US 8,318,746 B2

(12) United States Patent
Yasuma et al.

(10) Patent No.: US 8,318,746 B2
(45) Date of Patent: Nov. 27, 2012

(54) NITROGEN-CONTAINING FIVE-MEMBERED HETEROCYCLIC COMPOUND

(75) Inventors: Tsuneo Yasuma, Osaka (JP); Kentaro Hashimoto, Ibaraki (JP); Masahiro Ito, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 190 days.

(21) Appl. No.: 12/451,130

(22) PCT Filed: Apr. 25, 2008

(86) PCT No.: PCT/JP2008/058112
§ 371 (c)(1),
(2), (4) Date: Oct. 27, 2009

(87) PCT Pub. No.: WO2008/136428
PCT Pub. Date: Nov. 13, 2008

(65) Prior Publication Data
US 2010/0130446 A1    May 27, 2010

(30) Foreign Application Priority Data

Apr. 27, 2007  (JP) ................................ 2007-120136
Apr. 16, 2008  (JP) ................................ 2008-106925

(51) Int. Cl.
*A61K 31/496*   (2006.01)
*A61K 31/4427*  (2006.01)
*A61K 31/427*   (2006.01)
*C07D 403/14*   (2006.01)
*C07D 401/14*   (2006.01)
*C07D 277/20*   (2006.01)

(52) U.S. Cl. .................. 514/253.09; 514/343; 514/365; 544/364; 546/276.4; 548/202

(58) Field of Classification Search ............. 514/253.09, 514/343, 365; 544/364; 546/276.4; 548/202
See application file for complete search history.

(56) References Cited

U.S. PATENT DOCUMENTS

| 3,256,288 | A  | 6/1966  | Moyle et al.     |
| 3,354,173 | A  | 11/1967 | Godefroi         |
| 4,218,457 | A  | 8/1980  | Atsumi et al.    |
| 6,479,531 | B1 | 11/2002 | Kalindjian et al.|
| 2006/0111353 | A1 | 5/2006 | Weichert et al. |
| 2006/0211720 | A1 | 9/2006 | Glunz et al.    |
| 2008/0032996 | A1 | 2/2008 | Mitsuya et al.  |
| 2008/0070928 | A1 | 3/2008 | Nonoshita et al.|
| 2009/0247746 | A1 | 10/2009 | Yasuma et al.  |

FOREIGN PATENT DOCUMENTS

| EP | 2 077 267   |   | 7/2009  |        |
| JP | 5-155882    |   | 6/1993  |        |
| JP | 2002-296739 |   | 10/2002 |        |
| JP | 2006-515858 |   | 6/2006  |        |
| WO | WO 96/16040 | * | 5/1996  | ......... 548/200 |
| WO | 00/27823    |   | 5/2000  |        |
| WO | WO 2004/005283 | * | 1/2004 | ......... 548/200 |
| WO | 2005/063738 |   | 7/2005  |        |
| WO | 2005/090332 |   | 9/2005  |        |
| WO | 2006/062972 |   | 6/2006  |        |
| WO | 2006/112549 |   | 10/2006 |        |
| WO | 2007/028135 |   | 3/2007  |        |
| WO | 2007/061923 |   | 5/2007  |        |
| WO | 2007/075847 |   | 7/2007  |        |
| WO | 2007/104034 |   | 9/2007  |        |
| WO | 2008/047821 |   | 4/2008  |        |
| WO | 2008/050821 |   | 5/2008  |        |

OTHER PUBLICATIONS

Stadler, Daniel. Highly Diastereoselective Friedel—Crafts Alkylation Reactions via Chiral α-Functionalized Benzylic Carbocations. Chemistry—An Asian Journal 3(2), 272-284, Feb. 1, 2008.*
International Preliminary Report on Patentability (PCT/IB/338, PCT/IB/373) and Written Opinion of the International Searching Authority (PCT/ISA/237) issued Nov. 24, 2009 in International Application No. PCT/JP2008/058112, of which the present application is the U.S. National Stage.
Supplementary European Search Report dated Jul. 13, 2010 in Application No. EP 08 75 2146.
K. R. Guertin et al., "Small Molecule Glucokinase Activators as Glucose Lowering Agents: A New Paradigm for Diabetes Therapy", Current Medicinal Chemistry, vol. 13, pp. 1839-1843, 2006.
International Search Report issued Jun. 10, 2008 in International (PCT) Application No. PCT/JP2008/058112.
Nippon Kagaku Kaisha, 1975, No. 2, pp. 334-338, p. 336, compound 12.
W. G. O'Neal et al., "Studies in Chlorin Chemistry. II A Versatile Synthesis of Dihydrodipyrrins", J. Org. Chem., vol. 70, No. 18, pp. 7243-7251, 2005.
M. O. Senge, "Hydrogen Bonding and Conformation of 5-Substituted Dipyrromethanes—A Solid State Study", Heterocycles, vol. 65, No. 4, p. 797-808, 2005.
J. Setsune et al., "A Triangular Mixed-Valent $Cu^{II}Cu^{I}Cu^{I}$ Cluster Supported by the Tripod Ligand 2-Quinolyl-2,2'—dipyrrolylmethane", Angewandte Chemie, International Edition, vol. 39, No. 6, pp. 1115-1117, 2000.

(Continued)

*Primary Examiner* — Rebecca Anderson
*Assistant Examiner* — Samanatha Shterengarts
(74) *Attorney, Agent, or Firm* — Wenderoth, Lind & Ponack, L.L.P.

(57) ABSTRACT

The present invention provides a compound represented by the formula (I):

(I)

wherein each symbol is as defined in the specification, or a salt thereof. The compound of the present invention has a glucokinase activity, and is useful as a medicament such as an agent for the prophylaxis or treatment of diabetes, obesity and the like, and the like.

24 Claims, No Drawings

OTHER PUBLICATIONS

J. Setsune et al., "Synthesis and Atropisomerism of *meso*-Tetraarylporphyrins with Mixed *meso*-Aryl Groups Having *ortho*-Substituents", Tetrahedron, vol. 54, No. 8, pp. 1407-1424, 1998.

J. Setsune et al., "Self-Assembled Dimers of Copper(II) Complexes of Tripodal Dianionic Ligands, 2-Pyridyl-2,2'—dipyrrolymethanes", Inorganic Chemistry, vol. 36, No. 22, pp. 5135-5137, 1997.

C. M. Drain et al., "Self-assembly of a Bisporphyrin Supramolecular Cage Induced by Molecular Recognition Between Complementary Hydrogen Bonding Sites", Journal of Chemical Society, Chemical Communications, No. 3, pp. 243-245, 1993.

R. J. P. Corriu et al., "Silylamines in Organic Synthesis. Facile Synthetic Routes to Unsaturated Protected Primary Amines", Tetrahedron, vol. 48, No. 30, pp. 6231-6244, 1992.

D. H. Shih et al., "Preparation and Antibacterial Activity of $\Delta^1$-Thienamycin", Journal of Medical Chemistry, vol. 24, No. 5, pp. 639-643, 1981.

E. F. Godefroi et al., "DL-1-(1-Arylalkyl)imidazole-5-carboxylate Esters. A Novel Type of Hypnotic Agents", Journal of Medical Chemistry, vol. 8, No. 2, pp. 220-223, 1965.

STN Search Result by the Applicants, pp. 1-22.

STN Search Result by the Applicants, pp. 1-22, including CAS Nos. 303791-54-0, 930508-86-4, 746594-95-6, 438019-51-3, 438018-38-3, 779297-46-0 and 730926-85-9.

\* cited by examiner

NITROGEN-CONTAINING FIVE-MEMBERED HETEROCYCLIC COMPOUND

This application is a U.S. national stage of International Application No. PCT/JP2008/058112 filed Apr. 25, 2008.

TECHNICAL FIELD

The present invention relates to a nitrogen-containing 5-membered heterocyclic compound having a glucokinase activating action and useful as a therapeutic agent for diabetes and the like.

BACKGROUND OF THE INVENTION

Glucokinase (sometimes to be abbreviated as "GK" in the present specification) (EC2.7.1.1) is one of the 4 kinds of hexokinases found in mammals, and is also called hexokinase IV. GK is an enzyme that catalyzes conversion of glucose to glucose 6-phosphate, which is the first step of the glycolytic system. GK is mainly present in pancreatic β cell and the liver. In pancreatic β cell, it functions as a sensor of extracellular glucose concentration that defines glucose stimulated insulin secretion, and in the liver, enzyme reaction of GK becomes a rate determinant, which controls glycogen synthesis and gly-colysis. The three hexokinases (I, II and III) other than GK show the maximum enzyme activity at a glucose concentration of 1 mM or below, whereas GK shows low affinity for glucose and a Km value of 8-15 mM, which is close to the physiological blood glucose level. Therefore, intracellular glucose metabolism is promoted via GK, which corresponds to the changes in the blood glucose level from normal blood glucose (5 mM) to postprandial blood glucose (10-15 mM).

The hypothesis proposed by Matschinsky et al in 1984, "GK functions as a glucose sensor in pancreatic β cell and hepatocyte" has been demonstrated through analysis of glucokinase genetically-engineered mouse in recent years (see non-patent documents 1-5). That is, GK hetero-deficient mouse showed hyperglycemia state, and further, disordered insulin secretion reaction caused by stimulation with sugar. GK homo-deficient mouse dies soon after birth showing remarkable hyperglycemia and urinary sugar. On the other hand, GK overexpression mouse (hetero type) showed decreased blood glucose level, increased blood glucose clearance rate, increased liver glycogen content and the like. From these findings, it has been clarified that GK plays a key role in the systemic glucose homeostasis. In other words, when GK activity decreases, insufficient insulin secretion and lower liver glucose metabolism occur, which in turn causes the onset of impaired glucose tolerance or diabetes. Conversely, increased GK activity due to the activation or overexpression of GK promotes insulin secretion and liver glucose metabolism, which in turn increases systemic sugar utilization to improve glucose tolerance.

In addition, GK gene abnormality has been reported mainly in the family of Maturity Onset Diabetes of the Young called MODY2, and analysis thereof has clarified that GK functions as a glucose sensor and plays an important role in glucose homeostasis also in human (see non-patent document 6). In GK gene abnormality, due to the decreased affinity of GK for glucose (increased Km value) and decreased Vmax, the blood glucose threshold value of insulin secretion increases and the insulin secretory capacity decreases. In the liver, due to the decreased GK activity, decreased glucose uptake, promoted gluconeogenesis, decreased glycogen synthesis and liver insulin resistance are observed. On the other hand, a family with a mutation increasing the GK activity has also been found. In such family, fasting hypoglycemia associated with increased plasma insulin concentration is observed (see non-patent document 7).

As mentioned above, GK acts as a glucose sensor in mammals including human, and plays an important role in blood glucose regulation. On the other hand, control of blood glucose utilizing the glucose sensor system of GK is considered to open a new way of treating diabetes in many type 2 diabetes patients. Particularly, since a GK activating substance is expected to show insulin secretagogue action in the pancreatic β cell and glucose uptake promotion and glucose release suppressive action in the liver, such substance will be useful as a prophylactic or therapeutic drug for type 2 diabetes.

In recent years, it has been clarified that pancreatic p cell type glucokinase expresses locally in the feeding center (Ventromedial Hypothalamus: VMH) of rat brain. A subset of nerve cell present in VMH is called glucose responsive neuron, and plays an important role in the body weight control. From electrophysiological experiments, the neuron is activated in response to physiological changes in the glucose concentration (5-20 mM). However, since the glucose concentration sensor system of VHM is assumed to have a mechanism mediated by glucokinase as in the case of insulin secretion in the pancreatic β cell, different from pancreatic β cell and the liver, a medicament capable of activating glucokinase of VHM has a possibility of providing not only a blood glucose corrective effect but also improvement of obesity.

As mentioned above, a medicament having a GK activating action is useful as a prophylactic or therapeutic drug for diabetes or diabetes chronic complications such as retinopathy, nephropathy, neurosis, ischemic cardiac diseases, arteriosclerosis and the like, and further as a prophylactic or therapeutic drug for obesity.

As nitrogen-containing 5-membered heterocyclic compounds, the following compounds have been reported. However, none of the compounds has been reported to show a glucokinase activation.

Patent document 1 (WO2006/062972) discloses that a compound represented by

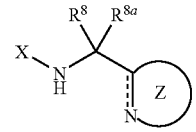

wherein $R^8$ is phenyl substituted by 0 to 5 particular substituents, and the like; $R^{8a}$ is H or $C_{1-4}$ alkyl; and

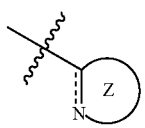

is a nitrogen-containing 5- or 6-membered heteroaryl, is a selective inhibitor of serine protease and useful for a thrombus obstructive disease and the like. In this reference, the following compound is disclosed.

Non-patent document 8 (Chemical Abstract Registry No.: 303791-54-0) discloses the following compound.

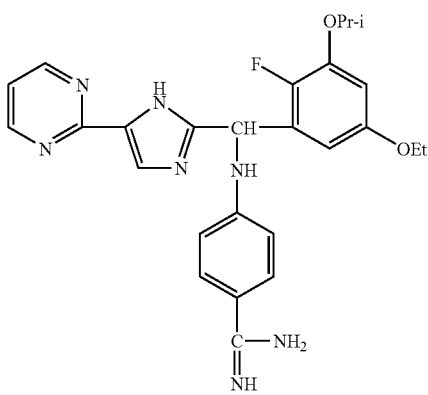

Non-patent document 9 (Journal of Organic Chemistry (2005), 70(18), 7243-7251) discloses the following compounds.

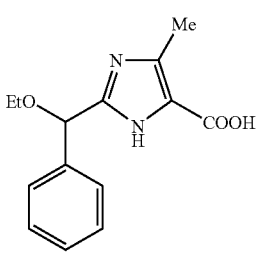

Non-patent document 10 (Heterocycles (2005), 65(4), 797-808) discloses the following compound.

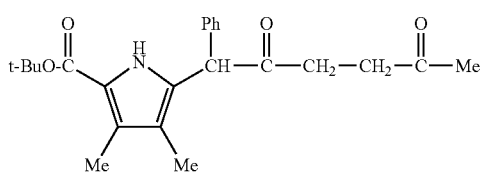

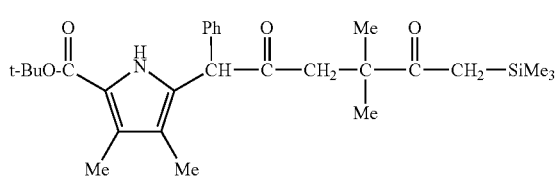

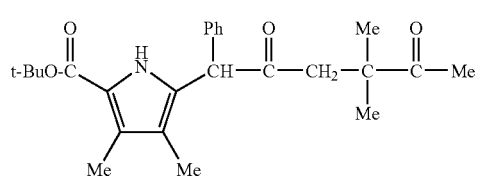

Patent document 2 (JP2002-296739) discloses the following compound.

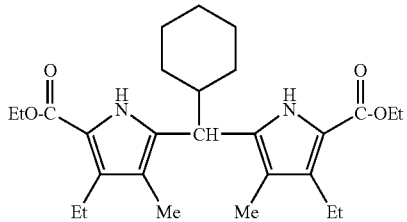

Patent document 3 (WO2000/27823) discloses the following compound.

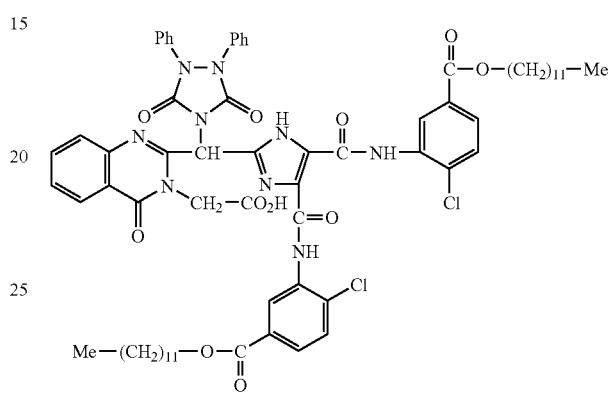

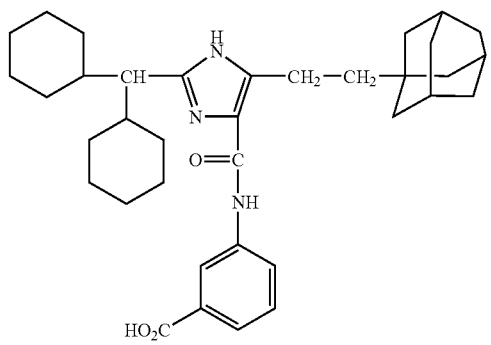

Non-patent document 11 (Angewandte Chemie, International Edition (2000), 39(6), 1115-1117) discloses the following compound.

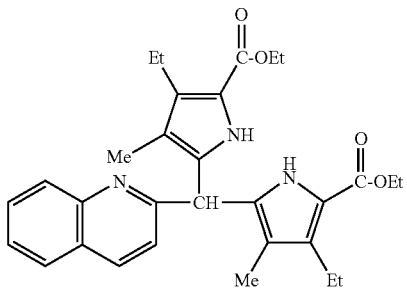

Non-patent document 12 (Tetrahedron (1998), 54(8), 1407-1424) discloses the following compound.

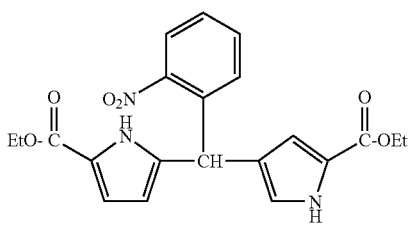

Non-patent document 13 (Inorganic Chemistry (1997), 36(22), 5135-5137) discloses the following compounds.

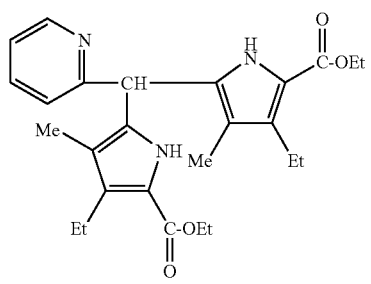

Patent document 4 (JP05-155882) discloses the following compounds.

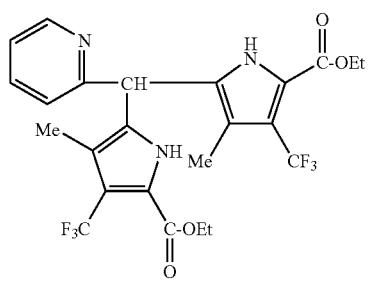

Non-patent document 14 (Journal of the Chemical Society, Chemical Communications (1993), (3), 243-5) discloses the following compounds.

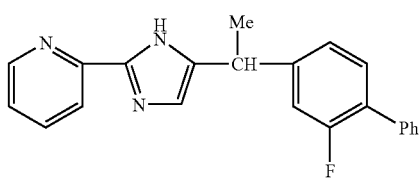

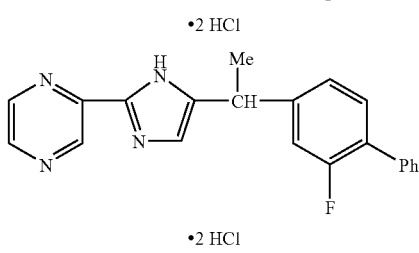

Non-patent document 15 (Tetrahedron (1992), 48(30), 6231-44) discloses the following compound.

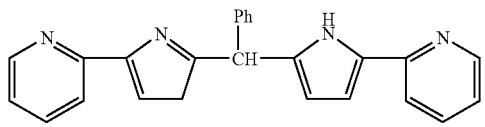

Non-patent document 16 (Journal of Medicinal Chemistry (1981), 24(5), 639-43) discloses the following compound.

Patent document 5 (U.S. Pat. No. 4,218,457) discloses the following compound.

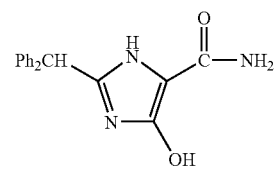

Non-patent document 17 (NIPPON KAGAKU KAISHI (1975), (2), 334-8) discloses the following compound.

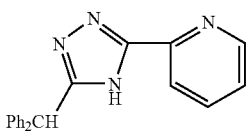

Patent document 6 (U.S. Pat. No. 3,256,288) discloses the following compound.

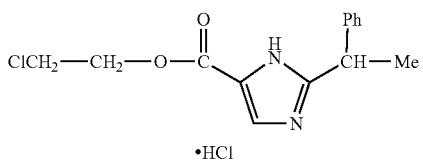

Patent document 7 (U.S. Pat. No. 3,354,173) discloses the following compounds.

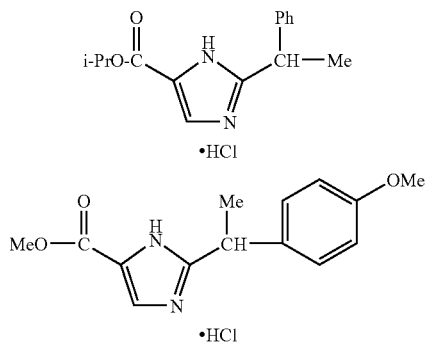

Non-patent document 18 (Journal of Medicinal Chemistry (1965), 8(2), 220-3) discloses the following compound.

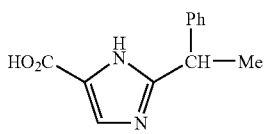

Non-patent document 19 (Chemical Abstract Registry No.: 930508-86-4) discloses the following compound.

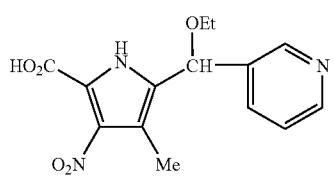

Non-patent document 20 (Chemical Abstract Registry No.: 746594-95-6) discloses the following compound.

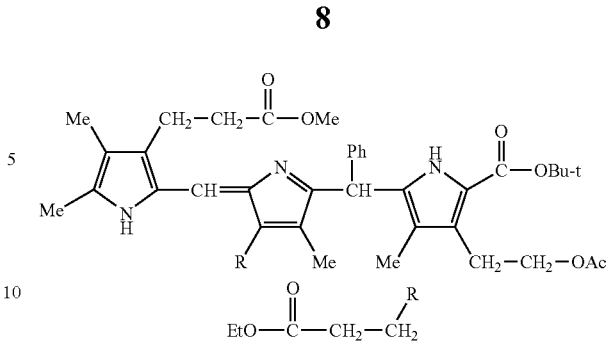

Non-patent document 21 (Chemical Abstract Registry No.: 438019-51-3) discloses the following compound.

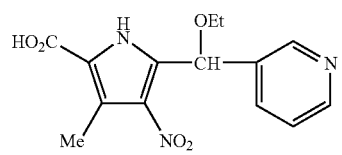

Non-patent document 22 (Chemical Abstract Registry No.: 438018-38-3) discloses the following compound.

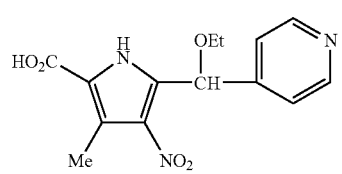

Non-patent document 23 (Chemical Abstract Registry No.: 779297-46-0)) discloses the following compound.

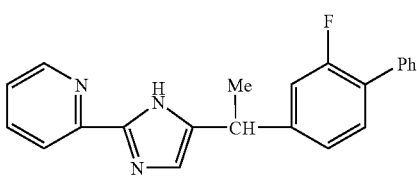

Non-patent document 24 (Chemical Abstract Registry No.: 730926-85-9) discloses the following compound.

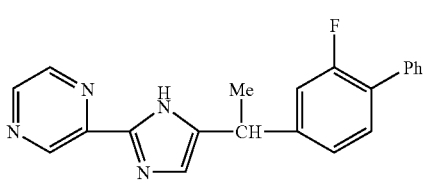

patent document 1: WO2006/062972
patent document 2: JP-A-2002-296739
patent document 3: WO2000/27823
patent document 4: JP-A-05-155882
patent document 5: U.S. Pat. No. 4,218,457
patent document 6: U.S. Pat. No. 3,256,288
patent document 7: U.S. Pat. No. 3,354,173
non-patent document 1: J. Biol. Chem. 1995, vol. 270, pp. 30253-30256 non-patent document 2: J. Biol. Chem. 1997, vol. 272, pp. 22564-22569
non-patent document 3: J. Biol. Chem. 1997, vol. 272, pp. 22570-22575
non-patent document 4: Japan Clinical, 2002, vol. 60, pp. 523-534
non-patent document 5: Cell 1995, vol. 83, pp. 69-78
non-patent document 6: Nature 1992, vol. 356, pp. 721-722 page
non-patent document 7: New England Journal Medicine 1998, vol. 338, pp. 226-230
non-patent document 8: Chemical Abstract Registry No.: 303791-54-0
non-patent document 9: Journal of Organic Chemistry (2005), 70(18), 7243-7251
non-patent document 10: Heterocycles (2005), 65(4), 797-808
non-patent document 11: Angewandte Chemie, International Edition (2000), 39(6), 1115-1117
non-patent document 12: Tetrahedron (1998), 54(8), 1407-1424
non-patent document 13: Inorganic Chemistry (1997), 36(22),
non-patent document 14: Journal of the Chemical Society, Chemical Communications (1993), (3), 243-5
non-patent document 15: Tetrahedron (1992), 48(30), 6231-44)
non-patent document 16: Journal of Medicinal Chemistry (1981), 24(5), 639-43
non-patent document 17: NIPPON KAGAKU KAISHI (1975), (2), 334-8
non-patent document 18: Journal of Medicinal Chemistry (1965), 8(2), 220-3
non-patent document 19: Chemical Abstract Registry No.: 930508-86-4
non-patent document 20: Chemical Abstract Registry No.: 746594-95-6
non-patent document 21: Chemical Abstract Registry No.: 438019-51-3
non-patent document 22: Chemical Abstract Registry No.: 438018-38-3
non-patent document 23: Chemical Abstract Registry No.: 779297-46-0
non-patent document 24: Chemical Abstract Registry No.: 730926-85-9

DISCLOSURE OF THE INVENTION

Problems to be Solved by the Invention

An object of the present invention is to provide a glucokinase activator useful as a medicament such as an agent for the prophylaxis or treatment of diabetes, obesity and the like, and the like.

Means of Solving the Problems

The present inventors have conducted intensive studies and found that a compound represented by the following formula (I):

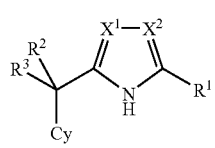

wherein
$R^1$ is
(i) a group represented by $-COR^4$ wherein
$R^4$ is an optionally substituted alkyl group, an optionally substituted cycloalkyl group, $-OR^5$ wherein $R^5$ is a hydrogen atom or an optionally substituted alkyl group, or an optionally substituted amino group, or
(ii) a 5- or 6-membered nitrogen-containing heterocyclic group represented by the formula

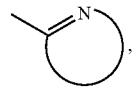

which is optionally substituted;
$R^2$ is an optionally substituted alkyl group, an optionally substituted 4- to 7-membered cyclic group, $-OR^6$ wherein $R^6$ is an optionally substituted alkyl group or an optionally substituted 4- to 7-membered cyclic group, or an optionally substituted amino group;
$R^3$ is a hydrogen atom or an optionally substituted alkyl group, or
$R^2$ and $R^3$ in combination
(i) optionally form, together with the carbon atom they are bonded to, cyclopropane substituted by an optionally substituted 4- to 7-membered cyclic group, or
(ii) optionally form $=N-OR^7$ or $=CH-R^7$ wherein $R^7$ is an optionally substituted alkyl group or an optionally substituted 4- to 7-membered cyclic group;
Cy is an optionally substituted 6-membered cyclic group, which is optionally condensed with an optionally substituted 5- or 6-membered ring; and
$X^1$ and $X^2$ are each independently an optionally substituted carbon atom, or a nitrogen atom,
or a salt thereof (sometimes to be abbreviated as "compound (I)" in the present specification) unexpectedly has a superior glucokinase activating action and superior actions in vivo (superior efficacy, low toxicity, superior metabolism stability and the like)), as well as superior properties of a pharmaceutical product such as stability and the like, and can be a safe and useful medicament, which resulted in the completion of the present invention.

Accordingly, the present invention relates to
[1] a compound represented by the formula (I) provided that (1) when Cy is a benzene ring, then $R^2$ should not be pyrrolyl;
(2) 4-{[(5-ethoxy-2-fluoro-3-isopropoxyphenyl)(5-pyrimidin-2-yl-1H-imidazol-2-yl)methyl]amino}benzenecarboximidamide,
2-[ethoxy(phenyl)methyl]-4-methyl-1H-imidazole-5-carboxylic acid,
tert-butyl 5-(2,5-dioxo-1-phenylhexyl)-3,4-dimethyl-1H-pyrrole-2-carboxylate,
tert-butyl 5-[4,4-dimethyl-2,5-dioxo-1-phenyl-6-(trimethylsilyl)hexyl]-3,4-dimethyl-1H-pyrrole-2-carboxylate,
tert-butyl 5-(4,4-dimethyl-2,5-dioxo-1-phenylhexyl)-3,4-dimethyl-1H-pyrrole-2-carboxylate,
diethyl 5,5'-(cyclohexylmethanediyl)bis(3-ethyl-4-methyl-1H-pyrrole-2-carboxylate),
[2-{[4,5-bis({2-chloro-5-[(dodecyloxy)carbonyl]phenyl}carbamoyl)-1H-imidazol-2-yl](3,5-dioxo-1,2-diphenyl-1,2,4-triazolidin-4-yl)methyl}-4-oxoquinazolin-3(4H)-yl]acetic acid,
3-({[2-(dicyclohexylmethyl)-5-(2-tricyclo[3.3.1.13,7]deca-1-ylethyl)-1H-imidazol-4-yl]carbonyl}amino)benzoic acid,
diethyl 5,5'-(quinolin-2-ylmethanediyl)bis(3-ethyl-4-methyl-1H-pyrrole-2-carboxylate),
ethyl 4-{[5-(ethoxycarbonyl)-1H-pyrrol-2-yl] (2-nitrophenyl)methyl}-1H-pyrrole-2-carboxylate, diethyl 5,5'-(pyridin-2-ylmethanediyl)bis(3-ethyl-4-methyl-1H-pyrrole-2-carboxylate),
diethyl 5,5'-(pyridin-2-ylmethanediyl)bis[4-methyl-3-(trifluoromethyl)-1H-pyrrole-2-carboxylate],
(2-fluorobiphenyl-4-yl)(2-pyridin-2-yl-1H-imidazol-5-yl)methanol,
(2-fluorobiphenyl-4-yl)(2-pyrazin-2-yl-1H-imidazol-5-yl)methanol,
5,5'-[(1-decyl-2,4-dioxo-1,2,3,4-tetrahydropyrimidin-5-yl)methanediyl]bis(3,4-diethyl-1H-pyrrole-2-carboxylic acid),
dibenzyl 5,5'-[(1-decyl-2,4-dioxo-1,2,3,4-tetrahydropyrimidin-5-yl)methanediyl]bis(3,4-diethyl-1H-pyrrole-2-carboxylate),
4-nitrobenzyl 3-hydroxy-5-(2-hydroxy-1-morpholin-4-yl-propyl)-1H-pyrrole-2-carboxylate,
2-(diphenylmethyl)-4-hydroxy-1H-imidazole-5-carboxamide,
3-[5-(diphenylmethyl)-4H-1,2,4-triazol-3-yl]pyridine,
2-chloroethyl 2-(1-phenylethyl)-1H-imidazole-5-carboxylate,
1-methylethyl 2-(1-phenylethyl)-1H-imidazole-5-carboxylate, methyl 2-[1-(4-methoxyphenyl)ethyl]-1H-imidazole-5-carboxylate,
2-(1-phenylethyl)-1H-imidazole-5-carboxylic acid,
5-[ethoxy(pyridin-3-yl)methyl]-4-methyl-3-nitro-1H-pyrrole-2-carboxylic acid,
tert-butyl 3-[2-(acetyloxy)ethyl]-5-{[(2E)-3-(3-ethoxy-3-oxopropyl)-2-{[3-(3-methoxy-3-oxopropyl)-4,5-dimethyl-1H-pyrrol-2-yl]methylidene}-4-methyl-2H-pyrrol-5-yl](phenyl)methyl}-4-methyl-1H-pyrrole-2-carboxylate,
5-[ethoxy(pyridin-3-yl)methyl]-3-methyl-4-nitro-1H-pyrrole-2-carboxylic acid,
5-[ethoxy(pyridin-4-yl)methyl]-3-methyl-4-nitro-1H-pyrrole-2-carboxylic acid,
2-{5-[1-(2-fluorobiphenyl-4-yl)ethyl]-1H-imidazol-2-yl}pyridine, and
2-{5-[1-(2-fluorobiphenyl-4-yl)ethyl]-1H-imidazol-2-yl}pyrazine
are excluded,
or a salt thereof;

[2] the compound of the above-mentioned [1], wherein $R^1$ is a 5- or 6-membered nitrogen-containing heterocyclic group represented by the formula

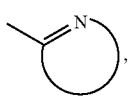

which is optionally substituted;
[3] the compound of the above-mentioned [1], wherein $R^2$ is an optionally substituted $C_{1-6}$ alkyl group;
[4] the compound of the above-mentioned [1], wherein $R^3$ is a hydrogen atom or a $C_{1-6}$ alkyl group;
[5] the compound of the above-mentioned [1], wherein Cy is an optionally substituted 6-membered aromatic group, which is optionally condensed with an optionally substituted 5- or 6-membered ring;
[6] the compound of the above-mentioned [1], wherein Cy is an optionally substituted 6-membered aromatic group;
[7] the compound of the above-mentioned [1], wherein $X^1$ is an optionally substituted carbon atom, or a nitrogen atom, and $X^2$ is an optionally substituted carbon atom;
[8] the compound of the above-mentioned [7], wherein $X^2$ is a carbon atom optionally substituted by one substituent selected from a halogen atom and a $C_{1-4}$ alkyl group optionally substituted by 1 to 3 $C_{1-6}$ alkoxy-carbonyl groups;
[9] the compound of the above-mentioned [1], wherein $X^1$ and $X^2$ are both optionally substituted carbon atoms;
[10] the compound of the above-mentioned [1], wherein $R^1$ is a 5- or 6-membered nitrogen-containing heterocyclic group represented by the formula

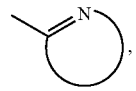

which is optionally substituted,
$R^2$ is an optionally substituted $C_{1-6}$ alkyl group, and
$X^1$ and $X^2$ are both optionally substituted carbon atoms;
[11] 3-{2-[5-(cyclobutylcarbonyl)-4-fluoro-1H-imidazol-2-yl]-2-[4-(cyclopropylsulfonyl)phenyl]ethyl}cyclopentanone or a salt thereof;
[12] 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol or a salt thereof;
[13] 1-[6-(5-{1-[4-(cyclopropylsulfonyl)phenyl]-2-(tetrahydro-2H-pyran-4-yl)ethyl}-1H-pyrrol-2-yl)pyridin-3-yl]ethane-1,2-diol or a salt thereof;
[14] 2-[6-(5-{1-[4-(cyclopropylsulfonyl)phenyl]-2-(tetrahydro-2H-pyran-4-yl)ethyl}-1H-pyrrol-2-yl)pyridin-3-yl]propane-1,3-diol or a salt thereof;
[15] 1-acetyl-4-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}piperazine or a salt thereof;
[16] 1-[6-(5-{1-[3-chloro-4-(methylsulfonyl)phenyl]-2-(tetrahydro-2H-pyran-4-yl)ethyl]-1H-pyrrol-2-yl)pyridin-3-yl]ethane-1,2-diol or a salt thereof;
[17] 1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol or a salt thereof;
[18] 1-[2-(5-[1-[4-(cyclopropylsulfonyl)phenyl]-2-(tetrahydro-2H-pyran-4-yl)ethyl]-1H-pyrrol-2-yl)-1,3-thiazol-5-yl]ethanol or a salt thereof;
[19] 1-[2-(5-{1-[3-chloro-4-(methylsulfonyl)phenyl]-2-(tetrahydro-2H-pyran-4-yl)ethyl}-1H-pyrrol-2-yl)-1,3-thiazol-5-yl]ethanol or a salt thereof;
[20] 3-(2-[3-chloro-4-(methylsulfonyl)phenyl]-2-{5-[5-(hydroxymethyl)pyridin-2-yl]-1H-pyrrol-2-yl}ethyl)cyclopentanone or a salt thereof;
[21] a prodrug of the compound of the above-mentioned [1];
[22] a medicament comprising compound (I) or a prodrug thereof;
[23] the medicament of the above-mentioned [22], which is a glucokinase activator;
[24] the medicament of the above-mentioned [22], which is an agent for the prophylaxis or treatment of diabetes or obesity;
[25] a method of activating a glucokinase in a mammal, which comprises administering compound (I) or a prodrug thereof in an amount effective for activating glucokinase to the mammal;
[26] a method for the prophylaxis or treatment of diabetes or obesity in a mammal, which comprises administering a therapeutically effective amount of compound (I) or a prodrug thereof to the mammal;
[27] use of compound (I) or a prodrug thereof for the production of a glucokinase activator;
[28] use of compound (I) or a prodrug thereof for the production of an agent for the prophylaxis or treatment of diabetes or obesity;

[A1] the compound of the above-mentioned [1], wherein $R^1$ is a 5- or 6-membered nitrogen-containing heterocyclic group represented by the formula

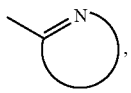

which is optionally substituted by a halogen atom, —OR', —SR', —SOR', —S(O)$_2$R', —COOR' wherein R' is a hydrogen atom or a substituent, an optionally substituted carbamoyl group or an optionally substituted $C_{1-6}$ alkyl group;
[A2] the compound of the above-mentioned [1], wherein $R^2$ is a $C_{1-6}$ alkyl group optionally substituted by an optionally substituted 4- to 7-membered cyclic group;
[A3] the compound of the above-mentioned [1], wherein $R^3$ is a hydrogen atom;
[A4] the compound of the above-mentioned [1], wherein $X^1$ and $X^2$ are each independently a carbon atom optionally substituted by a halogen atom, a cyano group, a $C_{1-6}$ alkyl group, a $C_{1-6}$ alkylsulfonyl group or an optionally substituted carbamoyl group, or a nitrogen atom;
[A5] the compound of the above-mentioned [1], wherein $R^1$ is
(i) a group represented by —COR$^4$
  wherein
  $R^4$ is an alkyl group, a cycloalkyl group, —OR$^5$ wherein $R^5$ is a hydrogen atom or an alkyl group, or an amino group, or
(ii) a 5- or 6-membered nitrogen-containing heterocyclic group represented by the formula

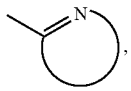

which is optionally substituted by a $C_{1-4}$ alkyl group,
$R^2$ is a $C_{1-6}$ alkyl group optionally substituted by a 4- to 7-membered cyclic group,
$R^3$ is a hydrogen atom,
Cy is a 6-membered aromatic group substituted by $C_{1-6}$ alkylsulfonyl or $C_{3-7}$ cycloalkylsulfonyl,
$X^1$ is a carbon atom or a nitrogen atom, and
$X^2$ is a carbon atom optionally substituted by a halogen atom or a $C_{1-4}$ alkyl group;
and the like.

EFFECT OF THE INVENTION

The glucokinase activator of the present invention has a superior glucokinase activating action, and it is useful as a medicament such as an agent for the prophylaxis or treatment of diabetes, obesity and the like, and the like.

DETAILED DESCRIPTION OF THE INVENTION

Unless otherwise specified, examples of the "halogen atom" in the present specification include a fluorine atom, a chlorine atom, a bromine atom and an iodine atom.
Unless otherwise specified, examples of the "optionally substituted hydrocarbon group" in the present specification include an "optionally substituted $C_{1-6}$ alkyl group", an "optionally substituted $C_{2-6}$ alkenyl group", an "optionally substituted $C_{2-6}$ alkynyl group", an "optionally substituted $C_{3-7}$ cycloalkyl group", an "optionally substituted $C_{6-14}$ aryl group", an "optionally substituted $C_{7-16}$ aralkyl group" and the like.

Unless otherwise specified, examples of the "$C_{1-6}$ alkyl group" in the present specification include methyl, ethyl, propyl, isopropyl, butyl, isobutyl, sec-butyl, tert-butyl, pentyl, isopentyl, neopentyl, hexyl and the like.
Unless otherwise specified, examples of the "$C_{2-6}$ alkenyl group" in the present specification include vinyl, propenyl, isopropenyl, 2-buten-1-yl, 2-methyl-1-propenyl, 4-penten-1-yl, 5-hexen-1-yl and the like.
Unless otherwise specified, examples of the "$C_{2-6}$ alkynyl group" include 2-butyn-1-yl, 4-pentyn-1-yl, 5-hexyn-1-yl and the like.
Unless otherwise specified, examples of the "$C_{3-7}$ cycloalkyl group" in the present specification include cyclopropyl, cyclobutyl, cyclopentyl, cyclohexyl, cycloheptyl and the like.
Unless otherwise specified, examples of the "$C_{6-14}$ aryl group" in the present specification include phenyl, 1-naphthyl, 2-naphthyl, 2-biphenylyl, 3-biphenylyl, 4-biphenylyl, 2-anthryl and the like.
Unless otherwise specified, examples of the "$C_{7-16}$ aralkyl group" in the present specification include benzyl, phenylethyl, 1-phenylethyl, diphenylmethyl, 1-naphthylmethyl, 2-naphthylmethyl, 2,2-diphenylethyl, 3-phenylpropyl, 3,3-diphenylpropyl, 4-phenylbutyl, 5-phenylpentyl, 2-biphenylylmethyl, 3-biphenylylmethyl, 4-biphenylylmethyl and the like.
Unless otherwise specified, examples of the "$C_{1-6}$ alkoxy group" in the present specification include methoxy, ethoxy, propoxy, isopropoxy, butoxy, isobutoxy, tert-butoxy, pentyloxy, hexyloxy and the like.
In addition, examples of the "$C_{1-10}$ alkoxy group" in the present specification include, besides the above-mentioned $C_{1-6}$ alkoxy group, heptyloxy, octyloxy, nonyloxy, decyloxy and the like.
Examples of the "heterocyclyloxy group" in the present specification include a hydroxy group substituted by the below-mentioned "heterocyclic group". Preferable examples of the heterocyclyloxy group include tetrahydropyranyloxy, thiazolyloxy, pyridyloxy, pyrazolyloxy, oxazolyloxy, thienyloxy, furyloxy, tetrahydrothiopyranyloxy, 1,1-dioxidotetrahydrothiopyranyloxy and the like.
Unless otherwise specified, examples of the "$C_{6-14}$ aryloxy group" in the present specification include phenoxy, 1-naphthyloxy, 2-naphthyloxy and the like.
Unless otherwise specified, examples of the "$C_{7-16}$ aralkyloxy group" in the present specification include benzyloxy, 2-phenylethyloxy, 1-phenylethyloxy and the like.
Unless otherwise specified, examples of the "tri-$C_{1-6}$ alkylsilyloxy group" in the present specification include trimethylsilyloxy, tert-butyl(dimethyl)silyloxy and the like.
Unless otherwise specified, examples of the "$C_{1-6}$ alkylsulfonyloxy group" in the present specification include methylsulfonyloxy, ethylsulfonyloxy and the like.
Examples of the "heterocyclylsulfonyloxy group" in the present specification include a sulfonyloxy group substituted by the below-mentioned "heterocyclic group". Preferable examples of the heterocyclylsulfonyloxy group include thienylsulfonyloxy, furylsulfonyloxy and the like.
Unless otherwise specified, examples of the "$C_{1-6}$ alkylthio group" in the present specification include methylthio, ethylthio, propylthio, isopropylthio, butylthio, sec-butylthio, tert-butylthio and the like. In addition, examples of the "$C_{1-10}$ alkylthio group" in the present specification include, in addition to the above-mentioned $C_{1-6}$ alkylthio group, heptylthio, octylthio, nonylthio, decylthio and the like.
Unless otherwise specified, examples of the "heterocyclylthio group" in the present specification include a mercapto group substituted by the below-mentioned "heterocyclic group". Preferable examples of the heterocyclylthio group include tetrahydropyranylthio, thiazolylthio, pyridylthio, pyrazolylthio, oxazolylthio, thienylthio, furylthio, tetrahydrothiopyranylthio, 1,1-dioxidotetrahydrothiopyranylthio and the like.

Unless otherwise specified, examples of the "$C_{6-14}$ arylthio group" in the present specification include phenylthio, 1-naphthylthio, 2-naphthylthio and the like.

Unless otherwise specified, examples of the "heterocyclic group" in the present specification include a 5- to 14-membered (monocyclic, bicyclic or tricyclic) heterocyclic group containing, as a ring-constituting atom besides carbon atoms, 1 to 4 hetero atoms selected from a nitrogen atom, a sulfur atom (the sulfur atom is optionally oxidized) and an oxygen atom, preferably (i) a 5- to 14-membered (preferably 5- to 10-membered) aromatic heterocyclic group, (ii) a 4- to 10-membered (preferably 4- to 7-membered) non-aromatic heterocyclic group and the like.

Specific examples thereof include aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), oxadiazolyl (e.g., 2-oxadiazolyl), quinolyl (e.g., 2-quinolyl, 3-quinolyl, 4-quinolyl, 5-quinolyl, 6-quinolyl, 8-quinolyl), isoquinolyl (e.g., 1-isoquinolyl, 3-isoquinolyl, 4-isoquinolyl, 5-isoquinolyl), pyrazinyl (e.g., 1-pyrazinyl, 2-pyrazinyl), pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), indolyl (e.g., 1-indolyl, 2-indolyl, 3-indolyl), indazolyl (e.g., 1-indazolyl, 3-indazolyl, 5-indazolyl), benzofuranyl (e.g., 2-benzofuranyl, 3-benzofuranyl), benzothiophenyl (e.g., 2-benzothiophenyl, 3-benzothiophenyl), benzothiazolyl (e.g., 2-benzothiazolyl), benzoxazolyl (e.g., 2-benzoxazolyl), benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl), benzotriazolyl (e.g., 1-benzotriazolyl, 5-benzotriazolyl), imidazo[1,2-a]pyridinyl (e.g., 2-imidazo[1,2-a]pyridinyl, 3-imidazo[1,2-a]pyridinyl, 6-imidazo[1,2-a]pyridinyl), imidazo[1,2-a]pyrimidinyl (e.g., 2-imidazo[1,2-a]pyrimidinyl, 3-imidazo[1,2-a]pyrimidinyl, 5-imidazo[1,2-a]pyrimidinyl), pyrrolo[2,3-b]pyridinyl (e.g., 2-1H-pyrrolo[2,3-b]pyridinyl, 3-1H-pyrrolo[2,3-b]pyridinyl, 4-1H-pyrrolo[2,3-b]pyridinyl), [1,2,4]triazolo[1,5-a]pyridinyl (e.g., 2-[1,2,4]triazolo[1,5-a]pyridinyl, 6-[1,2,4]triazolo[1,5-a]pyridinyl, 7-[1,2,4]triazolo[1,5-a]pyridinyl) and the like; non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl, 3-pyrrolidinyl), oxazolidinyl (e.g., 2-oxazolidinyl), dihydrooxadiazolyl (e.g., 2-dihydrooxadiazolyl), imidazolinyl (e.g., 1-imidazolinyl, 2-imidazolinyl, 4-imidazolinyl), imidazolidinyl (e.g., 3-imidazolidinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), 1-oxidothiomorpholinyl (e.g., 1-oxidothiomorpholino), 1,1-dioxidothiomorpholinyl (e.g., 1,1-dioxidothiomorpholino), tetrahydropyranyl (e.g., 2-tetrahydropyranyl, 3-tetrahydropyranyl, 4-tetrahydropyranyl), tetrahydrofuranyl (e.g., 2-tetrahydrofuranyl, 3-tetrahydrofuranyl), oxetanyl (e.g., 2-oxetanyl, 3-oxetanyl), oxopyrrolidinyl (e.g., 2-oxopyrrolidin-1-yl, 2-oxopyrrolidin-3-yl, 2-oxopyrrolidin-4-yl, 2-oxopyrrolidin-5-yl, 3-oxopyrrolidin-1-yl), dioxopyrrolidinyl (e.g., 2,5-dioxopyrrolidin-1-yl, 2,5-dioxopyrrolidin-3-yl), tetrahydrothiopyranyl (e.g., 2-tetrahydrothiopyranyl, 3-tetrahydrothiopyranyl, 4-tetrahydrothiopyranyl), 1,1-dioxidotetrahydrothiopyranyl (e.g., 1,1-dioxidotetrahydrothiopyran-2-yl, 1,1-dioxidotetrahydrothiopyran-3-yl, 1,1-dioxidotetrahydrothiopyran-4-yl), dihydrobenzofuranyl (e.g., 2,3-dihydro-1-benzofuran-4-yl, 2,3-dihydro-1-benzofuran-5-yl, 2,3-dihydro-1-benzofuran-6-yl, 2,3-dihydro-1-benzofuran-7-yl), benzodioxolyl (e.g., benzodioxol-5-yl), tetrahydrobenzo[c]azepinyl (e.g., 1,3,4,5-tetrahydrobenzo[c]azepin-2-yl), tetrahydroisoquinolinyl (e.g., 1,2,3,4-tetrahydroisoquinolin-2-yl) and the like; and the like.

In addition, the above-mentioned non-aromatic heterocyclic group may be a crosslinked non-aromatic heterocyclic group. Examples of the crosslinked non-aromatic heterocyclic group include 2,5-diazabicyclo[2.2.1]heptan-2-yl, 1-azabicyclo[2.2.2]octan-3-yl and the like.

Unless otherwise specified, examples of the "$C_{3-6}$ alkylsulfonyl group" in the present specification include methylsulfonyl, ethylsulfonyl and the like.

Unless otherwise specified, examples of the "$C_{3-7}$ cycloalkylsulfonyl group" in the present specification include cyclopropylsulfonyl, cyclobutylsulfonyl, cyclopentylsulfonyl and the like.

Unless otherwise specified, examples of the "$C_{6-14}$ arylsulfonyl group" in the present specification include phenylsulfonyl, 1-naphthylsulfonyl, 2-naphthylsulfonyl and the like.

Unless otherwise specified, examples of the "$C_{1-6}$ alkylsulfinyl group" in the present specification include methylsulfinyl, ethylsulfinyl and the like.

Unless otherwise specified, examples of the "$C_{6-14}$ arylsulfinyl group" in the present specification include phenylsulfinyl, 1-naphthylsulfinyl, 2-naphthylsulfinyl and the like.

Unless otherwise specified, examples of the "$C_{1-6}$ alkylcarbonyl group" in the present specification include acetyl, isobutanoyl, isopentanoyl and the like.

Unless otherwise specified, examples of the "$C_{6-14}$ arylcarbonyl group" in the present specification include benzoyl, 1-naphthylcarbonyl, 2-naphthylcarbonyl and the like.

Unless otherwise specified, examples of the "heterocyclylcarbonyl group" in the present specification include a carbonyl group substituted by the aforementioned "heterocyclic group". Examples thereof include pyrrolidinylcarbonyl, piperidinocarbonyl, piperazinylcarbonyl, morpholinocarbonyl, thiomorpholinocarbonyl, thienylcarbonyl, tetrahydrobenzo[c]azepinylcarbonyl, tetrahydroisoquinolinylcarbonyl and the like.

Unless otherwise specified, examples of the "optionally esterified carboxy group" in the present specification include a carboxy group, a $C_{1-6}$ alkoxy-carbonyl group (e.g., methoxycarbonyl, ethoxycarbonyl, propoxycarbonyl, tert-butoxycarbonyl), a $C_{6-19}$ aryloxy-carbonyl group (e.g., phenoxycarbonyl), a $C_{7-16}$ aralkyloxy-carbonyl group (e.g., benzyloxycarbonyl, 2-phenylethyloxycarbonyl) and the like.

Unless otherwise specified, examples of the "optionally halogenated $C_{1-6}$ alkyl group" in the present specification include the above-mentioned "$C_{1-6}$ alkyl group" optionally having 1 to 5 "halogen atoms" mentioned above. Examples thereof include methyl, ethyl, propyl, isopropyl, butyl, tert-butyl, isobutyl, trifluoromethyl and the like.

Unless otherwise specified, examples of the "optionally halogenated $C_{1-6}$ alkoxy group" in the present specification include the above-mentioned "$C_{1-6}$ alkoxy group" optionally having 1 to 5 "halogen atoms" mentioned above. Examples thereof include methoxy, ethoxy, isopropoxy, tert-butoxy, trifluoromethoxy and the like.

Unless otherwise specified, examples of the "mono- or di-$C_{1-6}$ alkyl-amino group" in the present specification include an amino group mono- or di-substituted by the above-mentioned "$C_{1-6}$ alkyl group". Examples thereof include methylamino, ethylamino, propylamino, dimethylamino, diethylamino and the like.

Unless otherwise specified, examples of the "mono- or di-$C_{3-7}$ cycloalkyl-amino group" in the present specification include an amino group mono- or di-substituted by the above-mentioned "$C_{3-7}$ cycloalkyl group". Examples thereof include cyclopropylamino and the like.

Unless otherwise specified, examples of the "mono- or di-$C_{6-14}$ aryl-amino group" in the present specification include an amino group mono- or di-substituted by the above-mentioned "$C_{6-14}$ aryl group". Examples thereof include phenylamino, diphenylamino, 1-naphthylamino, 2-naphthylamino and the like.

Unless otherwise specified, examples of the "mono- or di-$C_{7-16}$ aralkyl-amino group" in the present specification include an amino group mono- or di-substituted by the above-mentioned "$C_{7-16}$ aralkyl group". Examples thereof include benzylamino, 2-phenylethylamino and the like.

Unless otherwise specified, examples of the "N—$C_{1-6}$ alkyl-N—$C_{6-14}$ aryl-amino group" in the present specification include an amino group substituted by the above-mentioned "$C_{1-6}$ alkyl group" and the above-mentioned "$C_{6-14}$ aryl group". Examples thereof include N-methyl-N-phenylamino, N-ethyl-N-phenylamino and the like.

Unless otherwise specified, examples of the "N—$C_{1-6}$ alkyl-N—$C_{7-16}$ aralkyl-amino group" in the present specification include an amino group substituted by the above-mentioned "$C_{1-6}$ alkyl group" and the above-mentioned "$C_{7-16}$ aralkyl group". Examples thereof include N-methyl-N-benzylamino, N-ethyl-N-benzylamino and the like.

Unless otherwise specified, examples of the "mono- or di-($C_{1-6}$ alkyl-carbonyl)-amino group" in the present specification include an amino group mono- or di-substituted by the above-mentioned "$C_{1-6}$ alkyl-carbonyl group". Examples thereof include acetylamino and the like.

Unless otherwise specified, examples of the "N—$C_{1-6}$ alkyl-N—($C_{1-6}$ alkyl-carbonyl)-amino group" in the present specification include an amino group substituted by the above-mentioned "$C_{1-6}$ alkyl group" and the above-mentioned "$C_{1-6}$ alkyl-carbonyl group". Examples thereof include N-acetyl-N-methylamino, N-acetyl-N-ethylamino and the like.

Unless otherwise specified, examples of the "mono- or di-$C_{1-6}$ alkyl-carbamoyl group" in the present specification include a carbamoyl group mono- or di-substituted by the above-mentioned "$C_{1-6}$ alkyl group". Examples thereof include methylcarbamoyl, ethylcarbamoyl, dimethylcarbamoyl, diethylcarbamoyl, ethylmethylcarbamoyl and the like.

Unless otherwise specified, examples of the "mono- or di-$C_{6-14}$ aryl-carbamoyl group" in the present specification include a carbamoyl group mono- or di-substituted by the above-mentioned "$C_{6-14}$ aryl group". Examples thereof include phenylcarbamoyl, 1-naphthylcarbamoyl, 2-naphthylcarbamoyl and the like.

Unless otherwise specified, examples of the "mono- or di-$C_{3-7}$ cycloalkyl-carbamoyl group" in the present specification include a carbamoyl group mono- or di-substituted by the above-mentioned "$C_{3-7}$ cycloalkyl group". Examples thereof include cyclopropylcarbamoyl, cyclopentylcarbamoyl, cyclohexylcarbamoyl and the like.

Unless otherwise specified, examples of the "mono- or di-5- to 7-membered heterocyclyl-carbamoyl group" in the present specification include a carbamoyl group mono- or di-substituted by a 5- to 7-membered heterocyclic group. Examples of the 5- to 7-membered heterocyclic group include a 5- to 7-membered heterocyclic group, from among the above-mentioned "heterocyclic group". Preferable examples of the "mono- or di-5- to 7-membered heterocyclyl-carbamoyl group" include 2-pyridylcarbamoyl, 3-pyridylcarbamoyl, 4-pyridylcarbamoyl, 2-thienylcarbamoyl, 3-thienylcarbamoyl and the like.

Unless otherwise specified, examples of the "N—$C_{1-6}$ alkyl-N—$C_{1-6}$ alkoxy-carbamoyl group" in the present specification include a carbamoyl group substituted by the above-mentioned "$C_{1-6}$ alkyl group" and the above-mentioned "$C_{1-6}$ alkoxy group". Examples thereof include N-methyl-N-methoxycarbamoyl and the like.

Unless otherwise specified, examples of the "mono- or di-$C_{1-6}$ alkyl-sulfamoyl group" in the present specification include a sulfamoyl group mono- or di-substituted by the above-mentioned "$C_{1-6}$ alkyl group". Examples thereof include methylsulfamoyl, ethylsulfamoyl, dimethylsulfamoyl, diethylsulfamoyl and the like.

Unless otherwise specified, examples of the "mono- or di-$C_{6-14}$ aryl-sulfamoyl group" in the present specification include a sulfamoyl group mono- or di-substituted by the above-mentioned "$C_{6-14}$ aryl group". Examples thereof include phenylsulfamoyl, diphenylsulfamoyl, 1-naphthylsulfamoyl, 2-naphthylsulfamoyl and the like.

Unless otherwise specified, examples of the "$C_{1-6}$ alkoxy-$C_{1-6}$ alkoxy group" in the present specification include the above-mentioned "$C_{1-6}$ alkoxy group" having 1 to 5 "$C_{1-6}$ alkoxy groups" mentioned above. Examples thereof include methoxymethoxy, ethoxymethoxy, isopropoxymethoxy, tert-butoxy methoxy, methoxyethoxy, ethoxyethoxy, isopropoxyethoxy, tert-butoxy ethoxy and the like.

Unless otherwise specified, examples of the "nitrogen-containing heterocyclic group" in the present specification include a heterocyclic group containing at least one nitrogen atom, from among the above-mentioned "heterocyclic group".

Specific preferable examples of the nitrogen-containing heterocyclic group include, nitrogen-containing aromatic heterocyclic groups such as pyridyl, thiazolyl, oxazolyl, oxadiazolyl, quinolyl, isoquinolyl, pyrazinyl, pyrimidinyl, pyrrolyl, imidazolyl, pyrazolyl, pyridazinyl, isothiazolyl, isoxazolyl, triazolyl, tetrazolyl, indolyl, indazolyl, benzothiazolyl, benzoxazolyl, benzimidazolyl, benzotriazolyl, imidazopyridinyl, imidazopyrimidinyl, pyrrolopyridinyl, triazolopyridinyl and the like; nitrogen-containing non-aromatic heterocyclic groups such as azetidinyl, pyrrolidinyl, oxazolidinyl, dihydrooxadiazolyl, imidazolinyl, imidazolidinyl, piperidinyl, piperazinyl, morpholinyl, thiomorpholinyl, 1-oxidothiomorpholinyl, 1,1-dioxidothiomorpholinyl, tetrahydroquinolinyl, tetrahydroisoquinolinyl and the like; and the like.

Unless otherwise specified, examples of the "nitrogen-containing heterocyclylsulfonyl group" in the present specification include a sulfonyl group having the above-mentioned "nitrogen-containing heterocyclic group".

Specific preferable examples of the nitrogen-containing heterocyclylsulfonyl group include pyridylsulfonyl, thiazolylsulfonyl, oxazolylsulfonyl, oxadiazolylsulfonyl, quinolylsulfonyl, isoquinolylsulfonyl, pyrazinylsulfonyl, pyrimidinylsulfonyl, pyrrolylsulfonyl, imidazolylsulfonyl, pyrazolylsulfonyl, pyridazinylsulfonyl, isothiazolylsulfonyl, isoxazolylsulfonyl, triazolylsulfonyl, tetrazolylsulfonyl, indolylsulfonyl, indazolylsulfonyl, benzothiazolylsulfonyl, benzoxazolylsulfonyl, benzimidazolylsulfonyl, benzotriazolylsulfonyl, imidazopyridinylsulfonyl, imidazopyrimidinylsulfonyl, pyrrolopyridinylsulfonyl, triazolopyridinylsulfonyl, azetidinylsulfonyl, pyrrolidinylsulfonyl, oxazolidinylsulfonyl, dihydrooxadiazolylsulfonyl, imidazolinylsulfonyl, imidazolidinylsulfonyl, piperidinylsulfonyl, piperazinylsulfonyl, morpholinylsulfonyl, thiomorpholinylsulfonyl, 1-oxidothiomorpholinylsulfonyl, 1,1-dioxidothiomorpholinylsulfonyl, tetrahydroquinolinylsulfonyl, tetrahydroisoquinolinylsulfonyl and the like.

Unless otherwise specified, examples of the "nitrogen-containing heterocyclyl-amino group" in the present specification include an amino group mono- or di-substituted by the above-mentioned "nitrogen-containing heterocyclic group".

Specific preferable examples of the nitrogen-containing heterocyclyl-amino group include pyridylamino, thiazolylamino, oxazolylamino, oxadiazolylamino, quinolylamino, isoquinolylamino, pyrazinylamino, pyrimidinylamino, pyrrolylamino, imidazolylamino, pyrazolylamino, pyridazinylamino, isothiazolylamino, isoxazolylamino, triazolylamino, tetrazolylamino, indolylamino, indazolylamino, benzothiazolylamino, benzoxazolylamino, benzimidazolylamino, benzotriazolylamino, imidazopyridinylamino, imidazopyrimidinylamino, pyrrolopyridinylamino, triazolopyridinylamino, azetidinylamino, pyrrolidinylamino, oxazolidinylamino, dihydrooxadiazolylamino, imidazolinylamino, imidazolidinylamino, piperidinylamino, piperazinylamino, morpholinylamino, thiomorpholinylamino, 1-oxidothiomorpholinylamino, 1,1-dioxidothiomorpholinylamino, tetrahydroquinolinylamino, tetrahydroisoquinolinylamino and the like.

Unless otherwise specified, examples of the "$C_{1-6}$ alkyl-carbonyloxy" in the present specification include acetyloxy, propanoyloxy, butanoyloxy, isobutanoyloxy, pentanoyloxy, isopentanoyloxy and the like.

Unless otherwise specified, examples of the "$C_{1-4}$ alkylenedioxy group" in the present specification include methylenedioxy, ethylenedioxy and the like.

Examples of the "optionally substituted $C_{1-6}$ alkyl group", "optionally substituted $C_{2-6}$ alkenyl group", "optionally substituted $C_{2-6}$ alkynyl group", "optionally substituted $C_{1-10}$ alkoxy group (including the optionally substituted $C_{1-6}$ alkoxy group)", "optionally substituted $C_{1-6}$ alkylsulfonyloxy group" and "optionally substituted $C_{1-10}$ alkylthio group" in the present specification include a "$C_{1-6}$ alkyl group", a "$C_{2-6}$ alkenyl group", a "$C_{2-6}$ alkynyl group", a "$C_{1-10}$ alkoxy group (including a $C_{1-6}$ alkoxy group)", a "$C_{1-6}$ alkylsulfonyloxy group" and a "$C_{1-10}$ alkylthio group", each of which optionally has, at substitutable positions, 1 to 5 substituents selected from
(1) a halogen atom;
(2) a hydroxy group;
(3) an amino group;
(4) a nitro group;
(5) a cyano group;
(6) a heterocyclic group optionally substituted by 1 to 3 substituents selected from
  (a) a halogen atom,
  (b) a hydroxy group,
  (c) an amino group,
  (d) a nitro group,
  (e) a cyano group,
  (f) a $C_{1-6}$ alkyl group (the $C_{1-6}$ alkyl group is optionally substituted by 1 to 3 substituents selected from a halogen atom, a cyano group, a $C_{3-7}$ cycloalkyl group and a $C_{6-14}$ aryl group),
  (g) a $C_{2-6}$ alkenyl group (the $C_{2-6}$ alkenyl group is optionally substituted by a $C_{6-14}$ aryl group optionally having 1 to 3 halogen atoms),
  (h) a mono- or di-$C_{1-6}$ alkyl-amino group,
  (i) a $C_{6-14}$ aryl group (the $C_{6-14}$ aryl group optionally has 1 to 3 $C_{1-6}$ alkoxy groups),
  (j) a mono- or di-$C_{6-14}$ aryl-amino group,
  (k) a $C_{3-7}$ cycloalkyl group,
  (l) a $C_{1-6}$ alkoxy group,
  (m) a $C_{7-16}$ aralkyloxy group,
  (n) a $C_{1-6}$ alkoxy-$C_{1-6}$ alkoxy group,
  (o) a $C_{1-6}$ alkylthio group,
  (p) a $C_{1-6}$ alkylsulfinyl group,
  (q) a $C_{1-6}$ alkylsulfonyl group,
  (r) an optionally esterified carboxy group,
  (s) a carbamoyl group,
  (t) a thiocarbamoyl group,
  (u) a mono- or di-$C_{1-6}$ alkyl-carbamoyl group,
  (v) a mono- or di-$C_{6-14}$ aryl-carbamoyl group,
  (w) a sulfamoyl group,
  (x) a mono- or di-$C_{1-6}$ alkyl-sulfamoyl group,
  (y) a mono- or di-$C_{6-14}$ aryl-sulfamoyl group,
  (z) a heterocyclic group, and
  (aa) a $C_{1-6}$ alkyl-carbonyl group;
(7) a mono- or di-$C_{1-6}$ alkyl-amino group (the $C_{1-6}$ alkyl moiety is optionally substituted by 1 to 3 substituents selected from a hydroxy group, $C_{1-6}$ alkylthio and $C_{1-6}$ alkylsulfonyl);
(8) a mono- or di-$C_{3-7}$ cycloalkyl-amino group;
(9) a mono- or di-$C_{6-14}$ aryl-amino group (the $C_{6-14}$ aryl moiety is optionally substituted by 1 to 3 halogen atoms);
(10) a mono- or di-$C_{7-16}$ aralkyl-amino group;
(11) an N—$C_{1-6}$ alkyl-N—$C_{6-14}$ aryl-amino group;
(12) an N—$C_{1-6}$ alkyl-N—$C_{7-16}$ aralkyl-amino group;
(13) a $C_{3-7}$ cycloalkyl group optionally having 1 to 3 $C_{1-6}$ alkyl groups;
(14) a $C_{1-6}$ alkoxy group optionally substituted by 1 to 3 substituents selected from
  (a) a halogen atom, and
  (b) a $C_{1-6}$ alkoxy group;
(15) a $C_{1-6}$ alkylthio group optionally having 1 to 3 substituents selected from
  (a) a hydroxy group, and
  (b) a $C_{1-6}$ alkoxy group;
(16) a $C_{1-6}$ alkylsulfinyl group optionally having 1 to 3 $C_{1-6}$ alkoxy group0;
(17) a $C_{1-6}$ alkylsulfonyl group optionally substituted by 1 to 3 substituents selected from
  (a) a hydroxy group, and
  (b) a $C_{1-6}$ alkoxy group;
(18) a $C_{3-7}$ cycloalkylsulfonyl group;
(19) an optionally esterified carboxy group; (20) a carbamoyl group;
(21) a thiocarbamoyl group;
(22) a mono- or di-$C_{1-6}$ alkyl-carbamoyl group;
(23) a mono- or di-$C_{6-14}$ aryl-carbamoyl group;
(24) a mono- or di-5- to 7-membered heterocyclyl-carbamoyl group;
(25) an N—$C_{1-6}$ alkyl-N—$C_{1-6}$ alkoxy-carbamoyl group;
(26) a mono- or di-($C_{1-6}$ alkyl-carbonyl (the $C_{1-6}$ alkyl moiety optionally has 1 to 3 carboxy group0))-amino group;
(27) a $C_{6-14}$ aryloxy group optionally substituted by 1 to 3 substituents selected from
  (a) a halogen atom,
  (b) a hydroxy group,
  (c) an amino group,
  (d) a nitro group,
  (e) a cyano group,
  (f) an optionally halogenated $C_{1-6}$ alkyl group,
  (g) a mono- or di-$C_{1-6}$ alkyl-amino group,
  (h) a $C_{6-14}$ aryl group,
  (i) a mono- or di-$C_{6-14}$ aryl-amino group,
  (j) a $C_{3-7}$ cycloalkyl group,
  (k) a $C_{1-6}$ alkoxy group,
  (l) a $C_{1-6}$ alkoxy-$C_{1-6}$ alkoxy group,
  (m) a $C_{1-6}$ alkoxy-carbonyl group,
  (n) a $C_{1-6}$ alkylthio group,
  (o) a $C_{1-6}$ alkylsulfinyl group,
  (p) a $C_{1-6}$ alkylsulfonyl group,
  (q) an optionally esterified carboxy group,
  (r) a carbamoyl group,
  (s) a thiocarbamoyl group,
  (t) a mono- or di-$C_{1-6}$ alkyl-carbamoyl group,
  (u) a mono- or di-$C_{6-14}$ aryl-carbamoyl group, (v) a sulfamoyl group,
(w) a mono- or di-$C_{1-6}$ alkyl-sulfamoyl group, and
(x) a mono- or di-$C_{6-14}$ aryl-sulfamoyl group;
(28) a $C_{6-14}$ aryl group optionally substituted by 1 to 3 substituents selected from
  (a) a halogen atom,
  (b) a hydroxy group,
  (c) an amino group,
  (d) a nitro group,
  (e) a cyano group,
  (f) a $C_{1-6}$ alkyl group (the $C_{1-6}$ alkyl group is optionally substituted by 1 to 3 substituents selected from a halogen atom and a hydroxy group),
  (g) a mono- or di-$C_{1-6}$ alkyl-amino group,
  (h) a $C_{6-14}$ aryl group,
  (i) a mono- or di-$C_{6-14}$ aryl-amino group,
  (j) a mono- or di-($C_{1-6}$ alkyl-carbonyl)-amino group,
  (k) a $C_{3-7}$ cycloalkyl group,
  (l) a $C_{1-6}$ alkoxy group (the $C_{1-6}$ alkoxy group is optionally substituted by 1 to 3 halogen atoms),
  (m) a $C_{1-6}$ alkoxy-$C_{1-6}$ alkoxy group,
  (n) a $C_{1-6}$ alkylthio group,
  (o) a $C_{1-6}$ alkylsulfinyl group,
  (p) a $C_{1-6}$ alkylsulfonyl group,
  (q) an optionally esterified carboxy group,
  (r) a carbamoyl group,
  (s) a thiocarbamoyl group,
  (t) a mono- or di-$C_{1-6}$ alkyl-carbamoyl group,
  (u) a mono- or di-$C_{6-14}$ aryl-carbamoyl group,
  (v) a sulfamoyl group,
  (w) a mono- or di-$C_{1-6}$ alkyl-sulfamoyl group,
  (x) a mono- or di-$C_{6-14}$ aryl-sulfamoyl group,
  (y) a $C_{1-6}$ alkyl-carbonyl group,
  (z) a heterocyclic group, and
  (aa) a heterocyclyl-carbonyl group;
(29) a heterocyclyloxy group optionally substituted by 1 to 3% substituents selected from
  (a) a halogen atom,
  (b) a hydroxy group,
  (c) an amino group,
  (d) a nitro group,
  (e) a cyano group,
  (f) an optionally halogenated $C_{1-6}$ alkyl group,
  (g) a mono- or di-$C_{1-6}$ alkyl-amino group,
  (h) a $C_{6-14}$ aryl group,
  (i) a mono- or di-$C_{6-14}$ aryl-amino group,
  (j) a $C_{3-7}$ cycloalkyl group,
  (k) a $C_{1-6}$ alkoxy group,
  (l) a $C_{1-6}$ alkoxy-$C_{1-6}$ alkoxy group,
  (m) a $C_{1-6}$ alkylthio group,
  (n) a $C_{1-6}$ alkylsulfinyl group,
  (o) a $C_{1-6}$ alkylsulfonyl group,
  (p) an optionally esterified carboxy group,
  (q) a carbamoyl group,
  (r) a thiocarbamoyl group,
  (s) a mono- or di-$C_{1-6}$ alkyl-carbamoyl group,
  (t) a mono- or di-$C_{6-14}$ aryl-carbamoyl group,
  (u) a sulfamoyl group,
  (v) a mono- or di-$C_{1-6}$ alkyl-sulfamoyl group, and
  (w) a mono- or di-$C_{6-14}$ aryl-sulfamoyl group;
(30) a sulfamoyl group;
(31) a mono- or di-$C_{1-6}$ alkyl-sulfamoyl group;
(32) a mono- or di-$C_{6-14}$ aryl-sulfamoyl group;
(33) a $C_{7-16}$ aralkyloxy group optionally substituted by 1 to 3 substituents selected from
  (a) a halogen atom,
  (b) a hydroxy group,
  (c) an amino group,
  (d) a nitro group,
  (e) a cyano group,
  (f) an optionally halogenated $C_{1-6}$ alkyl group,
  (g) a mono- or di-$C_{1-6}$ alkyl-amino group,
  (h) a $C_{6-14}$ aryl group,
  (i) a mono- or di-$C_{6-14}$ aryl-amino group,
  (j) a $C_{3-7}$ cycloalkyl group,
  (k) a $C_{1-6}$ alkoxy group,
  (l) a $C_{1-6}$ alkoxy-$C_{1-6}$ alkoxy group,
  (m) a $C_{1-6}$ alkylthio group,
  (n) a $C_{1-6}$ alkylsulfinyl group,
  (o) a $C_{1-6}$ alkylsulfonyl group,
  (p) an optionally esterified carboxy group,
  (q) a carbamoyl group,
  (r) a thiocarbamoyl group,
  (s) a mono- or di-$C_{1-6}$ alkyl-carbamoyl group,
  (t) a mono- or di-$C_{6-14}$ aryl-carbamoyl group,
  (u) a sulfamoyl group,
  (v) a mono- or di-$C_{1-6}$ alkyl-sulfamoyl group, and
  (w) a mono- or di-$C_{6-14}$ aryl-sulfamoyl group;
(34) a $C_{1-6}$ alkylsulfonyloxy group;
(35) a tri-$C_{1-6}$ alkyl-silyloxy group;
(36) a heterocyclyl-carbonyl group;
(37) a $C_{6-14}$ aryl-carbonyl group;
(38) a $C_{6-14}$ arylthio group optionally substituted by 1 to 3 substituents selected from a halogen atom and a cyano group;
(39) a $C_{6-14}$ arylsulfinyl group optionally having 1 to 3 halogen atoms;
(40) a $C_{6-14}$ arylsulfonyl group optionally having 1 to 3 halogen atoms;
(41) a nitrogen-containing heterocyclylsulfonyl group;
(42) a heterocyclylthio group;
(43) a nitrogen-containing heterocyclyl-amino group optionally substituted by 1 to 3 substituents selected from a cyano group and a nitro group;
(44) a tert-butyl-diphenylsilyloxy group;
(45) a tert-butyl-dimethylsilyloxy group;
(46) $C_{1-6}$ alkyl-carbonyloxy optionally substituted by 1 to 3 substituents selected from an amino group optionally mono- or di-substituted by a $C_{1-6}$ alkoxy-carbonyl group; and the like.

Examples of the "optionally substituted $C_{3-7}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylsulfonyloxy group", "optionally substituted heterocyclylthio group", "optionally substituted $C_{6-14}$ arylthio group" and "optionally substituted $C_{7-16}$ aralkylthio group" in the present specification include a "$C_{3-7}$ cycloalkyl group", a "$C_{6-14}$ aryl group", a "$C_{7-16}$ aralkyl group", a "heterocyclic group", a "heterocyclyloxy group", a "$C_{6-14}$ aryloxy group", a "$C_{7-16}$ aralkyloxy group", a "heterocyclylsulfonyloxy group", a "heterocyclylthio group", a "$C_{6-14}$ arylthio group" and a "$C_{7-16}$ aralkylthio group", each of which optionally has, at substitutable positions, 1 to 5 substituents selected from
(1) a halogen atom;
(2) a hydroxy group;
(3) an amino group;
(4) a nitro group;
(5) a cyano group;
(6) an optionally substituted $C_{1-6}$ alkyl group;
(7) an optionally substituted $C_{2-6}$ alkenyl group;
(8) an optionally substituted $C_{2-6}$ alkynyl group;
(9) a $C_{6-14}$ aryl group optionally substituted by 1 to 3 substituents selected from
  (a) a halogen atom,
  (b) a hydroxy group,
  (c) an amino group, (d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(10) a $C_{6-14}$ aryloxy group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(11) a $C_{7-16}$ aralkyloxy group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(12) a heterocyclic group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(13) a mono- or di-$C_{1-6}$ alkyl-amino group;
(14) a mono- or di-$C_{6-14}$ aryl-amino group;
(15) a mono- or di-$C_{1-7-16}$ aralkyl-amino group;
(16) a mono- or di-($C_{1-6}$ alkoxy-carbonyl)-amino group;
(17) an N—$C_{1-6}$ alkyl-N—$C_{6-14}$ aryl-amino group;
(18) an N—$C_{1-6}$ alkyl-N—$C_{7-16}$ aralkyl-amino group;
(19) a $C_{3-7}$ cycloalkyl group;
(20) an optionally substituted $C_{1-6}$ alkoxy group;
(21) a $C_{1-6}$ alkylthio group optionally having 1 to 3 substituents selected from
(a) a hydroxy group,
(b) a carboxy group,
(c) a $C_{1-6}$ alkoxy group, and
(d) a $C_{1-6}$ alkoxy-carbonyl group;
(22) a $C_{1-6}$ alkylsulfinyl group optionally having 1 to 3 $C_{1-6}$ alkoxy group0;
(23) a $C_{1-6}$ alkylsulfonyl group optionally having 1 to 3 $C_{1-6}$ alkoxy group0;
(24) a $C_{3-7}$ cycloalkylsulfonyl group;
(25) an optionally esterified carboxy group;
(26) a carbamoyl group;
(27) a thiocarbamoyl group;
(28) a mono- or di-$C_{1-6}$ alkyl-carbamoyl group (the $C_{1-6}$ alkyl moiety is optionally substituted by 1 to 3 substituents selected from a hydroxy group and $C_{1-6}$ alkoxy);
(29) a mono- or di-$C_{6-14}$ aryl-carbamoyl group;
(30) a mono- or di-5- to 7-membered heterocyclyl-carbamoyl group;
(31) a mono- or di-$C_{3-7}$ cycloalkyl-carbamoyl group;
(32) an N—$C_{1-6}$ alkyl group-N—$C_{1-6}$ alkoxy-carbamoyl group;
(33) a sulfamoyl group;
(34) a mono- or di-$C_{1-6}$ alkyl-sulfamoyl group;
(35) a mono- or di-$C_{6-14}$ aryl-sulfamoyl group;
(36) a $C_{1-6}$ alkylsulfonyloxy group;
(37) a tri-$C_{1-6}$ alkyl-silyloxy group;
(38) a $C_{1-6}$ alkyl-carbonyl group;
(39) a heterocyclyl-carbonyl group;
(40) a heterocyclyloxy group optionally substituted by 1 to 3 substituents selected from
(a) a halogen atom,
(b) a hydroxy group,
(c) an amino group,
(d) a nitro group,
(e) a cyano group, (f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(41) a $C_{1-4}$ alkylenedioxy group optionally substituted by 1 to 3 phenyl;
(42) a mono- or di-($C_{1-6}$ alkyl-carbonyl)-amino group;
(43) an N—$C_{1-6}$ alkyl-N—($C_{1-6}$ alkyl-carbonyl)-amino group;
(44) a formyl group;
(45) an oxo group;
and the like.

Unless otherwise specified, examples of the "optionally substituted amino group" and "optionally substituted carbamoyl group" in the present specification include an "amino group" and a "carbamoyl group", each of which optionally has 1 or 2 substituents selected from
(1) an optionally substituted $C_{1-6}$ alkyl group;
(2) an optionally substituted $C_{2-6}$ alkenyl group;
(3) an optionally substituted $C_{2-6}$ alkynyl group;
(4) an optionally substituted $C_{3-7}$ cycloalkyl group;
(5) an optionally substituted $C_{6-14}$ aryl group;
(6) an optionally substituted $C_{1-6}$ alkoxy group;
(7) a $C_{1-6}$ alkyl-carbonyl group;
(8) a heterocyclyl-carbonyl group;
(9) a $C_{6-14}$ aryl-carbonyl group;
(10) an optionally substituted heterocyclic group;
(11) a sulfamoyl group;
(12) a mono- or di-$C_{1-6}$ alkyl-sulfamoyl group;
(13) a mono- or di-$C_{6-14}$ aryl-sulfamoyl group;
and the like.

When the "optionally substituted amino group" and "optionally substituted carbamoyl group" is an amino group and a carbamoyl group, each of which has two substituents, these substituents optionally form, together with the adjacent nitrogen atom, a nitrogen-containing heterocycle.

Examples of the "nitrogen-containing heterocycle" include a 5- to 7-membered nitrogen-containing heterocycle containing, as a ring constituting atom besides carbon atom, at least one nitrogen atom and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

Each symbol in the formula (I) is explained in detail in the following.

In the formula (I), $R^1$ is
(i) a group represented by —$COR^4$
wherein
$R^4$ is an optionally substituted alkyl group, an optionally substituted cycloalkyl group, —$OR^5$ wherein $R^5$ is a hydrogen atom or an optionally substituted alkyl group, or an optionally substituted amino group, or (ii) a 5- or 6-membered nitrogen-containing heterocyclic group represented by the formula

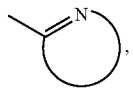

which is optionally substituted.

The "optionally substituted alkyl group" for $R^4$ may be a straight chain or a branched chain, and examples thereof include an optionally substituted $C_{1-6}$ alkyl group.

Examples of the "optionally substituted cycloalkyl group" for $R^4$ include an optionally substituted $C_{3-7}$ cycloalkyl group.

The "optionally substituted alkyl group" for $R^5$ may be a straight chain or a branched chain, and examples thereof include an optionally substituted $C_{1-5}$ alkyl group.

Examples of the "5- or 6-membered nitrogen-containing heterocyclic group" include
(1) a 5- or 6-membered nitrogen-containing heterocyclic group containing 1 to 3 nitrogen atoms;
(2) a 5- or 6-membered nitrogen-containing heterocyclic group containing one nitrogen atom and one or more (preferably 1 or 2) hetero atoms selected from an oxygen atom and a sulfur atom; and
(3) a 5- or 6-membered nitrogen-containing heterocyclic group containing two nitrogen atoms and one hetero atom selected from an oxygen atom and a sulfur atom.

Of these, a 5- or 6-membered nitrogen-containing aromatic heterocyclic group is preferable, and 2-imidazolyl, 4-imidazolyl, 2-thiazolyl, 2-thiadiazolyl, 3-pyrazolyl, 2-pyridyl, 2-pyrazinyl and the like are particularly preferable.

The "5- or 6-membered nitrogen-containing heterocyclic group" is optionally substituted, at substitutable position(s), by a substitutable number of (preferably 1 to 3) substituents.

Examples of the substituent include those similar to the substituents exemplified in the aforementioned "optionally substituted heterocyclic group". Of these, a halogen atom, —OR', —SR', —SOR', —S(O)₂R', —COOR' wherein R' is a hydrogen atom or a substituent, an optionally substituted carbamoyl group and an optionally substituted $C_{1-6}$ alkyl group are preferable.

Examples of the substituent for R' include an "optionally substituted $C_{1-6}$ alkyl group", an "optionally substituted heterocyclic group", an "optionally substituted $C_{6-14}$ aryl group", an "optionally substituted $C_{7-16}$ aralkyl group" and the like.

In one embodiment, re is preferably —$COR^4$
wherein
$R^4$ is an alkyl group, a cycloalkyl group, —$OR^5$ wherein $R^5$ is a hydrogen atom or an alkyl group, or an amino group.

In another embodiment, $R^1$ is preferably a 5- or 6-membered nitrogen-containing heterocyclic group (preferably a 5- or 6-membered nitrogen-containing aromatic heterocyclic group) represented by the formula

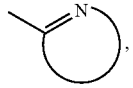

which is optionally substituted by a halogen atom, —OR', —SR', —SOR', —S(O)₂R', —COOR' wherein R' is a hydrogen atom or a substituent, an optionally substituted carbamoyl group or an optionally substituted $C_{1-6}$ alkyl group, more preferably a 5- or 6-membered nitrogen-containing heterocyclic group (preferably a 5- or 6-membered nitrogen-containing aromatic heterocyclic group) represented by the formula

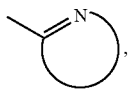

which is optionally substituted by a $C_{1-4}$ alkyl group.

In another embodiment, $R^1$ is preferably —$COR^4$
wherein
$R^4$ is
(1) a $C_{1-6}$ alkyl group (preferably ethyl, propyl, isopropyl, butyl),
(2) a $C_{3-7}$ cycloalkyl group (preferably cyclopropyl, cyclobutyl),
(3) —$OR^5$ wherein $R^5$ is a hydrogen atom or a $C_{1-6}$ alkyl group (preferably ethyl), or
(4) an amino group.

In another embodiment, $R^1$ is preferably a 5- or 6-membered nitrogen-containing heterocyclic group represented by the formula

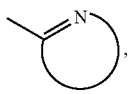

which is optionally substituted,
more preferably a 5- or 6-membered nitrogen-containing heterocyclic group (preferably a 5- or 6-membered nitrogen-containing aromatic heterocyclic group, more preferably 2-imidazolyl, 4-imidazolyl, 2-thiazolyl, 2-thiadiazolyl, 3-pyrazolyl, 2-pyridyl, 2-pyrazinyl) represented by the formula

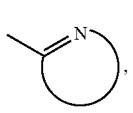

which is optionally substituted by 1 to 3 substituents selected from
(a) a $C_{1-4}$ alkyl group (preferably methyl, ethyl, isopropyl, isobutyl, tert-butyl) optionally substituted by 1 to 3 substituents selected from
 (a1) a hydroxy group,
 (a2) a $C_{1-6}$ alkoxy-carbonyl group (preferably methoxycarbonyl, ethoxycarbonyl),
 (a3) a heterocyclic group (preferably triazolyl, azetidinyl, pyrrolidinyl, imidazolidinyl, 1-oxidothiomorpholinyl, 1,1-dioxidothiomorpholinyl, piperidinyl, piperazinyl, morpholinyl, oxadiazolyl, dihydrooxadiazolyl, diazabicyclo[2.2.1]heptan-2-yl) optionally substituted by 1 to 3 substituents selected from a hydroxy group, a $C_{1-6}$ alkyl group (preferably methyl) optionally substituted by 1 to 3 $C_{6-14}$ aryl groups (preferably phenyl), a $C_{1-6}$ alkyl-carbonyl group (preferably acetyl), an oxo group and a halogen atom (preferably fluorine),
 (a4) a mono- or di-$C_{1-6}$ alkyl-amino group (the $C_{1-6}$ alkyl moiety is optionally substituted by 1 to 3 substituents selected from a hydroxy group, $C_{1-6}$ alkylthio (preferably ethylthio) and $C_{1-6}$ alkylsulfonyl (preferably ethylsulfonyl)),
 (a5) a nitrogen-containing heterocyclyl-amino group (preferably azabicyclo[2.2.2]octan-3-yl-amino),
 (a6) a tert-butyl-diphenylsilyloxy group,
 (a7) a $C_{1-6}$ alkyl-carbonyloxy group (preferably acetyloxy) optionally substituted by 1 to 3 substituents selected from an amino group optionally mono- or di-substituted by a $C_{1-6}$ alkoxy-carbonyl group (preferably tert-butoxycarbonyl),
 (a8) a cyano group,
 (a9) a carboxy group,
 (a10) a heterocyclyl-carbonyl group (preferably morpholinocarbonyl, azetidinylcarbonyl),
 (a11) a carbamoyl group,
 (a12) a mono- or di-$C_{1-6}$ alkyl-carbamoyl group,
 (a13) a $C_{1-6}$ alkylsulfonyl group (preferably methylsulfonyl, ethylsulfonyl) optionally substituted by 1 to 3 hydroxy groups,
 (a14) a $C_{1-6}$ alkoxy group (preferably methoxy, ethoxy) optionally substituted by 1 to 3 $C_{1-6}$ alkoxy groups (preferably methoxy),
 (a15) a halogen atom (preferably fluorine),
 (a16) a $C_{3-7}$ cycloalkyl group (preferably cyclobutyl), and
 (a17) a tert-butyl-dimethylsilyloxy group,
(b) a heterocyclic group (preferably dioxolanyl, tetrahydropyranyl) optionally substituted by 1 to 3 substituents selected from a hydroxy group and a $C_{1-6}$ alkyl group (preferably methyl),
(c) a halogen atom (preferably fluorine, bromine, chlorine),
(d) a $C_{2-6}$ alkenyl group (preferably vinyl, 2-methyl-1-propenyl) optionally substituted by 1 to 3 $C_{1-6}$ alkoxy-carbonyl groups (preferably ethoxycarbonyl),
(e) a formyl group,
(f) a $C_{1-6}$ alkylthio group (preferably methylthio, ethylthio) optionally substituted by 1 to 3 substituents selected from
 (f1) a hydroxy group,
 (f2) a carboxy group,
 (f3) a $C_{1-6}$ alkoxy group, and
 (f4) a $C_{1-6}$ alkoxy-carbonyl group (preferably ethoxycarbonyl),
(g) a carboxy group,
(h) a $C_{1-6}$ alkoxy group (preferably methoxy, ethoxy, propoxy, isopropoxy, isobutyloxy) optionally substituted by 1 to 3 substituents selected from
 (h1) a $C_{6-14}$ aryl group (preferably phenyl),
 (h2) a $C_{3-7}$ cycloalkyl group (preferably cyclopropyl),
 (h3) a $C_{1-6}$ alkyl-carbonyl group (preferably acetyl), and
 (h4) a hydroxy group,
(i) a hydroxy group,
(j) a $C_{1-6}$ alkoxy-carbonyl group (preferably methoxycarbonyl),
(k) a mono- or di-$C_{3-7}$ cycloalkyl (preferably cyclopropyl)-carbamoyl group,
(l) a mono- or di-$C_{1-6}$ alkyl (preferably ethyl, isobutyl)-carbamoyl group (the $C_{1-6}$ alkyl moiety is optionally substituted by 1 to 3 substituents selected from a hydroxy group and $C_{1-6}$ alkoxy (preferably ethoxy)),
(m) a heterocyclyl-carbonyl group (preferably morpholinocarbonyl, azetidinylcarbonyl),
(n) a $C_{1-6}$ alkyl-carbonyl group (preferably acetyl), and
(o) a carbamoyl group.

In the formula (I), $R^2$ is an optionally substituted alkyl group, an optionally substituted 4- to 7-membered cyclic group, —$OR^6$ wherein $R^6$ is an optionally substituted alkyl group or an optionally substituted 4- to 7-membered cyclic group, or an optionally substituted amino group.

In the formula (I), $R^3$ is a hydrogen atom or an optionally substituted alkyl group.

Alternatively, $R^2$ and $R^3$ in combination
(i) form, together with the carbon atom they are bonded to, cyclopropane substituted by an optionally substituted 4- to 7-membered cyclic group, or
(ii) form =N—OR$^7$ or =CH—R$^7$ wherein $R^7$ is an optionally substituted alkyl group or an optionally substituted 4- to 7-membered cyclic group.

The "optionally substituted alkyl group" for $R^2$ may be a straight chain or a branched chain, and examples thereof include an optionally substituted $C_{1-6}$ alkyl group.

Examples of the "4- to 7-membered cyclic group" of the "optionally substituted 4- to 7-membered cyclic group" for $R^2$ include a 4- to 7-membered homocyclic group and a 4- to 7-membered heterocyclic group. They may be saturated or unsaturated.

Examples of the "4- to 7-membered homocyclic group" include a 4- to 7-membered alicyclic hydrocarbon group and phenyl.

Examples of the "4- to 7-membered alicyclic hydrocarbon group" include
(1) a $C_{4-7}$ cycloalkyl group (e.g., cyclobutyl, cyclopentyl, cyclohexyl, cycloheptyl);
(2) a $C_{4-7}$ cycloalkenyl group (e.g., cyclobutenyl, cyclopentenyl, cyclohexenyl, cycloheptenyl); and
(3) a $C_{5-7}$ cycloalkadienyl group (e.g., 2,4-cyclopentadien-1-yl, 2,4-cyclohexadien-1-yl, 2,5-cyclohexadien-1-yl).

Examples of the "4- to 7-membered heterocyclic group" include a heterocyclic group containing one or more (preferably 1 to 4, more preferably 1 or 2) hetero atoms selected from an oxygen atom, a sulfur atom (the sulfur atom is optionally oxidized), a nitrogen atom and the like.

The "4- to 7-membered heterocyclic group" is preferably a 5- or 6-membered aromatic heterocyclic group or a 4- to 7-membered (preferably 5- or 6-membered) non-aromatic heterocyclic group (e.g., tetrahydrofuranyl, tetrahydropyranyl).

The "4- to 7-membered cyclic group" of the "optionally substituted 4- to 7-membered cyclic group" is optionally substituted, at substitutable position(s), by a substitutable number of (preferably 1 to 3) substituents.

Examples of the substituent include those similar to substituents exemplified in the "optionally substituted heterocyclic group". Of these, a alkylenedioxy group (preferably ethylenedioxy) optionally substituted by 1 to 3 phenyl groups, an oxo group and the like are preferable.

The "optionally substituted alkyl group" for $R^6$ may be a straight chain or a branched chain, and examples thereof include an optionally substituted $C_{1-6}$ alkyl group.

Examples of the "optionally substituted 4- to 7-membered cyclic group" for $R^6$ include those exemplified as the "optionally substituted 4- to 7-membered cyclic group" for $R^2$.

The "optionally substituted alkyl group" for $R^3$ may be a straight chain or a branched chain, and examples thereof include an optionally substituted $C_{1-6}$ alkyl group.

The "cyclopropane substituted by an optionally substituted 4- to 7-membered cyclic group" formed by $R^2$ and $R^3$ in combination together with the carbon atom they are bonded to can be represented by the following formula.

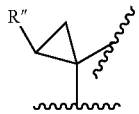

wherein R" is an optionally substituted 4- to 7-membered cyclic group.

Examples of the "optionally substituted 4- to 7-membered cyclic group" of the "cyclopropane substituted by an optionally substituted 4- to 7-membered cyclic group" formed by $R^2$ and $R^3$ in combination together with the carbon atom they are bonded to include those exemplified as the "optionally substituted 4- to 7-membered cyclic group" for $R^2$.

The "cyclopropane" of the "cyclopropane substituted by an optionally substituted 4- to 7-membered cyclic group" optionally has, at substitutable position(s), a substitutable number of (preferably 1 to 3) substituents, besides the optionally substituted 4- to 7-membered cyclic group.

Examples of the substituent include a halogen atom and an optionally substituted $C_{1-6}$ alkyl group.

When $R^2$ and $R^3$ in combination form =N—OR$^7$ or =CH—R$^7$, the "optionally substituted alkyl group" for $R^7$ may be a straight chain or a branched chain, and examples thereof include an optionally substituted $C_{1-6}$ alkyl group.

In this case, Examples of the "optionally substituted 4- to 7-membered cyclic group" for $R^7$ include those exemplified as the "optionally substituted 4- to 7-membered cyclic group" for $R^2$. Of these, a 4- to 7-membered non-aromatic heterocyclic group (e.g., tetrahydrofuranyl, tetrahydropyranyl) is preferable.

In one embodiment, the substituents that the "alkyl group" of the "optionally substituted alkyl group" for $R^2$ optionally has is preferably an optionally substituted 4- to 7-membered cyclic group. Examples of the "optionally substituted 4- to 7-membered cyclic group" include those exemplified as the "optionally substituted 4- to 7-membered cyclic group" for $R^2$.

In this embodiment, $R^2$ is preferably a $C_{1-6}$ alkyl group optionally substituted by an optionally substituted 4- to 7-membered cyclic group, more preferably a $C_{1-6}$ alkyl group optionally substituted by a 4- to 7-membered cyclic group.

In another embodiment, the substituents that the "alkyl group" of the "optionally substituted alkyl group" for $R^2$ optionally has is preferably an optionally substituted 4- to 7-membered cyclic group, more preferably
(a) a $C_{4-7}$ cycloalkyl group (preferably cyclopentyl) optionally substituted by 1 to 3 substituents selected from
  (a1) a $C_{1-4}$ alkylenedioxy group (preferably ethylenedioxy) optionally substituted by 1 to 3 phenyl groups, and
  (a2) an oxo group,
(b) a 4- to 7-membered (preferably 5- or 6-membered) non-aromatic heterocyclic group (preferably tetrahydrofuranyl, tetrahydropyranyl),
and the like.

In this embodiment, $R^2$ is preferably an optionally substituted $C_{1-6}$ alkyl group, more preferably a $C_{1-6}$ alkyl group optionally substituted by an optionally substituted 4- to 7-membered cyclic group, still more preferably a $C_{1-6}$ alkyl group (preferably methyl) optionally substituted by one substituent selected from
(a) a $C_{4-7}$ cycloalkyl group (preferably cyclopentyl) optionally substituted by 1 to 3 substituents selected from
  (a1) a $C_{1-2}$ alkylenedioxy group (preferably ethylenedioxy) optionally substituted by 1 to 3 phenyl groups, and
  (a2) an oxo group, and
(b) a 4- to 7-membered (preferably 5- or 6-membered) non-aromatic heterocyclic group (preferably tetrahydrofuranyl, tetrahydropyranyl).

$R^3$ is preferably a hydrogen atom or a $C_{1-6}$ alkyl group (preferably methyl), more preferably a hydrogen atom.

In the formula (I), Cy is an optionally substituted 6-membered cyclic group, which is optionally condensed with an optionally substituted 5- or 6-membered ring.

Examples of the "6-membered cyclic group" of the "optionally substituted 6-membered cyclic group, which is optionally condensed with an optionally substituted 5- or 6-membered ring" for Cy include a 6-membered cyclic group (e.g., phenyl, pyridyl, pyrimidyl, dihydropyridinyl), from among the "optionally substituted 4- to 7-membered cyclic group" for $R^2$. Of these, a 6-membered aromatic group is preferable, and phenyl and pyridyl (e.g., 2-pyridyl, 3-pyridyl, 4-pyridyl) are more preferable.

The "6-membered cyclic group" is optionally condensed with an optionally substituted 5- or 6-membered ring. Examples of the "5- or 6-membered ring" of the "optionally substituted 5- or 6-membered ring" include a ring (e.g., thiophene, pyrazole, thiazole, benzene, pyridine) corresponding to the 5- or 6-membered cyclic group exemplified as the "optionally substituted 4- to 7-membered cyclic group" for $R^2$.

The "6-membered cyclic group" and the "5- or 6-membered ring" optionally have, at substitutable position(s), a substitutable number of (preferably 1 to 3) substituents. Examples of the substituent include those similar to substituents exemplified in the "optionally substituted heterocyclic group".

In one embodiment, the substituent for the "6-membered cyclic group" and the "5- or 6-membered ring" is preferably $C_{1-6}$ alkylsulfonyl, $C_{3-7}$ cycloalkylsulfonyl and the like.

In this embodiment, Cy is preferably a 6-membered aromatic group substituted by $C_{1-6}$ alkylsulfonyl or $C_{3-7}$ cycloalkylsulfonyl.

In another embodiment, the substituent for the "6-membered cyclic group" and the "5- or 6-membered ring" is preferably
(a) $C_{1-6}$ alkylsulfonyl (preferably methylsulfonyl, ethylsulfonyl, propylsulfonyl) optionally substituted by 1 to 3 $C_{1-6}$ alkoxy groups (preferably methoxy),
(b) $C_{3-7}$ cycloalkylsulfonyl (preferably cyclopropylsulfonyl),
(c) a $C_{1-6}$ alkoxy-carbonyl group (preferably tert-butoxycarbonyl),
(d) a carboxy group,
(e) a mono- or di-$C_{3-7}$ cycloalkyl (preferably cyclopropyl)-carbamoyl group,
(f) a heterocyclyl-carbonyl group (preferably azetidinylcarbonyl),
(g) a carbamoyl group di-substituted by a $C_{1-6}$ alkyl group (preferably methyl) and a $C_{1-6}$ alkoxy group (preferably methoxy),
(h) a halogen atom (preferably fluorine, chlorine),
(i) a $C_{1-6}$ alkylthio group (preferably methylthio),
(j) a $C_{1-6}$ alkyl group (preferably methyl), and the like.

In this embodiment, Cy is preferably an optionally substituted 6-membered aromatic group, which is optionally condensed with an optionally substituted 5- or 6-membered ring, more preferably an optionally substituted 6-membered aromatic group, still more preferably a 6-membered aromatic group (preferably phenyl, pyridyl) substituted by 1 to 3 substituents selected from
(a) $C_{1-6}$ alkylsulfonyl (preferably methylsulfonyl, ethylsulfonyl, propylsulfonyl) optionally substituted by 1 to 3 $C_{1-6}$ alkoxy groups (preferably methoxy),
(b) $C_{3-7}$ cycloalkylsulfonyl (preferably cyclopropylsulfonyl),
(c) a $C_{1-6}$ alkoxy-carbonyl group (preferably tert-butoxycarbonyl),
(d) a carboxy group,
(e) a mono- or di-$C_{3-7}$ cycloalkyl (preferably cyclopropyl)-carbamoyl group,
(f) a heterocyclyl-carbonyl group (preferably azetidinylcarbonyl),
(g) a carbamoyl group di-substituted by a $C_{1-6}$ alkyl group (preferably methyl) and a $C_{1-6}$ alkoxy group (preferably methoxy),
(h) a halogen atom (preferably fluorine, chlorine),
(i) a $C_{1-6}$ alkylthio group (preferably methylthio), and
(j) a $C_{1-6}$ alkyl group (preferably methyl).

In the formula (I), $X^1$ and $X^2$ are each independently an optionally substituted carbon atom, or a nitrogen atom.

Examples of the substituent that the "carbon atom" of the "optionally substituted carbon atom" for $X^1$ or $X^2$ optionally has include those exemplified as the substituent that the "5- or 6-membered nitrogen-containing heterocyclic group" in $R^1$ optionally has.

In one embodiment, the substituent that the "carbon atom" of the "optionally substituted carbon atom" for $X^1$ or $X^2$ optionally has is preferably a halogen atom, a cyano group, a $C_{1-6}$ alkyl group, a $C_{1-6}$ alkylsulfonyl group, an optionally substituted carbamoyl group and the like. Of these, a halogen atom and a $C_{1-4}$ alkyl group are preferable.

In this embodiment, $X^1$ and $X^2$ are preferably each independently a carbon atom optionally substituted by a halogen atom, a cyano group, a $C_{1-6}$ alkyl group, a $C_{1-6}$ alkylsulfonyl group or an optionally substituted carbamoyl group, or a nitrogen atom,
more preferably $X^1$ is a carbon atom or a nitrogen atom, and $X^2$ is a carbon atom optionally substituted by a halogen atom or a $C_{1-4}$ alkyl group.

In another embodiment, the substituent that the "carbon atom" of the "optionally substituted carbon atom" for $X^1$ optionally has is preferably
(a) a $C_{1-6}$ alkoxy-carbonyl group (preferably ethoxycarbonyl),
(b) a carboxy group,
(c) a carbamoyl group,
(d) a mono- or di-$C_{1-6}$ alkyl-carbamoyl group,
(e) a cyano group,
(f) a mono- or di-($C_{1-6}$ alkoxy-carbonyl (preferably methoxycarbonyl))-amino group,
(g) a halogen atom (preferably fluorine, chlorine, iodine), and the like.

The substituent that the "carbon atom" of the "optionally substituted carbon atom" for $X^2$ optionally has is preferably
(a) a halogen atom (preferably fluorine, chlorine, bromine),
(b) a $C_{1-4}$ alkyl group (preferably methyl) optionally substituted by 1 to 3 $C_{1-6}$ alkoxy-carbonyl groups (preferably ethoxycarbonyl), and the like.

In this embodiment, the preferable combination of $X^1$ and $X^2$ is as follows;
(1) $X^1$ is an optionally substituted carbon atom, and $X^2$ is an optionally substituted carbon atom
[preferably
$X^1$ is a carbon atom optionally substituted by one substituent selected from
(a) a $C_{1-6}$ alkoxy-carbonyl group (preferably ethoxycarbonyl),
(b) a carboxy group,
(c) a carbamoyl group,
(d) a mono- or di-$C_{1-6}$ alkyl-carbamoyl group,
(e) a cyano group,
(f) a mono- or di-($C_{1-6}$ alkoxy-carbonyl (preferably methoxycarbonyl))-amino group, and
(g) a halogen atom (preferably fluorine, chlorine, iodine), and $X^2$ is a carbon atom optionally substituted by one substituent selected from
(a) a halogen atom (preferably fluorine, chlorine, bromine), and
(b) a $C_{1-4}$ alkyl group (preferably methyl) optionally substituted by 1 to 3 $C_{1-6}$ alkoxy-carbonyl group0 (preferably ethoxycarbonyl)]; or
(2) $X^1$ is a nitrogen atom, and $X^2$ is an optionally substituted carbon atom
[preferably
$X^1$ is a nitrogen atom, and
$X^2$ is a carbon atom optionally substituted by one substituent selected from (a) a halogen atom (preferably fluorine, chlorine, bromine), and (b) a $C_{1-4}$ alkyl group (preferably methyl) optionally substituted by 1 to 3 $C_{1-6}$ alkoxy-carbonyl groups (preferably ethoxycarbonyl)].

Of these, $X^1$ and $X^2$ are preferably both optionally substituted carbon atoms.

In compound (I), when Cy is a benzene ring, then $R^2$ should not be pyrrolyl; and compound (I) excluding the following compounds:

4-{[(5-ethoxy-2-fluoro-3-isopropoxyphenyl)(5-pyrimidin-2-yl-1H-imidazol-2-yl)methyl]amino}benzenecarboximidamide, 2-[ethoxy(phenyl)methyl]-4-methyl-1H-imidazole-5-carboxylic acid, tert-butyl 5-(2,5-dioxo-1-phenylhexyl)-3,4-dimethyl-1H-pyrrole-2-carboxylate, tert-butyl 5-[4,4-dimethyl-2,5-dioxo-1-phenyl-6-(trimethylsilyl)hexyl]-3,4-dimethyl-1H-pyrrole-2-carboxylate, tert-butyl 5-(4,4-dimethyl-2,5-dioxo-1-phenylhexyl)-3,4-dimethyl-1H-pyrrole-2-carboxylate, diethyl 5,5'-(cyclohexylmethanediyl)bis(3-ethyl-4-methyl-1H-pyrrole-2-carboxylate),

[2-{[4,5-bis({2-chloro-5-[(dodecyloxy)carbonyl]phenyl}carbamoyl)-1H-imidazol-2-yl](3,5-dioxo-1,2-diphenyl-1,2,4-triazolidin-4-yl)methyl}-4-oxoquinazolin-3(4H)-yl]acetic acid, 3-({[2-(dicyclohexylmethyl)-5-(2-tricyclo[3.3.1.13,7]deca-1-ylethyl)-1H-imidazol-4-yl]carbonyl}amino)benzoic acid, diethyl 5,5'-(quinolin-2-ylmethanediyl)bis(3-ethyl-4-methyl-1H-pyrrole-2-carboxylate), ethyl 4-{[5-(ethoxycarbonyl)-1H-pyrrol-2-yl](2-nitrophenyl)methyl}-1H-pyrrole-2-carboxylate, diethyl 5,5'-(pyridin-2-ylmethanediyl)bis(3-ethyl-4-methyl-1H-pyrrole-2-carboxylate), diethyl 5,5'-(pyridin-2-ylmethanediyl)bis[4-methyl-3-(trifluoromethyl)-1H-pyrrole-2-carboxylate], (2-fluorobiphenyl-4-yl)(2-pyridin-2-yl-1H-imidazol-5-yl)methanol, (2-fluorobiphenyl-4-yl)(2-pyrazin-2-yl-1H-imidazol-5-yl)methanol, 5,5'-[(1-decyl-2,4-dioxo-1,2,3,4-tetrahydropyrimidin-5-yl)methanediyl]bis(3,4-diethyl-1H-pyrrole-2-carboxylic acid), dibenzyl 5,5'-[(1-decyl-2,4-dioxo-1,2,3,4-tetrahydropyrimidin-5-yl)methanediyl]bis(3,4-diethyl-1H-pyrrole-2-carboxylate), 4-nitrobenzyl 3-hydroxy-5-(2-hydroxy-1-morpholin-4-ylpropyl)-1H-pyrrole-2-carboxylate, 2-(diphenylmethyl)-4-hydroxy-1H-imidazole-5-carboxamide, 3-[5-(diphenylmethyl)-4H-1,2,4-triazol-3-yl]pyridine, 2-chloroethyl 2-(1-phenylethyl)-1H-imidazole-5-carboxylate, 1-methylethyl 2-(1-phenylethyl)-1H-imidazole-5-carboxylate, methyl 2-[1-(4-methoxyphenyl)ethyl]-1H-imidazole-5-carboxylate, 2-(1-phenylethyl)-1H-imidazole-5-carboxylic acid, 5-[ethoxy(pyridin-3-yl)methyl]-4-methyl-3-nitro-1H-pyrrole-2-carboxylic acid, tert-butyl 3-[2-(acetyloxy)ethyl]-5-{[(2E)-3-(3-ethoxy-3-oxopropyl)-2-{[3-(3-methoxy-3-oxopropyl)-4,5-dimethyl-1H-pyrrol-2-yl]methylidene}-4-methyl-2H-pyrrol-5-yl](phenyl)methyl}-4-methyl-1H-pyrrole-2-carboxylate, 5-[ethoxy(pyridin-3-yl)methyl]-3-methyl-4-nitro-1H-pyrrole-2-carboxylic acid, 5-[ethoxy(pyridin-4-yl)methyl]-3-methyl-4-nitro-1H-pyrrole-2-carboxylic acid, 2-{5-[1-(2-fluorobiphenyl-4-yl)ethyl]-1H-imidazol-2-yl}pyridine, and 2-{5-[1-(2-fluorobiphenyl-4-yl)ethyl]-1H-imidazol-2-yl}pyrazine, and a salt thereof, is novel.

Specific preferable examples of the compound represented by the formula (I) include the following compounds.

(Compound A)
Compound (I) wherein
$R^1$ is
(i) a group represented by —$COR^4$
    wherein
    $R^4$ is an alkyl group, a cycloalkyl group, —$OR^5$ wherein $R^5$ is a hydrogen atom or an alkyl group, or an amino group, or
(ii) a 5- or 6-membered nitrogen-containing heterocyclic group (preferably a 5- or 6-membered nitrogen-containing aromatic heterocyclic group) represented by the formula

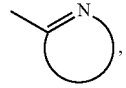

which is optionally substituted by a $C_{1-4}$ alkyl group,
$R^2$ is a $C_{1-6}$ alkyl group optionally substituted by a 4- to 7-membered cyclic group,
$R^3$ is a hydrogen atom,
Cy is a 6-membered aromatic group substituted by $C_{1-6}$ alkylsulfonyl or $C_{3-7}$ cycloalkylsulfonyl,
$X^1$ is a carbon atom or a nitrogen atom, and
$X^2$ is a carbon atom optionally substituted by a halogen atom or a $C_{1-4}$ alkyl group.

(Compound B)
Compound (I) wherein
$R^1$ is a 5- or 6-membered nitrogen-containing heterocyclic group (preferably a 5- or 6-membered nitrogen-containing aromatic heterocyclic group) represented by the formula

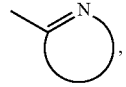

which is optionally substituted;
$R^2$ is an optionally substituted $C_{1-6}$ alkyl group; and
$X^1$ and $X^2$ are both optionally substituted carbon atoms.

(Compound B1)
Compound (I) wherein
$R^1$ is a 5- or 6-membered nitrogen-containing heterocyclic group (preferably a 5- or 6-membered nitrogen-containing aromatic heterocyclic group) represented by the formula

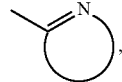

which is optionally substituted;
$R^2$ is an optionally substituted $C_{1-6}$ alkyl group;
$R^3$ is a hydrogen atom or a $C_{1-6}$ alkyl group;
Cy is an optionally substituted 6-membered aromatic group, which is optionally condensed with an optionally substituted 5- or 6-membered ring (preferably Cy is an optionally substituted 6-membered aromatic group);
$X^1$ is an optionally substituted carbon atom, or a nitrogen atom, and $X^2$ is an optionally substituted carbon atom.
(Compound B2)
Compound (B1) wherein
$X^1$ and $X^2$ are both optionally substituted carbon atoms.
(Compound B3)
Compound (B1) wherein
$X^1$ is a nitrogen atom, and
$X^2$ is a carbon atom optionally substituted by one substituent selected from a halogen atom, and a $C_{1-4}$ alkyl group optionally substituted by 1 to 3 $C_{1-6}$ alkoxy-carbonyl groups.
(Compound C1)
Compound (I) wherein
$R^1$ is
(i) a group represented by —$COR^4$
  wherein
  $R^4$ is
  (1) a $C_{1-6}$ alkyl group (preferably ethyl, propyl, isopropyl, butyl),
  (2) a $C_{3-7}$ cycloalkyl group (preferably cyclopropyl, cyclobutyl),
  (3) —$OR^5$ wherein $R^5$ is a hydrogen atom or a $C_{1-6}$ alkyl group, or
  (4) an amino group, or
(ii) a 5- or 6-membered nitrogen-containing heterocyclic group (preferably a 5- or 6-membered nitrogen-containing aromatic heterocyclic group, more preferably 2-imidazolyl, 4-imidazolyl, 2-thiazolyl, 2-thiadiazolyl, 3-pyrazolyl, 2-pyridyl, 2-pyrazinyl) represented by the formula

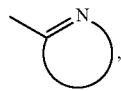

which is optionally substituted by 1 to 3 substituents selected from
(a) a $C_{1-4}$ alkyl group (preferably methyl, ethyl, isopropyl, isobutyl, tert-butyl) optionally substituted by 1 to 3 substituents selected from
  (a1) a hydroxy group,
  (a2) a $C_{1-6}$ alkoxy-carbonyl group (preferably methoxycarbonyl, ethoxycarbonyl),
  (a3) a heterocyclic group (preferably triazolyl, azetidinyl, pyrrolidinyl, imidazolidinyl, 1-oxidothiomorpholinyl, 1,1-dioxidothiomorpholinyl, piperidinyl, piperazinyl, morpholinyl, oxadiazolyl, dihydrooxadiazolyl, diazabicyclo[2.2.1]heptan-2-yl) optionally substituted by 1 to 3 substituents selected from a hydroxy group, a $C_{1-6}$ alkyl group (preferably methyl) optionally substituted by 1 to 3 $C_{6-14}$ aryl groups (preferably phenyl), a $C_{1-6}$ alkyl-carbonyl group (preferably acetyl), an oxo group and a halogen atom (preferably fluorine),
  (a4) a mono- or di-$C_{1-6}$ alkyl-amino group (the $C_{1-6}$ alkyl moiety is optionally substituted by 1 to 3 substituents selected from a hydroxy group, $C_{1-6}$ alkylthio (preferably ethylthio) and $C_{1-6}$ alkylsulfonyl (preferably ethylsulfonyl)),
  (a5) a nitrogen-containing heterocyclyl-amino group (preferably azabicyclo[2.2.2]octan-3-yl-amino),
  (a6) a tert-butyl-diphenylsilyloxy group,
  (a7) a $C_{1-6}$ alkyl-carbonyloxy group (preferably acetyloxy) optionally substituted by 1 to 3 substituents selected from an amino group optionally mono- or di-substituted by a $C_{1-6}$ alkoxy-carbonyl group (preferably tert-butoxycarbonyl),
  (a8) a cyano group,
  (a9) a carboxy group,
  (a10) a heterocyclyl-carbonyl group (preferably morpholinocarbonyl, azetidinylcarbonyl),
  (a11) a carbamoyl group,
  (a12) a mono- or di-$C_{1-6}$ alkyl-carbamoyl group,
  (a13) a $C_{1-6}$ alkylsulfonyl group (preferably methylsulfonyl, ethylsulfonyl) optionally substituted by 1 to 3 hydroxy groups,
  (a14) a $C_{1-6}$ alkoxy group (preferably methoxy, ethoxy) optionally substituted by 1 to 3 $C_{1-6}$ alkoxy groups (preferably methoxy),
  (a15) a halogen atom (preferably fluorine),
  (a16) a $C_{3-7}$ cycloalkyl group (preferably cyclobutyl), and
  (a17) a tert-butyl-dimethylsilyloxy group,
(b) a heterocyclic group (preferably dioxolanyl, tetrahydropyranyl) optionally substituted by 1 to 3 substituents selected from a hydroxy group and a $C_{1-6}$ alkyl group (preferably methyl),
(c) a halogen atom (preferably fluorine, bromine, chlorine),
(d) a $C_{2-6}$ alkenyl group (preferably vinyl, 2-methyl-21-propenyl) optionally substituted by 1 to 3 $C_{1-6}$ alkoxy-carbonyl groups (preferably ethoxycarbonyl),
(e) a formyl group,
(f) a $C_{1-6}$ alkylthio group (preferably methylthio, ethylthio) optionally substituted by 1 to 3 substituents selected from
  (f1) a hydroxy group,
  (f2) a carboxy group,
  (f3) a $C_{1-6}$ alkoxy group, and
  (f4) a $C_{1-6}$ alkoxy-carbonyl group (preferably ethoxycarbonyl),
(g) a carboxy group,
(h) a $C_{1-6}$ alkoxy group (preferably methoxy, ethoxy, propoxy, isopropoxy, isobutyloxy) optionally substituted by 1 to 3 substituents selected from
  (h1) a $C_{6-14}$ aryl group (preferably phenyl),
  (h2) a $C_{3-7}$ cycloalkyl group (preferably cyclopropyl),
  (h3) a $C_{1-6}$ alkyl-carbonyl group (preferably acetyl), and
  (h4) a hydroxy group,
(i) a hydroxy group,
(j) a $C_{1-6}$ alkoxy-carbonyl group (preferably methoxycarbonyl),
(k) a mono- or di-$C_{3-7}$ cycloalkyl (preferably cyclopropyl)-carbamoyl group,
(l) a mono- or di-$C_{1-6}$ alkyl (preferably ethyl, isobutyl)-carbamoyl group (the $C_{1-6}$ alkyl moiety is optionally substituted by 1 to 3 substituents selected from a hydroxy group and $C_{1-6}$ alkoxy (preferably ethoxy)),
(m) a heterocyclyl-carbonyl group (preferably morpholinocarbonyl, azetidinylcarbonyl),
(n) a $C_{1-6}$ alkyl-carbonyl group (preferably acetyl), and
(o) a carbamoyl group;
$R^2$ is a $C_{1-6}$ alkyl group (preferably methyl) optionally substituted by one substituent selected from
(a) a $C_{4-7}$ cycloalkyl group (preferably cyclopentyl) optionally substituted by 1 to 3 substituents selected from
  (a1) a $C_{1-4}$ alkylenedioxy group (preferably ethylenedioxy) optionally substituted by 1 to 3 phenyl groups, and
  (a2) an oxo group, and
(b) a 4- to 7-membered (preferably 5- or 6-membered) non-aromatic heterocyclic group (preferably tetrahydrofuranyl, tetrahydropyranyl);
$R^3$ is a hydrogen atom or a $C_{1-6}$ alkyl group (preferably methyl);
Cy is a 6-membered aromatic group (preferably phenyl, pyridyl) substituted by 1 to 3 substituents selected from
(a) $C_{1-6}$ alkylsulfonyl (preferably methylsulfonyl, ethylsulfonyl, propylsulfonyl) optionally substituted by 1 to 3 $C_{1-6}$ alkoxy groups (preferably methoxy),
(b) $C_{3-7}$ cycloalkylsulfonyl (preferably cyclopropylsulfonyl), (c) a $C_{1-6}$ alkoxy-carbonyl group (preferably tert-butoxycarbonyl),
(d) a carboxy group,
(e) a mono- or di-$C_{3-7}$ cycloalkyl (preferably cyclopropyl)-carbamoyl group,
(f) a heterocyclyl-carbonyl group (preferably azetidinylcarbonyl),
(g) a carbamoyl group di-substituted by a $C_{1-6}$ alkyl group (preferably methyl) and a $C_{1-6}$ alkoxy group (preferably methoxy),
(h) a halogen atom (preferably fluorine, chlorine),
(i) a $C_{1-6}$ alkylthio group (preferably methylthio), and
(j) a $C_{1-6}$ alkyl group (preferably methyl);
$X^1$ is
(1) a carbon atom optionally substituted by one substituent selected from
   (a) a $C_{1-6}$ alkoxy-carbonyl group (preferably ethoxycarbonyl),
   (b) a carboxy group,
   (c) a carbamoyl group,
   (d) a mono- or di-$C_{1-6}$ alkyl-carbamoyl group,
   (e) a cyano group,
   (f) a mono- or di-($C_{1-6}$ alkoxy-carbonyl (preferably methoxycarbonyl))-amino group, and
   (g) a halogen atom (preferably fluorine, chlorine, iodine), or
(2) a nitrogen atom; and
$X^2$ is a carbon atom optionally substituted by one substituent selected from
(a) a halogen atom (preferably fluorine, chlorine, bromine), and
(b) a $C_{1-4}$ alkyl group (preferably methyl) optionally substituted by 1 to 3 $C_{1-6}$ alkoxy-carbonyl groups (preferably ethoxycarbonyl).
(Compound C2)
Compound (C1) wherein
$R^1$ is a group represented by —$COR^4$
  wherein
  $R^4$ is
  (1) a $C_{1-6}$ alkyl group (preferably ethyl, propyl, isopropyl, butyl),
  (2) a $C_{3-7}$ cycloalkyl group (preferably cyclopropyl, cyclobutyl),
  (3) —$OR^5$ wherein $R^5$ is a hydrogen atom or a $C_{1-6}$ alkyl group, or
  (4) an amino group.
(Compound C3)
Compound (C1) wherein
$R^1$ is a 5- or 6-membered nitrogen-containing heterocyclic group (preferably a 5- or 6-membered nitrogen-containing aromatic heterocyclic group, more preferably 2-imidazolyl, 4-imidazolyl, 2-thiazolyl, 2-thiadiazolyl, 3-pyrazolyl, 2-pyridyl, 2-pyrazinyl) represented by the formula

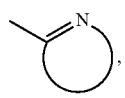, which is optionally substituted by 1 to 3 substituents selected from
(a) a $C_{1-4}$ alkyl group (preferably methyl, ethyl, isopropyl, isobutyl, tert-butyl) optionally substituted by 1 to 3 substituents selected from
  (a1) a hydroxy group,
  (a2) a $C_{1-6}$ alkoxy-carbonyl group (preferably methoxycarbonyl, ethoxycarbonyl),
  (a3) a heterocyclic group (preferably triazolyl, azetidinyl, pyrrolidinyl, imidazolidinyl, 1-oxidothiomorpholinyl, 1,1-dioxidothiomorpholinyl, piperidinyl, piperazinyl, morpholinyl, oxadiazolyl, dihydrooxadiazolyl, diazabicyclo[2.2.1]heptan-2-yl) optionally substituted by 1 to 3 substituents selected from a hydroxy group, a $C_{1-6}$ alkyl group (preferably methyl) optionally substituted by 1 to 3 $C_{6-14}$ aryl groups (preferably phenyl), a $C_{1-6}$ alkyl-carbonyl group (preferably acetyl), an oxo group and a halogen atom (preferably fluorine),
  (a4) a mono- or di-$C_{1-6}$ alkyl-amino group (the $C_{1-6}$ alkyl moiety is optionally substituted by 1 to 3 substituents selected from a hydroxy group, $C_{1-6}$ alkylthio (preferably ethylthio) and $C_{1-6}$ alkylsulfonyl (preferably ethylsulfonyl)),
  (a5) a nitrogen-containing heterocyclyl-amino group (preferably azabicyclo[2.2.2]octan-3-yl-amino),
  (a6) a tert-butyl-diphenylsilyloxy group,
  (a7) a $C_{1-6}$ alkyl-carbonyloxy group (preferably acetyloxy) optionally substituted by 1 to 3 substituents selected from an amino group optionally mono- or di-substituted by a $C_{1-6}$ alkoxy-carbonyl group (preferably tert-butoxycarbonyl),
  (a8) a cyano group,
  (a9) a carboxy group,
  (a10) a heterocyclyl-carbonyl group (preferably morpholinocarbonyl, azetidinylcarbonyl),
  (a11) a carbamoyl group,
  (a12) a mono- or di-$C_{1-6}$ alkyl-carbamoyl group,
  (a13) a $C_{1-6}$ alkylsulfonyl group (preferably methylsulfonyl, ethylsulfonyl) optionally substituted by 1 to 3 hydroxy groups,
  (a14) a $C_{1-6}$ alkoxy group (preferably methoxy, ethoxy) optionally substituted by 1 to 3 $C_{1-6}$ alkoxy groups (preferably methoxy),
  (a15) a halogen atom (preferably fluorine),
  (a16) a $C_{3-7}$ cycloalkyl group (preferably cyclobutyl), and
  (a17) a tert-butyl-dimethylsilyloxy group,
(b) a heterocyclic group (preferably dioxolanyl, tetrahydropyranyl) optionally substituted by 1 to 3 substituents selected from a hydroxy group and a $C_{1-6}$ alkyl group (preferably methyl),
(c) a halogen atom (preferably fluorine, bromine, chlorine),
(d) a $C_{2-6}$ alkenyl group (preferably vinyl, 2-methyl-1-propenyl) optionally substituted by 1 to 3 $C_{1-6}$ alkoxy-carbonyl groups (preferably ethoxycarbonyl),
(e) a formyl group,
(f) a $C_{1-6}$ alkylthio group (preferably methylthio, ethylthio) optionally substituted by 1 to 3 substituents selected from
  (f1) a hydroxy group,
  (f2) a carboxy group,
  (f3) a $C_{1-6}$ alkoxy group, and
  (f4) a $C_{1-6}$ alkoxy-carbonyl group (preferably ethoxycarbonyl),
(g) a carboxy group,
(h) a $C_{1-6}$ alkoxy group (preferably methoxy, ethoxy, propoxy, isopropoxy, isobutyloxy) optionally substituted by 1 to 3 substituents selected from
  (h1) a $C_{6-14}$ aryl group (preferably phenyl),
  (h2) a $C_{3-7}$ cycloalkyl group (preferably cyclopropyl),
  (h3) a $C_{1-6}$ alkyl-carbonyl group (preferably acetyl), and
  (h4) a hydroxy group,
(i) a hydroxy group,
(j) a $C_{1-6}$ alkoxy-carbonyl group (preferably methoxycarbonyl),
(k) a mono- or di-$C_{3-7}$ cycloalkyl (preferably cyclopropyl)-carbamoyl group,
(l) a mono- or di-$C_{1-6}$ alkyl (preferably ethyl, isobutyl)-carbamoyl group (the $C_{1-6}$ alkyl moiety is optionally substituted by 1 to 3 substituents selected from a hydroxy group and $C_{1-6}$ alkoxy (preferably ethoxy)), (m) a heterocyclyl-carbonyl group (preferably morpholinocarbonyl, azetidinylcarbonyl),
(n) a $C_{1-6}$ alkyl-carbonyl group (preferably acetyl), and
(o) a carbamoyl group.
(Compound C4)
Compound (C1), compound (C2) or compound (C3) wherein $X^1$ is a carbon atom optionally substituted by one substituent selected from
(a) a $C_{1-6}$ alkoxy-carbonyl group (preferably ethoxycarbonyl),
(b) a carboxy group,
(c) a carbamoyl group,
(d) a mono- or di-$C_{1-6}$ alkyl-carbamoyl group,
(e) a cyano group,
(f) a mono- or di-($C_{1-6}$ alkoxy-carbonyl (preferably methoxycarbonyl))-amino group, and
(g) a halogen atom (preferably fluorine, chlorine, iodine); and
$X^2$ is a carbon atom optionally substituted by one substituent selected from
(a) a halogen atom (preferably fluorine, chlorine, bromine), and
(b) a $C_{1-4}$ alkyl group (preferably methyl) optionally substituted by 1 to 3 $C_{1-6}$ alkoxy-carbonyl group0 (preferably ethoxycarbonyl).
(Compound C5)
Compound (C1), compound (C2) or compound (C3) wherein $X^1$ is a nitrogen atom; and
$X^2$ is a carbon atom optionally substituted by one substituent selected from
(a) a halogen atom (preferably fluorine, chlorine, bromine), and
(b) a $C_{1-4}$ alkyl group (preferably methyl) optionally substituted by 1 to 3 $C_{1-6}$ alkoxy-carbonyl groups (preferably ethoxycarbonyl).
(Compound D)
3-{2-[5-(cyclobutylcarbonyl)-4-fluoro-1H-imidazol-2-yl]-2-[4-(cyclopropylsulfonyl)phenyl]ethyl}cyclopentanone;
1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol;
1-[6-(5-{1-[4-(cyclopropylsulfonyl)phenyl]-2-(tetrahydro-2H-pyran-4-yl)ethyl}-1H-pyrrol-2-yl)pyridin-3-yl]ethane-1,2-diol;
2-[6-(5-{1-[4-(cyclopropylsulfonyl)phenyl]-2-(tetrahydro-2H-pyran-4-yl)ethyl}-1H-pyrrol-2-yl)pyridin-3-yl]propane-1,3-diol;
1-acetyl-4-[([6-(5-{1-[4-(cyclopropylsulfonyl)phenyl]-2-(tetrahydro-2H-pyran-4-yl)ethyl}-1H-pyrrol-2-yl)pyridin-3-yl]methyl]piperazine;
1-[6-(5-{1-[3-chloro-4-(methylsulfonyl)phenyl]-2-(tetrahydro-2H-pyran-4-yl)ethyl}-1H-pyrrol-2-yl)pyridin-3-yl]ethane-1,2-diol;
1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol;
1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethanol;
1-[2-(5-{1-[3-chloro-4-(methylsulfonyl)phenyl]-2-(tetrahydro-2H-pyran-4-yl)ethyl}-1H-pyrrol-2-yl)-1,3-thiazol-5-yl]ethanol; and
3-(2-[3-chloro-4-(methylsulfonyl)phenyl]-2-{5-[5-(hydroxymethyl)pyridin-2-yl]-1H-pyrrol-2-yl}ethyl)cyclopentanone;
and a salt thereof.

As the salt of compound (I), a pharmacologically acceptable salt is preferable. Examples of such salt include salts with inorganic bases, salts with organic bases, salts with inorganic acids, salts with organic acids, salts with basic or acidic amino acids and the like can be mentioned.

As preferable examples of the salt with inorganic base, alkali metal salts such as sodium salt, potassium salt and the like; alkaline earth metal salts such as calcium salt, magnesium salt and the like; and aluminum salts; ammonium salts and the like can be mentioned.

As preferable examples of the salt with organic base, salts with trimethylamine, triethylamine, pyridine, picoline, ethanolamine, diethanolamine, triethanolamine, dicyclohexylamine, N,N-dibenzylethylenediamine and the like can be mentioned.

As preferable examples of the salt with inorganic acid, salt with hydrochloric acid, hydrobromic acid, nitric acid, sulfuric acid, phosphoric acid and the like can be mentioned.

As preferable examples of the salt with organic acid, salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like can be mentioned.

As preferable examples of the salt with basic amino acid, salts with arginine, lysine, ornithine and the like can be mentioned.

As preferable examples of the salt with acidic amino acid, salts with aspartic acid, glutamic acid and the like can be mentioned.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc. Examples of the prodrug of compound (I) include a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. These compounds can be produced from compound (I) according to a method known per se.

A prodrug of the compound (I) may also be one which is converted into the compound (I) under a physiological condition, such as those described in *IYAKUHIN NO KAIHATSU* (Development of Pharmaceuticals), Vol. 7, Molecule Design, p. 163-198, Published by HIROKAWA SHOTEN (1990).

The compound (I) may be labeled with an isotope (e.g., $^3H$, $^{14}C$, $^{35}S$, $^{125}I$ etc.) and the like.

Moreover, a Deuterium-converted compound wherein $^1H$ has been converted to $^2H(D)$ is also encompassed in compound (I).

While a compound represented by the formula (I) and a salt thereof contain tautomer, any tautomer is encompassed in the present invention, and a compound represented by the formula (I) and a salt thereof may be any of solvate, hydrate, non-solvate and non-hydrate.

The compound (I) or a prodrug thereof (hereinafter sometimes to be abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys etc.) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; or solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, α-starch, dextrin, crystalline cellulose, low-substituted hydroxypropylcellulose, sodium carboxymethylcellulose, gum acacia, pullulan, light anhydrous silicic acid, synthetic aluminum silicate, magnesium aluminate metasilicate and the like.

Preferred examples of the lubricant include magnesium stearate, calcium stearate, talc, colloidal silica and the like.

Preferable examples of the binder include α-starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethylstarch, light anhydrous silicic acid, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferred examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agent include surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferred examples of the isotonicity agent include sodium chloride, glycerol, D-mannitol, D-sorbitol, glucose and the like.

Preferred examples of the buffer include buffers such as phosphate, acetate, carbonate, citrate and the like.

Preferred examples of the soothing agent include benzyl alcohol and the like.

Preferred examples of the preservative include p-oxybenzoates, chlorobutanol, benzyl alcohol, phenethyl alcohol, dehydroacetic acid, sorbic acid and the like.

Preferred examples of the antioxidant include sulfite, ascorbate and the like.

Preferable examples of the colorant include water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., beta carotene, chlorophil, ferric oxide red) and the like.

Preferable examples of the sweetening agent include saccharin sodium, dipotassium glycyrrhizinate, aspartame, stevia and the like.

Examples of the dosage form of the aforementioned pharmaceutical composition include oral preparations such as tablet (including sublingual tablet, orally disintegrating tablet), capsule (including soft capsule, microcapsule), granule, powder, troche, syrup, emulsion, suspension and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparations, pulmonary preparation (inhalant), eye drop and the like, each of which can be safely administered orally or parenterally (e.g., topical, rectal, intravenous administration etc.).

These preparations may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. Concrete production methods of preparations are described in detail in the following.

While the content of the compound of the present invention in the pharmaceutical composition varies depending on the dosage form, dose of the compound of the present invention and the like, it is, for example, about 0.1 to 100 wt %.

The compound of the present invention has a superior GK activating action, and can be used as an agent for the prophylaxis or treatment of various diseases for mammals (e.g., human, bovine, horse, dog, cat, monkey, mouse, rat, specifically human). In addition, as the compound of the present invention has a selective GK activating action, it shows low toxicity (e.g., acute toxicity, chronic toxicity, cardiotoxicity, carcinogenic, genetic toxicity), which causes fewer side effects.

The compound of the present invention can be used as an agent for the prophylaxis or treatment of diabetes (e.g., type 1 diabetes, type 2 diabetes, gestational diabetes, obese diabetes); an agent for the prophylaxis or treatment of hyperlipidemia (e.g., hypertriglyceridemia, hypercholesterolemia, hypoHDL-emia, postprandial hyperlipidemia); an agent for the prophylaxis or treatment of arteriosclerosis; an agent for the prophylaxis or treatment of impaired glucose tolerance [IGT (Impaired Glucose Tolerance)]; or an agent for preventing impaired glucose tolerance from progressing into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a casual blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, new diagnostic criteria of diabetes have been reported by ADA (American Diabetes Association) and WHO.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 100 mg/dl and less than 126 mg/dl is called IFG (Impaired Fasting Glucose). According to the report of WHO, among the IFG (Impaired Fasting Glucose), a condition showing a fasting blood glucose level (glucose 15 concentration of intravenous plasma) of not less than 110 mg/dl and less than 126 mg/dl is called IFG (Impaired Fasting Glycaemia).

The compound of the present invention can also be used as an agent for the prophylaxis or treatment of diabetes, borderline type, impaired glucose tolerance, IFG (Impaired Fasting Glucose) and IFG (Impaired Fasting Glycaemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycaemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, hypertension, polycystic ovary syndrome, renal disease (e.g., diabetic nephropathy, glomerulonephritis, glomerulosclerosis, nephrotic syndrome, hypertensive nephrosclerosis, end-stage m renal disorder), muscular dystrophy, myocardial infarction, angina pectoris, cerebrovascular disorder (e.g., cerebral infarction, cerebral apoplexy), glucose metabolism disorder, lipid metabolism abnormality, insulin resistance syndrome, syndrome X, metabolic syndrome (condition showing at least one of type 2 diabetes, impaired glucose tolerance and insulin resistance, and at least two of obesity, lipid metabolism abnormality, hypertension and microalbuminuria), Cushing's syndrome, hyperinsulinemia, perception disorder in hyperinsulinemia, tumor (e.g., leukemia, breast cancer, prostate cancer, skin cancer), irritable bowel syndrome, acute or chronic diarrhea, inflammatory disease (e.g., rheumatoid arthritis, spondylitis deformans, osteoarthritis, lumbago, gout, post-operative or post-traumatic inflammation, swelling, neuralgia, pharyngolaryngitis, cystitis, hepatitis (including nonalcoholic steatohepatitis), pneumonia, pancreatitis, inflammatory colitis, ulcerative colitis, gastric mucosa injury (including gastric mucosa injury caused by aspirin)), visceral obesity syndrome and the like.

The compound of the present invention can also be used for improving insulin resistance, promotion or increase of insulin secretion, decrease of visceral fat, suppression of visceral fat accumulation, improvement of glucose metabolism, improvement of lipid metabolism, suppression of oxidized LDL production, improvement of lipoprotein metabolism, improvement of coronary metabolism, prophylaxis or treatment of cardiovascular complications, prophylaxis or treatment of heart failure complications, lowering of blood remnant, prophylaxis or treatment of anovulation, prophylaxis or treatment of hirsutism, prophylaxis or treatment of hyperandrogenism, improvement of pancreatic ($\beta$ cell) function, pancreatic ($\beta$ cell) regeneration, promotion of pancreatic ($\beta$ cell) regeneration and the like.

The compound of the present invention can also be used for the secondary prevention and suppression of progression of various diseases mentioned above (e.g., cardiovascular event such as myocardial infarction etc.).

The compound of the present invention is particularly useful as an agent for the prophylaxis or treatment of type-2 diabetes, obese diabetes and the like.

While the dose of the compound of the present invention varies depending on the administration subject, administration route, target disease, condition and the like, the compound of the present invention is generally given in a single dose of about 0.01-100 mg/kg body weight, preferably 0.05-30 mg/kg body weight, more preferably 0.1-10 mg/kg body weight, in the case of, for example, oral administration to adult diabetic patients. This dose is desirably given 1 to 3 times a day.

The compound of the present invention can be used in combination with pharmaceutical agents such as therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antithrombotic agents, therapeutic agents for osteoporosis, antidementia agents, erectile dysfunction improvers, therapeutic agents for pollakiuria or urinary incontinence, therapeutic agents for dysuria and the like (hereinafter to be abbreviated as concomitant drug). The time of administration of the compound of the present invention and that of the concomitant drug are not limited, and they may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be determined as appropriate based on the dose clinically employed. The proportion of the compound of the present invention and the concomitant drug can be appropriately determined depending on the administration subject, administration route, target disease, condition, combination and the like. When, for example, the administration subject is human, the concomitant drug is used in an amount of 0.01-100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizer (e.g., pioglitazone or a salt thereof (preferably hydrochloride), rosiglitazone or a salt thereof (preferably maleate), Reglixane (JTT-501), Netoglitazone (MCC-555), DRF-2593, edaglitazone (BM-13.1258), KRP-297, R-119702, Rivoglitazone (CS-011), FK-614, compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), Ragaglitazar (N,N-622), muraglitazar (BMS-298585), ONO-5816, LM-4156, MBX-102, Naveglitazar (LY-519818), MX-6054, LY-510929, balaglitazone (N,N-2344), T-131 or a salt thereof, THR-0921), PPAR$\gamma$ agonist, PPARγ antagonist, PPARγ/α dual agonist, α-glucosidase inhibitor (e.g., voglibose, acarbose, miglitol, emiglitate), biguanide (e.g., phenformin, metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or calcium salt hydrate thereof], GPR40 agonist, GLP-1% receptor agonist [e.g., GLP-1, GLP-1MR agent, N,N-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitor (e.g., sodium vanadate), dipeptidyl peptidase IV inhibitor (e.g., Alogliptin or a salt thereof (preferably, benzoate), NVP-DPP-278, PT-100, P32/98, Vidagliptin (LAF-237), P93/01, TS-021, MK-431, Saxagliptin (BMS-477118)), β3 agonist (e.g., AJ-9677), gluconeogenesis inhibitor (e.g., glycogen phosphorylase inhibitor, glucose-6-phosphatase inhibitor, glucagon antagonist), SGLT (sodium-glucose cotransporter) inhibitor (e.g., T-1095), 11β-HSD1 inhibitor (e.g., BVT-3498), adiponectin or agonist thereof, IKK inhibitor (e.g., AS-2868), leptin resistance improving drugs, somatostatin receptor agonists (e.g., compounds described in WO01/25228, WO03/42204, WO98/44921, WO98/45285, WO99/22735) and the like can be mentioned.

Examples of the therapeutic agents for diabetic complications include aldose reductase inhibitors (e.g., Tolrestat, Epalrestat, Zenarestat, Zopolrestat, Minalrestat, Fidarestat, CT-112, Ranirestat (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), neuranagenesis stimulators (e.g., Y-128), PKC inhibitors (e.g., ruboxistaurin mesylate), AGE inhibitors (e.g., ALT-946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt, calcium salt)), squalene synthase inhibitors (e.g., compound described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agents include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compound described in WO01/82925 and WO01/87834); neuropeptide Y antagonists (e.g., CP-422935); cannabinoid receptor antagonists (e.g., SR-141716, SR-147778); ghrelin antagonists), pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), anticancer antibiotics (e.g., mitomycin, adriamycin), plant-derived anticancer agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agent include tacrine, donepezil, rivastigmine, galanthamine and the like.

Examples of the erectile dysfunction improvers include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The concomitant drug is preferably insulin preparation, insulin sensitizer, α-glucosidase inhibitor, biguanide, insulin secretagogue (preferably sulfonylurea) and the like.

Two or more kinds of the above-mentioned concomitant drugs may be used in an appropriate combination.

When the compound of the present invention is used in combination with a concomitant drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent for diabetic complications, therapeutic agent for hyperlipidemia and antihypertensive agent can be reduced whereby an adverse effect which may be caused by these agents can be prevented effectively.

Compound (I) can be produced, for example, by the methods shown in the following reaction schemes or methods according thereto.

Of the compound represented by the formula (I), the imidazole derivative can be produced, for example, by the method shown in the following Reaction Scheme 1.

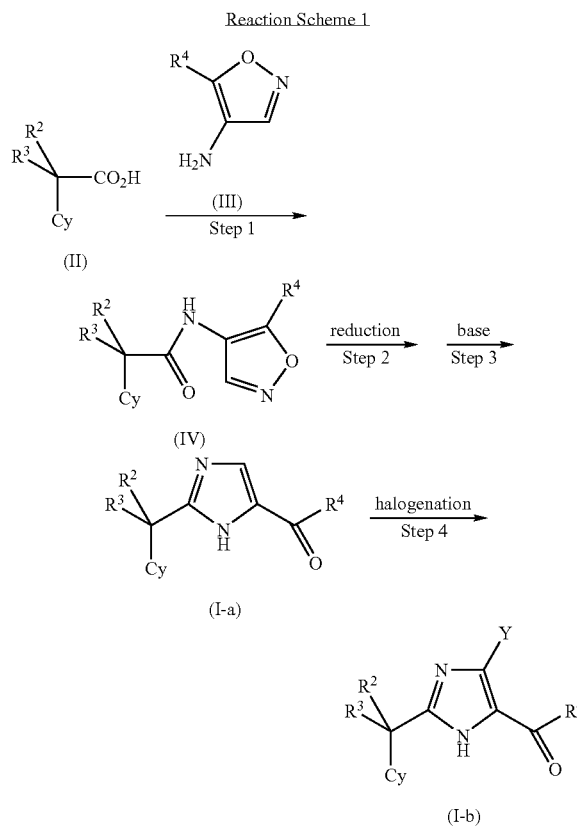

wherein Y is a halogen atom, and the other symbols are as defined above.

In this method, compound (II) is reacted with aminoisoxazole compound (III) to produce compound (IV), the isoxazole ring of compound (IV) is subjected to reductive cleavage, and then reacted in a base to produce compound (I-a), and compound (I-a) is subjected to halogenation to produced compound (I-b).

Compound (II) can be synthesized, for example, according to a known method described in WO00/58293, WO2006/016178 or the like.

Compound (III) can be synthesized according to a known method.

Step 1

Compound (IV) can be produced by reacting compound (II) or the reactive derivative of the carboxy group or a salt thereof with compound (III) or a salt thereof.

Examples of the reactive derivative of the carboxy group of compound (II) include 1) an acid chloride;
2) an acid azide;
3) a mixed acid anhydride with an acid (e.g., substituted phosphoric acids such as dialkylphosphoric acid, phenylphosphoric acid, diphenylphosphoric acid, dibenzylphosphoric acid, halogenated phosphoric acid and the like; dialkylphosphorous acid; sulfurous acid; thiosulfuric acid; sulfuric acid; sulfonic acids such as methanesulfonic acid and the like; aliphatic carboxylic acids such as acetic acid, propionic acid, butyric acid, isobutyric acid, pivalic acid, pentanoic acid, isopentanoic acid, trichloroacetic acid and the like; aromatic carboxylic acids such as benzoic acid and the like);
4) a symmetric acid anhydride;
5) an activated amide with imidazole, 4-substituted imidazole, dimethylpyrazole, triazole or tetrazole;
6) an activated ester such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxymethyl thioester, pyranyl ester, pyridyl ester, piperidyl ester, 8-quinolyl thioester and the like;
7) a ester with a N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole);

and the like. These reactive derivatives are appropriately determined according to the kind of compound (II) to be used.

Preferable examples of the salt of the reactive derivative of compound (II) include salts with a base, such as alkali metal salts (e.g., sodium salt, potassium salt and the like), alkaline earth metal salts (e.g., calcium salt, magnesium salt and the like), ammonium salts, organic base salts (e.g., trimethylamine salt, triethylamine salt, pyridine salt, picoline salt, dicyclohexylamine salt, N,N-dibenzylethylenediamine salt and the like) and the like.

This reaction is preferably carried out in a solvent inert to the reaction. While the solvent is not particularly limited as long as the reaction proceeds, examples of thereof include alcohols such as methanol, ethanol, propanol, isopropanol, butanol, tert-butyl alcohol and the like; ethers such as dioxane, tetrahydrofuran, diethyl ether, tert-butyl methyl ether, diisopropyl ether, ethylene glycol-diethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide; water and the like. These solvents may be used in a mixture of two or more kinds thereof at an appropriate ratio.

In this reaction, when compound (II) is used in the form of a free acid or a salt thereof, the reaction is preferably carried out in the presence of a conventional condensing agent such as a carbodiimide (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide and the like), N,N'-carbonylbis(2-methylimidazole), a trialkylphosphite, a polyphosphate (e.g., ethyl polyphosphate, isopropyl polyphosphate and the like), phosphorus oxychloride, diphenylphosphorylazide, thionyl chloride, oxalyl chloride, a lower alkyl haloformate (e.g., ethyl chloroformate, isopropyl chloroformate and the like), triphenylphosphine, 1-[bis(dimethylamino)methylene]-1H-1,2,3-triazolo(4,5-b)pyridinium 3-oxide hexafluorophosphate (HATU), N-hydroxybenzotriazole, 1-(p-chlorobenzenesulfonyloxy)-6-chloro-1H-benzotriazole, Vilsmeier-reagent (prepared by the reaction of N,N'-dimethylformamide and thionyl chloride, phosgene, trichloromethyl chloroformate, phosphorus oxychloride and the like), and the like.

This reaction can be carried out in the presence of a base, as necessary. Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal $C_{1-6}$ alkoxides such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithium diisopropylamide and the like, and the like.

The amount of compound (III) to be used is generally 1 to 10 mol, preferably 1 to 3 mol, per 1 mol of compound (II). The amount of the base to be used is generally 1 to 10 mol, preferably 1 to 3 mol, per 1 mol of compound (II).

The reaction temperature is generally –30° C. to 100° C. The reaction time is generally 0.5 to 20 hr.

When an mixed acid anhydride is used as a reactive derivative of compound (II), compound (II) can be reacted with a chloroformate (e.g., methyl chloroformate, ethyl chloroformate, isobutyl chloroformate) in the presence of a base (e.g., triethylamine, N-methylmorpholine, N,N-dimethylaniline, sodium hydrogen carbonate, sodium carbonate, potassium carbonate), and then reacted with compound (III).

This reaction is preferably carried out in a solvent inert to the reaction. While the solvent is not particularly limited as long as the reaction proceeds, examples of the solvent include ethers such as dioxane, tetrahydrofuran, diethyl ether, tert-butyl methyl ether, diisopropyl ether, ethylene glycol-diethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide and the like. These solvents may be used in a mixture of two or more kinds thereof at an appropriate ratio.

The amount of the chloroformate to be used is generally 1 to 10 mol, preferably 1 to 3 mol, per 1 mol of compound (III).

The reaction temperature is generally –30° C. to 100° C. The reaction time is generally 0.5 to 20 hr.

Compound (I-a) can be produced by subjecting compound (IV) to Step 2 and Step 3.

Step 2

The reduction reaction can be carried out by a hydrogenation reaction. In this case, for example, a catalyst such as palladium carbon, palladium black, platinum dioxide, Raney-nickel, Raney-cobalt and the like can be used. The amount of the catalyst to be used is about 5 to about 1000 wt %, preferably about 10 to about 300 wt %, per 1 mol of compound (IV). The hydrogenation reaction can also be carried out using various hydrogen sources instead of hydrogen gas. Examples of the hydrogen source include formic acid, ammonium formate, triethylammonium formate, sodium phosphinate, hydrazine and the like. The amount of the hydrogen source to be used is about 1 to about 10 mol, preferably about 1 to about 5 mol, per 1 mol of compound (IV).

The reduction reaction is preferably carried out using a solvent inert to the reaction. While the solvent is not particularly limited as long as the reaction proceeds, preferable examples thereof include alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propionic acid, trifluoroacetic acid, methanesulfonic acid and the like, and the like, and a mixed solvent thereof.

While the reaction time varies depending on the kind of the reagent and solvent to be used, it is generally about 10 min to about 100 hr, preferably about 30 min to about 50 hr. The reaction temperature is generally about –20 to about 100° C., preferably about 0 to about 80° C. When hydrogen gas is used, the reaction inner pressure is generally 1 atm to 100 atm, preferably 1 atm to 10 atm.

Step 3

In this step, compound (I-a) can be produced by reacting the resulting compound obtained in Step 2 with a base.

Examples of the base used for the reaction include alkali metal hydroxides such as sodium hydroxide, potassium hydroxide, hydroxide barium and the like; alkali metal carbonates such as sodium carbonate, potassium carbonate and the like; alkali metal alkoxides having 1 to 6 carbon atoms such as sodium methoxide, sodium ethoxide, potassium tert-butoxide and the like; organic bases such as triethylamine, imidazole, formamidine and the like, and the like. The amount of the base m to be used is about 0.5 to 10 mol, preferably about 0.5 to 6 mol, per 1 mol of the compound obtained in Step 2.

The reaction is advantageously carried out using a solvent inert to the reaction. While the solvent is not particularly limited as long as the reaction proceeds, preferable examples thereof include alcohols such as methanol, ethanol, 1-propanol, 2-propanol, tert-butyl alcohol and the like; ethers such as diethyl ether, diisopropyl ether, diphenyl ether, tetrahydrofuran, 1,4-dioxane, 1,2-dimethoxyethane and the like; amides such as N,N-dimethylformamide, N,N-dimethylacetamide, hexamethylphosphoric triamide and the like; water and the like, and a mixed solvent thereof.

While the reaction time varies depending on the kind of the compound obtained in Step 2, base or solvent, the reaction temperature and the like, it is generally about 10 min to about 100 hr, preferably about 30 min to about 24 hr. The reaction temperature is generally –20 to 200° C., preferably 20 to 100° C.

Step 4

Compound (I-b) can be produced by subjecting compound (I-a) to halogenation.

Examples of the halogenating agent used for the halogenation include the following reagents. Examples of the fluorinating agent include fluorine gas, trifluoroborane, cesium sulfate fluoride, xenon fluoride, hypofluorites, N-fluoropyridinium trifluoromethanesulfonate, N-fluorobis(trifluoromethanesulfonyl)imide, cobalt fluoride and the like.

Examples of the chlorinating agent include chlorine gas, N-chlorosuccinimide and the like. Examples of the brominating agent include bromine, dioxane-bromine complex, N-bromosuccinimide and the like. Examples of the iodinating agent include iodine, N-succinimide and the like.

Depending on the kind of the halogenating agent to be used, the reaction can be promoted by irradiation of light, addition of a radical initiator, and the like.

The reaction is advantageously carried out using a solvent inert to the reaction. While the solvent is not particularly limited as long as the reaction proceeds, preferable examples thereof include ethers such as diethyl ether, diisopropyl ether, diphenyl ether, tetrahydrofuran, 1,4-dioxane, 1,2-dimethoxyethane and the like; saturated hydrocarbons such as cyclohexane, hexane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; nitriles such as acetonitrile, propionitrile and the like; ketones such as acetone, ethyl methyl ketone and the like; sulfoxides such as dimethyl sulfoxide and the like, and the like, and a mixed solvent thereof.

While the reaction time varies depending on the kind of the reagent or solvent to be used, it is generally 10 min to 100 hr, preferably 30 min to 50 hr. The reaction temperature is generally −30 to 100° C., preferably 0 to 80° C.

The amount of the halogenating agent to be used is about 0.5 to about 5 mol, preferably about 1 to about 3 mol, per 1 mol of compound (I-a).

Of the compound represented by the formula (I), the pyrrole derivative can be produced, for example, by the method shown in the following Reaction Scheme 2.

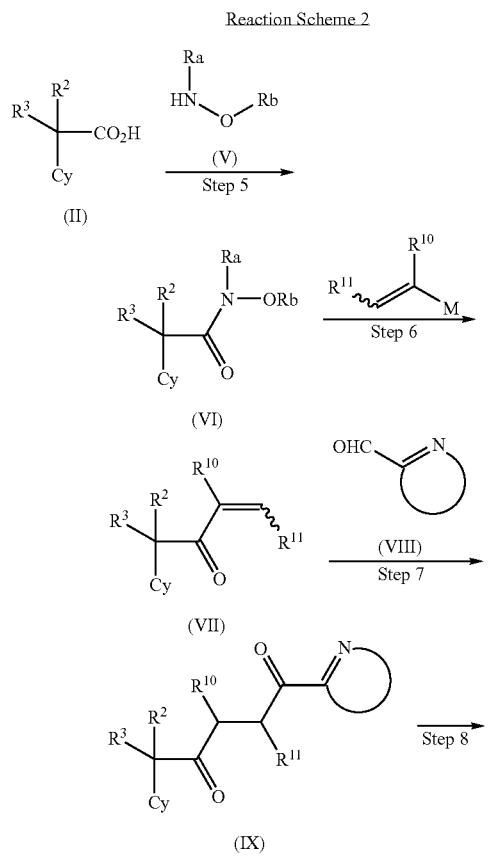

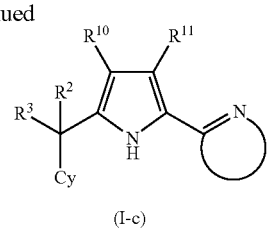

wherein Ra and Rb are each an optionally substituted alkyl group, $R^{10}$ and $R^{11}$ are each a hydrogen atom or an optionally substituted alkyl group, M is Na, K, Li, MgCl, MgBr, ZnCl or ZnBr, and the other symbols are as defined above.

Examples of the "optionally substituted alkyl group" for $R^{10}$, $R^{11}$, Ra or Rb include those similar to the aforementioned "optionally substituted $C_{1-6}$ alkyl group".

In this method, compound (II) is reacted with hydroxylamine compound (V) or a salt thereof to produce compound (VI), and compound (VI) is reacted with an alkenyl metal reagent to produce enone compound (VII). Then compound (VII) is reacted with aldehyde compound (VIII) to produce diketone compound (IX), and compound (IX) is subjected to a ring closure reaction to produce compound (I-c).

Compound (V) can be synthesized according to a known method.

Compound (VIII) can be synthesized according to a known method.

Step 5

In this step, compound (VI) is produced by reacting compound (II) or the reactive derivative of the carboxy group or a salt thereof with hydroxylamine compound (V) or a salt thereof, according to the method shown in Reaction Scheme 1, Step 1.

Step 6

In this step, enone compound (VII) is produced by reacting compound (VI) obtained in Step 5 with an alkenyl metal reagent.

Preferable examples of the alkenyl metal reagent include organic lithiums such as vinyllithium, 1-propenyllithium and the like; Grignard reagents such as vinylmagnesium bromide, vinylmagnesium chloride, 1-propenylmagnesium bromide and the like.

The reaction is advantageously carried out using a solvent inert to the reaction. While the solvent is not particularly limited as long as the reaction proceeds, preferable examples thereof include ethers such as diethyl ether, diisopropyl ether, diphenyl ether, tetrahydrofuran, 1,4-dioxane, 1,2-dimethoxyethane and the like; saturated hydrocarbons such as cyclohexane, hexane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; sulfoxides such as dimethyl sulfoxide and the like, and the like, and a mixed solvent thereof.

While the reaction time varies depending on the kind of the reagent or solvent to be used, it is generally 10 min to 100 hr, preferably 30 min to 50 hr. The reaction temperature is generally −70 to 100° C., preferably 0 to 80° C.

The amount of the alkenyl metal reagent to be used is about 0.5 to about 5 mol, preferably about 1 to about 3 mol, per 1 mol of compound (VI).

Step 7

In this step, diketone compound (IX) is produced by reacting enone compound (VII) obtained in Step 6 with aldehyde compound (VIII) in the presence of a thiazolium salt and a base.

Preferable examples of the thiazolium salt include 3-benzyl-5-(2-hydroxyethyl)-4-methyl-1,3-thiazol-3-ium chloride, 3-ethyl-5-(2-hydroxyethyl)-4-methyl-1,3-thiazol-3-ium bromide and the like.

Examples of the base include organic bases such as trimethylamine, triethylamine, diethylisopropylamine and the like, inorganic bases such as calcium carbonate, cesium carbonate, sodium hydroxide and the like.

The reaction is advantageously carried out without solvent or using a solvent inert to the reaction. While the solvent is not particularly limited as long as the reaction proceeds, preferable examples thereof include alcohols such as methyl alcohol, ethyl alcohol, t-butyl alcohol and the like; ethers such as diethyl ether, diisopropyl ether, diphenyl ether, tetrahydrofuran, 1,4-dioxane, 1,2-dimethoxyethane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; sulfoxides such as dimethyl sulfoxide and the like, and the like, and a mixed solvent thereof and the like.

While the reaction time varies depending on the kind of the reagent or solvent to be used, it is generally 10 min to 100 hr, preferably 30 min to 50 hr. The reaction temperature is generally 0 to 200° C., preferably 50 to 100° C.

The amount of the thiazolium salt and base to be used is about 0.5 to about 10 mol, preferably about 1 to about 3 mol, per 1 mol of compound, respectively.

Step 8

In this step, pyrrole compound (I-c) is produced by subjecting diketone compound (IX) obtained in Step 7 to a ring closure reaction in the presence of ammonia or an ammonium salt.

Preferable examples of the ammonium salt include ammonium salts with an inorganic acid such as ammonium sulfate, ammonium carbonate and the like, ammonium salts with an organic acid such as ammonium formate, ammonium acetate and the like.

The reaction is advantageously carried out without solvent or using a solvent inert to the reaction. While the solvent is not particularly limited as long as the reaction proceeds, preferable examples thereof include alcohols such as methanol, ethanol, 1-propanol, 2-propanol, tert-butyl alcohol and the like; halogenated hydrocarbons such as dichloromethane, chloroform, 1,2-dichloroethane and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propanoic acid, trifluoroacetic acid, methanesulfonic acid and the like, and the like, and a mixed solvent thereof.

While the reaction time varies depending on the kind of the reagent or solvent to be used, it is generally 10 min to 100 hr, preferably 30 min to 50 hr. The reaction temperature is generally –20 to 150° C., preferably 0 to 100° C.

The amount of the ammonia or ammonium salt to be used is about 0.5 to about 10 mol, preferably about 1 to about 3 mol, per 1 mol of compound (IX).

Of the compound represented by the formula (I), the pyrrole derivative can also be produced, for example, by the method shown the following Reaction Scheme 3.

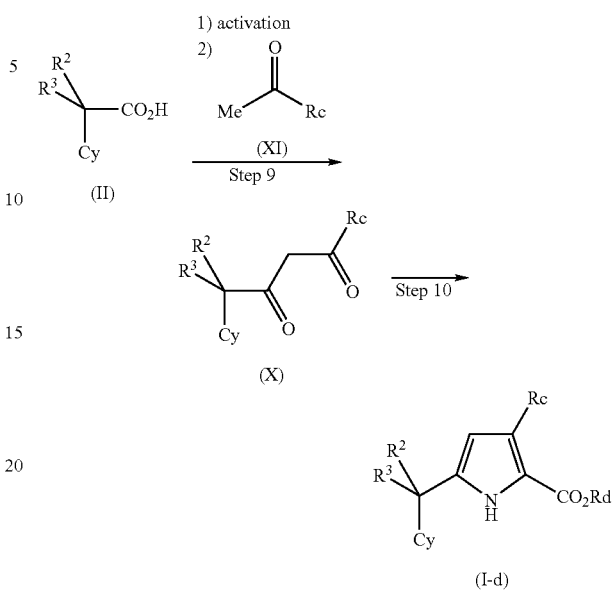

wherein Rc is a hydrogen atom, an optionally substituted alkyl group, an optionally substituted cyclic group or an optionally substituted carboxy group, Rd is an optionally substituted alkyl group, and the other symbols are as defined above.

Examples of the "optionally substituted alkyl group" for Rc or Rd include those similar to the "optionally substituted alkyl group" for $R^a$ or $R^b$.

Examples of the "optionally substituted cyclic group" for Rc include an optionally substituted $C_{3-7}$ cycloalkyl group, an optionally substituted $C_{6-14}$ aryl group, an optionally substituted heterocyclic group and the like.

Examples of the "optionally substituted carboxy group" for Rc include an optionally esterified carboxy group and the like.

Step 9

Compound (X) can be produced by reacting the reactive derivative of the carboxy group of compound (II) with ketone compound (XI) in the presence of a base.

Compound (XI) can be synthesized according to a known method.

Examples of the reactive derivative of the carboxy group of compound (II) include 1) an acid anhydride produced by reacting with oxalyl chloride and the like,
2) an activated amide with imidazole, 4-substituted imidazole, dimethylpyrazole, triazole or tetrazole and the like.

Examples of the base used for the reaction include metal hydrides such as sodium hydride, potassium hydride and the like; lithium amides such as lithiumdiisopropylamide and the like, and the like.

The amount of ketone compound (XI) to be used is generally 1 to 10 mol, preferably 1 to 3 mol, per 1 mol of compound (II). The amount of the base to be used is generally 1 to 10 mol, preferably 1 to 3 mol, per 1 mol of compound (II).

The reaction temperature is generally –30° C. to 100° C. The reaction time generally 0.5 to 20 hr.

When a mixed acid anhydride is used as a reactive derivative of compound (II), the reaction can also be carried out by reacting compound (II) with oxalyl chloride in the presence of a base (e.g., triethylamine, N-methylmorpholine, N,N-dimethylaniline, sodium hydrogen carbonate, sodium carbonate, potassium carbonate), and then reacting the resulting compound with ketone compound (XI).

The reaction is preferably carried out in a solvent inert to the reaction. While the solvent is not particularly limited as long as the reaction proceeds, preferable examples thereof include ethers such as dioxane, tetrahydrofuran, diethyl ether, tert-butyl methyl ether, diisopropyl ether, ethylene glycol-dimethyl ether and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide and the like. These solvents may be m used in a mixture of two or more kinds thereof at an appropriate ratio.

Step 10

Compound (I-d) can be produced, for example, by reacting compound (X)
1) with isonitrileacetate in the presence of a metal complex,
2) with glycinate or aminomalonate in the presence of an acid or a base, or
3) with hydroxyiminoacetate in the presence of zinc, a base and an acid.

Preferable examples of the metal complex in the above-mentioned 1) include rhodium carbonyl complex. The amount of the metal complex to be used is generally 0.01 to 1 mol, preferably 0.01 to 0.3 mol, per 1 mol of compound (X). The amount of the isonitrileacetate to be used is generally 1 to 10 mol, preferably 1 to 3 mol, per 1 mol of compound (X). The reaction temperature is generally −30° C. to 100° C.

Preferable examples of the acid in the above-mentioned 2) include organic acids such as formic acid, acetic acid, propionic acid and the like. Preferable examples of the base include organic bases such as piperidine, piperazine, morpholine and the like. The amount of the acid to be used is generally 1 to 10 mol, preferably 1 to 3 mol, per 1 mol of compound (X). The amount of the base to be used is generally 1 to 10 mol, preferably 1 to 3 mol, per 1 mol of compound (X). The amount of the glycinate or aminomalonate to be used is generally 1 to 10 mol, preferably 1 to 3 mol, per 1 mol of compound (X). The reaction temperature is generally −30° C. to 100° C.

Preferable examples of the acid in the above-mentioned 3) include organic acids such as formic acid, acetic acid, propionic acid and the like. Preferable examples of the base include metal salts with an organic acid such as sodium acetate, potassium acetate and the like. The amount of the acid to be used is generally 1 to 100 mol, preferably 1 to 30 mol, per 1 mol of compound (X). The amount of the base to be used is generally 1 to 10 mol, preferably 1 to 3 mol, per 1 mol of compound (X). The amount of the zinc and hydroxyiminoacetate to be used is 1 to 10 mol, preferably 1 to 3 mol, per 1 mol of compound (X), respectively. The reaction temperature is generally −30° C. to 100° C.

The reaction is advantageously carried out without solvent or using a solvent inert to the reaction. While the solvent is not particularly limited as long as the reaction proceeds, preferable examples thereof include alcohols such as methyl alcohol, ethyl alcohol, t-butyl alcohol and the like; ethers such as diethyl ether, diisopropyl ether, diphenyl ether, tetrahydrofuran, 1,4-dioxane, 1,2-dimethoxyethane and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; sulfoxides such as dimethyl sulfoxide and the like, and the like, and a mixed solvent thereof.

While the reaction time varies depending on the kind of the reagent or solvent to be used, it is generally 10 min to 100 hr, preferably 30 min to 50 hr. The reaction temperature is generally 0 to 200° C., preferably 0 to 100° C.

Of the compound represented by the formula (I), the imidazole derivative can also be produced, for example, by the method shown in the following Reaction Scheme 4

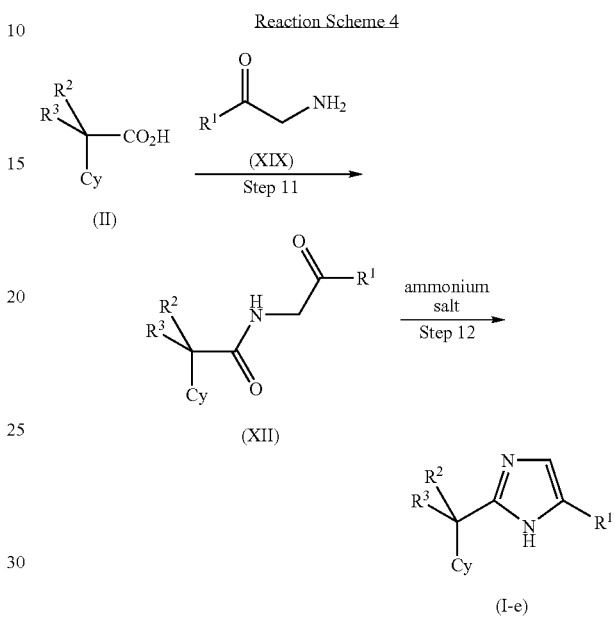

wherein each symbol is as defined above.

Step 11

Compound (XII) can be produced by reacting compound (II) or the reactive derivative of the carboxy group or a salt thereof with amine compound (XIX) or a salt thereof, according to the method shown in Reaction Scheme 1, Step 1.

Compound (XIX) can be synthesized according to a known method.

Step 12

Compound (I-e) can be produced by subjecting compound (XII) to a ring closure reaction, according to the method shown in Reaction Scheme 2, Step 8.

Compound (XV) which is compound (I) wherein $R^1$ is an optionally substituted thiazolyl group, can also be produced by the following method.

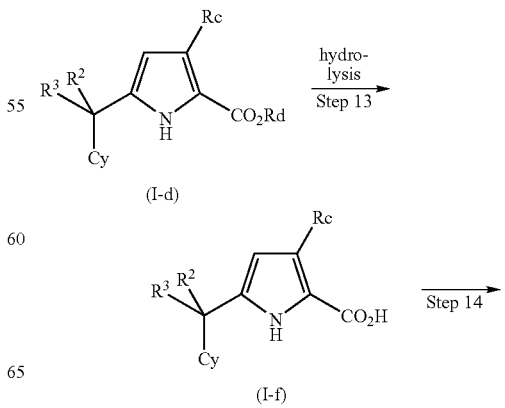

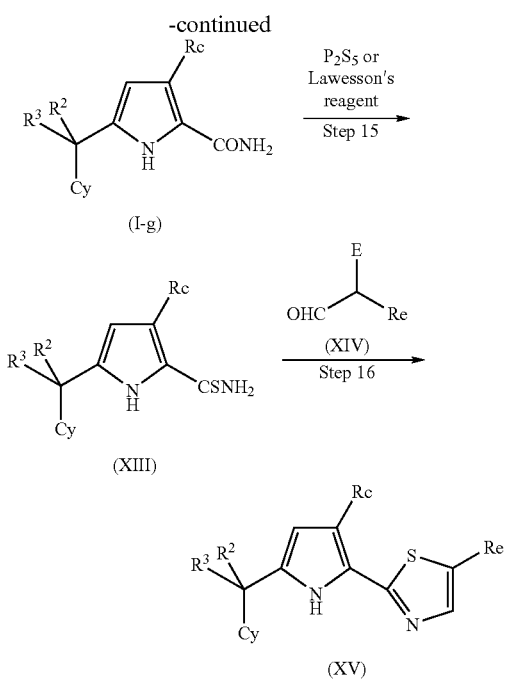

wherein E is a leaving group, Re is a hydrogen atom or an optionally substituted alkyl group, an optionally substituted cyclic group or an optionally substituted carboxy group, and the other symbols are as defined above.

Examples of the "leaving group" for E include a halogen atom; an optionally halogenated $C_{1-6}$ alkylsulfonyloxy group (e.g., methanesulfonyloxy, ethanesulfonyloxy, trichloromethanesulfonyloxy, trifluoromethanesulfonyloxy); $C_{6-10}$ arylsulfonyloxy group optionally having 1 to 3 substituents selected from a $C_{1-6}$ alkyl group, a $C_{1-6}$ alkoxy group and a nitro group (e.g., phenylsulfonyloxy, m-nitrophenylsulfonyloxy, p-toluenesulfonyloxy); a $C_{1-6}$ alkoxysulfonyloxy group; a $C_{6-10}$ aryloxysulfonyloxy group and the like.

Examples of the "optionally substituted alkyl group" for Re include those similar to the "optionally substituted alkyl group" for Ra or Rb.

Examples of the "optionally substituted cyclic group" and "optionally substituted carboxy group" for $R^e$ those similar to the "optionally substituted cyclic group" and "optionally substituted carboxy group" for Rc.

Step 13

Compound (I-f) can be produced by subjecting compound (I-d) to hydrolysis. The hydrolysis is carried out using an acid or a base, according to a conventional method.

Examples of the acid include mineral acids such as hydrochloric acid, sulfuric acid and the like; Lewis acids such as boron trichloride, boron tribromide and the like; organic acids such as trifluoroacetic acid, p-toluenesulfonic acid and the like, and the like. The Lewis acid can be used together with a thiol or a sulfide.

Examples of the base include alkali metal hydroxides such as lithium hydroxide, sodium hydroxide, potassium hydroxide, barium hydroxide and the like; alkali metal carbonates such as sodium carbonate, potassium carbonate and the like; alkali metal $C_{1-6}$ alkoxides such as sodium methoxide, sodium ethoxide, potassium tert-butoxide and the like; organic bases such as triethylamine, imidazole, formamidine and the like, and the like.

The amount of the acid or base to be used is generally about 0.5 to 10 mol, preferably about 0.5 to 6 mol, per 1 mol of compound (I-d).

The hydrolysis is carried out without a solvent or in a solvent inert to the reaction. While the solvent is not particularly limited as long as the reaction proceeds, preferable examples thereof include alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methyl ethyl ketone and the like; sulfoxides such as dimethyl sulfoxide and the like; water and the like. These solvents may be used in a mixture of two or more kinds thereof at an appropriate ratio.

The reaction time is generally 10 min to 60 hr, preferably 10 min to 12 hr. The reaction temperature is generally −10 to 200° C., preferably 0 to 120° C.

Step 14

Compound (I-g) can be produced by reacting compound (I-f) or the reactive derivative of the carboxy group or a salt thereof with ammonia or 1-hydroxybenztriazole-ammonia complex, according to the method shown in Reaction Scheme 1, Step 1.

Step 15

Compound (XIII) can be produced by reacting compound (I-g) with diphosphorus pentasulfide or the Lawesson's reagent.

This reaction is carried out without a solvent or in a solvent inert to the reaction. While the solvent is not particularly limited as long as the reaction proceeds, preferable examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like, and the like. These solvents may be used in a mixture of two or more kinds thereof at an appropriate ratio.

The amount of the diphosphorus pentasulfide or the Lawesson's reagent to be used is generally 0.5 to 10 mol, preferably 0.5 to 3 mol, per 1 mol of compound (I-g).

The reaction temperature is generally −30° C. to 100° C. The reaction time generally 0.5 to 20 hr.

Step 16

Compound (XV) can be produced by reacting compound (XIII) with compound (XIV).

Compound (XIV) can be synthesized according to a known method.

This reaction is carried out in the presence of an acid catalyst or a base, if desired.

Examples of the acid catalyst include mineral acids such as hydrochloric acid, sulfuric acid and the like; Lewis acids such as a boron trihalide (e.g., boron trichloride, boron trifluoride), a titanium tetrahalide (e.g., titanium tetrachloride, titanium tetrabromide), an aluminum halide (e.g., aluminum chloride, aluminum bromide) and the like; organic acids such as acetic acid, formic acid, trifluoroacetic acid and the like, and the like.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like.

This reaction is carried out without a solvent or in a solvent inert to the reaction. While the solvent is not particularly limited as long as the reaction proceeds, preferable examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like. These solvents may be used in a mixture of two or more kinds thereof at an appropriate ratio.

The amount of compound (XIV) and the acid catalyst to be used is generally 1 to 10 mol, preferably 1 to 3 mol, per 1 mol of compound (XIII), respectively.

While the reaction time varies depending on the kind and amount of compound (XIII), compound (XIV) and the acid catalyst to be used, it is generally about 1 hr to about 100 hr, preferably about 1 hr to about 50 hr. The reaction temperature is generally about −20 to about 120° C., preferably about 0 to about 80° C.

The amount of compound (XIV) and the base to be used is generally 1 to 10 mol, preferably 1 to 3 mol, per 1 mol of compound (XIII), respectively.

While the reaction time varies depending on the kind and amount of compound (XIII), compound (XIV) and the base to be used, it is generally about 1 hr to about 100 hr, preferably about 1 hr to about 50 hr. The reaction temperature is generally about −20 to about 120° C., preferably about 0 to about 80° C.

Compound (XVII) which is compound (I) wherein $R^1$ is an optionally substituted 1,3,4-thiadiazolyl group, can also be produced by the following method.

Step 17

Compound (I-h) can be produced by reacting compound (I-f) or the reactive derivative of the carboxy group or a salt thereof with compound (XVI) or a salt thereof, according to the method shown in Reaction Scheme 1, Step 1.

Compound (XVI) can be synthesized according to a known method.

Step 18

Compound (XVII) can be produced by reacting compound (I-h) with diphosphorus pentasulfide or the Lawesson's reagent, according to the method shown in Reaction Scheme 5, Step 15.

Step 19

Compound (I-i) can be produced by reacting compound (I-f) or the reactive derivative of the carboxy group or a salt thereof with hydrazine or a salt thereof, according to the method shown in Reaction Scheme 1, Step 1.

Step 20

Compound (I-h) can also be produced by reacting compound (I-i) with compound (XVIII), according to the method shown in, Reaction Scheme 1, Step 1.

Compound (XVIII) can be synthesized according to a known method.

Of the compound represented by the formula (I), the compound represented by the formula (I-aa) can be produced, for example, by the method shown in the following Reaction Scheme 7.

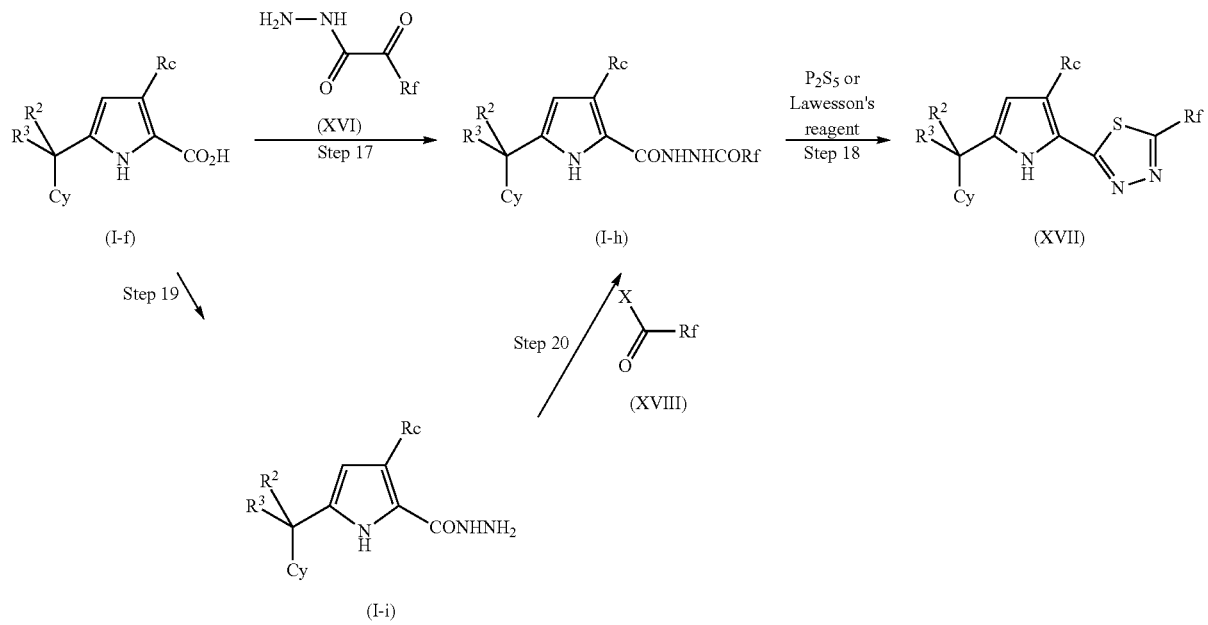

Reaction Scheme 6 wherein X is a halogen atom, Rf is a hydrogen atom or an optionally substituted alkyl group, an optionally substituted cyclic group or an optionally substituted carboxy group, and the other symbols are as defined above.

Examples of the "optionally substituted alkyl group" for Rf include those similar to the "optionally substituted alkyl group" for Ra or Rb.

Examples of the "optionally substituted cyclic group" and "optionally substituted carboxy group" for $R^f$ include those similar to the "optionally substituted cyclic group" and "optionally substituted carboxy group" for $R^c$.

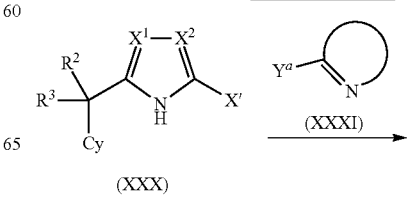

Reaction Scheme 7

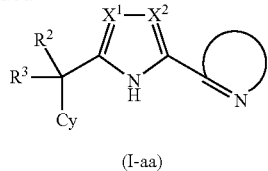

(I-aa)

wherein X' is a leaving group; $Y^a$ is a metal (e.g., potassium, sodium, lithium, magnesium, copper, water silver, zinc, m thallium, boron, tin and the like (the metal is optionally alkylated, hydroxylate, alkoxylated or complexed)); and the other symbols are as defined above.

Examples of the "leaving group" for X' include those similar to the "leaving group" for E. Specific preferable examples of X' include iodine, bromine, a trifluoromethanesulfonyloxy group, a phenylsulfonyloxy group, a m-nitrophenylsulfonyloxy group, a p-toluenesulfonyloxy group and the like.

In this method, compound (XXX) is reacted with compound (XXXI) in the presence of a base to produce compound (I-aa).

Examples of the base include alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogen carbonates such as sodium hydrogen carbonate, potassium hydrogen carbonate and the like; alkali metal phosphates such as tripotassium phosphate, trisodium phosphate and the like; alkali metal alkoxides having 1 to 6 carbon atoms such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithiumdiisopropylamide and the like, and the like.

The reaction of compound (XXX) with compound (XXXI) is advantageously carried out using a solvent inert to the reaction.

While the solvent is not particularly limited as long as the reaction proceeds, preferable examples thereof include alcohols such as methanol, ethanol, propanol, isopropanol, butanol, tert-butanol and the like; ethers such as dioxane, tetrahydrofuran, diethyl ether, tert-butyl methyl ether, diisopropyl ether, ethylene glycol-dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane, hexamethylphosphoramide, water and the like, a mixed solvent of two or more kinds thereof, and the like.

This reaction can be generally promoted by using a metal catalyst.

Examples of the metal catalyst include metal complexes having various ligands.

Examples of the metal complex include palladium compounds [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium-2,2'-bis(diphenylphosphino)-1,1'-binaphthyl, a complex of palladium(II) acetate and 1,1'-bis(diphenylphosphino)ferrocene, and the like]; nickel compounds [e.g., tetrakis(triphenylphosphine)nickel (0), bis(triethylphosphine)nickel (II) chloride, bis(triphenylphosphine)nickel (II) chloride and the like]; rhodium compounds [e.g., tris(triphenylphosphine)rhodium (III) chloride and the like]; cobalt compounds; copper compounds [e.g., copper oxide, copper(II) chloride and the like]; platinum compounds and the like. Of these, palladium compounds, nickel compounds and copper compounds are preferable.

The amount of the metal catalyst to be used is generally about 0.000001 to 5 mol, preferably about 0.0001 to 1 mol, per 1 mol of compound (XXX).

In this reaction, when a metal catalyst unstable to oxygen is used, the reaction is preferably carried out under inactive gas (e.g., argon, nitrogen) stream.

The amount of compound (XXXI) to be used is generally about 0.8 to 10 mol, preferably about 0.9 to 2 mol, per 1 mol of compound (XXX). The amount of the base to be used is about 1 to about 20 mol, preferably about 1 to about 5 mol.

The reaction temperature is generally about −10° C. to about 250° C., preferably about 0° C. to about 150° C.

While the reaction time varies depending on the kind of compound (XXX), compound (XXXI), the metal catalyst, base or solvent to be used; reaction temperature and the like, it is generally about 1 min to about 200 hr, preferably about 5 min to about 100 hr.

Compound (XXX) and compound (XXXI) can be synthesized, according to a method known per se.

Of the compound represented by the formula (I), the compound represented by the formula (I-aa) can also be produced, for example, by the method shown in the following Reaction Scheme 8.

Reaction Scheme 8

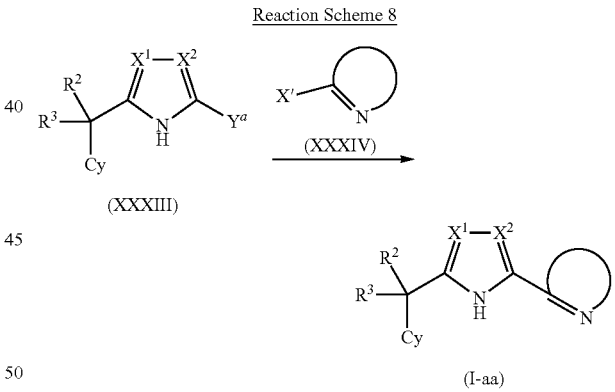

wherein each symbol is as defined above.

Compound (I) can be produced by reacting compound (XXXIII) with compound (XXXIV) in the presence of a base. This reaction can be carried out according to the method in the above-mentioned Reaction Scheme 7.

Compound (XXXIII) and compound (XXXIV) can be synthesized according to a method known per se.

In the product resulting from the above-mentioned reactions and compound (I), a functional group within a molecule can also be converted to a desired functional group by a combination of chemical reactions known per se. Examples of the chemical reaction here include oxidation reaction, reduction reaction, alkylation reaction, hydrolysis reaction, amination reaction, amidation reaction, esterification reaction, aryl coupling reaction, deprotection reaction and the like.

In the above-mentioned production methods, when the starting compound has an amino group, a carboxyl group, a hydroxy group, a carbonyl group or a mercapto group as a substituent, a protecting group generally used in peptide chemistry and the like may be introduced into these groups. By removing the protecting group as necessary after the reaction, the object compound can be obtained.

Examples of the amino-protecting group include formyl group, $C_{1-6}$ alkyl-carbonyl group (e.g., acetyl, propionyl), $C_{1-6}$ alkoxy-carbonyl group (e.g., methoxycarbonyl, ethoxycarbonyl, tert-butoxycarbonyl), benzoyl group, $C_{7-10}$ aralkyl-carbonyl group (e.g., benzylcarbonyl), $C_{7-14}$ aralkyloxy-carbonyl group (e.g., benzyloxycarbonyl, 9-fluorenylmethoxycarbonyl), trityl group, phthaloyl group, N,N-dimethylaminomethylene group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include $C_{1-6}$ alkyl group, $C_{7-10}$ aralkyl group (e.g., benzyl), phenyl group, trityl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include $C_{1-6}$ alkyl group, phenyl group, trityl group, $C_{7-10}$ aralkyl group (e.g., benzyl), formyl group, $C_{1-6}$ alkyl-carbonyl group, benzoyl group, $C_{7-10}$ aralkyl-carbonyl group (e.g., benzylcarbonyl), 2-tetrahydropyranyl group, 2-tetrahydrofuranyl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include cyclic acetal (e.g., 1,3-dioxane), acyclic acetal (e.g., di-$C_{1-6}$ alkylacetal) and the like.

Examples of the mercapto-protecting group include $C_{1-6}$ alkyl group, phenyl group, trityl group, $C_{7-10}$ aralkyl group (e.g., benzyl), $C_{1-6}$ alkyl-carbonyl group, benzoyl group, $C_{7-10}$ aralkyl-carbonyl group (e.g., benzylcarbonyl), $C_{1-6}$ alkoxy-carbonyl group, $C_{6-14}$ aryloxy-carbonyl group (e.g., phenyloxycarbonyl), $C_{7-14}$ aralkyloxy-carbonyl group (e.g., benzyloxycarbonyl, 9-fluorenylmethoxycarbonyl), 2-tetrahydropyranyl group, $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The compound of the present invention obtained according to the above-mentioned production method can be isolated and purified by a known means, for example, concentration, concentration under reduced pressure, solvent extraction, crystallization, recrystallization, phase transfer, chromatography and the like. In addition, various starting compounds used in each of the above-mentioned production methods can be isolated and purified by a known means such as those mentioned above and the like. Alternatively, the starting compounds may be directly used in the form of a reaction mixture without isolation as the starting materials of the next step.

For production of the compound of the present invention, when the starting compound can form a salt, the compound may be used in the form of a salt. Examples of such salt include those exemplified as the salts of compound (I).

When the compound of the present invention contains an optical isomer, a stereoisomer, a positional isomer or a rotational isomer, these are encompassed in the compound of the present invention, and obtained as a single product according to a synthesis method and separation method known per se. For example, when the compound of the present invention has an optical isomer, an optical isomer resolved from this compound is also encompassed in the compound of the present invention.

The compound of the present invention may be in the form of a crystal.

The crystal of the compound of the present invention (hereinafter sometimes to be abbreviated as the crystal of the present invention) can be produced by crystallization of the compound of the present invention according to a crystallization method known per se.

In the present specification, the melting point refers to that measured using, for example, micromelting point measuring apparatus (Yanako, MP-500D or Buchi, B-545) or DSC (differential scanning calorimetry) device (SEIKO, EXSTAR6000) and the like.

In general, melting points vary depending on measurement apparatuses, measurement conditions and the like. The crystal in the present specification may show a different melting point described in the present specification, as long as it is within general error range.

The crystal of the present invention is superior in physicochemical properties (e.g., melting point, solubility, stability and the like) and biological properties (e.g., pharmacokinetics (absorption, distribution, metabolism, excretion), efficacy expression and the like), and is extremely useful as a medicament.

EXAMPLES

The present invention is explained in detail in the following by referring to the following Reference Examples, Examples, Experimental Examples and Formulation Examples, which are not to be construed as limitative. In addition, the present invention may be modified without departing from the scope of invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. on proton NMR spectrum that could not be confirmed due to broad peak are not included in the data.

The other symbols used herein mean the following:
s: singlet
d: doublet
t: triplet
q: quartet
m: multiplet
br: broad
J: coupling constant
Hz: Hertz
$CDCl_3$: deuterated chloroform
DMSO-$d_6$: dimethyl sulfoxide-$d_6$
$^1$H-NMR: proton nuclear magnetic resonance
TFA: trifluoroacetic acid In the following Reference Examples and Examples, microwave synthesis apparatus, mass spectrum (MS) and nuclear magnetic resonance spectrum (NMR) were measured under the following conditions.

microwave synthesis apparatus: initiator manufactured by Biotage.

MS measurement device: Waters ZMD, Waters ZQ2000 or Micromass platform II.

ionization method: electron impact ionization method (Electron Spray Ionization: ESI) or high pressure chemical ionization method (Atmospheric Pressure Chemical Ionization: APCI). Unless otherwise specified, ESI was used.

NMR measurement tool: Varian Inc., Varian Gemini 200 (200 MHz), Varian Gemini 300 (300 MHz), Bruker BioSpin Corp., AVANCE 300.

In the following Reference Examples and Examples, purification by preparative HPLC was performed under the following conditions. When the compound has a basic functional group and trifluoroacetic acid is used for this operation, a neutralization operation and the like may be performed to obtain a free form.

preparative HPLC instrument: Gilson Inc., High-throughput purification system
column: YMC Combiprep ODS-A S-5 μm, 20×50 mm
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=90/10), 1.20 min (SOLUTION A/SOLUTION B=90/10), 4.75 min (SOLUTION A/SOLUTION B=0/100), 7.30 min (SOLUTION A/SOLUTION B=0/100), 7.40 min (SOLUTION A/SOLUTION B=90/10), 7.50 min (SOLUTION A/SOLUTION B=90/10).
flow rate: 25 ml/min, detection method: UV 220 nm
or
tool: Waters mass preparative system (UV Purification System)
Column: Develosil ODS-UG-10
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=95/5), 1.00 min (SOLUTION A/SOLUTION B=95/5), 2.00 min (SOLUTION A/SOLUTION B=80/20), 5.00 min (SOLUTION A/SOLUTION B=5/95), 5.10 min (SOLUTION A/SOLUTION B=0/100), 7.00 min (SOLUTION A/SOLUTION B=100/0)
flow rate: 150 ml/min, detection: UV 220 nm In the following Reference Examples and Examples, chiral preparative HPLC was performed using K-Prep manufactured by YMC, and chiral preparation by supercritical fluid chromatography (SFC) was performed using Multigram II manufactured by Mettler Toledo.

Reference Example 1A

Construction of Glucokinase (GK) Expression Vector

Plasmid DNA to be used for the expression of a protein (GST-hLGK1) containing GST (Glutathione S-transferase) added to the amino terminal of human liver GK in *Escherichia coli* was prepared as follows.

First, PCR (Polymerase Chain Reaction) was performed using human liver cDNA (Marathon Ready cDNA, Clontech Laboratories, Inc.) as a template and two kinds of synthetic DNAs (5'-CAGCTCTCCATCCAAGCAGCCGTTGCT-3' (SEQ ID NO: 1) and 5'-GGCGGCCTGGGTCCTGACAAG-3' (SEQ ID NO: 2)), and the obtained DNA fragment was closed using a TOPO TA Cloning Kit (Invitrogen Corporation). PCR was performed using the obtained plasmid DNA as a template and a synthetic DNA (5'-GGATCCATGCCCA-GACCAAGATCCCAACTCCCACAAC-CCAACTCCCAGGTAGAGCAGATCCT GGCAGAG-3' (SEQ ID NO: 3)) with a BamHI site added to immediately before the initiation codon, and a synthetic DNA (5'-GAAT-TCCTGGCCCAGCATACAGGC-3' (SEQ ID NO: 4)) with an EcoRI site added to immediately after the stop codon. The obtained DNA fragment was subcloned to pGEX6P-2 (Amersham Biosciences K.K.) cleaved with BamHI and EcoRI to give a plasmid (pGEX6P-2/hLGK1) for expression of human liver GK.

Reference Example 2A

Expression and Purification of GST-hLGK1

BL21 strain (Stratagene) transformed with pGEX6P-2/hLGK1% obtained in Reference Example 1A was cultured with shaking at 37° C. for 14 hr in a 200 ml Erlenmeyer flask containing 50 ml of 100 μg/ml ampicillin-containing LB medium. The culture medium (25 ml) was diluted with 225 ml of 100 μg/ml ampicillin-containing LB medium, and further cultured with shaking at 37° C. for 1 hr in a 1 L Erlenmeyer flask. After culture, the Erlenmeyer flask was cooled on ice, 125 μL of 100 mM isopropyl-thio-β-D-galactopyranoside (IPTG) was added (final concentration 50 μM), and cultured at 17° C. for 20 hr. The culture medium was centrifuged, and the obtained fungus was disrupted by ultrasonication. The object protein (GST-hLGK1) was purified from the supernatant using Glutathione Sepharose 4B (Amersham Biosciences K.K.).

Reference Example 1

3-cyclopentyl-N-methoxy-N-methyl-2-[4-(methylsulfonyl)phenyl]propanamide

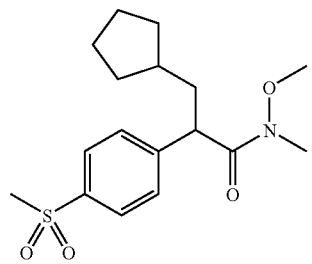

To a solution (80 mL) of N-methoxymethanamine hydrochloride (2.20 g) in N,N-dimethylformamide was added triethylamine (3.10 mL) for neutralization, and 3-cyclopentyl-2-[4-(methylsulfonyl)phenyl]propanoic acid (5.95 g), N-[3-(dimethylamino)propyl]-N'-ethylcarbodiimide hydrochloride (5.80 g) and 1-hydroxybenzotriazole (4.10 g) were added under ice-cooling. The reaction mixture was warmed to room temperature and stirred overnight. The reaction mixture was diluted with ethyl acetate, and washed with water, 1N aqueous hydrochloric acid solution and saturated aqueous sodium hydrogen carbonate. The ethyl acetate layer was dried (MgSO$_4$) and concentrated. The residue was subjected to silica gel column chromatography, and the title compound (6.07 g, yield 89%) was obtained as colorless amorphous crystals from a fraction eluted with ethyl acetate-hexane (1:1, volume ratio). MS: 340 (MH$^+$).

Reference Example 2

5-cyclopentyl-4-[(4-(methylsulfonyl)phenyl]pent-1-en-3-one

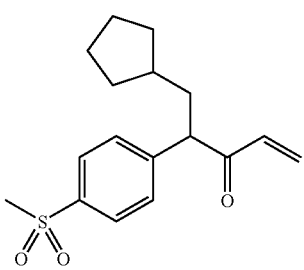

To a solution (10 mL) of 3-cyclopentyl-N-methoxy-N-methyl-2-[4-(methylsulfonyl)phenyl]propanamide (1.34 g) in tetrahydrofuran was added dropwise vinylmagnesium bromide (11.8 mL: 1.0M tetrahydrofuran solution) at room temperature. The reaction mixture was stirred overnight at room temperature, 1N hydrochloric acid was added, and the mixture was stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (790 mg, yield 65%) was obtained as colorless amorphous crystals from a fraction eluted with ethyl acetate-hexane (1:2, volume ratio). MS: 307 (MH$^+$).

Reference Example 3

6-cyclopentyl-5-[4-(methylsulfonyl)phenyl]-1-(1,3-thiazol-2-yl)hexane-1,4-dione

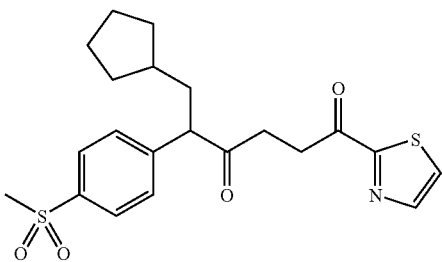

To a solution (5 mL) of 5-cyclopentyl-4-[4-(methylsulfonyl)phenyl]pent-1-en-3-one (790 mg) in ethanol were added 1,3-thiazole-2-carbaldehyde (275 μL), 3-benzyl-5-(2-hydroxyethyl)-4-methyl-1,3-thiazol-3-ium chloride (80 mg) and triethylamine (160 μL), and the mixture was stirred with heating under reflux for 8 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (850 mg, yield 79%) was obtained as colorless amorphous crystals from a fraction eluted with ethyl acetate-hexane (1:1, volume ratio). MS: 420 (MH$^+$).

Reference Example 4

6-cyclopentyl-5-[4-(methylsulfonyl)phenyl]-1-pyridin-2-ylhexane-1,4-dione

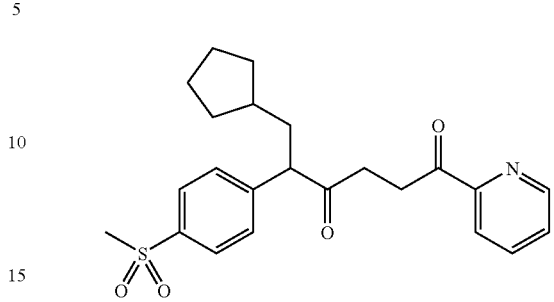

According to the method of Reference Example 3, the title compound (275 mg, yield 68%) was obtained as colorless amorphous crystals from 5-cyclopentyl-4-[4-(methylsulfonyl)phenyl]pent-1-en-3-one (300 mg) and pyridine-2-carbaldehyde (115 μL). MS: 414 (MH$^+$).

Reference Example 5

6-cyclopentyl-5-[4-(methylsulfonyl)phenyl]-1-pyrazin-2-ylhexane-1,4-dione

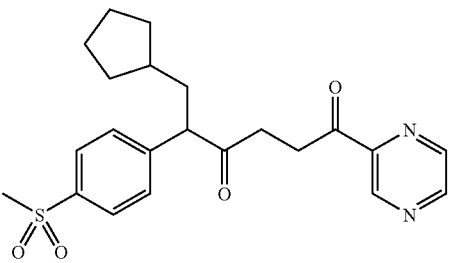

According to the method of Reference Example 3, the title 15 compound (340 mg, yield 84%) was obtained as colorless amorphous crystals from 5-cyclopentyl-4-[4-(methylsulfonyl)phenyl]pent-1-en-3-one (300 mg) and pyrazine-2-carbaldehyde (130 mg). MS: 415 (MH$^+$).

Reference Example 6

6-cyclopentyl-1-(1-methyl-1H-imidazol-2-yl)-5-[4-(methylsulfonyl)phenyl]hexane-1,4-dione

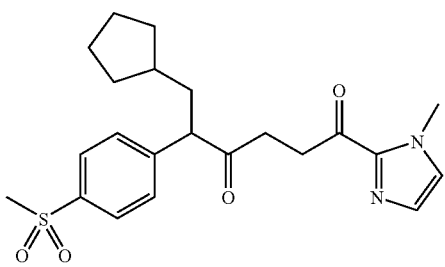

According to the method of Reference Example 3, the title compound (160 mg, yield 59%) was obtained as colorless amorphous crystals from 5-cyclopentyl-4-[4-(methylsulfonyl)phenyl]pent-1-en-3-one (200 mg) and 1-methyl-1H-imidazole-2-carbaldehyde (90 mg). MS: 417 (MH$^+$).

Reference Example 7

6-cyclopentyl-1-(1-methyl-1H-imidazol-4-yl)-5-[4-(methylsulfonyl)phenyl]hexane-1,4-dione

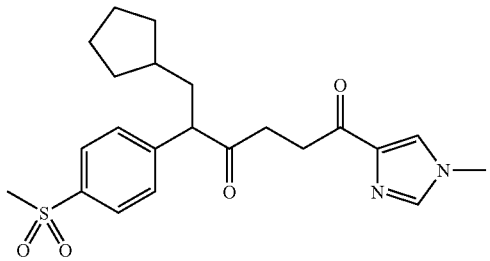

According to the method of Reference Example 3, the title compound (180 mg, yield 44%) was obtained as colorless amorphous crystals from 5-cyclopentyl-4-[4-(methylsulfonyl)phenyl]pent-1-en-3-one (300 mg) and 1-methyl-1H-imidazole-4-carbaldehyde (130 mg). MS: 417 (MH$^+$).

Reference Example 8

6-cyclopentyl-1-(1-methyl-1H-pyrazol-3-yl)-5-[4-(methylsulfonyl)phenyl]hexane-1,4-dione

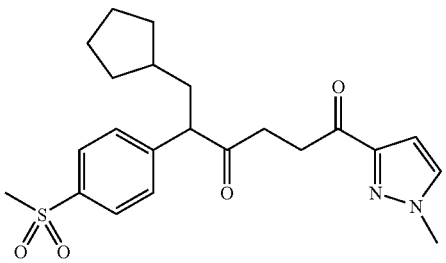

According to the method of Reference Example 3, the title compound (325 mg, yield 80%) was obtained as colorless amorphous crystals from 5-cyclopentyl-4-[4-(methylsulfonyl)phenyl]pent-1-en-3-one (300 mg) and 1-methyl-1H-pyrazole-3-carbaldehyde (130 mg). MS: 417 (MH$^+$).

Reference Example 9

2-[4-(cyclopropylsulfonyl)phenyl]-N-methoxy-N-methyl-3-(tetrahydro-2H-pyran-4-yl)propanamide

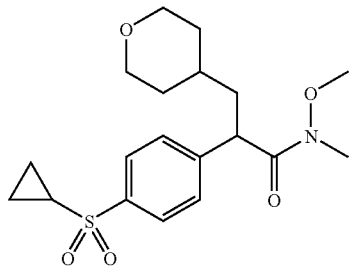

To a solution of N-methoxymethanamine hydrochloride (3.90 g) in N,N-dimethylformamide (100 mL) was added triethylamine (5.60 mL) for neutralization, and a solution of 2-[4-(cyclopropylsulfonyl)phenyl]-3-(tetrahydro-2H-pyran-4-yl)propanoic acid (11.23 g) in N,N-dimethylformamide (50 mL), N-[3-(dimethylamino)propyl]-N'-ethylcarbodiimide hydrochloride (9.60 g) and 1-hydroxybenzotriazole (6.80 g) were added under ice-cooling. The reaction mixture was warmed to room temperature and stirred overnight. The reaction mixture was diluted with ethyl acetate, and washed with water, 1N aqueous hydrochloric acid solution and saturated aqueous sodium hydrogen carbonate. The ethyl acetate layer was dried (MgSO$_4$) and concentrated. The residue was subjected to silica gel column chromatography, and the title compound (10.2 g, yield 81%) was obtained as colorless amorphous crystals from a fraction eluted with ethyl acetate-hexane (1:1, volume ratio). MS: 382 (MH$^+$).

$^1$H NMR (300 MHz, CDCl$_3$) δ0.99-1.08 (2 H, m), 1.23-1.72 (8 H, m), 2.03-2.14 (1 H, m), 2.40-2.50 (1 H, m), 3.17 (3 H, s), 3.25-4.37 (2 H, m), 3.54 (3 H, m), 3.88-3.97 (2 H, m), 4.23-4.32 (1 H, m), 7.49-7.54 (2 H, m), 7.81-7.86 (2 H, m).

Reference Example 10

4-[4-(cyclopropylsulfonyl)phenyl]-5-(tetrahydro-2H-pyran-4-yl)pent-1-en-3-one

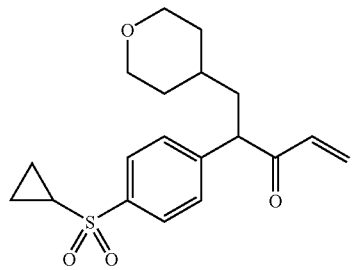

To a solution of 2-[4-(cyclopropylsulfonyl)phenyl]-N-methoxy-N-methyl-3-(tetrahydro-2H-pyran-4-yl)propanamide (10.2 g) in tetrahydrofuran (100 mL) was added dropwise vinylmagnesium bromide (1.0M tetrahydrofuran solution, 73 mL) under ice-cooling. The reaction mixture was stirred overnight at room temperature, 1M hydrochloric acid (80 mL) was added and the mixture was further stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (4.25 g, yield 46%) was obtained as colorless crystals from a fraction eluted with ethyl acetate-hexane (1:2, volume ratio). melting point 92-93° C. MS: 349 (MH$^+$).

$^1$H NMR (300 MHz, CDCl$_3$) δ1.00-1.09 (2 H, m), 1.22-1.76 (8 H, m), 2.04-2.15 (1 H, m), 2.41-2.51 (1 H, m), 3.23-3.34 (2H, m), 3.86-3.96 (2 H, m), 4.14 (1 H, t, J=7.4 Hz), 5.77 (1H, dd, J=2.9, 8.9 Hz), 6.25-6.42 (2 H, m), 7.38-7.44 (2 H, m), 7.83-7.88 (2 H, m).

Reference Example 11

5-[4-(cyclopropylsulfonyl)phenyl]-6-(tetrahydro-2H-pyran-4-yl)-1-(1,3-thiazol-2-yl)hexane-1,4-dione

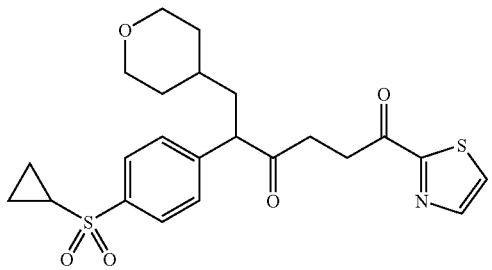

According to the method of Reference Example 3, the title compound (330 mg, yield 83%) was obtained as colorless amorphous crystals from 4-[4-(cyclopropylsulfonyl)phenyl]-5-(tetrahydro-2H-pyran-4-yl)pent-1-en-3-one (300 mg). MS: 462 (MH⁺).

Reference Example 12

6-cyclopentyl-5-[4-(methylsulfonyl)phenyl]hexane-2,4-dione

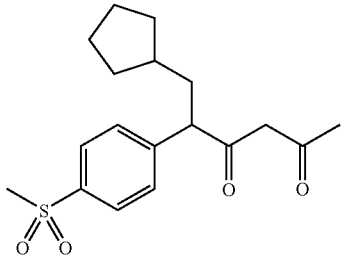

To a solution (15 mL) of 3-cyclopentyl-2-[4-(methylsulfonyl)phenyl]propanoic acid (5.00 g) in dichloromethane were added oxalyl chloride (7.30 mL) and a catalytic amount of N,N-dimethylformamide under ice-cooling and the mixture was stirred for 30 min. The reaction mixture was concentrated, and the residue was dissolved in tetrahydrofuran (15 mL). Thereto was added triethylamine (9.4% mL) at room temperature, and the mixture was stirred for 30 min. The resulting precipitate was filtered off, enolate separately prepared from acetone (1.08 g) and potassium hydride (2.71 g: 30% wt) in tetrahydrofuran (15 mL) was added to the filtrate at −78° C., and the mixture was stirred for 1 hr. is The reaction mixture was slowly warmed to room temperature, and the mixture was stirred overnight. The reaction mixture was diluted with ethyl acetate, 1N hydrochloric acid was added and the mixture was stirred for 30 min. The ethyl acetate layer was washed with saturated brine, dried (MgSO₄) and concentrated. The residue was subjected to preparative high performance liquid chromatography, and the title compound (1.60 g, yield 28%) was obtained as colorless amorphous crystals. MS: 337 (MH⁺).

Reference Example 13

5-{2-cyclopentyl-1-[4-(methylsulfonyl)phenyl]ethyl}-3-methyl-1H-pyrrole-2-carbothioamide

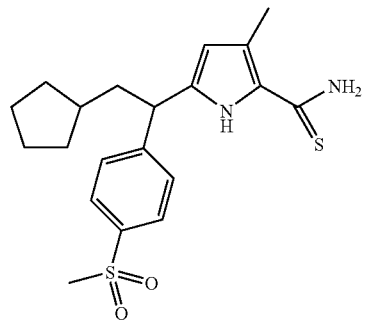

To a solution (10 mL) of 5-{2-cyclopentyl-1-[4-(methylsulfonyl)phenyl]ethyl}-3-methyl-1H-pyrrole-2-carboxamide (135 mg) in tetrahydrofuran was added Lawesson's reagent (156 mg), and the mixture was stirred for 3 hr at 55° C. After cooling to room temperature, the reaction mixture was concentrated, the residue was subjected to silica gel column chromatography, and the title compound (120 mg, yield 86%) was m obtained as yellow amorphous crystals from a fraction eluted with ethyl acetate-hexane (1:1, volume ratio). MS: 391 (MH⁺).

Reference Example 14

3-cyclopentyl-2-[4-(methylsulfonyl)phenyl]-N-(2-oxo-2-pyridin-2-ylethyl)propanamide

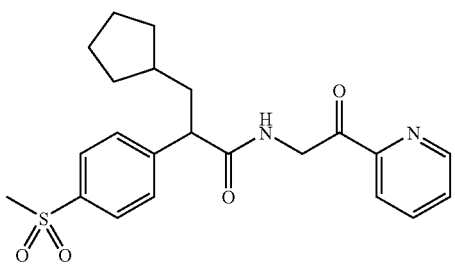

To a solution (10 mL) of 3-cyclopentyl-2-[4-(methylsulfonyl)phenyl]propanoic acid (564 mg) in dichloromethane solution were added oxalyl chloride (0.82 mL) and a catalytic amount of N,N-dimethylformamide under ice-cooling, and the mixture was stirred for 1 hr. The reaction mixture was concentrated to remove the residual oxalyl chloride. The residue was dissolved again in dichloromethane, collidine (0.76 mL) and 2-amino-1-pyridin-2-ylethanone dihydrochloride (400 mg) were added, and the mixture was stirred overnight. The reaction mixture was diluted with ethyl acetate and washed with water, 1N hydrochloric acid, saturated aqueous sodium hydrogen carbonate and saturated brine, dried (MgSO₄) and concentrated. The residue was subjected to preparative high performance liquid chromatography to give the title compound (350 mg, yield 44%) as colorless amorphous crystals. MS: 415 (MH⁺).

Reference Example 15

5-cyclopropylisoxazol-4-amine hydrochloride

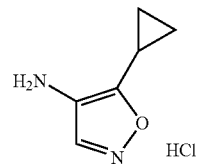

A mixture of 1-cyclopropylethanone (60 g) and N,N,N',N',N'',N''-hexamethylmethanetriamine (103 g) was stirred at 120° C. for 20 hr. The reaction mixture was cooled to room temperature, and concentrated under reduced pressure. To an aqueous solution (200 mL) of the residue was added hydroxyammonium chloride (75 g), and the mixture was heated under reflux for 2 hr. The reaction mixture was extracted with diethyl ether, and the extract was washed successively with water and saturated brine, dried over anhydrous sodium sulfate, and concentrated under reduced pressure. The residue was applied to silica gel column chromatography (diethyl ether), and the obtained crude product was dissolve in trifluoroacetic anhydride (310 ml). Ammonium nitrate (51.3 g) was gradually added, and the reaction mixture as stirred at room temperature for 1 hr. The reaction mixture was concentrated under reduced pressure, saturated aqueous sodium hydrogen carbonate solution was added to the residue, and the mixture was extracted with diethyl ether. The extract was washed successively with saturated sodium hydrogen carbonate, water and saturated brine, dried over anhydrous magnesium sulfate and concentrated under reduced pressure. The residue was applied to silica gel column chromatography (ethyl acetate), and the obtained crude product was suspended in water (1300 mL). Ammonium chloride (624 g) and zinc powder (250 g) were added, and the mixture was stirred at room temperature for 2 hr. The reaction mixture was extracted with ethyl acetate. The extract was washed successively with water and saturated brine, dried over anhydrous sodium sulfate, and concentrated under reduced pressure. The residue was purified by NH-silica gel column chromatography (ethyl acetate:hexane=10:90-60:40, volume ratio). The purified product was treated with a 4N hydrochloric acid ethyl acetate solution to give the title compound (23.8 g, yield of 5 steps 25%) as pale-pink crystals.

$^1$H NMR (300 MHz, DMSO-$d_6$) δ1.00-1.07 (2 H, m), 1.08-1.18 (2H, m), 2.36-2.47 (1 H, m), 8.63 (1 H, s), 10.29 (2 H, brs).

Reference Example 16

5-cyclobutylisoxazol-4-amine hydrochloride

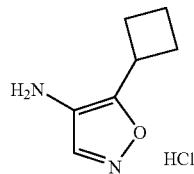

According to the method of Reference Example 1, the title compound (2.36 g, yield of 5 steps 5%) was obtained as colorless crystals from 1-cyclobutylethanone (29.7 g).

$^1$H NMR (300 MHz, DMSO-$d_6$) δ 1.83-2.12 (2 H, m), 2.23-2.38 (4 H, m), 3.79-4.09 (1 H, m), 8.61 (1 H, s), 9.86 (2 H, brs).

Reference Example 17

Methyl [4-s (cyclopropylsulfonyl)phenyl]acetate

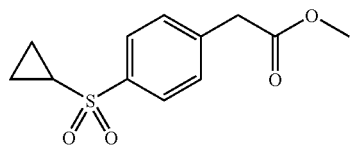

To a solution of ethyl [4-(cyclopropylsulfonyl)phenyl] (oxo)acetate (10.5 g) in a mixed solvent of tetrahydrofuran (160 mL) and methanol (80 mL) was added 2N aqueous sodium hydroxide solution (40 mL), and the mixture was stirred at room temperature for 48 hr. The reaction mixture was acidified with 1N hydrochloric acid, and extracted with ethyl acetate. The extract was washed with saturated brine, dried over anhydrous magnesium sulfate and concentrated under reduced pressure. The residue was cooled to −78° C., hydrazine monohydrate (8.65 mL) was added, and the mixture was warmed to room temperature. The reaction mixture was stirred at 80° C. for 10 min, and cooled to room temperature. Potassium hydroxide (6.00 g) was added to the reaction mixture, and the mixture was stirred at 100° C. for 16 hr. Water was added to the reaction mixture, and the aqueous layer was washed with diethyl ether. The aqueous layer was acidified with 1N hydrochloric acid, and the mixture was extracted with ethyl acetate. The extract was washed with saturated brine, dried over anhydrous magnesium sulfate and concentrated under reduced pressure. The residue was washed with saturated brine, dried over anhydrous magnesium sulfate and concentrated under reduced pressure. The residue was dissolved in methanol (200 mL), conc. sulfuric acid (5 mL) was added, and the mixture was heated under reflux for 16 hr. The reaction mixture was concentrated under reduced pressure, and the residue was diluted with ethyl acetate. The mixture was washed successively with saturated aqueous sodium hydrogen carbonate solution, water and saturated brine, dried over anhydrous magnesium sulfate and concentrated under reduced pressure. The residue was purified by silica gel column chromatography (ethyl acetate:hexane=10:90-50:50, volume ratio) to give the title compound (6.80 g, 72%) as colorless crystals.

$^1$H NMR (300 MHz, CDCl$_3$) δ0.99-1.08 (2 H, m), 1.31-1.39 (2 H, m), 2.40-2.50 (1 H, m), 3.70-3.76 (5 H, m), 7.48 (2 H, d, J=8.5 Hz), 7.86 (2 H, d, J=8.5 Hz).

Reference Example 18

Methyl 3-cyclopentyl-2-[4-(cyclopropylsulfonyl) phenyl]propanoate

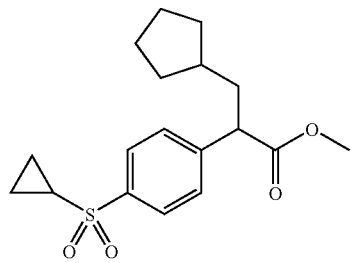

A solution of diisopropylamine (1.67 mL) in a mixed solvent of dry tetrahydrofuran (15 mL) and 1,3-dimethyl-3,4,5, 6-tetrahydro-2(1H)-pyrimidinone (5 mL) was cooled to −78° C. and purged with nitrogen. A 1.6M n-butyllithium hexane solution (7.38 mL) was added dropwise to the reaction mixture, and the mixture was stirred at −78° C. for 30 min. To the reaction mixture were added a solution of methyl [4-(cyclopropylsulfonyl)phenyl]acetate (2.85 g) in a mixed solvent of dry tetrahydrofuran (15 mL) and 1,3-dimethyl-3,4,5,6-tetrahydro-2(1H)-pyrimidinone (5 mL), and the mixture was stirred at −78° C. for 30 min. To the reaction mixture was added a solution (10 mL) of iodomethylcyclopentane (2.81 g) in dry tetrahydrofuran, and the mixture was stirred at −78° C. for 1 hr. The reaction mixture was warmed to room temperature, and the mixture was stirred at room temperature for 2 hr. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:

Reference Example 19

3-cyclopentyl-2-[4-(cyclopropylsulfonyl)phenyl]propanoic acid

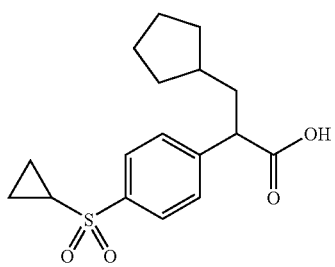

To a solution of methyl 3-cyclopentyl-2-[4-(cyclopropylsulfonyl)phenyl]propanoate (1.95 g) in a mixed solvent of tetrahydrofuran (40 mL) and methanol (20 mL) was added 2N aqueous sodium hydroxide solution (10 mL), and the mixture was stirred at 50° C. for 3 hr. The reaction mixture was acidified with 1N hydrochloric acid, and the mixture was extracted with ethyl acetate. The extract was washed with saturated brine, dried over anhydrous magnesium sulfate and concentrated under reduced pressure. The residue was recrystallized from hexane-diethyl ether to give the title compound (1.67 g, 89%) as colorless crystals. MS: 323 (MH$^+$).

Reference Example 20

3-cyclopentyl-N-(5-isopropylisoxazol-4-yl)-2-[4-(methylsulfonyl)phenyl]propanamide

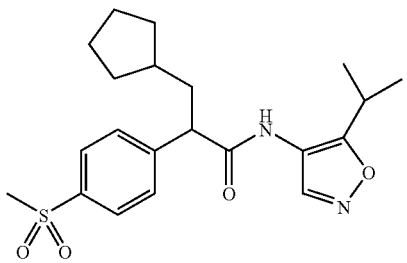

To a solution (15 ml) of 3-cyclopentyl-2-[4-(methylsulfonyl)phenyl]propanoic acid (2.00 g) in N,N-dimethylformamide were added N,N-diisopropylethylamine (3.49% mL), 1-[bis(dimethylamino)methylene]-1H-1,2,3-triazolo(4,5-b)pyridinium 3-oxide hexafluorophosphate (2.82 g) and 5-isopropylisoxazol-4-amine hydrochloride (1.15 g), and the mixture was stirred at room temperature for 48 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=30:70-100:0, volume ratio) to give the title compound (2.50 g, 92%) as colorless amorphous crystals. MS: 405 (MH$^+$).

Reference Example 21

3-cyclopentyl-N-(5-cyclopropylisoxazol-4-yl)-2-[4-(methylsulfonyl)phenyl]propanamide

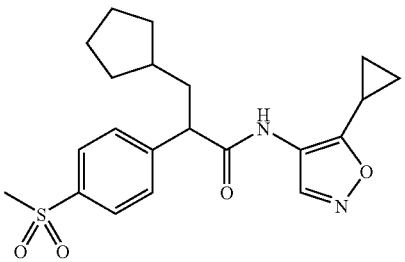

According to the method of Reference Example 20, the title compound (2.58 g, 81%) was obtained as colorless amorphous crystals from 3-cyclopentyl-2-[4-(methylsulfonyl)phenyl]propanoic acid (2.35 g) and 5-cyclopropylisoxazol-4-amine hydrochloride (1.40 g). MS: 403 (MH$^+$).

Reference Example 22

N-(5-cyclobutylisoxazol-4-yl)-3-cyclopentyl-2-[4-(methylsulfonyl)phenyl]propanamide

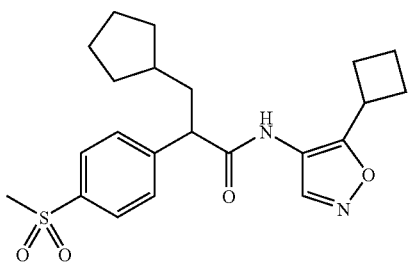

According to the method of Reference Example 20, the title compound (2.38 g, 93%) was obtained as colorless amorphous crystals from 3-cyclopentyl-2-[4-(methylsulfonyl)phenyl]propanoic acid (1.82 g) and 5-cyclobutylisoxazol-4-amine hydrochloride (1.13 g). MS: 417 (MH$^+$).

Reference Example 23

3-cyclopentyl-N-(5-cyclopropylisoxazol-4-yl)-2-[4-(cyclopropylsulfonyl)phenyl]propanamide

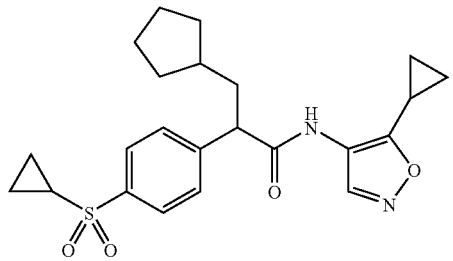

According to the method of Reference Example 20, the title compound (1.81 g, 82%) was obtained as colorless amorphous crystals from 3-cyclopentyl-2-[4-(cyclopropylsulfonyl)phenyl]propanoic acid (1.67 g) and 5-cyclopropylisoxazol-4-amine hydrochloride (0.915 g). MS: 429 (MH$^+$).

Reference Example 24

N-(5-cyclopropylisoxazol-4-yl)-2-[4-(methylsulfonyl)phenyl]-3-(tetrahydro-2H-pyran-4-yl)propanamide

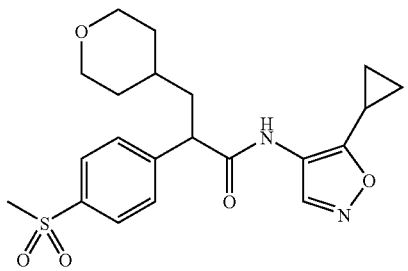

According to the method of Reference Example 20, the title compound (4.45 g, 83%) was obtained as colorless amorphous crystals from 2-[4-(methylsulfonyl)phenyl]-3-(tetrahydro-2H-pyran-4-yl)propanoic acid (1.67 g) and 5-cyclopropylisoxazol-4-amine hydrochloride (2.15 g). MS: 419 (MH$^+$).

Reference Example 25

N-(5-cyclopropylisoxazol-4-yl)-2-[4-(cyclopropylsulfonyl)phenyl]-3-(tetrahydro-2H-pyran-4-yl)propanamide

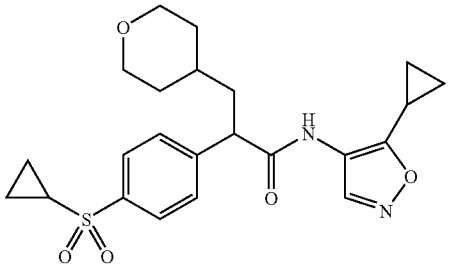

According to the method of Reference Example 20, the title compound (1.90 g, 85%) was obtained as a yellow oil from 2-[4-(cyclopropylsulfonyl)phenyl]-3-(tetrahydro-2H-pyran-4-yl)propanoic acid (1.70 g) and 5-cyclopropylisoxazol-4-amine hydrochloride (0.887 g). MS: 445 (MH$^+$).

Reference Example 26

5-[4-(cyclopropylsulfonyl)phenyl]-1-(pyridin-2-yl)-6-(tetrahydro-2H-pyran-4-yl)hexane-1,4-dione

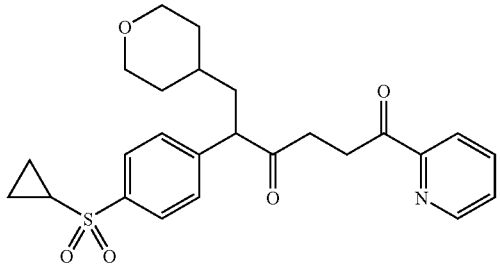

To a solution of 4-[4-(cyclopropylsulfonyl)phenyl]-5-(tetrahydro-2H-pyran-4-yl)pent-1-en-3-one (300 mg) in ethanol (5 mL) were added pyridine-2-carbaldehyde (100 μL), 3-benzyl-5-(2-hydroxyethyl)-4-methyl-1,3-thiazol-3-ium chloride (25 mg) and triethylamine (52 μL), and the mixture was stirred with heating under reflux for 2 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (220 mg, yield 56%) was obtained as a brown oil from a fraction eluted with ethyl acetate-hexane (4:1, volume ratio). MS: 456 (MH$^+$).

Reference Example 27

Ethyl [2-(1,3-dioxolan-2-yl)-1,3-thiazol-5-yl](oxo)acetate

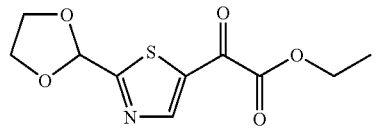

To a solution of 2-(1,3-dioxolan-2-yl)-1,3-thiazole (14.2 g) in tetrahydrofuran (400 mL) was slowly added a 1.6M n-butyllithium hexane solution (62 mL) at −78° C. The reaction mixture was stirred for 30 min, diethyl oxalate (16.5 g) was added, and the mixture was further stirred for 2 hr. The reaction mixture was warmed to room temperature, 1M hydrochloric acid was added, and the mixture was extracted with ethyl acetate. The ethyl acetate layer was washed with saturated aqueous sodium hydrogen carbonate and saturated brine, dried (MgSO$_4$) and concentrated. The residue was subjected to silica gel column chromatography, and the title compound (12.2 g, yield 52%) was obtained as a pale-yellow oil from a fraction eluted with ethyl acetate-hexane (2:3, volume ratio). MS: 258 (MH$^+$).

Reference Example 28

1-[2-(1,3-dioxolan-2-yl)-1,3-thiazol-5-yl]ethane-1,2-diol

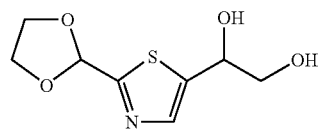

To a solution of ethyl [2-(1,3-dioxolan-2-yl)-1,3-thiazol-5-yl](oxo)acetate (2.00 g) in ethanol (20 mL) was slowly added sodium borohydride (0.50 g). The reaction mixture was stirred at room temperature for 1 hr, 6M hydrochloric acid was added, and the mixture was extracted with ethyl acetate. The ethyl acetate layer was washed with saturated brine, dried (MgSO$_4$) and concentrated to give the title compound (1.50 g, yield 89%) as a colorless oil. MS: 218 (MH$^+$).

Reference Example 29

5-(2,2-dimethyl-1,3-dioxolan-4-yl)-1,3-thiazole-2-carbaldehyde

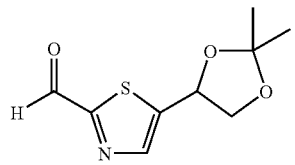

To a solution of 1-[2-(1,3-dioxolan-2-yl)-1,3-thiazol-5-yl]ethane-1,2-diol (1.50 g) in acetone (10 mL) were added water (1 mL) and pyridinium p-toluenesulfonate (0.52 g) and the mixture was stirred with heating under reflux overnight. The reaction mixture was extracted with ethyl acetate, and the ethyl acetate layer was washed with saturated brine, dried (MgSO$_4$) and concentrated to give a crude product (1.20 g). To a solution of the obtained crude product (1.20 g) in acetone (80 mL) was added pyridinium p-toluenesulfonate (1.80 g), and the mixture was stirred with heating under reflux overnight. The reaction mixture was concentrated, the residue was dissolved in ethyl acetate, and the solution was washed with water. The ethyl acetate layer was washed with saturated aqueous sodium hydrogen carbonate and saturated brine, dried (MgSO$_4$) and concentrated. The residue was subjected to silica gel column chromatography, and the title compound (0.50 g, yield 34%) was obtained as a yellow oil from a fraction eluted with ethyl acetate-hexane (2:3, volume ratio). MS: 214 (MH$^+$).

Reference Example 30

5-[4-(cyclopropylsulfonyl)phenyl]-1-[5-(2,2-dimethyl-1,3-dioxolan-4-yl)-1,3-thiazol-2-yl]-6-(tetrahydro-2H-pyran-4-yl)hexane-1,4-dione

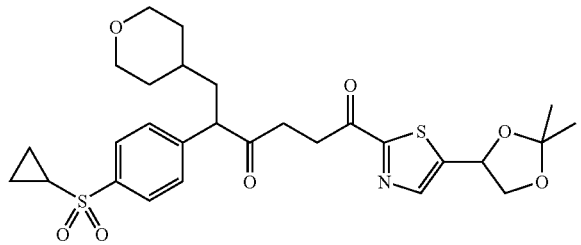

To a solution of 4-[4-(cyclopropylsulfonyl)phenyl]-5-(tetrahydro-2H-pyran-4-yl)pent-1-en-3-one (2.00 g) in ethanol (20 mL) were added 5-(2,2-dimethyl-1,3-dioxolan-4-yl)-1,3-thiazole-2-carbaldehyde (1.50 g), 3-benzyl-5-(2-hydroxyethyl)-4-methyl-1,3-thiazol-3-ium chloride (170 mg) and triethylamine (345 μL), and the mixture was stirred with heating under reflux for 2 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (950 mg, yield 30%) was obtained as a pale-yellow amorphous solid from a fraction eluted with ethyl acetate-hexane (4:1, volume ratio). MS: 562 (MH$^+$).

$^1$H NMR (300 MHz, CDCl$_3$) δ 0.99-1.10 (2 H, m), 1.20-1.41 (6 H, m), 1.46 (3 H, s), 1.52 (3 H, s), 1.60-1.78 (2 H, m), 1.96-2.14 (1 H, m), 2.40-2.55 (1 H, m), 2.67-2.82 (1 H, m), 2.83-3.01 (1 H, m), 3.19-3.35 (3 H, m), 3.36-3.52 (1 H, m), 3.80-4.05 (4 H, m), 4.38 (1 H, dd, J=6.2, 8.5 Hz), 5.36 (1 H, t, J=6.2 Hz), 7.44 (2 H, d, J=8.3 Hz), 7.84 (1 H, s), 7.88 (2 H, d, J=8.3 Hz).

Reference Example 31

5-[4-(cyclopropylsulfonyl)phenyl]-1-(5-fluoropyridin-2-yl)-6-(tetrahydro-2H-pyran-4-yl)hexane-1,4-dione

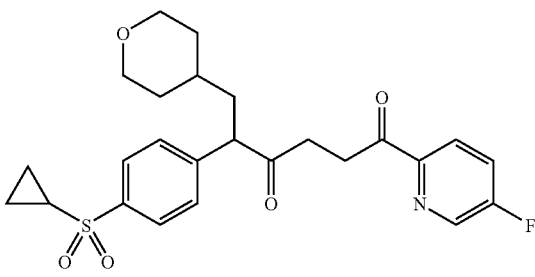

To a solution of 4-[4-(cyclopropylsulfonyl)phenyl]-5-(tetrahydro-2H-pyran-4-yl)pent-1-en-3-one (300 mg) in ethanol (5 mL) were added 5-fluoropyridine-2-carbaldehyde (130 mg), 3-benzyl-5-(2-hydroxyethyl)-4-methyl-1,3-thiazol-3-ium chloride (26 mg) and triethylamine (52 μL), and the mixture was stirred with heating under reflux for 2 hr. After cooling to room temperature, the reaction mixture was diluted with ethyl acetate and washed with water. The ethyl acetate layer was washed with saturated brine, dried (MgSO$_4$) and concentrated. The residue was subjected to preparative HPLC to give the title compound (65 mg, yield 16%) as a brown oil. MS: 474 (MH$^+$).

Reference Example 32

5-[4-(methylsulfonyl)phenyl]-1-(pyridin-2-yl)-6-(tetrahydro-2H-pyran-4-yl)hexane-1,4-dione

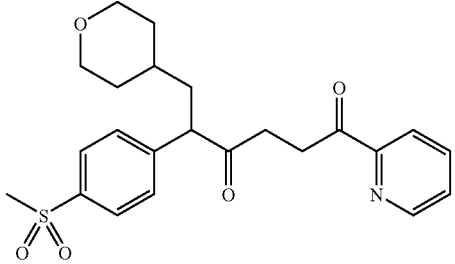

To a solution of 4-[4-(methylsulfonyl)phenyl]-5-(tetrahydro-2H-pyran-4-yl)pent-1-en-3-one (500 mg) in ethanol (5 mL) were added pyridine-2-carbaldehyde (180 μL), 3-benzyl-5-(2-hydroxyethyl)-4-methyl-1,3-thiazol-3-ium chloride (46 mg) and triethylamine (95 μL), and the mixture was stirred with heating under reflux for 2 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (525 mg, yield 79%) was

Reference Example 33

1-(5-bromopyridin-2-yl)-5-[4-(cyclopropylsulfonyl)phenyl]-6-(tetrahydro-2H-pyran-4-yl)hexane-1,4-dione

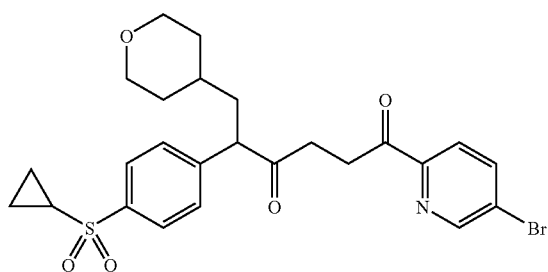

To a solution of 4-[4-(cyclopropylsulfonyl)phenyl]-5-(tetrahydro-2H-pyran-4-yl)pent-1-en-3-one (1.00 g) in ethanol (10 mL) were added 5-bromopyridine-2-carbaldehyde (640 mg), 3-benzyl-5-(2-hydroxyethyl)-4-methyl-1,3-thiazol-3-ium chloride (85 mg) and triethylamine (175 μL), and the mixture was stirred with heating under reflux overnight. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (1.29 g, yield 84%) was obtained as a yellow amorphous solid from a fraction eluted with ethyl acetate-hexane (3:2, volume ratio). MS: 536 (MH$^+$).
$^1$H NMR (300 MHz, CDCl$_3$) δ0.98-1.12 (2 H, m), 1.27-1.44 (5 H, m), 1.58-1.77 (3 H, m), 1.96-2.15 (1 H, m), 2.41-2.55 (1H, m), 2.65-2.81 (1 H, m), 2.84-2.98 (1 H, m), 3.21-3.40 (3 H, m), 3.43-3.57 (1 H, m), 3.92 (2 H, d, J=11.7 Hz), 4.03 (1 H, t, J=7.6 Hz), 7.45 (2 H, d, J=8.3 Hz), 7.83-7.91 (3 H, m), 7.93-8.00 (1 H, m), 8.71 (1 H, d, J=2.3 Hz).

Reference Example 34

Diethyl [6-(1,3-dioxolan-2-yl)pyridin-3-yl]malonate

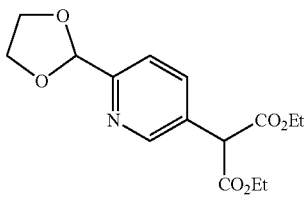

To a solution of 5-bromo-2-(1,3-dioxolan-2-yl)pyridine (2.00 g) in 1,4-dioxane (30 mL) were added diethyl malonate (1.6 mL), palladium acetate (II) (195 mg), di-tert-butyl(2'-methylbiphenyl-2-yl)phosphane (600 mg) and tripotassium phosphate (4.30 g), and the mixture was heated under reflux under argon atmosphere overnight. After cooling to room temperature, the reaction mixture was diluted with ethyl acetate, and the insoluble material was filtered off through celite. The filtrate was concentrated, and the residue was subjected to silica gel column chromatography, and the title compound (1.95 g, yield 72%) was obtained as a brown oil from a fraction eluted with ethyl acetate-hexane (1:1, volume ratio). MS: 310 (MH$^+$).
$^1$H NMR (300 MHz, CDCl$_3$) δ1.26 (6 H, t, J=7.2 Hz), 4.02-4.31 (8 H, m), 4.64 (1 H, s), 5.87 (1 H, s), 7.56 (1 H, d, J=8.1 Hz), 7.90 (1 H, dd, J=2.3, 8.1 Hz), 8.58 (1 H, d, J=1.9 Hz).

Reference Example 35

Diethyl (6-{5-[4-(cyclopropylsulfonyl)phenyl]-4-oxo-6-(tetrahydro-2H-pyran-4-yl)hexanoyl}pyridin-3-yl)malonate

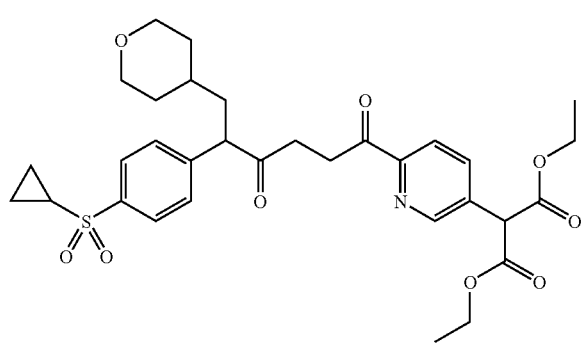

To a solution of diethyl [6-(1,3-dioxolan-2-yl)pyridin-3-yl]malonate (1.00 g) in tetrahydrofuran (10 mL) was added 3M hydrochloric acid (10 mL), and the mixture was stirred at 50° C. for 4 hr. After cooling to room temperature, the reaction mixture was diluted with ethyl acetate, and washed with saturated aqueous sodium hydrogen carbonate. The ethyl acetate layer was washed with saturated brine, dried (MgSO$_4$) and concentrated to give a crude product (170 mg). To a solution of the obtained crude product (170 mg) and 4-[4-(cyclopropylsulfonyl)phenyl]-5-(tetrahydro-2H-pyran-4-yl)pent-1-en-3-one (200 mg) in ethanol (5 mL) were added 3-benzyl-5-(2-hydroxyethyl)-4-methyl-1,3-thiazol-3-ium chloride (17 mg) and triethylamine (35 μL), and the mixture was stirred with heating under reflux for 2 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (150 mg, yield 43%) was obtained as a colorless amorphous solid from a fraction eluted with ethyl acetate-hexane (3:2, volume ratio). MS: 614 (MH$^+$).

Reference Example 36

5-(1,3-dioxolan-2-yl)pyridine-2-carbaldehyde

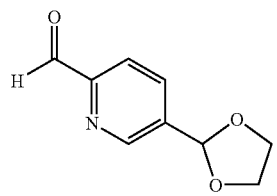

To a solution of 2-bromo-5-(1,3-dioxolan-2-yl)pyridine (9.60 g) in tetrahydrofuran (150 mL) was slowly added a 1.6M n-butyllithium hexane solution (28.7 mL) at −78° C. The reaction mixture was stirred for 30 min, N,N-dimethylformamide (3.9 mL) in tetrahydrofuran (50 mL) was added, and the mixture was warmed to room temperature and stirred for 30 min. Water was added to the reaction mixture, and the mixture was extracted with ethyl acetate solution. The ethyl acetate layer was washed with saturated brine, dried (MgSO$_4$) and concentrated. The residue was subjected to silica gel column chromatography, and the title compound (2.70 g, yield 36%) was obtained as a pale-yellow amorphous solid from a fraction eluted with ethyl acetate-hexane (1:2, volume ratio). MS: 180 (MH$^+$).

Reference Example 37

5-[4-(cyclopropylsulfonyl)phenyl]-1-[5-(1,3-dioxolan-2-yl)pyridin-2-yl]-6-(tetrahydro-2H-pyran-4-yl)hexane-1,4-dione

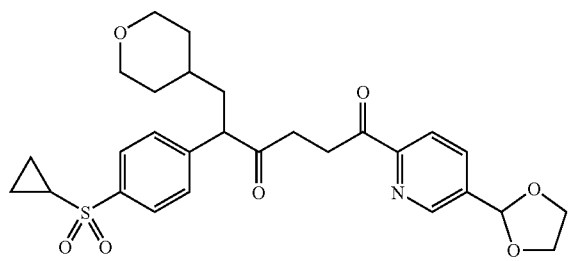

To a solution of 4-[4-(cyclopropylsulfonyl)phenyl]-5-(tetrahydro-2H-pyran-4-yl)pent-1-en-3-one (4.40 g) in ethanol (50 mL) were added 5-(1,3-dioxolan-2-yl)pyridine-2-carbaldehyde (2.70 g), 3-benzyl-5-(2-hydroxyethyl)-4-methyl-1,3-thiazol-3-ium chloride (375 mg) and triethylamine (755 μL), and the mixture was stirred with heating under reflux for 2 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (4.40 g, yield 67%) was obtained as a colorless amorphous solid from a fraction eluted with ethyl acetate-hexane (2:1, volume ratio). MS: 528 (MH$^+$).

Reference Example 38

1-(5-bromopyridin-2-yl)-5-[4-(methylsulfonyl)phenyl]-6-(tetrahydro-2H-pyran-4-yl)hexane-1,4-dione

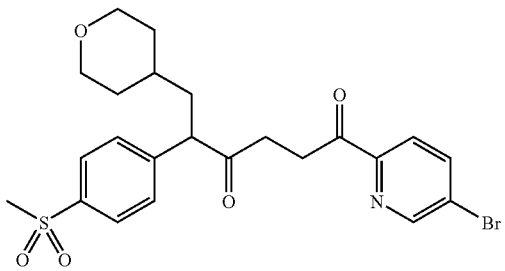

To a solution of 4-[4-(methylsulfonyl)phenyl]-5-(tetrahydro-2H-pyran-4-yl)pent-1-en-3-one (3.00 g) in ethanol (50 mL) were added 5-bromopyridine-2-carbaldehyde (2.10 g), 3-benzyl-5-(2-hydroxyethyl)-4-methyl-1,3-thiazol-3-ium chloride (280 mg) and triethylamine (560 μL), and the mixture was stirred with heating under reflux overnight. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (3.89 g, yield 82%) was obtained as a colorless amorphous solid from a fraction eluted with ethyl acetate-hexane (2:1, volume ratio). MS: 510 (MH$^+$).

Reference Example 39

Tert-butyl 4-{2-[methoxy(methyl)amino]-2-oxoethyl}benzoate

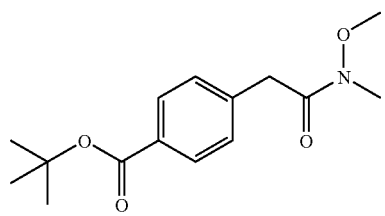

To a solution of N-methoxymethanamine hydrochloride (5.00 g) in N,N-dimethylformamide (200 mL) was added triethylamine (7.1 mL), and the mixture was stirred at room temperature for 30 min. [4-(tert-Butoxycarbonyl)phenyl]acetic acid (10.0 g), 1-ethyl-3-(3-dimethylaminopropyl)carbodiimide hydrochloride (12.2 g) and 1-hydroxybenzotriazole (8.60 g) were added to the reaction mixture under ice-cooling, and the mixture was stirred overnight at room temperature. The reaction mixture was diluted with ethyl acetate, washed with 1M hydrochloric acid, saturated aqueous sodium hydrogen carbonate and saturated brine, dried (MgSO$_4$) and concentrated. The residue was subjected to silica gel column chromatography, and the title compound (9.50 g, yield 80%) was obtained as a colorless amorphous solid from a fraction eluted with ethyl acetate-hexane (3:2, volume ratio). MS: 280 (MH$^+$).

Reference Example 40

Tert-butyl 4-{2-[methoxy(methyl)amino]-2-oxo-1-(tetrahydro-2H-pyran-4-ylmethyl)ethyl}benzoate

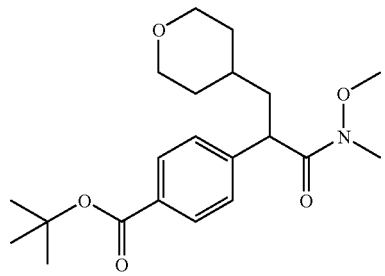

Lithium diisopropylamide (2M tetrahydrofuran solution, 6.9 mL) was diluted with tetrahydrofuran (20 mL), a solution of tert-butyl 4-{2-[methoxy(methyl)amino]-2-oxoethyl}benzoate (3.70 g) in a mixed solvent of tetrahydrofuran (20 mL) and 1,3-dimethyl-3,4,5,6-tetrahydro-2(1H)-pyrimidinone (12 mL) were added at −78° C., and the mixture was stirred for 1 hr. To the reaction mixture was added a solution of 4-(iodomethyl)tetrahydro-2H-pyran (3.30 g) in tetrahydrofuran m (20 mL) at −78° C. and the mixture was stirred for 3 hr. The mixture was slowly warmed to room temperature, and stirred overnight. A saturated aqueous ammonium chloride solution was added to the reaction mixture, and the mixture was extracted with ethyl acetate. The ethyl acetate layer was washed with saturated brine, dried (MgSO$_4$) and concentrated. The residue was subjected to silica gel column chromatography, and the title compound (3.81 g, yield 76%) was obtained as a colorless amorphous solid from a fraction eluted with ethyl acetate-hexane (1:1, volume ratio). MS: 378 (MH$^+$).

Reference Example 41

Tert-butyl 4-[2-oxo-1-(tetrahydro-2H-pyran-4-ylmethyl)but-3-en-1-yl]benzoate

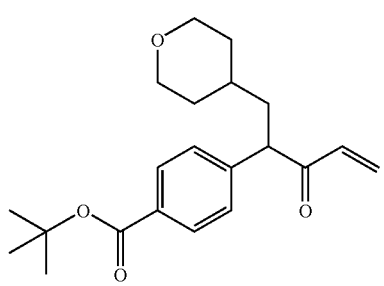

To a solution of tent-butyl 4-{2-[methoxy(methyl)amino]-2-oxo-1-(tetrahydro-2H-pyran-4-ylmethyl)ethyl}benzoate (3.81 g) in tetrahydrofuran (50 mL) was added vinylmagnesium bromide (1.0M tetrahydrofuran solution, 30 mL) at −78° C., and the mixture was stirred for 45 min. The reaction mixture was slowly warmed to room temperature, and further stirred for 4 hr. An excess amount of 1M hydrochloric acid was added to the reaction mixture, and the mixture was extracted with ethyl acetate. The ethyl acetate layer was washed with saturated aqueous sodium hydrogen carbonate and saturated brine, dried (MgSO$_4$) and concentrated. The residue was subjected to silica gel column chromatography, and the title compound (3.20 g, yield 91%) was obtained as a colorless amorphous solid from a fraction eluted with ethyl acetate-hexane (2:3, volume ratio). MS: 345 (MH$^+$).

Reference Example 42

Tert-butyl 4-[2,5-dioxo-1-(tetrahydro-2H-pyran-4-ylmethyl)-5-{5-[(tetrahydro-2H-pyran-2-yloxy)methyl]-1,3-thiazol-2-yl}pentyl]benzoate

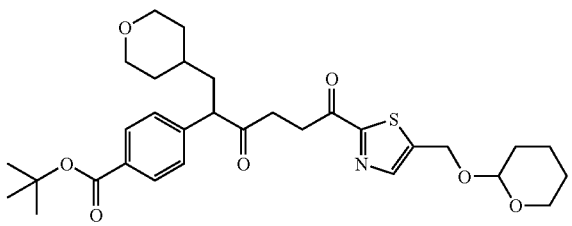

To a solution of tert-butyl 4-[2-oxo-1-(tetrahydro-2H-pyran-4-ylmethyl)but-3-en-1-yl]benzoate (1.50 g) in ethanol (15 mL) were added 5-[(tetrahydro-2H-pyran-2-yloxy)methyl]-1,3-thiazole-2-carbaldehyde (1.20 g), 3-benzyl-5-(2-hydroxyethyl)-4-methyl-1,3-thiazol-3-ium chloride (130 mg) and triethylamine (260 μL), and the mixture was stirred with heating under reflux for 4 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (2.37 g, yield 95%) was obtained as a colorless amorphous solid from a fraction eluted with ethyl acetate-hexane (1:1, volume ratio). MS: 488 (MH$^+$).

Reference Example 43

4-({[tert-butyl(diphenyl)silyl]oxy}methyl)pyridine-2-carbaldehyde

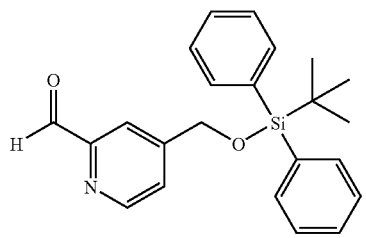

To a solution of 2-bromo-4-({[tert-butyl(diphenyl)silyl]oxy}methyl)pyridine (8.50 g) in diethyl ether (80 mL) was slowly added a 1.6M n-butyllithium hexane solution (13.0 mL) at −78° C. The reaction mixture was stirred for 30 min, a solution of N,N-dimethylformamide (1.85 mL) in tetrahydrofuran (20 mL) was added, and the mixture was warmed to room temperature and stirred for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography, and the title compound (2.16 g, yield 29%) was obtained as a colorless amorphous solid from a fraction eluted with ethyl acetate-hexane (1:4, volume ratio). MS: 376 (MH$^+$).

Reference Example 44

1-[4-({[tert-butyl(diphenyl)silyl]oxy}methyl)pyridin-2-yl]-5-[4-(methylsulfonyl)phenyl]-6-(tetrahydro-2H-pyran-4-yl)hexane-1,4-dione

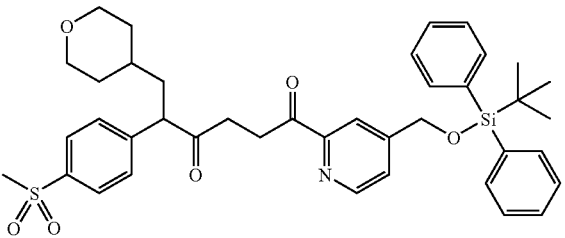

To a solution of 4-[4-(methylsulfonyl)phenyl]-5-(tetrahydro-2H-pyran-4-yl)pent-1-en-3-one (1.00 g) in ethanol (15 mL) were added 4-({[tert-butyl(diphenyl)silyl]oxy}methyl)pyridine-2-carbaldehyde (1.40 g), 3-benzyl-5-(2-hydroxyethyl)-4-methyl-1,3-thiazol-3-ium chloride (95.0 mg) and triethylamine (190 μL), and the mixture was stirred with heating under reflux for 4 hr under argon atmosphere. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (1.90 g, yield 88%)

was obtained as a brown oil from a fraction eluted with ethyl acetate-hexane (2:1, volume ratio). MS: 698 (MH+).

Reference Example 45

1-(6-bromopyridin-3-yl)ethane-1,2-diol

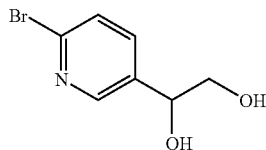

To a solution of ethyl (6-bromopyridin-3-yl)(oxo)acetate (1.00 g) in ethanol (20 mL) was slowly added sodium borohydride (250 mg). The reaction mixture was stirred at room temperature for 4 hr, diluted with ethyl acetate and washed with water. The ethyl acetate layer was washed with saturated brine, dried (MgSO$_4$) and concentrated to give the title compound (650 mg, yield 77%) as a colorless oil. MS: 220 (MH+).

Reference Example 46

2-bromo-5-(2,2-dimethyl-1,3-dioxolan-4-yl)pyridine

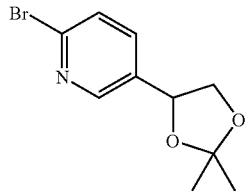

To a solution of 1-(6-bromopyridin-3-yl)ethane-1,2-diol (4.20 g) in acetone (80 mL) was added pyridinium p-toluenesulfonate (1.50 g), and the mixture was stirred with heating under reflux for 3 hr. The reaction mixture was diluted with ethyl acetate and washed with water. The ethyl acetate layer was washed with saturated brine, dried (MgSO$_4$) and concentrated to give the title compound (4.12 g, yield 72%) as a pale-yellow solid. MS: 260 (MH+).

Reference Example 47

5-(2,2-dimethyl-1,3-dioxolan-4-yl)pyridine-2-carbaldehyde

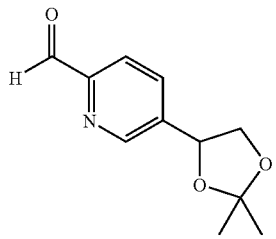

To a solution of 2-bromo-5-(2,2-dimethyl-1,3-dioxolan-4-yl)pyridine (4.12 g) in diethyl ether (100 mL) was slowly added a 1.6M n-butyllithium hexane solution (10 mL) at −78° C. The reaction mixture was stirred for 30 min, and N,N-dimethylformamide (1.40 g) was added. The reaction mixture was warmed to room temperature over 1 hr, and stirred overnight. Water was added to the reaction mixture, and the mixture was extracted with ethyl acetate. The ethyl acetate layer was washed with saturated brine, dried (MgSO$_4$) and concentrated. The residue was subjected to silica gel column chromatography, and the title compound (900 mg, yield 27%) was obtained as a pale-yellow oil from a fraction eluted with ethyl acetate-hexane (1:4, volume ratio). MS: 208 (MH+).

Reference Example 48

1-[5-(2,2-dimethyl-1,3-dioxolan-4-yl)pyridin-2-yl]-5-[4-(methylsulfonyl)phenyl]-6-(tetrahydro-2H-pyran-4-yl)hexane-1,4-dione

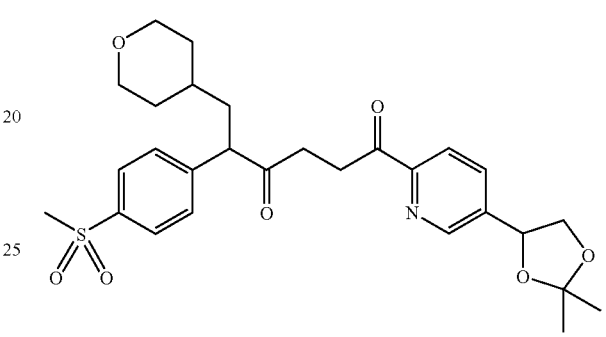

To a solution (10 mL) of 4-[4-(methylsulfonyl)phenyl]-5-(tetrahydro-2H-pyran-4-yl)pent-1-en-3-one (500 mg) in ethanol were added 5-(2,2-dimethyl-1,3-dioxolan-4-yl)pyridine-2-carbaldehyde (350 mg), 3-benzyl-5-(2-hydroxyethyl)-4-methyl-1,3-thiazol-3-ium chloride (45.0 mg) and triethylamine (93 μL), and the mixture was stirred with heating under reflux for 4 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (232 mg, yield 28%) was obtained as a pale-yellow amorphous solid from a fraction eluted with ethyl acetate-hexane (2:1, volume ratio). MS: 530 (MH+).

Reference Example 49

1-[5-(2,2-dimethyl-1,3-dioxolan-4-yl)pyridin-2-yl]-5-[3-fluoro-4-(methylsulfanyl)phenyl]-6-(tetrahydro-2H-pyran-4-yl)hexane-1,4-dione

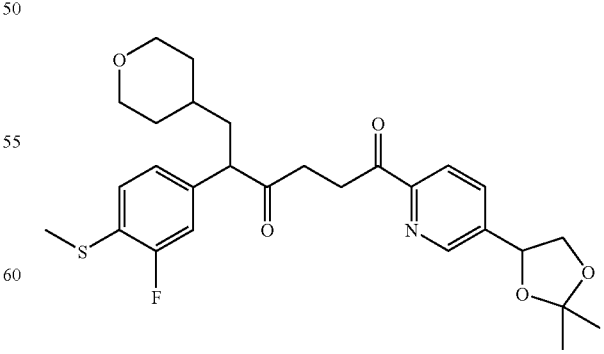

To a solution of 4-[3-fluoro-4-(methylsulfanyl)phenyl]-5-(tetrahydro-2H-pyran-4-yl)pent-1-en-3-one (430 mg) in a mixed solvent of ethanol (3 mL) and tetrahydrofuran (3 mL) were added 5-(2,2-dimethyl-1,3-dioxolan-4-yl)pyridine-2- carbaldehyde (290 mg), 3-benzyl-5-(2-hydroxyethyl)-4-methyl-1,3-thiazol-3-ium chloride (41.0 mg) and triethylamine (84 μL), and the mixture was stirred with heating under reflux under argon atmosphere for 4 hr. After cooling to room temperature, the reaction mixture was diluted with ethyl acetate and washed with water. The ethyl acetate layer was washed with saturated brine, dried (MgSO₄) and concentrated. The residue was subjected to silica gel column chromatography, and the title compound (510 mg, yield 71%) was obtained as a pale-yellow amorphous solid from a fraction eluted with ethyl acetate-hexane (1:1, volume ratio). MS: 516 (MH⁺).

Reference Example 50

5-[3-chloro-4-(methylsulfonyl)phenyl]-1-[5-(2,2-dimethyl-1,3-dioxolan-4-yl)pyridin-2-yl]-6-(tetrahydro-2H-pyran-4-yl)hexane-1,4-dione

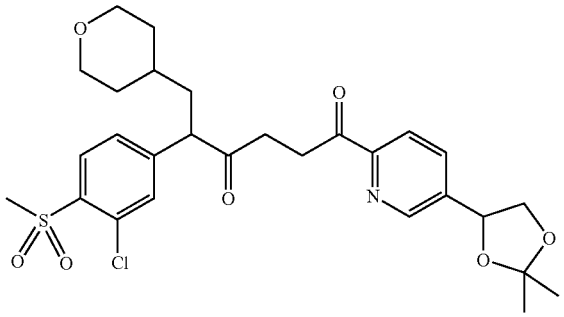

To a solution of 4-[3-chloro-4-(methylsulfonyl)phenyl]-5-(tetrahydro-2H-pyran-4-yl)pent-1-en-3-one (500 mg) in a mixed solvent of ethanol (3 mL) and tetrahydrofuran (3 mL) were added 5-(2,2-dimethyl-1,3-dioxolan-4-yl)pyridine-2-carbaldehyde (320 mg), 3-benzyl-5-(2-hydroxyethyl)-4-methyl-1,3-thiazol-3-ium chloride (42.0 mg) and triethylamine (84 μL), and the mixture was stirred with heating under reflux for 4 hr under argon atmosphere. After cooling to room temperature, the reaction mixture was diluted with ethyl acetate and washed with water. The ethyl acetate layer was washed with saturated brine, dried (MgSO₄) and concentrated. The residue was subjected to silica gel column chromatography, and the title compound (620 mg, yield 78%) was obtained as a pale-brown amorphous solid from a fraction eluted with ethyl acetate-hexane (2:1, volume ratio). MS: 566 (MH⁺).

Reference Example 51

(2E)-2-[4-(cyclopropylsulfonyl)phenyl]-N-methoxy-N-methyl-3-(tetrahydro-2H-pyran-4-yl)propan-2-enamide

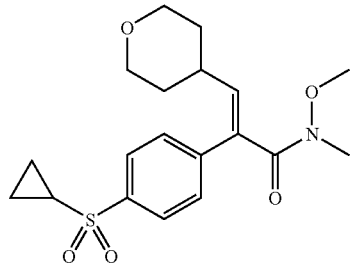

To a solution of N-methoxymethanamine hydrochloride (350 mg) in N,N-dimethylformamide (10 mL) was added triethylamine (500 μL), and the mixture was stirred at room temperature for 30 min. (2E)-2-[4-(Cyclopropylsulfonyl)phenyl]-3-(tetrahydro-2H-pyran-4-yl)propan-2-enoic acid (1.00 g), 1-ethyl-3-(3-dimethylaminopropyl)carbodiimide hydrochloride (860 mg) and 1-hydroxybenzotriazole (600 mg) were added to the reaction mixture under ice-cooling, and the mixture was stirred at room temperature for 4 hr. The reaction mixture was diluted with ethyl acetate, washed with 1M hydrochloric acid, saturated aqueous sodium hydrogen carbonate and saturated brine, dried (MgSO₄) and concentrated to give a crude product (1.15 g) of the title compound as colorless crystals. MS: 380 (MH⁺).

Reference Example 52

(1E)-2-[4-(cyclopropylsulfonyl)phenyl]-1-(tetrahydro-2H-pyran-4-yl)penta-1,4-dien-3-one

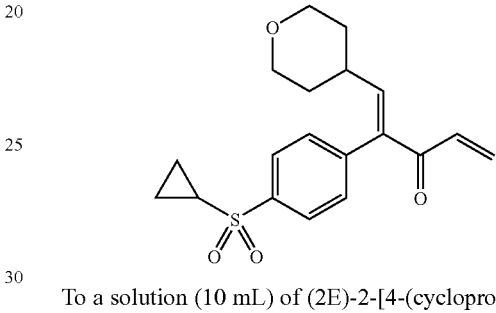

To a solution (10 mL) of (2E)-2-[4-(cyclopropylsulfonyl)phenyl]-N-methoxy-N-methyl-3-(tetrahydro-2H-pyran-4-yl)propan-2-enamide (1.13 g) in tetrahydrofuran was added vinylmagnesium bromide (1.0M tetrahydrofuran solution, 9 mL) under ice-cooling, and the mixture was warmed to room temperature and stirred overnight. An excess amount of 1M hydrochloric acid was added to the reaction mixture, and the mixture was extracted with ethyl acetate. The ethyl acetate layer was washed with saturated aqueous sodium hydrogen carbonate and saturated brine, dried (MgSO₄) and concentrated. The residue was subjected to silica gel column chromatography, and the title compound (426 mg, yield 41%) was obtained as a colorless oil from a fraction eluted with ethyl acetate-hexane (3:2, volume ratio). MS: 347 (MH⁺).

Reference Example 53

(5E)-5-[4-(cyclopropylsulfonyl)phenyl]-6-(tetrahydro-2H-pyran-4-yl)-1-(1,3-thiazol-2-yl)hex-5-ene-1,4-dione

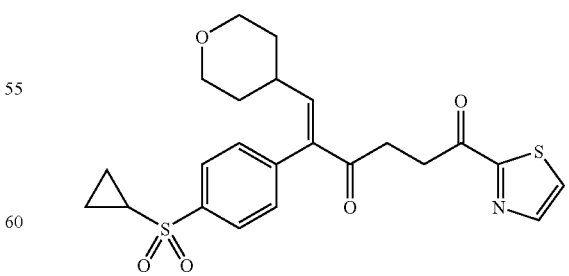

To a solution of (1E)-2-[4-(cyclopropylsulfonyl)phenyl]-1-(tetrahydro-2H-pyran-4-yl)penta-1,4-dien-3-one (425 mg) in ethanol (5 mL) were added 1,3-thiazole-2-carbaldehyde (130 μL), 3-benzyl-5-(2-hydroxyethyl)-4-methyl-1,3-thiazol-3-ium chloride (36.0 mg) and triethylamine (75 μL), and the mixture was stirred with heating under reflux for 4 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (278 mg, yield 49%) was obtained as a colorless amorphous solid from a fraction eluted with ethyl acetate-hexane (2:1, volume ratio). MS: 460 (MH$^+$).

Reference Example 54

2-[4-(cyclopropylsulfonyl)phenyl]-1-(tetrahydro-2H-pyran-4-yl)hex-4-en-3-one

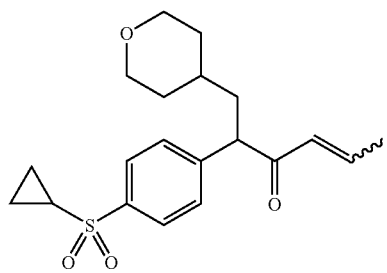

To a solution of 2-[4-(cyclopropylsulfonyl)phenyl]-N-methoxy-N-methyl-3-(tetrahydro-2H-pyran-4-yl)propanamide (1.00 g) in tetrahydrofuran (10 mL) was added 1-propenylmagnesium bromide (0.5M tetrahydrofuran solution, 17.2 mL) under ice-cooling, and the mixture was warmed to room temperature and stirred for 3 hr. The reaction mixture was poured into a mixture of concentrated hydrochloric acid (5 mL) and ice (100 g), and the mixture was stirred for 15 min. The mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (632 mg, yield 61%) was obtained as a colorless oil from a fraction eluted with ethyl acetate-hexane (4:1, volume ratio). MS: 363 (MH$^+$).

Reference Example 55

5-[4-(cyclopropylsulfonyl)phenyl]-2-methyl-1-(pyridin-2-yl)-6-(tetrahydro-2H-pyran-4-yl)hexane-1,4-dione

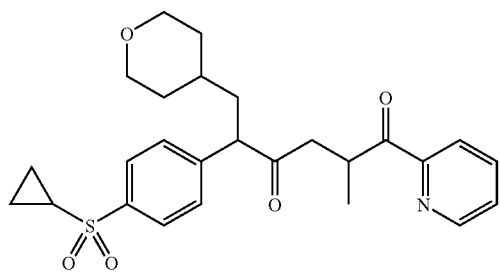

To a solution of 2-[4-(cyclopropylsulfonyl)phenyl]-1-(tetrahydro-2H-pyran-4-yl)hex-4-en-3-one (200 mg) in a mixed solvent of ethanol (3 mL) and tetrahydrofuran (3 mL) were added pyridine-2-carbaldehyde (71.0 mg), 3-benzyl-5-(2-hydroxyethyl)-4-methyl-1,3-thiazol-3-ium chloride (16.0 mg) and triethylamine (33 μL), and the mixture was stirred under argon atmosphere at 80° C. for 3 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (180 mg, yield 69%) was obtained as a pale-yellow oil from a fraction eluted with ethyl acetate-hexane (4:1, volume ratio). MS: 470 (MH$^+$).

Reference Example 56

1-[5-(1-{[tert-butyl(dimethyl)silyl]oxy}ethyl)pyridin-2-yl]-5-[4-(cyclopropylsulfonyl)phenyl]-2-methyl-6-(tetrahydro-2H-pyran-4-yl)hexane-1,4-dione


To a solution of 2-[4-(cyclopropylsulfonyl)phenyl]-1-(tetrahydro-2H-pyran-4-yl)hex-4-en-3-one (180 mg) in a mixed solvent of ethanol (3 mL) and tetrahydrofuran (3 mL) were added 5-(1-{[tert-butyl(dimethyl)silyl]oxy}ethyl)pyridine-2-carbaldehyde (158 mg), 3-benzyl-5-(2-hydroxyethyl)-4-methyl-1,3-thiazol-3-ium chloride (14.7 mg) and triethylamine (29.9 μL), and the mixture was stirred with heating under reflux under argon atmosphere for 3 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (180 mg, yield 58%) was obtained as a pale-yellow oil from a fraction eluted with ethyl acetate-hexane (1:1, volume ratio). MS: 628 (MH$^+$).

Reference Example 57

5-[4-(cyclopropylsulfonyl)phenyl]-1-[5-(1,2-dihydroxy-2-methylpropyl)pyridin-2-yl]-2-methyl-6-(tetrahydro-2H-pyran-4-yl)hexane-1,4-dione

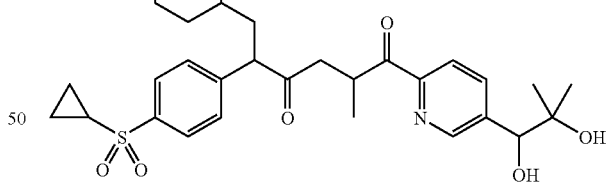

To a solution of 2-[4-(cyclopropylsulfonyl)phenyl]-1-(tetrahydro-2H-pyran-4-yl)hex-4-en-3-one (200 mg) in a mixed solvent of ethanol (3 mL) and tetrahydrofuran (3 mL) were added 5-(1,2-dihydroxy-2-methylpropyl)pyridine-2-carbaldehyde (129 mg), 3-benzyl-5-(2-hydroxyethyl)-4-methyl-1,3-thiazol-3-ium chloride (16.4 mg) and triethylamine (33.2 μL), and the mixture was stirred with heating under reflux under argon m atmosphere for 3 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (235 mg, yield 76%) was obtained as a yellow amorphous solid from a fraction eluted with ethyl acetate. MS: 558 (MH$^+$).

Reference Example 58

Ethyl [4-(cyclopropylsulfonyl)phenyl]acetate

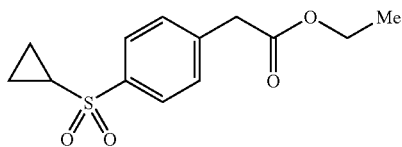

To a solution of ethyl [4-(cyclopropylsulfonyl)phenyl](oxo)acetate (20.1 g) in a mixed solvent of tetrahydrofuran (140 mL) and methanol (70 mL) was added 2M aqueous sodium hydroxide solution (70 mL), and the mixture was stirred at room temperature for 16 hr. The reaction mixture was acidified with 1M hydrochloric acid and extracted with ethyl acetate. The extract was washed with saturated brine, dried over anhydrous sodium sulfate, and concentrated under reduced pressure. The residue was cooled to −78° C., hydrazine monohydrate (17.3 mL) was added, and the mixture was warmed to room temperature by stirring. The reaction mixture was stirred at 80° C. for 10 min and cooled to room temperature. Potassium hydroxide (12.0 g) was added to the reaction mixture, and the mixture was stirred at 100° C. for 16 hr. Water was added to the reaction mixture, and the aqueous layer was washed with diethyl ether. The aqueous layer was acidified with 1M hydrochloric acid, and the mixture was extracted with ethyl acetate. The extract was washed with saturated brine, dried over anhydrous magnesium sulfate and concentrated under reduced pressure. To a solution of the residue in ethanol (500 mL) was added thionyl chloride (6.23 mL) under ice-cooling, and the mixture was warmed to room temperature and stirred at room temperature for 16 hr. The reaction mixture was concentrated under reduced pressure, and the residue was recrystallized from hexane-ether to give the title compound (13.7 g, yield 72%) as colorless crystals. melting point 102-104° C.

Reference Example 59

Ethyl 2-[4-(cyclopropylsulfonyl)phenyl]-3-[(2R,3R,7R)-2,3-diphenyl-1,4-dioxaspiro[4.4]non-7-yl]propanoate

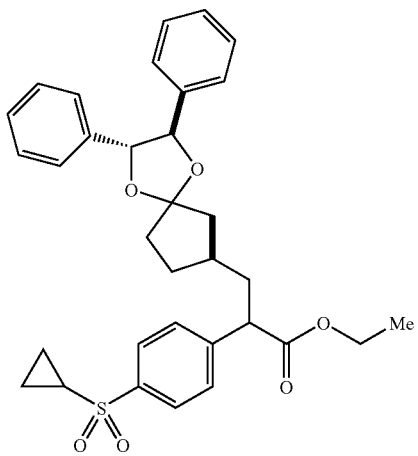

In the same manner as in Reference Example 18, the title compound (20.2 g, yield 71%) was obtained as a colorless amorphous solid from ethyl [4-(cyclopropylsulfonyl)phenyl]acetate (13.7 g) and (2R,3R,7S)-7-(iodomethyl)-2,3-diphenyl-1,4-dioxaspiro[4.4]nonane (23.6 g).

$^1$H NMR (CDCl$_3$) δ0.98-1.07 (2 H, m), 1.18-1.27 (3 H, m), 1.31-1.39 (2 H, m), 1.42-1.60 (2 H, m), 1.68-1.82 (1 H, m), 1.86-2.10 (3 H, m), 2.15-2.39 (3 H, m), 2.40-2.50 (1H, m), 3.71 (1 H, t, J=7.6 Hz), 4.04-4.24 (2 H, m), 4.64-4.73 (2 H, m), 7.15-7.24 (4 H, m), 7.27-7.35 (6 H, m), 7.49-7.57 (2 H, m), 7.81-7.90 (2 H, m).

Reference Example 60

2-[4-(cyclopropylsulfonyl)phenyl]-3-[(2R,3R,7R)-2,3-diphenyl-1,4-dioxaspiro[4.4]non-7-yl]propanoic acid

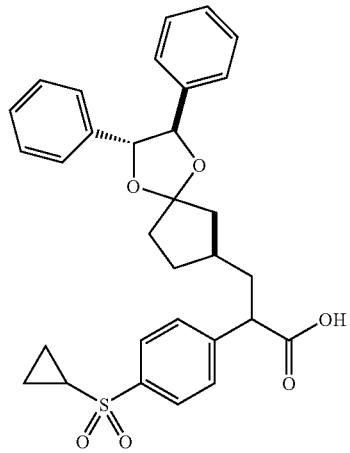

In the same manner as in Reference Example 19, the title compound (19.2 g, quantitatively) was obtained as a colorless amorphous solid from ethyl 2-[4-(cyclopropylsulfonyl)phenyl]-3-[(2R,3R,7R)-2,3-diphenyl-1,4-dioxaspiro[4.4]non-7-yl]propanoate (20.2 g).

$^1$H NMR (DMSO-d$_6$) δ0.97-1.14 (4 H, m), 1.32-1.48 (1 H, m), 1.64-1.76 (1 H, m), 1.77-1.99 (4 H, m), 2.03-2.16 (2 H, m), 2.17-2.29 (1 H, m), 2.79-2.90 (1 H, m), 3.72-3.79 (1 H, m), 4.66-4.74 (2 H, m), 7.15-7.24 (4 H, m), 7.29-7.40 (6 H, m), 7.58-7.66 (2 H, m), 7.82-7.90 (2 H, m), 12.64 (1 H, s).

Reference Example 61

2-[4-(cyclopropylsulfonyl)phenyl]-3-[(2R,3R,7R)-2,3-diphenyl-1,4-dioxaspiro[4.4]non-7-yl]-N-methoxy-N-methylpropanamide

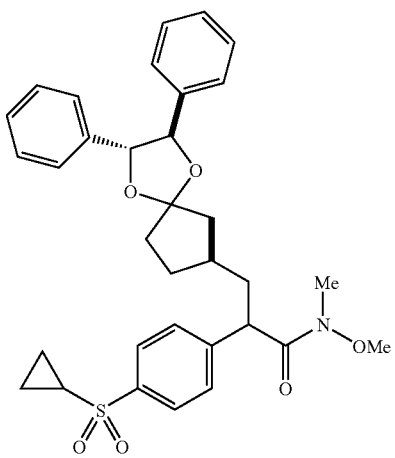

In the same manner as in Reference Example 1, the title compound (6.00 g, quantitatively) was obtained as a colorless oil from 2-[4-(cyclopropylsulfonyl)phenyl]-3-[(2R,3R,7R)-2,3-diphenyl-1,4-dioxaspiro[4.4]non-7-yl]propanoic acid (5.52 g). MS: 576 (MH$^+$).

Reference Example 62

4-[4-(cyclopropylsulfonyl)phenyl]-5-[(2R,3R,7R)-2,3-diphenyl-1,4-dioxaspiro[4.4]non-7-yl]pent-1-en-3-one

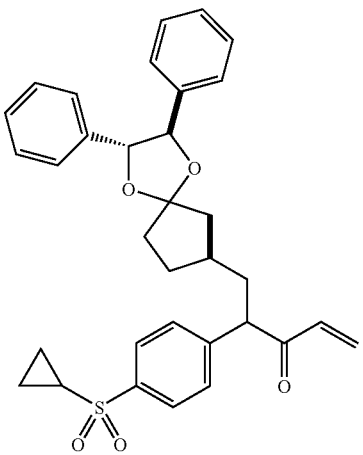

In the same manner as in Reference Example 2, the title compound (3.13 g, yield 52%) was obtained as a colorless amorphous solid from 2-[4-(cyclopropylsulfonyl)phenyl]-3-[(2R,3R,7R)-2,3-diphenyl-1,4-dioxaspiro[4.4]non-7-yl]-N-methoxy-N-methylpropanamide (6.00 g).

$^1$H NMR (CDCl$_3$) δ0.97-1.07 (2 H, m), 1.31-1.39 (2 H, m), 1.42-1.55 (1 H, m), 1.67-1.82 (1 H, m), 1.82-2.09 (3 H, m), 2.10-2.40 (4 H, m), 2.39-2.51 (1 H, m), 4.03-4.12 (1H, m), 4.63-4.74 (2 H, m), 5.72-5.80 (1 H, m), 6.26-6.44 (2 H, m), 7.14-7.24 (4 H, m), 7.27-7.37 (6 H, m), 7.39-7.49 (2 H, m), 7.81-7.90 (2 H, m).

Reference Example 63

Ethyl 4-[4-(cyclopropylsulfonyl)phenyl]-3-oxo-5-(tetrahydro-2H-pyran-4-yl)pentanoate

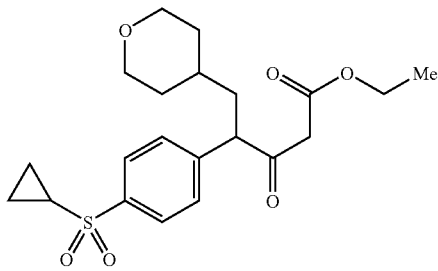

To a solution of 2-[4-(cyclopropylsulfonyl)phenyl]-3-(tetrahydro-2H-pyran-4-yl)propanoic acid (5.71 g) in tetrahydrofuran (30 mL) was added 1,1'-carbonyldiimidazole (3.29 g), and the mixture was purged with nitrogen, and stirred at room temperature for 2 hr. To the reaction solution were added magnesium dichloride (1.61 g) and malonic acid monoethyl ester potassium salt (2.88 g), and the mixture was stirred at 60° C. for 2 hr. The reaction mixture was acidified with 1M hydrochloric acid, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=20:80-60:40, volume ratio) to give the title compound (4.45 g, yield 64%) as a colorless oil. MS: 409 (MH$^+$).

Reference Example 64

Ethyl 4-[4-(cyclopropylsulfonyl)phenyl]-3-oxo-2-[2-oxo-2-(1,3-thiazol-2-yl)ethyl]-5-(tetrahydro-2H-pyran-4-yl)pentanoate

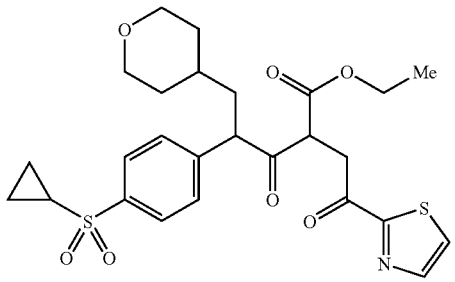

A suspension of sodium hydride (60%, oil, 241 mg) in tetrahydrofuran (15 mL) was purged with nitrogen, a solution of ethyl 4-[4-(cyclopropylsulfonyl)phenyl]-3-oxo-5-(tetrahydro-2H-pyran-4-yl)pentanoate (2.05 g) in tetrahydrofuran (15 mL) was added under ice-cooling, and the reaction solution was stirred at 0° C. for 15 min. A solution of 2-bromo-1-(1,3-thiazol-2-yl)ethanone (1.24 g) in tetrahydrofuran (20 mL) was added dropwise at 0° C. to the reaction mixture. The reaction solution was warmed to room temperature, and stirred at room temperature for 20 hr. A saturated aqueous ammonium chloride solution was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=40:60-100:0, volume ratio) and preparative HPLC to give the title compound (0.637 g, yield 24%) as a colorless oil. MS: 534 (MH$^+$).

Reference Example 65

5-(benzyloxy)pyridine-2-carbaldehyde

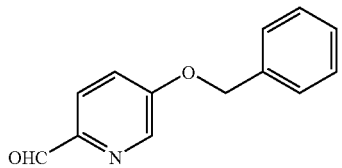

A solution of 6-bromopyridin-3-ol (4.20 g) in N,N-dimethylformamide (100 mL) was purged with nitrogen, sodium hydride (60%, oil, 1.06 g) was added under ice-cooling, and the mixture was stirred at 0° C. for 15 min. Benzyl bromide (3.15 mL) was added to the reaction mixture, and the mixture was warmed to room temperature, and stirred at room temperature for 16 hr. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=10:90-50:50, volume ratio) to give a colorless oil. A solution of the obtained oil in toluene (10 mL) was added to a solution of tributylmagnesium ate complex in toluene-tetrahydrofuran-hexane prepared from a 1.6M n-butyllithium hexane solution (8.4 mL) and a 2.0M butylmagnesium chloride tetrahydrofuran solution (3.4 mL) in at −10° C., and the mixture was stirred at −10° C. for 2.5 hr. N,N-dimethylformamide (1.59 mL) was added to the reaction mixture, and the mixture was warmed to room temperature and stirred at room temperature for 2 hr. 10% Aqueous citric acid solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=5:95-50:50, volume ratio) to give the title compound (1.00 g, yield 17%) as a colorless oil. MS: 214 (MH$^+$).

Reference Example 66

2-[4-(ethylsulfonyl)phenyl]-3-(tetrahydro-2H-pyran-4-yl)propanoic acid

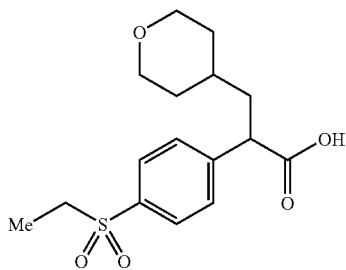

To a solution of 1-bromo-4-(ethylsulfonyl)benzene (1.50 g) in 1,4-dioxane (20 mL) were added diethyl malonate (1.16 g), potassium phosphate (3.84 g), biphenyl-2-yl(di-tert-butyl)phosphine (108 mg) and palladium acetate (II) (40 mg). The reaction solution was purged with argon, and the mixture was heated under reflux for 12 hr. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=10:90-50:50, volume ratio) to give a colorless oil. A solution of the obtained oil in N,N-dimethylformamide (20 mL) was purged with nitrogen, sodium hydride (60%, oil, 213 mg) was added under ice-cooling, and the mixture was stirred at 0° C. for 15 min. To the reaction solution was added a solution of 4-(iodomethyl)tetrahydro-2H-pyran (1.15 g) in N,N-dimethylformamide (10 mL) at 0° C., and the mixture was stirred for 3 hr at 90° C. The reaction mixture was concentrated under reduced pressure, saturated aqueous ammonium chloride solution was added to the residue, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=10:90-40:60, volume ratio) to give a colorless oil. To a solution of the obtained oil in a mixed solvent of tetrahydrofuran (40 mL) and methanol (20 mL) was added 2M aqueous sodium hydroxide solution (10 mL), and the mixture was stirred at 60° C. for 3 hr. The reaction solution was cooled to room temperature, and acidified with 1M hydrochloric acid, and the mixture was extracted with ethyl acetate. The extract was washed successively with water and saturated brine, dried over anhydrous magnesium sulfate and concentrated under reduced pressure. The residue was recrystallized from hexane-ethyl acetate to give the title compound (1.33 g, yield 67%) as colorless crystals. MS: 327 (MH$^+$).

Reference Example 67

4-[4-(ethylsulfonyl)phenyl]-5-(tetrahydro-2H-pyran-4-yl)pent-1-en-3-one

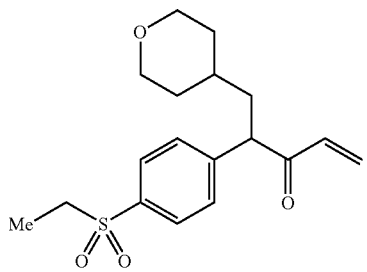

To a solution of 2-[4-(ethylsulfonyl)phenyl]-3-(tetrahydro-2H-pyran-4-yl)propanoic acid (1.30 g) in N,N-dimethylformamide (20 mL) were added N-methoxymethanamine hydrochloride (582 mg), triethylamine (1.67 mL), N-[3-(dimethylamino)propyl]-N'-ethylcarbodiimide hydrochloride (840 mg) and 1-hydroxybenzotriazole (670 mg), and the mixture was stirred at room temperature for 3 days. Water was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=50:50-0:100, volume ratio) to give a colorless oil. A solution of the obtained oil in tetrahydrofuran (40 mL) was purged with nitrogen, and a 1.0M vinylmagnesium bromide tetrahydrofuran solution (12 mL) was added under ice-cooling. The reaction solution was warmed to room temperature, and the mixture was stirred at room temperature for 1 hr. The reaction mixture was added to 1M hydrochloric acid, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=20:80-80:20, volume ratio) to give the title compound (1.20 g, yield 90%) as a colorless oil. MS: 337 (MH$^+$).

Reference Example 68

2-{4-[(3-methoxypropyl)sulfonyl]phenyl}-3-(tetrahydro-2H-pyran-4-yl)propanoic acid

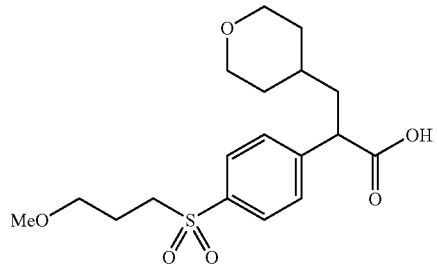

In the same manner as in Reference Example 66, the title compound (6.10 g, yield 84%) as a colorless oil from 1-bromo-4-[(3-methoxypropyl)sulfonyl]benzene (5.62 g). MS: 371 (MH+).

Reference Example 69

4-{4-[(3-methoxypropyl)sulfonyl]phenyl}-5-(tetrahydro-2H-pyran-4-yl)pent-1-en-3-one

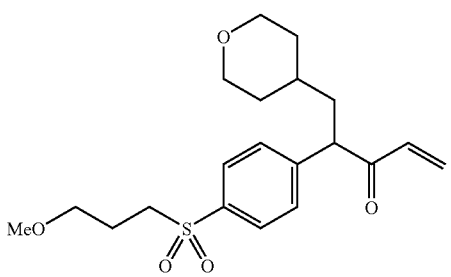

In the same manner as in Reference Example 67, the title compound (4.44 g, yield 72%) as a colorless oil from 2-{4-[(3-methoxypropyl)sulfonyl]phenyl}-3-(tetrahydro-2H-pyran-4-yl)propanoic acid (6.10 g). MS: 381 (MH+).

Reference Example 70

2-bromo-5-(2-methylprop-1-en-1-yl)pyridine

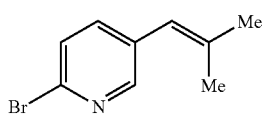

To a solution of (1-methylethyl)(triphenyl)phosphonium iodide (72.2 g) in N,N-dimethylformamide (200 mL) was added a solution of potassium tert-butoxide (20.1 g) in N,N-dimethylformamide (100 mL) under ice-cooling, and the mixture was stirred at 0° C. for 30 min. To the reaction solution was added dropwise at 0° C. a solution of 6-bromopyridine-3-carbaldehyde (20.8 g) in N,N-dimethylformamide (200 mL). The reaction solution was warmed to room temperature, and the mixture was stirred at room temperature for 16 hr. A saturated aqueous ammonium chloride solution was added to the reaction mixture, and the mixture was extracted with diethyl ether. The extract was washed successively with water and saturated brine, dried over anhydrous sodium sulfate, and concentrated under reduced pressure. The residue was purified by silica gel column chromatography (ethyl acetate:hexane=1:99-40:60, volume ratio) to give the title compound (16.2, yield 68%) as a colorless oil.

$^1$H NMR (CDCl$_3$) δ1.84 (3 H, d, J=1.3 Hz), 1.92 (3 H, d, J=1.3 Hz), 6.14 (1 H, s), 7.34-7.45 (2 H, m), 8.22 (1 H, d, J=2.3 Hz).

Reference Example 71

5-(2-methylprop-1-en-1-yl)pyridine-2-carbaldehyde

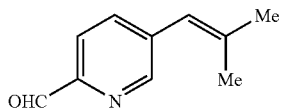

Under a nitrogen atmosphere, a 2.0M butylmagnesium chloride tetrahydrofuran solution (11.2 mL) was diluted with tetrahydrofuran (200 mL). The reaction solution was cooled to −10° C., a 1.6M n-butyllithium hexane solution (28.1 mL) was added dropwise, and the mixture was stirred at −10° C. for 10 min. To the reaction solution was added dropwise a solution (50 mL) of 2-bromo-5-(2-methylprop-1-en-1-yl)pyridine (11.9 g) in tetrahydrofuran, and the mixture was stirred at −10° C. for 30 min. To the reaction solution was added N,N-dimethylformamide (8.65 mL), and the mixture was stirred at −10° C. for 3 hr. A saturated aqueous ammonium chloride solution was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=1:99-10:90, volume ratio) to give the title compound (7.47 g, yield 83%) as a pale-yellow oil.

$^1$H NMR (CDCl$_3$) δ1.93 (3 H, s), 1.99 (3 H, s), 6.29 (1 H, s), 7.71 (1 H, d, J=8.0 Hz), 7.93 (1 H, d, J=8.0 Hz), 8.65 (1 H, s), 10.06 (1 H, s).

Reference Example 72

5-(1,2-dihydroxy-2-methylpropyl)pyridine-2-carbaldehyde

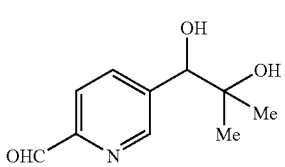

To a solution of 5-(2-methylprop-1-en-1-yl)pyridine-2-carbaldehyde (9.40 g) in a mixed solvent of dimethylsulfoxide (230 mL) and water (1.89 mL) was added N-bromosuccinimide (18.7 g) at 0° C. The reaction solution was warmed to room temperature and stirred at room temperature for 1 hr. To the reaction mixture was added saturated aqueous sodium hydrogen carbonate solution, and the mixture was extracted with ethyl acetate. The extract was washed successively with water and saturated brine, dried over anhydrous sodium sulfate, and concentrated under reduced pressure. To a solution of the residue in tetrahydrofuran (200 mL) was added 4.5M aqueous sulfuric acid solution, and the mixture was stirred at room temperature for 3 hr. The reaction mixture was neutralized with aqueous sodium hydroxide solution and saturated aqueous sodium hydrogen carbonate solution, and the mixture was extracted with ethyl acetate. The extract was washed successively with water and saturated brine, dried over anhydrous sodium sulfate, and concentrated under reduced pressure. The residue was purified by silica gel column chroma-

Reference Example 73

2-(1-[(benzyloxy)methyl]-5-{1-[4-(cyclopropylsulfonyl)phenyl]-2-(tetrahydro-2H-pyran-4-yl)ethyl}-1H-pyrrol-2-yl)-5-bromopyridine

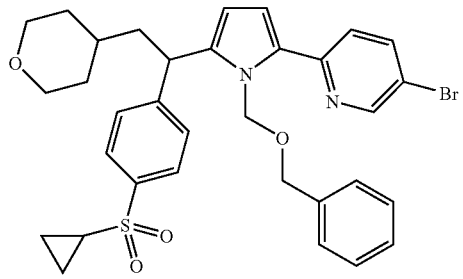

To a solution of 5-bromo-2-(5-{1-[4-(cyclopropylsulfonyl)phenyl]-2-(tetrahydro-2H-pyran-4-yl)ethyl}-1H-pyrrol-2-yl)pyridine (3.00 g) in N,N-dimethylformamide (25 mL) was added sodium hydride (60%, oil, 279 mg) under ice-cooling, and the mixture was stirred at 0° C. for 10 min. To the reaction solution was added [(chloromethoxy)methyl]benzene (0.970 mL), and the mixture was stirred at 0° C. for 3 hr. A saturated aqueous ammonium chloride solution was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=10:90-50:50, volume ratio) to give the title compound (2.91 g, yield 79%) as a colorless amorphous solid.

$^1$H NMR (CDCl$_3$) δ0.96-1.06 (2 H, m), 1.22-1.41 (4 H, m), 1.45-1.68 (5 H, m), 1.69-1.82 (1 H, m), 1.97-2.10 (1 H, m), 2.35-2.47 (1 H, m), 3.14-3.35 (2 H, m), 3.79-3.95 (2H, m), 4.21-4.48 (3 H, m), 5.31 (1 H, d, J=10.6 Hz), 6.09 (1H, d, J=10.6 Hz), 6.32 (1 H, d, J=3.8 Hz), 6.60 (1 H, d, J=3.8 Hz), 7.03-7.12 (2 H, m), 7.22-7.31 (3 H, m), 7.43 (1 H, d, J=8.7 Hz), 7.72-7.78 (3 H, m), 8.41 (1 H, d, J=2.3 Hz).

Reference Example 74

Ethyl [6-(methylsulfanyl)pyridin-3-yl]acetate

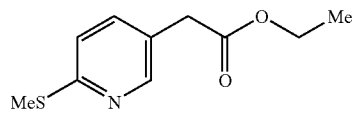

To a solution of ethyl (6-chloropyridin-3-yl)acetate (10.7 g) in N,N-dimethylformamide (100 mL) was added sodium methanethiolate (11.3 g), and the mixture was stirred at room temperature for 23 hr. The reaction mixture was diluted with ethyl acetate, washed successively with water and saturated brine, dried over anhydrous sodium sulfate, and concentrated under reduced pressure. The residue was purified by silica gel column chromatography (ethyl acetate:hexane=5:95-50:50, volume ratio) to give the title compound (4.55 g, yield 40%) as a colorless oil. MS: 212 (MH$^+$).

Reference Example 75

Ethyl 2-[6-(methylsulfanyl)pyridin-3-yl]-3-(tetrahydro-2H-pyran-4-yl)propanoate

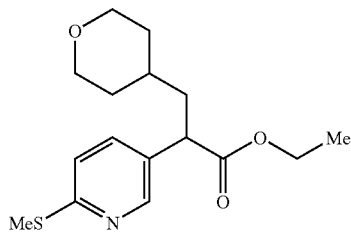

A solution of N,N-diisopropylamine (3.65 mL) in tetrahydrofuran (50 mL) was purged with nitrogen, a 1.6M n-butyllithium hexane solution (16.1 mL) was added at −78° C., and the mixture was stirred at −78° C. for 30 min. To the reaction solution was added dropwise a solution of ethyl [6-(methylsulfanyl)pyridin-3-yl]acetate (4.55 g) in tetrahydrofuran (40 mL), and the mixture was stirred at −78° C. for 30 min. To the reaction solution was added a solution of 4-(iodomethyl)tetrahydro-2H-pyran (5.83 mL) in tetrahydrofuran (40 mL), and the mixture was stirred at −78° C. for 2 hr. The reaction solution was warmed to room temperature, and stirred at room temperature for 3 days. A saturated aqueous ammonium chloride solution was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=10:90-50:50, volume ratio) to give the title compound (3.90 g, yield 59%) as a pale-yellow oil. MS: 310 (MH$^+$).

Reference Example 76

N-methoxy-N-methyl-2-[6-(methylsulfanyl)pyridin-3-yl]-3-(tetrahydro-2H-pyran-4-yl)propanamide

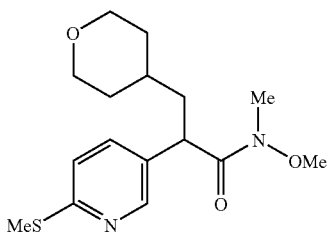

To a solution of ethyl 2-[6-(methylsulfanyl)pyridin-3-yl]-3-(tetrahydro-2H-pyran-4-yl)propanoate (3.90 g) in a mixed solvent of tetrahydrofuran (80 mL) and methanol (40 mL) was added 2M aqueous sodium hydroxide solution (20 mL), and the mixture was stirred at 50° C. for 2 hr. The reaction mixture was acidified with 10% aqueous citric acid solution, and extracted with ethyl acetate. The extract was washed successively with water and saturated brine, dried over anhydrous sodium sulfate, and concentrated under reduced pressure. To a solution of the residue in N,N-dimethylformamide (25 mL) were added N-methoxymethanamine hydrochloride (1.36 g), triethylamine (5.28 mL), N-[3-(dimethylamino)propyl]-N'-ethylcarbodiimide hydrochloride (2.66 g) and 1-hydroxybenzotriazole (2.13 g), and the mixture was stirred at room temperature for 24 hr. The reaction mixture was concentrated, and the residue was purified by silica gel column chromatography (ethyl acetate:hexane=50:50-0:100, volume ratio) and basic silica gel column chromatography (ethyl acetate:hexane=30:70-100:0, volume ratio) to give the title compound (2.80 g, yield 68%) as a colorless oil. MS: 325 (MH$^+$).

Reference Example 77

4-[6-(methylsulfanyl)pyridin-3-yl]-5-(tetrahydro-2H-pyran-4-yl)pent-1-en-3-one

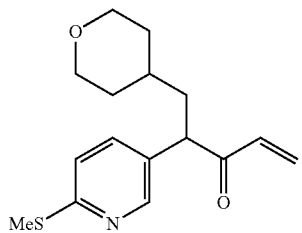

A solution of N-methoxy-N-methyl-2-[6-(methylsulfanyl)pyridin-3-yl]-3-(tetrahydro-2H-pyran-4-yl)propanamide (2.80 g) in tetrahydrofuran (30 mL) was purged with nitrogen, a 1.0M vinylmagnesium bromide tetrahydrofuran solution was added under ice-cooling, and the mixture was stirred at 0° C. for 30 min, and at room temperature for 6 hr. The reaction mixture was poured into saturated aqueous ammonium chloride solution, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=5:95-50:50, volume ratio) to give the title compound (1.00 g, yield 34%) as a colorless oil. MS: 292 (MH$^+$).

Reference Example 78

2-(4,5-diiodo-1H-imidazol-2-yl)pyridine

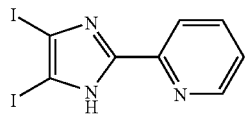

To a solution of 2-(1H-imidazol-2-yl)pyridine (11.3 g) in N,N-dimethylformamide (250 mL) was added N-succinimide (37.5 g), and the mixture was stirred at room temperature for 24 hr and at 80° C. for 4 hr. Water was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate) and basic silica gel column chromatography (ethyl acetate) to give the title compound (26.8 g, yield 86%) as pale-brown crystals. melting point 177-179° C.

Reference Example 79

2-(4,5-diiodo-1-{[2-(trimethylsilyl)ethoxy]methyl}-1H-imidazol-2-yl)pyridine

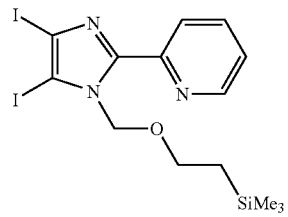

A solution of 2-(4,5-diiodo-1H-imidazol-2-yl)pyridine (8.00 g) in N,N-dimethylformamide (80 mL) was purged with nitrogen, sodium hydride (60%, oil, 972 mg) was added under ice-cooling, and the mixture was stirred at 0° C. for 15 min. To the reaction solution was added [2-(chloromethoxy)ethyl](trimethyl)silane (4.28 mL), and the mixture was stirred at 0° C. for 30 min. The reaction solution was warmed to room temperature, and stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=1:99-40:60, volume ratio) to give the title compound (9.00 g, yield 85%) as a pale-yellow oil.
$^1$H NMR (CDCl$_3$) δ-0.12 (9 H, s), 0.79-0.90 (2 H, m), 3.43-3.58 (2 H, m), 6.21 (2 H, s), 7.25-7.32 (1 H, m), 7.75-7.82 (1 H, m), 8.13-8.18 (1 H, m), 8.57-8.62 (1 H, m).

Reference Example 80

2-(5-iodo-1H-imidazol-2-yl)pyridine

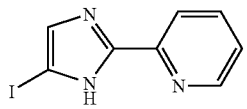

To a solution of 2-(4,5-diiodo-1H-imidazol-2-yl)pyridine (18.6 g) in a mixed solvent of N,N-dimethylformamide (200 mL) and water (100 ml) was added sodium sulfite (35.4 g), and the mixture was stirred at 120° C. for 24 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=1:99-20:80, volume ratio) to give the title compound (11.2 g, yield 88%) as colorless crystals. melting point 175-179° C.

Reference Example 81

2-(4-chloro-5-iodo-1H-imidazol-2-yl)pyridine

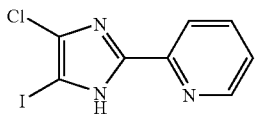

To 5% aqueous sodium chlorite solution (180 mL) was added sodium hydroxide (737 mg) and completely dissolved. To the reaction solution was added 2-(5-iodo-1H-imidazol-2-yl)pyridine (5.00 g), and the mixture was stirred at room temperature for 24 hr. The reaction mixture was adjusted to pH 3 to 4 with 1M hydrochloric acid, and the mixture was extracted with ethyl acetate. The extract was washed successively with water and saturated brine, dried over anhydrous sodium sulfate, and concentrated under reduced pressure. The residue was purified by basic silica gel column chromatography (ethyl acetate:hexane=30:70-100:0, volume ratio) to give the title compound (3.57 g, yield 63%) as colorless crystals. melting point 188-189° C.

Reference Example 82

2-(4-chloro-5-iodo-1-{[2-(trimethylsilyl)ethoxy]methyl}-1H-imidazol-2-yl)pyridine

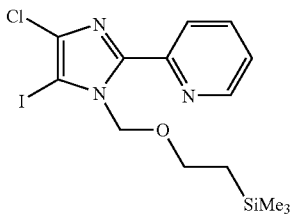

In the same manner as in Reference Example 79, the title compound (4.55 g, yield 91%) was obtained as a colorless oil from 2-(4-chloro-5-iodo-1H-imidazol-2-yl)pyridine (3.52 g). MS: 436 (MH$^+$).

Reference Example 83

3-chloro-4-(methylsulfanyl)benzaldehyde

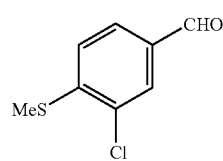

A solution of 3-chloro-4-fluorobenzaldehyde (50.0 g) in N,N-dimethylformamide (350 mL) was cooled to −10° C., and sodium methanethiolate (25 g) was added. The reaction solution was warmed to room temperature, and stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was recrystallized from hexane-ethyl acetate to give the title compound (33.6 g, yield 59%) as colorless crystals. The mother liquor was concentrated under reduced pressure, and the residue was purified by silica gel column chromatography (ethyl acetate:hexane=5:95-30:70, volume ratio) and recrystallized from hexane-ethyl acetate to give the title compound (12.3 g, yield 21%) as colorless crystals. melting point 58-59° C.

Reference Example 84

[3-chloro-4-(methylsulfanyl)phenyl](morpholin-4-yl)acetonitrile

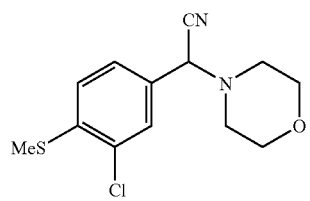

To a solution of 3-chloro-4-(methylsulfanyl)benzaldehyde (12.3 g) in tetrahydrofuran (50 mL) were added morpholine (13.4 mL), p-toluenesulfonic acid monohydrate (10.8 g) and a solution of potassium cyanide (4.50 g) in water (10 mL), and the mixture was heated under reflux for 16 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate), and recrystallized from hexane-ethyl acetate to give the title compound (14.0 g, yield 95%) as colorless crystals.
$^1$H NMR (CDCl$_3$) δ2.50 (3 H, s), 2.58 (4 H, t, J=4.6 Hz), 3.66-3.81 (4 H, m), 4.76 (1 H, s), 7.17 (1 H, d, J=8.3 Hz), 7.43 (1 H, dd, J=1.3, 8.3 Hz), 7.53 (1 H, d, J=1.3 Hz).

Reference Example 85

1-[3-chloro-4-(methylsulfanyl)phenyl]-2-(tetrahydro-2H-pyran-4-yl)ethanone

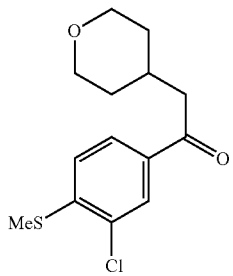

A solution of [3-chloro-4-(methylsulfanyl)phenyl](morpholin-4-yl)acetonitrile (2.70 g) in N,N-dimethylformamide (30 mL) was purged with nitrogen, sodium hydride (60%, oil, 420 mg) was added under ice-cooling, and the mixture was stirred at 0° C. for 10 min. To the reaction solution was added a solution of 4-(iodomethyl)tetrahydro-2H-pyran (2.37 g) in N,N-dimethylformamide (10 mL), and the mixture was stirred at 0° C. for 30 min. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=10:90-70:30, volume ratio) to give a yellow oil. A mixture of the obtained oil and 80% aqueous acetic acid solution (100 mL) was stirred at 100° C. for 8 hr. The reaction mixture was neutralized with saturated aqueous sodium carbonate solution, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=5:95-50:50, volume ratio) to give the title compound (2.20 g, yield 81%) as yellow crystals. MS: 285 (MH$^+$).

Reference Example 86

1-[3-chloro-4-(methylsulfanyl)phenyl]-1-(4-iodo-2-(pyridin-2-yl)-1-{[2-(trimethylsilyl)ethoxy]methyl}-1H-imidazol-5-yl)-2-(tetrahydro-2H-pyran-4-yl)ethanol

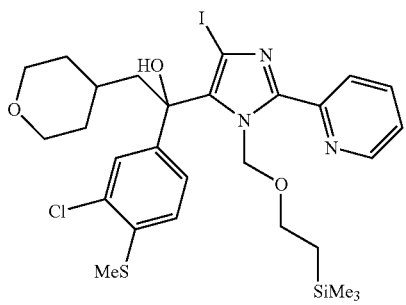

A solution of 2-(4,5-diiodo-1-{[2-(trimethylsilyl)ethoxy]methyl}-1H-imidazol-2-yl)pyridine (1.53 g) in tetrahydrofuran (15 mL) was purged with nitrogen, and a 3.0M ethylmagnesium bromide diethyl ether solution (1.01 ml) was added under ice-cooling. The reaction solution was warmed to room temperature, and the mixture was stirred at room temperature for 30 min. To the reaction solution was added dropwise a solution of 1-[3-chloro-4-(methylsulfanyl)phenyl]-2-(tetrahydro-2H-pyran-4-yl)ethanone (691 mg) in tetrahydrofuran (10 mL) at 0° C. The reaction solution was warmed to room temperature, and stirred at room temperature for 4 hr. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=10:90-100:0, volume ratio) to give the title compound (0.521 g, yield 31%) as a colorless oil. MS: 686 (MH$^+$).

Reference Example 87

1-[3-chloro-4-(methylsulfanyl)phenyl]-1-(4-chloro-2-pyridin-2-yl-1-{[2-(trimethylsilyl)ethoxy]methyl}-1H-imidazol-5-yl)-2-(tetrahydro-2H-pyran-4-yl)ethanol

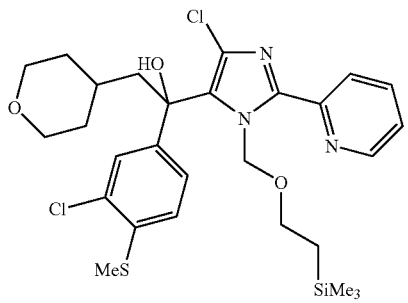

In the same manner as in Reference Example 86, the title compound (1.47 g, yield 55%) was obtained as a colorless amorphous solid from 2-(4-chloro-5-iodo-1-{[2-(trimethylsilyl)ethoxy]methyl}-1H-imidazol-2-yl)pyridine (2.35 g) and 1-[3-chloro-4-(methylsulfanyl)phenyl]-2-(tetrahydro-2H-pyran-4-yl)ethanone (1.28 g). MS: 594 (MH$^+$).

Reference Example 88

Ethyl (2-bromo-1,3-thiazol-4-yl)(oxo) acetate

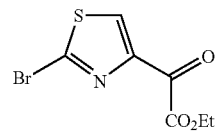

To a mixture of ethyl (2-amino-1,3-thiazol-4-yl)(oxo)acetate (8.33 g), copper(II) bromide (9.80 g) and acetonitrile (60 mL) was added at 0° C. tert-butyl nitrite (7.16 g) over 1 hr, and the mixture was stirred at room temperature for 2 hr. The reaction mixture was concentrated, and the obtained residue was subjected to silica gel column chromatography, and the title compound (7.17 g, yield 65%) was obtained as a yellow oil from a fraction eluted with ethyl acetate-hexane (1:6, volume ratio). MS: 266 (MH$^+$).

Reference Example 89

2-bromo-4-(2,2-dimethyl-1,3-dioxolan-4-yl)-1,3-thiazole

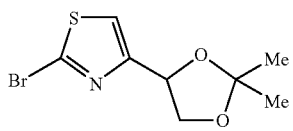

To a solution of ethyl (2-bromo-1,3-thiazol-4-yl)(oxo)acetate (7.17 g) in ethanol (50 mL) was slowly added at 0° C. sodium borohydride (2.28 g), and the mixture was stirred at 0° C. for 1 hr, then at room temperature for 2 hr. To the reaction mixture was slowly added a solution of citric acid (11.6 g) in water (30 mL). After completion of hydrogen gas generation, the inorganic salt was filtered off, and the filtrate was extracted 5 times with ethyl acetate. The ethyl acetate layers were combined, dried (MgSO$_4$) and concentrated to give a colorless oil (6.55 g). A mixture of the obtained oil (6.55 g), 2,2-dimethoxypropane (5.64 g), p-toluenesulfonic acid monohydrate (0.26 g) and acetone (80 mL) was stirred with heating under reflux for 1 hr. The reaction mixture was concentrated, and the residue was subjected to silica gel column chromatography, and the title compound (6.10 g, yield 85%) was obtained as a colorless oil from a fraction eluted with ethyl acetate-hexane (1:6, volume ratio).

$^1$H NMR (300 MHz, CDCl$_3$) δ1.46 (3 H, s), 1.52 (3 H, s), 3.99 (1H, dd, J=6.3, 8.4 Hz), 4.37 (1 H, dd, J=6.6, 8.4 Hz), 5.20 (1H, ddd, J=0.9, 6.3, 6.6 Hz), 7.23 (1 H, d, J=0.9 Hz).

Reference Example 90

4-(2,2-dimethyl-1,3-dioxolan-4-yl)-1,3-thiazole-2-carbaldehyde

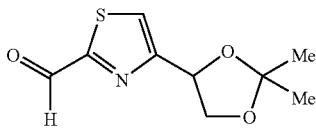

To a solution of 2-bromo-4-(2,2-dimethyl-1,3-dioxolan-4-yl)-1,3-thiazole (3.00 g) in tetrahydrofuran (40 mL) was slowly added a 1.6M n-butyllithium hexane solution (7.8 mL) at −70° C. under a nitrogen atmosphere. The reaction mixture was stirred at −70° C. for 1 hr, and N,N-dimethylformamide (2.50 g) was added. The reaction mixture was warmed to room temperature, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography, and the title compound (1.03 g, yield 42%) was obtained as a colorless oil from a fraction eluted with ethyl acetate-hexane (1:5, volume ratio).

$^1$H NMR (300 MHz, CDCl$_3$) δ1.49 (3 H, s), 1.53 (3 H, s), 4.05 (1H, dd, J=6.6, 8.4 Hz), 4.44 (1 H, dd, J=6.6, 8.4 Hz), 5.33 (1H, t, J=6.6 Hz), 7.72 (1 H, d, J=1.1 Hz), 9.94 (1 H, t, J=1.1 Hz).

Reference Example 91

5-[4-(cyclopropylsulfonyl)phenyl]-1-[4-(2,2-dimethyl-1,3-dioxolan-4-yl)-1,3-thiazol-2-yl]-6-(tetrahydro-2H-pyran-4-yl)hexane-1,4-dione

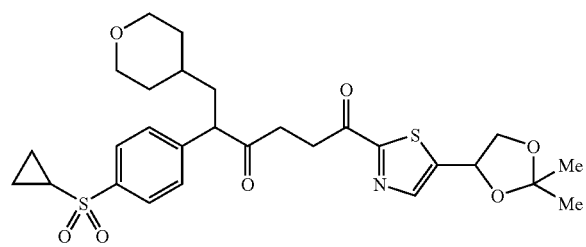

A mixture of 4-[4-(cyclopropylsulfonyl)phenyl]-5-(tetrahydro-2H-pyran-4-yl)pent-1-en-3-one (0.50 g), 4-(2,2-dimethyl-1,3-dioxolan-4-yl)-1,3-thiazole-2-carbaldehyde (0.37 g), 3-benzyl-5-(2-hydroxyethyl)-4-methyl-1,3-thiazol-3-ium chloride (43 mg), triethylamine (0.09 mL) and ethanol (6 mL) was stirred with heating under reflux for 2 hr. The reaction mixture was concentrated, the residue was subjected to basic silica gel column chromatography, and the title compound (0.47% g, yield 60%) was obtained as a yellow oil from a fraction eluted with ethyl acetate-hexane (2:1, volume ratio). MS: 562 (MH$^+$).

Reference Example 92

5-[(tetrahydro-2H-pyran-2-yloxy)methyl]-1,3-thiazole

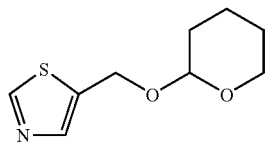

A mixture of 2-chloro-5-[(tetrahydro-2H-pyran-2-yloxy)methyl]-1,3-thiazole (10.4 g), 10% palladium carbon (containing 50% water, 2.0 g), potassium carbonate (6.2 g) and methanol (10 mL) was stirred under hydrogen atmosphere (5 atm) at 60° C. for 10 hr. The insoluble material was filtered off, and the filtrate was concentrated. Water was added to the residue, and the mixture was extracted with ethyl acetate. The ethyl acetate layer was washed with saturated brine, dried (MgSO$_4$) and concentrated. The obtained residue was subjected to silica gel column chromatography, and the title compound (6.97 g, yield 79%) was obtained as a colorless oil from a fraction eluted with ethyl acetate-hexane (1:2, volume ratio).

$^1$H NMR (300 MHz, CDCl$_3$) δ1.48-1.90 (6 H, m), 3.52-3.60 (1 H, m), 3.84-3.93 (1 H, m), 4.72 (1 H, t, J=3.3 Hz), 4.77 (1 H, d, J=12.6 Hz), 4.94 (1 H, dd, J=0.9, 12.6 Hz), 7.80 (1 H, d, J=0.9 Hz), 8.78 (1 H, s).

Reference Example 93

5-[(tetrahydro-2H-pyran-2-yloxy)methyl]-1,3-thiazole-2-carbaldehyde

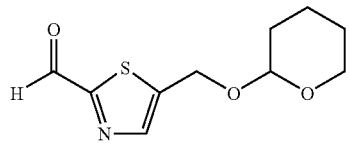

To a solution of 5-[(tetrahydro-2H-pyran-2-yloxy)methyl]-1,3-thiazole (7.44 g) in tetrahydrofuran (100 mL) was slowly added a 1.6M n-butyllithium hexane solution (25.6 mL) at −70° C. under a nitrogen atmosphere. The reaction mixture was stirred at −70° C. for 30 min and N,N-dimethylformamide (8.0 g) was added. The reaction mixture was warmed to room temperature, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography, and the title compound (6.91 g, yield 82%) was obtained as a yellow oil from a fraction eluted with ethyl acetate-hexane (1:4, volume ratio). MS: 228 (MH⁺).

Reference Example 94

5-[4-(cyclopropylsulfonyl)phenyl]-6-(tetrahydro-2H-pyran-4-yl)-1-{5-[(tetrahydro-2H-pyran-2-yloxy)methyl]-1,3-thiazol-2-yl}hexane-1,4-dione

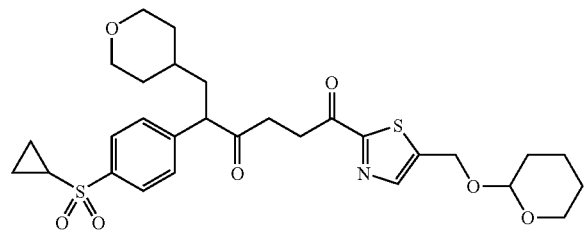

A mixture of 4-[4-(cyclopropylsulfonyl)phenyl]-5-(tetrahydro-2H-pyran-4-yl)pent-1-en-3-one (1.84 g), 5-[(tetrahydro-2H-pyran-2-yloxy)methyl]-1,3-thiazole-2-carbaldehyde (1.32 g), 3-benzyl-5-(2-hydroxyethyl)-4-methyl-1,3-thiazol-3-ium chloride (0.14 g), triethylamine (0.32 mL), tetrahydrofuran (5 mL) and ethanol (10 mL) was stirred with heating under reflux for 2 hr. The reaction mixture was concentrated, and the residue was subjected to basic silica gel column chromatography, and the title compound (2.43 g, yield 80%) was obtained as a yellow oil from a fraction eluted with ethyl acetate-hexane (2:1, volume ratio). MS: 576 (MH⁺).

Reference Example 95

5-[4-(cyclopropylsulfonyl)phenyl]-1-[5-(hydroxymethyl)-1,3-thiazol-2-yl]-6-(tetrahydro-2H-pyran-4-yl)hexane-1,4-dione

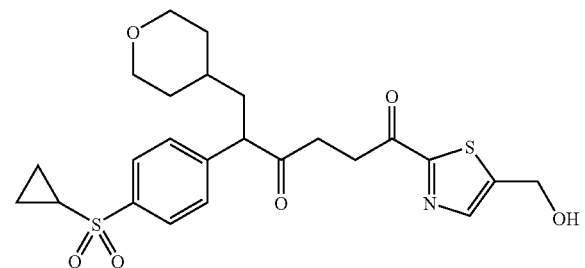

A mixture of 5-[4-(cyclopropylsulfonyl)phenyl]-6-(tetrahydro-2H-pyran-4-yl)-1-{5-[(tetrahydro-2H-pyran-2-yloxy)methyl]-1,3-thiazol-2-yl}hexane-1,4-dione (3.35 g), 1M hydrochloric acid (6 mL) and tetrahydrofuran (10 mL) was stirred overnight at room temperature. To the reaction mixture was added saturated aqueous sodium hydrogen carbonate, and the mixture was extracted with ethyl acetate. The ethyl acetate layer was washed with saturated brine, dried (MgSO₄) and concentrated. The obtained residue was subjected to silica gel column chromatography, and the title compound (1.83 g, yield 73%) was obtained as a colorless oil from a fraction eluted with ethyl acetate. MS: 492 (MH⁺).

Reference Example 96

2-(1,3-dioxolan-2-yl)-1,3-thiazole-5-carbaldehyde

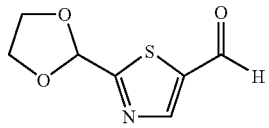

To a solution of 2-(1,3-dioxolan-2-yl)-1,3-thiazole (10.00 g) in tetrahydrofuran (150 mL) was slowly added a 1.6M n-butyllithium hexane solution (44 mL) at −70° C. under a nitrogen atmosphere. The reaction mixture was stirred at −70° C. for 1 hr and N,N-dimethylformamide (14 g) was added. The reaction mixture was warmed to room temperature, 10% aqueous citric acid solution was added, and the mixture was extracted with ethyl acetate. The ethyl acetate layer was washed with saturated brine, dried (MgSO₄) and concentrated. The obtained residue was subjected to silica gel column chromatography, and the title compound (6.64 g, yield 56%) was obtained as a colorless oil from a fraction eluted with ethyl acetate-hexane (3:2, volume ratio). MS: 186 (MH⁺).

Reference Example 97

1-[2-(1,3-dioxolan-2-yl)-1,3-thiazol-5-yl]ethanol

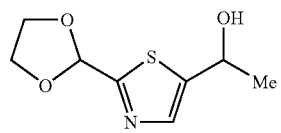

To a solution of 2-(1,3-dioxolan-2-yl)-1,3-thiazole-5-carbaldehyde (2.25 g) in tetrahydrofuran (20 mL) was slowly added a 1.13M methyllithium diethyl ether solution (12.0 mL) at 0° C. under a nitrogen atmosphere. The reaction mixture was stirred at 0° C. for 30 min, 10% aqueous citric acid solution was added, and the mixture was extracted with ethyl acetate. The ethyl acetate layer was washed with saturated brine, dried (MgSO₄) and concentrated. The obtained residue was subjected to silica gel column chromatography, and the title compound (1.96 g, yield 80%) was obtained as a colorless oil from a fraction eluted with ethyl acetate-hexane (1:2, volume ratio). MS: 202 (MH⁺).

Reference Example 98

5-(1-hydroxyethyl)-1,3-thiazole-2-carbaldehyde

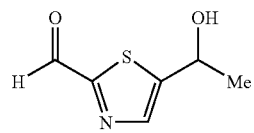

A mixture of 1-[2-(1,3-dioxolan-2-yl)-1,3-thiazol-5-yl]ethanol (1.96 g), 1M hydrochloric acid (8 mL) and acetone (20 mL) was stirred with heating under reflux for 3 hr. To the reaction mixture was added saturated aqueous sodium hydrogen carbonate, and the mixture was extracted with ethyl acetate. The ethyl acetate layer was washed with saturated brine, dried (MgSO$_4$) and concentrated. The obtained residue was subjected to silica gel column chromatography, and the title compound (0.60 g, yield 39%) was obtained as a colorless oil from a fraction eluted with ethyl acetate-hexane (2:1, volume ratio). MS: 158 (MH$^+$).

Reference Example 99

5-[4-(cyclopropylsulfonyl)phenyl]-1-[5-(1-hydroxyethyl)-1,3-thiazol-2-yl]-6-(tetrahydro-2H-pyran-4-yl)hexane-1,4-dione

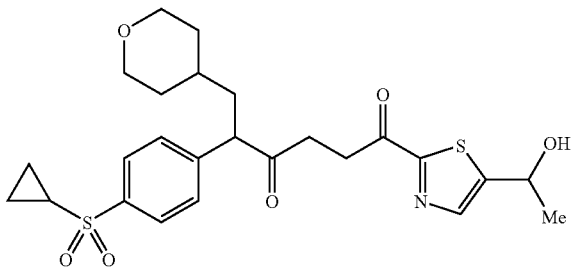

A mixture of 4-[4-(cyclopropylsulfonyl)phenyl]-5-(tetrahydro-2H-pyran-4-yl)pent-1-en-3-one (1.00 g), 5-(1-hydroxyethyl)-1,3-thiazole-2-carbaldehyde (0.47 g), 3-benzyl-5-(2-hydroxyethyl)-4-methyl-1,3-thiazol-3-ium chloride (77 mg), triethylamine (0.16 mL), tetrahydrofuran (6 ml) and ethanol (6 mL) was stirred with heating under reflux for 2 hr. The reaction mixture was concentrated, the residue was subjected to basic silica gel column chromatography, and eluted with ethyl acetate, and the fraction was concentrated. The residue was subjected to silica gel column chromatography, and the title compound (1.36 g, yield 94%) was obtained as a colorless oil from a fraction eluted with ethyl acetate-hexane (9:1, volume ratio). MS: 506 (MH$^+$).

Reference Example 100

1-[2-(1,3-dioxolan-2-yl)-1,3-thiazol-5-yl]-2-methoxyethanone

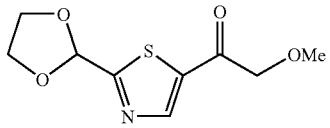

To a solution of 2-(1,3-dioxolan-2-yl)-1,3-thiazole (2.20 g) in tetrahydrofuran (50 mL) was slowly added a 1.6M n-butyllithium hexane solution (9.6 mL) at −70° C. under a nitrogen atmosphere. The reaction mixture was stirred at −70° C. for 1 hr, and methyl methoxyacetate (2.91 g) was added. The reaction mixture was warmed to room temperature, water was added, and the mixture was extracted with ethyl acetate. The ethyl acetate layer was washed with saturated brine, dried (MgSO$_4$) and concentrated. The obtained residue was subjected to silica gel column chromatography, and the title compound (2.00 g, yield 62%) was obtained as yellow crystals from a fraction eluted with ethyl acetate-hexane (1:1, volume ratio). melting point 65-66° C.

Reference Example 101

1-[2-(1,3-dioxolan-2-yl)-1,3-thiazol-5-yl]-2-methoxyethanol

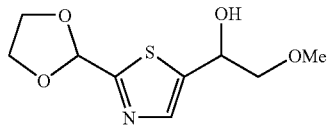

To a solution of 1-[2-(1,3-dioxolan-2-yl)-1,3-thiazol-5-yl]-2-methoxyethanone (2.00 g) in a mixed solvent of tetrahydrofuran (10 mL) and ethanol (10 mL) was slowly added sodium borohydride (0.18 g) at 0° C., and the mixture was stirred at room temperature for 30 min. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography, the title compound (1.84 g, yield 91%) was obtained as a colorless oil from a fraction eluted with ethyl acetate. MS: 232 (MH$^+$).

Reference Example 102

5-(1-hydroxy-2-methoxyethyl)-1,3-thiazole-2-carbaldehyde

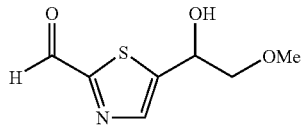

A mixture of 1-[2-(1,3-dioxolan-2-yl)-1,3-thiazol-5-yl]-2-methoxyethanol (1.84 g), 1M hydrochloric acid (8 mL) and acetone (20 mL) was stirred with heating under reflux for 3 hr. To the reaction mixture was added saturated aqueous sodium hydrogen carbonate, and the mixture was extracted with ethyl acetate. The ethyl acetate layer was washed with saturated brine, dried (MgSO$_4$) and concentrated. The obtained residue was subjected to silica gel column chromatography, and the title compound (1.04 g, yield 70%) was obtained as a colorless oil from a fraction eluted with ethyl acetate-hexane (2:1, volume ratio). MS: 188 (MH$^+$).

Reference Example 103

5-[4-(cyclopropylsulfonyl)phenyl]-1-[5-(1-hydroxy-2-methoxyethyl)-1,3-thiazol-2-yl]-6-(tetrahydro-2H-pyran-4-yl)hexane-1,4-dione

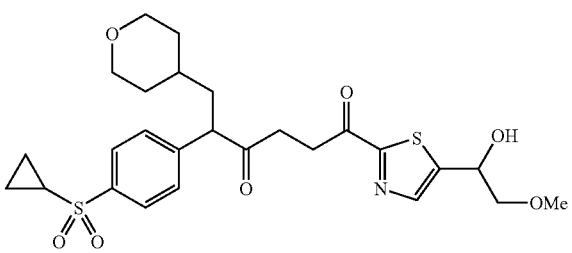

A mixture of 4-[4-(cyclopropylsulfonyl)phenyl]-5-(tetrahydro-2H-pyran-4-yl)pent-1-en-3-one (1.00 g), 5-(1-hydroxy-2-methoxyethyl)-1,3-thiazole-2-carbaldehyde (0.56 g), 3-benzyl-5-(2-hydroxyethyl)-4-methyl-1,3-thiazol-3-ium chloride (77 mg), triethylamine (0.16 mL), tetrahydro-

Reference Example 104

[2-(1,3-dioxolan-2-yl)-1,3-thiazol-5-yl]methanol

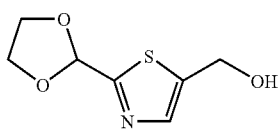

To a solution of 2-(1,3-dioxolan-2-yl)-1,3-thiazole-5-carbaldehyde (7.00 g) in methanol (30 mL) was slowly added sodium borohydride (0.53 g) at 0° C., and the mixture was stirred at 0° C. for 30 min. Water was added to the reaction mixture, and the mixture was extracted with ethyl acetate. The ethyl acetate layer was washed with saturated brine, dried (MgSO$_4$) and concentrated. The obtained residue was subjected to silica gel column chromatography, and the title compound (6.59 g, yield 93%) was obtained as a colorless oil from a fraction eluted with ethyl acetate. MS: 188 (MH$^+$).

Reference Example 105

2-(1,3-dioxolan-2-yl)-5-[(2-methoxyethoxy)methyl]-1,3-thiazole

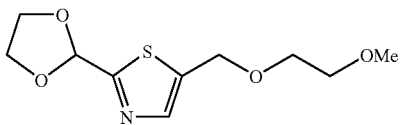

To a mixture of [2-(1,3-dioxolan-2-yl)-1,3-thiazol-5-yl]methanol (1.02 g), 1-bromo-2-methoxyethane (1.14 g), tetrahydrofuran (6 mL) and N,N-dimethylacetamide (6 mL) was slowly added sodium hydride (60%, oil, 0.28 g) at 0° C. The reaction mixture was stirred at room temperature overnight, water was added, and the mixture was extracted with ethyl acetate. The ethyl acetate layer was washed with saturated brine, dried (MgSO$_4$) and concentrated. The obtained residue was subjected to basic silica gel column chromatography, and the title compound (0.40 g, yield 29%) was obtained as a colorless oil from a fraction eluted with ethyl acetate-hexane (1:3, volume ratio). MS: 246 (MH$^+$).

Reference Example 106

5-[(2-methoxyethoxy)methyl]-1,3-thiazole-2-carbaldehyde

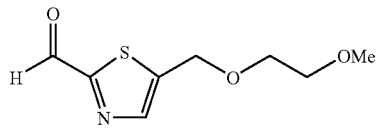

A mixture of 2-(1,3-dioxolan-2-yl)-5-[(2-methoxyethoxy)methyl]-1,3-thiazole (0.40 g), 1M hydrochloric acid (2 mL) and acetone (10 mL) was stirred with heating under reflux for 4 hr. To the reaction mixture was added saturated aqueous sodium hydrogen carbonate, and the mixture was extracted with ethyl acetate. The ethyl acetate layer was washed with saturated brine, dried (MgSO$_4$) and concentrated. The obtained residue was subjected to silica gel column chromatography, and the title compound (0.26 g, yield 81%) was obtained as a colorless oil from a fraction eluted with ethyl acetate-hexane (3:1, volume ratio).

$^1$H NMR (300 MHz, CDCl$_3$) δ 3.39 (3 H, s), 3.55-3.60 (2 H, m), 3.67-3.71 (2 H, m), 4.84 (2 H, d, J=0.6 Hz), 7.97 (1H, s), 9.93 (1 H, s).

Reference Example 107

5-[4-(cyclopropylsulfonyl)phenyl]-1-{5-[(2-methoxyethoxy)methyl]-1,3-thiazol-2-yl}-6-(tetrahydro-2H-pyran-4-yl)hexane-1,4-dione

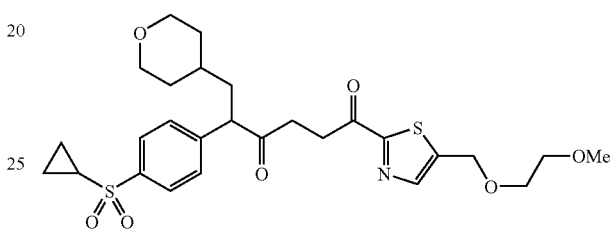

A mixture of 4-[4-(cyclopropylsulfonyl)phenyl]-5-(tetrahydro-2H-pyran-4-yl)pent-1-en-3-one (0.43 g), 5-[(2-methoxyethoxy)methyl]-1,3-thiazole-2-carbaldehyde (0.26 g), 3-benzyl-5-(2-hydroxyethyl)-4-methyl-1,3-thiazol-3-ium chloride (32 mg), triethylamine (0.07 mL), tetrahydrofuran (4 mL) and ethanol (4 mL) was stirred with heating under reflux for 2 hr. The reaction mixture was concentrated, and the residue was subjected to basic silica gel column chromatography, and the title compound (0.52 g, yield 79%) was obtained as a colorless oil from a fraction eluted with ethyl acetate-hexane (4:1, volume ratio). MS: 550 (MH$^+$).

Reference Example 108

2-[2-(1,3-dioxolan-2-yl)-1,3-thiazol-5-yl]-1,1-dimethoxypropan-2-ol

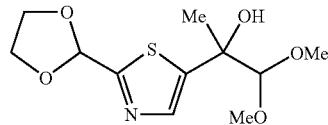

To a solution of 2-(1,3-dioxolan-2-yl)-1,3-thiazole (1.00 g) in tetrahydrofuran (20 mL) was slowly added a 1.6M n-butyllithium hexane solution (4.5 mL) at −70° C. under a nitrogen atmosphere. The reaction mixture was stirred at −70° C. for 30 min, and 1,1-dimethoxypropan-2-one (1.50 g) was added. The reaction mixture was warmed to room temperature, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography, and the title compound (1.58 g, yield 90%) was obtained as a yellow oil from a fraction eluted with ethyl acetate-hexane (9:1, volume ratio). MS: 276 (MH$^+$).

Reference Example 109

5-(1-hydroxy-2,2-dimethoxy-1-methylethyl)-1,3-thiazole-2-carbaldehyde

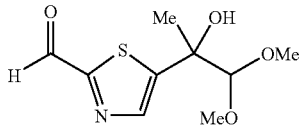

A mixture of 2-[2-(1,3-dioxolan-2-yl)-1,3-thiazol-5-yl]-1,1-dimethoxypropan-2-ol (1.58 g), 1M hydrochloric acid (5 ml) and acetone (15 mL) was stirred overnight at 60° C. To the reaction mixture was added saturated aqueous sodium hydrogen carbonate, and the mixture was extracted with ethyl acetate. The ethyl acetate layer was washed with saturated brine, dried ($MgSO_4$) and concentrated. The obtained residue was subjected to silica gel column chromatography, and the title compound (0.94 g, yield 71%) was obtained as colorless crystals from a fraction eluted with ethyl acetate-hexane (4:1, volume ratio). melting point 98-99° C.

Reference Example 110

5-[4-(cyclopropylsulfonyl)phenyl]-1-[5-(1-hydroxy-2,2-dimethoxy-1-methylethyl)-1,3-thiazol-2-yl]-6-(tetrahydro-2H-pyran-4-yl)hexane-1,4-dione

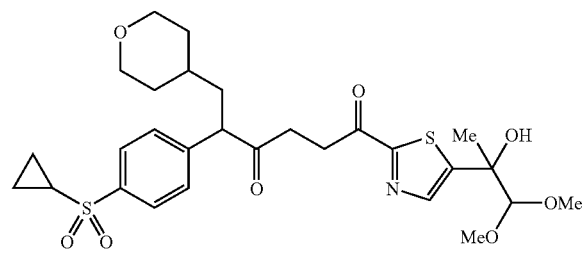

A mixture of 4-[4-(cyclopropylsulfonyl)phenyl]-5-(tetrahydro-2H-pyran-4-yl)pent-1-en-3-one (1.00 g), 5-(1-hydroxy-2,2-dimethoxy-1-methylethyl)-1,3-thiazole-2-carbaldehyde (0.73 g), 3-benzyl-5-(2-hydroxyethyl)-4-methyl-1,3-thiazol-3-ium chloride (77 mg), triethylamine (0.16 mL), tetrahydrofuran (8 mL) and ethanol (8 mL) was stirred with heating under reflux for 2 hr. The reaction mixture was concentrated, and the residue was subjected to basic silica gel column chromatography, and the title compound (1.14 g, yield 69%) was obtained as a colorless oil from a fraction eluted with ethyl acetate-hexane (9:1, volume ratio). MS: 580 ($MH^+$).

Reference Example 111

1-[2-(1,3-dioxolan-2-yl)-1,3-thiazol-5-yl]-2,2,2-trifluoroethanol

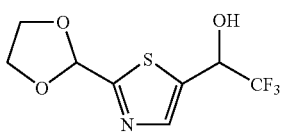

To a solution of 2-(1,3-dioxolan-2-yl)-1,3-thiazole (2.00 g) in tetrahydrofuran (50 mL) was slowly added a 1.6M n-butyllithium hexane solution (8.7 mL) at −70° C. under a nitrogen atmosphere. The reaction mixture was stirred at −70° C. for 30 min, and ethyl trifluoroacetate (5.4 g) was added. The reaction mixture was warmed to room temperature, 10% aqueous citric acid solution was added, and the mixture was extracted with ethyl acetate. The ethyl acetate layer was washed with saturated brine, dried ($MgSO_4$) and concentrated. The obtained residue was dissolved in methanol (30 mL), and sodium borohydride (0.27 g) was added by small portions at 0° C. The reaction mixture was stirred at 0° C. for 30 min, 10% aqueous citric acid solution was added, and the mixture was extracted with ethyl acetate. The ethyl acetate layer was washed with saturated brine, dried ($MgSO_4$) and concentrated. The obtained residue was subjected to silica gel column chromatography, and the title compound (2.56 g, yield 79%) was obtained as a yellow oil from a fraction eluted with ethyl acetate-hexane (1:1, volume ratio). MS: 256 ($MH^+$).

Reference Example 112

5-(2,2,2-trifluoro-1-hydroxyethyl)-1,3-thiazole-2-carbaldehyde

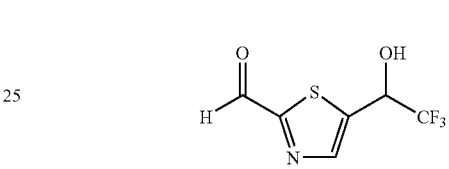

A mixture of 1-[2-(1,3-dioxolan-2-yl)-1,3-thiazol-5-yl]-2,2,2-trifluoroethanol (2.56 g), 1M hydrochloric acid (10 mL) and tetrahydrofuran (10 mL) was stirred with heating under reflux for 6 hr. Water was added to the reaction mixture, and the mixture was extracted with ethyl acetate. The ethyl acetate layer was washed with saturated brine, dried ($MgSO_4$) and concentrated. The obtained residue was subjected to silica gel column chromatography, and the title compound (1.69 g, yield 80%) was obtained as colorless crystals from a fraction eluted with ethyl acetate-hexane (4:1, volume ratio). melting point 64-66° C.

Reference Example 113

5-[4-(cyclopropylsulfonyl)phenyl]-6-(tetrahydro-2H-pyran-4-yl)-1-[5-(2,2,2-trifluoro-1-hydroxyethyl)-1,3-thiazol-2-yl]hexane-1,4-dione

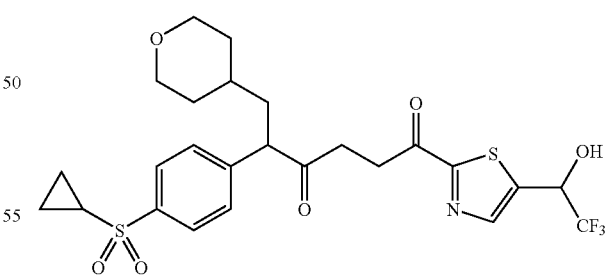

A mixture of 4-[4-(cyclopropylsulfonyl)phenyl]-5-(tetrahydro-2H-pyran-4-yl)pent-1-en-3-one (0.30 g), 5-(2,2,2-trifluoro-1-hydroxyethyl)-1,3-thiazole-2-carbaldehyde (0.20 g), 3-benzyl-5-(2-hydroxyethyl)-4-methyl-1,3-thiazol-3-ium chloride (23 mg), triethylamine (0.05 mL), tetrahydrofuran (4 mL) and ethanol (2 mL) was stirred with heating under reflux for 2 hr. The reaction mixture was concentrated, and the residue was subjected to silica gel column chromatography, and the title compound (0.45 g, yield 90%) was obtained as a colorless oil from a fraction eluted with ethyl acetate-hexane (4:1, volume ratio). MS: 560 (MH+).

Reference Example 114

1-[5-(1-hydroxyethyl)-1,3-thiazol-2-yl]-5-[4-(methylsulfonyl)phenyl]-6-(tetrahydro-2H-pyran-4-yl)hexane-1,4-dione

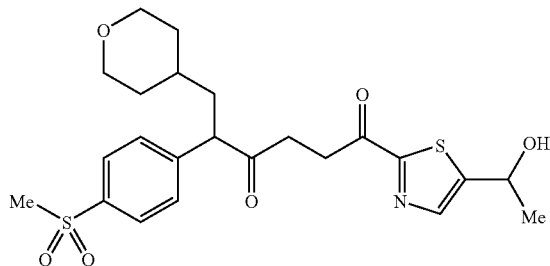

A mixture of 4-[4-(methylsulfonyl)phenyl]-5-(tetrahydro-2H-pyran-4-yl)pent-1-en-3-one (0.50 g), 5-(1-hydroxyethyl)-1,3-thiazole-2-carbaldehyde (0.28 g), 3-benzyl-5-(2-hydroxyethyl)-4-methyl-1,3-thiazol-3-ium chloride (43 mg), triethylamine (0.09 mL), tetrahydrofuran (6 mL) and ethanol (6 mL) was stirred with heating under reflux for 2 hr. The reaction mixture was concentrated, the residue was subjected to basic silica gel column chromatography, and eluted with ethyl acetate, and the fraction was concentrated. The residue was subjected to silica gel column chromatography, and the title compound (0.57 g, yield 75%) was obtained as a colorless oil from a fraction eluted with ethyl acetate. MS: 480 (MH+).

Reference Example 115

5-[3-chloro-4-(methylsulfonyl)phenyl]-1-[5-(1-hydroxyethyl)-1,3-thiazol-2-yl]-6-(tetrahydro-2H-pyran-4-yl)hexane-1,4-dione

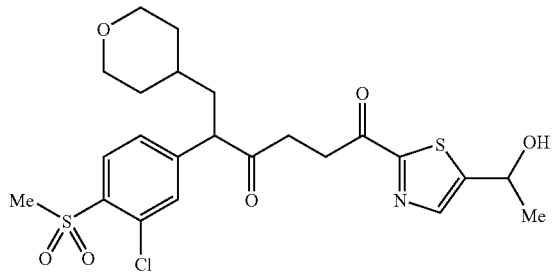

A mixture of 4-[3-chloro-4-(methylsulfonyl)phenyl]-5-(tetrahydro-2H-pyran-4-yl)pent-1-en-3-one (0.56 g), 5-(1-hydroxyethyl)-1,3-thiazole-2-carbaldehyde (0.30 g), 3-benzyl-5-(2-hydroxyethyl)-4-methyl-1,3-thiazol-3-ium chloride (43 mg), triethylamine (0.09 mL), tetrahydrofuran (4 mL) and ethanol (4 mL) was stirred with heating under reflux for 3 hr. The reaction mixture was concentrated, the residue was subjected to basic silica gel column chromatography, and eluted with ethyl acetate, and the fraction was concentrated. The residue was subjected to silica gel column chromatography, and the title compound (0.66 g, yield 81%) was obtained as a pale-yellow oil from a fraction eluted with ethyl acetate. MS: 514 (MH+).

$^1$H NMR (300 MHz, CDCl$_3$) δ1.20-1.38 (3 H, m), 1.50-1.72 (6 H, m), 1.98-2.10 (1 H, m), 2.64 (1 H, t, J=5.0 Hz), 2.73-2.99 (2 H, m), 3.20-3.50 (7 H, m), 3.86-4.02 (3 H, m), 5.16-5.25 (1 H, m), 7.34 (1 H, td, J=1.5, 8.1 Hz), 7.44 (1 H, d, J=1.5 Hz), 7.78 (1 H, dd, J=0.9, 2.7 Hz), 8.08 (1 H, dd, 1.5, 8.1 Hz).

Reference Example 116

Ethyl [2-(1,3-dioxolan-2-yl)-1,3-thiazol-5-yl](hydroxy)acetate

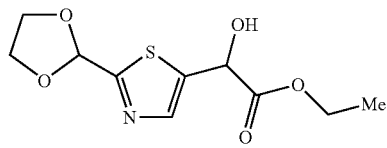

A suspension of sodium borohydride (6.18 g) and DL-tartaric acid (24.5 g) in tetrahydrofuran (250 mL) was stirred at 80° C. for 2 hr. The reaction mixture was cooled to 0° C., ethyl [2-(1,3-dioxolan-2-yl)-1,3-thiazol-5-yl](oxo)acetate (10.49 g) was added, and the mixture was stirred at room temperature for 2 days. The reaction mixture was slowly poured into ice (100 g), and the mixture was extracted with ethyl acetate. The ethyl acetate layer was washed with saturated brine, dried (MgSO$_9$) and concentrated. The obtained residue was subjected to silica gel column chromatography, and the title compound (8.43 g, yield 80%) was obtained as a colorless oil from a fraction eluted with ethyl acetate-hexane (4:1, volume ratio). MS: 260 (MH+).

Reference Example 117

1-[2-(1,3-dioxolan-2-yl)-1,3-thiazol-5-yl]-2-methylpropane-1,2-diol

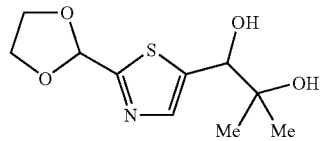

To a solution of ethyl [2-(1,3-dioxolan-2-yl)-1,3-thiazol-5-yl] (hydroxy)acetate (1.37 g) in tetrahydrofuran (25 mL) was slowly added a 3M methylmagnesium bromide diethyl ether solution (7.0 mL) at 0° C. The reaction mixture was stirred at room temperature for 1 hr, 10% aqueous citric acid solution was added, and the mixture was extracted with ethyl acetate. The ethyl acetate layer was washed with saturated brine, dried (MgSO$_4$) and concentrated. The obtained residue was subjected to silica gel column chromatography, and the title compound (0.33 g, yield 25%) was obtained as colorless crystals from a fraction eluted with ethyl acetate. melting point 130-131° C.

Reference Example 118

5-(1,2-dihydroxy-2-methylpropyl)-1,3-thiazole-2-carbaldehyde

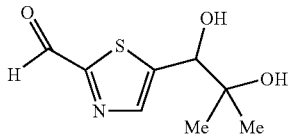

A mixture of 1-[2-(1,3-dioxolan-2-yl)-1,3-thiazol-5-yl]-2-methylpropane-1,2-diol (0.33 g), 1M hydrochloric acid (1 mL), water (2 mL) and tetrahydrofuran (6 mL) was stirred at 60° C. for 6 hr. To the reaction mixture was added saturated aqueous sodium hydrogen carbonate, and the mixture was extracted with ethyl acetate. The ethyl acetate layer was washed with saturated brine, dried (MgSO$_4$) and concentrated. The obtained residue was subjected to silica gel column chromatography, and the title compound (0.21 g, yield 77%) was obtained as a yellow oil from a fraction eluted with ethyl acetate. MS: 202 (MH$^+$).

Reference Example 119

5-[4-(cyclopropylsulfonyl)phenyl]-1-[5-(1,2-dihydroxy-2-methylpropyl)-1,3-thiazol-2-yl]-6-(tetrahydro-2H-pyran-4-yl)hexane-1,4-dione

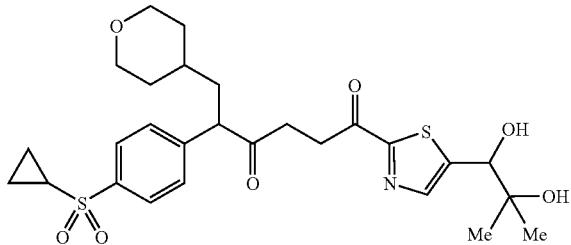

A mixture of 4-[4-(cyclopropylsulfonyl)phenyl]-5-(tetrahydro-2H-pyran-4-yl)pent-1-en-3-one (0.35 g), 5-(1,2-dihydroxy-2-methylpropyl)-1,3-thiazole-2-carbaldehyde (0.21 g), 3-benzyl-5-(2-hydroxyethyl)-4-methyl-1,3-thiazol-3-ium chloride (27 mg), triethylamine (0.06 mL), tetrahydrofuran (4 mL) and ethanol (4 mL) was stirred with heating under reflux for 1 hr. The reaction mixture was concentrated, and the residue was subjected to silica gel column chromatography, and the title compound (0.52 g, yield 95%) was obtained as a colorless oil from a fraction eluted with ethyl acetate. MS: 550 (MH$^+$).

Reference Example 120

1-[5-(1,2-dihydroxy-2-methylpropyl)-1,3-thiazol-2-yl]-5-[4-(methylsulfonyl)phenyl]-6-(tetrahydro-2H-pyran-4-yl)hexane-1,4-dione

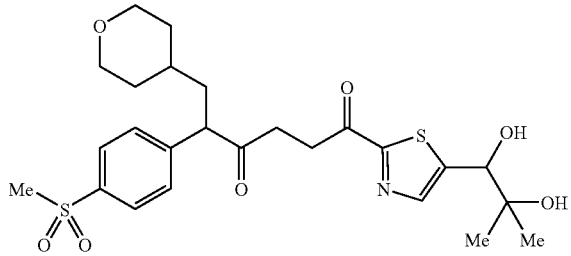

A mixture of 4-[4-(methylsulfonyl)phenyl]-5-(tetrahydro-2H-pyran-4-yl)pent-1-en-3-one (0.50 g), 5-(1,2-dihydroxy-2-methylpropyl)-1,3-thiazole-2-carbaldehyde (0.32 g), 3-benzyl-5-(2-hydroxyethyl)-4-methyl-1,3-thiazol-3-ium chloride (43 mg), triethylamine (0.09 mL), tetrahydrofuran (6 mL) and ethanol (6 mL) was stirred with heating under reflux for 1 hr. The reaction mixture was concentrated, the residue was subjected to basic silica gel column chromatography, and eluted with tetrahydrofuran, and the fraction was concentrated. The residue was subjected to silica gel column chromatography, and the title compound (0.51 g, yield 61%) was obtained as a colorless oil from a fraction eluted with ethyl acetate. MS: 524 (MH$^+$).

Reference Example 121

1-[5-(1,2-dihydroxy-2-methylpropyl)pyridin-2-yl]-5-[5-(methylsulfanyl)pyridin-2-yl]-6-(tetrahydro-2H-pyran-4-yl)hexane-1,4-dione

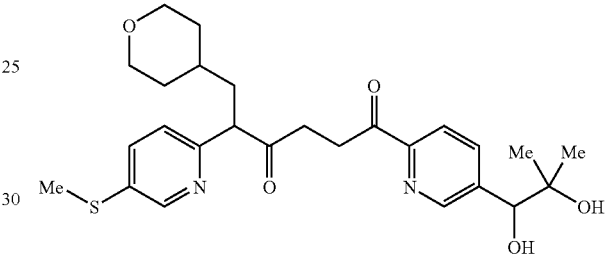

A mixture of 4-[5-(methylsulfanyl)pyridin-2-yl]-5-(tetrahydro-2H-pyran-4-yl)pent-1-en-3-one (0.50 g), 5-(1,2-dihydroxy-2-methylpropyl)pyridine-2-carbaldehyde (0.32 g), 3-benzyl-5-(2-hydroxyethyl)-4-methyl-1,3-thiazol-3-ium chloride (43 mg), triethylamine (0.09 mL), tetrahydrofuran (6 mL) and ethanol (6 mL) was stirred with heating under reflux for 1 hr. The reaction mixture was concentrated, and the residue was subjected to silica gel column chromatography, and the title compound (0.51 g, yield 61%) was obtained as a colorless oil from a fraction eluted with ethyl acetate. MS: 524 (MH$^+$).

Reference Example 122

1-(6-bromopyridin-3-yl)-2-methoxyethanone

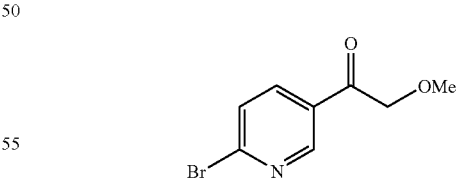

To a suspension of 2,5-dibromopyridine (50.0 g) in diethyl ether (1 L) was added under nitrogen atmosphere a 1.6M n-butyllithium hexane solution (140 mL) at −70° C. over 20 min. The reaction mixture was stirred at −70° C. for 30 min, methyl methoxyacetate (44.0 g) was added at −70 to −45° C. over 15 min. The reaction mixture was warmed to room temperature, 2M hydrochloric acid (110 mL) was added, and the diethyl ether layer was separated. The aqueous layer was extracted with ethyl acetate, the ethyl acetate layer was combined with the diethyl ether layer, and the layers were washed

Reference Example 123

1-(6-bromopyridin-3-yl)-2-methoxyethanol

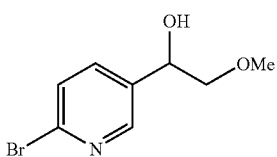

To a mixture of 1-(6-bromopyridin-3-yl)-2-methoxyethanone (15.85 g), tetrahydrofuran (15 mL) and ethanol (15 mL) was slowly added sodium borohydride (0.97 g) at room temperature, and the mixture was stirred at room temperature for 30 min. To the reaction mixture was added 10% aqueous citric acid solution, and the mixture was extracted with ethyl acetate. The ethyl acetate layer was washed with saturated brine, dried (MgSO$_4$) and concentrated. The obtained residue was subjected to silica gel column chromatography, and the title compound (15.26 g, yield 96%) was obtained as a yellow oil from a fraction eluted with ethyl acetate. MS: 234 (MH$^+$).

Reference Example 124

2-bromo-5-[2-methoxy-1-(tetrahydro-2H-pyran-2-yloxy)ethyl]pyridine

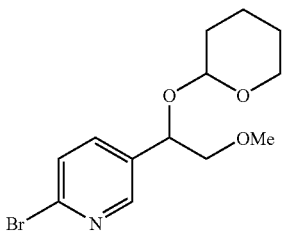

To a mixture of 1-(6-bromopyridin-3-yl)-2-methoxyethanol (15.26 g), p-toluenesulfonic acid monohydrate (0.63 g) and tetrahydrofuran (65 ml) was added 3,4-dihydro-2H-pyran (7.76 g) at room temperature over 30 min, and the mixture was stirred for 2 hr. To the reaction mixture was added saturated aqueous sodium hydrogen carbonate, and the mixture was extracted with ethyl acetate. The ethyl acetate layer was washed with saturated brine, dried (MgSO$_4$) and concentrated. The obtained residue was subjected to silica gel column chromatography, and the title compound (19.66 g, yield 94%) was obtained as a colorless oil from a fraction eluted with ethyl acetate-hexane (2:3, volume ratio). MS: 318 (MH$^+$).

with saturated brine, dried (MgSO$_4$) and concentrated. Cold ether was added to the obtained residue, and the resulting crystals were collected by filtration, washed with cold ether and dried to give the title compound (15.85 g, yield 33%) as colorless crystals. melting point 110-112° C.

Reference Example 125

5-[2-methoxy-1-(tetrahydro-2H-pyran-2-yloxy)ethyl]pyridine-2-carbaldehyde

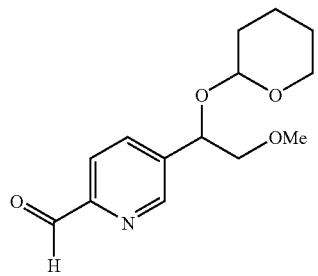

To tetrahydrofuran (250 mL) cooled to −20° C. were successively added a 2M butylmagnesium chloride tetrahydrofuran solution (11.2 mL) and a 1.6M n-butyllithium hexane solution (28.0 mL). The reaction mixture was stirred at −20° C. for 10 min, and a solution of 2-bromo-5-[2-methoxy-1-(tetrahydro-2H-pyran-2-yloxy)ethyl]pyridine (17.66 g) in tetrahydrofuran (15 mL) was added at −20° C. to −10° C. over 20 min. The reaction mixture was stirred at −10° C. for 30 min and N,N-dimethylformamide (8.2 g) was added. The reaction mixture was warmed to room temperature, saturated aqueous ammonium chloride solution was added, and the mixture was extracted with ethyl acetate. The ethyl acetate layer was washed with saturated brine, dried (MgSO$_4$) and concentrated. The obtained residue was subjected to silica gel column chromatography, and the title compound (9.48 g, yield 64%) was obtained as a yellow oil from a fraction eluted with ethyl acetate-hexane (1:1, volume ratio). MS: 266 (MH$^+$).

Reference Example 126

5-[4-(cyclopropylsulfonyl)phenyl]-1-{5-[2-methoxy-1-(tetrahydro-2H-pyran-2-yloxy)ethyl]pyridin-2-yl}-6-(tetrahydro-2H-pyran-4-yl)hexane-1,4-dione

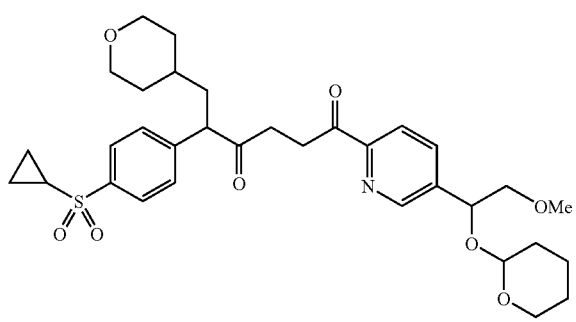

A mixture of 4-[4-(cyclopropylsulfonyl)phenyl]-5-(tetrahydro-2H-pyran-4-yl)pent-1-en-3-one (0.50 g), 5-[2-methoxy-1-(tetrahydro-2H-pyran-2-yloxy)ethyl]pyridine-2-carbaldehyde (0.42 g), 3-benzyl-5-(2-hydroxyethyl)-4-methyl-1,3-thiazol-3-ium chloride (38 mg), triethylamine (0.1 mL), tetrahydrofuran (5 mL) and ethanol (5 mL) was stirred with heating under reflux for 2 hr. The reaction mixture was concentrated, and the residue was subjected to silica gel column chromatography, and the title compound (0.70 g, yield 79%)

was obtained as a pale-yellow oil from a fraction eluted with ethyl acetate-hexane (2:1, volume ratio). MS: 614 (MH$^+$).

Reference Example 127

1-{5-[2-methoxy-1-(tetrahydro-2H-pyran-2-yloxy) ethyl]pyridin-2-yl}-5-[4-(methylsulfonyl)phenyl]-6-(tetrahydro-2H-pyran-4-yl)hexane-1,4-dione

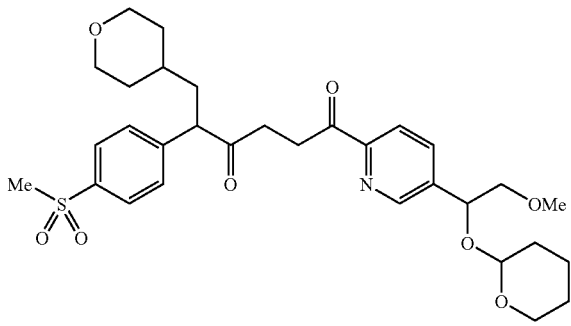

A mixture of 4-[4-(methylsulfonyl)phenyl]-5-(tetrahydro-2H-pyran-4-yl)pent-1-en-3-one (1.07 g), 5-[2-methoxy-1-(tetrahydro-2H-pyran-2-yloxy)ethyl]pyridine-2-carbaldehyde (0.97 g), 3-benzyl-5-(2-hydroxyethyl)-4-methyl-1,3-thiazol-3-ium chloride (90 mg), triethylamine (0.23 mL), tetrahydrofuran (8 mL) and ethanol (8 mL) was stirred with heating under reflux for 1 hr. The reaction mixture was concentrated, and the residue was subjected to silica gel column chromatography, and the title compound (1.05 g, yield 54%) was obtained as a yellow oil from a fraction eluted with ethyl acetate-hexane (2:1, volume ratio). MS: 588 (MH$^+$).

Reference Example 128

Ethyl (4-formyl-1H-imidazol-1-yl)acetate

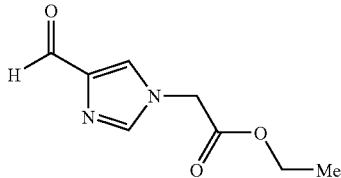

To a suspension of sodium hydride (60%, oil, 1.40 g) in tetrahydrofuran (80 mL) was slowly added 1H-imidazole-4-carbaldehyde (3.00 g) at room temperature. The reaction mixture was stirred at room temperature until hydrogen gas generation stopped, and ethyl bromoacetate (4.5 mL) was added over 30 min. The reaction mixture was stirred at room temperature overnight, and ethanol (5 mL) was added. The insoluble material was filtered off, and the filtrate was concentrated. The obtained residue was subjected to silica gel column chromatography, and the title compound (3.94 g, yield 69%) was obtained as a yellow oil from a fraction eluted with tetrahydrofuran-hexane (5:1, volume ratio). MS: 183 (MH$^+$).

Reference Example 129

Ethyl (4-{5-[4-(cyclopropylsulfonyl)phenyl]-4-oxo-6-(tetrahydro-2H-pyran-4-yl)hexanoyl}-1H-imidazol-1-yl)acetate

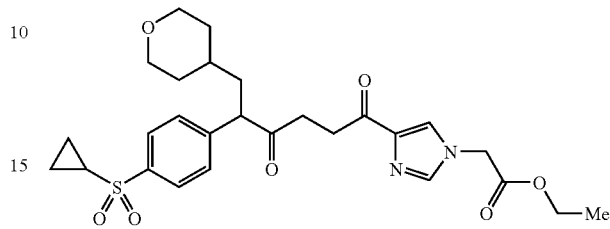

A mixture of 4-[4-(cyclopropylsulfonyl)phenyl]-5-(tetrahydro-2H-pyran-4-yl)pent-1-en-3-one (0.77 g), ethyl (4-formyl-1H-imidazol-1-yl)acetate (0.45 g), 3-benzyl-5-(2-hydroxyethyl)-4-methyl-1,3-thiazol-3-ium chloride (60 mg), triethylamine (0.12 mL), tetrahydrofuran (4 mL) and ethanol (4 mL) was stirred with heating under reflux for 1 hr. The reaction mixture was concentrated, and the residue was subjected to basic silica gel column chromatography, and the title compound (0.90 g, yield 77%) was obtained as a yellow oil from a fraction eluted with ethyl acetate. MS: 531 (Me).

Reference Example 130

(5E)-5-[4-(cyclopropylsulfonyl)phenyl]-1-[5-(1,2-dihydroxy-2-methylpropyl)pyridin-2-yl]-6-(tetrahydro-2H-pyran-4-yl)hex-5-ene-1,4-dione

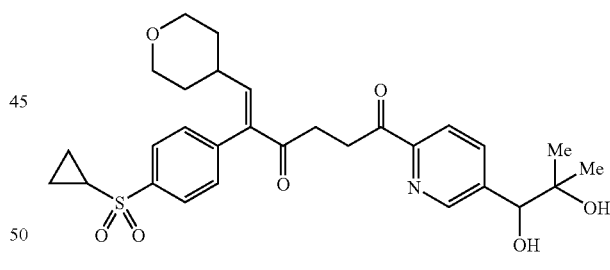

A mixture of (1E)-2-[4-(cyclopropylsulfonyl)phenyl]-1-(tetrahydro-2H-pyran-4-yl)penta-1,4-dien-3-one (4.16 g), 5-(1,2-dihydroxy-2-methylpropyl)pyridine-2-carbaldehyde (2.58 g), 3-benzyl-5-(2-hydroxyethyl)-4-methyl-1,3-thiazol-3-ium chloride (0.32 g), triethylamine (0.84 mL), tetrahydrofuran (10 mL) and ethanol (10 mL) was stirred with heating under reflux for 2 hr. The reaction mixture was concentrated, and the residue was subjected to basic silica gel column chromatography, and the title compound (0.70 g, yield 79%) was obtained as yellow crystals from a fraction eluted with ethyl acetate. melting point 102-104° C.

Reference Example 131

Ethyl [3-chloro-4-(methylsulfonyl)phenyl]acetate

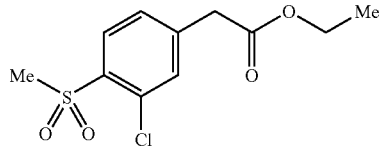

To a solution of [3-chloro-4-(methylsulfanyl)phenyl]acetic acid (35.5 g) in ethanol (410 mL) was added thionyl chloride (23.9 mL) under ice-cooling, and the mixture was warmed to room temperature and stirred at room temperature for 16 hr. The reaction mixture was diluted with ethyl acetate, washed successively with saturated aqueous sodium hydrogen carbonate solution, water and saturated brine, dried over anhydrous magnesium sulfate and concentrated under reduced pressure. To a solution of the obtained residue in ethyl acetate (330 mL) was added m-chlorobenzoic acid (74.0 g) under ice-cooling, and the mixture was stirred at 0° C. for 30 min, and at room temperature for 1 hr. m-Chlorobenzoic acid (74.0 g) was added to the reaction solution under ice-cooling, and the mixture was stirred at room temperature for 2 hr. To the reaction mixture were added saturated aqueous sodium hydrogen carbonate solution and 1M aqueous sodium thiosulfate solution, and the mixture was extracted with ethyl acetate. The extract was washed successively with saturated aqueous sodium hydrogen carbonate solution, water and saturated brine, dried over anhydrous magnesium sulfate and concentrated under reduced pressure. The residue was purified by silica gel column chromatography (ethyl acetate:hexane=10:90-50:50, volume ratio) to give the title compound (40.0 g, yield 88%) as colorless crystals.

$^1$H NMR (300 MHz, CDCl$_3$) δ1.28 (3 H, t, J=7.2 Hz), 3.26 (3 H, s), 3.68 (2 H, s), 4.19 (2 H, q, J=7.2 Hz), 7.39 (1 H, dd, J=1.5, 8.1 Hz), 7.51 (1 H, d, J=1.5 Hz), 8.11 (1 H, d, J=8.1 Hz).

Reference Example 132

Ethyl 2-[3-chloro-4-(methylsulfonyl)phenyl]-3-[(2R, 3R,7R)-2,3-diphenyl-1,4-dioxaspiro[4.4]non-7-yl]propanoate

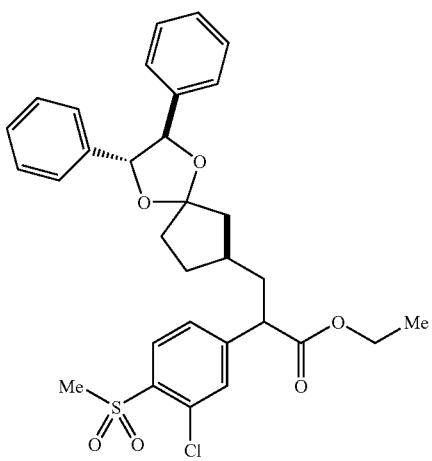

In the same manner as in Reference Example 18, the title compound (19.1 g, 66%) was obtained as a colorless oil from ethyl [3-chloro-4-(methylsulfonyl)phenyl]acetate (14.1 g) and (2R,3R,7S)-7-(iodomethyl)-2,3-diphenyl-1,4-dioxaspiro[4.4]nonane (23.6 g).

$^1$H NMR (300 MHz, CDCl$_3$) δ1.18-1.29 (3 H, m), 1.43-1.59 (1 H, m), 1.68-1.80 (1 H, m), 1.83-2.10 (4 H, m), 2.13-2.39 (3H, m), 3.26 (3 H, s), 3.67 (1 H, t, J=7.6 Hz), 4.04-4.25 (2 H, m), 4.61-4.74 (2 H, m), 7.14-7.24 (4 H, m), 7.27-7.37 (6 H, m), 7.40-7.46 (1 H, m), 7.53-7.57 (1 H, m), 8.06-8.14 (1 H, m).

Reference Example 133

2-[3-chloro-4-(methylsulfonyl)phenyl]-3-[(2R,3R, 7R)-2,3-diphenyl-1,4-dioxaspiro[4.4]non-7-yl]propanoic acid

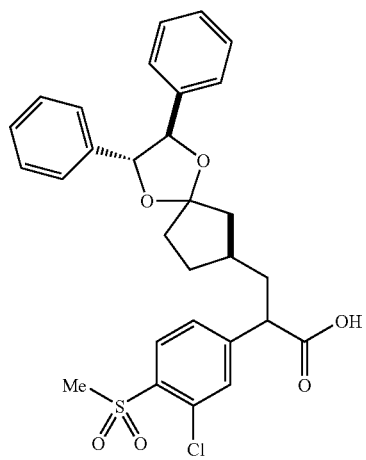

To a solution of ethyl 2-[3-chloro-4-(methylsulfonyl)phenyl]-3-[(2R,3R,7R)-2,3-diphenyl-1,4-dioxaspiro[4.4]non-7-yl]propanoate in a mixed solvent of tetrahydrofuran (200 mL) and methanol (100 mL) was added 2M aqueous sodium hydroxide solution (50 mL), and the mixture was stirred at room temperature for 16 hr. The reaction mixture was concentrated under reduced pressure, the residue was acidified with 10% aqueous citric acid solution, and the mixture was extracted with ethyl acetate. The extract was washed with saturated brine, dried over anhydrous magnesium sulfate and concentrated under reduced pressure. The residue was purified by silica gel column chromatography (ethyl acetate:hexane=30:70-70:30, volume ratio) to give the title compound (17.6 g, yield 97%) as a colorless amorphous solid.

$^1$H NMR (300 MHz, CDCl$_3$) δ1.39-1.58 (1 H, m), 1.66-1.82 (1 H, m), 1.85-2.11 (4 H, m), 2.15-2.39 (4 H, m), 3.25 (3 H, s), 3.71 (1 H, t, J=7.5 Hz), 4.63-4.73 (2 H, m), 7.14-7.23 (4 H, m), 7.27-7.35 (6 H, m), 7.40-7.48 (1 H, m), 7.53-7.58 (1 H, m), 8.07-8.15 (1 H, m).

Reference Example 134

2-[3-chloro-4-(methylsulfonyl)phenyl]-3-[(2R,3R,7R)-2,3-diphenyl-1,4-dioxaspiro[4.4]non-7-yl]-N-methoxy-N-methylpropaneamide

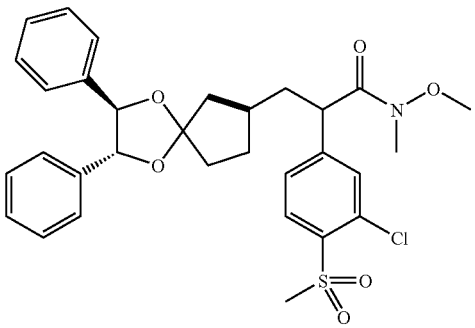

A solution of N-methoxymethanamine hydrochloride (936 mg) in acetonitrile (40 mL) was neutralized with triethylamine (3.35 mL), and 2-[3-chloro-4-(methylsulfonyl)phenyl]-3-[(2R,3R,7R)-2,3-diphenyl-1,4-dioxaspiro[4.4]non-7-yl]propanoic acid (4.33 g), N-[3-(dimethylamino)propyl]-N'-ethylcarbodiimide hydrochloride (2.30 g) and 1-hydroxybenzotriazole (612 mg) were added under ice-cooling. The reaction mixture was stirred overnight at room temperature, diluted with ethyl acetate, and washed with water and saturated aqueous sodium hydrogen carbonate. The ethyl acetate layer was dried ($MgSO_4$) and concentrated. The residue was subjected to silica gel column chromatography, and the title compound (3.05 g, yield 69%) was obtained as a colorless amorphous solid from a fraction eluted with ethyl acetate-hexane (3:1, volume ratio).

$^1$H NMR (300 MHz, $CDCl_3$) δ1.40-2.42 (9 H, m), 3.18 (3 H, d, J=2.7 Hz), 3.25 (3 H, s), 3.61 (3 H, d, J=4.2 Hz), 4.12-4.22 (1 H, m), 4.69 (2 H, s), 7.15-7.24 (4 H, m), 7.28-7.36 (6 H, m), 7.41-7.48 (1 H, m), 7.59 (1 H, dd, J=1.5, 4.5 Hz), 8.08 (1 H, dd, J=4.5, 8.0 Hz).

Reference Example 135

4-[3-chloro-4-(methylsulfonyl)phenyl]-5-[(2R,3R,7R)-2,3-diphenyl-1,4-dioxaspiro[4.4]non-7-yl]pent-1-en-3-one

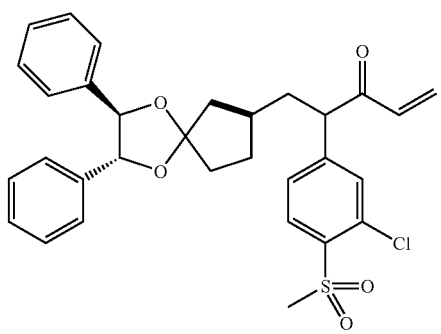

A solution of 2-[3-chloro-4-(methylsulfonyl)phenyl]-3-[(2R,3R,7R)-2,3-diphenyl-1,4-dioxaspiro[4.4]non-7-yl]-N-methoxy-N-methylpropaneamide (3.05 g) in tetrahydrofuran (30 mL) was cooled to 0° C., and vinylmagnesium bromide (1.0M tetrahydrofuran solution, 22.1 mL) was added dropwise. The reaction mixture was stirred at room temperature for 4 hr, and poured into 1M hydrochloric acid, and the mixture was stirred for 30 min. The reaction mixture was extracted with ethyl acetate, and the ethyl acetate layer was washed with saturated aqueous sodium hydrogen carbonate and saturated brine, dried ($MgSO_4$) and concentrated. The residue was subjected to silica gel column chromatography, and the title compound (2.58 g, yield 90%) was obtained as a colorless amorphous solid from a fraction eluted with ethyl acetate-hexane (1:1, volume ratio).

$^1$H NMR (300 MHz, $CDCl_3$) δ1.36-2.38 (9 H, m), 3.26 (3 H, s), 4.03-4.09 (1 H, m), 4.62-4.73 (2 H, m), 5.77-5.85 (1 H, m), 6.25-6.44 (2 H, m), 7.15-7.23 (4 H, m), 7.27-7.40 (7 H, m), 7.47 (1 H, dd, J=1.6, 5.9 Hz), 8.10 (1 H, dd, J=4.7, 8.1 Hz).

Reference Example 136

5-[3-chloro-4-(methylsulfonyl)phenyl]-6-[(2R,3R,7R)-2,3-diphenyl-1,4-dioxaspiro[4.4]non-7-yl]-1-(pyridin-2-yl)hexane-1,4-dione

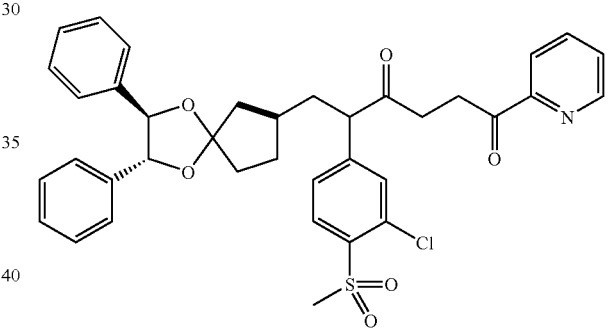

To a solution of 4-[3-chloro-4-(methylsulfonyl)phenyl]-5-[(2R,3R,7R)-2,3-diphenyl-1,4-dioxaspiro[4.4]non-7-yl]pent-1-en-3-one (882 mg) in ethanol (5 mL) were added pyridine-2-carbaldehyde (183 µL), 3-benzyl-5-(2-hydroxyethyl)-4-methyl-1,3-thiazol-3-ium chloride (47.5 mg) and triethylamine (96 µL), and the mixture was stirred with heating under reflux for 1.5 hr. The reaction mixture was cooled to room temperature, diluted with ethyl acetate and washed with water. The ethyl acetate layer was dried ($MgSO_4$) and concentrated. The residue was subjected to silica gel column chromatography, and the title compound (698 mg, yield 66%) was obtained as a pale-yellow amorphous solid from a fraction eluted with ethyl acetate-hexane (1:1, volume ratio).

$^1$H NMR (300 MHz, $CDCl_3$) δ1.41-1.53 (1 H, m), 1.69-1.80 (1 H, m), 1.84-2.09 (4 H, m), 2.13-2.41 (3 H, m), 2.69-2.84 (1H, m), 2.86-3.02 (1 H, m), 3.27 (3 H, s), 3.36-3.63 (2 H, m), 3.96 (1 H, t, J=7.4 Hz), 4.63-4.74 (2 H, m), 7.17-7.24 (4 H, m), 7.28-7.53 (9 H, m), 7.76-7.85 (1 H, m), 7.93-8.01 (1 H, m), 8.12 (1 H, dd, J=5.1, 8.1 Hz), 8.63-8.70 (1 H, m).

Reference Example 137

5-[3-chloro-4-(methylsulfonyl)phenyl]-6-[(2R,3R,7R)-2,3-diphenyl-1,4-dioxaspiro[4.4]non-7-yl]-1-{5-[(tetrahydro-2H-pyran-2-yloxy)methyl]-1,3-thiazol-2-yl}hexane-1,4-dione

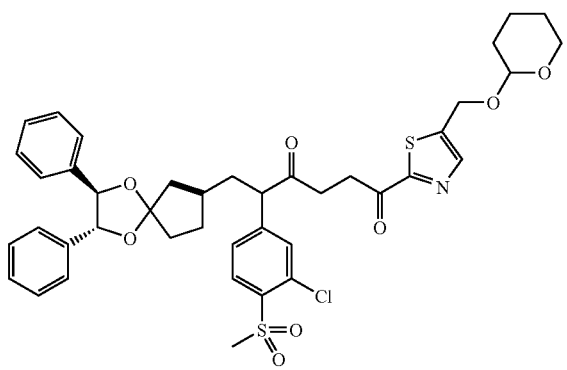

To a solution of 4-[3-chloro-4-(methylsulfonyl)phenyl]-5-[(2R,3R,7R)-2,3-diphenyl-1,4-dioxaspiro[4.4]non-7-yl]pent-1-en-3-one (525 mg) in ethanol (3 mL) were added 5-[(tetrahydro-2H-pyran-2-yloxy)methyl]-1,3-thiazole-2-carbaldehyde (259 mg), 3-benzyl-5-(2-hydroxyethyl)-4-methyl-1,3-thiazol-3-ium chloride (28.3 mg) and triethylamine (57 μL), and the mixture was stirred with heating under reflux for 1.5 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (416 mg, yield 56%) was obtained as a pale-yellow amorphous solid from a fraction eluted with ethyl acetate-hexane (1:1, volume ratio).

$^1$H NMR (300 MHz, CDCl$_3$) δ1.41-2.40 (15 H, m), 2.71-2.84 (1 H, m), 2.88-3.02 (1 H, m), 3.20-3.61 (6 H, m), 3.79-3.96 (2 H, m), 4.62-4.80 (4 H, m), 4.90-4.98 (1 H, m), 7.12-7.43 (11 H, m), 7.49 (1 H, dd, J=1.4, 6.5 Hz), 7.84 (1 H, s), 8.12 (1 H, dd, J=5.1, 8.1 Hz).

Reference Example 138

2-[3-chloro-4-(methylsulfonyl)phenyl]-N-methoxy-N-methyl-3-(tetrahydro-2H-pyran-4-yl)propanamide

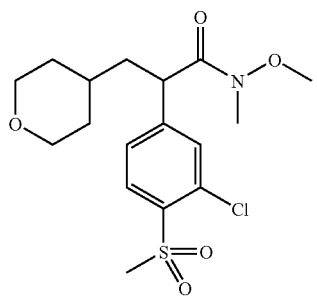

A solution of N-methoxymethanamine hydrochloride (2.75 g) in acetonitrile (120 mL) was neutralized with triethylamine (9.83 mL), 2-[3-chloro-4-(methylsulfonyl)phenyl]-3-(tetrahydro-2H-pyran-4-yl)propanoic acid (8.16 g), N-[3-(dimethylamino)propyl]-N'-ethylcarbodiimide hydrochloride (6.77 g) and 1-hydroxybenzotriazole (541 mg) were added under ice-cooling. The reaction mixture was stirred overnight at room temperature, diluted with ethyl acetate, and washed with water and saturated aqueous sodium hydrogen carbonate. The ethyl acetate layer was dried (MgSO$_4$) and concentrated. The residue was subjected to silica gel column chromatography, and the title compound (8.64 g, yield 94%) was obtained as a colorless amorphous solid from a fraction eluted with ethyl acetate-hexane (9:1, volume ratio).

$^1$H NMR (300 MHz, CDCl$_3$) δ1.17-1.72 (7 H, m), 2.02-2.15 (1 H, m), 3.18 (3 H, s), 3.23-3.39 (5 H, m), 3.60 (3 H, s), 3.88-3.99 (2 H, m), 4.23 (1 H, t, J=7.4 Hz), 7.42 (1 H, dd, J=1.7, 8.1 Hz), 7.56 (1 H, d, J=1.5 Hz), 8.09 (1 H, d, J=8.3 Hz).

Reference Example 139

4-[3-chloro-4-(methylsulfonyl)phenyl]-5-(tetrahydro-2H-pyran-4-yl)pent-1-en-3-one

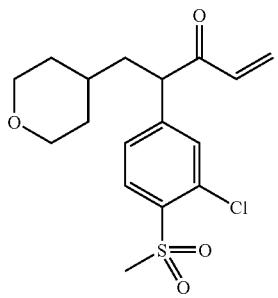

A solution of 2-[3-chloro-4-(methylsulfonyl)phenyl]-N-methoxy-N-methyl-3-(tetrahydro-2H-pyran-4-yl)propanamide (8.64 g) in tetrahydrofuran (90 mL) was cooled to 0° C., and vinylmagnesium bromide (1.0M tetrahydrofuran solution, 88.8 mL) was added dropwise. The reaction mixture was stirred at room temperature for 3 hr, and added to 1M hydrochloric acid, and the mixture was stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (7.15 g, yield 90%) was obtained as a pale-yellow amorphous solid from a fraction eluted with ethyl acetate-hexane (1:1, volume ratio).

$^1$H NMR (300 MHz, CDCl$_3$) δ1.19-1.75 (6 H, m), 2.00-2.15 (1 H, m), 3.23-3.36 (5 H, m), 3.87-3.99 (1 H, m), 4.06-4.18 (1 H, m), 5.83 (1 H, dd, J=3.1, 8.4 Hz), 6.26-6.45 (2 H, m), 7.34 (1H, dd, J=1.7, 8.1 Hz), 7.44 (1 H, d, J=1.7 Hz), 8.11 (1H, d, J=8.1 Hz).

Reference Example 140

5-[3-chloro-4-(methylsulfonyl)phenyl]-1-(pyridin-2-yl)-6-(tetrahydro-2H-pyran-4-yl)hexane-1,4-dione

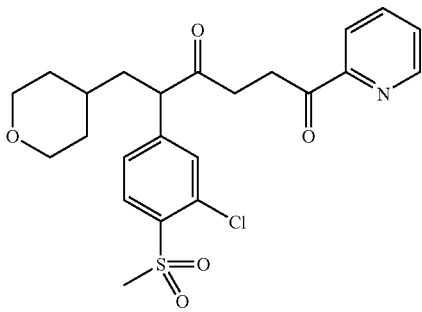

To a solution of 4-[3-chloro-4-(methylsulfonyl)phenyl]-5-(tetrahydro-2H-pyran-4-yl)pent-1-en-3-one (1.03 g) in ethanol (10 mL) were added pyridine-2-carbaldehyde (329 µL), 3-benzyl-5-(2-hydroxyethyl)-4-methyl-1,3-thiazol-3-ium chloride (85.5 mg) and triethylamine (173 µL), and the mixture was stirred with heating under reflux for 1 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (1.13 g, yield 84%) was obtained as a pale-yellow amorphous solid from a fraction eluted with ethyl acetate-hexane (9:1, volume ratio).

$^1$H NMR (300 MHz, CDCl$_3$) δ1.19-1.45 (3 H, m), 1.53-1.75 (3 m), 2.01-2.16 (1 H, m), 2.68-2.82 (1 H, m), 2.86-3.01 (1 H, m), 3.24-3.65 (7 H, m), 3.90-3.98 (1 H, m), 4.03 (1 H, t, J=7.5 Hz), 7.35-7.41 (1 H, m), 7.45-7.52 (2 H, m), 7.78-7.88 (1 H, m), 7.99 (1 H, dd, J=0.9, 7.9 Hz), 8.12 (1 H, d, J=8.1 Hz), 8.64-8.70 (1 H, m).

Reference Example 141

5-[3-chloro-4-(methylsulfonyl)phenyl]-6-(tetrahydro-2H-pyran-4-yl)-1-[5-[(tetrahydro-2H-pyran-2-yloxy)methyl]-1,3-thiazol-2-yl]hexane-1,4-dione

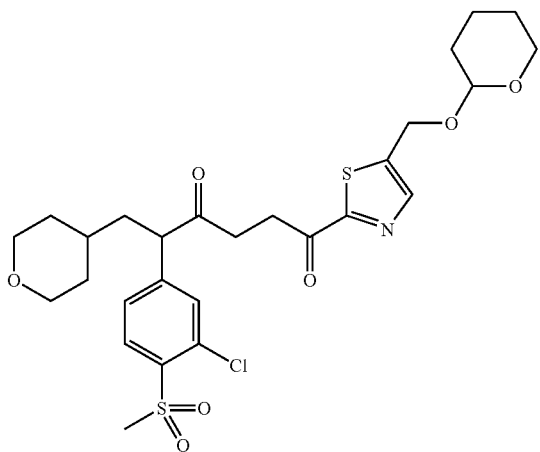

To a solution of 4-[3-chloro-4-(methylsulfonyl)phenyl]-5-(tetrahydro-2H-pyran-4-yl)pent-1-en-3-one (526 mg) in ethanol (6 mL) were added 5-[(tetrahydro-2H-pyran-2-yloxy)methyl]-1,3-thiazole-2-carbaldehyde (402 mg), 3-benzyl-5-(2-hydroxyethyl)-4-methyl-1,3-thiazol-3-ium chloride (43.7 mg) and triethylamine (88 µL), and the mixture was stirred with heating under reflux for 1 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (366 mg, yield 43%) was obtained as a pale-yellow amorphous solid from a fraction eluted with ethyl acetate-hexane (9:1, volume ratio).

$^1$H NMR (300 MHz, CDCl$_3$) δ1.21-1.42 (3 H, m), 1.48-1.90 (9 H, m), 1.97-2.12 (1 H, m), 2.68-2.83 (1 H, m), 2.86-3.00 (1 H, m), 3.25-3.62 (8 H, m), 3.79-4.03 (4 H, m), 4.70-4.80 (2 H, m), 4.92-4.99 (1 H, m), 7.36 (1 H, dd, J=1.7, 8.3 Hz), 7.46 (1 H, d, J=1.5 Hz), 7.85 (1 H, s), 8.12 (1 H, d, J=8.1 Hz).

Reference Example 142

5-[3-chloro-4-(methylsulfonyl)phenyl]-6-[(2R,3R,7R)-2,3-diphenyl-1,4-dioxaspiro[4.4]non-7-yl]-1-(pyrazin-2-yl)hexane-1,4-dione

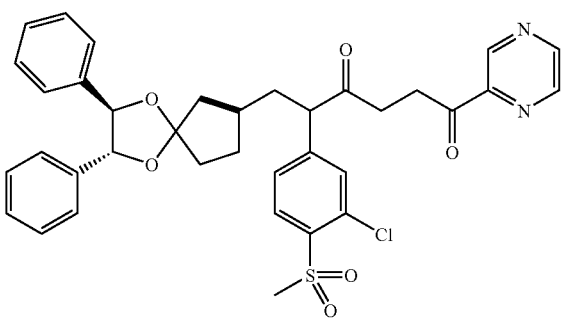

To a solution of 4-[3-chloro-4-(methylsulfonyl)phenyl]-5-[(2R,3R,7R)-2,3-diphenyl-1,4-dioxaspiro[4.4]non-7-yl]pent-1-en-3-one (539 mg) in ethanol (5 mL) were added pyrazine-2-carbaldehyde (126 mg), 3-benzyl-5-(2-hydroxyethyl)-4-methyl-1,3-thiazol-3-ium chloride (29.0 mg) and triethylamine (59 µL), and the mixture was stirred with heating under reflux for 1 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (284 mg, yield 44%) was obtained as a pale-yellow amorphous solid from a fraction eluted with ethyl acetate-hexane (2:1, volume ratio).

$^1$H NMR (300 MHz, CDCl$_3$) δ1.38-2.43 (9 H, m), 2.72-2.86 (1H, m), 2.89-3.06 (1 H, m), 3.27 (3 H, s), 3.32-3.57 (2 H, m), 3.90-3.99 (1 H, m), 4.62-4.77 (2 H, m), 7.12-7.35 (10 H, m), 7.37-7.44 (1 H, m), 7.48-7.53 (1 H, m), 8.09-8.17 (1 H, m), 8.63 (1 H, d, J=0.9 Hz), 8.75 (1 H, d, J=2.3 Hz), 9.14-9.21 (1 H, m).

Reference Example 143

5-[3-chloro-4-(methylsulfonyl)phenyl]-1-[5-(1,3-dioxolan-2-yl)pyridin-2-yl]-6-[(2R,3R,7R)-2,3-diphenyl-1,4-dioxaspiro[4.4]non-7-yl]hexane-1,4-dione

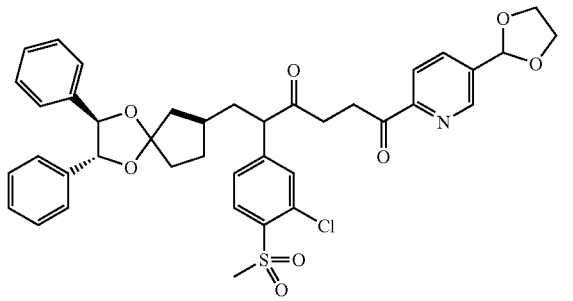

To a solution of 4-[3-chloro-4-(methylsulfonyl)phenyl]-5-[(2R,3R,7R)-2,3-diphenyl-1,4-dioxaspiro[4.4]non-7-yl]pent-1-en-3-one (624 mg) in ethanol (5 mL) were added 5-(1,3-dioxolan-2-yl)pyridine-2-carbaldehyde (244 mg), 3-benzyl-5-(2-hydroxyethyl)-4-methyl-1,3-thiazol-3-ium chloride (33.7 mg) and triethylamine (68 μL), and the mixture was stirred with heating under reflux for 1 hr. After cooling to room temperature, the reaction mixture was diluted with ethyl acetate and washed with water. The ethyl acetate layer was dried (MgSO₄) and concentrated. The residue was subjected to silica gel column chromatography, and the title compound (276 mg, yield 33%) was obtained as a pale-yellow amorphous solid from a fraction eluted with ethyl acetate-hexane (2:1, volume ratio).

$^1$H NMR (300 MHz, CDCl₃) δ1.38-2.42 (9H, m), 2.69-2.84 (1H, m), 2.87-3.01 (1 H, m), 3.27 (3 H, s), 3.36-3.62 (2 H, m), 3.90-4.00 (1 H, m), 4.03-4.18 (4 H, m), 4.63-4.74 (2 H, m), 5.91 (1 H, s), 7.16-7.23 (4 H, m), 7.28-7.43 (7 H, m), 7.48-7.53 (1 H, m), 7.87-7.92 (1 H, m), 7.95-8.01 (1 H, m), 8.09-8.15 (1 H, m), 8.74 (1 H, s).

Reference Example 144

Ethyl [5-(methylsulfanyl)pyridin-2-yl] (oxo) acetate

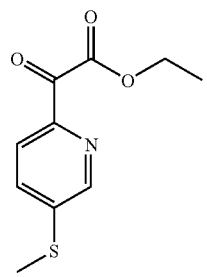

A solution of n-butyllithium (1.6M hexane solution, 10.6 mL) in toluene (10 mL) was cooled to −45° C. and purged with nitrogen. n-Butylmagnesium chloride (2.0M tetrahydrofuran solution, 4.22 mL) was added dropwise to the reaction mixture, and the mixture was stirred at 0° C. for 30 min. To the reaction mixture was added dropwise a solution of 2-bromo-5-(methylsulfanyl)pyridine (4.30 g) in toluene (40 mL), and the mixture was stirred at −20° C. for 2.5 hr. To the reaction mixture was added diethyl oxalate (4.29 mL), and the mixture was stirred at room temperature for 24 hr. A saturated aqueous ammonium chloride solution was added to the reaction mixture, and the mixture was extracted with ethyl acetate. The extract was washed with saturated brine, dried over anhydrous magnesium sulfate and concentrated under reduced pressure. The residue was subjected to silica gel column chromatography, and the title compound (2.05 g, yield 43%) was obtained as a yellow amorphous solid from a fraction eluted with ethyl acetate-hexane (1:2, volume ratio).

$^1$H NMR (300 MHz, CDCl₃) δ1.41 (3 H, t, J=7.2 Hz), 2.58 (3 H, s), 4.47 (2 H, q, J=7.2 Hz), 7.64 (1 H, dd, J=2.4, 8.3 Hz), 7.97-8.03 (1 H, m), 8.54 (1 H, d, J=2.3 Hz).

Reference Example 145

Ethyl 2-[5-(methylsulfanyl)pyridin-2-yl]-3-(tetrahydro-2H-pyran-4-yl)-2-propenoate

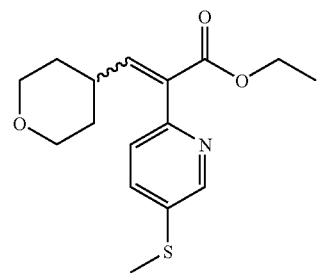

To a solution of triphenyl(tetrahydro-2H-pyran-4-ylmethyl)phosphonium iodide (5.11 g) in dry tetrahydrofuran (20 mL) was added lithium hexamethyldisilazide (1.1M tetrahydrofuran solution, 9.1 mL), and the mixture was stirred at 15° C. for 2 hr. To the reaction mixture was added a solution of ethyl [5-(methylsulfanyl)pyridin-2-yl](oxo)acetate (2.05 g) in dry tetrahydrofuran (20 mL), and the mixture was stirred at room temperature for 16 hr. A saturated aqueous ammonium chloride solution was added to the reaction mixture, and the mixture was extracted with ethyl acetate. The extract was washed with saturated brine, dried over anhydrous magnesium sulfate and concentrated under reduced pressure. The residue was subjected to silica gel column chromatography, and the title compound (2.41 g, yield 86%) was obtained as yellow amorphous crystals from a fraction eluted with ethyl acetate-hexane (1:2, volume ratio).

$^1$H NMR (300 MHz, CDCl₃) δ1.13-1.78 (11 H, m), 1.95-2.15 (2 H, m), 3.21-3.38 (2 H, m), 3.78-3.94 (2 H, m), 4.14 (2H, q, J=7.2 Hz), 7.21 (1H, d, J=8.5 Hz), 7.52 (1 H, dd, J=2.5, 8.4 Hz), 8.44 (1 H, d, J=2.4 Hz).

Reference Example 146

Ethyl 2-[5-(methylsulfanyl)pyridin-2-yl]-3-(tetrahydro-2H-pyran-4-yl)propanoate

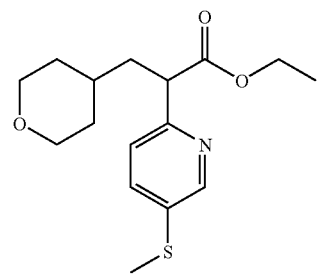

To a solution of ethyl 2-[5-(methylsulfanyl)pyridin-2-yl]-3-(tetrahydro-2H-pyran-4-yl)-2-propenoate (2.41 g) in methanol (20 mL) was added sodium borohydride (890 mg), and the mixture was stirred at room temperature for 3 hr. A saturated aqueous ammonium chloride solution was added to the reaction mixture, and the mixture was extracted with ethyl acetate. The extract was dried over anhydrous magnesium to sulfate and concentrated under reduced pressure. The residue was subjected to silica gel column chromatography, and the title compound (1.44 g, yield 59%) was obtained as a yellow amorphous solid from a fraction eluted with ethyl acetate-hexane (2:1, volume ratio).

$^1$H NMR (300 MHz, CDCl$_3$) δ1.11-1.51 (6 H, m), 1.53-1.72 (2 H, m), 1.77-1.92 (1 H, m), 2.00-2.13 (1 H, m), 2.50 (3 H, s), 3.21-3.39 (2H, m), 3.85-3.98 (3 H, m), 4.07-4.25 (2 H, m), 7.20-7.31 (1H, m), 7.54 (1 H, dd, J=2.4, 8.2 Hz), 8.44 (1 H, s).

Reference Example 147

N-methoxy-N-methyl-2-[5-(methylsulfanyl)pyridin-2-yl]-3-(tetrahydro-2H-pyran-4-yl)propanamide

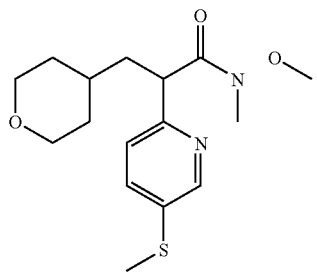

A solution of N-methoxymethanamine hydrochloride (1.48 g) in toluene (15 mL) was cooled to 0° C., and trimethylaluminum (1.4M hexane solution, 10.9 mL) was added dropwise. The reaction mixture was stirred at room temperature for 1.5 hr, and a solution of ethyl 2-[5-(methylsulfanyl) pyridin-2-yl]-3-(tetrahydro-2H-pyran-4-yl)propanoate (1.57 g) in toluene (15 mL) was added dropwise. The reaction mixture was stirred at room temperature for 6 hr, saturated aqueous sodium hydrogen carbonate and saturated aqueous Rochelle salt solution were added and the mixture was stirred for 1 hr. The reaction mixture was extracted with ethyl acetate, and the ethyl acetate layer was washed with saturated brine, dried (MgSO$_4$) and concentrated. The residue was subjected to silica gel column chromatography, and the title compound (404 mg, yield 25%) was obtained as a pale-yellow amorphous solid from a fraction eluted with ethyl acetate-hexane (9:1, volume ratio).

$^1$H NMR (300 MHz, CDCl$_3$) δ1.20-1.52 (3 H, m), 1.55-1.81 (3 H, m), 2.00-2.13 (1 H, m), 2.49 (3 H, s), 3.19 (3 H, s), 3.25-3.38 (2 H, m), 3.58 (3 H, s), 3.92 (2 H, dd, J=2.6, 11.9 Hz), 4.36-4.51 (1 H, m), 7.34 (1 H, dd, J=0.8, 8.3 Hz), 7.54 (1 H, dd, J=2.4, 8.3 Hz), 8.41 (1 H, d, J=1.9 Hz).

Reference Example 148

4-[5-(methylsulfanyl)pyridin-2-yl]-5-(tetrahydro-2H-pyran-4-yl)pent-1-en-3-one

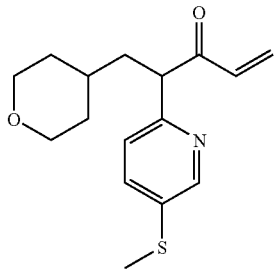

A solution of N-methoxy-N-methyl-2-[5-(methylsulfanyl) pyridin-2-yl]-3-(tetrahydro-2H-pyran-4-yl)propanamide (404 mg) in tetrahydrofuran (5 mL) was cooled to 0° C., and vinylmagnesium bromide (1.0M tetrahydrofuran solution, 5.0 mL) was added dropwise thereto. The reaction mixture was stirred at room temperature for 2 hr, and poured into 1M hydrochloric acid, and the mixture was stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (168 mg, yield 46%) was obtained as a pale-yellow amorphous solid from a fraction eluted with ethyl acetate-hexane (1:1, volume ratio).

$^1$H NMR (300 MHz, CDCl$_3$) δ1.19-1.88 (6 H, m), 2.06 (1 H, td, J=7.0, 13.9 Hz), 2.50 (3 H, s), 3.21-3.35 (2 H, m), 3.83-3.99 (2 H, m), 4.29 (1 H, t, J=7.5 Hz), 5.74 (1 H, dd, J=2.4, 9.3 Hz), 6.29-6.48 (2 H, m), 7.13 (1 H, dd, J=0.8, 8.3 Hz), 7.52 (1 H, dd, J=2.4, 8.3 Hz), 8.44 (1 H, d, J=1.9 Hz).

Reference Example 149

5-[5-(methylsulfanyl)pyridin-2-yl]-1-(pyridin-2-yl)-6-(tetrahydro-2H-pyran-4-yl)hexane-1,4-dione

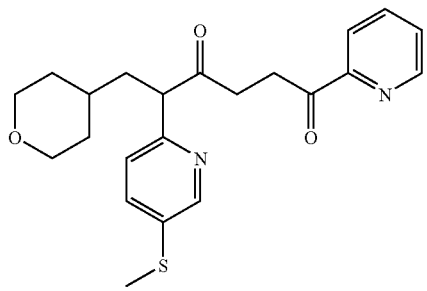

To a solution of 4-[5-(methylsulfanyl)pyridin-2-yl]-5-(tetrahydro-2H-pyran-4-yl)pent-1-en-3-one (55.4 mg) in ethanol (1 mL) were added pyridine-2-carbaldehyde (21.7 μL), 3-benzyl-5-(2-hydroxyethyl)-4-methyl-1,3-thiazol-3-ium chloride (5.6 mg) and triethylamine (11.4 μL), and the mixture was stirred with heating under reflux for 2 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (27.7 mg, yield 37%) was obtained as a pale-yellow amorphous solid from a fraction eluted with ethyl acetate-hexane (2:1, volume ratio).

$^1$H NMR (300 MHz, CDCl$_3$) δ1.18-1.45 (3 H, m), 1.51-1.72 (2 H, m), 1.75-1.88 (1 H, m), 2.01-2.14 (1 H, m), 2.51 (3H, s), 2.73-2.99 (2 H, m), 3.22-3.60 (4H, m), 3.86-3.99 (2 H, m), 4.08-4.19 (1 H, m), 7.18 (1 H, d, J=8.3 Hz), 7.42-7.50 (1 H, m), 7.55 (1 H, dd, J=2.7, 8.3 Hz), 7.76-7.86 (1 H, m), 7.98 (1 H, d, J=8.0 Hz), 8.46 (1 H, d, J=1.9 Hz), 8.66 (1 H, d, J=4.2 Hz).

Reference Example 150

2-[3-fluoro-4-(methylsulfanyl)phenyl]-N-methoxy-N-methyl-3-(tetrahydro-2H-pyran-4-yl)propanamide

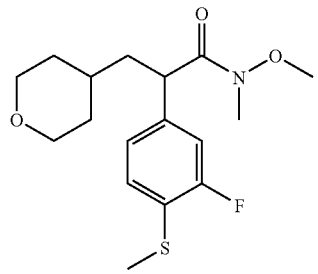

A solution of N-methoxymethanamine hydrochloride (467 mg) in acetonitrile (16 mL) was neutralized with triethylamine (1.82 mL), and 2-[3-fluoro-4-(methylsulfanyl)phenyl]-3-(tetrahydro-2H-pyran-4-yl)propanoic acid (1.30 g), N-[3-(dimethylamino)propyl]-N'-ethylcarbodiimide hydrochloride (918 mg) and 1-hydroxybenzotriazole (73.4 mg) were added under ice-cooling. The reaction mixture was warmed to room temperature and stirred overnight. The reaction mixture was diluted with ethyl acetate, and washed with water and saturated aqueous sodium hydrogen carbonate. The ethyl acetate layer was dried (MgSO$_4$) and concentrated. The residue was subjected to silica gel column chromatography, and the title compound (1.33 g, yield 89%) was obtained as a colorless amorphous solid from a fraction eluted with ethyl acetate-hexane (9:1, volume ratio).

$^1$H NMR (300 MHz, CDCl$_3$) δ1.19-1.49 (3 H, m), 1.52-1.71 (3 H, m), 1.93-2.03 (1 H, m), 2.45 (3 H, s), 3.16 (3 H, s), 3.25-3.38 (2 H, m), 3.54 (3 H, s), 3.88-3.97 (2 H, m), 4.05-4.20 (1 H, m), 7.00-7.10 (2 H, m), 7.20 (1 H, t, J=8.0 Hz).

Reference Example 151

4-[3-fluoro-4-(methylsulfanyl)phenyl]-5-(tetrahydro-2H-pyran-4-yl)pent-1-en-3-one

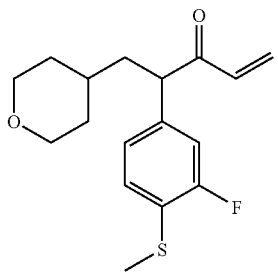

A solution of 2-[3-fluoro-4-(methylsulfanyl)phenyl]-N-methoxy-N-methyl-3-(tetrahydro-2H-pyran-4-yl)propanamide (1.33 g) in tetrahydrofuran (15.6 mL) was cooled to 0° C., and vinylmagnesium bromide (1.0M tetrahydrofuran solution, 15.6 mL) was added dropwise thereto. The reaction mixture was stirred at room temperature for 4 hr and poured into 1M hydrochloric acid, and the mixture was stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (1.12 g, yield 93%) was obtained as a pale-yellow amorphous solid from a fraction eluted with ethyl acetate-hexane (2:1, volume ratio).

$^1$H NMR (300 MHz, CDCl$_3$) δ1.20-1.73 (6 H, m), 1.94-2.06 (1 H, m), 2.46 (3 H, s), 3.18-3.36 (2 H, m), 3.86-4.00 (3 H, m), 5.72 (1 H, dd, J=2.5, 9.3 Hz), 6.20-6.43 (2 H, m), 6.87-7.00 (2 H, m), 7.21 (1 H, t, J=8.0 Hz).

Reference Example 152

5-[3-fluoro-4-(methylsulfanyl)phenyl]-1-(pyridin-2-yl)-6-(tetrahydro-2H-pyran-4-yl)hexane-1,4-dione

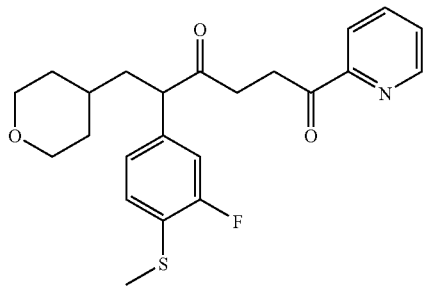

To a solution of 4-[3-fluoro-4-(methylsulfanyl)phenyl]-5-(tetrahydro-2H-pyran-4-yl)pent-1-en-3-one (225 mg) in ethanol (3.6 mL) were added pyridine-2-carbaldehyde (83.2 μL), 3-benzyl-5-(2-hydroxyethyl)-4-methyl-1,3-thiazol-3-ium chloride (21.6 mg) and triethylamine (43.7 μL), and the mixture was stirred with heating under reflux for 2 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (127 mg, yield 42%) was obtained as a pale-yellow amorphous solid from a fraction eluted with ethyl acetate-hexane (2:1, volume ratio).

$^1$H NMR (300 MHz, CDCl$_3$) δ1.18-1.76 (6 H, m), 1.93-2.04 (1 H, m), 2.47 (3 H, s), 2.66-2.79 (1 H, m), 2.82-2.95 (1 H, m), 3.22-3.42 (3 H, m), 3.48-3.61 (1 H, m), 3.82-3.98 (3 H, m), 6.91-7.04 (2 H, m), 7.23 (1 H, t, J=7.9 Hz), 7.41-7.51 (1 H, m), 7.77-7.86 (1 H, m), 7.94-8.03 (1 H, m), 8.63-8.69 (1 H, m).

Reference Example 153

5-[3-fluoro-4-(methylsulfanyl)phenyl]-1-(pyrazin-2-yl)-6-(tetrahydro-2H-pyran-4-yl)hexane-1,4-dione

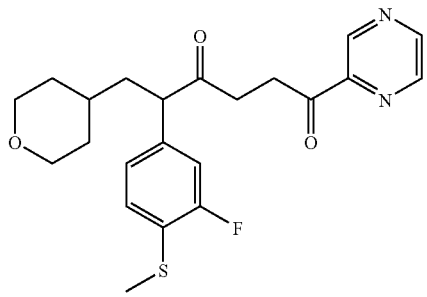

To a solution of 4-[3-fluoro-4-(methylsulfanyl)phenyl]-5-(tetrahydro-2H-pyran-4-yl)pent-1-en-3-one (433 mg) in ethanol (7 mL) were added pyrazine-2-carbaldehyde (182 mg), 3-benzyl-5-(2-hydroxyethyl)-4-methyl-1,3-thiazol-3-ium chloride (41.5 mg) and triethylamine (84.1 μL), and the mixture was stirred with heating under reflux for 2 hr. After cooling to room temperature, the reaction mixture was diluted with ethyl acetate and washed with water. The ethyl acetate layer was dried (MgSO$_4$) and concentrated. The residue was

Reference Example 154

Methyl 2-[4-(methylsulfonyl)phenyl]-3-(tetrahydrofuran-3-yl)propanoate

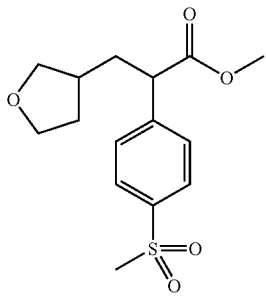

A solution of diisopropylamine (2.94 mL) in dry tetrahydrofuran (42 mL) was cooled to −78° C. and purged with nitrogen. To the reaction mixture was added dropwise a 1.6M n-butyllithium hexane solution (12.1 mL), and the mixture was stirred at −78° C. for 30 min. To the reaction mixture was added a solution of methyl [4-(methylsulfonyl)phenyl]acetate (4.00 g) in a mixed solvent of dry tetrahydrofuran (42 mL) and 1,3-dimethyl-3,4,5,6-tetrahydro-2(1H)-pyrimidinone (14 mL), and the mixture was stirred at −78° C. for 1 hr. To the reaction mixture was added a solution of 3-(iodomethyl)tetrahydrofuran (4.45 g) in 1,3-dimethyl-3,4,5,6-tetrahydro-2(1H)-pyrimidinone (4 mL), and the mixture was stirred at −78° C. for 30 min. The reaction mixture was warmed to room temperature, and stirred at room temperature for 64 hr. A saturated aqueous ammonium chloride solution was added to the reaction mixture, and the mixture was extracted with ethyl acetate. The extract was washed with saturated brine, dried over anhydrous magnesium sulfate and concentrated under reduced pressure. The residue was subjected to silica gel column chromatography, and the title compound (3.61 g, yield 66%) was obtained as a colorless amorphous solid from a fraction eluted with ethyl acetate-hexane (3:1, volume ratio).

$^1$H NMR (300 MHz, CDCl$_3$) δ1.43-1.65 (1 H, m), 1.82-2.29 (4 H, m), 3.05 (3 H, s), 3.27-3.42 (1 H, m), 3.60-3.95 (7 H, m), 7.52 (2 H, d, J=8.3 Hz), 7.91 (2 H, d, J=8.3 Hz).

Reference Example 155

2-[4-(methylsulfonyl)phenyl]-3-(tetrahydrofuran-3-yl)propanoic acid

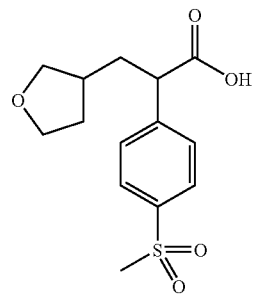

To a solution of methyl 2-[4-(methylsulfonyl)phenyl]-3-(tetrahydrofuran-3-yl)propanoate (3.61 g) in a mixed solvent of methanol (46 mL) was added 2M aqueous sodium hydroxide solution (11.6 mL), and the mixture was stirred at 50° C. for 16 hr. The reaction mixture was acidified with 6M hydrochloric acid, and extracted with ethyl acetate. The extract was washed with saturated brine, dried over anhydrous magnesium sulfate, and concentrated under reduced pressure to give the title compound (3.12 g, 90%) as colorless crystals.

$^1$H NMR (300 MHz, CDCl$_3$) δ1.41-1.57 (1 H, m), 1.73-2.13 (4 H, m), 3.13-3.36 (4 H, m), 3.48-3.84 (4 H, m), 7.56-7.64 (2 H, m), 7.89 (2 H, d, J=8.3 Hz), 12.65 (1 H, s).

Reference Example 156

N-methoxy-N-methyl-2-[4-(methylsulfonyl)phenyl]-3-(tetrahydrofuran-3-yl)propanamide

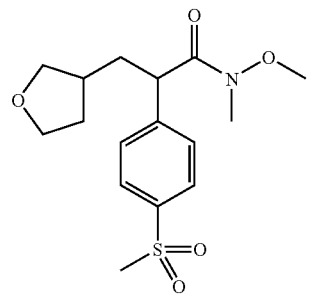

To a solution of N-methoxymethanamine hydrochloride (1.22 g) in acetonitrile (40 mL) was added triethylamine (4.35 mL) for neutralization, and 2-[4-(methylsulfonyl)phenyl]-3-(tetrahydrofuran-3-yl)propanoic acid (3.12 g), N-[3-(dimethylamino)propyl]-N'-ethylcarbodiimide hydrochloride (2.40 g) and 1-hydroxybenzotriazole (191 mg) were added under ice-cooling. The reaction mixture was stirred overnight at room temperature, diluted with ethyl acetate, and washed with water and saturated aqueous sodium hydrogen carbonate. The ethyl acetate layer was dried (MgSO$_4$) and concentrated. The residue was subjected to silica gel column chromatography, and the title compound (2.96 g, yield 83%) was obtained as a colorless amorphous solid from a fraction eluted with ethyl acetate-hexane (9:1, volume ratio).

--- subjected to silica gel column chromatography, and the title compound (438 mg, yield 75%) was obtained as a pale-yellow amorphous solid from a fraction eluted with ethyl acetate-hexane (2:1, volume ratio).

$^1$H NMR (300 MHz, CDCl$_3$) δ1.18-1.43 (3 H, m), 1.48-1.76 (3 H, m), 1.92-2.04 (1 H, m), 2.48 (3 H, s), 2.68-2.98 (2 H, m), 3.23-3.38 (3 H, m), 3.42-3.57 (1 H, m), 3.81-3.99 (3 H, m), 6.91-7.04 (2 H, m), 7.20-7.26 (1 H, m), 8.63 (1 H, dd, J=1.6, 2.5 Hz), 8.75 (1 H, d, J=2.4 Hz), 9.18 (1 H, d, J=1.5 Hz).

$^1$H NMR (300 MHz, CDCl$_3$) δ1.42-2.28 (5 H, m), 3.03-4.06 (8 H, m), 5.78 (1 H, dd, J=3.4, 7.9 Hz), 6.25-6.43 (2 H, m), 7.45 (2 H, d, J=8.3 Hz), 7.86-7.96 (2 H, m).

Reference Example 157

4-[4-(methylsulfonyl)phenyl]-5-(tetrahydrofuran-3-yl)pent-1-en-3-one

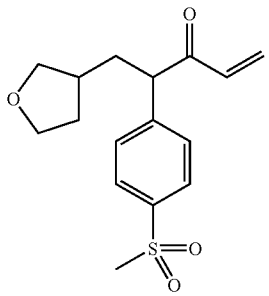

A solution of N-methoxy-N-methyl-2-[4-(methylsulfonyl)phenyl]-3-(tetrahydrofuran-3-yl)propanamide (2.96 g) in tetrahydrofuran (34.6 mL) was cooled to 0° C., vinylmagnesium bromide (1.0M tetrahydrofuran solution, 34.6 ml) was added dropwise thereto. The reaction mixture was stirred at room temperature for 4 hr, and poured into 1M hydrochloric acid, and the mixture was stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (2.06 g, yield 77%) was obtained as a colorless amorphous solid from a fraction eluted with ethyl acetate-hexane (9:1, volume ratio).

$^1$H NMR (300 MHz, CDCl$_3$) δ1.42-2.28 (5 H, m), 3.03-4.06 (8 H, m), 5.78 (1 H, dd, J=3.4, 7.9 Hz), 6.25-6.43 (2 H, m), 7.45 (2 H, d, J=8.3 Hz), 7.86-7.96 (2 H, m).

Reference Example 158

5-[4-(methylsulfonyl)phenyl]-1-(pyridin-2-yl)-6-(tetrahydrofuran-3-yl)hexane-1,4-dione

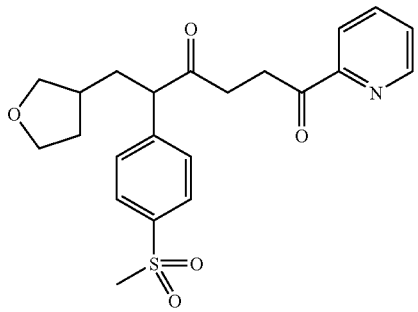

To a solution of 4-[4-(methylsulfonyl)phenyl]-5-(tetrahydrofuran-3-yl)pent-1-en-3-one (229 mg) in ethanol (3.6 mL) were added pyridine-2-carbaldehyde (84.8 mg), 3-benzyl-5-(2-hydroxyethyl)-4-methyl-1,3-thiazol-3-ium chloride (22.0 mg) and triethylamine (44.5 μL), and the mixture was stirred with heating under reflux for 3 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (43.5 mg, yield 14%) was obtained as a pale-yellow amorphous solid from a fraction eluted with ethyl acetate-hexane (19:1, volume ratio).

$^1$H NMR (300 MHz, CDCl$_3$) δ1.42-1.61 (1 H, m), 1.75-2.31 (4 H, m), 2.61-2.78 (1 H, m), 2.83-2.98 (1 H, m), 3.07 (3H, s), 3.22-3.99 (7 H, m), 7.41-7.53 (3 H, m), 7.79-7.86 (1 H, m), 7.89-8.02 (3 H, m), 8.64-8.69 (1 H, m).

Reference Example 159

5-[4-(methylsulfonyl)phenyl]-1-(pyrazin-2-yl)-6-(tetrahydrofuran-3-yl)hexane-1,4-dione

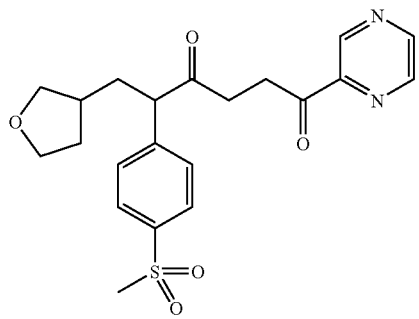

To a solution of 4-[4-(methylsulfonyl)phenyl]-5-(tetrahydrofuran-3-yl)pent-1-en-3-one (523 mg) in ethanol (8.5 mL) were added pyrazine-2-carbaldehyde (220 mg), 3-benzyl-5-(2-hydroxyethyl)-4-methyl-1,3-thiazol-3-ium chloride (50.5 mg) and triethylamine (102 μL), and the mixture was stirred with heating under reflux for 3 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (100 mg, yield 14%) was obtained as a pale-yellow amorphous solid from a fraction eluted with ethyl acetate-hexane (19:1, volume ratio).

$^1$H NMR (300 MHz, CDCl$_3$) δ1.37-1.61 (1 H, m), 1.78-2.29 (4 H, m), 2.67-2.81 (1 H, m), 2.88-3.00 (1 H, m), 3.08 (3 H, s), 3.26-3.58 (3 H, m), 3.64-3.97 (4 H, m), 7.48 (2 H, d, J=8.3 Hz), 7.95 (2 H, d, J=8.5 Hz), 8.64 (1 H, dd, J=1.5, 2.4 Hz), 8.76 (1 H, d, J=2.4 Hz), 9.18 (1 H, d, J=1.3 Hz).

Reference Example 160

Ethyl [2-({[tert-butyl (diphenyl)silyl]oxy}acetyl)hydrazino](oxo)acetate

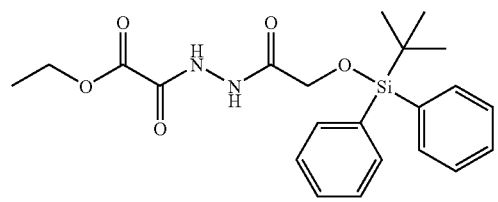

To a solution of ethyl hydrazino(oxo)acetate (3.58 g) in acetonitrile (100 mL) were successively added triethylamine (6.86 mL), {[tert-butyl(diphenyl)silyl]oxy}acetic acid (7.74 g), N-[3-(dimethylamino)propyl]-N'-ethylcarbodiimide hydrochloride (5.20 g) and 1-hydroxybenzotriazole (415 mg) under ice-cooling. The reaction mixture was warmed to room temperature and stirred overnight. The reaction mixture was diluted with ethyl acetate, washed with water and saturated aqueous sodium hydrogen carbonate. The ethyl acetate layer was dried (MgSO$_4$) and concentrated. The residue was subjected to silica gel column chromatography, and the title compound (3.20 g, yield 30%) was obtained as a colorless amorphous solid from a fraction eluted with ethyl acetate-hexane (1:1, volume ratio).

$^1$H NMR (300 MHz, CDCl$_3$) δ1.12 (9 H, s), 1.41 (3 H, t, J=7.2 Hz), 4.27 (2 H, s), 4.41 (2 H, q, J=7.2 Hz), 7.37-7.50 (6 H, m), 7.64 (4 H, dd, J=1.7, 7.8 Hz), 9.25 (1 H, brs), 9.50 (1 H, brs).

Reference Example 161

Ethyl 5-({[tert-butyl(diphenyl)silyl]oxy}methyl)-1,3,4-thiadiazole-2-carboxylate

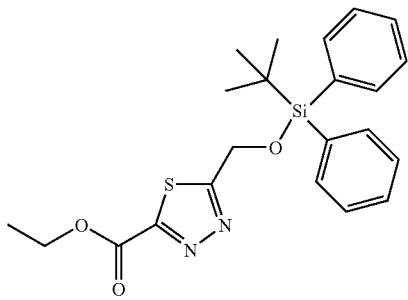

To a solution of ethyl [2-({[tert-butyl(diphenyl)silyl]oxy}acetyl)hydrazino](oxo)acetate (3.20 g) in tetrahydrofuran (30 mL) was added Lawesson's reagent (3.02 g), and the mixture was stirred at room temperature for 24 hr. The reaction mixture was concentrated, and the residue was subjected to silica gel column chromatography, and the title compound (3.05 g, yield 96%) was obtained as a colorless amorphous solid from a fraction eluted with ethyl acetate-hexane (1:1, volume ratio).

$^1$H NMR (300 MHz, CDCl$_3$) δ1.12 (9 H, s), 1.47 (3 H, t, J=7.0 Hz), 4.53 (2 H, q, J=7.2 Hz), 5.11 (2 H, s), 7.35-7.51 (6 H, m), 7.60-7.70 (4 H, m).

Reference Example 162

[5-({[tert-butyl(diphenyl)silyl]oxy}methyl)-1,3,4-thiadiazol-2-yl]methanol

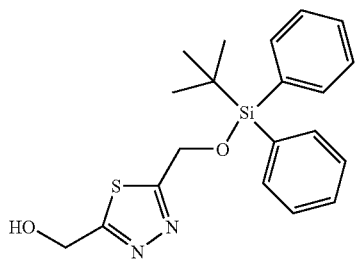

To a solution of ethyl 5-({[tert-butyl(diphenyl)silyl]oxy}methyl)-1,3,4-thiadiazole-2-carboxylate (998 mg) in methanol (12 ml) was added sodium borohydride (177 mg), and the mixture was stirred at 0° C. for 1 hr. A saturated aqueous ammonium chloride solution was added to the reaction mixture, and the mixture was extracted with ethyl acetate. The extract was dried over anhydrous magnesium sulfate and concentrated under reduced pressure. The residue was subjected to silica gel column chromatography, and the title compound (738 mg, yield 82%) was obtained as a colorless amorphous solid from a fraction eluted with ethyl acetate-hexane (2:1, volume ratio).

$^1$H NMR (300 MHz, CDCl$_3$) δ1.10 (9 H, s), 5.02-5.11 (4 H, m), 7.35-7.51 (6 H, m), 7.67 (4 H, dd, J=1.5, 8.0 Hz).

Reference Example 163

5-({[tert-butyl(diphenyl)silyl]oxy}methyl)-1,3,4-thiadiazole-2-carbaldehyde

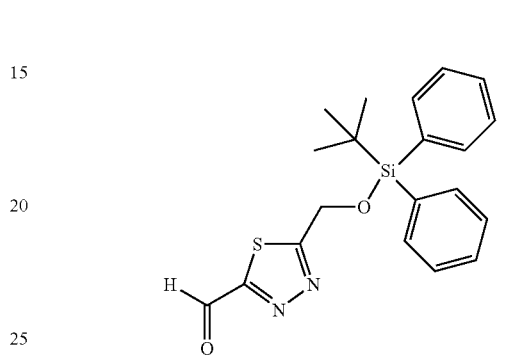

To a solution of [5-({[tert-butyl(diphenyl)silyl]oxy}methyl)-1,3,4-thiadiazol-2-yl]methanol (242 mg) in toluene (2 mL) was added manganese dioxide (693 mg), and the mixture was stirred at room temperature for 1 hr. The reaction mixture was filtered through celite, and the filtrate was concentrated to give the title compound (171 mg) as a colorless amorphous solid.

$^1$H NMR (300 MHz, CDCl$_3$) δ1.12 (9 H, s), 5.13 (2 H, s), 7.36-7.51 (6 H, m), 7.62-7.70 (4 H, m), 10.20 (1 H, s).

Reference Example 164

1-[5-({[tert-butyl(diphenyl)silyl]oxy}methyl)-1,3,4-thiadiazol-2-yl]-5-[4-(cyclopropylsulfonyl)phenyl]-6-(tetrahydro-2H-pyran-4-yl)hexane-1,4-dione

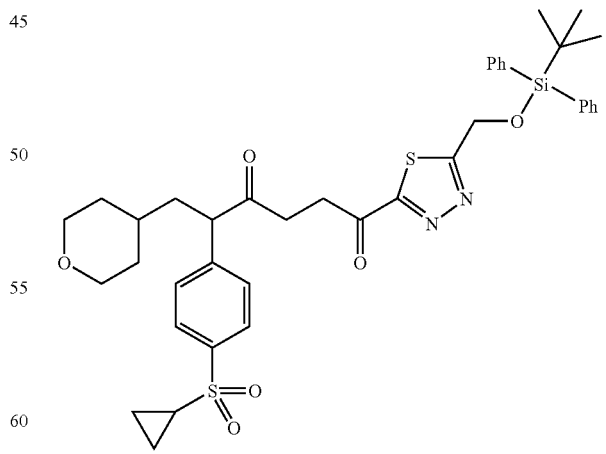

To a solution of 4-[4-(cyclopropylsulfonyl)phenyl]-5-(tetrahydro-2H-pyran-4-yl)pent-1-en-3-one (141 mg) in a mixed solvent of ethanol (1 mL) and tetrahydrofuran (1 mL) were added 5-({[tert-butyl(diphenyl)silyl]oxy}methyl)-1,3,4-thiadiazole-2-carbaldehyde (171 mg), 3-benzyl-5-(2-hydroxyethyl)-4-methyl-1,3-thiazol-3-ium chloride (12.1 mg) and triethylamine (24.4 μL), and the mixture was stirred with heating under reflux for 3 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (168 mg, yield 57%) was obtained as white crystals from a fraction eluted with ethyl acetate-hexane (19:1, volume ratio).

$^1$H NMR (300 MHz, CDCl$_3$) δ1.00-1.73 (18 H, m), 2.01-2.14 (1 H, m), 2.42-2.55 (1 H, m), 2.71-3.03 (2 H, m), 3.19-3.61 (4 H, m), 3.88-4.06 (3 H, m), 5.09 (2 H, s), 7.36-7.52 (8 H, m), 7.63-7.70 (4 H, m), 7.86-7.94 (2 H, m).

Reference Example 165

Methyl 2-[4-(methylsulfonyl)phenyl]-3-(tetrahydrofuran-2-yl)propanoate

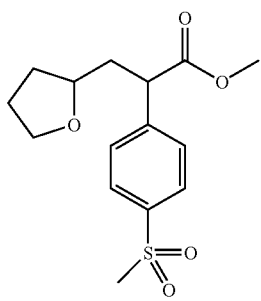

A solution of diisopropylamine (3.43 mL) in dry tetrahydrofuran (45 mL) was cooled to −78° C. and purged with nitrogen. A 1.6M n-butyllithium hexane solution (13.1 mL) was added dropwise to the reaction mixture, and the mixture was stirred at −78° C. for 30 min. To the reaction mixture was added a solution of methyl [4-(methylsulfonyl)phenyl]acetate (4.00 g) in a mixed solvent of dry tetrahydrofuran (45 mL) and 1,3-dimethyl-3,4,5,6-tetrahydro-2(1H)-pyrimidinone (15 mL), and the mixture was stirred at −78° C. for 1 hr. To the reaction mixture was added a solution of 2-(iodomethyl)tetrahydrofuran (4.05 g) in 1,3-dimethyl-3,4,5,6-tetrahydro-2(1H)-pyrimidinone (5 mL), and the mixture was stirred at −78° C. for 30 min. The reaction mixture was warmed to room temperature, and stirred at room temperature 2 for 4 hr. A saturated aqueous ammonium chloride solution was added to the reaction mixture, and the mixture was extracted with ethyl acetate. The extract was washed with saturated brine, dried over anhydrous magnesium sulfate and concentrated under reduced pressure. The residue was subjected to silica gel column chromatography, and the title compound (1.94 g, yield 35%) was obtained as a colorless amorphous solid from a fraction eluted with ethyl acetate-hexane (3:1, volume ratio).

$^1$H NMR (300 MHz, CDCl$_3$) δ1.41-2.46 (7 H, m), 3.05 (3 H, s), 3.52-4.05 (4 H, m), 7.46-7.61 (2 H, m), 7.83-7.98 (2 H, m).

Reference Example 166

2-[4-(methylsulfonyl)phenyl]-3-(tetrahydrofuran-2-yl)propanoic acid

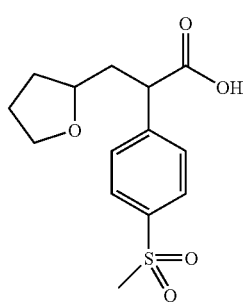

To a solution of methyl 2-[4-(methylsulfonyl)phenyl]-3-(tetrahydrofuran-2-yl)propanoate (1.94 g) in methanol (25 mL) was added 2M aqueous sodium hydroxide solution (6.21 mL), and the mixture was stirred at 50° C. for 16 hr. The reaction mixture was acidified with 6M hydrochloric acid, and extracted with ethyl acetate. The extract was washed with saturated brine, dried over anhydrous magnesium sulfate, and concentrated under reduced pressure to give the title compound (1.69 g, 91%) as colorless crystals.

$^1$H NMR (300 MHz, CDCl$_3$) δ1.41-2.46 (7 H, m), 3.05 (3 H, s), 3.52-4.05 (4 H, m), 7.46-7.61 (2 H, m), 7.83-7.98 (2 H, m).

Reference Example 167

N-methoxy-N-methyl-2-[4-(methylsulfonyl)phenyl]-3-(tetrahydrofuran-2-yl)propanamide

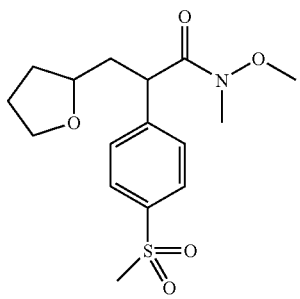

A solution of N-methoxymethanamine hydrochloride (662 mg) in acetonitrile (23 mL) was neutralized with triethylamine (2.34 mL), and 2-[4-(methylsulfonyl)phenyl]-3-(tetrahydrofuran-3-yl)propanoic acid (1.69 g), N-[3-(dimethylamino)propyl]-N'-ethylcarbodiimide hydrochloride (1.30 g) and 1-hydroxybenzotriazole (104 mg) were added under ice-cooling. The reaction mixture was stirred overnight at room temperature, diluted with ethyl acetate, and washed with water and saturated aqueous sodium hydrogen carbonate. The ethyl acetate layer was dried (MgSO$_4$) and concentrated. The residue was subjected to silica gel column chromatography, and the title compound (1.68 g, yield 87%) was obtained as a colorless amorphous solid from a fraction eluted with ethyl acetate-hexane (99:1, volume ratio).

$^1$H NMR (300 MHz, CDCl$_3$) δ1.38-2.57 (6 H, m), 3.00-3.24 (6 H, m), 3.47-3.91 (6 H, m), 4.30-4.55 (1 H, m), 7.46-7.63 (1 H, m), 7.82-7.93 (2 H, m).

Reference Example 168

4-[4-(methylsulfonyl)phenyl]-5-(tetrahydrofuran-2-yl)pent-1-en-3-one

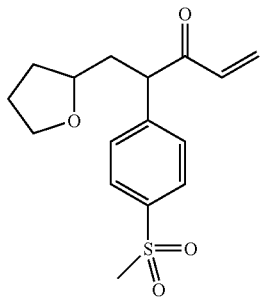

A solution of N-methoxy-N-methyl-2-[4-(methylsulfonyl)phenyl]-3-(tetrahydrofuran-2-yl)propanamide (1.68 g) in tetrahydrofuran (19.7 mL) was cooled to 0° C., and vinylmagnesium bromide (1.0M tetrahydrofuran solution, 19.7 mL) was added dropwise thereto. The reaction mixture was stirred at room temperature for 3 hr, and poured into 1M hydrochloric acid, and the mixture was stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (930 mg, yield 61%) was obtained as a colorless amorphous solid from a fraction eluted with ethyl acetate-hexane (9:1, volume ratio). MS: 309 (MH$^+$).

Reference Example 169

5-[4-(methylsulfonyl)phenyl]-1-(pyridin-2-yl)-6-(tetrahydrofuran-2-yl)hexane-1,4-dione

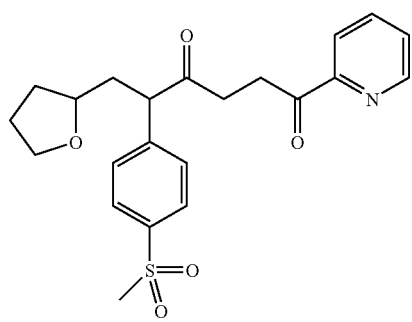

To a solution of 4-[4-(methylsulfonyl)phenyl]-5-(tetrahydrofuran-2-yl)pent-1-en-3-one (930 mg) in a mixed solvent of ethanol (7.5 mL) and tetrahydrofuran (7.5 mL) were added pyridine-2-carbaldehyde (323 μL), 3-benzyl-5-(2-hydroxyethyl)-4-methyl-1,3-thiazol-3-ium chloride (89.6 mg) and triethylamine (181 μL), and the mixture was stirred with heating under reflux for 3 hr. After cooling to room temperature, the reaction mixture was diluted with ethyl acetate and washed with water. The ethyl acetate layer was dried (MgSO$_9$) and concentrated. The residue was subjected to silica gel column chromatography, and the title compound (302 mg, yield 24%) was obtained as a pale-yellow amorphous solid from a fraction eluted with ethyl acetate-hexane (19:1, volume ratio). MS: 416 (MH$^+$).

Reference Example 170

Ethyl 2-methyl-2-[5-(methylsulfanyl)pyridin-2-yl]-3-(tetrahydro-2H-pyran-4-yl)propanoate

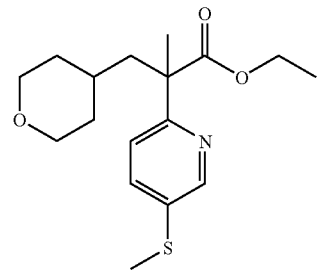

To a solution of ethyl 2-[5-(methylsulfanyl)pyridin-2-yl]-3-(tetrahydro-2H-pyran-4-yl)propanoate (1.18 g) in dry tetrahydrofuran (7.6 mL) was added lithium hexamethyldisilazide (1.1M tetrahydrofuran solution, 4.49 mL), and the mixture was stirred at 0° C. for 30 min. To the reaction mixture was added methyl iodide (473 μL), and the mixture was stirred at room temperature for 30 min. A saturated aqueous ammonium chloride solution was added to the reaction mixture, and the mixture was extracted with ethyl acetate. The extract was washed with saturated brine, dried over anhydrous magnesium sulfate and concentrated under reduced pressure. The residue was subjected to silica gel column chromatography, and the title compound (1.11 g, yield 90%) was obtained as a colorless amorphous solid from a fraction eluted with ethyl acetate-hexane (1:2, volume ratio).

$^1$H NMR (300 MHz, CDCl$_3$) δ1.13-1.78 (11 H, m), 1.95-2.15 (2 H, m), 3.21-3.38 (2 H, m), 3.78-3.94 (2 H, m), 4.14 (2 H, q, J=7.2 Hz), 7.21 (1 H, d, J=8.5 Hz), 7.52 (1 H, dd, J=2.5, 8.4 Hz), 8.44 (1 H, d, J=2.4 Hz).

Reference Example 171

N-methoxy-N,2-dimethyl-2-[5-(methylsulfanyl)pyridin-2-yl]-3-(tetrahydro-2H-pyran-4-yl)propanamide

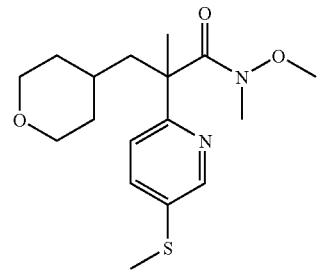

A solution of N-methoxymethanamine hydrochloride (1.00 g) in toluene (10 mL) was cooled to 0° C., and trimethylaluminum (1.4M hexane solution, 7.36 mL) was added dropwise thereto. The reaction mixture was stirred at room temperature for 1.5 hr, and a solution (10 mL) of ethyl 2-methyl-2-[5-(methylsulfanyl)pyridin-2-yl]-3-(tetrahydro-2H-pyran-4-yl)propanoate (1.11 g) in toluene was added dropwise thereto. The reaction mixture was stirred at room temperature for 24 hr, saturated aqueous sodium hydrogen carbonate and saturated aqueous Rochelle salt solution were added and the mixture was stirred for 1 hr. The reaction mixture was extracted with ethyl acetate, and the ethyl acetate layer was washed with saturated brine, dried (MgSO$_4$) and concentrated. The residue was subjected to silica gel column chromatography, and the title compound (401 mg, yield 35%) was obtained as white crystals from a fraction eluted with ethyl acetate-hexane (9:1, volume ratio).

$^1$H NMR (300 MHz, CDCl$_3$) δ1.18-1.69 (8 H, m), 1.91 (1 H, dd, J=5.1, 14.2 Hz), 2.24 (1 H, dd, J=5.9, 14.2 Hz), 2.50 (3 H, s), 2.79 (3 H, s), 3.12 (3 H, s), 3.24-3.39 (2 H, m), 3.78-3.91 (2 H, m), 7.18 (1 H, d, J=8.3 Hz), 7.55 (1 H, dd, J=2.7, 8.3 Hz), 8.47 (1 H, d, J=2.3 Hz).

Reference Example 172

4-methyl-4-[5-(methylsulfanyl)pyridin-2-yl]-5-(tetrahydro-2H-pyran-4-yl)pent-1-en-3-one

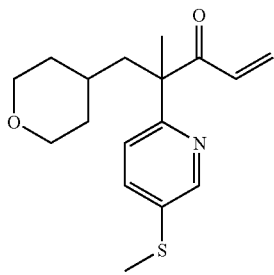

A solution of N-methoxy-N,2-dimethyl-2-[5-(methylsulfanyl)pyridin-2-yl]-3-(tetrahydro-2H-pyran-4-yl)propanamide (401 mg) in tetrahydrofuran (4.8 mL) was cooled to 0° C., and vinylmagnesium bromide (1.0M tetrahydrofuran solution, 4.76 mL) was added dropwise thereto. The reaction mixture was stirred at room temperature for 3 hr, and poured into 1M hydrochloric acid, and the mixture was stirred for 30 min. The reaction mixture was extracted with ethyl acetate, and the ethyl acetate layer was washed with saturated aqueous sodium hydrogen carbonate and saturated brine, dried (MgSO$_4$) and concentrated. The residue was subjected to silica gel column chromatography, and the title compound (250 mg, yield 69%) was obtained as a colorless amorphous solid from a fraction eluted with ethyl acetate-hexane (1:1, volume ratio).

$^1$H NMR (300 MHz, CDCl$_3$) δ1.08-1.64 (8 H, m), 1.91-2.15 (2 H, m), 2.51 (3 H, s), 3.16-3.36 (2 H, m), 3.73-3.90 (2 H, m), 5.52 (1 H, dd, J=2.7, 9.5 Hz), 6.17-6.39 (2 H, m), 7.14 (1 H, d, J=8.3 Hz), 7.52 (1 H, dd, J=2.7, 8.3 Hz), 8.45 (1 H, d, J=2.7 Hz).

Reference Example 173

5-methyl-5-[5-(methylsulfanyl)pyridin-2-yl]-1-(pyridin-2-yl)-6-(tetrahydro-2H-pyran-4-yl)hexane-1,4-dione

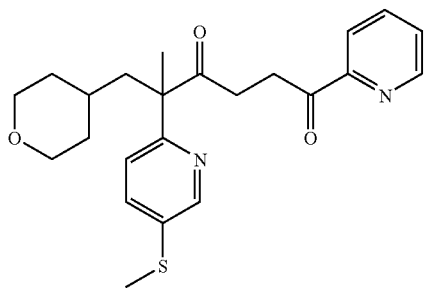

To a solution of 4-methyl-4-[5-(methylsulfanyl)pyridin-2-yl]-5-(tetrahydro-2H-pyran-4-yl)pent-1-en-3-one (77.8 mg) in a mixed solvent of ethanol (0.6 mL) and tetrahydrofuran (0.6 mL) were added pyridine-2-carbaldehyde (48.5 μL), 3-benzyl-5-(2-hydroxyethyl)-4-methyl-1,3-thiazol-3-ium chloride (6.9 mg) and triethylamine (14.2 μL), and the mixture was stirred with heating under reflux for 3 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (60.7 mg, yield 58%) was obtained as a pale-yellow amorphous solid from a fraction eluted with ethyl acetate-hexane (1:2, volume ratio).

$^1$H NMR (300 MHz, CDCl$_3$) δ1.09-1.19 (2 H, m), 1.24-1.69 (6 H, m), 1.94-2.14 (2 H, m), 2.52 (3 H, s), 2.57-2.70 (1 H, m), 2.73-2.85 (1 H, m), 3.14-3.56 (4 H, m), 3.72-3.90 (2 H, m), 7.22-7.26 (1 H, m), 7.42-7.48 (1 H, m), 7.55 (1 H, dd, J=2.4, 8.3 Hz), 7.77-7.85 (1 H, m), 7.95-8.01 (1 H, m), 8.45-8.49 (1 H, m), 8.64-8.69 (1 H, m).

Reference Example 174

1-[5-(1-hydroxy-2-methoxyethyl)-1,3-thiazol-2-yl]-5-[5-(methylsulfanyl)pyridin-2-yl]-6-(tetrahydro-2H-pyran-4-yl)hexane-1,4-dione

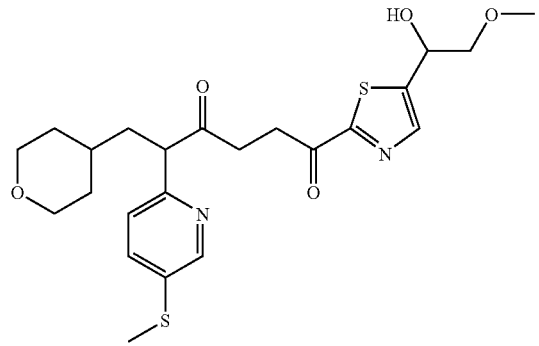

To a solution of 4-[5-(methylsulfanyl)pyridin-2-yl]-5-(tetrahydro-2H-pyran-4-yl)pent-1-en-3-one (168 mg) in a mixed solvent of ethanol (1.5 mL) and tetrahydrofuran (1.5 mL) were added 5-(1-hydroxy-2-methoxyethyl)-1,3-thiazole-2-carbaldehyde (119 mg), 3-benzyl-5-(2-hydroxyethyl)-4-methyl-1,3-thiazol-3-ium chloride (15.5 mg) and triethylamine (32.1 μL), and the mixture was stirred with heating under reflux for 2 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (103 mg, yield 37%) was obtained as a pale-yellow amorphous solid from a fraction eluted with ethyl acetate-hexane (19:1, volume ratio).

$^1$H NMR (300 MHz, CDCl$_3$) δ1.17-1.42 (3 H, m), 1.49-1.88 (3 H, m), 1.99-2.13 (1 H, m), 2.51 (3 H, s), 2.73-2.98 (2 H, m), 3.02-3.48 (8 H, m), 3.53 (1 H, dd, J=7.0, 9.4 Hz), 3.63-3.69 (1 H, m), 3.85-3.96 (2 H, m), 4.10 (1 H, t, J=7.5 Hz), 5.17 (1 H, dd, J=3.7, 6.9 Hz), 7.16 (1 H, d, J=8.1 Hz), 7.55 (1 H, dd, J=2.5, 8.2 Hz), 7.86 (1 H, s), 8.45 (1 H, d, J=2.4 Hz).

Reference Example 175

5-chloro-2-(1,3-dioxolan-2-yl)-1,3-thiazole

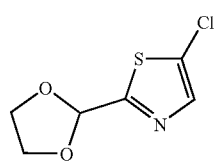

A solution of 2-(1,3-dioxolan-2-yl)-1,3-thiazole (2.00 g) in tetrahydrofuran (50 mL) was cooled to −78° C. and purged with nitrogen. n-Butyllithium (1.6M hexane solution, 9.56 mL) was added dropwise to the reaction mixture, and the mixture was stirred for 30 min. To the reaction mixture was added carbon tetrachloride (6.13 mL), and the mixture was stirred at 0° C. for 1 hr. Water was added to the reaction mixture, and the mixture was extracted with ethyl acetate. The extract was washed with saturated brine, dried over anhydrous magnesium sulfate and concentrated under reduced pressure. The residue was subjected to silica gel column chromatography, and the title compound (1.81 g, yield 74%) was obtained as a yellow amorphous solid from a fraction eluted with ethyl acetate-hexane (1:4, volume ratio).

$^1$H NMR (300 MHz, CDCl$_3$) δ4.02-4.20 (4 H, m), 6.02 (1 H, s), 7.60 (1 H, s).

Reference Example 176

5-chloro-1,3-thiazole-2-carbaldehyde

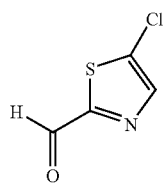

To a solution of 5-chloro-2-(1,3-dioxolan-2-yl)-1,3-thiazole (1.81 g) in tetrahydrofuran (5 mL) was added 1M hydrochloric acid (5 mL), and the mixture was stirred with heating under reflux for 8 hr. After cooling to room temperature, the mixture was neutralized with saturated aqueous sodium hydrogen carbonate solution. The reaction mixture was diluted with diethyl ether and washed with saturated brine. The ethyl acetate layer was dried (MgSO$_4$) and concentrated. The residue was subjected to silica gel column chromatography, and the title compound (1.02 g, yield 73%) was obtained as pale-yellow crystals from a fraction eluted with ethyl acetate-hexane (1:4, volume ratio).

$^1$H NMR (300 MHz, CDCl$_3$) δ7.92 (1 H, s), 9.85 (1 H, s).

Reference Example 177

1-(5-chloro-1,3-thiazol-2-yl)-5-[5-(methylsulfanyl)pyridin-2-yl]-6-(tetrahydro-2H-pyran-4-yl)hexane-1,4-dione

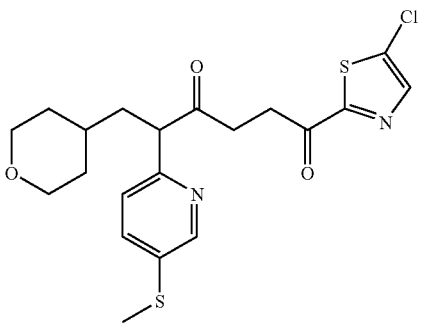

To a solution of 4-[5-(methylsulfanyl)pyridin-2-yl]-5-(tetrahydro-2H-pyran-4-yl)pent-1-en-3-one (85.0 mg) in a mixed solvent of ethanol (1.5 mL) and tetrahydrofuran (1.5 mL) were added 5-chloro-1,3-thiazole-2-carbaldehyde (86.0 mg), 3-benzyl-5-(2-hydroxyethyl)-4-methyl-1,3-thiazol-3-ium chloride (7.9 mg) and triethylamine (16.3 µL), and the mixture was stirred with heating under reflux for 2 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (98.4 mg, yield 77%) was obtained as a pale-yellow amorphous solid from a fraction eluted with ethyl acetate-hexane (1:1, volume ratio).

$^1$H NMR (300 MHz, CDCl$_3$) δ1.18-1.42 (2 H, m), 1.47-1.70 (3 H, m), 1.74-1.87 (1 H, m), 1.98-2.10 (1 H, m), 2.52 (3 H, s), 2.73-2.99 (2 H, m), 3.16-3.41 (4 H, m), 3.86-3.97 (2 H, m), 4.09 (1 H, dd, J=7.0, 8.3 Hz), 7.15 (1 H, dd, J=0.8, 8.3 Hz), 7.55 (1 H, dd, J=2.4, 8.1 Hz), 7.76 (1 H, s), 8.45 (1 H, d, J=1.9 Hz).

Reference Example 178

2-bromo-5-(1-{[tert-butyl(dimethyl)silyl]oxy}ethyl)pyridine

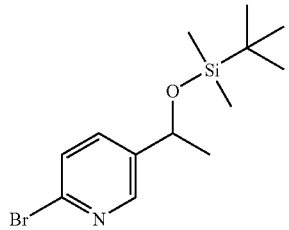

A solution of 2,5-dibromopyridine (7.11 g) in diethyl ether (120 mL) was cooled to −78° C. and purged with nitrogen. n-Butyllithium (1.6M hexane solution, 20.6 mL) was added dropwise to the reaction mixture and the mixture was stirred for 1 hr. To the reaction mixture was added acetoaldehyde (2.53 mL), and the mixture was stirred at 0° C. for 1 hr. To the reaction mixture was added a solution of tert-butyl(dimethyl)silyl trifluoromethanesulfonate (9.19 ml) in tetrahydrofuran (40 mL), and the mixture was stirred at 0° C. for 15 min. To the reaction mixture was added saturated aqueous sodium hydrogen carbonate, and the mixture was extracted with diethyl ether. The extract was washed with saturated brine, dried (MgSO$_4$) and concentrated. The residue was subjected to silica gel column chromatography, and the title compound (6.72 g, yield 71%) was obtained as a pale-yellow amorphous solid from a fraction eluted with ethyl acetate-hexane (1:9, volume ratio).

$^1$H NMR (300 MHz, CDCl$_3$) δ-0.09 (3 H, s), 0.00 (3 H, s), 0.82 (9H, s), 1.33 (3 H, d, J=6.4 Hz), 4.80 (1 H, q, J=6.3 Hz), 7.34-7.38 (1 H, m), 7.45-7.50 (1 H, m), 8.24 (1 H, d, J=2.3 Hz).

Reference Example 179

5-(1-{[tert-butyl(dimethyl)silyl]oxy}ethyl)pyridine-2-carbaldehyde

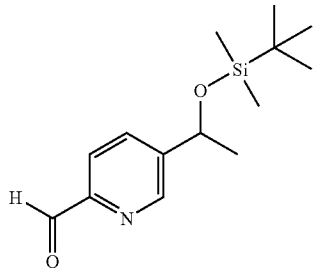

A solution of 2-bromo-5-(1-{[tert-butyl(dimethyl)silyl]oxy}ethyl)pyridine (6.72 g) in toluene (100 mL) was cooled to −78° C. and purged with nitrogen. n-Butyllithium (1.6M hexane solution, 15.9 mL) was added dropwise to the reaction mixture, and the mixture was stirred for 1 hr. To the reaction mixture was added N,N-dimethylformamide (8.21 mL), and the mixture was stirred at room temperature for 1 hr. Water was added to the reaction mixture, and the mixture was extracted with diethyl ether. The extract was washed with saturated brine, dried (MgSO$_4$) and concentrated. The residue was subjected to silica gel column chromatography, and the title compound (2.98 g, yield 53%) was obtained as a pale-yellow amorphous solid from a fraction eluted with ethyl acetate-hexane (1:19, volume ratio).

$^1$H NMR (300 MHz, CDCl$_3$) δ0.00 (3 H, s), 0.09 (3 H, s), 0.91 (9 H, s), 1.46 (3 H, d, J=6.4 Hz), 4.99 (1 H, q, J=6.2 Hz), 7.82-7.88 (1 H, m), 7.92-7.97 (1 H, m), 8.74 (1 H, d, J=1.9 Hz), 10.07 (1 H, s).

Reference Example 180

1-[5-(1-{[tert-butyl(dimethyl)silyl]oxy}ethyl)pyridin-2-yl]-5-[5-(methylsulfanyl)pyridin-2-yl]-6-(tetrahydro-2H-pyran-4-yl)hexane-1,4-dione

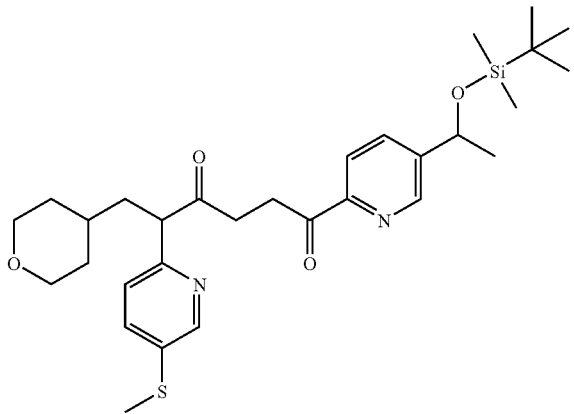

To a solution of 4-[5-(methylsulfanyl)pyridin-2-yl]-5-(tetrahydro-2H-pyran-4-yl)pent-1-en-3-one (93.1 mg) in a mixed solvent of ethanol (1.5 mL) and tetrahydrofuran (1.5 mL) were added 5-(1-{[tert-butyl(dimethyl)silyl]oxy}ethyl)pyridine-2-carbaldehyde (169 mg), 3-benzyl-5-(2-hydroxyethyl)-4-methyl-1,3-thiazol-3-ium chloride (8.6 mg) and triethylamine (17.8 μL), and the mixture was stirred with heating under reflux for 2 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (123 mg, yield 69%) was obtained as a pale-yellow amorphous solid from a fraction eluted with ethyl acetate-hexane (1:3, volume ratio).

$^1$H NMR (300 MHz, CDCl$_3$) δ-0.09 (3 H, s), 0.00 (3 H, s), 0.82 (9 H, s), 1.11-1.38 (6 H, m), 1.44-1.64 (2 H, m), 1.67-1.84 (1 H, m), 1.92-2.05 (1 H, m), 2.43 (3 H, s), 2.64-2.76 (1 H, m), 2.77-2.91 (1 H, m), 3.13-3.35 (3 H, m), 3.37-3.51 (1 H, m), 3.78-3.88 (2 H, m), 4.06 (1 H, t, J=7.5 Hz), 4.88 (1 H, q, J=6.3 Hz), 7.10 (1 H, d, J=8.3 Hz), 7.47 (1 H, dd, J=2.4, 8.3 Hz), 7.70 (1 H, dd, J=2.1, 8.1 Hz), 7.87 (1 H, d, J=8.1 Hz), 8.37 (1 H, d, J=2.3 Hz), 8.53 (1 H, d, J=2.1 Hz).

Reference Example 181

3-cyclopentyl-N-methoxy-N-methyl-2-[5-(methylsulfanyl)pyridin-2-yl]propanamide

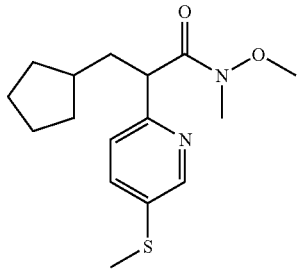

A solution of 2-methyl-5-(methylsulfanyl)pyridine (1.95 g) in tetrahydrofuran (40 mL) was cooled to −78° C. and purged with nitrogen. n-Butyllithium (1.6M hexane solution, 8.75 mL) was added dropwise to the reaction mixture, and the mixture was stirred for 15 min. To the reaction mixture was added a solution of (iodomethyl)cyclopentane (2.94 g) in tetrahydrofuran (16 ml), and the mixture was stirred at 0° C. for 30 min. The reaction mixture was cooled again to −78° C., n-butyllithium (1.6M hexane solution, 8.75 mL) was added dropwise, and the mixture was stirred at 0° C. for 30 min. To the reaction mixture was added methoxy(methyl)carbamoyl chloride (2.60 g), and the mixture was stirred at 0° C. for 30 min. Water was added to the reaction mixture, and the mixture was extracted with ethyl acetate. The ethyl acetate layer was dried (MgSO$_4$) and concentrated. The residue was subjected to silica gel column chromatography, and the title compound (1.70 g, yield 40%) was obtained as a yellow amorphous solid from a fraction eluted with ethyl acetate-hexane (3:1, volume ratio).

30 $^1$H NMR (300 MHz, CDCl$_3$) δ0.77-1.91 (10 H, m), 2.02-2.20 (1 H, m), 2.48 (3 H, s), 3.19 (3 H, s), 3.61 (3 H, s), 4.25-4.46 (1 H, m), 7.36 (1 H, d, J=8.3 Hz), 7.54 (1 H, dd, J=2.3, 8.3 Hz), 8.42 (1 H, d, J=2.3 Hz).

Reference Example 182

5-cyclopentyl-4-[5-(methylsulfanyl)pyridin-2-yl]pent-1-en-3-one

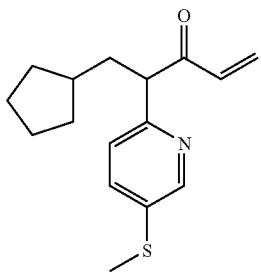

A solution of 3-cyclopentyl-N-methoxy-N-methyl-2-[5-(methylsulfanyl)pyridin-2-yl]propanamide (350 mg) in tetrahydrofuran (4.5 mL) was cooled to 0° C., and vinylmagnesium bromide (1.0M tetrahydrofuran solution, 4.54 mL) was added dropwise thereto. The reaction mixture was stirred at room temperature for 1 hr, and poured into 1M hydrochloric acid, and the mixture was stirred for 30 min. The reaction mixture was extracted with ethyl acetate, and the ethyl acetate layer was washed with saturated aqueous sodium hydrogen carbonate, dried (MgSO$_4$) and concentrated. The residue was subjected to silica gel column chromatography, and the title compound (171 mg, yield 54%) was obtained as a pale-yellow amorphous solid from a fraction eluted with ethyl acetate-hexane (2:1, volume ratio).

$^1$H NMR (300 MHz, CDCl$_3$) δ1.00-2.19 (11 H, m), 2.49 (3 H, s), 4.22 (1 H, t, J=7.4 Hz), 5.73 (1 H, dd, J=1.9, 9.5 Hz), 6.27-6.51 (2 H, m), 7.16 (1 H, d, J=8.3 Hz), 7.52 (1 H, dd, J=2.7, 8.3 Hz), 8.44 (1 H, d, J=2.7 Hz).

Reference Example 183

1-[5-(1-{[tert-butyl(dimethyl)silyl]oxy}ethyl)pyridin-2-yl]-6-cyclopentyl-5-[5-(methylsulfanyl)pyridin-2-yl]hexane-1,4-dione

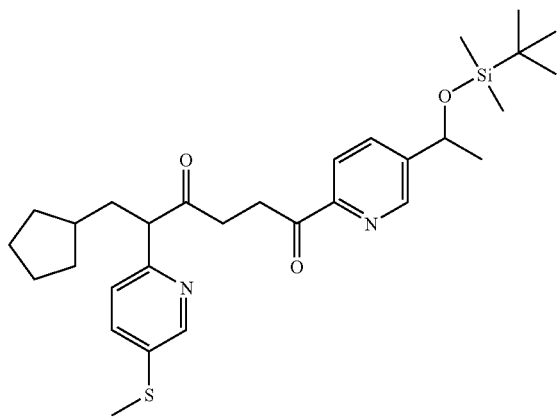

To a solution of 5-cyclopentyl-4-[5-(methylsulfanyl)pyridin-2-yl]pent-1-en-3-one (455 mg) in a mixed solvent of ethanol (8 mL) and tetrahydrofuran (8 mL) were added 5-(1-{[tert-butyl(dimethyl)silyl]oxy}ethyl)pyridine-2-carbaldehyde (878% mg), 3-benzyl-5-(2-hydroxyethyl)-4-methyl-1,3-thiazol-3-ium chloride (44.5 mg) and triethylamine (92.0 μL), and the mixture was stirred with heating under reflux for 2 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (848 mg, yield 95%) was obtained as a pale-yellow amorphous solid from a fraction eluted with ethyl acetate-hexane (1:3, volume ratio).

$^1$H NMR (300 MHz, CDCl$_3$) δ0.00 (3 H, s), 0.09 (3 H, s), 0.91 (9H, s), 1.03-1.21 (2 H, m), 1.35-1.98 (11 H, m), 2.06-2.17 (1 H, m), 2.77-3.02 (2 H, m), 3.31-3.43 (0 H, m), 3.45-3.57 (1 H, m), 4.06 (1H, dd, J=6.6, 8.5 Hz), 4.97 (1 H, q, J=6.4 Hz), 7.21 (1 H, d, J=8.3 Hz), 7.56 (1 H, dd, J=2.4, 8.3 Hz), 7.78 (1 H, dd, J=2.1, 8.1 Hz), 7.96 (1 H, d, J=8.1 Hz), 8.47 (1 H, d, J=2.4 Hz), 8.61 (1 H, d, J=2.1 Hz).

Reference Example 184

1-(6-bromopyridin-3-yl)-2-{[tert-butyl(dimethyl)silyl]oxy}ethanol

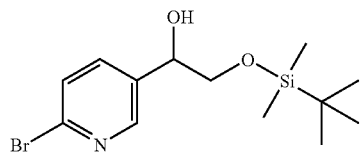

A solution of 2,5-dibromopyridine (2.64 g) in diethyl ether (75 mL) was cooled to −78° C. and purged with nitrogen. n-Butyllithium (1.6M hexane solution, 11.3 mL) was added dropwise to the reaction mixture, and the mixture was stirred for 1 hr. To the reaction mixture was added {[tert-butyl(dimethyl)silyl]oxy}acetoaldehyde (3.00 g), and the mixture was stirred at 0° C. for 1 hr. To the reaction mixture was added saturated aqueous sodium hydrogen carbonate, and the mixture was extracted with diethyl ether. The extract was washed with saturated brine, dried (MgSO$_4$) and concentrated. The residue was subjected to silica gel column chromatography, and the title compound (1.58 g, yield 43%) was obtained as a pale-yellow amorphous solid from a fraction eluted with ethyl acetate-hexane (1:3, volume ratio).

$^1$H NMR (300 MHz, CDCl$_3$) δ-0.01 (3 H, s), 0.00 (3 H, s), 0.83 (9 H, s), 2.91 (1 H, d, J=3.0 Hz), 3.47 (1 H, dd, J=7.9, 10.0 Hz), 3.70 (1 H, dd, J=3.8, 10.0 Hz), 4.69 (1 H, ddd, J=3.4, 3.6, 7.5 Hz), 7.38-7.42 (1 H, m), 7.53 (1 H, dd, J=2.4, 8.3 Hz), 8.29 (1 H, d, J=2.4 Hz).

Reference Example 185

5-(1,2-bis{[tert-butyl(dimethyl)silyl]oxy}ethyl)-2-bromopyridine

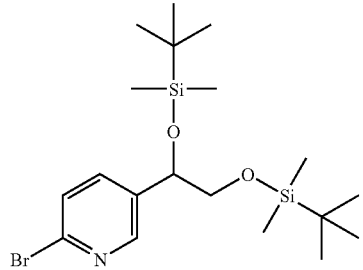

A solution of 1-(6-bromopyridin-3-yl)-2-{[tert-butyl(dimethyl)silyl]oxy}ethanol (1.58 g) and 2,6-lutidine (0.83 mL) in dichloromethane (15 mL) was cooled to 0° C., tert-butyl(dimethyl)silyl trifluoromethanesulfonate (1.31 mL) was added dropwise, and the mixture was stirred for 1 hr. To the reaction mixture was added saturated aqueous sodium hydrogen carbonate, and the mixture was extracted with diethyl ether. The extract was washed with saturated brine, dried (MgSO$_4$) and concentrated. The residue was subjected to silica gel column chromatography, and the title compound (1.79 g, yield 84%) was obtained as a pale-yellow amorphous solid from a fraction eluted with ethyl acetate-hexane (1:19, volume ratio).

$^1$H NMR (300 MHz, CDCl$_3$) δ -0.03 (3 H, s), 0.00 (6 H, s), 0.11 (3 H, s), 0.87 (9 H, s), 0.92 (9 H, s), 3.51 (1 H, dd, J=6.5, 9.9 Hz), 3.75 (1 H, dd, J=6.0, 9.8 Hz), 4.70 (1 H, t, J=6.2 Hz), 7.45-7.49 (1 H, m), 7.60 (1 H, dd, J=2.4, 8.3 Hz), 8.37 (1 H, d, J=2.1 Hz).

Reference Example 186

5-(1,2-bis{[tert-butyl(dimethyl)silyl]oxy}ethyl)pyridine-2-carbaldehyde

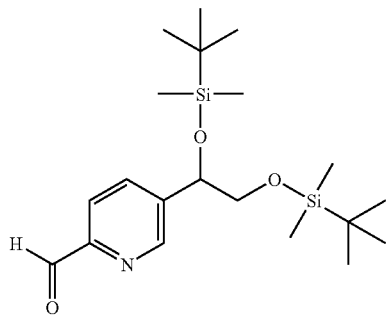

A solution of 5-(1,2-bis{[tert-butyl(dimethyl)silyl]oxy}ethyl)-2-bromopyridine (1.79 g) in toluene (20 mL) was cooled to −78° C. and purged with nitrogen. n-Butyllithium (1.6M hexane solution, 2.76 mL) was added dropwise to the reaction mixture, and the mixture was stirred for 1 hr. To the reaction mixture was added N,N-dimethylformamide (1.55 mL), and the mixture was stirred at room temperature for 1 hr. Water was added to the reaction mixture, and the mixture was extracted with diethyl ether. The extract was washed with saturated brine, dried (MgSO$_4$) and concentrated. The residue was subjected to silica gel column chromatography, and the title compound (1.07 g, yield 68%) was obtained as a yellow amorphous solid from a fraction eluted with ethyl acetate-hexane (1:19, volume ratio).

$^1$H NMR (300 MHz, CDCl$_3$) δ -0.04 (3 H, s), −0.00 (3 H, s), 0.02 (3H, s), 0.14 (3 H, s), 0.87 (9 H, s), 0.94 (9 H, s), 3.58 (1 H, dd, J=6.7, 9.9 Hz), 3.82 (1 H, dd, J=5.9, 9.9 Hz), 4.84 (1 H, t, J=6.2 Hz), 7.89-7.95 (1 H, m), 7.97-8.02 (1 H, m), 8.81 (1 H, d, J=1.9 Hz), 10.13 (1 H, s).

Reference Example 187

1-[5-(1,2-bis{[tert-butyl(dimethyl)silyl]oxy}ethyl)pyridin-2-yl]-6-cyclopentyl-5-[5-(methylsulfanyl)pyridin-2-yl]hexane-1,4-dione

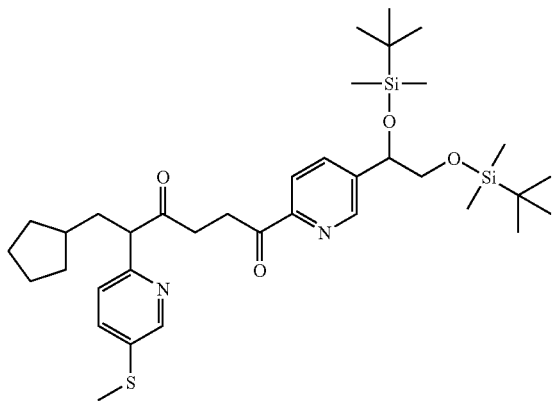

To a solution of 5-cyclopentyl-4-[5-(methylsulfanyl)pyridin-2-yl]pent-1-en-3-one (464 mg) in a mixed solvent of ethanol (8 mL) and tetrahydrofuran (8 mL) were added 5-(1,2-bis{[tert-butyl(dimethyl)silyl]oxy}ethyl)pyridine-2-carbaldehyde (1.07 g), 3-benzyl-5-(2-hydroxyethyl)-4-methyl-1,3-thiazol-3-ium chloride (45.3 mg) and triethylamine (93.7 μL), and the mixture was stirred with heating under reflux for 1 hr. After cooling to room temperature, the reaction mixture was diluted with ethyl acetate and washed with water. The ethyl acetate layer was dried (MgSO$_4$) and concentrated. The residue was subjected to silica gel column chromatography, and the title compound (682 mg, yield 60%) was obtained as a pale-yellow amorphous solid from a fraction eluted with ethyl acetate-hexane (1:4, volume ratio).

$^1$H NMR (300 MHz, CDCl$_3$) δ -0.04 (3 H, s), −0.01 (3 H, s), 0.00 (3 H, s), 0.12 (3 H, s), 0.87 (9 H, s), 0.92 (9 H, s), 1.04-1.25 (2 H, m), 1.44-2.02 (8 H, m), 2.10-2.21 (1 H, m), 2.55 (3 H, s), 2.76-3.06 (2 H, m), 3.35-3.62 (3 H, m), 3.77 (1 H, dd, J=6.0, 10.0 Hz), 4.09 (1 H, dd, J=6.6, 8.5 Hz), 4.81 (1 H, t, J=6.1 Hz), 7.24 (1 H, d, J=8.3 Hz), 7.59 (1H, dd, J=2.4, 8.3 Hz), 7.83 (1 H, dd, J=2.0, 8.2 Hz), 7.99 (1 H, d, J=8.1 Hz), 8.50 (1 H, d, J=2.3 Hz), 8.66 (1 H, d, J=1.9 Hz).

Reference Example 188

1-[5-({[tert-butyl(diphenyl)silyl]oxy}methyl)-1,3,4-thiadiazol-2-yl]-5-[4-(methylsulfonyl)phenyl]-6-(tetrahydro-2H-pyran-4-yl)hexane-1,4-dione

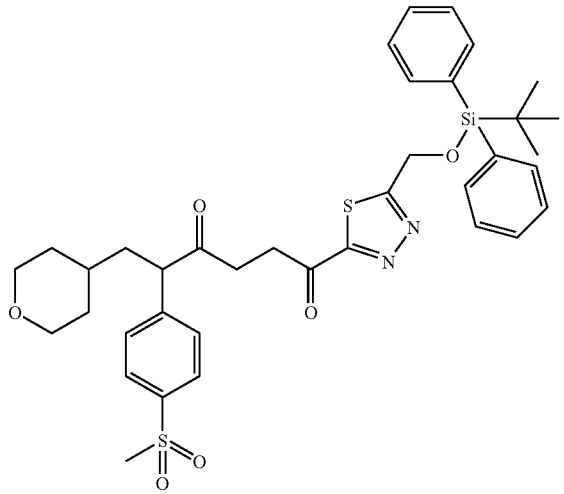

To a solution of 4-[4-(methylsulfonyl)phenyl]-5-(tetrahydro-2H-pyran-4-yl)pent-1-en-3-one (1.97 g) in a mixed solvent of ethanol (20 mL) and tetrahydrofuran (20 mL) were added 5-({[tert-butyl(diphenyl)silyl]oxy}methyl)-1,3,4-thiadiazole-2-carbaldehyde (1.51 g), 3-benzyl-5-(2-hydroxyethyl)-4-methyl-1,3-thiazol-3-ium chloride (139 mg) and triethylamine (281 μL), and the mixture was stirred with heating under reflux for 30 min and cooled to room temperature. The reaction mixture was diluted with ethyl acetate and washed with water. The ethyl acetate layer was washed with saturated brine, dried (MgSO$_4$) and concentrated. The residue was subjected to silica gel column chromatography, and the title compound (1.95 g, yield 59%) was obtained as a colorless amorphous solid from a fraction eluted with ethyl acetate-hexane (1:1, volume ratio).

$^1$H NMR (300 MHz, CDCl$_3$) δ 1.11 (9 H, s), 1.24-1.38 (2 H, m), 1.52-1.78 (4 H, m), 2.07 (1 H, ddd, J=6.7, 6.8, 13.8 Hz), 2.83 (1 H, dd, J=5.1, 6.6 Hz), 2.93 (1 H, dd, J=4.8, 7.4 Hz), 3.09 (3 H, s), 3.23-3.40 (2 H, m), 3.40-3.62 (2 H, m), 3.93 (2

H, d, J=11.1 Hz), 4.02 (1 H, t, J=7.5 Hz), 5.09 (2H, s), 7.36-7.53 (8 H, m), 7.63-7.70 (4 H, m), 7.95 (2 H, d, J=8.3 Hz).

Reference Example 189

Tert-butyl 2-{1-[4-(cyclopropylsulfonyl)phenyl]-2-(tetrahydro-2H-pyran-4-yl)ethyl}-5-(5-formylpyridin-2-yl)-1H-pyrrole-1-carboxylate

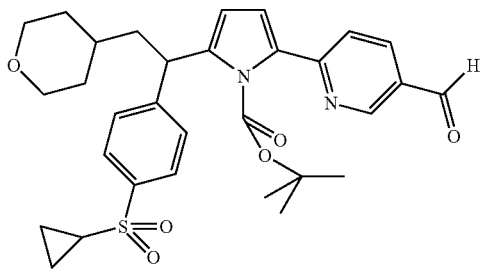

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (5 g) in acetonitrile (100 mL) were added di-tert-butyl dicarbonate (2.82 g) and 4-dimethylaminopyridine (0.1 g), and the mixture was stirred at room temperature for 16 hr. The reaction mixture was concentrated, and the residue was subjected to silica gel column chromatography, and the title compound (4.4 g, yield 72%) was obtained as a yellow amorphous solid from a fraction eluted with hexane-ethyl acetate (1:1, volume ratio). MS: 565 (MH$^+$).

Reference Example 190

Tert-butyl 2-{1-[4-(cyclopropylsulfonyl)phenyl]-2-(tetrahydro-2H-pyran-4-yl)ethyl}-5-[5-(hydroxymethyl)pyridin-2-yl]-1H-pyrrole-1-carboxylate

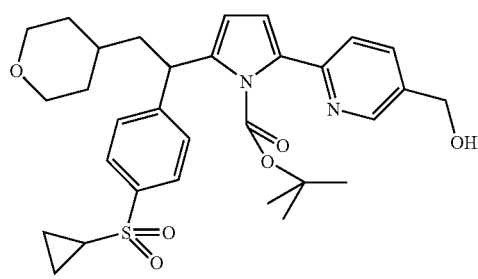

To a solution of tert-butyl 2-{1-[4-(cyclopropylsulfonyl)phenyl]-2-(tetrahydro-2H-pyran-4-yl)ethyl}-5-(5-formylpyridin-2-yl)-1H-pyrrole-1-carboxylate (3 g) in ethanol (10 mL) was added sodium borohydride (221 mg), and the mixture was stirred at room temperature for 10 min. Saturated aqueous sodium hydrogen carbonate solution was added to the reaction mixture, and the mixture was extracted with ethyl acetate. The ethyl acetate layer was washed with saturated brine, dried (MgSO$_4$) and concentrated. The residue was subjected to silica gel column chromatography, and the title compound (3 g, yield 100%) was obtained as a pale-yellow amorphous solid from a fraction eluted with hexane-ethyl acetate (1:1, volume ratio). MS: 567 (MH$^+$).

Example 1

2-(5-{2-cyclopentyl-1-[4-(methylsulfonyl)phenyl]ethyl}-1H-pyrrol-2-yl)-1,3-thiazole

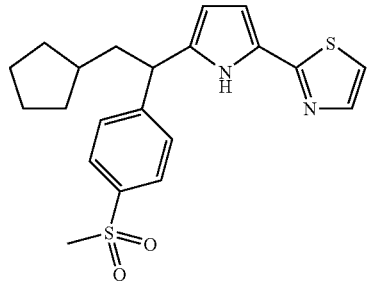

To a solution (5 mL) of 6-cyclopentyl-5-[4-(methylsulfonyl)phenyl]-1-(1,3-thiazol-2-yl)hexane-1,4-dione (300 mg) in N,N-dimethylformamide was added ammonium acetate (310 mg), and the mixture was stirred at 100° C. for 1.5 hr. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (150 mg, yield 53%) was obtained as colorless amorphous crystals from a fraction eluted with ethyl acetate-hexane (1:1, volume ratio). MS: 401 (MH$^+$).

Example 2

2-(5-{2-cyclopentyl-1-[4-(methylsulfonyl)phenyl]ethyl}-1H-pyrrol-2-yl)pyridine

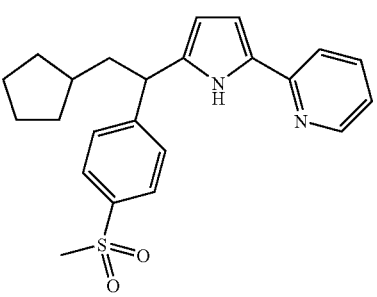

According to the method of Example 1, the title compound (230 mg, yield 88%) was obtained as colorless amorphous crystals from 6-cyclopentyl-5-[4-(methylsulfonyl)phenyl]-1-pyridin-2-ylhexane-1,4-dione (275 mg) and ammonium acetate (260 mg). MS: 395 (MH$^+$).

Example 3

2-(5-{2-cyclopentyl-1-[4-(methylsulfonyl)phenyl]ethyl}-1H-pyrrol-2-yl)pyrazine

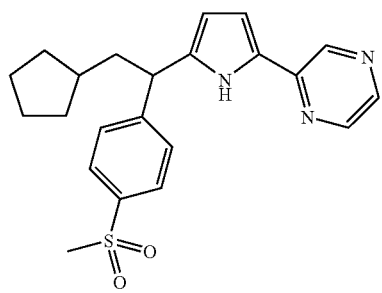

According to the method of Example 1, the title compound (250 mg, yield 77%) was obtained as colorless amorphous crystals from 6-cyclopentyl-5-[4-(methylsulfonyl)phenyl]-1-pyrazin-2-ylhexane-1,4-dione (340 mg) and ammonium acetate (320 mg). MS: 396 (MH$^+$).

Example 4

2-(5-{2-cyclopentyl-1-[4-(methylsulfonyl)phenyl]ethyl}-1H-pyrrol-2-yl)-1-methyl-1H-imidazole

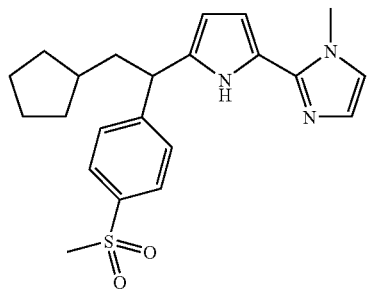

According to the method of Example 1, the title compound (75 mg, yield 49%) was obtained as colorless amorphous crystals from 6-cyclopentyl-1-(1-methyl-1H-imidazol-2-yl)-5-[4-(methylsulfonyl)phenyl]hexane-1,4-dione (160 mg) and ammonium acetate (150 mg). MS: 398 (MH$^+$).

Example 5

4-(5-{2-cyclopentyl-1-[4-(methylsulfonyl)phenyl]ethyl}-1H-pyrrol-2-yl)-1-methyl-1H-imidazole

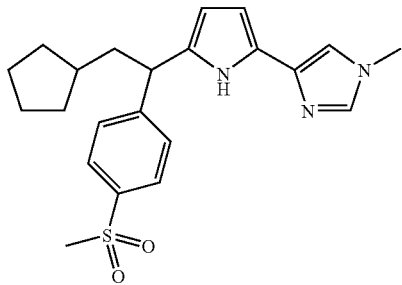

According to the method of Example 1, the title compound (90 mg, yield 49%) was obtained as colorless amorphous crystals from 6-cyclopentyl-1-(1-methyl-1H-imidazol-4-yl)-5-[4-(methylsulfonyl)phenyl]hexane-1,4-dione (180 mg) and ammonium acetate (170 mg). MS: 398 (MH$^+$).

Example 6

3-(5-{2-cyclopentyl-1-[4-(methylsulfonyl)phenyl]ethyl}-1H-pyrrol-2-yl)-1-methyl-1H-pyrazole

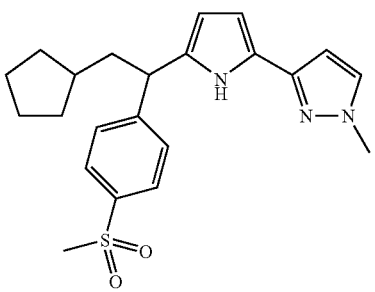

According to the method of Example 1, the title compound (133 mg, yield 43%) was obtained as colorless amorphous crystals from 6-cyclopentyl-1-(1-methyl-1H-pyrazol-3-yl)-5-[4-(methylsulfonyl)phenyl]hexane-1,4-dione (325 mg) and ammonium acetate (300 mg). MS: 398 (MH$^+$).

Example 7

2-{5-[1-[4-(cyclopropylsulfonyl)phenyl]-2-(tetrahydro-2H-pyran-4-yl)ethyl]-1H-pyrrol-2-yl}-1,3-thiazole

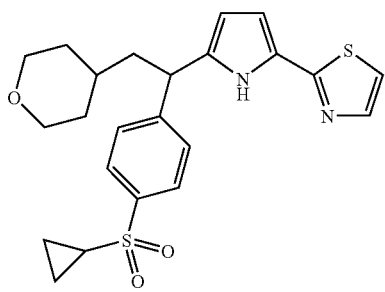

According to the method of Example 1, the title compound (60 mg, yield 19%) was obtained as colorless amorphous crystals from 5-[4-(cyclopropylsulfonyl)phenyl]-6-(tetrahydro-2H-pyran-4-yl)-1-(1,3-thiazol-2-yl)hexane-1,4-dione (330 mg). MS: 443 (MH$^+$).

Example 8

Ethyl 5-{2-cyclopentyl-1-[4-(methylsulfonyl)phenyl]ethyl}-3-methyl-1H-pyrrole-2-carboxylate

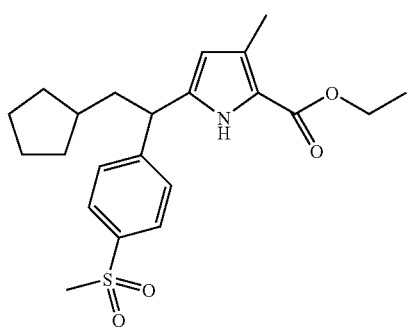

To a solution (5 mL) of 6-cyclopentyl-5-[4-(methylsulfonyl)phenyl]hexane-2,4-dione (1.60 g) in toluene were added ethyl isocyanoacetate (0.29 g) and dodecacarbonyltetrarhodium(0) complex (55 mg), and the mixture was stirred under argon atmosphere at 80° C. overnight. After cooling to room temperature, the reaction mixture was concentrated, and the residue was subjected to NH silica gel column chromatography, and the title compound (0.44 g, yield 43%) was obtained as colorless amorphous crystals from a fraction eluted with ethyl acetate-hexane (1:1, volume ratio). MS: 404 (MH$^+$).

Example 9

5-{2-cyclopentyl-1-[4-(methylsulfonyl)phenyl]ethyl}-3-methyl-1H-pyrrole-2-carboxylic acid

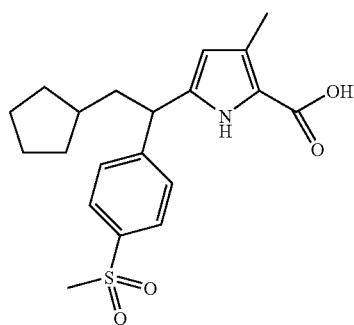

To a solution (10 mL) of ethyl 5-{2-cyclopentyl-1-[4-(methylsulfonyl)phenyl]ethyl}-3-methyl-1H-pyrrole-2-carboxylate (200 mg) in tetrahydrofuran was added an aqueous solution (2 mL) of lithium hydroxide monohydrate (65 mg), and the mixture was stirred at 50° C. overnight. The reaction mixture was slowly warmed to room temperature and stirred overnight. After cooling to room temperature, the reaction mixture was neutralized with 1N hydrochloric acid. The ethyl acetate layer was washed with water and saturated brine, dried (MgSO$_4$) and concentrated to give the title compound (165 mg, yield 89%) as white crystals. melting point 127° C.

Example 10

5-{2-cyclopentyl-1-[4-(methylsulfonyl)phenyl]ethyl}-3-methyl-1H-pyrrole-2-carboxamide

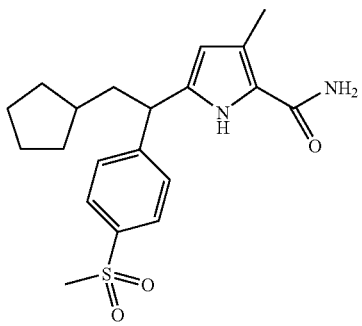

To a solution (5 mL) of 5-{2-cyclopentyl-1-[4-(methylsulfonyl)phenyl]ethyl}-3-methyl-1H-pyrrole-2-carboxylic acid (160 mg) in N,N-dimethylformamide were added under ice-cooling N-[3-(dimethylamino)propyl]-N'-ethylcarbodiimide hydrochloride (125 mg) and 1-hydroxybenzotriazole-ammonia complex (100 mg). The reaction mixture was slowly warmed to room temperature, and stirred overnight. The reaction mixture was diluted with ethyl acetate, and washed with saturated aqueous sodium hydrogen carbonate. The ethyl acetate layer was washed with saturated brine, dried (MgSO$_4$) and concentrated. The residue was subjected to silica gel column chromatography, and the title compound (155 mg, yield 97%) was obtained as colorless amorphous crystals from a fraction eluted with ethyl acetate-hexane (4:1, volume ratio). MS: 375 (MH$^+$).

Example 11

2-(5-{2-cyclopentyl-1-[4-(methylsulfonyl)phenyl]ethyl}-3-methyl-1H-pyrrol-2-yl)-1,3-thiazole

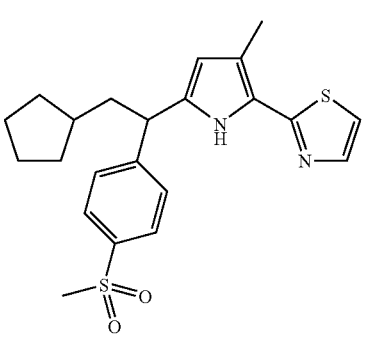

To a solution (3 mL) of 5-{2-cyclopentyl-1-[4-(methylsulfonyl)phenyl]ethyl}-3-methyl-1H-pyrrole-2-carbothioamide (120 mg) in N,N-dimethylacetamide was added 2-bromo-1,1-diethoxyethane (125 mg), and the mixture was stirred at 60° C. for 2 hr, then at 100° C. for 4 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (60 mg, yield 47%) was

Example 12

2-(2-{2-cyclopentyl-1-[4-(methylsulfonyl)phenyl]ethyl}-1H-imidazol-5-yl)pyridine

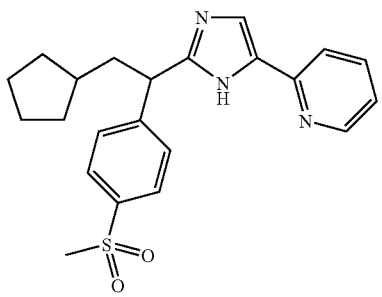

To a solution (10 mL) of 3-cyclopentyl-2-[4-(methylsulfonyl)phenyl]-N-(2-oxo-2-pyridin-2-ylethyl)propanamide (330 mg) in acetic acid was added ammonium acetate (310 mg), and the mixture was stirred with heating under reflux for 4 hr. After cooling to room temperature, the reaction mixture was concentrated, the residue was diluted with ethyl acetate, and the mixture was washed with saturated aqueous sodium hydrogen carbonate. The ethyl acetate layer was concentrated, and the residue was subjected to preparative high performance liquid chromatography to give the title compound (80 mg, yield 25%) as colorless amorphous crystals. MS: 396 (MH$^+$).

Example 13

1-(2-{2-cyclopentyl-1-[4-(methylsulfonyl)phenyl]ethyl}-1H-imidazol-5-yl)-2-methylpropan-1-one

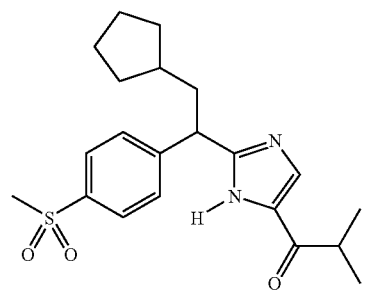

To a solution (40 mL) of 3-cyclopentyl-N-(5-isopropylisoxazol-4-yl)-2-[4-(methylsulfonyl)phenyl]propanamide (2.50 g) in ethanol was added 10% palladium carbon (containing 50% water, 0.500 g) and the mixture was stirred under hydrogen atmosphere (5 atm) for 4 hr. The reaction mixture was filtered to remove the catalyst, sodium hydroxide (0.261 g) was added to the filtrate, and the mixture was heated under reflux for 1 hr. To the reaction mixture was added ammonium chloride (0.430 g), and the mixture was cooled to room temperature, and stirred at room temperature for 16 hr. The reaction solution was concentrated, the obtained residue was suspended in acetone, and the suspension was filtered to remove insoluble materials. The filtrate was concentrated, and the obtained residue was purified by silica gel column chromatography (ethyl acetate:hexane=50:50-100:0, volume ratio), and recrystallized from ethyl acetate-hexane to give the title compound (1.20 g, yield 50%) as colorless crystals. melting point 171-172° C.

Example 14

1-(2-{2-cyclopentyl-1-[4-(methylsulfonyl)phenyl]ethyl}-4-fluoro-1H-imidazol-5-yl)-2-methylpropan-1-one

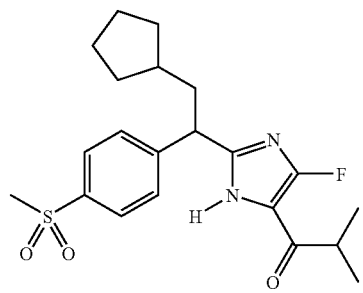

To a solution (13 mL) of 1-(2-{2-cyclopentyl-1-[4-(methylsulfonyl)phenyl]ethyl}-1H-imidazol-5-yl)-2-methylpropan-1-one (0.507 g) in acetonitrile was added xenon difluoride (0.440 g), and the mixture was heated under reflux for 4 hr. The reaction mixture was diluted with ethyl acetate, washed successively with water and saturated brine, dried over anhydrous magnesium sulfate and concentrated under reduced pressure. The residue was purified by silica gel column chromatography (ethyl acetate:hexane=5:95-40:60, volume ratio) and recrystallized from diethyl ether-hexane to give the title compound (0.07 g, yield 13%) as colorless crystals. melting point 161-162° C.

Example 15

(2-{2-cyclopentyl-1-[4-(methylsulfonyl)phenyl]ethyl}-1H-imidazol-5-yl)(cyclopropyl)methanone

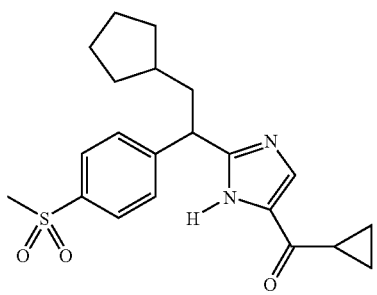

According to the method of Example 13, the title compound (5.09 g, yield 82%) was obtained as colorless crystals from 3-cyclopentyl-N-(5-cyclopropylisoxazol-4-yl)-2-[4-(methylsulfonyl)phenyl]propanamide (6.43 g). melting point 165-166° C.

Example 16

1-(2-{2-cyclopentyl-1-[4-(methylsulfonyl)phenyl]ethyl}-1H-imidazol-5-yl)butan-1-one

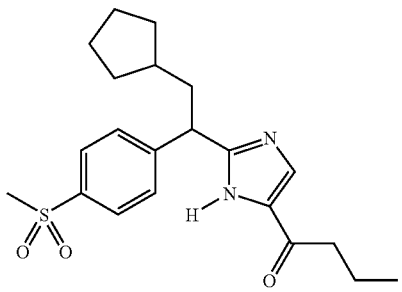

In Example 15, the title compound (0.236 g, yield 4%) was simultaneously obtained as colorless crystal byproduct by purification by silica gel column chromatography (ethyl acetate:hexane=50:50-100:0, volume ratio) and recrystallization from ethyl acetate-hexane. melting point 159-163° C.

Example 17

1-(2-{2-cyclopentyl-1-[4-(methylsulfonyl)phenyl]ethyl}-4-fluoro-1H-imidazol-5-yl)butan-1-one

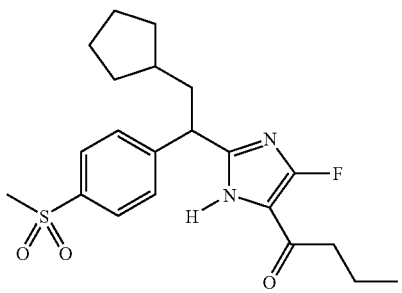

According to the method of Example 14, the title compound (0.010 g, yield 5%) was obtained as colorless crystals from 1-(2-{2-cyclopentyl-1-[4-(methylsulfonyl)phenyl]ethyl}-1H-imidazol-5-yl)butan-1-one (0.200 g). melting point 70-73° C.

Example 18

(4-chloro-2-{2-cyclopentyl-1-[4-(methylsulfonyl)phenyl]ethyl}-1H-imidazol-5-yl)(cyclopropyl)methanone

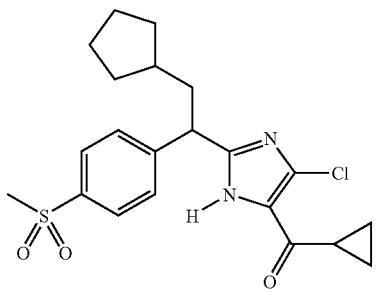

To a solution (12 mL) of (2-{2-cyclopentyl-1-[4-(methylsulfonyl)phenyl]ethyl}-1H-imidazol-5-yl)(cyclopropyl)methanone in 1,2-dichloroethane was added N-chlorosuccinimide (0.091 g) and the mixture was stirred at 100° C. for 6 hr. To the reaction mixture were successively added saturated aqueous sodium hydrogen carbonate solution and 1 mol/L aqueous sodium thiosulfate solution, and the mixture was extracted with ethyl acetate. The extract was washed successively with water and saturated brine, dried over anhydrous magnesium sulfate and concentrated under reduced pressure. The residue was successively purified by silica gel column chromatography (ethyl acetate:hexane=10:90-50:50, volume ratio) and thin layer chromatography (ethyl acetate:hexane=50:50), and recrystallized from diisopropyl ether-hexane to give the title compound (0.016 g, yield 9%) as colorless crystals. melting point 95-97° C.

Example 19

(4-bromo-2-{2-cyclopentyl-1-[4-(methylsulfonyl)phenyl]ethyl}-1H-imidazol-5-yl)(cyclopropyl)methanone

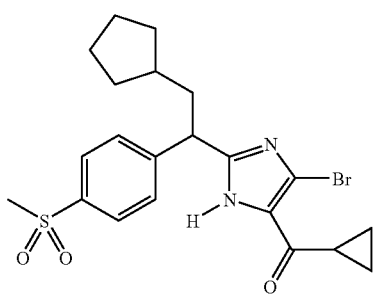

To a solution (5 mL) of (2-{2-cyclopentyl-1-[4-(methylsulfonyl)phenyl]ethyl}-1H-imidazol-5-yl)(cyclopropyl)methanone (0.038 g) in N,N-dimethylformamide was added N-bromosuccinimide (0.024 g) and the mixture was stirred at 50° C. for 16 hr. The reaction mixture was diluted with ethyl acetate, washed successively with water and saturated brine, dried over anhydrous magnesium sulfate and concentrated under reduced pressure. The residue was purified by silica gel column chromatography (ethyl acetate:hexane=10:90-50:50, volume ratio) and recrystallized from diisopropyl ether-hexane to give the title compound (0.026 g, yield 56%) as colorless crystals. melting point 160-161° C.

Example 20

(2-{2-cyclopentyl-1-[4-(methylsulfonyl)phenyl]ethyl}-4-fluoro-1H-imidazol-5-yl)(cyclopropyl)methanone

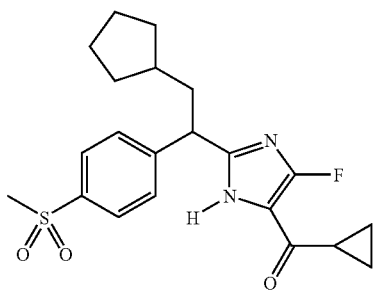

To a solution (20 mL) of (4-bromo-2-{2-cyclopentyl-1-[4-(methylsulfonyl)phenyl]ethyl}-1H-imidazol-5-yl)(cyclopropyl)methanone (0.367 g) in toluene were added tetrakistriphenylphosphinepalladium(0) (271 mg) and hexamethylditin(IV) (1.16 g) and the mixture was purged with nitrogen and heated under reflux for 24 hr. The reaction mixture was diluted with ethyl acetate and filtered through celite, and the filtrate was concentrated under reduced pressure. The residue was dissolved in acetonitrile (10 mL), N-fluoro-N'-chloromethyltriethylenediamine bis(tetrafluoroborate) (2.52 g) was added, and the mixture was stirred at room temperature for 1 hr, at 50° C. for 3 hr, and at 80° C. for 2 hr. The reaction mixture was diluted with ethyl acetate, and filtered through celite, and the filtrate was concentrated under reduced pressure. The residue was purified by silica gel column chromatography (ethyl acetate:hexane=10:90-70:30, volume ratio). The obtained crude product was dissolved in ethanol (10 mL), 10% palladium carbon (containing 50% water, 0.050 g) was added, and the mixture was purged with under hydrogen atmosphere, and stirred at room temperature for 6 hr. The reaction mixture was filtered, and the filtrate was concentrated under reduced pressure. The residue was purified by silica gel column chromatography (ethyl acetate:hexane=20:80-80:20, volume ratio), and recrystallized from diisopropyl ether-hexane to give the title compound (0.012 g, yield 4%) as colorless crystals. melting point 160-162° C.

Example 21

Cyclobutyl(2-{2-cyclopentyl-1-[4-(methylsulfonyl)phenyl]ethyl}-1H-imidazol-5-yl)methanone

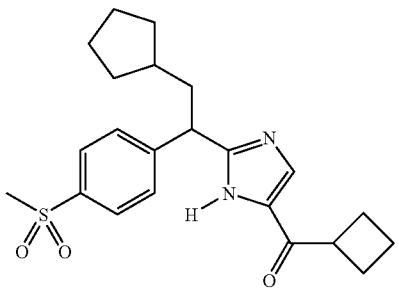

According to the method of Example 13, the title compound (1.75 g, yield 77%) was obtained as colorless crystals from N-(5-cyclobutylisoxazol-4-yl)-3-cyclopentyl-2-[4-(methylsulfonyl)phenyl]propanamide (2.35 g). melting point 194-196° C.

Example 22

Cyclobutyl(2-{2-cyclopentyl-1-[4-(methylsulfonyl)phenyl]ethyl}-4-fluoro-1H-imidazol-5-yl)methanone

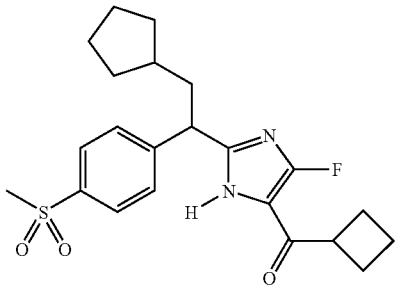

According to the method of Example 14, the title compound (0.042 g, yield 13%) was obtained as colorless crystals from cyclobutyl(2-{2-cyclopentyl-1-[4-(methylsulfonyl)phenyl]ethyl}-1H-imidazol-5-yl)methanone (0.306 g). melting point 78-80° C.

Example 23

(2-{2-cyclopentyl-1-[4-(cyclopropylsulfonyl)phenyl]ethyl}-1H-imidazol-5-yl)(cyclopropyl)methanone

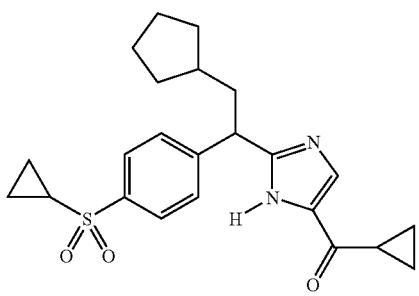

According to the method of Example 13, the title compound (1.45 g, yield 84%) was obtained as colorless crystals from 3-cyclopentyl-N-(5-cyclopropylisoxazol-4-yl)-2-[4-(cyclopropylsulfonyl)phenyl]propanamide (1.81 g). melting point 85-89° C.

Example 24

(2-{2-cyclopentyl-1-[4-(cyclopropylsulfonyl)phenyl]ethyl}-4-fluoro-1H-imidazol-5-yl)(cyclopropyl)methanone

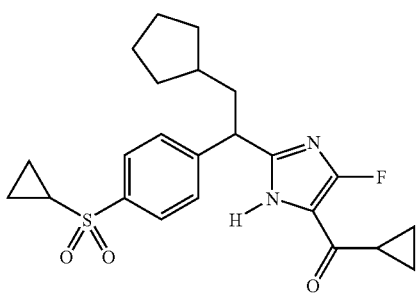

According to the method of Example 14, the title compound (0.048 g, yield 12%) was obtained as colorless crystals from (2-{2-cyclopentyl-1-[4-(cyclopropylsulfonyl)phenyl]ethyl}-1H-imidazol-5-yl)(cyclopropyl)methanone (0.395 g). melting point 79-82° C.

Example 25

{4-chloro-2-[1-[4-(methylsulfonyl)phenyl]-2-(tetrahydro-2H-pyran-4-yl)ethyl]-1H-imidazol-5-yl}(cyclopropyl)methanone

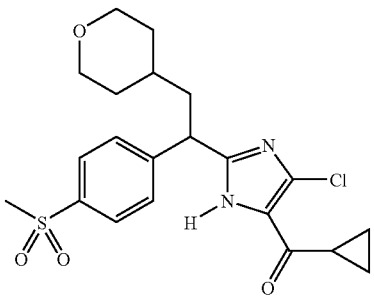

According to the method of Example 18, the title compound (0.048 g, yield 21%) was obtained as colorless crystals from cyclopropyl{2-[1-[4-(methylsulfonyl)phenyl]-2-(tetrahydro-2H-pyran-4-yl)ethyl]-1H-imidazol-5-yl}methanone (0.214 g). melting point 213-215° C.

Example 26

Cyclopropyl{4-fluoro-2-[1-[4-(methylsulfonyl)phenyl]-2-(tetrahydro-2H-pyran-4-yl)ethyl]-1H-imidazol-5-yl}methanone

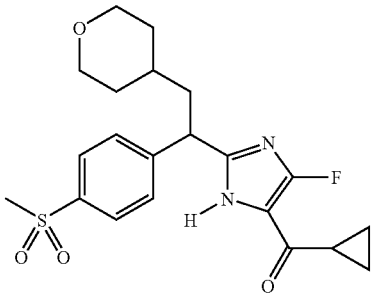

According to the method of Example 14, the title compound (0.022 g, yield 7%) was obtained as colorless crystals from cyclopropyl{2-[1-[4-(methylsulfonyl)phenyl]-2-(tetrahydro-2H-pyran-4-yl)ethyl]-1H-imidazol-5-yl}methanone (0.300 g). melting point 127-130° C.

Example 27

Cyclopropyl{2-[1-[4-(cyclopropylsulfonyl)phenyl]-2-(tetrahydro-2H-pyran-4-yl)ethyl]-4-fluoro-1H-imidazol-5-yl}methanone

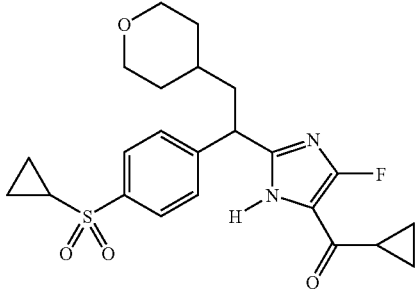

According to the method of Example 14, the title compound (0.026 g, yield 8%) was obtained as colorless crystals from cyclopropyl{2-[1-[4-(cyclopropylsulfonyl)phenyl]-2-(tetrahydro-2H-pyran-4-yl)ethyl]-1H-imidazol-5-yl}methanone (0.300 g). melting point 115-118° C.

Example 28

(3R)-3-{2-[5-(cyclobutylcarbonyl)-1H-imidazol-2-yl]-2-[4-(cyclopropylsulfonyl)phenyl]ethyl}cyclopentanone

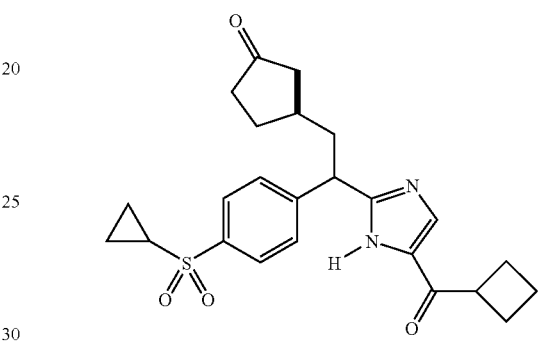

To a solution (30 mL) of 2-[4-(cyclopropylsulfonyl)phenyl]-3-[(1R)-3-oxocyclopentyl]propanic acid in N,N-dimethylformamide were added N,N-diisopropylethylamine (1.89 mL), 1-[bis(dimethylamino)methylene]-1H-1,2,3-triazolo(4,5-b)pyridinium 3-oxide hexafluorophosphate (1.52 g) and 5-cyclobutylisoxazol-4-amine hydrochloride (0.669 g), and the mixture was stirred at room temperature for 20 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=70:30-100:0, volume ratio). The obtained crude product was dissolved in ethanol (30 mL), palladium carbon (1.00 g) was added, and the mixture was purged with hydrogen (5 atm) and stirred at room temperature for 2 hr and at 50° C. for 2 hr. The reaction mixture was filtered to remove the catalyst, sodium hydroxide (0.160 g) was added to the filtrate, and the mixture was heated under reflux for 1.5 hr. To the reaction mixture was added ammonium chloride (0.243 g), and the mixture was cooled to room temperature and stirred at room temperature for 16 hr. The reaction mixture was concentrated, the obtained residue was suspended in acetone and the suspension was filtered to remove insoluble materials. The filtrate was concentrated, and the obtained residue was purified by silica gel column chromatography (ethyl acetate:hexane=60:40-100:0, volume ratio) to give the title compound (0.720 g, yield of 3 steps 45%) as a colorless oil. MS: 441 (MH+).

Example 29

(3R)-3-{2-[5-(cyclobutylcarbonyl)-4-fluoro-1H-imidazol-2-yl]-2-[4-(cyclopropylsulfonyl)phenyl]ethyl}cyclopentanone

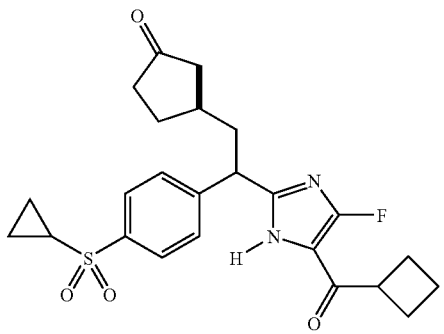

To a solution (16 mL) of (3R)-3-{2-[5-(cyclobutylcarbonyl)-1H-imidazol-2-yl]-2-[4-(cyclopropylsulfonyl)phenyl]ethyl}cyclopentanone (0.720 g) in acetonitrile was added xenon difluoride (0.552 g), and the mixture was heated under reflux for 4 hr. The reaction mixture was poured into ice water, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=30:70-100:0, volume ratio), and recrystallized from diethyl ether-hexane to give the title compound (0.035 g, yield 5%) as colorless crystals. melting point 85-88° C.

$^1$H NMR (300 MHz, CDCl$_3$) 0.98-1.12 (2 H, m), 1.24-1.43 (2 H, m), 1.77-2.22 (8 H, m), 2.22-2.57 (8 H, m), 3.75-3.90 (1 H, m), 4.21-4.33 (1 H, m), 7.51-7.60 (2 H, m), 7.82-7.89 (2 H, m), 10.91 (0.5 H, s), 11.06 (0.5 H, s).

Example 30

Cyclopropyl{2-[1-[4-(methylsulfonyl)phenyl]-2-(tetrahydro-2H-pyran-4-yl)ethyl]-1H-imidazol-5-yl}methanone

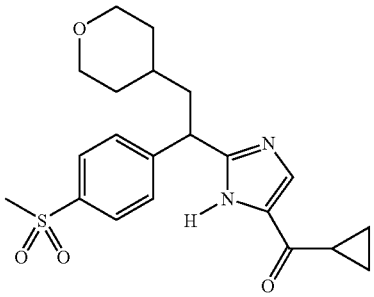

According to the method of Example 13, the title compound (3.86 g, 90%) was obtained as colorless amorphous crystals from N-(5-cyclopropylisoxazol-4-yl)-2-[4-(methylsulfonyl)phenyl]-3-(tetrahydro-2H-pyran-4-yl)propanamide (4.43 g). MS: 403 (MH$^+$).

Example 31

Cyclopropyl{2-[1-[4-(cyclopropylsulfonyl)phenyl]-2-(tetrahydro-2H-pyran-4-yl)ethyl]-1H-imidazol-5-yl}methanone

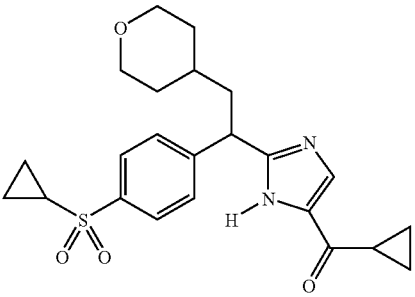

According to the method of Example 13, the title compound (1.20 g, 67%) was obtained as colorless crystals from N-(5-cyclopropylisoxazol-4-yl)-2-[4-(cyclopropylsulfonyl)phenyl]-3-(tetrahydro-2H-pyran-4-yl)propanamide (1.85 g). melting point 79-83° C.

Example 32

2-(5-{1-[4-(cyclopropylsulfonyl)phenyl]-2-(tetrahydro-2H-pyran-4-yl)ethyl}-1H-pyrrol-2-yl)pyridine

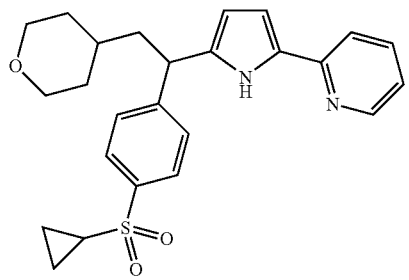

To a solution of 5-[4-(cyclopropylsulfonyl)phenyl]-1-(pyridin-2-yl)-6-(tetrahydro-2H-pyran-4-yl)hexane-1,4-dione (220 mg) in N,N-dimethylformamide (5 mL) was added ammonium acetate (190 mg), and the mixture was stirred at 100° C. for 1 hr. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, from a fraction eluted with ethyl acetate-hexane (3:1, volume ratio) to give a crude product. The obtained crude product was subjected to basic silica gel column chromatography, and the title compound (95 mg, yield 45%) was obtained as a pale-yellow amorphous solid from a fraction eluted with ethyl acetate-hexane (1:1, volume ratio). MS: 437 (MH$^+$).

$^1$H NMR (300 MHz, CDCl$_3$) δ0.94-1.09 (2 H, m), 1.24-1.50 (6 H, m), 1.51-1.58 (1 H, m), 1.80-1.95 (1 H, m), 2.00-2.14 (1H, m), 2.37-2.49 (1 H, m), 3.18-3.35 (2 H, m), 3.84-3.98 (2 H, m), 4.17 (1 H, t, J=7.9 Hz), 6.15 (1 H, t, J=3.1 Hz), 6.65 (1 H, dd, J=2.5, 3.5 Hz), 6.96-7.04 (1 H, m), 7.40 (2 H, d, J=8.3 Hz), 7.47-7.53 (1 H, m), 7.55-7.64 (1 H, m), 7.82 (2 H, d, J=8.5 Hz), 8.30-8.43 (1 H, m), 9.29 (1 H, brs).

Example 33

2-(5-{1-[4-(cyclopropylsulfonyl)phenyl]-2-(tetrahydro-2H-pyran-4-yl)ethyl}-1H-pyrrol-2-yl)-5-(2,2-dimethyl-1,3-dioxolan-4-yl)-1,3-thiazole

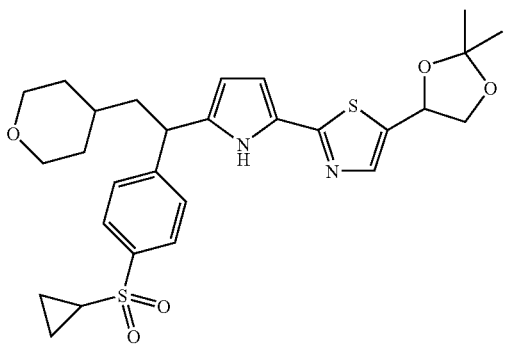

To a solution of 5-[4-(cyclopropylsulfonyl)phenyl]-1-[5-(2,2-dimethyl-1,3-dioxolan-4-yl)-1,3-thiazol-2-yl]-6-(tetrahydro-2H-pyran-4-yl)hexane-1,4-dione (730 mg) in acetic acid (15 mL) was added ammonium acetate (1.60 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (470 mg, yield 67%) was obtained as a pale-yellow amorphous solid from a fraction eluted with ethyl acetate-hexane (4:1, volume ratio). MS: 543 (MH$^+$).

$^1$H NMR (300 MHz, CDCl$_3$) δ0.96-1.10 (2 H, m), 1.28-1.40 (5 H, m), 1.45 (3 H, s), 1.52 (3 H, s), 1.56-1.60 (1 H, m), 1.63-1.69 (1 H, m), 1.89 (1 H, s), 1.97-2.13 (1 H, m), 2.37-2.53 (1 H, m), 3.18-3.37 (2 H, m), 3.78-3.98 (3 H, m), 4.13 (1 H, t, J=7.2 Hz), 4.26-4.37 (1 H, m), 5.30 (1 H, t, J=6.4 Hz), 6.12 (1 H, t, J=3.2 Hz), 6.61 (1 H, dd, J=2.6, 3.6 Hz), 7.37 (2 H, d, J=8.5 Hz), 7.47 (1 H, s), 7.82 (2 H, d, J=8.3 Hz), 9.05 (1 H, brs).

Example 34

1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol

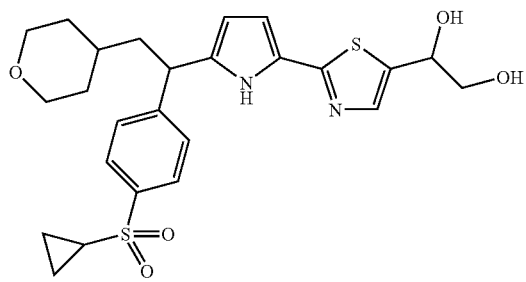

To a solution of 2-(5-{1-[4-(cyclopropylsulfonyl)phenyl]-2-(tetrahydro-2H-pyran-4-yl)ethyl}-1H-pyrrol-2-yl)-5-(2,2-dimethyl-1,3-dioxolan-4-yl)-1,3-thiazole (470 mg) in tetrahydrofuran (3 mL) was added 1M hydrochloric acid (3 mL), and the mixture was stirred at room temperature for 3 days. The reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to preparative HPLC to give the title compound (280 mg, yield 64%) as a colorless amorphous solid. MS: 503 (MH$^+$).

$^1$H NMR (300 MHz, CDCl$_3$) δ0.95-1.10 (2 H, m), 1.26-1.43 (5 H, m), 1.53 (3 H, brs), 1.79-1.94 (1 H, m), 1.95-2.07 (1H, m), 2.36-2.53 (1 H, m), 3.26 (2 H, t, J=11.5 Hz), 3.66-3.76 (1 H, m), 3.78-3.97 (4 H, m), 4.06-4.17 (1 H, m), 5.00 (1 H, dd, J=6.6, 4.0 Hz), 6.11 (1 H, t, J=3.0 Hz), 6.54-6.63 (1 H, m), 7.35 (3 H, d, J=8.3 Hz), 7.81 (2 H, d, J=8.3 Hz), 9.41 (1 H, brs).

Example 35

2-(5-{1-[4-(cyclopropylsulfonyl)phenyl]-2-(tetrahydro-2H-pyran-4-yl)ethyl}-1H-pyrrol-2-yl)-5-fluoropyridine

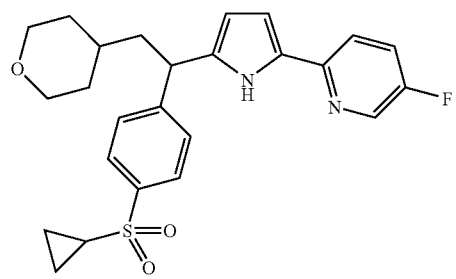

To a solution of 5-[4-(cyclopropylsulfonyl)phenyl]-1-(5-fluoropyridin-2-yl)-6-(tetrahydro-2H-pyran-4-yl)hexane-1,4-dione (65 mg) in acetic acid (3 mL) was added ammonium acetate (170 mg), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (35 mg, yield 56%) was obtained as a pale-yellow amorphous solid from a fraction eluted with ethyl acetate-hexane (3:2, volume ratio). MS: 455 (MH$^+$).

$^1$H NMR (300 MHz, CDCl$_3$) δ0.95-1.09 (2 H, m), 1.20-1.46 (5 H, m), 1.60-1.72 (2 H, m), 1.82-1.97 (1 H, m), 2.00-2.15 (1 H, m), 2.37-2.53 (1 H, m), 3.29 (2 H, t, J=11.5 Hz), 3.84-3.98 (2 H, m), 4.17 (1 H, t, J=7.8 Hz), 6.14 (1 H, t, J=3.2 Hz), 6.58 (1 H, t, J=2.8 Hz), 7.29-7.54 (4 H, m), 7.83 (2 H, d, J=8.3 Hz), 8.24 (1 H, d, J=2.3 Hz), 9.04 (1 H, brs).

Example 36

2-(5-{1-[4-(methylsulfonyl)phenyl]-2-(tetrahydro-2H-pyran-4-yl)ethyl}-1H-pyrrol-2-yl)pyridine

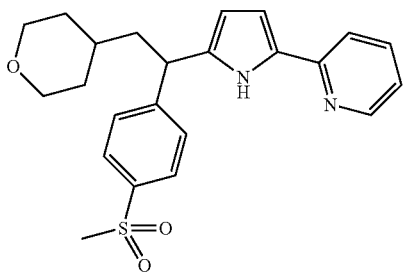

To a solution of 5-[4-(methylsulfonyl)phenyl]-1-(pyridin-2-yl)-6-(tetrahydro-2H-pyran-4-yl)hexane-1,4-dione (525 mg) in acetic acid (6 mL) was added ammonium acetate (1.50 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (430 mg, yield 86%) was obtained as a colorless amorphous solid from a fraction eluted with ethyl acetate-hexane (2:1, volume ratio). MS: 411 (MH$^+$).

$^1$H NMR (300 MHz, CDCl$_3$) δ1.24-1.50 (3 H, m), 1.56 (1H, brs), 1.67 (1 H, brs), 1.80-1.96 (1 H, m), 2.00-2.13 (1 H, m), 3.03 (3 H, s), 3.28 (2 H, t, J=11.5 Hz), 3.84-3.98 (2H, m), 4.17 (1 H, t, J=8.0 Hz), 6.14 (1 H, t, J=3.0 Hz), 6.55-6.71 (1 H, m), 6.91-7.07 (1 H, m), 7.40 (2 H, d, J=8.3 Hz), 7.46-7.54 (1 H, m), 7.55-7.66 (1 H, m), 7.86 (2 H, d, J=8.3 Hz), 8.38 (1 H, d, J=4.9 Hz), 9.33 (1 H, brs).

Example 37

5-bromo-2-(5-[1-[4-(cyclopropylsulfonyl)phenyl]-2-(tetrahydro-2H-pyran-4-yl)ethyl]-1H-pyrrol-2-yl)pyridine

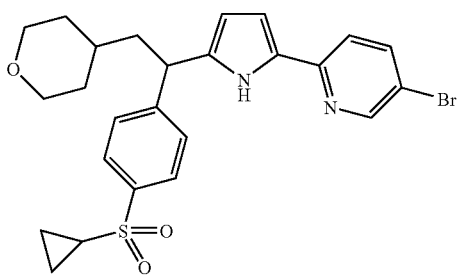

To a solution (10 mL) of 1-(5-bromopyridin-2-yl)-5-[4-(cyclopropylsulfonyl)phenyl]-6-(tetrahydro-2H-pyran-4-yl)hexane-1,4-dione (1.29 g) in acetic acid (10 mL) was added ammonium acetate (3.00 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (1.12 g, yield 96%) was obtained as a white amorphous solid from a fraction eluted with ethyl acetate-hexane (1:1, volume ratio). MS: 517 (MH$^+$).

$^1$H NMR (300 MHz, CDCl$_3$) δ0.93-1.12 (2 H, m), 1.27-1.49 (5 H, m), 1.59-1.72 (2 H, m), 1.78-1.96 (1 H, m), 1.98-2.15 (1 H, m), 2.36-2.52 (1 H, m), 3.18-3.37 (2 H, m), 3.83-3.99 (2 H, m), 4.17 (1 H, t, J=7.9 Hz), 6.15 (1 H, t, J=3.1 Hz), 6.64 (1 H, dd, J=3.6, 2.6 Hz), 7.31-7.45 (3 H, m), 7.70 (1 H, dd, J=2.4, 8.6 Hz), 7.83 (2 H, d, J=8.3 Hz), 8.35-8.48 (1 H, m), 9.12 (1 H, brs).

Example 38

Optically Active Form of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol

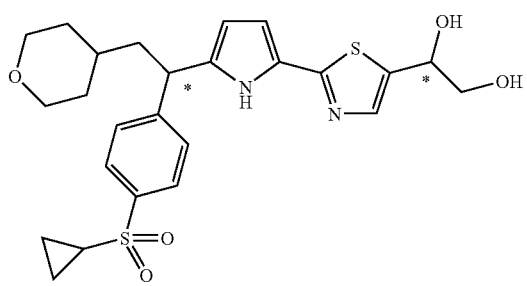

1-[2-(5-{1-[4-(Cyclopropylsulfonyl)phenyl]-2-(tetrahydro-2H-pyran-4-yl)ethyl}-1H-pyrrol-2-yl)-1,3-thiazol-5-yl]ethane-1,2-diol (200 mg) was dissolved in hexane-ethanol (800:200, volume ratio, 888 mL), and the solution was subjected to HPLC using CHIRALCEL OD (50 mmID×500 mL, manufactured by DAICEL CHEMICAL INDUSTRY LTD.). Using hexane-ethanol (800:200, volume ratio) as a mobile phase, the solution was eluted at flow rate 80 mL/min and at 30° C. and the fraction was separated at retention time 59.9 min, and concentrated. The obtained solid (enantiomeric excess 99%) was dissolved in ethyl acetate and the insoluble material was filtered off. The filtration was concentrated to give the title compound (47.0 mg) as a colorless amorphous solid. MS: 503 (MH$^+$).

Example 3.9

Optically Active Form of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol

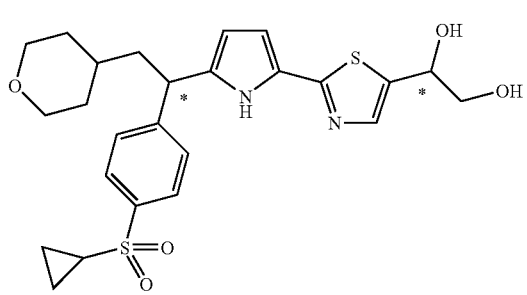

1-[2-(5-{1-[4-(Cyclopropylsulfonyl)phenyl]-2-(tetrahydro-2H-pyran-4-yl)ethyl}-1H-pyrrol-2-yl)-1,3-thiazol-5-yl]ethane-1,2-diol (200 mg) was dissolved in hexane-ethanol (800:200, volume ratio, 888 mL), and the solution was subjected to HPLC using CHIRALCEL OD (50 mmID×500 mL, manufactured by DAICEL CHEMICAL INDUSTRY LTD.). Using hexane-ethanol (800:200, volume ratio) as a mobile phase, the solution was eluted at flow rate 80 mL/min and at 30° C., and the fraction was separated at retention time 78.3 min, and concentrated. The obtained solid (enantiomeric excess 98.6%) was dissolved in ethyl acetate and the insoluble material was filtered off. The filtration was concentrated to give the title compound (47.9 mg) as a colorless amorphous solid. MS: 503 (MH⁺).

Example 40

Optically Active Form of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol

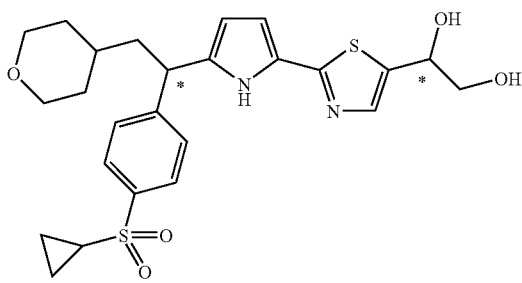

1-[2-(5-{1-[4-(Cyclopropylsulfonyl)phenyl]-2-(tetrahydro-2H-pyran-4-yl)ethyl}-1H-pyrrol-2-yl)-1,3-thiazol-5-yl]ethane-1,2-diol (200 mg) was dissolved in hexane-ethanol (800:200, volume ratio, 888 mL), and the solution was subjected to HPLC using CHIRALCEL OD (50 mmID×500 mL, manufactured by DAICEL CHEMICAL INDUSTRY LTD.). Using hexane-ethanol (800:200, volume ratio) as a mobile phase, the solution was eluted at flow rate 80 mL/min and at 30° C., and the fraction was separated at retention time 101.7 min, and concentrated. The obtained solid (enantiomeric excess 99%) was dissolved in ethyl acetate and the insoluble material was filtered off. The filtration was concentrated to give the title compound (55.2 mg) as a colorless amorphous solid. MS: 503 (MH⁺).

Example 41

Optically Active Form of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol

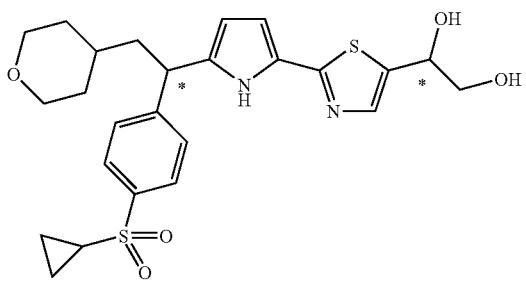

1-[2-(5-{1-[4-(Cyclopropylsulfonyl)phenyl]-2-(tetrahydro-2H-pyran-4-yl)ethyl}-1H-pyrrol-2-yl)-1,3-thiazol-5-yl]ethane-1,2-diol (200 mg) was dissolved in hexane-ethanol (800:200, volume ratio, 888 mL), and the solution was subjected to HPLC using CHIRALCEL OD (50 mmID×500 mL, manufactured by DAICEL CHEMICAL INDUSTRY LTD.). Using hexane-ethanol (800:200, volume ratio) as a mobile phase, the solution was eluted at flow rate 80 mL/min and at 30° C., and the fraction was separated at retention time 115.7 min, and concentrated. The obtained solid (enantiomeric excess 98.4%) was dissolved in ethyl acetate and the insoluble material was filtered off. The filtration was concentrated to give the title compound (52.7 mg) as a colorless amorphous solid. MS: 503 (MH⁺).

Example 42

1-[6-(5-{1-[4-(cyclopropylsulfonyl)phenyl]-2-(tetrahydro-2H-pyran-4-yl)ethyl}-1H-pyrrol-2-yl)pyridin-3-yl]ethane-1,2-diol

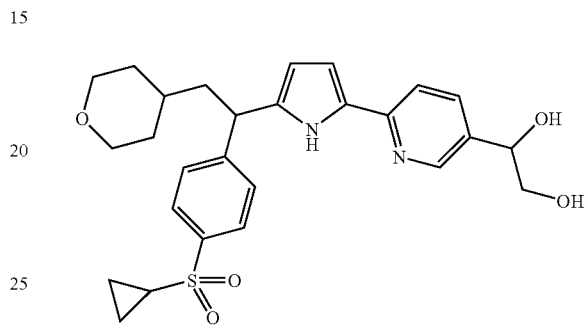

To a solution of 2-(5-{1-[4-(cyclopropylsulfonyl)phenyl]-2-(tetrahydro-2H-pyran-4-yl)ethyl}-1H-pyrrol-2-yl)-5-ethenylpyridine (110 mg) in a mixed solvent of tert-butyl alcohol (1.5 mL) and water (1.5 mL) was added AD-mix-α (350 mg; Aldrich), and the mixture was stirred under ice-cooling for 4 hr. Sodium sulfite (30 mg) was added and the mixture was stirred for 30 min. The reaction mixture was diluted with methyl acetate, washed with water and saturated brine, dried (MgSO₄) and concentrated. The residue was subjected to preparative HPLC to give the title compound (47 mg, yield 40%) as a yellow amorphous solid. MS: 497 (MH⁺).

¹H NMR (300 MHz, CDCl₃) δ 0.94-1.07 (2 H, m), 1.16-1.23 (1H, m), 1.29-1.45 (5 H, m), 1.62-1.70 (1 H, m), 1.89 (1 H, d, J=6.4 Hz), 2.04-2.13 (1 H, m), 2.36-2.50 (1 H, m), 3.20-3.35 (2 H, m), 3.56-3.69 (1 H, m), 3.70-3.81 (1 H, m), 3.91 (2 H, d, J=11.7 Hz), 4.13-4.23 (1 H, m), 4.79 (1 H, dd, J=3.4, 8.0 Hz), 6.15 (1 H, brs), 6.60-6.68 (1 H, m), 7.38 (2 H, dd, J=1.9, 8.3 Hz), 7.49 (1 H, d, J=8.0 Hz), 7.57-7.68 (1H, m), 7.81 (2 H, d, J=8.0 Hz), 8.32 (1 H, s), 9.38 (1 H, brs).

Example 43

Optically Active Form of 1-[6-(5-{1-[4-(cyclopropylsulfonyl)phenyl]-2-(tetrahydro-2H-pyran-4-yl)ethyl}-1H-pyrrol-2-yl)pyridin-3-yl]ethane-1,2-diol

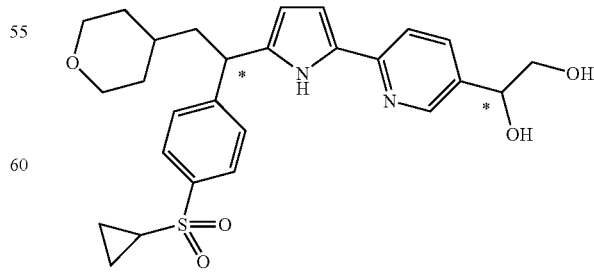

1-[6-(5-{1-[4-(Cyclopropylsulfonyl)phenyl]-2-(tetrahydro-2H-pyran-4-yl)ethyl}-1H-pyrrol-2-yl)pyridin-3-yl]

Example 44

Optically Active Form of 1-[6-(5-{1-[4-(cyclopropyl-sulfonyl)phenyl]-2-(tetrahydro-2H-pyran-4-yl)ethyl}-1H-pyrrol-2-yl)pyridin-3-yl]ethane-1,2-diol

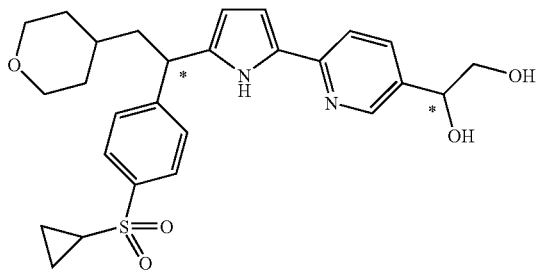

1-[6-(5-{1-[4-(Cyclopropylsulfonyl)phenyl]-2-(tetrahydro-2H-pyran-4-yl)ethyl}-1H-pyrrol-2-yl)pyridin-3-yl]ethane-1,2-diol (1100 mg) was dissolved in ethanol (55 mL), and the solution was subjected to supercritical fluid chromatography using CHIRALPAK AS-H (20 mmID×250 mL, manufactured by DAICEL CHEMICAL INDUSTRY LTD.). Using carbon dioxide-methanol-isopropylamine (500:500:0.5, volume ratio) as a mobile phase, the solution was eluted at flow rate 50 mL/min, at 100 bar and at 35° C., and the fraction was separated at retention time 2.3 min, and concentrated. The obtained solid was dissolved again in ethanol (27 mL), and the solution was subjected to supercritical fluid chromatography using CHIRALCEL OD-H (20 mmID×250 mL, manufactured by DAICEL CHEMICAL INDUSTRY LTD.). Using carbon dioxide-methanol (500:500, volume ratio) as a mobile phase, the solution was eluted at flow rate 50 mL/min, at 100 bar and at 35° C., and the fraction was separated at retention time 4.4 min, and concentrated. The obtained solid (diastereomeric excess 99%) was dissolved in ethyl acetate and the insoluble material was filtered off. The filtration was concentrated to give the title compound (229 mg) as a colorless amorphous solid. MS: 497 (MH$^+$).

Example 45

Optically Active Form of 1-[6-(5-{1-[4-(cyclopropyl-sulfonyl)phenyl]-2-(tetrahydro-2H-pyran-4-yl)ethyl}-1H-pyrrol-2-yl)pyridin-3-yl]ethane-1,2-diol

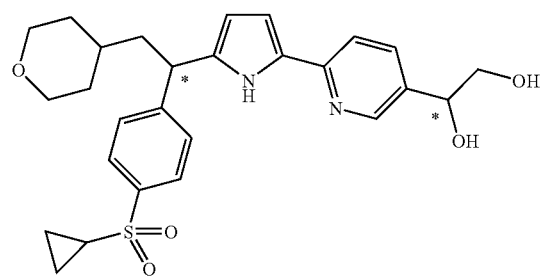

1-[6-(5-{1-[4-(Cyclopropylsulfonyl)phenyl]-2-(tetrahydro-2H-pyran-4-yl)ethyl}-1H-pyrrol-2-yl)pyridin-3-yl]ethane-1,2-diol (1100 mg) was dissolved in ethanol (55 mL), and the solution was subjected to supercritical fluid chromatography using CHIRALPAK AS-H (20 mmID×250 mL, manufactured by DAICEL CHEMICAL INDUSTRY LTD.). Using carbon dioxide-methanol-isopropylamine (500:500:0.5, volume ratio) as a mobile phase, the solution was eluted at flow rate 50 mL/min, at 100 bar and at 35° C., and the fraction was separated at retention time 3.2 min, and concentrated. The obtained solid (diastereomeric excess 99%) was dissolved in ethyl acetate and the insoluble material was filtered off. The filtration was concentrated to give the title compound (228 mg) as a colorless amorphous solid. MS: 497 (MH$^+$).

Example 46

Optically Active Form of 1-[6-(5-{1-[4-(cyclopropyl-sulfonyl)phenyl]-2-(tetrahydro-2H-pyran-4-yl)ethyl}-1H-pyrrol-2-yl)pyridin-3-yl]ethane-1,2-diol

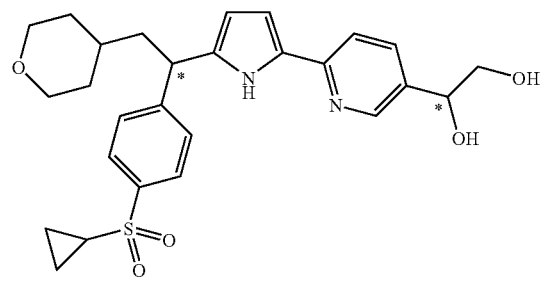

1-[6-(5-{1-[4-(Cyclopropylsulfonyl)phenyl]-2-(tetrahydro-2H-pyran-4-yl)ethyl}-1H-pyrrol-2-yl)pyridin-3-yl]ethane-1,2-diol (1100 mg) was dissolved in ethanol (55 mL), and the solution was subjected to supercritical fluid chromatography using CHIRALPAK AS-H (20 mmID×250 mmL, manufactured by DAICEL CHEMICAL INDUSTRY LTD.). Using carbon dioxide-methanol-isopropylamine (500:500:0.5, volume ratio) as a mobile phase, the solution was eluted at flow rate 50 mL/min, at 100 bar and at 35° C., and the fraction was separated at retention time 4.3 min, and concentrated. The obtained solid (diastereomeric excess 99%) was dissolved in ethyl acetate and the insoluble material was filtered off. The filtration was concentrated to give the title compound (211 mg) as a colorless amorphous solid. MS: 497 (MH+).

Example 47

Optically Active Form of 2-(5-{2-cyclopentyl-1-[4-(methylsulfonyl)phenyl]ethyl}-1H-pyrrol-2-yl)-1,3-thiazole

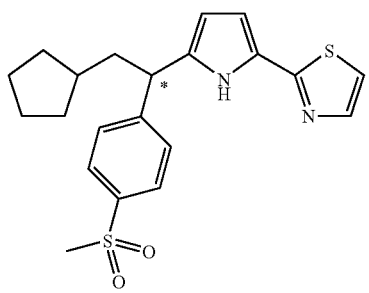

2-(5-{2-Cyclopentyl-1-[4-(methylsulfonyl)phenyl]ethyl}-1H-pyrrol-2-yl)-1,3-thiazole (218 mg) was dissolved in hexane-ethanol (850:150, volume ratio, 109 mL), and the solution was subjected to HPLC using CHIRALPAK AD (50 mmID×500 mL, manufactured by DAICEL CHEMICAL INDUSTRY LTD.). Using hexane-ethanol (850:150, volume ratio) as a mobile phase, the solution was eluted at flow rate 80 mL/min and at 30° C., and the fraction was separated at retention time 71.5 min, and concentrated. The obtained solid (enantiomeric excess 99.9%) was dissolved in ethyl acetate and the insoluble material was filtered off. The filtration was concentrated to give the title compound (105 mg) as a colorless amorphous solid. MS: 401 (MH+).

Example 48

Optically Active Form of 2-(5-{2-cyclopentyl-1-[4-(methylsulfonyl)phenyl]ethyl}-1H-pyrrol-2-yl)-1,3-thiazole

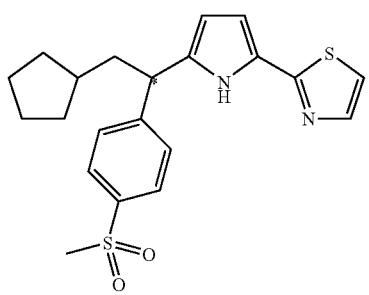

2-(5-{2-Cyclopentyl-1-[4-(methylsulfonyl)phenyl]ethyl}-1H-pyrrol-2-yl)-1,3-thiazole (218 mg) was dissolved in hexane-ethanol (850:150, volume ratio, 109 mL), and the solution was subjected to HPLC using CHIRALPAK AD (50 mmID×500 mL, manufactured by DAICEL CHEMICAL INDUSTRY LTD.). Using hexane-ethanol (850:150, volume ratio) as a mobile phase, the solution was eluted at flow rate 80 mL/min and at 30° C., and the fraction was separated at retention time 126.7 min, and concentrated. The obtained solid (enantiomeric excess 99.9%) was dissolved in ethyl acetate and the insoluble material was filtered off. The filtration was concentrated to give the title compound (102 mg) as a colorless amorphous solid. MS: 401 (MH+).

Example 49

2-(5-{1-[4-(cyclopropylsulfonyl)phenyl]-2-[(2R,3R,7R)-2,3-diphenyl-1,4-dioxaspiro[4.4]non-7-yl]ethyl}-1H-pyrrol-2-yl)pyridine

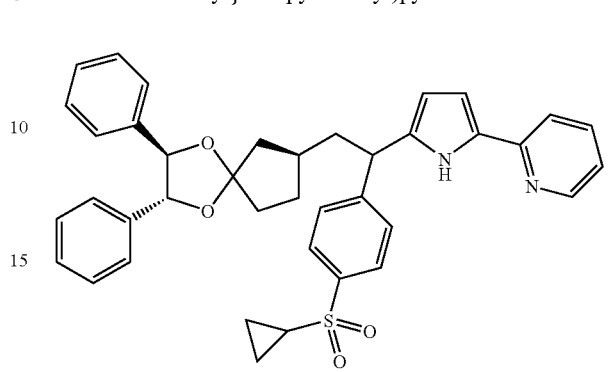

To a solution of 4-[4-(cyclopropylsulfonyl)phenyl]-5-[(2R,3R,7R)-2,3-diphenyl-1,4-dioxaspiro[4.4]non-7-yl]pent-1-en-3-one (500 mg) in ethanol (5 mL) were added pyridine-2-carbaldehyde (107 µL), 3-benzyl-5-(2-hydroxyethyl)-4-methyl-1,3-thiazol-3-ium chloride (28 mg) and triethylamine (56 µL), and the mixture was stirred with heating under reflux for 2 hr. After cooling to room temperature, the reaction mixture was diluted with ethyl acetate and washed with water. The ethyl acetate layer was washed with saturated brine, dried (MgSO$_4$) and concentrated to give a crude product (610 mg). To a solution of the obtained crude product (610 mg) in acetic acid (5 mL) was added ammonium acetate (1135 mg), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to preparative HPLC to give the title compound (70 mg, yield 12%) as a colorless amorphous solid. MS: 631 (MH+).

$^1$H NMR (300 MHz, CDCl$_3$) δ0.91-1.07 (2 H, m), 1.12-1.27 (1H, m), 1.33 (2 H, d, J=4.7 Hz), 1.67-1.85 (1 H, m), 1.88-2.02 (2 H, m), 2.05 (2 H, s), 2.19-2.33 (3 H, m), 2.36-2.55 (1 H, m), 4.04-4.16 (1 H, m), 4.69 (2 H, t, J=2.8 Hz), 6.16 (1H, t, J=3.1 Hz), 6.58-6.68 (1 H, m), 6.94-7.04 (1 H, m), 7.13-7.24 (4 H, m), 7.27-7.35 (6 H, m), 7.39-7.52 (3H, m), 7.53-7.64 (1 H, m), 7.74-7.87 (2 H, m), 8.38 (1 H, dd, J=2.1, 4.7 Hz), 9.21 (1 H, d, J=0.8 Hz).

Example 50

(3R)-3-{2-[4-(cyclopropylsulfonyl)phenyl]-2-(5-(pyridin-2-yl)-1H-pyrrol-2-yl)ethyl}cyclopentanone

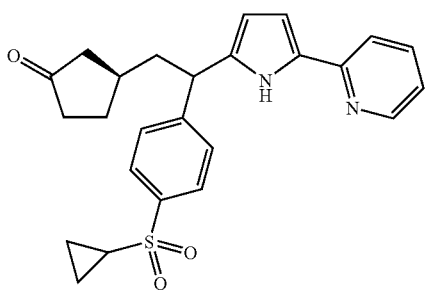

To a solution of 2-(5-{1-[4-(cyclopropylsulfonyl)phenyl]-2-[(2R,3R,7R)-2,3-diphenyl-1,4-dioxaspiro[4.4]non-7-yl]ethyl}-1H-pyrrol-2-yl)pyridine (70 mg) in tetrahydrofuran (3 mL) was added 1M hydrochloric acid (3 mL), and the mixture was stirred overnight at room temperature. The reaction mixture was diluted with ethyl acetate, and washed with saturated aqueous sodium hydrogen carbonate. The ethyl acetate layer was washed with saturated brine, dried (MgSO₄) and concentrated. The residue was subjected to silica gel column chromatography, and the title compound (45 mg, yield 94%) was obtained as a colorless amorphous solid from a fraction eluted with ethyl acetate-hexane (2:1, volume ratio). MS: 435 (MH⁺).

¹H NMR (300 MHz, CDCl₃) δ0.96-1.10 (2 H, m), 1.28-1.40 (2H, m), 1.49-1.57 (1 H, m), 1.74-1.95 (1 H, m), 2.00-2.52 (8H, m), 4.02-4.19 (1 H, m), 6.17 (1 H, t, J=3.2 Hz), 6.58-6.69 (1 H, m), 6.94-7.07 (1 H, m), 7.41 (2 H, dd, J=2.7, 8.3 Hz), 7.45-7.54 (1 H, m), 7.55-7.67 (1 H, m), 7.83 (2 H, d, J=8.3 Hz), 8.38 (1 H, d, J=5.3 Hz), 9.31 (1 H, brs).

Example 51

2-(5-{1-[4-(cyclopropylsulfonyl)phenyl]-2-(tetrahydro-2H-pyran-4-yl)ethyl}-1H-pyrrol-2-yl)-5-ethenylpyridine

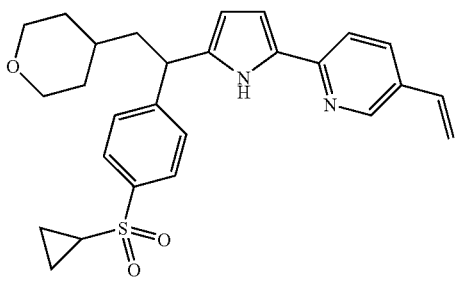

To a solution of 5-bromo-2-(5-{1-[4-(cyclopropylsulfonyl)phenyl]-2-(tetrahydro-2H-pyran-4-yl)ethyl}-1H-pyrrol-2-yl)pyridine (200 mg) in toluene (2 mL) were added tributyl(vinyl)tin (115 µL) and tetrakistriphenylphosphinepalladium(0) (40 mg), and the mixture was stirred under argon atmosphere at 110° C. overnight. After cooling to room temperature, the reaction mixture was concentrated, and the residue was subjected to silica gel column chromatography. The title compound (120 mg, yield 67%) was obtained as a yellow amorphous solid from a fraction eluted with ethyl acetate-hexane (1:1, volume ratio). MS: 463 (MH⁺).

¹H NMR (300 MHz, CDCl₃) δ0.97-1.09 (2 H, m), 1.25-1.51 (5H, m), 1.52-1.58 (1 H, m), 1.62-1.71 (1 H, m), 1.82-1.95 (1H, m), 1.99-2.14 (1 H, m), 2.37-2.49 (1 H, m), 3.28 (2H, t, J=11.7 Hz), 3.83-3.98 (2 H, m), 4.16 (1 H, t, J=8.0 Hz), 5.30 (1 H, d, J=11.0 Hz), 5.75 (1 H, d, J=17.4 Hz), 6.15 (1H, t, J=3.2 Hz), 6.58-6.72 (2 H, m), 7.38 (2 H, d, J=8.3 Hz), 7.46 (1 H, d, J=8.3 Hz), 7.68 (1 H, dd, J=1.9, 8.3 Hz), 7.81 (2 H, d, J=8.0 Hz), 8.36 (1 H, d, J=1.9 Hz), 9.29 (1 H, brs).

Example 52

Diethyl [6-(5-{1-[4-(cyclopropylsulfonyl)phenyl]-2-(tetrahydro-2H-pyran-4-yl)ethyl}-1H-pyrrol-2-yl)pyridin-3-yl]malonate

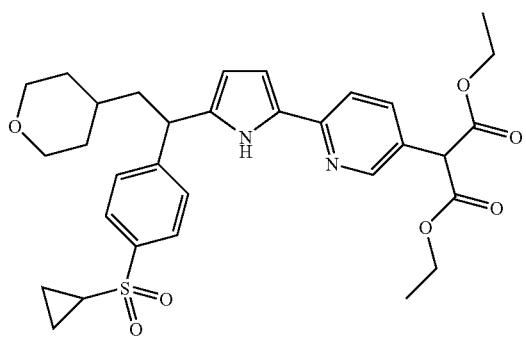

To a solution (5 mL) of diethyl (6-{5-[4-(cyclopropylsulfonyl)phenyl]-4-oxo-6-(tetrahydro-2H-pyran-4-yl)hexanoyl}pyridin-3-yl)malonate (150 mg) in acetic acid was added ammonium acetate (300 mg), and the mixture was stirred at 110° C. for 40 min. After cooling to room temperature, the reaction mixture was diluted with ethyl acetate and washed with water. The ethyl acetate layer was washed with saturated aqueous sodium hydrogen carbonate and saturated brine, dried (MgSO₄) and concentrated. The residue was subjected to silica gel column chromatography, and the title compound (120 mg, yield 83%) was obtained as a colorless amorphous solid from a fraction eluted with ethyl acetate-hexane (1.5:1, volume ratio). MS: 595 (MH⁺).

¹H NMR (300 MHz, CDCl₃) δ0.96-1.09 (2 H, m), 1.20-1.30 (7H, m), 1.31-1.46 (5 H, m), 1.60-1.72 (2 H, m), 1.81-1.96 (1H, m), 2.00-2.12 (1 H, m), 2.38-2.50 (1 H, m), 3.20-3.38 (2 H, m), 3.92 (2 H, d, J=11.7 Hz), 4.10-4.31 (5 H, m), 6.15 (1 H, t, J=3.1 Hz), 6.66 (1 H, dd, J=2.4, 3.6 Hz), 7.39 (2H, d, J=8.3 Hz), 7.50 (1 H, d, J=8.5 Hz), 7.73 (1 H, dd, J=2.3, 8.5 Hz), 7.78-7.86 (2 H, m), 8.34 (1 H, d, J=1.9 Hz), 9.20 (1 H, brs).

Example 53

2-[6-(5-{1-[4-(cyclopropylsulfonyl)phenyl]-2-(tetrahydro-2H-pyran-4-yl)ethyl}-1H-pyrrol-2-yl)pyridin-3-yl]propane-1,3-diol

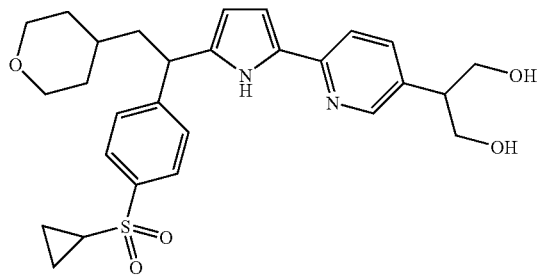

A solution of diethyl [6-(5-{1-[4-(cyclopropylsulfonyl)phenyl]-2-(tetrahydro-2H-pyran-4-yl)ethyl}-1H-pyrrol-2-yl)pyridin-3-yl]malonate (100 mg) in tetrahydrofuran (1.5 mL) was added to a suspension of lithium aluminum hydride (15 mg) in tetrahydrofuran (1.5 mL) under ice-cooling, and the mixture was stirred for 2 hr. Lithium aluminum hydride (30 mg) was further added, and the mixture was stirred with heating under reflux overnight. After cooling to room temperature, the reaction mixture was diluted with tetrahydrofuran, and the reaction was quenched with sodium sulfate decahydrate. The reaction mixture was filtered through celite, and the filtrate was concentrated. The residue was subjected to preparative HPLC to give the title compound (15 mg, yield 15%) as a yellow amorphous solid. MS: 511 (MH$^+$).

$^1$H NMR (300 MHz, CDCl$_3$) δ0.91-1.09 (2 H, m), 1.11-1.23 (2H, m), 1.23-1.41 (4 H, m), 1.40-1.56 (2 H, m), 1.58-1.76 (3H, m), 1.81-1.98 (1 H, m), 2.08 (1 H, d, J=1.7 Hz), 2.53-3.03 (2 H, m), 3.54-3.68 (1 H, m), 3.70-3.99 (5 H, m), 4.21-4.42 (1 H, m), 6.12 (1 H, t, J=3.2 Hz), 6.57-6.76 (1H, m), 7.45-7.67 (4 H, m), 7.74-7.91 (3 H, m), 8.26 (1H, brs).

Example 54

6-(5-{1-[4-(cyclopropylsulfonyl)phenyl]-2-(tetrahydro-2H-pyran-4-yl)ethyl}-1H-pyrrol-2-yl)pyridine-3-carbaldehyde

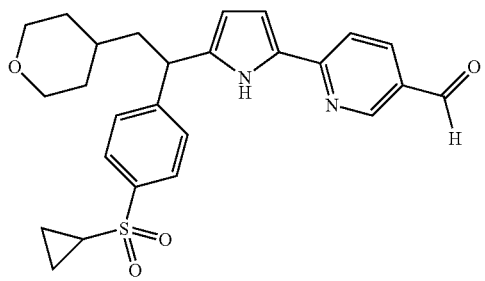

To a solution of 5-[4-(cyclopropylsulfonyl)phenyl]-1-[5-(1,3-dioxolan-2-yl)pyridin-2-yl]-6-(tetrahydro-2H-pyran-4-yl)hexane-1,4-dione (4.40 g) in acetic acid (35 mL) was added ammonium acetate (10.3 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (3.22 g, yield 83%) was obtained as a yellow amorphous solid from a fraction eluted with ethyl acetate-hexane (2:1, volume ratio). MS: 465 (MH$^+$).

$^1$H NMR (300 MHz, CDCl$_3$) δ0.95-1.09 (2 H, m), 1.31-1.52 (5H, m), 1.61-1.71 (2 H, m), 1.86-2.00 (1 H, m), 2.05-2.14 (1H, m), 2.38-2.51 (1 H, m), 3.29 (2 H, t, J=11.4 Hz), 3.86-3.99 (2 H, m), 4.21 (1 H, t, J=8.0 Hz), 6.22 (1 H, t, J=3.2 Hz), 6.77-6.88 (1 H, m), 7.41 (2 H, d, J=8.3 Hz), 7.58 (1H, d, J=8.3 Hz), 7.85 (2 H, d, J=8.3 Hz), 8.05 (1 H, dd, J=2.3, 8.3 Hz), 8.81 (1 H, d, J=1.5 Hz), 9.33 (1 H, brs), 9.97 (1H, s).

Example 55

2-{[6-(5-{1-[4-(cyclopropylsulfonyl)phenyl]-2-(tetrahydro-2H-pyran-4-yl)ethyl}-1H-pyrrol-2-yl)pyridin-3-yl]sulfanyl}ethanol

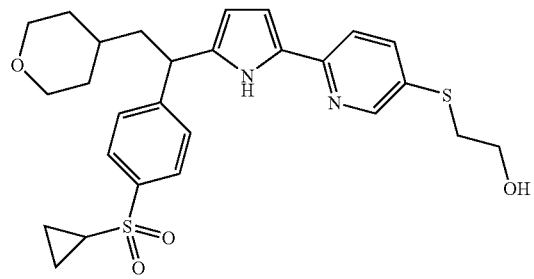

To a solution of 5-bromo-2-(5-{1-[4-(cyclopropylsulfonyl)phenyl]-2-(tetrahydro-2H-pyran-4-yl)ethyl}-1H-pyrrol-2-yl)pyridine (200 mg) in N,N-dimethylformamide (1 mL) were added 2-sulfanylethanol (63 μL) and tetrakistriphenylphosphinepalladium(0) (230 mg), and the mixture was stirred using a microwave synthesis apparatus at 120° C. for 3 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (114 mg, yield 57%) was obtained as a colorless amorphous solid from a fraction eluted with ethyl acetate-hexane (4:1, volume ratio). MS: 513 (MH$^+$).

$^1$H NMR (300 MHz, CDCl$_3$) δ0.93-1.11 (2 H, m), 1.25-1.48 (5H, m), 1.60-1.73 (2 H, m), 1.80-1.95 (1 H, m), 2.00-2.19 (2H, m), 2.36-2.52 (1 H, m), 3.05 (2 H, t, J=5.9 Hz), 3.19-3.37 (2 H, m), 3.73 (2 H, d, J=4.5 Hz), 3.84-3.99 (2 H, m), 4.09-4.23 (1 H, m), 6.15 (1 H, t, J=3.2 Hz), 6.57-6.73 (1H, m), 7.41 (3 H, dd, J=10.6, 8.3 Hz), 7.66 (1 H, dd, J=2.3, 8.3 Hz), 7.82 (2 H, d, J=8.3 Hz), 8.41 (1 H, d, J=2.3 Hz), 9.23 (1 H, brs).

Example 56

Ethyl {[6-(5-{1-[4-(cyclopropylsulfonyl)phenyl]-2-(tetrahydro-2H-pyran-4-yl)ethyl}-1H-pyrrol-2-yl)pyridin-3-yl]sulfanyl}acetate

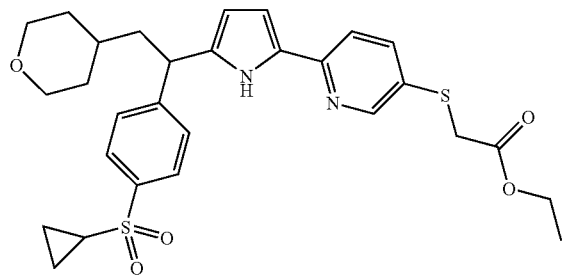

To a solution of 5-bromo-2-(5-{1-[4-(cyclopropylsulfonyl)phenyl]-2-(tetrahydro-2H-pyran-4-yl)ethyl}-1H-pyrrol-2-yl)pyridine (200 mg) in N,N-dimethylformamide (1 mL) were added ethyl sulfanylacetate (98 μL) and tetrakistriphenylphosphinepalladium(0) (230 mg), and the mixture was stirred using a microwave synthesis apparatus at 120° C. for 3 hr. After cooling to room temperature, the reaction mixture was diluted with ethyl acetate and washed with water. The ethyl acetate layer was washed with saturated brine, dried (MgSO$_4$) and concentrated. The residue was subjected to silica gel column chromatography, and the title compound (117 mg, yield 54%) was obtained as a yellow amorphous solid from a fraction eluted with ethyl acetate-hexane (3:2, volume ratio). MS: 555 (MH$^+$).

$^1$H NMR (300 MHz, CDCl$_3$) δ0.95-1.09 (2 H, m), 1.22 (3 H, t, J=7.2 Hz), 1.29-1.46 (5 H, m), 1.64 (2 H, d, J=19.7 Hz), 1.78-1.96 (1 H, m), 1.99-2.13 (1 H, m), 2.37-2.52 (1H, m), 3.18-3.37 (2 H, m), 3.54 (2 H, s), 3.83-3.99 (2 H, m), 4.06-4.24 (3 H, m), 6.15 (1 H, t, J=3.2 Hz), 6.60-6.71 (1H, m), 7.41 (3 H, t, J=8.7 Hz), 7.70 (1 H, dd, J=2.3, 8.7 Hz), 7.83 (2 H, d, J=8.3 Hz), 8.45 (1 H, d, J=1.5 Hz), 9.16 (1H, brs).

Example 57

{[6-(5-{1-[4-(cyclopropylsulfonyl)phenyl]-2-(tetrahydro-2H-pyran-4-yl)ethyl}-1H-pyrrol-2-yl)pyridin-3-yl]sulfanyl}acetic acid

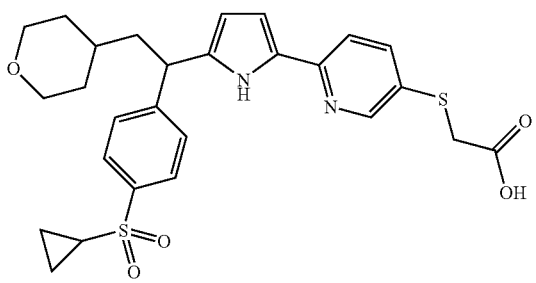

To a solution of ethyl {[6-(5-{1-[4-(cyclopropylsulfonyl)phenyl]-2-(tetrahydro-2H-pyran-4-yl)ethyl}-1H-pyrrol-2-yl)pyridin-3-yl]sulfanyl}acetate (75 mg) in methanol (3 mL) was added 2M aqueous sodium hydroxide solution (170 μL), and the mixture was stirred at 50° C. for 2 hr. After cooling to room temperature, the reaction mixture was neutralized with 1M hydrochloric acid, and the mixture was extracted with ethyl acetate. The ethyl acetate layer was washed with saturated brine, dried (MgSO$_4$) and concentrated to give the title compound (50 mg, yield 70%) as a pale-yellow amorphous solid. MS: 527 (MH$^+$).

$^1$H NMR (300 MHz, CDCl$_3$) δ0.91-1.07 (2 H, m), 1.25-1.39 (4H, m), 1.52-1.69 (2 H, m), 1.73-1.95 (1 H, m), 1.98-2.16 (1H, m), 2.33-2.51 (1 H, m), 3.26 (3 H, t, J=11.7 Hz), 3.56 (2H, brs), 3.90 (2 H, d, J=11.4 Hz), 4.26 (1 H, t, J=7.8 Hz), 6.08-6.19 (1 H, m), 6.64-6.84 (1 H, m), 7.44 (2 H, d, J=8.3 Hz), 7.53 (1 H, d, J=8.7 Hz), 7.71-7.88 (3 H, m), 8.63 (1 H, s), 11.48 (1 H, d, J=5.7 Hz).

Example 58

[6-(5-{1-[4-(cyclopropylsulfonyl)phenyl]-2-(tetrahydro-2H-pyran-4-yl)ethyl}-1H-pyrrol-2-yl)pyridin-3-yl]methanol

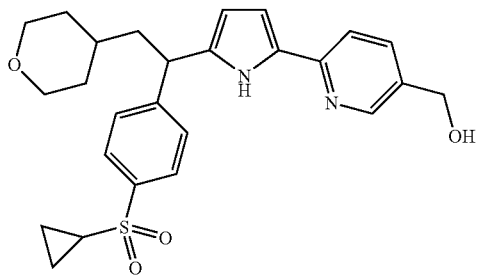

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in a mixed solvent of tetrahydrofuran (1 mL) and methanol (1 mL) was added sodium borohydride (55.0 mg), and the mixture was stirred at room temperature for 30 min. Water was added to the reaction mixture, and the mixture was extracted with ethyl acetate. The ethyl acetate layer was m washed with saturated brine, dried (MgSO$_4$) and concentrated. The residue was subjected to silica gel column chromatography, and the title compound (166 mg, yield 83%) was obtained as a colorless amorphous solid from a fraction eluted with ethyl acetate-hexane (4:1, volume ratio). MS: 467 (MH$^+$).

$^1$H NMR (300 MHz, CDCl$_3$) δ0.95-1.08 (2 H, m), 1.25-1.47 (5H, m), 1.51-1.58 (1 H, m), 1.64-1.71 (1 H, m), 1.79-1.96 (2H, m), 2.00-2.15 (1 H, m), 2.37-2.49 (1 H, m), 3.19-3.36 (2 H, m), 3.83-3.97 (2 H, m), 4.16 (1 H, t, J=8.0 Hz), 4.66 (2 H, s), 6.15 (1 H, t, J=3.0 Hz), 6.57-6.71 (1 H, m), 7.38 (2 H, d, J=8.3 Hz), 7.46-7.54 (1 H, m), 7.58-7.68 (1 H, m), 7.81 (2 H, d, J=8.3 Hz), 8.33 (1 H, d, J=1.9 Hz), 9.38 (1H, brs).

Example 59

4-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}thiomorpholine 1-oxide

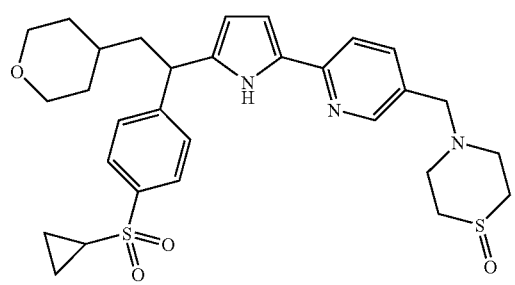

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in 1,2-dichloroethane (5 mL) was added thiomorpholine 1-oxide (155 mg), and the mixture was stirred at room temperature for 30 min. To the reaction mixture was added sodium triacetoxyborohydride (280 mg), and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to silica gel column chromatography, and the title compound (87 mg, yield 36%) was obtained as a colorless amorphous solid from a fraction eluted with ethyl acetate. MS: 568 (MH$^+$).

$^1$H NMR (300 MHz, CDCl$_3$) δ0.96-1.09 (2 H, m), 1.26 (1 H, t, J=7.4 Hz), 1.30-1.47 (4 H, m), 1.53-1.59 (1 H, m), 1.65-1.71 (1 H, m), 1.83-1.97 (1 H, m), 2.02-2.15 (1 H, m), 2.37-2.50 (1 H, m), 2.62-2.93 (6 H, m), 2.99-3.13 (2H, m), 3.28 (2 H, t, J=11.7 Hz), 3.54 (2 H, s), 3.85-3.99 (2H, m), 4.07-4.23 (1 H, m), 6.15 (1 H, t, J=3.2 Hz), 6.61-6.68 (1 H, m), 7.40 (2 H, d, J=8.0 Hz), 7.44-7.62 (2 H, m), 7.82 (2 H, d, J=8.3 Hz), 8.30 (1 H, s), 9.19 (1 H, brs).

Example 60

2-[{[6-(5-{1-[4-(cyclopropylsulfonyl)phenyl]-2-(tetrahydro-2H-pyran-4-yl)ethyl}-1H-pyrrol-2-yl)pyridin-3-yl]methyl}(methyl)amino]ethanol

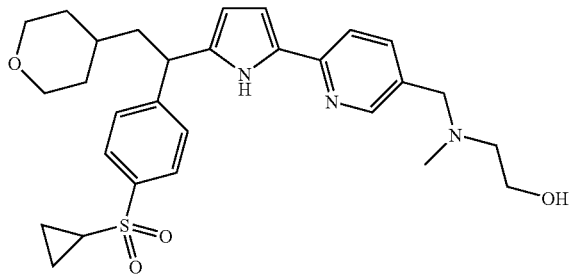

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in 1,2-dichloroethane (5 mL) was added 2-(methylamino)ethanol (80 μL), and the mixture was stirred at room temperature for 30 min. To the reaction mixture was added sodium triacetoxyborohydride (280 mg), and the mixture was stirred overnight at room temperature. The reaction mixture was diluted with ethyl acetate, washed with saturated aqueous sodium hydrogen carbonate and saturated brine, dried ($MgSO_4$) and concentrated. The residue was subjected to silica gel column chromatography, and the title compound (181 mg, yield 80%) was obtained as a colorless amorphous solid from a fraction eluted with ethyl acetate. MS: 524 ($MH^+$).

$^1$H NMR (300 MHz, $CDCl_3$) δ0.96-1.08 (2 H, m), 1.28-1.44 (5H, m), 1.54-1.58 (1 H, m), 1.62-1.72 (2 H, m), 1.81-1.96 (1H, m), 2.00-2.14 (1 H, m), 2.22 (3 H, s), 2.37-2.50 (1H, m), 2.59 (2 H, t, J=5.3 Hz), 3.21-3.36 (2 H, m), 3.52 (2H, s), 3.62 (2 H, t, J=5.3 Hz), 3.92 (2 H, d, J=11.7 Hz), 4.18 (1H, t, J=8.0 Hz), 6.15 (1 H, t, J=3.0 Hz), 6.59-6.68 (1 H, m), 7.40 (2 H, d, J=8.3 Hz), 7.44-7.50 (1 H, m), 7.52-7.60 (1H, m), 7.82 (2 H, d, J=8.3 Hz), 8.28 (1 H, d, J=1.5 Hz), 9.21 (1 H, brs).

Example 61

4-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}morpholine

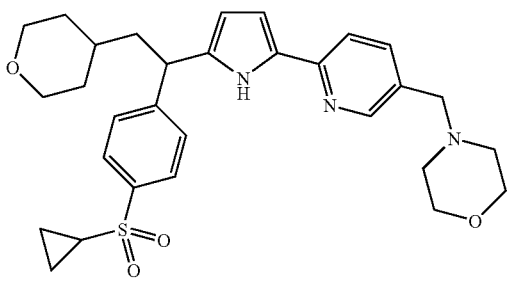

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in 1,2-dichloroethane (5 mL) was added morpholine (240 μL), and the mixture was stirred at room temperature for 30 min. To the reaction mixture was added sodium triacetoxyborohydride (280 mg), and the mixture was stirred at room temperature for 4 hr. The reaction mixture was diluted with ethyl acetate, washed with saturated aqueous sodium hydrogen carbonate and saturated brine, dried ($MgSO_4$) and concentrated. The residue was subjected to silica gel column chromatography, and the title compound (192 mg, yield 83%) was obtained as a pale-yellow amorphous solid from a fraction eluted with ethyl acetate-hexane (2:1, volume ratio). MS: 536 ($MH^+$).

$^1$H NMR (300 MHz, $CDCl_3$) δ0.94-1.10 (2 H, m), 1.26 (1 H, t, J=7.0 Hz), 1.30-1.47 (4 H, m), 1.52-1.58 (1 H, m), 1.61-1.70 (1 H, m), 1.81-1.96 (1 H, m), 2.00-2.14 (1 H, m), 2.37-2.48 (5 H, m), 3.20-3.36 (2 H, m), 3.41-3.48 (2H, m), 3.62-3.74 (4 H, m), 3.92 (2 H, d, J=12.1 Hz), 4.06-4.23 (1 H, m), 6.15 (1 H, t, J=3.2 Hz), 6.60-6.66 (1 H, m), 7.40 (2 H, d, J=8.3 Hz), 7.44-7.50 (1 H, m), 7.59 (1 H, dd, J=2.1, 8.1 Hz), 7.82 (2 H, d, J=8.3 Hz), 8.30 (1 H, s), 9.19 (1 H, brs).

Example 62

1-acetyl-4-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}piperazine

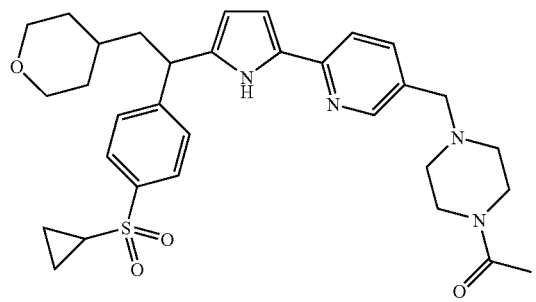

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (100 mg) in 1,2-dichloroethane (5 mL) was added 1-acetylpiperazine (65 mg), and the mixture was stirred at room temperature for 30 min. To the reaction mixture was added sodium triacetoxyborohydride (140 mg), and the mixture was stirred at room temperature for 4 hr. The reaction mixture was diluted with ethyl acetate, washed with saturated aqueous sodium hydrogen carbonate and saturated brine, dried ($MgSO_4$) and concentrated. The residue was subjected to silica gel column chromatography, and the title compound (114 mg, yield 92%) was obtained as a colorless amorphous solid from a fraction eluted with ethyl acetate-methanol (19:1, volume ratio). MS: 577 ($MH^+$).

$^1$H NMR (300 MHz, $CDCl_3$) δ0.97-1.08 (2 H, m), 1.23-1.48 (5H, m), 1.53-1.58 (1 H, m), 1.65-1.71 (1 H, m), 1.83-1.96 (1H, m), 2.07 (3 H, s), 2.36-2.49 (5 H, m), 3.28 (2 H, t, J=11.5 Hz), 3.39-3.49 (4 H, m), 3.56-3.63 (2 H, m), 3.92 (2 H, d, J=11.4 Hz), 4.13-4.22 (1 H, m), 6.15 (1 H, t, J=3.2 Hz), 6.64 (1 H, t, J=3.0 Hz), 7.40 (2 H, d, J=8.3 Hz), 7.44-7.50 (1 H, m), 7.54-7.61 (1 H, m), 7.82 (2 H, d, J=8.3 Hz), 8.29 (1 H, s), 9.18 (1 H, brs).

Example 63

4-{[6-(5-[(1-[4-(cyclopropylsulfonyl)phenyl]-2-(tetrahydro-2H-pyran-4-yl)ethyl]-1H-pyrrol-2-yl)pyridin-3-yl]methyl}thiomorpholine 1,1-dioxide

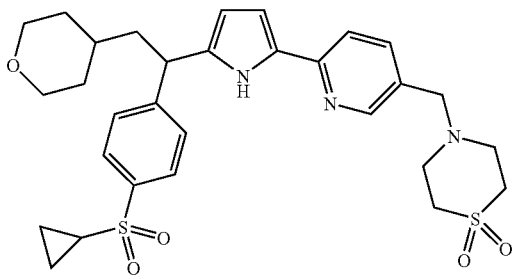

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in 1,2-dichloroethane (5 mL) was added thiomorpholine 1,1-dioxide (135 mg), and the mixture was stirred at room temperature for 30 min. To the reaction mixture was added sodium triacetoxyborohydride (280 mg), and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to silica gel column chromatography, and the title compound (108 mg, yield 43%) was obtained as a colorless amorphous solid from a fraction eluted with ethyl acetate. MS: 584 (MH$^+$).

$^1$H NMR (300 MHz, CDCl$_3$) δ0.96-1.10 (2 H, m), 1.23-1.46 (5H, m), 1.60-1.72 (2 H, m), 1.83-1.99 (1 H, m), 2.01-2.14 (1 H, m), 2.38-2.50 (1 H, m), 3.01 (8 H, dd, J=6.2, 18.4 Hz), 3.21-3.35 (2 H, m), 3.61 (2 H, s), 3.86-3.99 (2 H, m), 4.07-4.24 (1 H, m), 6.16 (1 H, t, J=3.0 Hz), 6.61-6.69 (1H, m), 7.41 (2 H, d, J=8.3 Hz), 7.45-7.51 (1 H, m), 7.53-7.60 (1 H, m), 7.83 (2 H, d, J=8.3 Hz), 8.29 (1 H, d, J=1.5 Hz), 9.15 (1 H, brs).

Example 64

(1S,4S)-2-benzyl-5-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}-2,5-diazabicyclo[2.2.1]heptane

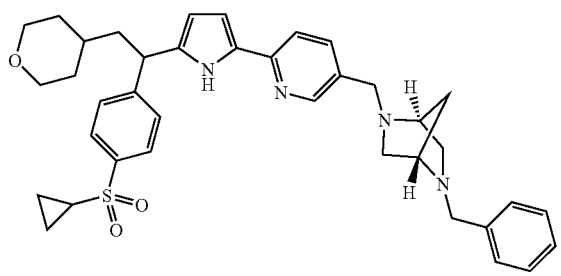

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in 1,2-dichloroethane (5 mL) were added (1S,4S)-2-benzyl-2,5-diazabicyclo[2.2.1]heptane dibromate (350 mg) and triethylamine (310 μL), and the mixture was stirred at room temperature for 30 min. To the reaction mixture was added sodium triacetoxyborohydride (280 mg), and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to basic silica gel column chromatography, and the title compound (172 mg, yield 63%) was obtained as a colorless amorphous solid from a fraction eluted with ethyl acetate-hexane (3:1, volume ratio). MS: 637 (MH$^+$).

$^1$H NMR (300 MHz, CDCl$_3$) δ0.93-1.08 (2 H, m), 1.26-1.45 (4H, m), 1.53-1.63 (1 H, m), 1.69-1.80 (2 H, m), 1.80-1.96 (1H, m), 2.00-2.14 (1 H, m), 2.36-2.51 (1 H, m), 2.57-2.71 (2 H, m), 2.77-2.88 (2 H, m), 3.19-3.36 (4 H, m), 3.59-3.79 (4 H, m), 3.84-3.97 (2 H, m), 4.17 (1 H, t, J=8.0 Hz), 6.14 (1 H, t, J=3.0 Hz), 6.58-6.67 (1 H, m), 7.18-7.25 (1H, m), 7.27-7.49 (7 H, m), 7.63 (1 H, dd, J=1.9, 8.3 Hz), 7.81 (2 H, d, J=8.3 Hz), 8.34 (1 H, d, J=1.5 Hz), 9.22 (1H, brs).

Example 65

(1S,4S)-2-[([6-(5-[(1-[4-(cyclopropylsulfonyl)phenyl]-2-(tetrahydro-2H-pyran-4-yl)ethyl]-1H-pyrrol-2-yl)pyridin-3-yl]methyl]-2,5-diazabicyclo[2.2.1]heptane

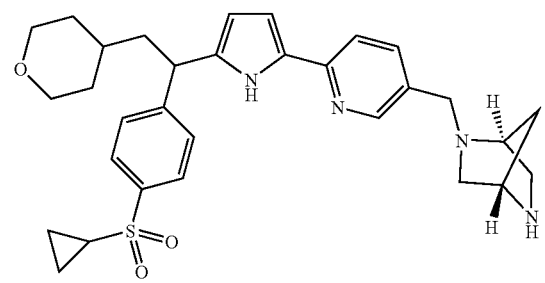

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (300 mg) in 1,2-dichloroethane (5 mL) were added (1S,4S)-2,5-diazabicyclo[2.2.1]heptane dibromate (390 mg) and triethylamine (460 μL), and the mixture was stirred at room temperature for 30 min. To the reaction mixture was added sodium triacetoxyborohydride (415 mg), and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to preparative HPLC to give the title compound (95 mg, yield 27%) as a colorless amorphous solid. MS: 547 (MH$^+$).

$^1$H NMR (300 MHz, CDCl$_3$) δ0.90-1.46 (9 H, m), 1.52-1.70 (3H, m), 1.85 (1 H, d, J=6.4 Hz), 2.02-2.15 (1 H, m), 2.55 (2H, d, J=7.6 Hz), 2.68 (1 H, d, J=9.5 Hz), 2.73-2.86 (1 H, m), 3.15 (2 H, t, J=11.5 Hz), 3.21-3.30 (2 H, m), 3.64 (2 H, q, J=13.8 Hz), 3.72-3.86 (2 H, m), 4.27-4.42 (1 H, m), 5.96-6.20 (1 H, m), 6.56-6.69 (1 H, m), 7.49-7.67 (4 H, m), 7.79 (2 H, d, J=8.3 Hz), 8.36 (1 H, d, J=1.5 Hz), 11.25 (1H, brs).

Example 66

(1S,4S)-2-acetyl-5-{[6-(5-[1-[4-(cyclopropylsulfonyl)phenyl]-2-(tetrahydro-2H-pyran-4-yl)ethyl]-1H-pyrrol-2-yl)pyridin-3-yl]methyl}-2,5-diazabicyclo[2.2.1]heptane

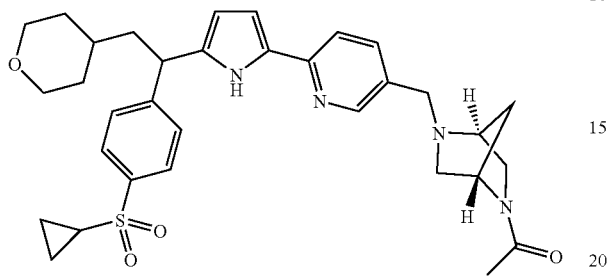

To a solution of (1S,4S)-2-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}-2,5-diazabicyclo[2.2.1]heptane (29.0 mg) in dichloromethane (5 mL) were added acetyl chloride (6 μL) and triethylamine (23 μL) under ice-cooling, and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to preparative HPLC to give the title compound (10.0 mg, yield 32%) as a colorless amorphous solid. MS: 589 (MH$^+$).

$^1$H NMR (300 MHz, CDCl$_3$) δ0.96-1.10 (2 H, m), 1.30-1.44 (5H, m), 1.59-1.69 (2 H, m), 1.74-1.96 (5 H, m), 2.06 (3 H, d, J=6.8 Hz), 2.37-2.57 (1 H, m), 2.60-3.04 (2 H, m), 3.21-3.36 (3 H, m), 3.45-3.58 (2 H, m), 3.62-3.76 (2 H, m), 3.92 (2 H, d, J=11.3 Hz), 4.09-4.26 (1 H, m), 6.15 (1 H, t, J=2.7 Hz), 6.57-6.70 (1 H, m), 7.40 (2 H, d, J=8.3 Hz), 7.43-7.50 (1 H, m), 7.55-7.65 (1 H, m), 7.82 (2 H, d, J=8.5 Hz), 8.21-8.39 (1 H, m), 9.24 (1 H, brs).

Example 67

N-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}-1-azabicyclo[2.2.2]octan-3-amine

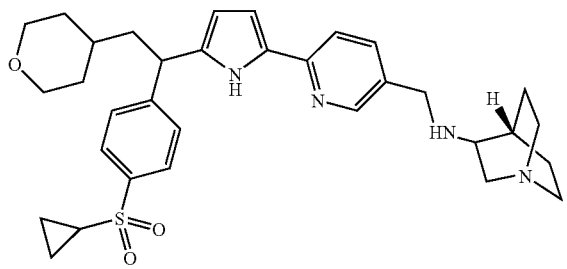

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (100 mg) in 1,2-dichloroethane (5 mL) were added 1-azabicyclo[2.2.2]octan-3-amine dihydrochloride (100 mg) and triethylamine (150 μL), and the mixture was stirred at room temperature for 30 min. To the reaction mixture was added sodium triacetoxyborohydride (65.0 mg), and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to preparative HPLC to give the title compound (30.0 mg, yield 24%) as a colorless amorphous solid. MS: 575 (MH$^+$).

$^1$H NMR (300 MHz, CDCl$_3$) δ0.93-1.12 (4 H, m), 1.24 (4 H, d, J=5.1 Hz), 1.60 (3 H, d, J=5.1 Hz), 1.72-1.93 (3 H, m), 1.98-2.14 (1 H, m), 2.30-2.44 (1 H, m), 2.57-2.86 (6 H, m), 2.90-3.03 (1 H, m), 3.15 (3 H, t, J=11.6 Hz), 3.53-3.69 (2H, m), 3.79 (2 H, d, J=9.2 Hz), 4.36 (1 H, t, J=7.9 Hz), 6.01-6.14 (1 H, m), 6.57-6.68 (1 H, m), 7.50-7.69 (4 H, m), 7.79 (2 H, d, J=8.3 Hz), 8.36 (1 H, d, J=1.3 Hz), 11.26 (1H, brs).

Example 68

(3S)-1-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}-3-methylpiperazine

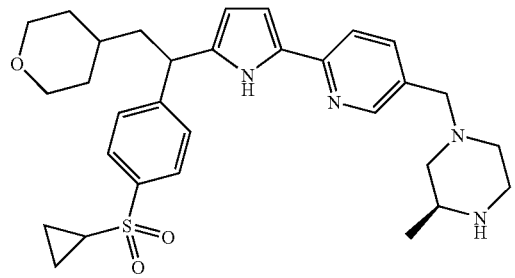

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (250 mg) in tetrahydrofuran (10 mL) was added (2S)-2-methylpiperazine (270 mg), and the mixture was stirred at room temperature for 30 min. To the reaction mixture was added sodium triacetoxyborohydride (230 mg), and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to preparative HPLC to give the title compound (111 mg, yield 38%) as a colorless amorphous solid. MS: 549 (MH$^+$).

$^1$H NMR (300 MHz, CDCl$_3$) δ0.98-1.03 (2 H, m), 1.05 (3 H, d, J=6.2 Hz), 1.29-1.49 (5 H, m), 1.52-1.70 (3 H, m), 1.82-1.97 (2 H, m), 2.05-2.15 (2 H, m), 2.36-2.49 (1 H, m), 2.66-2.79 (2 H, m), 2.81-3.05 (3 H, m), 3.19-3.36 (2H, m), 3.40-3.50 (2 H, m), 3.84-4.00 (2 H, m), 4.12-4.23 (1. H, m), 6.15 (1 H, t, J=3.0 Hz), 6.63 (1 H, dd, J=2.4, 3.5 Hz), 7.40 (2 H, d, J=8.3 Hz), 7.44-7.50 (1 H, m), 7.52-7.63 (1H, m), 7.75-7.88 (2 H, m), 8.29 (1 H, d, J=1.5 Hz), 9.22 (1H, brs).

Example 69

(2S)-1-acetyl-4-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}-2-methylpiperazine

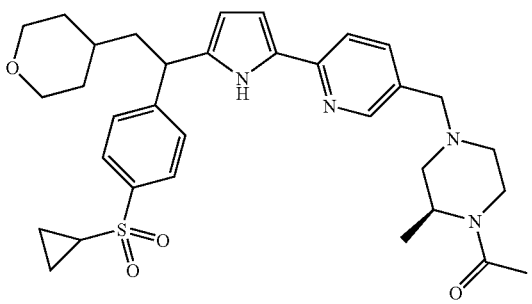

To a solution of acetic acid (5.6 μL) in tetrahydrofuran (2 mL) were added 1-ethyl-3-(3-dimethylaminopropyl)carbodiimide hydrochloride (25.0 mg), 1-hydroxybenzotriazole (18.0 mg) and N-methylmorpholine (30 μL), and the mixture was stirred at room temperature for 30 min. To to the reaction mixture was added a solution of (3S)-1-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}-3-methylpiperazine (45.0 mg) in tetrahydrofuran (1 mL), and the mixture was stirred overnight at room temperature. The reaction mixture was diluted with ethyl acetate, washed with water and saturated brine, dried (MgSO$_4$) and concentrated. The residue was subjected to basic silica gel column chromatography, and the title compound (43.0 mg, yield 90%) was obtained as a pale-yellow amorphous solid from a fraction eluted with ethyl acetate. MS: 591 (MH$^+$).

$^1$H NMR (300 MHz, CDCl$_3$) δ0.93-1.11 (2 H, m), 1.14-1.52 (10H, m), 1.54-1.61 (1 H, m), 1.66-1.71 (1 H, m), 1.81-1.97 (1 H, m), 1.97-2.21 (6 H, m), 2.36-2.49 (1 H, m), 2.54-2.68 (1 H, m), 2.70-2.85 (1 H, m), 3.19-3.61 (5 H, m), 3.93 (2 H, d, J=11.4 Hz), 4.13-4.25 (1 H, m), 6.15 (1H, brs), 6.58-6.68 (1 H, m), 7.41 (2 H, d, J=8.0 Hz), 7.44-7.51 (1 H, m), 7.59 (1 H, dd, J=2.1, 8.1 Hz), 7.82 (2 H, d, J=8.3 Hz), 8.31 (1 H, d, J=1.5 Hz), 9.20 (1 H, brs).

Example 70

(2S)-4-acetyl-1-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}-2-methylpiperazine

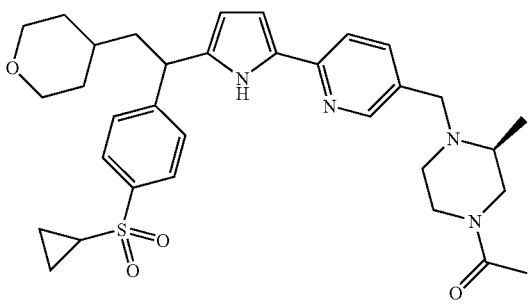

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in 1,2-dichloroethane (3 mL) was added (3S)-1-acetyl-3-methylpiperazine (140 mg), and the mixture was stirred at room temperature for 30 min. To the reaction mixture was added sodium triacetoxyborohydride (273 mg), and the mixture was stirred at room temperature for 3 hr. The reaction mixture was diluted with ethyl acetate, washed with saturated aqueous sodium hydrogen carbonate and saturated brine, dried (MgSO$_4$) and concentrated. The residue was subjected to basic silica gel column chromatography, and the title compound (184 mg, yield 72%) was obtained as a colorless amorphous solid from a fraction eluted with ethyl acetate. MS: 591 (MH$^+$).

$^1$H NMR (300 MHz, CDCl$_3$) δ0.94-1.07 (2 H, m), 1.14 (3 H, d, J=6.2 Hz), 1.24-1.50 (5 H, m), 1.54-1.60 (1 H, m), 1.65-1.71 (1 H, m), 1.83-1.98 (1 H, m), 1.99-2.18 (5 H, m), 2.35-2.55 (2 H, m), 2.58-2.71 (1 H, m), 2.77-3.36 (5H, m), 3.48 (1 H, q, J=7.0 Hz), 3.82-4.00 (3 H, m), 4.07-4.24 (2 H, m), 6.15 (1 H, t, J=3.1 Hz), 6.63 (1 H, t, J=2.8 Hz), 7.40 (2 H, d, J=8.3 Hz), 7.44-7.50 (1 H, m), 7.54-7.62 (1H, m), 7.82 (2 H, d, J=8.3 Hz), 8.30 (1 H, s), 9.18 (1 H, brs).

Example 71

1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropan-1-ol

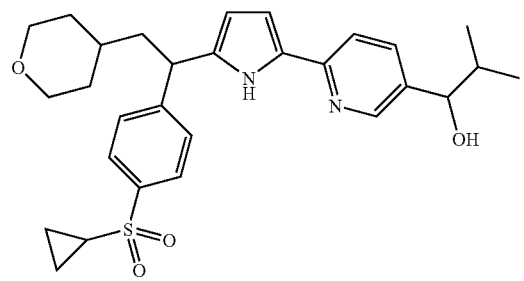

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (100 mg) in tetrahydrofuran (3 mL) was added (2-methylethyl)magnesium bromide (1M tetrahydrofuran solution, 650 μL), and the mixture was stirred at −20° C. for 30 min and then overnight at room temperature. Water was added to the reaction mixture, and the mixture was extracted with ethyl acetate. The ethyl acetate layer was washed with saturated brine, dried (MgSO$_4$) and concentrated. The residue was subjected to preparative HPLC to give the title compound (40.0 mg, yield 37%) as a pale-yellow amorphous solid. MS: 509 (MH$^+$).

$^1$H NMR (300 MHz, CDCl$_3$) δ0.81 (3 H, d, J=6.8 Hz), 0.92-1.11 (5 H, m), 1.27-1.45 (5 H, m), 1.63-1.74 (2 H, m), 1.82-1.99 (3 H, m), 2.00-2.16 (1 H, m), 2.35-2.51 (1 H, m), 3.28 (2 H, t, J=11.5 Hz), 3.92 (2 H, d, J=11.7 Hz), 4.17 (1H, t, J=8.0 Hz), 4.38 (1 H, d, J=6.4 Hz), 6.15 (1 H, brs), 6.59-6.70 (1 H, m), 7.40 (2 H, d, J=8.0 Hz), 7.44-7.52 (1 H, m), 7.54-7.63 (1 H, m), 7.82 (2 H, d, J=8.3 Hz), 8.22-8.34 (1H, m), 9.26 (1 H, brs).

Example 72

6-(5-{1-[4-(cyclopropylsulfonyl)phenyl]-2-(tetrahydro-2H-pyran-4-yl)ethyl}-1H-pyrrol-2-yl)pyridine-3-carboxylic acid

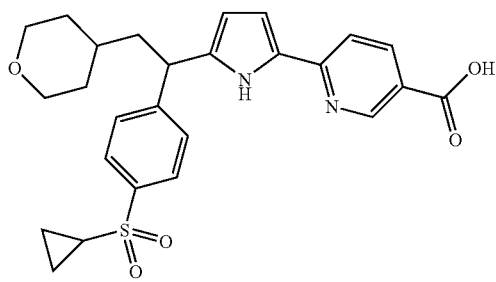

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (100 mg) in acetone (5 mL) was added an aqueous solution (1 mL) of potassium permanganate (45.0 mg), and the mixture was stirred overnight at room temperature. To the reaction mixture was added sodium sulfite, and the mixture was extracted with ethyl acetate. The ethyl acetate layer was washed with saturated brine, dried (MgSO$_4$) and concentrated to give the title compound (50.0 mg, yield 49%) as a pale-yellow amorphous solid. MS: 481 (MH$^+$).

$^1$H NMR (300 MHz, CDCl$_3$) δ0.77-1.08 (2 H, m), 1.23-1.48 (5H, m), 1.56-1.74 (2 H, m), 1.87-2.03 (1 H, m), 2.07-2.25 (1H, m), 2.31-2.49 (1 H, m), 3.15-3.41 (2 H, m), 3.78-4.01 (2 H, m), 4.36 (1 H, t, J=7.8 Hz), 6.06-6.35 (1 H, m), 6.84-6.93 (1 H, m), 7.50 (2 H, d, J=8.3 Hz), 7.70 (1 H, d, J=8.7 Hz), 7.82 (2 H, d, J=8.3 Hz), 8.33 (1 H, dd, J=2.1, 8.5 Hz), 9.12 (1 H, d, J=1.9 Hz), 11.09 (1 H, brs).

Example 73

5-bromo-2-(5-{1-[4-(methylsulfonyl)phenyl]-2-(tetrahydro-2H-pyran-4-yl)ethyl}-1H-pyrrol-2-yl)pyridine

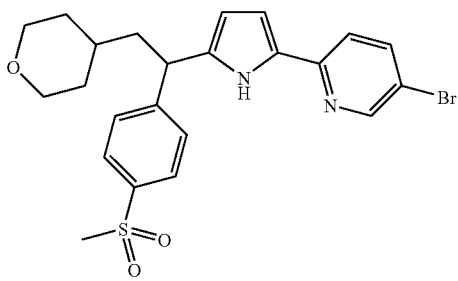

To a solution of 1-(5-bromopyridin-2-yl)-5-[4-(methylsulfonyl)phenyl]-6-(tetrahydro-2H-pyran-4-yl)hexane-1,4-dione (3.89 g) in acetic acid (40 mL) was added ammonium acetate (9.50 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (3.20 g, yield 86%) was obtained as a colorless amorphous solid from a fraction eluted with ethyl acetate-hexane (1:1, volume ratio). MS: 491 (MH$^+$).

$^1$H NMR (300 MHz, CDCl$_3$) δ1.29-1.53 (3 H, m), 1.60-1.71 (2H, m), 1.80-1.96 (1 H, m), 1.99-2.15 (1 H, m), 3.02-3.06 (3H, m), 3.28 (2 H, t, J=11.5 Hz), 3.83-3.99 (2 H, m), 4.06-4.23 (1 H, m), 6.14 (1 H, t, J=3.2 Hz), 6.63 (1 H, t, J=3.0 Hz), 7.33-7.44 (3 H, m), 7.70 (1 H, dd, J=2.3, 8.7 Hz), 7.87 (2 H, d, J=8.0 Hz), 8.42 (1 H, d, J=2.3 Hz), 9.16 (1 H, brs).

Example 74

5-ethenyl-2-(5-{1-[4-(methylsulfonyl)phenyl]-2-(tetrahydro-2H-pyran-4-yl)ethyl}-1H-pyrrol-2-yl)pyridine

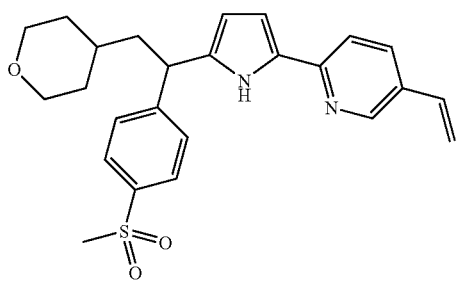

To a solution of 5-bromo-2-(5-{1-[4-(methylsulfonyl)phenyl]-2-(tetrahydro-2H-pyran-4-yl)ethyl}-1H-pyrrol-2-yl)pyridine (1.50 g) in toluene (20 mL) were added tributyl(vinyl)tin (900 µL) and tetrakistriphenylphosphinepalladium(0) (315 mg), and the mixture was stirred under argon atmosphere at 110° C. overnight. After cooling to room temperature, the reaction mixture was concentrated, and the residue was subjected to silica gel column chromatography. The title compound (950 mg, yield 71%) was obtained as a yellow amorphous solid from a fraction eluted with ethyl acetate-hexane (1:1, volume ratio). MS: 437 (MH$^+$).

$^1$H NMR (300 MHz, CDCl$_3$) δ1.29-1.50 (3 H, m), 1.56 (1 H, brs), 1.66 (1 H, brs), 1.80-1.96 (1 H, m), 2.00-2.16 (1 H, m), 3.03 (3 H, s), 3.16-3.36 (2 H, m), 3.81-3.99 (2 H, m), 4.10-4.22 (1 H, m), 5.30 (1 H, d, J=11.0 Hz), 5.75 (1 H, d, J=17.8 Hz), 6.14 (1 H, t, J=3.2 Hz), 6.56-6.74 (2 H, m), 7.40 (2 H, d, J=8.3 Hz), 7.46 (1 H, d, J=8.3 Hz), 7.68 (1H, dd, J=2.3, 8.3 Hz), 7.85 (2 H, d, J=8.0 Hz), 8.36 (1 H, d, J=1.9 Hz), 9.36 (1 H, brs).

Example 75

Tert-butyl 4-[1-{5-[5-(hydroxymethyl)-1,3-thiazol-2-yl]-1H-pyrrol-2-yl}-2-(tetrahydro-2H-pyran-4-yl)ethyl]benzoate

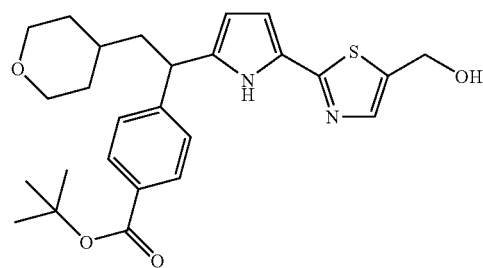

To a solution of tert-butyl 4-[2,5-dioxo-1-(tetrahydro-2H-pyran-4-ylmethyl)-5-{5-[(tetrahydro-2H-pyran-2-yloxy)methyl]-1,3-thiazol-2-yl}pentyl]benzoate (2.24 g) in acetic acid (15 mL) was added ammonium acetate (4.85 g), and the mixture was stirred at 110° C. for 45 min. After cooling to room temperature, the reaction mixture was diluted with ethyl acetate and washed with water. The ethyl acetate layer was m washed with saturated aqueous sodium hydrogen carbonate and saturated brine, dried (MgSO$_4$) and concentrated. The residue was subjected to silica gel column chromatography, and the title compound (1.30 g, yield 71%) was obtained as a pale-yellow amorphous solid from a fraction eluted with ethyl acetate-hexane (3:2, volume ratio). MS: 469 (MH$^+$).

$^1$H NMR (300 MHz, CDCl$_3$) δ1.28-1.42 (3 H, m), 1.45-1.53 (1H, m), 1.55-1.60 (9 H, m), 1.63-1.70 (1 H, m), 1.83-2.03 (2H, m), 2.13 (1 H, t, J=5.9 Hz), 3.25 (2 H, t, J=11.4 Hz), 3.84-3.96 (2 H, m), 4.03-4.16 (1 H, m), 4.80 (2 H, d, J=5.7 Hz), 6.07 (1 H, t, J=3.0 Hz), 6.55-6.61 (1 H, m), 7.24 (2 H, d, J=8.3 Hz), 7.39 (1 H, s), 7.92 (2 H, d, J=8.3 Hz), 9.09 (1H, brs).

Example 76

4-[1-{5-[5-(hydroxymethyl)-1,3-thiazol-2-yl]-1H-pyrrol-2-yl}-2-(tetrahydro-2H-pyran-4-yl)ethyl]benzoic acid

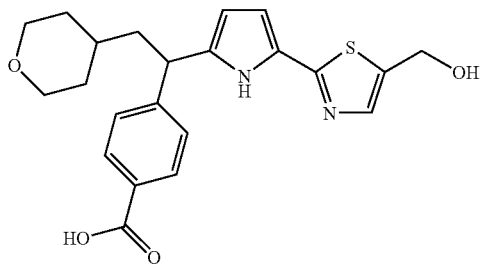

To a solution of tert-butyl 4-[1-{5-[5-(hydroxymethyl)-1,3-thiazol-2-yl]-1H-pyrrol-2-yl}-2-(tetrahydro-2H-pyran-4-yl)ethyl]benzoate (200 mg) in dichloromethane (10 mL) was added trifluoroacetic acid (2 mL) under ice-cooling, and the mixture was stirred at room temperature for 3 hr. The reaction mixture was concentrated and subjected to preparative HPLC to give the title compound (60.0 mg, yield 34%) as a pale-yellow solid. MS: 413 (MH$^+$).

$^1$H NMR (300 MHz, CDCl$_3$) δ1.06-1.42 (3 H, m), 1.58 (2 H, d, J=11.4 Hz), 1.75-1.93 (1 H, m), 1.95-2.12 (1 H, m), 3.14 (2 H, t, J=10.4 Hz), 3.78 (2 H, d, J=10.6 Hz), 4.24 (1 H, t, J=8.0 Hz), 4.62 (2 H, s), 5.48 (1 H, brs), 5.98-6.12 (1H, m), 6.51 (1 H, t, J=3.0 Hz), 7.37-7.54 (3 H, m), 7.86 (2H, d, J=8.3 Hz), 11.55 (1 H, brs), 12.79 (1 H, brs).

Example 77

N-cyclopropyl-4-[1-{5-[5-(hydroxymethyl)-1,3-thiazol-2-yl]-1H-pyrrol-2-yl}-2-(tetrahydro-2H-pyran-4-yl)ethyl] benzamide

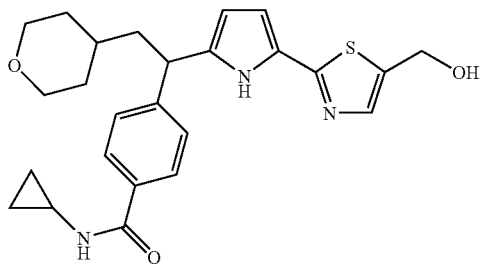

To a solution of 4-[1-{5-[5-(hydroxymethyl)-1,3-thiazol-2-yl]-1H-pyrrol-2-yl}-2-(tetrahydro-2H-pyran-4-yl)ethyl]benzoic acid (270 mg) in N,N-dimethylformamide (5 mL) were added 1-ethyl-3-(3-dimethylaminopropyl)carbodiimide hydrochloride (140 mg), 1-hydroxybenzotriazole (100 mg) and N-methylmorpholine (215 μL), and the mixture was stirred for 1 hr. To the reaction mixture was added cyclopropylamine (50 μL), and the mixture was stirred overnight at room temperature. The reaction mixture was diluted with ethyl acetate and washed with 1M hydrochloric acid. The obtained aqueous layer was neutralized with 1M aqueous sodium hydroxide solution, and the mixture was extracted with ethyl acetate. The ethyl acetate layer was washed with saturated brine, dried (MgSO$_4$) and concentrated. The residue was subjected to silica gel column chromatography, and the title compound (210 mg, yield 71%) was obtained as a pale-yellow amorphous solid from a fraction eluted with ethyl acetate. MS: 452 (MH$^+$).

$^1$H NMR (300 MHz, CDCl$_3$) δ0.54-0.67 (2 H, m), 0.79-0.94 (2H, m), 1.24-1.40 (3 H, m), 1.42-1.53 (1 H, m), 1.60 (1 H, d, J=12.5 Hz), 1.80-2.01 (2 H, m), 2.66 (1 H, d, J=3.4 Hz), 2.82-2.92 (1 H, m), 3.16-3.29 (2 H, m), 3.87 (2 H, dd, J=4.7, 10.0 Hz), 4.02 (1 H, t, J=7.8 Hz), 4.77 (2 H, s), 6.06 (1 H, t, J=3.2 Hz), 6.27 (1 H, d), 6.55-6.62 (1 H, m), 7.17 (2 H, d, J=8.3 Hz), 7.29 (1 H, s), 7.59 (2 H, d, J=8.3 Hz), 9.50 (1 H, brs).

Example 78

[2-(5-{1-[4-(azetidin-1-ylcarbonyl)phenyl]-2-(tetrahydro-2H-pyran-4-yl)ethyl}-1H-pyrrol-2-yl)-1,3-thiazol-5-yl]methanol

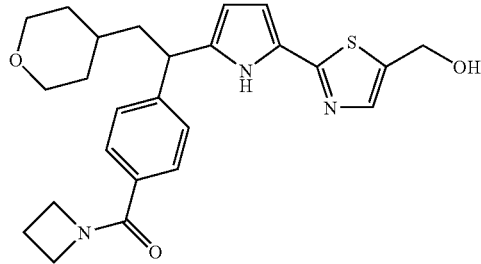

To a solution of 4-[1-{5-[5-(hydroxymethyl)-1,3-thiazol-2-yl]-1H-pyrrol-2-yl}-2-(tetrahydro-2H-pyran-4-yl)ethyl] benzoic acid (100 mg) in N,N-dimethylformamide (5 mL) were added 1-ethyl-3-(3-dimethylaminopropyl)carbodiimide hydrochloride (70.0 mg) and 1-hydroxybenzotriazole (50.0 mg), and the mixture was stirred for 30 min. To the reaction mixture was added azetidine (21.0 mg), and the mixture was stirred overnight at room temperature. The reaction mixture was diluted with ethyl acetate and washed with 1M hydrochloric acid. The ethyl acetate layer was washed with saturated aqueous sodium hydrogen carbonate and saturated brine, dried (MgSO$_4$) and concentrated. The residue was subjected to silica gel column chromatography, and the title compound (30.0 mg, yield 28%) was obtained as a colorless amorphous solid from a fraction eluted with ethyl acetate-methanol (9:1, volume ratio). MS: 452 (MH$^+$).

$^1$H NMR (300 MHz, CDCl$_3$) δ1.23-1.43 (4 H, m), 1.46-1.57 (1H, m), 1.80-2.07 (2 H, m), 2.25-2.40 (2 H, m), 2.41-2.55 (1H, m), 3.17-3.33 (2 H, m), 3.89 (2 H, dd, J=4.7, 10.4 Hz), 4.05 (1 H, t, J=8.0 Hz), 4.14-4.38 (4 H, m), 4.77 (2 H, s), 6.09 (1 H, t, J=3.0 Hz), 6.56-6.62 (1 H, m), 7.20 (2 H, d, J=8.0 Hz), 7.29 (1 H, s), 7.55 (2 H, d, J=8.3 Hz), 9.34 (1H, brs).

Example 79

4-[1-{5-[5-(hydroxymethyl)-1,3-thiazol-2-yl]-1H-pyrrol-2-yl}-2-(tetrahydro-2H-pyran-4-yl)ethyl]-N-methoxy-N-methylbenzamide

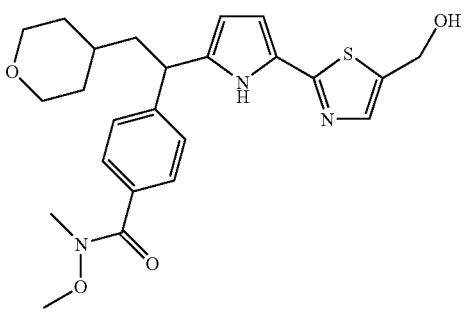

To a solution of 4-[1-{5-[5-(hydroxymethyl)-1,3-thiazol-2-yl]-1H-pyrrol-2-yl}-2-(tetrahydro-2H-pyran-4-yl)ethyl]benzoic acid (200 mg) in N,N-dimethylformamide (5 mL) were added 1-ethyl-3-(3-dimethylaminopropyl)carbodiimide hydrochloride (140 mg), 1-hydroxybenzotriazole (100 mg) and N-methylmorpholine (160 μL), and the mixture was stirred for 1% hr. To the reaction mixture was added N-methoxymethanamine hydrochloride (60.0 mg), and the mixture was stirred overnight at room temperature. The reaction mixture was diluted with ethyl acetate and washed with 1M hydrochloric acid. The ethyl acetate layer was washed with saturated aqueous sodium hydrogen carbonate and saturated brine, dried (MgSO₄) and concentrated. The residue was subjected to silica gel column chromatography, and the title compound (92.0 mg, yield 42%) was obtained as a pale-yellow amorphous solid from a fraction eluted with ethyl acetate-methanol (19:1, volume ratio). MS: 456 (MH⁺).

¹H NMR (300 MHz, CDCl₃) δ1.20-1.46 (4 H, m), 1.54 (1 H, d, J=11.7 Hz), 1.82-2.04 (2 H, m), 2.29 (1 H, brs), 3.18-3.31 (2 H, m), 3.35 (3 H, s), 3.56 (3 H, s), 3.90 (2 H, dd, J=5.1, 10.4 Hz), 4.01-4.12 (1 H, m), 4.79 (2 H, s), 6.10 (1 H, t, J=3.0 Hz), 6.56-6.62 (1 H, m), 7.22 (2 H, d, J=8.3 Hz), 7.35 (1 H, s), 7.62 (2 H, d, J=8.3 Hz), 9.25 (1 H, brs).

Example 80

4-({[tert-butyl(diphenyl)silyl]oxy}methyl)-2-(5-1-[4-(methylsulfonyl)phenyl]-2-(tetrahydro-2H-pyran-4-yl)ethyl)-1H-pyrrol-2-yl)pyridine

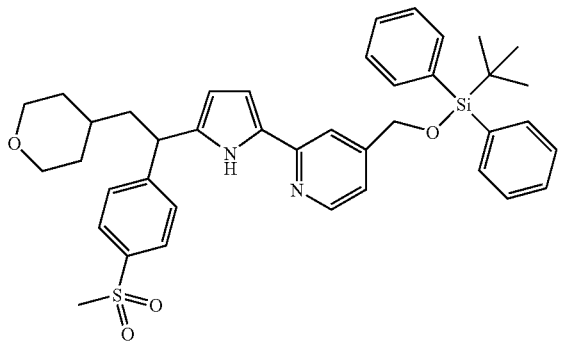

To a solution of 1-[4-({[tert-butyl(diphenyl)silyl]oxy}methyl)pyridin-2-yl]-5-[4-(methylsulfonyl)phenyl]-6-(tetrahydro-2H-pyran-4-yl)hexane-1,4-dione (1.90 g) in acetic acid (15 mL) was added ammonium acetate (3.40 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO₄) and concentrated. The residue was subjected to silica gel column chromatography, and the title compound (900 mg, yield 49%) was obtained as a colorless amorphous solid from a fraction eluted with ethyl acetate-hexane (2:1, volume ratio). MS: 679 (MH⁺).

¹H NMR (300 MHz, CDCl₃) δ1.10-1.14 (9 H, m), 1.24-1.51 (4H, m), 1.63-1.72 (1 H, m), 1.83-1.96 (1 H, m), 2.03-2.17 (1H, m), 3.04 (3 H, s), 3.22-3.37 (2 H, m), 3.85-4.00 (2H, m), 4.17 (1 H, q, J=7.3 Hz), 4.74 (2 H, s), 6.14 (1 H, t, J=2.9 Hz), 6.60 (1 H, dd, J=2.3, 3.4 Hz), 6.99 (1 H, dd, J=5.2, 1.4 Hz), 7.33-7.47 (8 H, m), 7.53 (1 H, s), 7.63-7.72 (4H, m), 7.83-7.91 (2 H, m), 8.28-8.35 (1 H, m), 9.29 (1H, brs).

Example 81

[2-(5-{1-[4-(methylsulfonyl)phenyl]-2-(tetrahydro-2H-pyran-4-yl)ethyl}-1H-pyrrol-2-yl)pyridin-4-yl]methanol

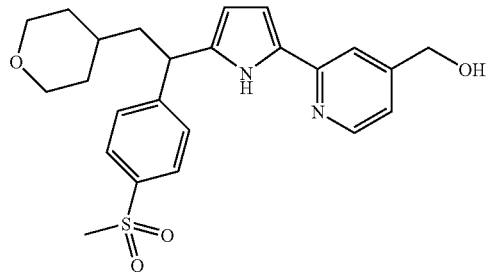

To a solution of 4-({[tert-butyl(diphenyl)silyl]oxy}methyl)-2-(5-{1-[4-(methylsulfonyl)phenyl]-2-(tetrahydro-2H-pyran-4-yl)ethyl}-1H-pyrrol-2-yl)pyridine (870 mg) in tetrahydrofuran (10 mL) was added tetrabutylammonium fluoride (1M tetrahydrofuran solution, 1.54 mL), and the mixture was stirred at room temperature for 1 hr. The reaction mixture was diluted with ethyl acetate and washed with water. The ethyl acetate layer was washed with saturated aqueous sodium hydrogen carbonate and saturated brine, dried (MgSO₄) and concentrated. The residue was subjected to silica gel column chromatography, and the title compound (533 mg, yield 95%) was obtained as a colorless amorphous solid from a fraction eluted with ethyl acetate. MS: 441 (MH⁺).

¹H NMR (300 MHz, CDCl₃) δ1.28-1.50 (3 H, m), 1.53-1.58 (1H, m), 1.65-1.70 (1 H, m), 1.80-1.95 (1 H, m), 1.99-2.13 (2H, m), 3.03 (3 H, s), 3.19-3.36 (2 H, m), 3.82-3.98 (2H, m), 4.12-4.22 (1 H, m), 4.72 (2 H, s), 6.14 (1 H, t, J=3.0 Hz), 6.62-6.70 (1 H, m), 6.98 (1 H, dd, J=1.5, 5.3 Hz), 7.40 (2 H, d, J=8.3 Hz), 7.50 (1 H, s), 7.85 (2 H, d, J=8.3 Hz), 8.32 (1 H, d, J=5.3 Hz), 9.39 (1 H, brs).

Example 82

2-(5-{1-[4-(methylsulfonyl)phenyl]-2-(tetrahydro-2H-pyran-4-yl)ethyl}-1H-pyrrol-2-yl)pyridine-4-carbaldehyde

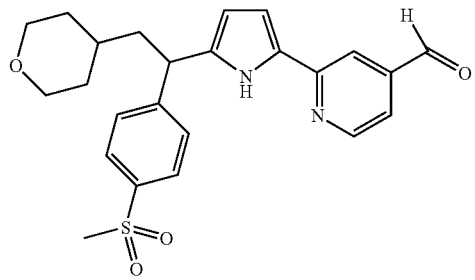

To a solution of [2-(5-{1-[4-(methylsulfonyl)phenyl]-2-(tetrahydro-2H-pyran-4-yl)ethyl}-1H-pyrrol-2-yl)pyridin-4-yl]methanol (457 mg) in acetonitrile (10 mL) was added Dess-Martin reagent (530 mg), and the mixture was stirred at room temperature for 4 hr. The reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (380 mg, yield 83%) was obtained as a yellow amorphous solid from a fraction eluted with ethyl acetate-hexane (1:1, volume ratio).

$^1$H NMR (300 MHz, CDCl$_3$) δ1.30-1.51 (3 H, m), 1.55-1.60 (1H, m), 1.66-1.72 (1 H, m), 1.85-1.99 (1 H, m), 2.05-2.15 (1H, m), 3.05 (3 H, s), 3.29 (2 H, t, J=11.4 Hz), 3.88-3.99 (2H, m), 4.16-4.24 (1 H, m), 6.19 (1 H, t, J=3.2 Hz), 6.75-6.80 (1 H, m), 7.36-7.47 (3 H, m), 7.82-7.92 (3 H, m), 8.60 (1 H, d, J=5.7 Hz), 9.24 (1 H, brs), 10.05 (1 H, s).

Example 83

1-acetyl-4-{[2-(5-{1-[4-(methylsulfonyl)phenyl]-2-(tetrahydro-2H-pyran-4-yl)ethyl}-1H-pyrrol-2-yl)pyridin-4-yl]methyl}piperazine

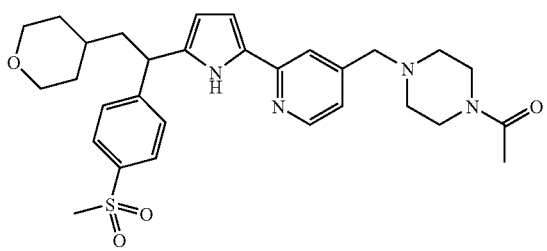

To a solution of 2-(5-{1-[4-(methylsulfonyl)phenyl]-2-(tetrahydro-2H-pyran-4-yl)ethyl}-1H-pyrrol-2-yl)pyridine-4-carbaldehyde (170 mg) in 1,2-dichloroethane (5 mL) was added 1-acetylpiperazine (115 mg), and the mixture was stirred at room temperature for 30 min. To the reaction mixture was added sodium triacetoxyborohydride (250 mg), and the mixture was stirred overnight at room temperature. The reaction mixture was diluted with ethyl acetate, washed with saturated aqueous sodium hydrogen carbonate and saturated brine, dried (MgSO$_4$) and concentrated. The residue was subjected to basic silica gel column chromatography, and the title compound (180 mg, yield 85%) was obtained as a pale-yellow amorphous solid from a fraction eluted with ethyl acetate-methanol (19:1, volume ratio). MS: 551 (MH$^+$).

$^1$H NMR (300 MHz, CDCl$_3$) δ1.29-1.50 (3 H, m), 1.54-1.60 (1H, m), 1.82-1.97 (1 H, m), 2.08 (3 H, s), 2.36-2.50 (4 H, m), 3.04 (3 H, s), 3.20-3.37 (2 H, m), 3.40-3.53 (4 H, m), 3.58-3.69 (2 H, m), 3.86-3.99 (2 H, m), 4.14-4.22 (1H, m), 6.15 (1 H, t, J=3.0 Hz), 6.59-6.72 (1 H, m), 6.93-7.06 (1 H, m), 7.36-7.53 (3 H, m), 7.87 (2 H, d, J=8.3 Hz), 8.32 (1 H, d, J=4.5 Hz), 9.28 (1 H, brs).

Example 84

1-[2-(5-{1-[4-(methylsulfonyl)phenyl]-2-(tetrahydro-2H-pyran-4-yl)ethyl}-1H-pyrrol-2-yl)pyridin-4-yl]ethanol

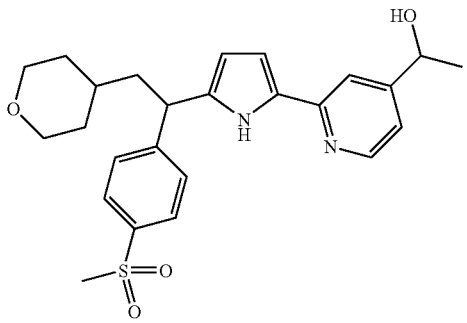

To a solution of 2-(5-{1-[4-(methylsulfonyl)phenyl]-2-(tetrahydro-2H-pyran-4-yl)ethyl}-1H-pyrrol-2-yl)pyridine-4-carbaldehyde (210 mg) in tetrahydrofuran (5 mL) was added methylmagnesium bromide (3M diethyl ether solution, 0.5 mL) at 0° C., and the mixture was stirred overnight at room temperature. The reaction mixture was diluted with ethyl acetate and washed with water. The ethyl acetate layer was washed with saturated brine, dried (MgSO$_4$) and concentrated. The residue was subjected to silica gel column chromatography, and the title compound (165 mg, yield 76%) was obtained as a yellow amorphous solid from a fraction eluted with ethyl acetate. MS: 455 (MH$^+$).

$^1$H NMR (300 MHz, CDCl$_3$) δ1.28-1.44 (3 H, m), 1.49 (3 H, d, J=6.4 Hz), 1.53-1.58 (1 H, m), 1.63-1.70 (1 H, m), 1.79-1.95 (1 H, m), 1.96-2.15 (2 H, m), 3.03 (3 H, s), 3.20-3.36 (2 H, m), 3.86-3.99 (2 H, m), 4.11-4.25 (1 H, m), 4.88 (1 H, q, J=6.4 Hz), 6.14 (1 H, t, J=3.0 Hz), 6.62-6.72 (1 H, m), 7.00 (1 H, d, J=5.3 Hz), 7.41 (2 H, d, J=8.3 Hz), 7.51 (1 H, s), 7.86 (2 H, d, J=8.7 Hz), 8.33 (1 H, d, J=4.5 Hz), 9.32 (1 H, brs).

Example 85

1-[6-(5-{1-[4-(cyclopropylsulfonyl)phenyl]-2-(tetrahydro-2H-pyran-4-yl)ethyl}-1H-pyrrol-2-yl)pyridin-3-yl]ethanol

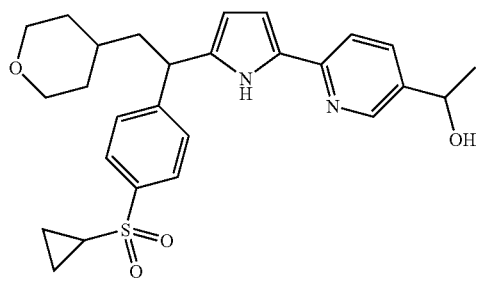

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (200 mg) in tetrahydrofuran (5 mL) was added methylmagnesium bromide (3M diethyl ether solution, 450 μL) at 0° C., and the mixture was stirred overnight at room temperature. Water was added to the reaction mixture, and the mixture was extracted with ethyl acetate. The ethyl acetate layer was washed with saturated brine, dried (MgSO$_4$) and concentrated. The residue was subjected to silica gel column chromatography, and the title compound (83.0 mg, yield 40%) was obtained as a pale-yellow amorphous solid from a fraction eluted with ethyl acetate. MS: 481 (MH$^+$).

$^1$H NMR (300 MHz, CDCl$_3$) δ0.96-1.08 (2 H, m), 1.24-1.42 (5H, m), 1.48-1.52 (3 H, m), 1.54-1.58 (1 H, m), 1.65-1.71 (1H, m), 1.80-1.96 (2 H, m), 2.00-2.16 (1 H, m), 2.37-2.51 (1 H, m), 3.21-3.36 (2 H, m), 3.86-3.98 (2 H, m), 4.17 (1H, t, J=7.9 Hz), 4.90 (1 H, q, J=6.4 Hz), 6.15 (1 H, t, J=3.1 Hz), 6.64 (1 H, dd, J=2.4, 3.4 Hz), 7.39 (2 H, d, J=8.3 Hz), 7.49 (1 H, d, J=8.3 Hz), 7.61-7.69 (1 H, m), 7.81 (2 H, d, J=8.5 Hz), 8.30-8.40 (1 H, m), 9.34 (1 H, brs).

Example 86

2-[6-(5-{1-[4-(cyclopropylsulfonyl)phenyl]-2-(tetrahydro-2H-pyran-4-yl)ethyl}-1H-pyrrol-2-yl)pyridin-3-yl]-2-hydroxyethyl N-(tert-butoxycarbonyl)glycinate

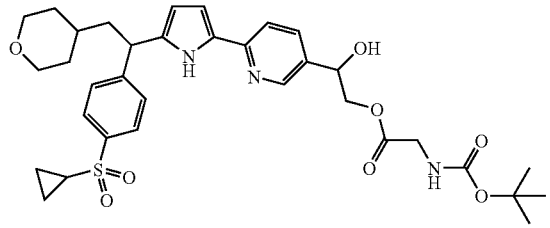

To a solution of 1-[6-(5-{1-[4-(cyclopropylsulfonyl)phenyl]-2-(tetrahydro-2H-pyran-4-yl)ethyl}-1H-pyrrol-2-yl)pyridin-3-yl]ethane-1,2-diol (245 mg) in N,N-dimethylformamide (5 mL) were added N-(tert-butoxycarbonyl)glycine (86.0 mg), 1-ethyl-3-(3-dimethylaminopropyl)carbodiimide hydrochloride (115 mg), 1-hydroxybenzotriazole (80.0 mg) and N-methylmorpholine (162 μL) under ice-cooling, and the mixture was stirred overnight at room temperature. The reaction mixture was diluted with ethyl acetate, washed with water and saturated brine, dried (MgSO$_4$) and concentrated. The residue was subjected to silica gel column chromatography, and the title compound (110 mg, yield 34%) was obtained as a colorless amorphous solid from a fraction eluted with ethyl acetate-hexane (2:1, volume ratio). MS: 654 (MH$^+$).

Example 87

2-[6-(5-{1-[4-(cyclopropylsulfonyl)phenyl]-2-(tetrahydro-2H-pyran-4-yl)ethyl}-1H-pyrrol-2-yl)pyridin-3-yl]-2-hydroxyethyl glycinate dihydrochloride

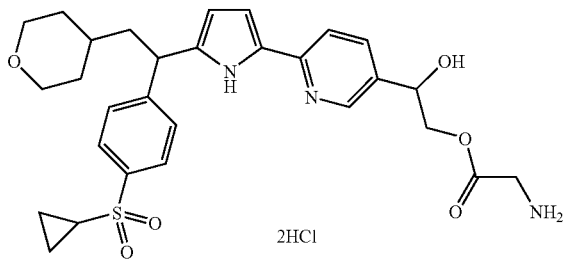

To a solution of 2-[6-(5-{1-[4-(cyclopropylsulfonyl)phenyl]-2-(tetrahydro-2H-pyran-4-yl)ethyl}-1H-pyrrol-2-yl)pyridin-3-yl]-2-hydroxyethyl N-(tert-butoxycarbonyl)glycinate (245 mg) in ethyl acetate (5 mL) was added 4M hydrogen chloride-ethyl acetate solution (210 μL), and the mixture was stirred overnight at room temperature. The reaction mixture was diluted with diethyl ether, and the resulting precipitate was collected by filtration and dried to give the title compound (44.1 mg, yield 41%) as a pale-yellow solid. MS: 554 (MH$^+$).

$^1$H NMR (300 MHz, DMSO-d$_6$) δ0.91-1.40 (7 H, m), 1.60 (2H, brs), 1.84-1.97 (1 H, m), 2.16 (1 H, brs), 2.68-2.89 (1H, m), 3.15 (2 H, t, J=11.5 Hz), 3.53-3.94 (9 H, m), 4.24-4.46 (3 H, m), 4.97 (1 H, t, J=4.9 Hz), 6.18-6.34 (1 H, m), 7.59-7.71 (2 H, m), 7.82 (2 H, d, J=8.3 Hz), 8.14 (1 H, brs), 8.32 (3 H, brs), 8.43-8.52 (1 H, m).

Example 88

1-[6-(5-{1-[4-(methylsulfonyl)phenyl]-2-(tetrahydro-2H-pyran-4-yl)ethyl}-1H-pyrrol-2-yl)pyridin-3-yl]ethane-1,2-diol

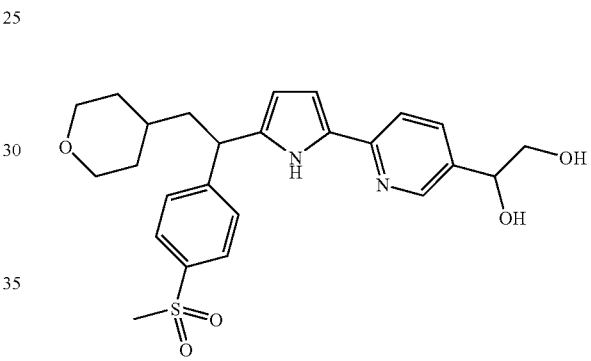

To a solution of 1-[5-(2,2-dimethyl-1,3-dioxolan-4-yl)pyridin-2-yl]-5-[4-(methylsulfonyl)phenyl]-6-(tetrahydro-2H-pyran-4-yl)hexane-1,4-dione (232 mg) in acetic acid (5 mL) was added ammonium acetate (540 mg), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated to give a crude product (218 mg). To a solution of the obtained crude product in tetrahydrofuran (5 mL) was added 1M hydrochloric acid (5 mL), and the mixture was stirred at 50° C. for 4 hr. The reaction mixture was diluted with ethyl acetate and washed with saturated aqueous sodium hydrogen carbonate. The ethyl acetate layer was washed with saturated brine, dried (MgSO$_4$) and concentrated. The residue was subjected to preparative HPLC to give the title compound (155 mg, yield 78%) as a colorless amorphous solid. MS: 471 (MH$^+$).

$^1$H NMR (300 MHz, CDCl$_3$) δ1.25-1.46 (3 H, m), 1.50-1.57 (1H, m), 1.65 (1 H, d, J=1.9 Hz), 1.78-1.97 (1 H, m), 1.97-2.13 (1 H, m), 2.31 (1 H, brs), 2.75 (1 H, brs), 2.97-3.09 (3H, m), 3.18-3.35 (2 H, m), 3.55-3.68 (1 H, m), 3.70-3.80 (1H, m), 3.91 (2 H, d, J=12.1 Hz), 4.05-4.23 (1 H, m), 4.79 (1H, dd, J=3.8, 8.0 Hz), 6.14 (1 H, t, J=3.0 Hz), 6.57-6.71 (1H, m), 7.40 (2 H, d, J=8.3 Hz), 7.49 (1 H, d, J=8.3 Hz), 7.58-7.70 (1 H, m), 7.85 (2 H, d, J=8.3 Hz), 9.42 (2 H, brs).

Example 89

1-[6-(5-{1-[3-fluoro-4-(methylsulfanyl)phenyl]-2-(tetrahydro-2H-pyran-4-yl)ethyl}-1H-pyrrol-2-yl)pyridin-3-yl]ethane-1,2-diol

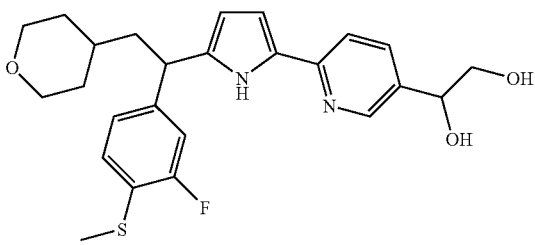

To a solution of 1-[5-(2,2-dimethyl-1,3-dioxolan-4-yl)pyridin-2-yl]-5-[3-fluoro-4-(methylsulfanyl)phenyl]-6-(tetrahydro-2H-pyran-4-yl)hexane-1,4-dione (500 mg) in acetic acid (5 mL) was added ammonium acetate (1.20 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated to give a crude product (400 mg). To a solution of the obtained crude product (400 mg) in tetrahydrofuran (5 mL) was added 1M hydrochloric acid (5 mL), and the mixture was stirred at 50° C. for 3 hr. The reaction mixture was diluted with ethyl acetate, and washed with saturated aqueous sodium hydrogen carbonate. The ethyl acetate layer was washed with saturated brine, dried (MgSO$_4$) and concentrated to give the title compound (367 mg, quantitatively) as a pale-brown amorphous solid. MS: 457 (MH$^+$).

$^1$H NMR (300 MHz, CDCl$_3$) δ1.21-1.40 (3 H, m), 1.50-1.71 (4H, m), 1.79-1.91 (1 H, m), 1.93-2.03 (1 H, m), 2.44 (3 H, s), 3.20-3.34 (2 H, m), 3.58-3.68 (1 H, m), 3.70-3.79 (1H, m), 3.84-3.96 (2 H, m), 4.03 (1 H, t, J=8.0 Hz), 4.78 (1H, dd, J=3.6, 7.8 Hz), 6.10 (1 H, t, J=3.2 Hz), 6.57-6.66 (1H, m), 6.85-7.01 (2 H, m), 7.19 (1 H, t, J=8.0 Hz), 7.47 (1H, d, J=8.3 Hz), 7.55-7.66 (1 H, m), 8.31 (1 H, s), 9.31 (1H, brs).

Example 90

1-[6-(5-{1-[3-fluoro-4-(methylsulfonyl)phenyl]-2-(tetrahydro-2H-pyran-4-yl)ethyl}-1H-pyrrol-2-yl)pyridin-3-yl]ethane-1,2-diol

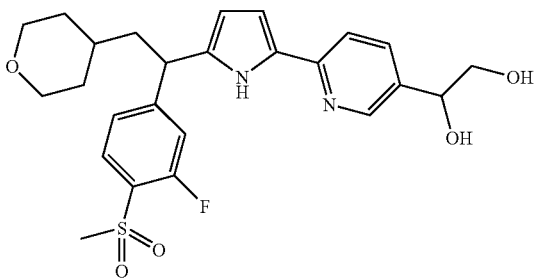

To a solution of 1-[6-(5-{1-[3-fluoro-4-(methylsulfanyl)phenyl]-2-(tetrahydro-2H-pyran-4-yl)ethyl}-1H-pyrrol-2-yl)pyridin-3-yl]ethane-1,2-diol (367 mg) in a mixed solvent of tetrahydrofuran (3 mL), methanol (3 mL) and water (3 mL) was added Oxone (registered trademark) (593 mg), and the mixture was stirred at room temperature for 2 hr. The reaction mixture was diluted with ethyl acetate, and washed with saturated aqueous sodium hydrogen carbonate. The ethyl acetate layer was washed with saturated brine, dried (MgSO$_4$) and concentrated to give the title compound (330 mg, 84%) as a pale-yellow amorphous solid. MS: 489 (MH$^+$).

$^1$H NMR (300 MHz, CDCl$_3$) δ1.27-1.50 (3 H, m), 1.51-1.72 (5H, m), 1.77-1.91 (1 H, m), 1.96-2.04 (1 H, m), 3.19 (3 H, s), 3.22-3.34 (2 H, m), 3.57-3.67 (1 H, m), 3.70-3.79 (1H, m), 3.85-3.97 (2 H, m), 4.79 (1 H, dd, J=3.4, 8.0 Hz), 6.14 (1 H, t, J=3.2 Hz), 6.59-6.68 (1 H, m), 7.04 (1 H, d, J=11.0 Hz), 7.14 (1 H, dd, J=1.5, 8.0 Hz), 7.50 (1 H, d, J=8.3 Hz), 7.60-7.68 (1 H, m), 7.84 (1 H, t, J=7.6 Hz), 8.31 (1 H, s), 9.62 (1 H, brs).

Example 91

1-[6-(5-{1-[3-chloro-4-(methylsulfonyl)phenyl]-2-(tetrahydro-2H-pyran-4-yl)ethyl}-1H-pyrrol-2-yl)pyridin-3-yl]ethane-1,2-diol

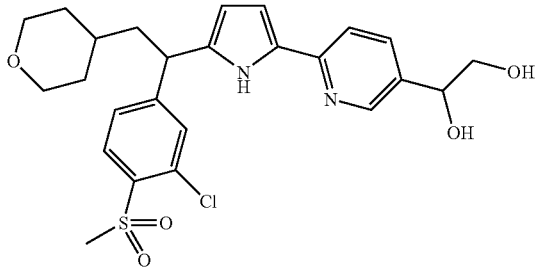

To a solution of 5-[3-chloro-4-(methylsulfonyl)phenyl]-1-[5-(2,2-dimethyl-1,3-dioxolan-4-yl)pyridin-2-yl]-6-(tetrahydro-2H-pyran-4-yl)hexane-1,4-dione (620 mg) in acetic acid (5 mL) was added ammonium acetate (1.36 g), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated to give a crude product (660 mg). To a solution of the obtained crude product (660 mg) in tetrahydrofuran (5 mL) was added 1M hydrochloric acid (5 mL), and the mixture was stirred at 50° C. for 3 hr. The reaction mixture was diluted with ethyl acetate, and washed with saturated aqueous sodium hydrogen carbonate. The ethyl acetate layer was washed with saturated brine, dried (MgSO$_4$) and concentrated. The residue was subjected to silica gel column chromatography, and the title compound (500 mg, yield 90%) was obtained as a pale-yellow amorphous solid from a fraction eluted with ethyl acetate-methanol (9:1, volume ratio). MS: 507 (MH$^+$). $^1$H NMR (300 MHz, CDCl$_3$) δ1.24-1.48 (3H, m), 1.51-1.62 (3 H, m), 1.74-1.89 (1 H, m), 1.95-2.09 (1H, m), 2.38 (1 H, brs), 3.01 (1 H, s), 3.19-3.34 (5 H, m), 3.55-3.66 (1 H, m), 3.69-3.80 (1 H, m), 3.85-3.97 (2H, m), 4.02-4.14 (1 H, m), 4.78 (1 H, dd, J=7.8, 3.6 Hz), 6.61-6.68 (1 H, m), 7.24 (1 H, dd, J=8.1, 1.7 Hz), 7.32 (1 H, d, J=1.5 Hz), 7.50 (1 H, d, J=8.3 Hz), 7.59-7.67 (1 H, m), 7.97-8.05 (1 H, m), 8.30 (1 H, s), 9.71 (1 H, brs).

Example 92

2-{5-[(E)-1-[4-(cyclopropylsulfonyl)phenyl]-2-(tetrahydro-2H-pyran-4-yl)ethenyl]-1H-pyrrol-2-yl}-1,3-thiazole

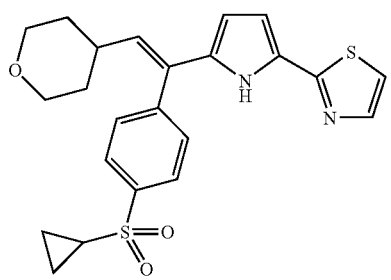

To a solution of (5E)-5-[4-(cyclopropylsulfonyl)phenyl]-6-(tetrahydro-2H-pyran-4-yl)-1-(1,3-thiazol-2-yl)hex-5-ene-1,4-dione (278 mg) in acetic acid (5 mL) was added ammonium acetate (750 mg), and the mixture was stirred at 110° C. for 45 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (133 mg, yield 50%) was obtained as a pale-yellow amorphous solid from a fraction eluted with ethyl acetate-hexane (3:2, volume ratio). MS: 441 (MH$^+$).

$^1$H NMR (300 MHz, CDCl$_3$) δ1.05-1.17 (2 H, m), 1.38-1.63 (6H, m), 2.10-2.32 (1 H, m), 2.49-2.66 (1 H, m), 3.17-3.35 (2 H, m), 3.91 (2 H, dd, J=3.0, 10.6 Hz), 5.81-5.98 (2 H, m), 6.61 (1 H, dd, J=2.3, 3.8 Hz), 7.16 (1 H, d, J=3.0 Hz), 7.45 (2 H, d, J=8.3 Hz), 7.66 (1 H, d, J=3.0 Hz), 7.96 (2 H, d, J=8.3 Hz), 9.20 (1 H, brs).

Example 93

2-(5-{1-[4-(cyclopropylsulfonyl)phenyl]-2-(tetrahydro-2H-pyran-4-yl)ethyl}-3-methyl-1H-pyrrol-2-yl)pyridine

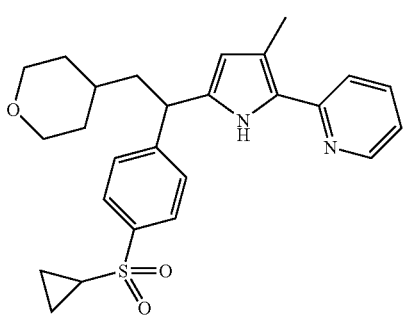

To a solution of 5-[4-(cyclopropylsulfonyl)phenyl]-2-methyl-1-(pyridin-2-yl)-6-(tetrahydro-2H-pyran-4-yl)hexane-1,4-dione (180 mg) in acetic acid (5 mL) was added ammonium acetate (472 mg), and the mixture was stirred at 110° C. for 30 min. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (140 mg, yield 81%) was obtained as a colorless amorphous solid from a fraction eluted with ethyl acetate-hexane (2:1, volume ratio). MS: 451 (MH$^+$).

$^1$H NMR (300 MHz, CDCl$_3$) δ0.96-1.07 (2 H, m), 1.27-1.37 (4H, m), 1.37-1.52 (1 H, m), 1.60-1.70 (2 H, m), 1.80-1.94 (1H, m), 1.97-2.12 (1 H, m), 2.34-2.40 (3 H, m), 2.40-2.49 (1 H, m), 3.21-3.37 (2 H, m), 3.85-3.99 (2 H, m), 4.06-4.19 (1 H, m), 5.98 (1 H, d, J=3.4 Hz), 6.99 (1 H, dd, J=4.9, 6.4 Hz), 7.40 (2 H, d, J=8.3 Hz), 7.46 (1 H, d, J=8.0 Hz), 7.56-7.68 (1 H, m), 7.82 (2 H, d, J=8.3 Hz), 8.42 (1 H, d, J=4.2 Hz), 9.22 (1 H, brs).

Example 94

5-(1-{[tert-butyl(dimethyl)silyl]oxy}ethyl)-2-(5-{1-[4-(cyclopropylsulfonyl)phenyl]-2-(tetrahydro-2H-pyran-4-yl)ethyl}-3-methyl-1H-pyrrol-2-yl)pyridine

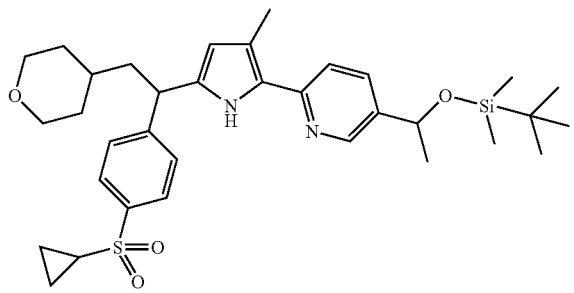

To a solution of 1-[5-(1-{[tert-butyl(dimethyl)silyl]oxy}ethyl)pyridin-2-yl]-5-[4-(cyclopropylsulfonyl)phenyl]-2-methyl-6-(tetrahydro-2H-pyran-4-yl)hexane-1,4-dione (180 mg) in acetic acid (5 mL) was added ammonium acetate (354 mg), and the mixture was stirred at 90° C. for 1 hr. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (130 mg, yield 74%) was obtained as a pale-yellow amorphous solid from a fraction eluted with ethyl acetate-hexane (1:1, volume ratio). MS: 609 (MH$^+$).

$^1$H NMR (300 MHz, CDCl$_3$) δ0.85-0.92 (9 H, m), 0.95-1.09 (3H, m), 1.22-1.30 (2 H, m), 1.30-1.37 (5 H, m), 1.41 (4 H, d, J=6.2 Hz), 1.60-1.72 (2 H, m), 1.79-1.94 (1 H, m), 1.99-2.14 (1 H, m), 2.34-2.39 (3 H, m), 2.40-2.51 (1 H, m), 3.20-3.37 (3 H, m), 3.86-3.99 (2 H, m), 4.07-4.19 (2H, m), 4.86 (1 H, d, J=6.2 Hz), 5.97 (1 H, d, J=3.0 Hz), 7.42 (3H, t, J=7.9 Hz), 7.57-7.66 (1 H, m), 7.77-7.89 (2 H, m), 8.37 (1 H, d, J=2.1 Hz), 9.11 (1 H, brs).

Example 95

1-[6-(5-{1-[4-(cyclopropylsulfonyl)phenyl]-2-(tetrahydro-2H-pyran-4-yl)ethyl}-3-methyl-1H-pyrrol-2-yl)pyridin-3-yl]ethanol

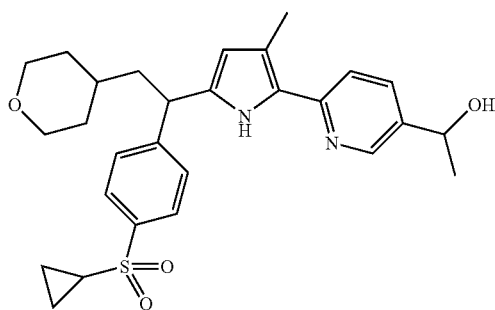

To a solution (5 mL) of 5-(1-{[tert-butyl(dimethyl)silyl]oxy}ethyl)-2-(5-{1-[4-(cyclopropylsulfonyl)phenyl]-2-(tetrahydro-2H-pyran-4-yl)ethyl}-3-methyl-1H-pyrrol-2-yl)pyridine (130 mg) in tetrahydrofuran (5 mL) was added tetrabutylammonium fluoride (1M tetrahydrofuran solution, 256 µL), and the mixture was stirred overnight at room temperature. The reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (83.0 mg, yield 79%) was obtained as a pale-yellow amorphous solid from a fraction eluted with ethyl acetate-hexane (3:1, volume ratio). MS: 495 (MH$^+$).

$^1$H NMR (300 MHz, CDCl$_3$) δ0.96-1.08 (2 H, m), 1.24-1.43 (5H, m), 1.51 (3 H, d, J=6.4 Hz), 1.60-1.70 (2 H, m), 1.78-1.94 (2 H, m), 1.97-2.10 (1 H, m), 2.37 (3 H, s), 2.40-2.49 (1H, m), 3.21-3.35 (2 H, m), 3.85-3.97 (2 H, m), 4.06-4.18 (1 H, m), 4.91 (1 H, q, J=6.4 Hz), 5.98 (1 H, d, J=3.0 Hz), 7.39 (2 H, d, J=8.3 Hz), 7.46 (1 H, d, J=8.3 Hz), 7.63-7.71 (1 H, m), 7.81 (2 H, d, J=8.3 Hz), 8.39 (1 H, s), 9.24 (1H, brs).

Example 96

1-[6-(5-{1-[4-(cyclopropylsulfonyl)phenyl]-2-(tetrahydro-2H-pyran-4-yl)ethyl}-3-methyl-1H-pyrrol-2-yl)pyridin-3-yl]-2-methylpropane-1,2-diol

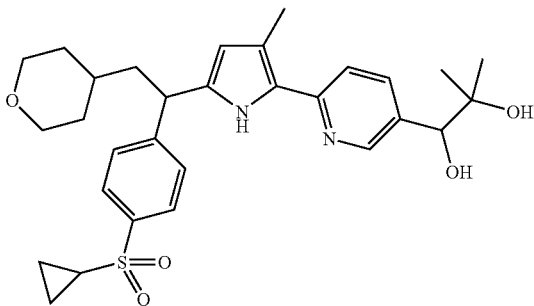

To a solution of 5-[4-(cyclopropylsulfonyl)phenyl]-1-[5-(1,2-dihydroxy-2-methylpropyl)pyridin-2-yl]-2-methyl-6-(tetrahydro-2H-pyran-4-yl)hexane-1,4-dione (235 mg) in acetic acid (5 mL) was added ammonium acetate (519 mg), and the mixture was stirred at 90° C. for 1 hr. After cooling to room temperature, the reaction mixture was diluted with ethyl acetate and washed with water. The ethyl acetate layer was washed with saturated aqueous sodium hydrogen carbonate and saturated brine, dried (MgSO$_4$) and concentrated. The residue was subjected to silica gel column chromatography, and the title compound (150 mg, yield 66%) was obtained as a pale-yellow amorphous solid from a fraction eluted with ethyl acetate. MS: 539 (MH$^+$).

$^1$H NMR (300 MHz, CDCl$_3$) δ0.95-1.05 (2 H, m), 1.08 (3 H, s), 1.22-1.28 (3 H, m), 1.29-1.40 (4 H, m), 1.40-1.50 (1H, m), 1.60-1.70 (2 H, m), 1.78-1.94 (1 H, m), 1.96-2.11 (2H, m), 2.35-2.39 (3 H, m), 2.40-2.49 (1 H, m), 2.71 (1H, brs), 3.20-3.36 (2 H, m), 3.86-3.97 (2 H, m), 4.04-4.16 (1 H, m), 4.45-4.53 (1 H, m), 5.98 (1 H, d, J=2.3 Hz), 7.38 (2 H, dd, J=1.9, 8.5 Hz), 7.45 (1 H, d, J=8.3 Hz), 7.62-7.74 (1 H, m), 7.76-7.86 (2 H, m), 8.35 (1 H, dd, J=2.0, 5.7 Hz), 9.27 (1 H, brs).

Example 97

1-[2-(4-chloro-5-{1-[4-(cyclopropylsulfonyl)phenyl]-2-(tetrahydro-2H-pyran-4-yl)ethyl}-1H-pyrrol-2-yl)-1,3-thiazol-5-yl]ethanol

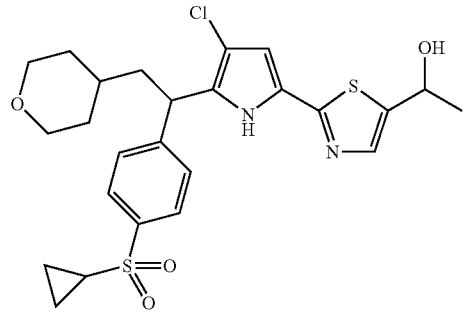

To a solution of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethanol (300 mg) in tetrahydrofuran (5 mL) was added N-chlorosuccinimide (82.3 mg) at 0° C., and the mixture was stirred at 50° C. overnight. After cooling to room temperature, the reaction mixture was diluted with ethyl acetate, and washed with saturated aqueous sodium hydrogen carbonate. The ethyl acetate layer was washed with saturated brine, dried (MgSO$_4$) and concentrated. The residue was subjected to preparative HPLC to give a mixture of the title compound and a positional isomer thereof (210 mg). The mixture of the obtained positional isomers was dissolved in hexane-2-propanol (700:300, volume ratio, 18.8 mL), and the solution was subjected to HPLC using CHIRALPAK AD (50 mmID×500 mL, manufactured by DAICEL CHEMICAL INDUSTRY LTD.). Using hexane-2-propanol (700:300, volume ratio) as a mobile phase, the solution was eluted at flow rate 60 mL/min and at 30° C., and the fraction was separated at retention time 22.0 min, and concentrated. The obtained solid was dissolved in ethyl acetate and the insoluble material was filtered off. The filtration was concentrated to give the title compound (85.9 mg, yield 27%) as a colorless amorphous solid. MS: 521 (MH$^+$).

$^1$H NMR (300 MHz, CDCl$_3$) δ0.95-1.08 (2 H, m), 1.28-1.44 (6H, m), 1.50-1.63 (4 H, m), 1.83-2.08 (2 H, m), 2.36-2.49 (2H, m), 3.18-3.34 (2 H, m), 3.83-3.98 (2 H, m), 4.40 (1H, dd, J=9.1, 7.3 Hz), 5.14 (1 H, d, J=6.6 Hz), 6.55 (1 H, d, J=2.6 Hz), 7.41 (3 H, dd, J=3.8, 4.7 Hz), 7.80 (2 H, d, J=8.3 Hz), 9.57 (1 H, brs).

Example 98

1-[2-(3-chloro-5-{1-[4-(cyclopropylsulfonyl)phenyl]-2-(tetrahydro-2H-pyran-4-yl)ethyl}-1H-pyrrol-2-yl)-1,3-thiazol-5-yl]ethanol

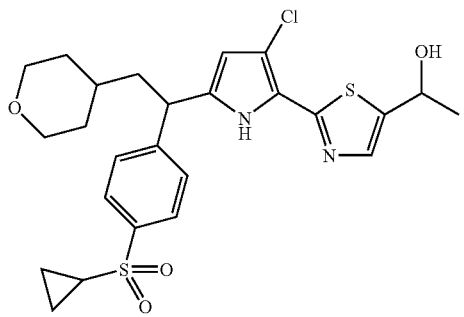

To a solution (5 mL) of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethanol (300 mg) in tetrahydrofuran was added N-chlorosuccinimide (82.3 mg) at 0° C., and the mixture was stirred at 50° C. overnight. After cooling to room temperature, the reaction mixture was diluted with ethyl acetate, and washed with saturated aqueous sodium hydrogen carbonate. The ethyl acetate layer was washed with saturated brine, dried (MgSO$_4$) and concentrated. The residue was subjected to preparative HPLC to give a mixture of the title compound and a positional isomer thereof (210 mg). The mixture of the obtained positional isomers was dissolved in hexane-2-propanol (700:300, volume ratio, 18.8 mL), and the solution was subjected to HPLC using CHIRALPAK AD (50 mmID×500 mL, manufactured by DAICEL CHEMICAL INDUSTRY LTD.). Using hexane-2-propanol (700:300, volume ratio) as a mobile phase, the solution was eluted at flow rate 60 mL/min and at 30° C., and the both fractions were separated at retention times 41.0 min and 55.0 min, and concentrated. The obtained solid was dissolved in ethyl acetate, and the insoluble material was filtered off. The filtration was concentrated to give the title compound (93.2 mg, yield 29%) as a colorless amorphous solid. MS: 521 (MH$^+$).

$^1$H NMR (300 MHz, CDCl$_3$) δ0.98-1.09 (2 H, m), 1.26-1.45 (6H, m), 1.48-1.62 (4 H, m), 1.77-1.91 (1 H, m), 1.92-2.05 (1H, m), 2.34 (1 H, brs), 2.39-2.51 (1 H, m), 3.17-3.34 (2H, m), 3.86-3.96 (2 H, m), 4.05 (1 H, t, J=7.9 Hz), 5.12-5.24 (1 H, m), 6.14 (1 H, d, J=2.8 Hz), 7.33 (2 H, d, J=8.3 Hz), 7.46 (1 H, s), 7.77-7.85 (2 H, m), 9.36 (1 H, d, J=1.3 Hz).

Example 99

1-[2-(5-{1-[4-(cyclopropylsulfonyl)phenyl]-2-(tetrahydro-2H-pyran-4-yl)ethyl}-4-fluoro-1H-pyrrol-2-yl)-1,3-thiazol-5-yl]ethanol

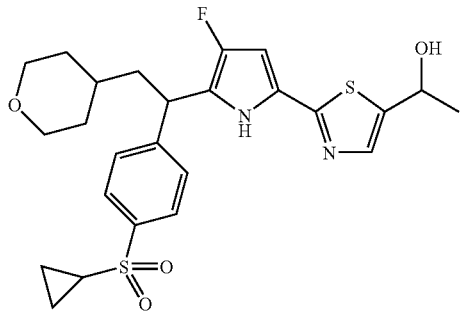

To a solution of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethanol (420 mg) in dichloromethane (5 mL) was added 2,6-dichloro-1-fluoropyridinium trifluoromethanesulfonate (410 mg), and the mixture was stirred at room temperature for 3 hr. The reaction mixture was diluted with ethyl acetate, and washed with saturated aqueous sodium hydrogen carbonate. The ethyl acetate layer was washed with saturated brine, dried (MgSO$_4$) and concentrated. The residue was subjected to preparative HPLC to give a mixture of the title compound and a positional isomer thereof (35.0 mg). The mixture of the obtained positional isomers was dissolved in hexane-ethanol (850:150, volume ratio, 114 mL), and the solution was subjected to HPLC using TSK GEL SHILICA-60 (20 mmID×250 mL, manufactured by Tosoh Corporation-silica). Using hexane-ethanol (850:150, volume ratio) as a mobile phase, the solution was eluted at flow rate 20 mL/min and at room temperature, and the fraction was separated at retention time 34.5 min, and concentrated. The obtained solid was dissolved in ethyl acetate and the insoluble material was filtered off. The filtration was concentrated to give the title compound (18.1 mg, yield 3%) as a colorless amorphous solid. MS: 505 (MH$^+$).

$^1$H NMR (300 MHz, CDCl$_3$) δ0.96-1.09 (2 H, m), 1.23-1.43 (7H, m), 1.54-1.63 (3 H, m), 1.81-1.95 (1 H, m), 2.00-2.16 (1H, m), 2.35 (1 H, d, J=4.5 Hz), 2.38-2.48 (1 H, m), 3.28 (2H, t, J=11.0 Hz), 3.92 (2 H, d, J=11.7 Hz), 4.23 (1 H, dd, J=7.2, 9.1 Hz), 5.06-5.20 (1 H, m), 6.36 (1 H, d, J=2.7 Hz), 7.35-7.45 (3 H, m), 7.81 (2 H, d, J=8.3 Hz), 9.03 (1 H, brs).

Example 100

1-[2-(5-{1-[4-(cyclopropylsulfonyl)phenyl]-2-(tetrahydro-2H-pyran-4-yl)ethyl}-3-fluoro-1H-pyrrol-2-yl)-1,3-thiazol-5-yl]ethanol

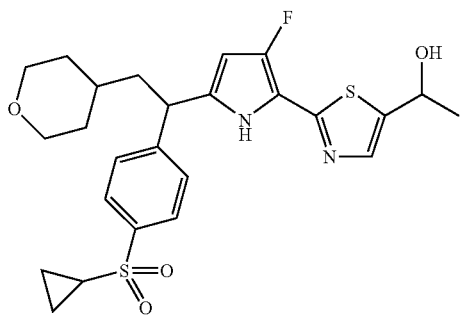

To a solution of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethanol (420 mg) in dichloromethane (5 mL) was added 2,6-dichloro-1-fluoropyridinium trifluoromethanesulfonate (410 mg), and the mixture was stirred at room temperature for 3 hr. The reaction mixture was diluted with ethyl acetate, and washed with saturated aqueous sodium hydrogen carbonate. The ethyl acetate layer was washed with saturated brine, dried (MgSO$_4$) and concentrated. The residue was subjected to preparative HPLC to give a mixture of the title compound and a positional isomer thereof (35.0 mg). The mixture of the obtained positional isomers was dissolved in hexane-ethanol (850:150, volume ratio, 114 mL), and the solution was subjected to HPLC using TSK GEL SHILICA-60 (20 mm ID×250 mL, manufactured by Tosoh Corporation silica). Using hexane-ethanol (850:150, volume ratio) as a mobile phase, the solution was eluted at flow rate 20 mL/min and at room temperature, and the fraction was separated at retention time 39.0 min, and concentrated. The obtained solid was dissolved in ethyl acetate and the insoluble material was filtered off. The filtration was concentrated to give the title compound (26.8 mg, yield 4%) as a colorless amorphous solid. MS: 505 (MH⁺).

¹H NMR (300 MHz, CDCl₃) δ0.91-1.12 (2 H, m), 1.25-1.41 (5H, m), 1.51 (1 H, t, J=10.6 Hz), 1.60 (4 H, d, J=6.4 Hz), 1.77-1.89 (1 H, m), 1.89-2.03 (1 H, m), 2.37-2.55 (1 H, m), 2.72 (1 H, d, J=4.5 Hz), 3.16-3.39 (2 H, m), 3.91 (2 H, d, J=11.4 Hz), 4.01 (1 H, t, J=8.0 Hz), 5.08-5.23 (1 H, m), 5.93 (1 H, d, J=2.7 Hz), 7.31 (2 H, d, J=8.3 Hz), 7.39 (1H, s), 7.81 (2 H, d, J=8.3 Hz), 9.11-9.24 (1 H, m).

Example 101

2-(5-{1-[4-(cyclopropylsulfonyl)phenyl]-2-[(2R,3R,7R)-2,3-diphenyl-1,4-dioxaspiro[4.4]non-7-yl]ethyl}-1H-pyrrol-2-yl)-1,3-thiazole

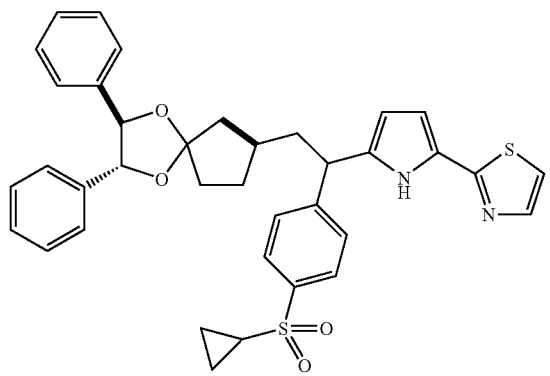

To a solution of 4-[4-(cyclopropylsulfonyl)phenyl]-5-[(2R,3R,7R)-2,3-diphenyl-1,4-dioxaspiro[4.4]non-7-yl]pent-1-en-3-one (1.70 g) in ethanol (10 mL) were added 1,3-thiazole-2-carbaldehyde (0.33 mL), 3-benzyl-5-(2-hydroxyethyl)-4-methyl-1,3-thiazol-3-ium chloride (93 mg) and triethylamine (0.19 mL), and the mixture was heated under reflux for 12 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=20:80-60:40, volume ratio) to give a colorless oil. To a solution of the obtained oil in N,N-dimethylformamide (20 mL) was added ammonium acetate (820 mg), and the mixture was stirred at 100° C. for 1.5 hr. The reaction mixture was diluted with ethyl acetate, washed successively with water and saturated brine, dried over anhydrous magnesium sulfate and concentrated under reduced pressure. The residue was purified by basic silica gel column chromatography (ethyl acetate:hexane=10:90-80:20, volume ratio) to give the title compound (0.100 g, yield 5%) as a colorless oil. MS: 637 (MH⁺).

¹H NMR (CDCl₃) 0.97-1.07 (2 H, m), 1.30-1.38 (2 H, m), 1.44-1.57 (1 H, m), 1.70-1.84 (1 H, m), 1.87-2.16 (4 H, m), 2.16-2.38 (3 H, m), 2.39-2.50 (1 H, m), 4.03-4.11 (1H, m), 4.64-4.73 (2 H, m), 6.11-6.17 (1 H, m), 6.59-6.66 (1H, m), 7.11 (1 H, dd, J=1.4, 3.4 Hz), 7.15-7.23 (4 H, m), 7.27-7.35 (6 H, m), 7.36-7.43 (2 H, m), 7.59 (1 H, dd, J=2.1, 3.4 Hz), 7.78-7.85 (2 H, m), 9.10 (1 H, s).

Example 102

(3R)-3-{2-[4-(cyclopropylsulfonyl)phenyl]-2-[5-(1,3-thiazol-2-yl)-1H-pyrrol-2-yl]ethyl}cyclopentanone

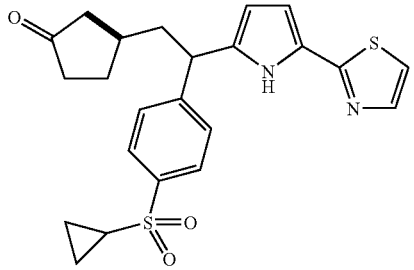

To a solution of 2-(5-{1-[4-(cyclopropylsulfonyl)phenyl]-2-[(2R,3R,7R)-2,3-diphenyl-1,4-dioxaspiro[4.4]non-7-yl]ethyl}-1H-pyrrol-2-yl)-1,3-thiazole (0.100 g) in 1,4-dioxane (2 mL) was added 4.5M aqueous sulfuric acid solution (2 mL) at room temperature, and the mixture was stirred at room temperature for 4 hr. To the reaction mixture was added saturated aqueous sodium hydrogen carbonate solution, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=20:80-80:20, volume ratio), and recrystallized from diethyl ether-hexane to give the title compound (0.03 g, yield 43%) as colorless crystals. MS: 441 (MH⁺). melting point 165-167° C.

Example 103

Ethyl 2-{1-[4-(cyclopropylsulfonyl)phenyl]-2-(tetrahydro-2H-pyran-4-yl)ethyl}-5-(1,3-thiazol-2-yl)-1H-pyrrole-3-carboxylate

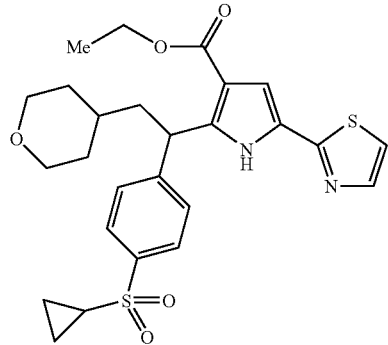

To a solution of ethyl 4-[4-(cyclopropylsulfonyl)phenyl]-3-oxo-2-[2-oxo-2-(1,3-thiazol-2-yl)ethyl]-5-(tetrahydro-2H-pyran-4-yl)pentanoate (0.190 g) in acetic acid (5 mL) was added ammonium acetate (0.411 g) at room temperature, and the mixture was stirred at 100° C. for 15 hr. To the reaction mixture was added saturated aqueous sodium hydrogen carbonate solution, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=30:70-70:30, volume ratio) to give the title compound (0.126 g, yield 68%) as a colorless amorphous solid. MS: 515 (MH⁺). melting point 178-179° C.

Example 104

2-{1-[4-(cyclopropylsulfonyl)phenyl]-2-(tetrahydro-2H-pyran-4-yl)ethyl}-5-(1,3-thiazol-2-yl)-1H-pyrrole-3-carboxylic acid

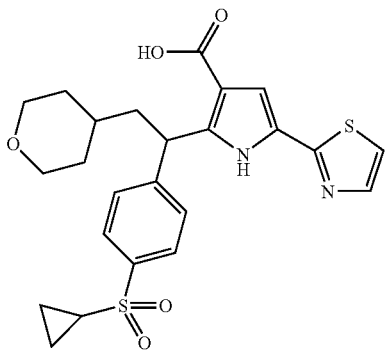

To a solution of ethyl 2-[(1-[4-(cyclopropylsulfonyl)phenyl]-2-(tetrahydro-2H-pyran-4-yl)ethyl]-5-(1,3-thiazol-2-yl)-1H-pyrrole-3-carboxylate (0.326 g) in a mixed solvent of tetrahydrofuran (20 mL) and ethanol (10 mL) was added 4M aqueous lithium hydroxide solution (5 mL), and the mixture was heated under reflux for 70 hr. The reaction mixture was acidified with 1M hydrochloric acid, and extracted with ethyl acetate. The extract was washed successively with water and saturated brine, dried over anhydrous magnesium sulfate and concentrated under reduced pressure. The residue was purified by silica gel column chromatography (ethyl acetate:hexane=65:35-100:0, volume ratio), and recrystallized from hexane-ethyl acetate to give the title compound (0.155 g, yield 50%) as colorless crystals. MS: 487 (MH$^+$). melting point 153-155° C.

Example 105

2-{1-[4-(cyclopropylsulfonyl)phenyl]-2-(tetrahydro-2H-pyran-4-yl)ethyl}-N,N-dimethyl-5-(1,3-thiazol-2-yl)-1H-pyrrole-3-carboxamide

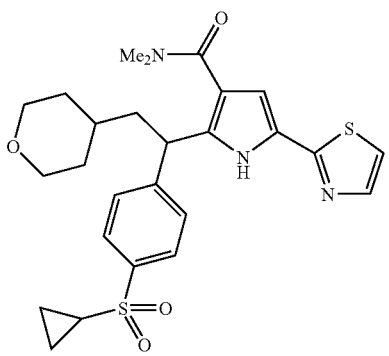

To a solution of 2-{1-[4-(cyclopropylsulfonyl)phenyl]-2-(tetrahydro-2H-pyran-4-yl)ethyl}-5-(1,3-thiazol-2-yl)-1H-pyrrole-3-carboxylic acid (0.066 g) in N,N-dimethylformamide (5 mL) were added N,N-dimethylamine (0.038 mL), O-(benzotriazol-1-yl)-N,N,N',N'-tetramethyluronium hexafluorophosphate (57 mg) and N,N-diisopropylethylamine (0.069 mL), and the mixture was stirred at room temperature for 16 hr. To the reaction mixture was added 1M hydrochloric acid, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=70:30-100:0, volume ratio), and recrystallized from hexane-ethyl acetate to give the title compound (0.058 g, yield 84%) as colorless crystals. MS: 514 (MH$^+$). melting point 180-182° C.

Example 106

2-{1-[4-(cyclopropylsulfonyl)phenyl]-2-(tetrahydro-2H-pyran-4-yl)ethyl}-5-(1,3-thiazol-2-yl)-1H-pyrrole-3-carboxamide

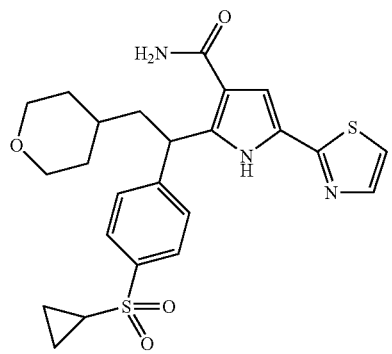

To a solution of 2-{1-[4-(cyclopropylsulfonyl)phenyl]-2-(tetrahydro-2H-pyran-4-yl)ethyl}-5-(1,3-thiazol-2-yl)-1H-pyrrole-3-carboxylic acid (0.090 g) in N,N-dimethylformamide (9 mL) were added N-[3-(dimethylamino)propyl]-N'-ethylcarbodiimide hydrochloride (71 mg) and 1-hydroxybenzotriazole ammonium salt (0.056 g), and the mixture was stirred at room temperature for 16 hr. The reaction mixture was concentrated under reduced pressure, and the residue was suspended in ethyl acetate. The suspension was washed successively with water and saturated brine, dried over anhydrous sodium sulfate, and concentrated under reduced pressure. The residue was purified by basic silica gel column chromatography (ethyl acetate:hexane=70:30-100:0, volume ratio), and recrystallized from hexane-ethyl acetate to give the title compound (0.058 g, yield 65%) as colorless crystals. MS: 486 (MH$^+$). melting point 241-243° C.

Example 107

2-{1-[4-(cyclopropylsulfonyl)phenyl]-2-(tetrahydro-2H-pyran-4-yl)ethyl}-5-(1,3-thiazol-2-yl)-1H-pyrrole-3-carbonitrile

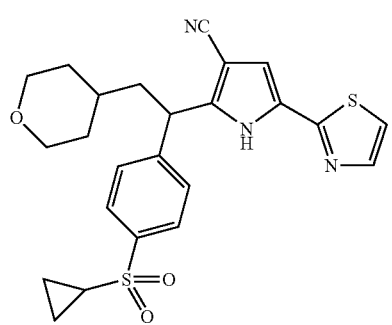

To a solution of 2-{1-[4-(cyclopropylsulfonyl)phenyl]-2-(tetrahydro-2H-pyran-4-yl)ethyl}-5-(1,3-thiazol-2-yl)-1H-pyrrole-3-carboxamide (0.147 g) in N,N-dimethylformamide (5 mL) was added cyanuroyl chloride (0.061 g) under ice-cooling, m and the mixture was warmed to room temperature and stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=30:70-70:30, volume ratio), and recrystallized from hexane-diethyl ether to give the title compound (0.093 g, yield 66%) as colorless crystals. MS: 468 (MH$^+$). melting point 114-116° C.

Example 108

2-(5-{1-[4-(ethylsulfonyl)phenyl]-2-(tetrahydro-2H-pyran-4-yl)ethyl}-1H-pyrrol-2-yl)pyridine

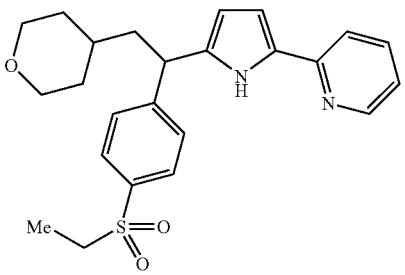

To a solution of 4-[4-(ethylsulfonyl)phenyl]-5-(tetrahydro-2H-pyran-4-yl)pent-1-en-3-one (0.409 g) in ethanol (15 mL) were added pyridine-2-carbaldehyde (0.139 mL), 3-benzyl-5-(2-hydroxyethyl)-4-methyl-1,3-thiazol-3-ium chloride (36 mg) and triethylamine (0.073 mL), and the mixture was heated under reflux for 1 hr. Water was added to the reaction mixture, and the mixture was extracted with ethyl acetate. The extract was washed successively with water and saturated brine, dried over anhydrous sodium sulfate, and concentrated under m reduced pressure. The residue was purified by silica gel column chromatography (ethyl acetate:hexane=30:70-80:20, volume ratio) to give a colorless oil. To a solution of the obtained oil in acetic acid (10 mL) was added ammonium acetate (356 mg), and the mixture was stirred at 110° C. for 3 hr. The reaction mixture was neutralized with saturated aqueous sodium hydrogen carbonate solution, and extracted with ethyl acetate. The extract was washed successively with water and saturated brine, dried over anhydrous magnesium sulfate and concentrated under reduced pressure. The residue was purified by silica gel column chromatography (ethyl acetate:hexane=10:90-80:20, volume ratio) to give the title compound (0.350 g, yield 69%) as a colorless amorphous solid. MS: 425 (MH$^+$).

$^1$H NMR (CDCl$_3$) 1.21-1.50 (6 H, m), 1.55-1.70 (2 H, m), 1.82-1.95 (1 H, m), 2.01-2.13 (1 H, m), 3.03-3.16 (2 H, m), 3.28 (2 H, t, J=11.5 Hz), 3.87-3.98 (2 H, m), 4.13-4.20 (1H, m), 6.12-6.18 (1 H, m), 6.63-6.67 (1 H, m), 6.97-7.04 (1 H, m), 7.41 (2 H, d, J=8.3 Hz), 7.47-7.53 (1 H, m), 7.55-7.65 (1 H, m), 7.82 (2 H, d, J=8.3 Hz), 8.38 (1 H, d, J=4.5 Hz), 9.32 (1 H, s).

Example 109

2-{5-[1-{4-[(3-methoxypropyl)sulfonyl]phenyl}-2-(tetrahydro-2H-pyran-4-yl)ethyl]-1H-pyrrol-2-yl}pyridine

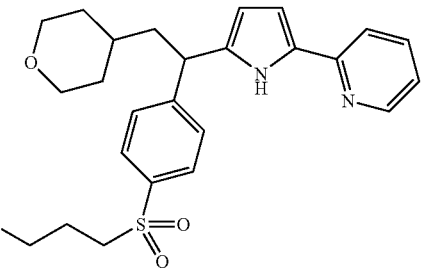

To a solution of 4-{4-[(3-methoxypropyl)sulfonyl]phenyl}-5-(tetrahydro-2H-pyran-4-yl)pent-1-en-3-one (0.450 g) in ethanol (20 mL) were added pyridine-2-carbaldehyde (0.135 mL), 3-benzyl-5-(2-hydroxyethyl)-4-methyl-1,3-thiazol-3-ium chloride (35 mg) and triethylamine (0.071 mL), and the mixture was heated under reflux for 1 hr. The reaction mixture was concentrated under reduced pressure, and the residue was purified by silica gel column chromatography (ethyl acetate:hexane=40:60-100:0, volume ratio) to give a colorless oil. To a solution of the obtained oil in acetic acid (10 mL) was added ammonium acetate (355 mg), and the mixture was stirred at 110° C. for 1.5 hr. The reaction mixture was neutralized with saturated aqueous sodium hydrogen carbonate solution, and extracted with ethyl acetate. The extract was washed successively with water and saturated brine, dried over anhydrous magnesium sulfate and concentrated under reduced pressure. The residue was purified by silica gel column chromatography (ethyl acetate:hexane=40:60-100:0, volume ratio) to give the title compound (0.400 g, yield 72%) as a colorless amorphous solid. MS: 425 (MH$^+$).

$^1$H NMR (CDCl$_3$) 1.23-1.70 (7 H, m), 1.82-2.15 (4 H, m), 3.13-3.21 (2 H, m), 3.23-3.34 (5 H, m), 3.41 (2 H, t, J=5.9 Hz), 3.87-3.97 (2 H, m), 4.18 (1 H, t, J=7.9 Hz), 6.13 (1 H, t, J=3.1 Hz), 6.62-6.68 (1 H, m), 6.97-7.04 (1 H, m), 7.41 (1H, d, J=8.5 Hz), 7.47-7.52 (1 H, m), 7.56-7.64 (1 H, m), 7.83 (1 H, d, J=8.5 Hz), 8.35-8.41 (1 H, m), 9.26 (1 H, s).

Example 110

5-(benzyloxy)-2-(5-{1-[4-(cyclopropylsulfonyl)phenyl]-2-(tetrahydro-2H-pyran-4-yl)ethyl}-1H-pyrrol-2-yl)pyridine

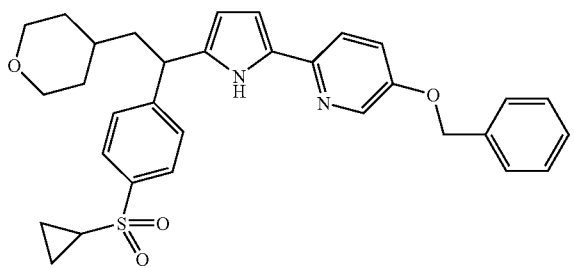

To a solution of 4-[4-(cyclopropylsulfonyl)phenyl]-5-(tetrahydro-2H-pyran-4-yl)pent-1-en-3-one (1.56 g) in ethanol (60 mL) were added 5-(benzyloxy)pyridine-2-carbaldehyde (1.00 g), 3-benzyl-5-(2-hydroxyethyl)-4-methyl-1,3-thiazol-3-ium chloride (132 mg) and triethylamine (0.269 mL), and the mixture was heated under reflux for 2 hr. Water was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=20:80-100:0, volume ratio) to give colorless crystals. To a solution of the obtained crystals in acetic acid (40 mL) was added ammonium acetate (3.02 g), and the mixture was stirred at 110° C. for 2 hr. The reaction mixture was neutralized with saturated aqueous sodium hydrogen carbonate solution, and extracted with ethyl acetate. The extract was washed successively with water and saturated brine, dried over anhydrous magnesium sulfate and concentrated under reduced pressure. The residue was purified by silica gel column chromatography (ethyl acetate:hexane=5:95-50:50, volume ratio) to give the title compound (1.97 g, yield 82%) as a pale-green amorphous solid. MS: 543 (MH$^+$).

$^1$H NMR (CDCl$_3$) 0.97-1.06 (2 H, m), 1.29-1.52 (6 H, m), 1.63 (2 H, s), 1.82-1.93 (1 H, m), 2.01-2.12 (1 H, m), 2.38-2.49 (1 H, m), 3.22-3.33 (2 H, m), 3.86-3.97 (2 H, m), 4.10-4.19 (1 H, m), 5.09 (2 H, s), 6.09-6.15 (1 H, m), 6.48-6.54 (1 H, m), 7.19-7.25 (1 H, m), 7.30-7.46 (7H, m), 7.81 (2 H, d, J=8.5 Hz), 8.15 (1 H, d, J=2.4 Hz), 9.11 (1 H, s).

Example 111

6-(5-{1-[4-(cyclopropylsulfonyl)phenyl]-2-(tetrahydro-2H-pyran-4-yl)ethyl}-1H-pyrrol-2-yl)pyridin-3-ol

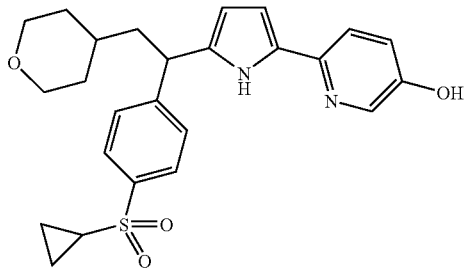

To a solution of 5-(benzyloxy)-2-(5-[1-[4-(cyclopropylsulfonyl)phenyl]-2-(tetrahydro-2H-pyran-4-yl)ethyl]-1H-pyrrol-2-yl)pyridine (1.97 g) in a mixed solvent of ethanol (30 mL) and tetrahydrofuran (30 mL) was added 10% palladium carbon (200 mg), and the mixture was stirred at room temperature for 16 hr under a hydrogen atmosphere. The reaction mixture was filtered, and the filtrate was concentrated under reduced pressure. The residue was purified by silica gel column chromatography (ethyl acetate:hexane=20:80-80:20, volume ratio) to give the title compound (1.62 g, yield 99%) as a yellow amorphous solid. MS: 453 (MH$^+$).

$^1$H NMR (CDCl$_3$) 0.95-1.04 (2 H, m), 1.23-1.48 (5 H, m), 1.52-1.66 (2 H, m), 1.79-1.92 (1 H, m), 1.97-2.08 (1 H, m), 2.36-2.47 (1 H, m), 3.21-3.32 (2 H, m), 3.90 (2 H, d, J=9.2 Hz), 4.08-4.14 (1 H, m), 6.09 (1 H, t, J=3.1 Hz), 6.52 (1 H, dd, J=3.5, 2.5 Hz), 7.14 (1 H, dd, J=2.8, 8.9 Hz), 7.35 (2 H, d, J=8.3 Hz), 7.44 (1 H, d, J=8.9 Hz), 7.77 (2 H, d, J=8.3 Hz), 8.02 (1 H, d, J=2.5 Hz), 9.39 (1 H, s).

Example 112

5-(cyclopropylmethoxy)-2-(5-{1-[4-(cyclopropylsulfonyl)phenyl]-2-(tetrahydro-2H-pyran-4-yl)ethyl}-1H-pyrrol-2-yl)pyridine

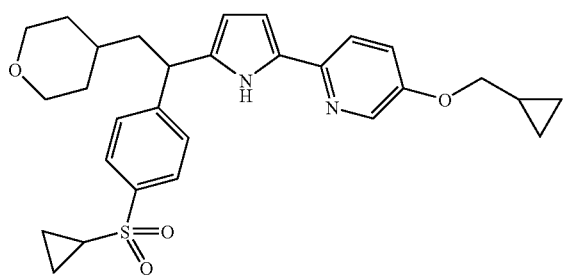

To a solution of 6-(5-{1-[4-(cyclopropylsulfonyl)phenyl]-2-(tetrahydro-2H-pyran-4-yl)ethyl}-1H-pyrrol-2-yl)pyridin-3-ol (0.260 g) in tetrahydrofuran (10 mL) were added cyclopropylmethanol (83 mg), tributylphosphine (0.29 mL) and 1,1'-(azodicarbonyl)dipiperidine (290 mg), and the mixture was stirred at room temperature for 16 hr. The reaction mixture was concentrated under reduced pressure, the residue was dissolved in toluene (10 mL), and hexane (10 mL) was added. The obtained suspension was filtered to remove the precipitate, and the filtrate was concentrated under reduced pressure. The residue was purified by silica gel column chromatography (ethyl acetate:hexane=20:80-70:30, volume ratio) to give the title compound (0.240 g, yield 83%) as a colorless amorphous solid. MS: 507 (MH$^+$).

$^1$H NMR (CDCl$_3$) 0.32-0.40 (2 H, m), 0.62-0.71 (2 H, m), 0.97-1.06 (2 H, m), 1.19-1.51 (6 H, m), 1.54-1.71 (2 H, m), 1.79-1.96 (1 H, m), 2.00-2.14 (1 H, m), 2.38-2.51 (1H, m), 3.22-3.35 (2 H, m), 3.83 (2 H, d, J=7.0 Hz), 3.87-3.98 (2 H, m), 4.07-4.21 (1 H, m), 6.12 (1 H, t, J=3.0 Hz), 6.51 (1 H, dd, J=2.5, 3.5 Hz), 7.17 (1 H, dd, J=3.0, 8.8 Hz), 7.36-7.47 (3 H, m), 7.81 (2 H, d, J=8.3 Hz), 8.09 (1 H, d, J=2.5 Hz), 9.07 (1 H, s).

Example 113

2-(5-{1-[4-(cyclopropylsulfonyl)phenyl]-2-(tetrahydro-2H-pyran-4-yl)ethyl}-1H-pyrrol-2-yl)-5-ethoxypyridine

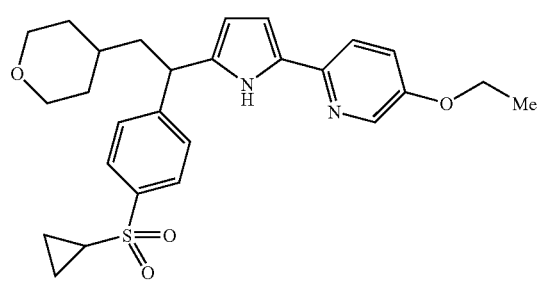

To a solution of 6-(5-{1-[4-(cyclopropylsulfonyl)phenyl]-2-(tetrahydro-2H-pyran-4-yl)ethyl}-1H-pyrrol-2-yl)pyridin- 3-ol (0.260 g) in tetrahydrofuran (10 mL) were added ethanol (0.067 tributylphosphine (0.29 mL) and 1,1'-(azodicarbonyl)dipiperidine (290 mg), and the mixture was stirred at room temperature for 16 hr. The reaction mixture was concentrated under reduced pressure, the residue was dissolved in toluene (10 mL), and hexane (10 mL) was added. The obtained suspension was filtered to remove the precipitate, and the filtrate was concentrated under reduced pressure. The residue was purified by silica gel column chromatography (ethyl acetate:hexane=20:80-70:30, volume ratio) to give the title compound (0.220 g, yield 80%) as a colorless amorphous solid. MS: 481 (MH$^+$).

$^1$H NMR (CDCl$_3$) 0.98-1.07 (2 H, m), 1.19-1.54 (8 H, m), 1.54-1.71 (2 H, m), 1.81-1.94 (1 H, m), 2.00-2.12 (1 H, m), 2.38-2.49 (1 H, m), 3.22-3.34 (2 H, m), 3.88-3.96 (2H, m), 4.06 (2 H, q, J=7.0 Hz), 4.16 (1 H, t, J=7.7 Hz), 6.07-6.15 (1 H, m), 6.51 (1 H, dd, J=2.5, 3.5 Hz), 7.16 (1 H, dd, J=2.9, 8.8 Hz), 7.35-7.47 (3 H, m), 7.77-7.87 (2 H, m), 8.08 (1 H, d, J=2.5 Hz), 9.07 (1 H, s).

Example 114

2-(5-[(1-[4-(cyclopropylsulfonyl)phenyl]-2-(tetrahydro-2H-pyran-4-yl)ethyl]-1H-pyrrol-2-yl)-5-(1-methylethoxy)pyridine

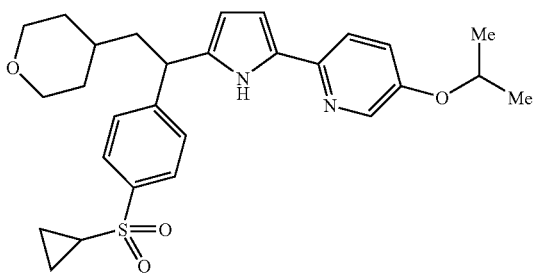

To a solution of 6-(5-[(1-[4-(cyclopropylsulfonyl)phenyl]-2-(tetrahydro-2H-pyran-4-yl)ethyl]-1H-pyrrol-2-yl)pyridin-3-ol (0.260 g) in tetrahydrofuran (10 mL) were added 2-propanol (0.088 mL), tributylphosphine (0.29 mL) and 1,1'-(azodicarbonyl)dipiperidine (290 mg), and the mixture was stirred at room temperature for 16 hr. The reaction mixture was concentrated under reduced pressure, the residue was dissolved in toluene (10 mL), and hexane (10 mL) was added. The obtained suspension was filtered to remove the precipitate, and the filtrate was concentrated under reduced pressure. The residue was purified by silica gel column chromatography (ethyl acetate:hexane=20:80-70:30, volume ratio) to give the title compound (0.220 g, yield 78%) as a colorless amorphous solid. MS: 495 (MH$^+$).

$^1$H NMR (CDCl$_3$) 0.97-1.07 (2 H, m), 1.22-1.50 (11 H, m), 1.59 (2 H, s), 1.82-1.94 (1 H, m), 2.00-2.13 (1 H, m), 2.38-2.50 (1 H, m), 3.22-3.35 (2 H, m), 3.87-3.98 (2H, m), 4.16 (1 H, t, J=7.7 Hz), 4.46-4.59 (1 H, m), 6.09-6.14 (1 H, m), 6.51 (1 H, dd, J=2.6, 3.4 Hz), 7.15 (1 H, dd, J=2.6, 8.9 Hz), 7.36-7.47 (3 H, m), 7.81 (2 H, d, J=8.5 Hz), 8.07 (1 H, d, J=2.6 Hz), 9.06 (1 H, s).

Example 115

1-{[6-(5-{1-[4-(cyclopropylsulfonyl)phenyl]-2-(tetrahydro-2H-pyran-4-yl)ethyl}-1H-pyrrol-2-yl)pyridin-3-yl]oxy}propan-2-one

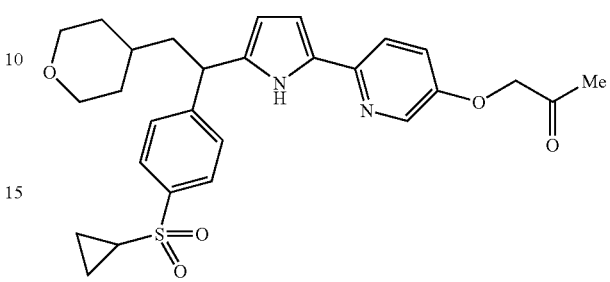

To a solution of 6-(5-{1-[4-(cyclopropylsulfonyl)phenyl]-2-(tetrahydro-2H-pyran-4-yl)ethyl}-1H-pyrrol-2-yl)pyridin-3-ol (0.052 g) in acetone (5 mL) were added chloroacetone (0.01 mL), potassium carbonate (18 mg) and potassium iodide (2 mg), and the mixture was heated under reflux for 11 hr. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=20:80-100:0, volume ratio) to give the title compound (0.038 g, yield 64%) as a colorless amorphous solid. MS: 509 (MH$^+$).

$^1$H NMR (CDCl$_3$) 0.98-1.07 (2 H, m), 1.29-1.47 (5 H, m), 1.59 (3 H, s), 1.82-1.95 (1 H, m), 2.01-2.13 (1 H, m), 2.29 (3H, s), 2.39-2.50 (1 H, m), 3.23-3.34 (2 H, m), 3.88-3.98 (2 H, m), 4.09-4.19 (1 H, m), 4.58 (2 H, s), 6.11-6.15 (1 H, m), 6.53 (1 H, dd, J=2.4, 3.5 Hz), 7.16 (1 H, dd, J=2.4, 8.8 Hz), 7.37-7.48 (3 H, m), 7.82 (1 H, d, J=8.5 Hz), 8.09 (1 H, d, J=2.4 Hz), 9.05 (1 H, s).

Example 116

1-{[6-(5-{1-[4-(cyclopropylsulfonyl)phenyl]-2-(tetrahydro-2H-pyran-4-yl)ethyl}-1H-pyrrol-2-yl)pyridin-3-yl]oxy}-2-methylpropan-2-ol

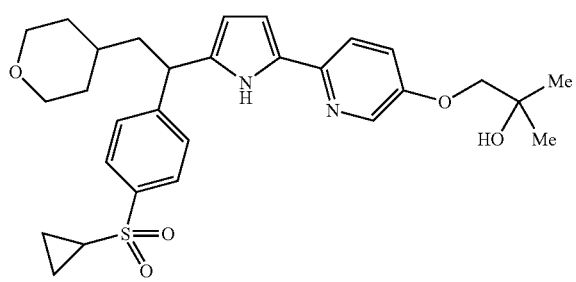

A solution of 1-{[6-(5-{1-[4-(cyclopropylsulfonyl)phenyl]-2-(tetrahydro-2H-pyran-4-yl)ethyl}-1H-pyrrol-2-yl)pyridin-3-yl]oxy}propan-2-one (0.160 g) in tetrahydrofuran (5 mL) was purged with nitrogen, a 1.0M methylmagnesium bromide diethyl ether solution (1.0 mL) was added under ice-cooling, and the mixture was stirred at 0° C. for 30 min. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=30:70-100:0, volume ratio), and recrystallized from hexane-ethyl acetate to give the title compound (0.114 g, yield 69%) as colorless crystals. MS: 525 (MH⁺). melting point 110-112° C.

Example 117

1-{[6-(5-{1-[4-(cyclopropylsulfonyl)phenyl]-2-(tetrahydro-2H-pyran-4-yl)ethyl}-1H-pyrrol-2-yl)pyridin-3-yl]oxy}propan-2-ol

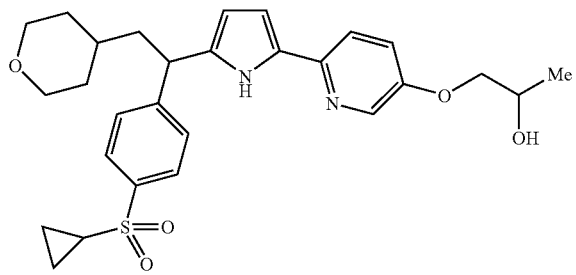

To a solution of 1-[([6-(5-{1-[4-(cyclopropylsulfonyl)phenyl]-2-(tetrahydro-2H-pyran-4-yl)ethyl]-1H-pyrrol-2-yl)pyridin-3-yl]oxy}propan-2-one (0.050 g) in a mixed solvent of tetrahydrofuran (5 mL) and ethanol (1 mL) was added sodium borohydride (18 mg) under ice-cooling. The reaction solution was warmed to room temperature, and stirred at room temperature for 10 hr. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=30:70-100:0, volume ratio), and recrystallized from hexane-ethyl acetate to give the title compound (0.039 g, yield 78%) as colorless crystals. MS: 511 (MH⁺). melting point 116-118° C.

Example 118

Methyl 6-(5-{1-[4-(cyclopropylsulfonyl)phenyl]-2-(tetrahydro-2H-pyran-4-yl)ethyl}-1H-pyrrol-2-yl)pyridine-3-carboxylate

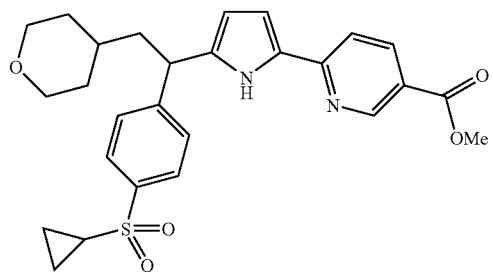

To a solution of 4-[4-(cyclopropylsulfonyl)phenyl]-5-(tetrahydro-2H-pyran-4-yl)pent-1-en-3-one (2.47 g) in ethanol (35 mL) were added methyl 6-formylpyridine-3-carboxylate (1.29 g), 3-benzyl-5-(2-hydroxyethyl)-4-methyl-1,3-thiazol-3-ium chloride (191 mg) and triethylamine (0.397 mL), and the mixture was stirred at 70° C. for 2.5 hr. Water was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=20:80-70:30, volume ratio) to give colorless crystals. To a solution of the obtained crystals in acetic acid (50 mL) was added ammonium acetate (3.41 g), and the mixture was stirred at 110° C. for 2 hr. The reaction mixture was neutralized with saturated aqueous sodium hydrogen carbonate solution, and extracted with ethyl acetate. The extract was washed successively with water and saturated brine, dried over anhydrous magnesium sulfate and concentrated under reduced pressure. The residue was purified by silica gel column chromatography (ethyl acetate:hexane=20:80-80:20, volume ratio), and recrystallized from hexane-ethyl acetate to give the title compound (1.76 g, yield 50%) as pale-yellow crystals. MS: 495 (MH⁺). melting point 150-152° C.

Example 119

N-cyclopropyl-6-(5-{1-[4-(cyclopropylsulfonyl)phenyl]-2-(tetrahydro-2H-pyran-4-yl)ethyl}-1H-pyrrol-2-yl)pyridine-3-carboxamide

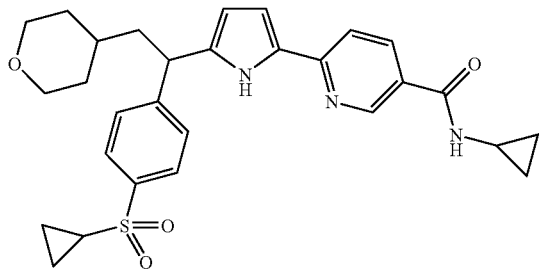

To a solution of 6-(5-{1-[4-(cyclopropylsulfonyl)phenyl]-2-(tetrahydro-2H-pyran-4-yl)ethyl}-1H-pyrrol-2-yl)pyridine-3-carboxylic acid (0.168 g) in N,N-dimethylformamide (5 mL) were added cyclopropylamine (0.036 mL), triethylamine (0.146 mL), N-[3-(dimethylamino)propyl]-N'-ethylcarbodiimide hydrochloride (102 mg) and 1-hydroxybenzotriazole (81 mg), and the mixture was stirred at room temperature for 3 days. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=30:70-100:30, volume ratio), and recrystallized from hexane-ethyl acetate to give the title compound (0.106 g, yield 58%) as colorless crystals. MS: 520 (MH⁺). melting point 134-136° C.

Example 120

5-(azetidin-1-ylcarbonyl)-2-(5-[(1-[4-(cyclopropyl-sulfonyl)phenyl]-2-(tetrahydro-2H-pyran-4-yl)ethyl]-1H-pyrrol-2-yl)pyridine

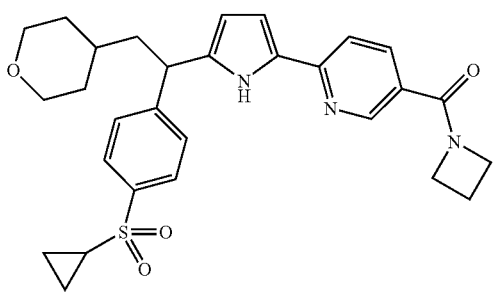

To a solution of 6-(5-{1-[4-(cyclopropylsulfonyl)phenyl]-2-(tetrahydro-2H-pyran-4-yl)ethyl}-1H-pyrrol-2-yl)pyridine-3-carboxylic acid (0.210 g) in N,N-dimethylformamide (5 mL) were added azetidine hydrochloride (61 mg), triethylamine (0.305 ml), N-[3-(dimethylamino)propyl]-N'-ethylcarbodiimide hydrochloride (125 mg) and 1-hydroxybenzotriazole (100 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=40:60-100:0, volume ratio) and recrystallized from hexane-ethyl acetate to give the title compound (0.101 g, yield 44%) as colorless crystals. MS: 520 (MH$^+$). melting point 109-110° C.

Example 121

5-(morpholin-4-ylcarbonyl)-2-(5-[1-[4-(cyclopropyl-sulfonyl)phenyl]-2-(tetrahydro-2H-pyran-4-yl)ethyl]-1H-pyrrol-2-yl)pyridine

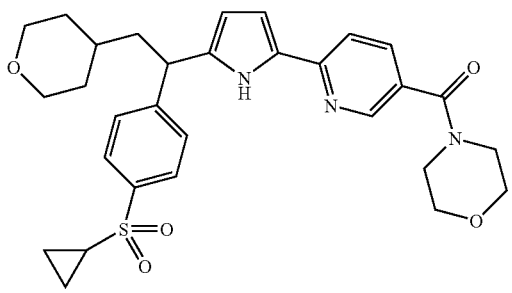

To a solution of 6-(5-{1-[4-(cyclopropylsulfonyl)phenyl]-2-(tetrahydro-2H-pyran-4-yl)ethyl}-1H-pyrrol-2-yl)pyridine-3-carboxylic acid (0.155 g) in N,N-dimethylformamide (5 mL) were added morpholine (0.056 mL), triethylamine (0.135 mL), N-[3-(dimethylamino)propyl]-N'-ethylcarbodiimide hydrochloride (93 mg) and 1-hydroxybenzotriazole (74 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=40:60-100:0, volume ratio) and recrystallized from hexane-ethyl acetate to give the title compound (0.106 g, yield 60%) as colorless crystals. MS: 550 (MH$^+$). melting point 114-116° C.

Example 122

6-(5-{1-[4-(cyclopropylsulfonyl)phenyl]-2-(tetrahydro-2H-pyran-4-yl)ethyl}-1H-pyrrol-2-yl)-N-(2-ethoxyethyl)pyridine-3-carboxamide

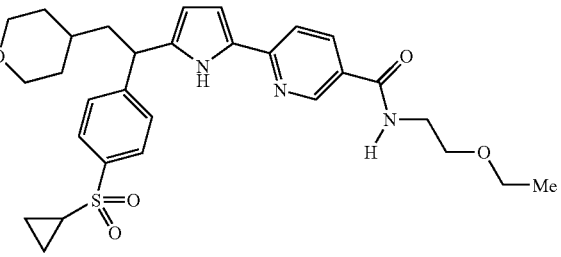

To a solution of 6-(5-[(1-[4-(cyclopropylsulfonyl)phenyl]-2-(tetrahydro-2H-pyran-4-yl)ethyl]-1H-pyrrol-2-yl)pyridine-3-carboxylic acid (0.170 g) in N,N-dimethylformamide (5 mL) were added 2-ethoxyethylamine (0.056 mL), triethylamine (0.247 mL), N-[3-(dimethylamino)propyl]-N'-ethylcarbodiimide hydrochloride (101 mg) and 1-hydroxybenzotriazole (81 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=40:60-100:0, volume ratio) and recrystallized from hexane-ethyl acetate to give the title compound (0.029 g, yield 15%) as colorless crystals. MS: 552 (MH$^+$). melting point 87-90° C.

Example 123

6-(5-[1-[4-(cyclopropylsulfonyl)phenyl]-2-(tetrahydro-2H-pyran-4-yl)ethyl]-1H-pyrrol-2-yl)-N-(2-hydroxy-2-methylpropyl)pyridine-3-carboxamide

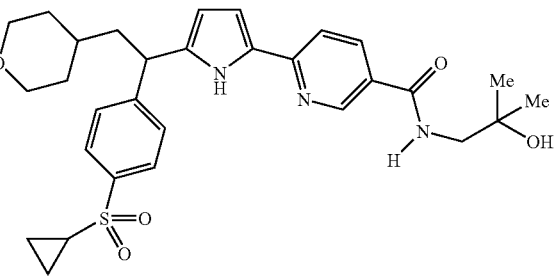

To a solution of 6-(5-{1-[4-(cyclopropylsulfonyl)phenyl]-2-(tetrahydro-2H-pyran-4-yl)ethyl}-1H-pyrrol-2-yl)pyridine-3-carboxylic acid (0.205 g) in N,N-dimethylformamide (5 mL) were added 1-amino-2-methyl-propan-2-ol (76 mg), triethylamine (0.18 mL), N-[3-(dimethylamino)propyl]-N'-ethylcarbodiimide hydrochloride (123 mg) and 1-hydroxybenzotriazole (98 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column 15 chromatography (ethyl acetate:hexane=40:60-100:0, volume ratio) and recrystallized from hexane-ethyl acetate to give the title compound (0.126 g, yield 53%) as colorless crystals. MS: 552 (MH+). melting point 126-128° C.

Example 124

6-(5-{1-[4-(cyclopropylsulfonyl)phenyl]-2-(tetrahydro-2H-pyran-4-yl)ethyl}-1H-pyrrol-2-yl)pyridine-3-carboxamide

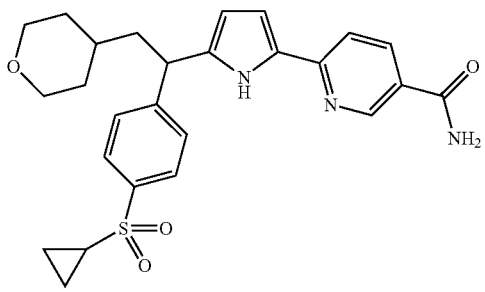

To a solution of 6-(5-{1-[4-(cyclopropylsulfonyl)phenyl]-2-(tetrahydro-2H-pyran-4-yl)ethyl}-1H-pyrrol-2-yl)pyridine-3-carboxylic acid (0.212 g) in N,N-dimethylformamide (5 mL) were added ammonium chloride (117 mg), triethylamine (0.62 mL), N-[3-(dimethylamino)propyl]-N'-ethylcarbodiimide hydrochloride (169 mg) and 1-hydroxybenzotriazole (135 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=40:60-100:0, volume ratio) and recrystallized from hexane-ethyl acetate to give the title compound (0.080 g, yield 38%) as colorless crystals. MS: 480 (MH+). melting point 136-138° C.

Example 125

2-[6-(5-{1-[4-(cyclopropylsulfonyl)phenyl]-2-(tetrahydro-2H-pyran-4-yl)ethyl}-1H-pyrrol-2-yl)pyridin-3-yl]propan-2-ol

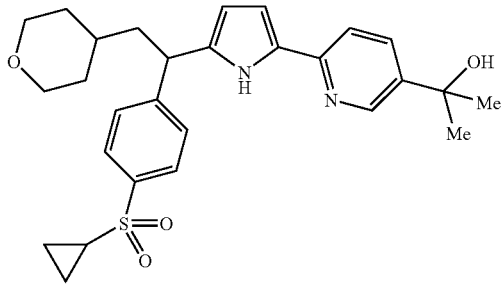

To a solution of 6-(5-{1-[4-(cyclopropylsulfonyl)phenyl]-2-(tetrahydro-2H-pyran-4-yl)ethyl}-1H-pyrrol-2-yl)pyridine-3-carboxylic acid (0.500 g) in N,N-dimethylformamide (10 mL) were added N-methoxymethanamine hydrochloride (152 mg), triethylamine (0.436 mL), N-[3-(dimethylamino)propyl]-N'-ethylcarbodiimide hydrochloride (300 mg) and 1-hydroxybenzotriazole (239 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=30:70-100:0, volume ratio) to give a colorless oil. A solution of the obtained oil in tetrahydrofuran (5 mL) was purged with nitrogen, and a 1.0M methylmagnesium bromide tetrahydrofuran solution (1.5 mL) was added under ice-cooling. The reaction solution was warmed to room temperature, and stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=30:70-100:0, volume ratio) to give a colorless oil. A solution of the obtained oil in tetrahydrofuran (3 mL) was purged with nitrogen, a 1.0M methylmagnesium bromide tetrahydrofuran solution (5.0 mL) was added under ice-cooling, and the mixture was stirred at 0° C. for 4 hr. A saturated aqueous ammonium chloride solution was added to the reaction mixture, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=30:70-100:0, volume ratio) and recrystallized from hexane-ethyl acetate to give the title compound (0.096 g, yield 19%) as colorless crystals. MS: 495 (MH+). melting point 112-114° C.

Example 126

2-(5-{1-[4-(cyclopropylsulfonyl)phenyl]-2-(tetrahydro-2H-pyran-4-yl)ethyl}-1H-pyrrol-2-yl)-5-(2-methylprop-1-en-1-yl)pyridine

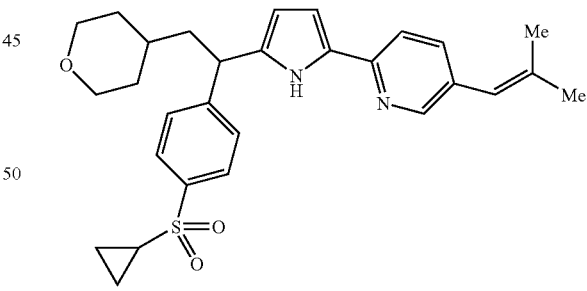

A solution of 4-[4-(cyclopropylsulfonyl)phenyl]-5-(tetrahydro-2H-pyran-4-yl)pent-1-en-3-one (1.20 g) in a mixed solvent of tetrahydrofuran (15 mL) and ethanol (15 mL) was deaerated, 5-(2-methylprop-1-en-1-yl)pyridine-2-carbaldehyde (0.666 g), 3-benzyl-5-(2-hydroxyethyl)-4-methyl-1,3-thiazol-3-ium chloride (93 mg) and triethylamine (0.192 mL) were added, and the mixture was stirred at 70° C. for 1.5 hr under a nitrogen atmosphere. Water was added to the reaction mixture, and the mixture was extracted with ethyl acetate. The extract was washed successively with water and saturated brine, dried over anhydrous magnesium sulfate and concentrated under reduced pressure. To a solution of the residue in acetic acid (50 mL) was added ammonium acetate (2.65 g),

Example 127

1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol

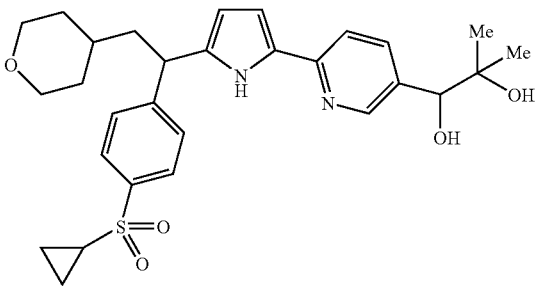

To a solution of 2-(5-[(1-[4-(cyclopropylsulfonyl)phenyl]-2-(tetrahydro-2H-pyran-4-yl)ethyl]-1H-pyrrol-2-yl)-5-(2-methylprop-1-en-1-yl)pyridine (1.04 g) in acetone (12 mL) were added N-methylmorpholine-N-oxide (372 mg) and 4% aqueous osmium tetraoxide solution (3.89 mL), and the mixture was stirred at room temperature for 4 hr. To the reaction mixture was added 1M aqueous sodium thiosulfate solution, and the mixture was stirred at room temperature for 30 min and extracted with ethyl acetate. The extract was washed successively with water and saturated brine, dried over anhydrous magnesium sulfate and concentrated under reduced pressure. The residue was successively purified by silica gel column chromatography (ethyl acetate:hexane=50:50-100:0, volume ratio) and basic silica gel column chromatography (ethyl acetate:hexane=50:50-100:0, volume ratio) to give the title compound (0.178 g, yield 16%) as a colorless amorphous solid. MS: 525 (MH$^+$).

$^1$H NMR (CDCl$_3$) 0.98-1.06 (2 H, m), 1.08 (3 H, s), 1.22-1.29 (4 H, m), 1.30-1.38 (3 H, m), 1.38-1.70 (6 H, m), 1.83-1.95 (1 H, m), 1.99-2.12 (2 H, m), 2.39-2.49 (1 H, m), 2.70 (1 H, d, J=3.0 Hz), 3.22-3.33 (1 H, m), 3.88-3.97 (1H, m), 4.13-4.21 (1 H, m), 4.50 (1 H, d, J=3.0 Hz), 6.13-6.17 (1 H, m), 6.63-6.67 (1 H, m), 7.40 (1 H, d, J=7.3 Hz), 7.48 (1 H, d, J=8.3 Hz), 7.63-7.71 (1 H, m), 7.82 (2 H, d, J=8.3 Hz), 8.33 (1 H, dd, J=2.0, 4.6 Hz), 9.27 (1 H, s).

Example 128

[6-(5-{1-[4-(cyclopropylsulfonyl)phenyl]-2-(tetrahydro-2H-pyran-4-yl)ethyl}-1H-pyrrol-2-yl)pyridin-3-yl]acetonitrile

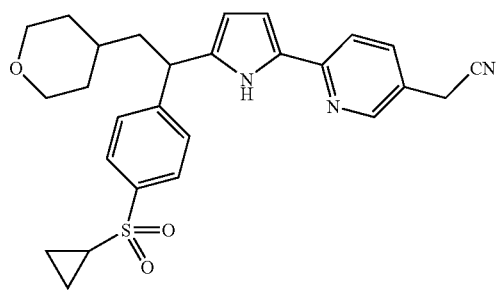

To a solution of [6-(5-{1-[4-(cyclopropylsulfonyl)phenyl]-2-(tetrahydro-2H-pyran-4-yl)ethyl}-1H-pyrrol-2-yl)pyridin-3-yl]methanol (0.500 g) in tetrahydrofuran (10 mL) were added acetone cyanohydrin (202 mg), tributylphosphine (466 mg) and 1,1'-(azodicarbonyl)dipiperidine (540 mg), and the mixture was stirred at room temperature for 12 hr. The reaction mixture was suspended in ethyl acetate and filtered to remove the precipitate, and the filtrate, and the suspension was concentrated under reduced pressure. The residue was successively purified by silica gel column chromatography (ethyl acetate:hexane=20:80-100:0, volume ratio) and basic silica gel column chromatography (ethyl acetate:hexane=20:80-100:0, volume ratio), and recrystallized from hexane-ethyl acetate to give the title compound (0.116 g, yield 23%) as colorless crystals. MS: 476 (MH$^+$). melting point 139-141° C.

Example 129

[6-(5-{1-[4-(cyclopropylsulfonyl)phenyl]-2-(tetrahydro-2H-pyran-4-yl)ethyl}-1H-pyrrol-2-yl)pyridin-3-yl]acetic acid

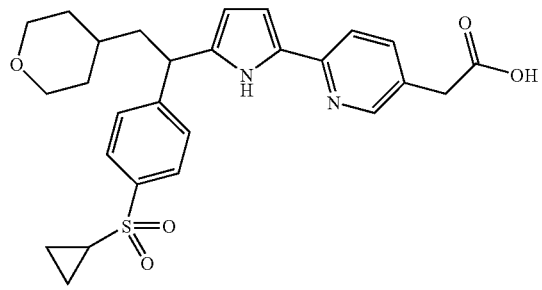

To a solution of [6-(5-{1-[4-(cyclopropylsulfonyl)phenyl]-2-(tetrahydro-2H-pyran-4-yl)ethyl}-1H-pyrrol-2-yl)pyridin-3-yl]acetonitrile (0.200 g) in a mixed solvent of tetrahydrofuran (3 mL) and ethanol (3 mL) was added 4M aqueous sodium hydroxide solution (3 mL), and the mixture was stirred at 90° C. for 16 hr. The reaction mixture was acidified with acetic acid, and extracted with ethyl acetate. The extract was washed successively with water and saturated brine, dried over anhydrous sodium sulfate, and concentrated under reduced pressure. The residue was purified by silica gel column chromatography (ethyl acetate:methanol=100:0-80:20,

Example 130

4-{[6-(5-{1-[4-(cyclopropylsulfonyl)phenyl]-2-(tetrahydro-2H-pyran-4-yl)ethyl}-1H-pyrrol-2-yl)pyridin-3-yl]acetyl}morpholine

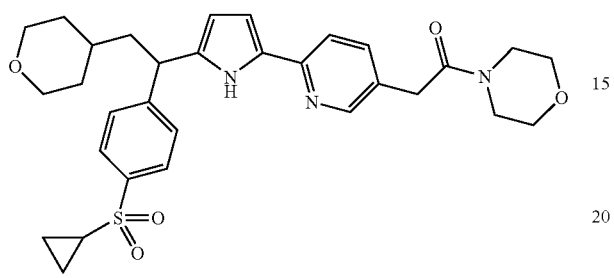

To a solution of [6-(5-{1-[4-(cyclopropylsulfonyl)phenyl]-2-(tetrahydro-2H-pyran-4-yl)ethyl}-1H-pyrrol-2-yl)pyridin-3-yl]acetic acid (0.200 g) in N,N-dimethylformamide (5 mL) were added morpholine (0.053 mL), triethylamine (0.169 mL), N-[3-(dimethylamino)propyl]-N'-ethylcarbodiimide hydrochloride (116 mg) and 1-hydroxybenzotriazole (93 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:hexane=40:60-100:0, volume ratio) and recrystallized from hexane-acetone to give the title compound (0.174 g, yield 76%) as pale-yellow crystals. MS: 564 (MH$^+$). melting point 202-203° C.

Example 131

5-(2-(azetidin-1-yl)-2-oxoethyl)-2-(5-{1-[4-(cyclopropylsulfonyl)phenyl]-2-(tetrahydro-2H-pyran-4-yl)ethyl}-1H-pyrrol-2-yl)pyridine

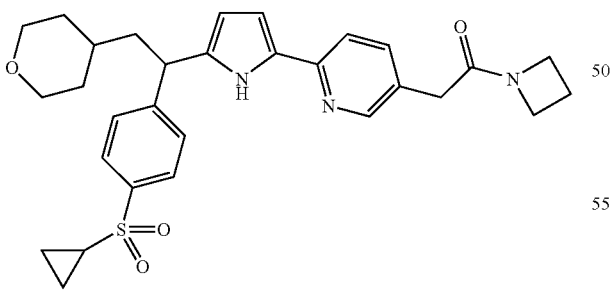

To a solution of [6-(5-{1-[4-(cyclopropylsulfonyl)phenyl]-2-(tetrahydro-2H-pyran-4-yl)ethyl}-1H-pyrrol-2-yl)pyridin-3-yl]acetic acid (0.200 g) in N,N-dimethylformamide (5 mL) were added azetidine hydrochloride (57 mg), triethylamine (0.169 mL), N-[3-(dimethylamino)propyl]-N'-ethylcarbodiimide hydrochloride (116 mg) and 1-hydroxybenzotriazole (93 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated under reduced pressure. The residue was purified by basic silica gel column chromatography (ethyl acetate:methanol=100:0-80:20, volume ratio) and recrystallized from hexane-ethyl acetate to give the title compound (0.115 g, yield 53%) as colorless crystals. MS: 534 (MH$^+$). melting point 94-98° C.

Example 132

2-[6-(5-{1-[4-(cyclopropylsulfonyl)phenyl]-2-(tetrahydro-2H-pyran-4-yl)ethyl}-1H-pyrrol-2-yl)pyridin-3-yl]acetamide

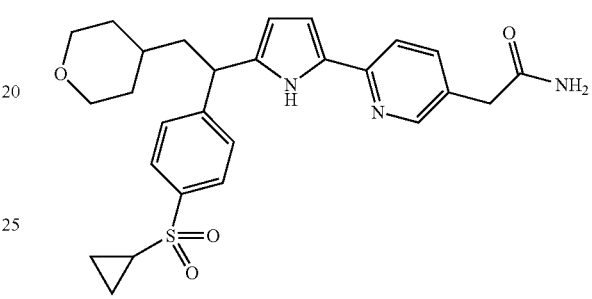

To a solution of [6-(5-{1-[4-(cyclopropylsulfonyl)phenyl]-2-(tetrahydro-2H-pyran-4-yl)ethyl}-1H-pyrrol-2-yl)pyridin-3-yl]acetic acid (0.320 g) in N,N-dimethylformamide (6 mL) were added 1-hydroxybenzotriazole ammonia complex (234 mg), triethylamine (0.271 mL) and N-[3-(dimethylamino)propyl]-N'-ethylcarbodiimide hydrochloride (186 mg), and the mixture was stirred at room temperature for 16 hr. Water was added to the reaction mixture, and the mixture was extracted with ethyl acetate. The extract was washed successively with water and saturated brine, dried over anhydrous magnesium sulfate and concentrated, under reduced pressure. The residue was purified by basic silica gel column chromatography (ethyl acetate:hexane=50:50-100:0, volume ratio) and recrystallized from hexane-acetone to give the title compound (0.240 g, yield 75%) as colorless crystals. MS: 494 (MH$^+$). melting point 151-153° C.

Example 133

1-[6-(5-{1-[3-chloro-4-(methylsulfonyl)phenyl]-2-(tetrahydro-2H-pyran-4-yl)ethyl}-1H-pyrrol-2-yl)pyridin-3-yl]-2-methylpropane-1,2-diol

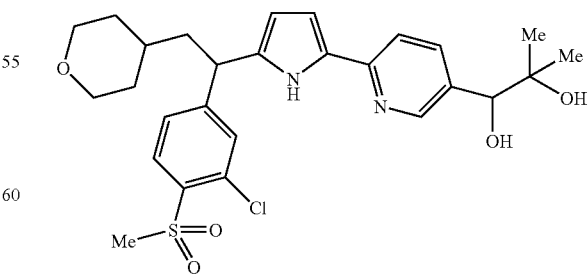

A solution of 4-[3-chloro-4-(methylsulfonyl)phenyl]-5-(tetrahydro-2H-pyran-4-yl)pent-1-en-3-one (0.600 g) in a mixed solvent of ethanol (5 mL) and tetrahydrofuran (5 mL) was deaerated, and 5-(1,2-dihydroxy-2-methylpropyl)pyridine-2-carbaldehyde (491 mg), 3-benzyl-5-(2-hydroxyethyl)-4-methyl-1,3-thiazol-3-ium chloride (45 mg) and triethylamine (0.093 mL) were added. The reaction solution was purged with nitrogen, and stirred at 70° C. for 1 hr. Water was added to the reaction mixture, and the mixture was extracted with ethyl acetate. The extract was washed successively with water and saturated brine, dried over anhydrous sodium sulfate, and concentrated under reduced pressure. To a solution of the residue in acetic acid (15 mL) was added ammonium acetate (647 mg), and the mixture was stirred at 110° C. for 2 hr. The reaction mixture was neutralized with saturated aqueous sodium hydrogen carbonate solution, and extracted with ethyl acetate. The extract was washed successively with water and saturated brine, dried over anhydrous sodium sulfate, and concentrated under reduced pressure. The residue was purified by silica gel column chromatography (ethyl acetate:hexane=30:70-100:0, volume ratio) and recrystallized from hexane-ethyl acetate to give the title compound (0.777 g, yield 87%) as colorless crystals. MS: 533 (MH$^+$). melting point 138-140° C.

Example 134

2-methyl-1-[6-(5-{1-[4-(methylsulfonyl)phenyl]-2-(tetrahydro-2H-pyran-4-yl)ethyl}-1H-pyrrol-2-yl)pyridin-3-yl]propane-1,2-diol

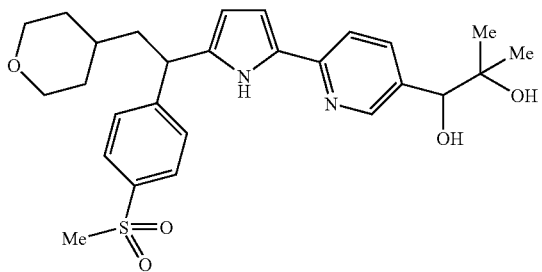

A solution of 4-[4-(methylsulfonyl)phenyl]-5-(tetrahydro-2H-pyran-4-yl)pent-1-en-3-one (1.79 g) in a mixed solvent of ethanol (30 mL) and tetrahydrofuran (30 mL) was deaerated, and 5-(1,2-dihydroxy-2-methylpropyl)pyridine-2-carbaldehyde (1.52 g), 3-benzyl-5-(2-hydroxyethyl)-4-methyl-1,3-thiazol-3-ium chloride (150 mg) and triethylamine (0.310 mL) were added. The reaction solution was purged with nitrogen, and the mixture was stirred at 70° C. for 1.5 hr. Water was added to the reaction mixture, and the mixture was extracted with ethyl acetate. The extract was washed successively with water and saturated brine, dried over anhydrous sodium sulfate, and concentrated under reduced pressure. To a solution of the residue in acetic acid (150 mL) was added ammonium acetate (4.28 g), and the mixture was stirred at 110° C. for 2 hr. The reaction mixture was neutralized with saturated aqueous sodium hydrogen carbonate solution, and extracted with ethyl acetate. The extract was washed successively with water and saturated brine, dried over anhydrous sodium sulfate, and concentrated under reduced pressure. The residue was purified by silica gel column chromatography (ethyl acetate:hexane=20:80-100:0, volume ratio) to give the title compound (1.79 g, yield 65%) as a colorless amorphous solid. MS: 499 (MH$^+$).

$^1$H NMR (CDCl$_3$) 1.07 (3 H, s), 1.23 (3 H, s), 1.25-1.70 (6H, m), 1.81-1.95 (1 H, m), 2.00-2.13 (1 H, m), 2.80 (1 H, s), 3.03 (3 H, s), 3.22-3.34 (2 H, m), 3.87-3.96 (2 H, m), 4.12-4.19 (1 H, m), 4.48 (1 H, s), 6.12-6.16 (1 H, m), 6.63-6.66 (1 H, m), 7.39 (2 H, d, J=7.9 Hz), 7.47 (1 H, d, J=8.3 Hz), 7.63-7.71 (1 H, m), 7.85 (2 H, d, J=8.3 Hz), 8.31 (1 H, dd, J=1.9, 4.7 Hz), 9.38 (1 H, s).

Example 135

4-[6-(5-[(1-[4-(cyclopropylsulfonyl)phenyl]-2-(tetrahydro-2H-pyran-4-yl)ethyl]-1H-pyrrol-2-yl)pyridin-3-yl]tetrahydro-2H-pyran-4-ol

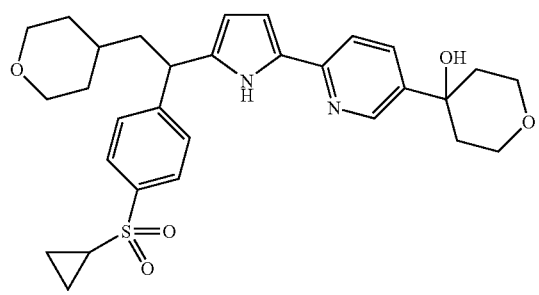

A solution of 2-(1-[(benzyloxy)methyl]-5-{1-[4-(cyclopropylsulfonyl)phenyl]-2-(tetrahydro-2H-pyran-4-yl)ethyl}-1H-pyrrol-2-yl)-5-bromopyridine (0.710 g) in tetrahydrofuran (12 mL) was purged with nitrogen, a 1.6M n-butyllithium hexane solution (0.74 mL) was added at −78° C., and the mixture was stirred at −78° C. for 30 min. To the reaction solution was added tetrahydro-4H-pyran-4-one (0.11 mL), and the mixture was stirred at −78° C. for 3 hr. The reaction mixture was warmed to room temperature, and stirred at room temperature for 1 hr. A saturated aqueous ammonium chloride solution was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=20:80-80:20, volume ratio) to give a yellow oil. To a solution of the obtained oil in a mixed solvent of tetrahydrofuran (4 mL) and ethanol (4 mL) was added 20% palladium hydroxide-carbon (100 mg), and the mixture was purged with hydrogen, and stirred at room temperature for 24 hr. The reaction mixture was filtered, and the filtrate was concentrated under reduced pressure. To a solution of the residue in tetrahydrofuran (10 mL) was added 2M aqueous sodium hydroxide solution, and the mixture was heated under reflux for 3 hr. A saturated aqueous ammonium chloride solution was added to the reaction mixture, and the m mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=70:30-100:0, volume ratio) to give the title compound (0.074 g, yield 12%) as colorless crystals. MS: 537 (MH$^+$).

$^1$H NMR (CDCl$_3$) δ1.13-1.70 (19 H, m), 1.82-1.93 (1 H, m), 2.01-2.13 (1 H, m), 3.28 (2 H, t, J=11.7 Hz), 3.65-3.78 (4H, m), 3.92 (2 H, d, J=11.7 Hz), 4.12-4.21 (1 H, m), 6.13 (1 H, t, J=3.1 Hz), 6.64 (1 H, dd, J=3.6, 2.4 Hz), 6.97-7.03 (1H, m), 7.38 (2 H, d, J=8.5 Hz), 7.47-7.52 (1 H, m).

Example 136

2-(methylsulfanyl)-5-[1-(5-(pyridin-2-yl)-1H-pyrrol-2-yl)-2-(tetrahydro-2H-pyran-4-yl)ethyl]pyridine

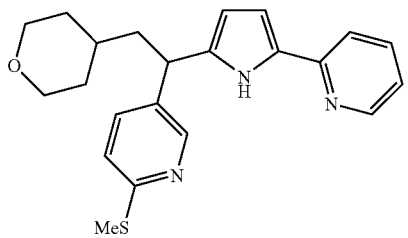

To a solution of 4-[6-(methylsulfanyl)pyridin-3-yl]-5-(tetrahydro-2H-pyran-4-yl)pent-1-en-3-one (0.485 g) in ethanol (16 mL) were added pyridine-2-carbaldehyde (0.189 mL), 3-benzyl-5-(2-hydroxyethyl)-4-methyl-1,3-thiazol-3-ium chloride (49 mg) and triethylamine (0.189 mL), and the mixture was heated under reflux for 2 hr. Water was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=5:95-60:40, volume ratio) to give a colorless oil. To a solution of the obtained oil in acetic acid (15 mL) was added ammonium acetate (1.28 g), and the mixture was stirred at 110° C. for 3 hr. The reaction mixture was neutralized with saturated aqueous sodium hydrogen carbonate solution, and extracted with ethyl acetate. The extract was washed successively with water and saturated brine, dried over anhydrous sodium sulfate, and concentrated under reduced pressure. The residue was purified by silica gel column chromatography (ethyl acetate:hexane=5:95-40:60, volume ratio) to give the title compound (0.365 g, yield 58%) as a colorless oil. MS: 380 (MH$^+$).

$^1$H NMR (300 MHz, CDCl$_3$) δ1.22-1.49 (3 H, m), 1.56 (1 H, d, J=12.4 Hz), 1.67 (1 H, d, J=12.4 Hz), 1.80-1.93 (1 H, m), 1.96-2.09 (1 H, m), 2.55 (3 H, s), 3.22-3.33 (2 H, m), 3.85-3.97 (2 H, m), 4.01-4.08 (1 H, m), 6.06-6.11 (1H, m), 6.59-6.64 (1 H, m), 6.95-7.02 (1 H, m), 7.11 (1 H, d, J=8.3 Hz), 7.34 (1 H, dd, J=2.4, 8.3 Hz), 7.45-7.51 (1 H, m), 7.55-7.63 (1 H, m), 8.31-8.40 (2 H, m), 9.37 (1 H, s).

Example 137

2-(methylsulfonyl)-5-[1-(5-(pyridin-2-yl)-1H-pyrrol-2-yl)-2-(tetrahydro-2H-pyran-4-yl)ethyl]pyridine

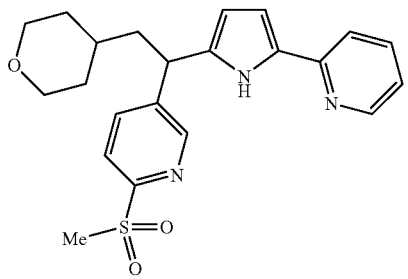

To a solution of 2-(methylsulfanyl)-5-[1-(5-(pyridin-2-yl)-1H-pyrrol-2-yl)-2-(tetrahydro-2H-pyran-4-yl)ethyl]pyridine (0.365 g) in a mixed solvent of tetrahydrofuran (10 mL), methanol (5 mL) and water (5 mL) was added Oxone (registered trade mark, 1.77 g), and the mixture was stirred at room temperature for 2 hr. To the reaction mixture was added saturated aqueous sodium hydrogen carbonate solution, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=20:80-80:20, volume ratio) and recrystallized from hexane-ethyl acetate to give the title compound (0.200 g, yield 51%) as colorless crystals. MS: 412 (MH$^+$). melting point 89-90° C.

Example 138

Optically Active Form of 1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol

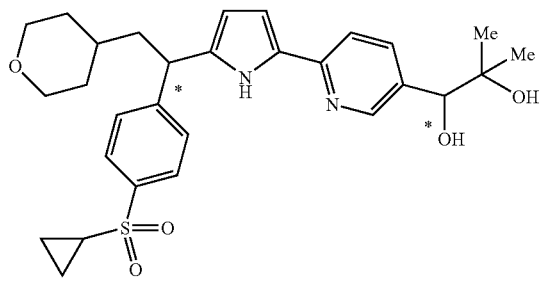

1-[6-(5-{1-[4-(Cyclopropylsulfonyl)phenyl]-2-(tetrahydro-2H-pyran-4-yl)ethyl}-1H-pyrrol-2-yl)pyridin-3-yl]-2-methylpropane-1,2-diol (129 mg) was dissolved in methanol to prepare a solution of 1.0 mg/mL concentration. The solution was subjected to supercritical fluid chromatography using CHIRALCEL OD-H (LA060, 4.6 mmID×250 mL). Using carbon dioxide-methanol-diethylamine (600:400:1, volume ratio) as a mobile phase, the solution was eluted at flow rate 2.35 mL/min and at 40° C., and the fraction was separated at retention time 6.38 min, and concentrated to give the title compound (20.6 mg) as a colorless amorphous solid. MS: 499 (MH$^+$).

Example 139

Optically Active Form of 1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol

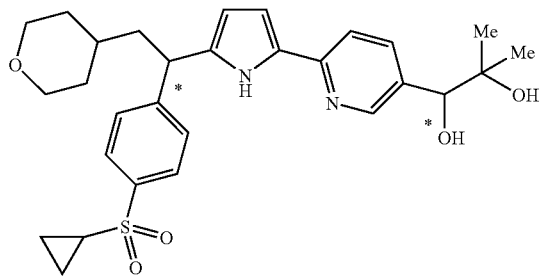

1-[6-(5-{1-[4-(Cyclopropylsulfonyl)phenyl]-2-(tetrahydro-2H-pyran-4-yl)ethyl}-1H-pyrrol-2-yl)pyridin-3-yl]-2-methylpropane-1,2-diol (129 mg) was dissolved in methanol to prepare a solution of 1.0 mg/mL concentration. The solution was subjected to supercritical fluid chromatography using CHIRALCEL OD-H (LA060, 4.6 mmID×250 mL). Using carbon dioxide-methanol-diethylamine (600:400:1, volume ratio) as a mobile phase, the solution was eluted at flow rate 2.35 mL/min and at 40° C., and the fraction was separated at retention time 7.90 min, and concentrated to give the title compound (18.3 mg) as a colorless amorphous solid. MS: 499 (MH⁺).

Example 140

Optically Active Form of 1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol

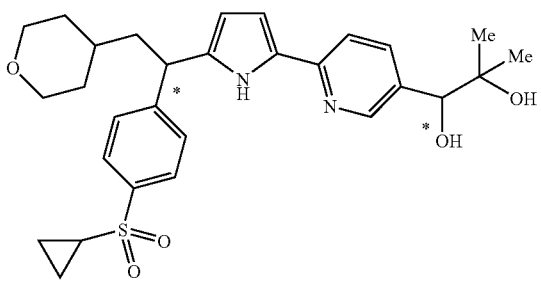

1-[6-(5-{1-[4-(Cyclopropylsulfonyl)phenyl]-2-(tetrahydro-2H-pyran-4-yl)ethyl}-1H-pyrrol-2-yl)pyridin-3-yl]-2-methylpropane-1,2-diol (129 mg) was dissolved in methanol to prepare a solution of 1.0 mg/mL concentration. The solution was subjected to supercritical fluid chromatography using CHIRALCEL OD-H (LA060, 4.6 mmID×250 mL). Using carbon dioxide-methanol-diethylamine (600:400:1, volume ratio) as a mobile phase, the solution was eluted at flow rate 2.35 mL/min and at 40° C., and the fraction was separated at retention time 9.77 min, and concentrated. The obtained solid was dissolved again in methanol to prepare a solution of 5.0 mg/mL concentration. The solution was subjected to supercritical fluid chromatography using CHIRALPAK AS-H (LA005, 20 mmID×250 mL). Using carbon dioxide-methanol-diethylamine (600:400:1, volume ratio) as a mobile phase, the solution was eluted at flow rate 50 mL/min and at 35° C., and the fraction was separated at retention time 3.05 min, and concentrated to give the title compound (16.8 mg) as a colorless amorphous solid. MS: 499 (MH⁺).

Example 141

Optically Active Form of 1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol

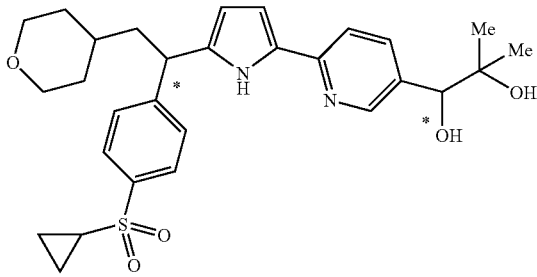

1-[6-(5-{1-[4-(Cyclopropylsulfonyl)phenyl]-2-(tetrahydro-2H-pyran-4-yl)ethyl}-1H-pyrrol-2-yl)pyridin-3-yl]-2-methylpropane-1,2-diol (129 mg) was dissolved in methanol to prepare a solution of 1.0 mg/mL concentration. The solution was subjected to supercritical fluid chromatography using CHIRALCEL OD-H (LA060, 4.6 mmID×250 mL). Using carbon dioxide-methanol-diethylamine (600:400:1, volume ratio) as a mobile phase, the solution was eluted at flow rate 2.35 mL/min and at 40° C., and the fraction was separated at retention time 9.77 min, and concentrated. The obtained solid was dissolved again in methanol to prepare a solution of 5.0 mg/mL concentration. The solution was subjected to supercritical fluid chromatography using CHIRALPAK AS-H (LA005, 20 mmID×250 mL). Using carbon dioxide-methanol-diethylamine (600:400:1, volume ratio) as a mobile phase, the solution was eluted at flow rate 50 mL/min and at 35° C., and the fraction was separated at retention time 4.97 min, and concentrated to give the title compound (17.3 mg) as a colorless amorphous solid. MS: 499 (MH⁺).

Example 142

2-(5-[(1-[4-(cyclopropylsulfonyl)phenyl]-2-(tetrahydro-2H-pyran-4-yl)ethyl]-1H-pyrrol-2-yl)-4-(2,2-dimethyl-1,3-dioxolan-4-yl)-1,3-thiazole

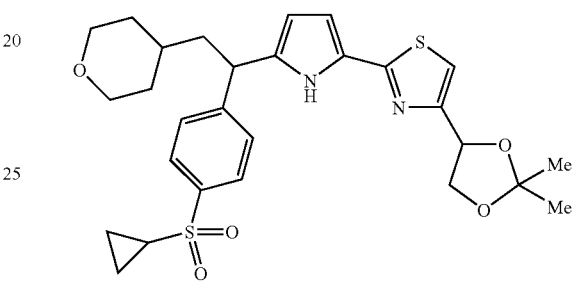

A mixture of 5-[4-(cyclopropylsulfonyl)phenyl]-1-[4-(2,2-dimethyl-1,3-dioxolan-4-yl)-1,3-thiazol-2-yl]-6-(tetrahydro-2H-pyran-4-yl)hexane-1,4-dione (0.47 g), ammonium acetate (1.00 g) and acetic acid (6 mL) was stirred at 100° C. for 1 hr. The reaction mixture was neutralized with saturated aqueous sodium hydrogen carbonate, and extracted with ethyl acetate. The ethyl acetate layer was washed with saturated brine, dried (MgSO₄) and concentrated. The residue was subjected to silica gel column chromatography, and the title compound (0.19 g, yield 42%) was obtained as a colorless amorphous solid from a fraction eluted with ethyl acetate-hexane (2:1, volume ratio). MS: 543 (MH⁺).
¹H NMR (300 MHz, CDCl₃) δ0.99-1.07 (2 H, m), 1.24-1.71 (13 H, m), 1.80-2.10 (2 H, m), 2.40-2.50 (1 H, m), 3.21-3.34 (2 H, m), 3.86-4.00 (3 H, m), 4.07-4.16 (1 H, m), 4.26-4.34 (1 H, m), 5.15 (1 H, t, J=6.5 Hz), 6.09-6.13 (1 H, m), 6.58-6.62 (1 H, m), 7.04 (1 H, d, J=0.6 Hz), 7.30-7.37 (2 H, m), 7.77-7.84 (2 H, m), 9.13 (1 H, brs).

Example 143

1-[2-(5-{1-[4-(cyclopropylsulfonyl)phenyl]-2-(tetrahydro-2H-pyran-4-yl)ethyl}-1H-pyrrol-2-yl)-1,3-thiazol-4-yl]ethane-1,2-diol

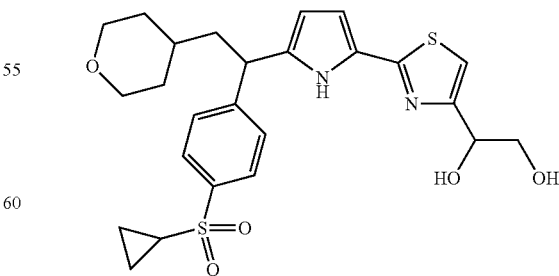

A mixture of 2-(5-{1-[4-(cyclopropylsulfonyl)phenyl]-2-(tetrahydro-2H-pyran-4-yl)ethyl}-1H-pyrrol-2-yl)-4-(2,2-dimethyl-1,3-dioxolan-4-yl)-1,3-thiazole (0.19 g), 1M hydrochloric acid (4 mL) and tetrahydrofuran (6 mL) was stirred at 50° C. for 2 hr. To the reaction mixture was added saturated aqueous sodium hydrogen carbonate, and the mixture was extracted with ethyl acetate. The ethyl acetate layer was m washed with saturated brine, dried (MgSO₄) and concentrated to give the title compound (1.83 g, yield 73%) as a colorless amorphous solid. MS: 503 (MH⁺).

¹H NMR (300 MHz, CDCl₃) δ0.98-1.07 (2 H, m), 1.24-1.70 (7 H, m), 1.80-2.10 (2 H, m), 2.40-2.50 (1 H, m), 2.90 (1 H, brs), 3.20-3.34 (3 H, m), 3.75-3.96 (4 H, m), 4.07-4.17 (1 H, m), 4.73-4.80 (1 H, m), 6.12 (1 H, t, J=3.5 Hz), 6.63 (1 H, dd, J=2.4, 3.5 Hz), 7.00 (1 H, s), 7.32-7.38 (2 H, m), 7.78-7.83 (2 H, m), 9.38 (1 H, brs).

Example 144

[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol

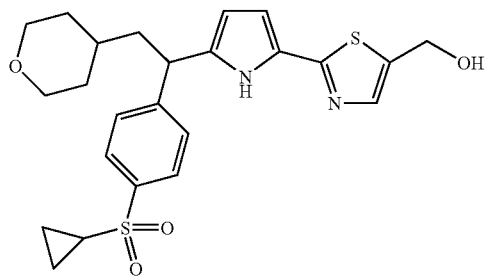

A mixture of 5-[4-(cyclopropylsulfonyl)phenyl]-1-[5-(hydroxymethyl)-1,3-thiazol-2-yl]-6-(tetrahydro-2H-pyran-4-yl)hexane-1,4-dione (0.50 g), ammonium acetate (0.39 g) and acetic acid (4 mL) was stirred at 100° C. for 1 hr. The reaction mixture was neutralized with saturated aqueous sodium hydrogen carbonate, and extracted with ethyl acetate. The ethyl acetate layer was washed with saturated brine, dried (MgSO₄) and concentrated. The residue was subjected to silica gel column chromatography, and the title compound (0.45 g, yield 95%) was obtained as a colorless amorphous solid from a fraction eluted with tetrahydrofuran-hexane (5:1, volume ratio). MS: 473 (MH⁺).

¹H NMR (300 MHz, CDCl₃) δ0.99-1.07 (2 H, m), 1.22-1.65 (7 H, m), 1.78-2.07 (2 H, m), 2.39-2.49 (1 H, m), 2.74 (1 H, brs), 3.20-3.30 (2 H, m), 3.85-3.94 (3 H, m), 4.09 (1 H, t, J=7.8 Hz), 4.79 (2 H, brs), 6.10 (1 H, t, J=3.3 Hz), 6.60 (1 H, dd, J=2.4, 3.3 Hz), 7.30-7.36 (3 H, m), 7.75-7.80 (2 H, m), 9.60 (1 H, brs).

Example 145

4-{[2-(5-[1-[4-(cyclopropylsulfonyl)phenyl]-2-(tetrahydro-2H-pyran-4-yl)ethyl]-1H-pyrrol-2-yl)-1,3-thiazol-5-yl]methyl}morpholine hydrochloride

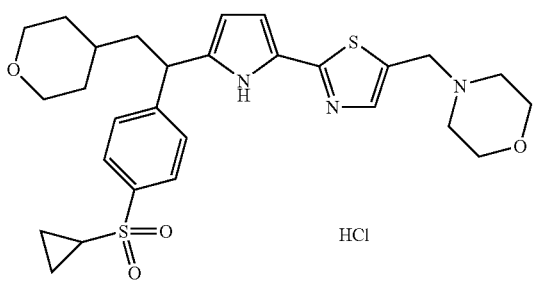

To a mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.40 g), N,N-dimethylformamide (two drops) and tetrahydrofuran (6 mL) was added thionyl chloride (0.12 mL) at 0° C. The reaction mixture was stirred at 0° C. for 1 hr and concentrated. The obtained residue was dissolved in tetrahydrofuran (2 mL), and the solution was added to a mixture of morpholine (0.22 mL), sodium hydrogen carbonate (0.21 g) and N,N-dimethylformamide (6 mL) at 0° C. The reaction mixture was stirred at room temperature for 1 hr, water was added, and the mixture was extracted with ethyl acetate. The ethyl acetate layer was washed with saturated brine, dried (MgSO₄) and concentrated. The residue was subjected to silica gel column chromatography to give a colorless amorphous solid from a fraction eluted with tetrahydrofuran-hexane (2:1, volume ratio). The obtained amorphous solid was dissolved in ethyl acetate, and 4M hydrogen chloride-ethyl acetate solution (0.6 mL) was added. The precipitated crystals were collected by filtration, and dried to give the title compound (0.45 g, yield 95%) as yellow crystals. MS: 542 (MH⁺).

¹H NMR (300 MHz, DMSO-d₆) δ0.96-1.40 (7 H, m), 1.54-1.65 (2H, m), 1.80-1.92 (1 H, m), 2.03-2.16 (1 H, m), 2.74-2.86 (1 H, m), 2.96-3.35 (6 H, m), 3.68-4.02 (6 H, m), 4.32 (1 H, t, J=7.7 Hz), 4.58 (2 H, s), 6.16 (1 H, dd, J=2.7, 3.6 Hz), 6.64 (1 H, dd, J=2.7, 3.6 Hz), 7.56-7.62 (2 H, m), 7.77-7.83 (3 H, m), 11.61 (1 H, brs), 11.79 (1 H, brs).

Example 146

2-(5-{1-[4-(cyclopropylsulfonyl)phenyl]-2-(tetrahydro-2H-pyran-4-yl)ethyl}-1H-pyrrol-2-yl)-5-[(methylsulfonyl)methyl]-1,3-thiazole

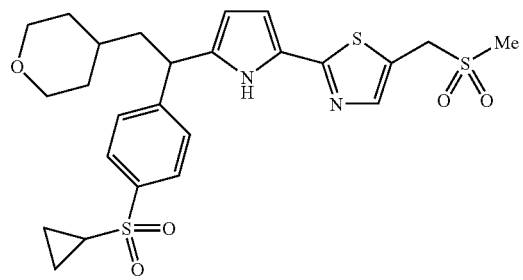

To a mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.16 g), N,N-dimethylformamide (two drops) and tetrahydrofuran (6 mL) was added thionyl chloride (0.05 mL) at 0° C. The reaction mixture was stirred at 0° C. for 1 hr, and concentrated. The obtained residue was dissolved in tetrahydrofuran (2 mL), and added to a mixture of sodium methanesulfinate (70 mg), potassium carbonate (47 mg) and N,N-dimethylformamide (4 mL) at 0° C. The reaction mixture was stirred at room temperature for 1 hr, water was added, and the mixture was extracted with ethyl acetate. The ethyl acetate layer was washed with saturated brine, dried (MgSO₄) and concentrated. The residue was subjected to silica gel column chromatography, and the title compound (0.12 g, yield 65%) was 15 obtained as a colorless amorphous solid from a fraction eluted with tetrahydrofuran-hexane (3:1, volume ratio). MS: 535 (MH⁺).

$^1$H NMR (300 MHz, CDCl$_3$) δ0.98-1.07 (2 H, m), 1.22-1.65 (7 H, m), 1.77-2.05 (2 H, m), 2.40-2.50 (1 H, m), 2.90 (3 H, s), 3.19-3.31 (2 H, m), 3.84-3.94 (2 H, m), 4.10 (1 H, t, J=8.0 Hz), 4.43 (2 H, s), 6.12 (1 H, t, J=3.0 Hz), 6.63 (1 H, dd, J=2.6, 3.5 Hz), 7.26-7.34 (2 H, m), 7.45 (1 H, s), 7.63-7.79 (2 H, m), 9.88 (1 H, brs).

Example 147

1-{[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methyl}imidazolidine-2,4-dione

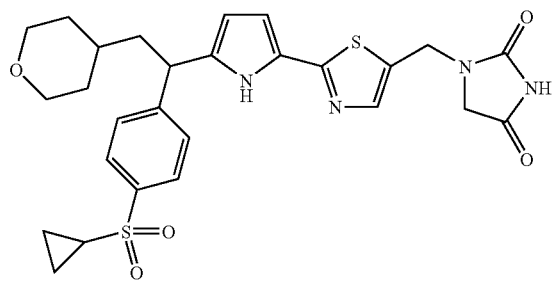

To a mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.77 g), N,N-dimethylformamide (two drops) and tetrahydrofuran (6 mL) was added thionyl chloride (0.24 mL) at 0° C. The reaction mixture was stirred at 0° C. for 1 hr and concentrated. The obtained residue was dissolved in tetrahydrofuran (2 mL) and the solution was added to a mixture of glycine ethyl ester hydrochloride (0.57 g), potassium carbonate (0.80 g) and N,N-dimethylformamide (6 mL) at 0° C. The reaction mixture was stirred at room temperature for 1 hr, water was added, and the mixture was extracted with ethyl acetate. The ethyl acetate layer was washed with saturated brine, dried (MgSO$_4$) and concentrated. The residue was subjected to silica gel column chromatography to give a yellow amorphous solid from a fraction eluted with ethyl acetate. A mixture of the obtained amorphous solid, sodium cyanate (0.04 g) and water (2 mL) was adjusted to pH 4-5 with acetic acid, and the mixture was stirred at 60° C. overnight. Sodium cyanate (0.02 g) was added, and the mixture was stirred at 80° C. for 2 hr and at 100° C. overnight. Water was added to the reaction mixture, and the mixture was extracted with ethyl acetate. The ethyl acetate layer was washed with saturated brine, dried (MgSO$_4$) and concentrated. The residue was subjected to silica gel column chromatography, and the title compound (0.17 g, yield 63%) was obtained as yellow crystals from a fraction eluted with tetrahydrofuran-hexane (3:1, volume ratio). melting point 184-185° C. MS: 555 (MH$^+$).

Example 148

[2-(5-{1-[4-(cyclopropylsulfonyl)phenyl]-2-(tetrahydro-2H-pyran-4-yl)ethyl}-1H-pyrrol-2-yl)-1,3-thiazol-5-yl]acetonitrile

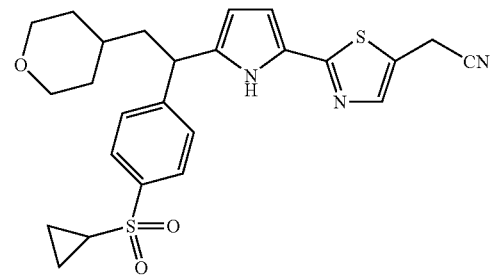

To a mixture of [2-(5-{1-[4-(cyclopropylsulfonyl)phenyl]-2-(tetrahydro-2H-pyran-4-yl)ethyl}-1H-pyrrol-2-yl)-1,3-s thiazol-5-yl]methanol (0.45 g), N,N-dimethylformamide (two drops) and tetrahydrofuran (6 mL) was added thionyl chloride (0.14 mL) at 0° C. The reaction mixture was stirred at 0° C. for 1 hr and concentrated. The obtained residue was dissolved in tetrahydrofuran (2 mL), and the solution was added to a mixture of sodium cyanide (93 mg), potassium carbonate (0.26 g) and N,N-dimethylformamide (6 mL) at 0° C. The reaction mixture was stirred at room temperature for 2 hr, water was added, and the mixture was extracted with ethyl acetate. The ethyl acetate layer was washed with saturated brine, dried (MgSO$_4$) and concentrated. The residue was subjected to silica gel column chromatography, and the title compound (0.23 g, yield 51%) was obtained as a yellow amorphous solid from a fraction eluted with ethyl acetate-hexane (9:1, volume ratio). MS: 482 (MH$^+$).

$^1$H NMR (300 MHz, CDCl$_3$) δ1.00-1.10 (2 H, m), 1.24-1.67 (7 H, m), 1.79-2.08 (2 H, m), 2.40-2.50 (1 H, m), 3.20-3.33 (2H, m), 3.85-3.96 (4 H, m), 4.10 (1 H, t, J=7.8 Hz), 6.12 (1H, t, J=3.0 Hz), 6.61 (1 H, dd, J=3.0, 3.9 Hz), 7.27-7.34 (2H, m), 7.43 (1 H, t, J=1.1 Hz), 7.75-7.82 (2 H, m), 9.52 (1 H, brs).

Example 149

[2-(5-{1-[4-(cyclopropylsulfonyl)phenyl]-2-(tetrahydro-2H-pyran-4-yl)ethyl}-1H-pyrrol-2-yl)-1,3-thiazol-5-yl]acetic acid

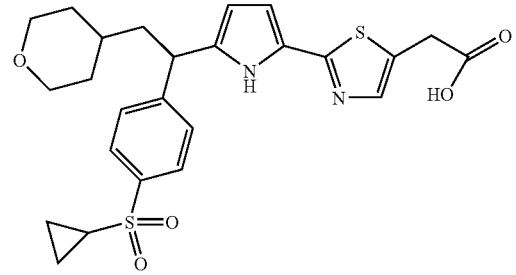

A mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]acetonitrile (0.23 g), 2M aqueous sodium hydroxide solution (0.50 mL), tetrahydrofuran (4 mL) and ethanol (4 mL) was stirred with heating under reflux for 6 hr. Water was added to the reaction mixture, and the mixture was washed

Example 150

2-(5-{1-[4-(cyclopropylsulfonyl)phenyl]-2-(tetrahydro-2H-pyran-4-yl)ethyl}-1H-pyrrol-2-yl)-5-[(3,3-difluoropyrrolidin-1-yl)methyl]-1,3-thiazole dihydrochloride

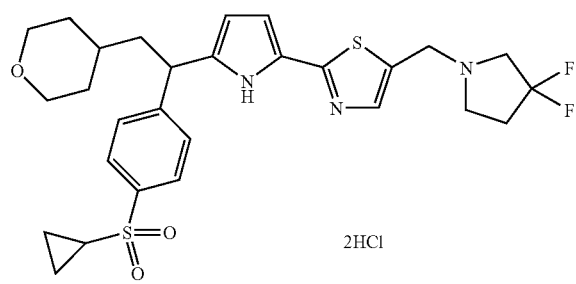

To a mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.30 g), N,N-dimethylformamide (two drops) and tetrahydrofuran (6 mL) was added thionyl chloride (0.09 mL) at 0° C. The reaction mixture was stirred at 0° C. for 1 hr and concentrated. The obtained residue was dissolved in tetrahydrofuran (2 mL), and the solution was added to a mixture of 3,3-difluoropyrrolidine hydrochloride (0.18 g), potassium carbonate (0.17 g) and N,N-dimethylformamide (6 mL) at 0° C. The reaction mixture was stirred at room temperature for 2 hr, water was added, and the mixture was extracted with ethyl acetate. The ethyl acetate layer was washed with saturated brine, dried (MgSO$_4$) and concentrated. The residue was subjected to basic silica gel column chromatography, and a yellow amorphous solid was obtained from a fraction eluted with ethyl acetate-hexane (3:1, volume ratio). The obtained amorphous solid was dissolved in ethyl acetate, and 4M hydrogen chloride-ethyl acetate solution (0.5 mL) was added. The precipitated crystals were collected by filtration, and dried to give the title compound (0.17 g, yield 43%) as a yellow amorphous solid. MS: 562 (MH$^+$).

$^1$H NMR (300 MHz, DMSO-d$_6$) δ0.98-1.42 (7 H, m), 1.60 (2 H, brt, J=10.2 Hz), 1.79-1.92 (1 H, m), 2.02-2.16 (1 H, m), 2.50-2.70 (2 H, m), 2.75-2.85 (1 H, m), 3.15 (2 H, brt, J=11.6 Hz), 3.53 (2 H, brs), 3.72-3.87 (4 H, m), 4.32 (1 H, t, J=7.8 Hz), 4.67 (2 H, s), 6.12 (2 H, brs), 6.17 (1 H, t, J=2.9 Hz), 6.66 (1 H, t, J=2.9 Hz), 7.55-7.62 (2 H, m), 7.77-7.83 (2H, m), 7.85 (1 H, s), 11.82 (1 H, brs).

Example 151

1-[2-(5-{1-[4-(cyclopropylsulfonyl)phenyl]-2-(tetrahydro-2H-pyran-4-yl)ethyl]-1H-pyrrol-2-yl)-1,3-thiazol-5-yl]ethanol

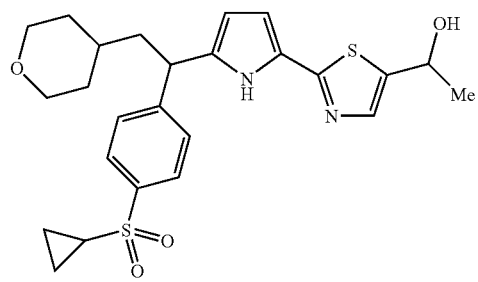

A mixture of 5-[4-(cyclopropylsulfonyl)phenyl]-1-[5-(1-hydroxyethyl)-1,3-thiazol-2-yl]-6-(tetrahydro-2H-pyran-4-yl)hexane-1,4-dione (1.36 g), ammonium acetate (1.33 g) and acetic acid (15 mL) was stirred at 100° C. for 2 hr. The reaction mixture was neutralized with 8M aqueous sodium hydroxide solution, and extracted with ethyl acetate. The ethyl acetate layer was concentrated, 2M aqueous sodium hydroxide solution (4 mL), tetrahydrofuran (8 mL) and methanol (8 mL) were added to the residue, and the mixture was stirred with heating under reflux for 2 hr. Water was added to the reaction mixture, and the mixture was extracted with ethyl acetate. The ethyl acetate layer was washed with saturated brine, dried (MgSO$_4$) and concentrated. The residue was subjected to basic silica gel column chromatography, and the title compound (0.43 g, yield 33%) was obtained as a yellow amorphous solid from a fraction eluted with ethyl acetate-hexane (4:1, volume ratio). MS: 487 (MH$^+$).

$^1$H NMR (300 MHz, CDCl$_3$) δ0.98-1.06 (2 H, m), 1.23-1.68 (10H, m), 1.80-2.08 (2 H, m), 2.39-2.48 (1 H, m), 2.50 (1H, brd, J=3.3 Hz), 3.20-3.31 (2 H, m), 3.85-3.94 (2 H, m), 4.10 (1 H, t, J=7.7 Hz), 5.05-5.46 (1 H, m), 6.09 (1 H, t, J=3.6 Hz), 6.58 (1 H, dd, J=2.4, 3.6 Hz), 7.30-7.36 (3 H, m), 7.75-7.81 (2 H, m), 9.40 (1 H, brs).

Example 152

1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]-2-methoxyethanol

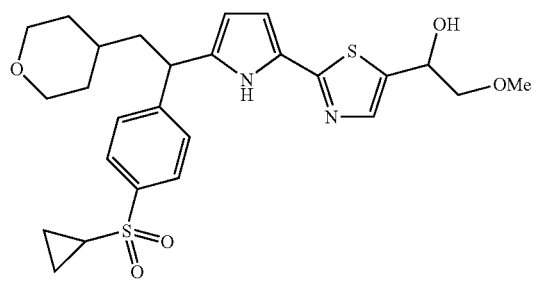

A mixture of 5-[4-(cyclopropylsulfonyl)phenyl]-1-[5-(1-hydroxy-2-methoxyethyl)-1,3-thiazol-2-yl]-6-(tetrahydro-2H-pyran-4-yl)hexane-1,4-dione (1.36 g), ammonium acetate (1.33 g) and acetic acid (15 mL) was stirred at 100° C. for 2 hr. The reaction mixture was neutralized with 8M aqueous sodium hydroxide solution, and extracted with ethyl acetate. The ethyl acetate layer was concentrated, 2M aqueous sodium hydroxide solution (1.3 mL), tetrahydrofuran (6 mL) and methanol (6 mL) were added to the residue, and the mixture was stirred with heating under reflux for 2 hr. Water was added to the reaction mixture, and the mixture was extracted with ethyl acetate. The ethyl acetate layer was washed with saturated brine, dried (MgSO$_4$) and concentrated. The residue was subjected to basic silica gel column chromatography, and the title compound (1.27 g, yield 90%) was obtained as a yellow amorphous solid from a fraction eluted with ethyl acetate-hexane (4:1, volume ratio). MS: 517 (MH$^+$).

$^1$H NMR (300 MHz, CDCl$_3$) δ0.98-1.06 (2 H, m), 1.23-1.65 (7 H, m), 1.77-2.06 (2 H, m), 2.39-2.48 (1 H, m), 3.19-3.35 (3H, m), 3.44 (3 H, s), 3.50-3.66 (2 H, m), 3.85-3.94 (2 H, m), 4.09 (1 H, t, J=7.8 Hz), 5.06-5.12 (1 H, m), 6.09 (1 H, dd, J=2.8, 3.5 Hz), 6.58 (1 H, dd, J=2.8, 3.5 Hz), 7.28-7.36 (2 H, m), 7.43 (1 H, t, J=0.6 Hz), 7.75-7.80 (2 H, m), 9.51 (1 H, brs).

Example 153

2-(5-[1-[4-(cyclopropylsulfonyl)phenyl]-2-(tetrahydro-2H-pyran-4-yl)ethyl]-1H-pyrrol-2-yl)-5-[(2-methoxyethoxy)methyl]-1,3-thiazole

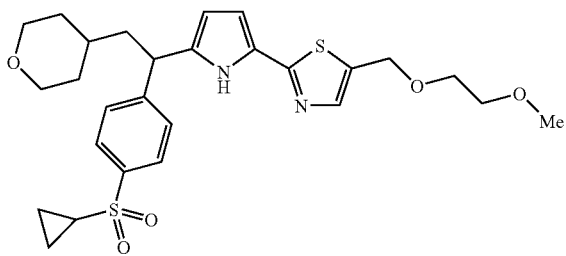

A mixture of 5-[4-(cyclopropylsulfonyl)phenyl]-1-[5-[(2-methoxyethoxy)methyl]-1,3-thiazol-2-yl]-6-(tetrahydro-2H-pyran-4-yl)hexane-1,4-dione (0.52 g), ammonium acetate (0.55 g) and acetic acid (6 mL) was stirred at 100° C. for 2 hr. The reaction mixture was neutralized with 8M aqueous sodium hydroxide solution, and extracted with ethyl acetate. The ethyl acetate layer was washed with saturated brine, dried (MgSO$_4$) and concentrated. The residue was subjected to silica gel column chromatography, and the title compound (0.47 g, yield 94%) was obtained as a yellow resin from a fraction eluted with tetrahydrofuran-hexane (1:4, volume ratio). MS: 531 (MH$^+$).

$^1$H NMR (300 MHz, CDCl$_3$) δ0.99-1.07 (2 H, m), 1.25-1.44 (5 H, m), 1.52-1.69 (2 H, m), 1.82-1.93 (1 H, m), 1.98-2.09 (1H, m), 2.40-2.49 (1 H, m), 3.22-3.32 (2 H, m), 3.38 (3 H, s), 3.52-3.64 (4 H, m), 3.86-3.95 (2 H, m), 4.12 (1 H, t, J=8.0 Hz), 4.70 (2 H, s), 6.11 (1 H, t, J=3.6 Hz), 6.59 (1 H, dd, J=2.4, 3.6 Hz), 7.32-7.38 (2 H, m), 7.43 (1 H, d, J=0.9 Hz), 7.77-7.84 (2 H, m), 9.17 (1 H, brs).

Example 154

1-{[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methyl}-4-methylpiperidin-4-ol

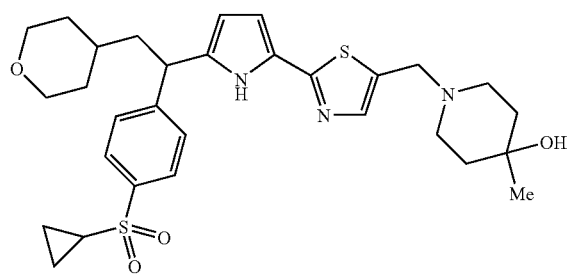

To a mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.30 g), N,N-dimethylformamide (two drops) and tetrahydrofuran (6 mL) was added thionyl chloride (0.09 mL) at 0° C. The reaction mixture was stirred at 0° C. for 1 hr and concentrated. The obtained residue was dissolved in tetrahydrofuran (2 mL), and the solution was added to a mixture of 4-methylpiperidin-4-ol (0.20 g), potassium carbonate (0.17 g) and N,N-dimethylformamide (6 mL) at 0° C. The reaction mixture was stirred at room temperature overnight, water was added, and the mixture was extracted with ethyl acetate. The ethyl acetate layer was washed with saturated brine, dried (MgSO$_4$) and concentrated. The residue was subjected to basic silica gel column chromatography, and the title compound (0.22 g, yield 62%) was obtained as a yellow amorphous solid from a fraction eluted with tetrahydrofuran-hexane (4:1, volume ratio). MS: 570 (MH$^+$). $^1$H NMR (300 MHz, CDCl$_3$) δ0.96-1.06 (2 H, m), 1.20-1.86 (15H, m), 1.92-2.05 (1 H, m), 2.36-2.63 (5 H, m), 3.17-3.30 (2H, m), 3.67 (2 H, s), 3.83-3.93 (2 H, m), 4.06 (1 H, t, J=8.0 Hz), 6.07 (1 H, t, J=2.9 Hz), 6.55 (1 H, t, J=2.9 Hz), 7.25-7.32 (3 H, m), 7.71-7.77 (2 H, m), 10.02 (1 H, brs).

Example 155

1-acetyl-4-{[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methyl}piperazine hydrochloride

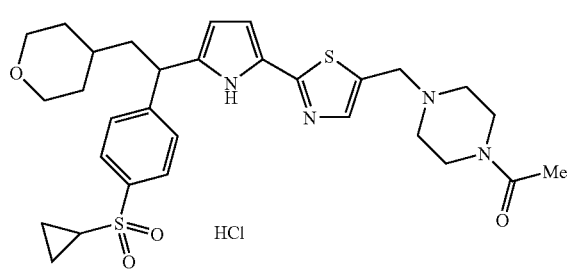

To a mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.30 g), N,N-dimethylformamide (two drops) and tetrahydrofuran (6 mL) was added thionyl chloride (0.09 mL) at 0° C. The reaction mixture was stirred at 0° C. for 1 hr and concentrated. The obtained residue was dissolved in tetrahydrofuran (2 mL) and the solution was added to a mixture of 1-acetylpiperazine (0.20 g), potassium carbonate (0.17 g) and N,N-dimethylformamide (6 mL) at 0° C. The reaction mixture was stirred at room temperature for 2 hr, water was added, and the mixture was extracted with ethyl acetate. The ethyl acetate layer was washed with saturated brine, dried (MgSO$_4$) and concentrated. The residue was subjected to basic silica gel column chromatography, and a yellow amorphous solid was obtained from a fraction eluted with ethyl acetate-hexane (3:1, volume ratio). The obtained amorphous solid was dissolved in ethyl acetate, and 4M hydrogen chloride-ethyl acetate solution (1.0 mL) was added. The precipitated crystals were collected by filtration, and dried to give the title compound (0.17 g, yield 43%) as yellow crystals. melting point 156-158° C. MS: 583 (MH$^+$).

Example 156

1-{[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methyl}piperidin-4-one hydrochloride

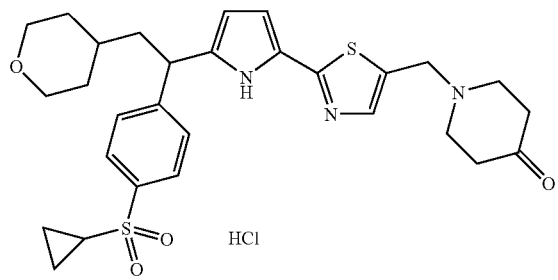

To a mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.30 g), N,N-dimethylformamide (two drops) and tetrahydrofuran (6 mL) was added thionyl chloride (0.09 mL) at 0° C. The reaction mixture was stirred at 0° C. for 1 hr and concentrated. The obtained residue was dissolved in tetrahydrofuran (2 mL) and the solution was added to a mixture of piperidine-4,4-diol hydrochloride (0.19 g), potassium carbonate (0.17 g) and N,N-dimethylformamide (6 mL) at 0° C. The reaction mixture was stirred at room temperature overnight, water was added, and the mixture was extracted with ethyl acetate. The ethyl acetate layer was washed with saturated brine, dried (MgSO$_4$) and concentrated. The residue was subjected to basic silica gel column chromatography to give a yellow amorphous solid from a fraction eluted with tetrahydrofuran-hexane (3:1, volume ratio). The obtained amorphous solid was dissolved in ethyl acetate, and 4M hydrogen chloride-ethyl acetate solution (1.0 mL) was added. The precipitated crystals were collected by filtration, and dried to give the title compound (0.21 g, yield 57%) as yellow crystals. melting point 146-148° C. MS: 554 (MH$^+$).

Example 157

1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]-N,N-dimethylethanamine dihydrochloride

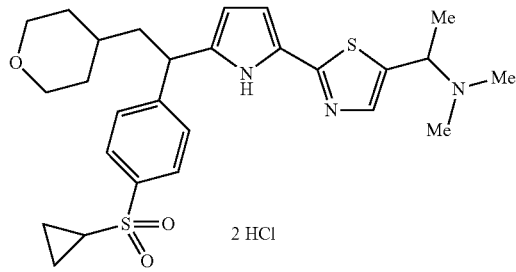

To a mixture of 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethanol (0.26 g), N,N-dimethylformamide (two drops) and tetrahydrofuran (6 mL) was added thionyl chloride (0.08 mL) at 0° C. The reaction mixture was stirred at room temperature for 2 hr, thionyl chloride (0.08 mL) was added, and the mixture was stirred at 60° C. for 3 hr. The reaction mixture was concentrated, and the obtained residue was dissolved in tetrahydrofuran (1 mL) and the solution was added to a mixture of a 2M dimethylamine tetrahydrofuran solution (0.80 mL), potassium carbonate (0.15 g) and N,N-dimethylformamide (4 mL) at 0° C. The reaction mixture was stirred at room temperature overnight, water was added, and the mixture was extracted with ethyl acetate. The ethyl acetate layer was washed with saturated brine, dried (MgSO$_4$) and concentrated. The residue was subjected to basic silica gel column chromatography to give a yellow oil from a fraction eluted with tetrahydrofuran-hexane (3:2, volume ratio). The obtained oil was dissolved in ethyl acetate, and 4M hydrogen chloride-ethyl acetate solution (0.5 mL) was added. The precipitated crystals were collected by filtration, and dried to give the title compound (0.14 g, yield 45%) as yellow crystals. melting point 147-148° C. MS: 513 (M$^+$).

Example 158

2-(5-{1-[4-(cyclopropylsulfonyl)phenyl]-2-(tetrahydro-2H-pyran-4-yl)ethyl}-1H-pyrrol-2-yl)-1,3-thiazole-5-carbaldehyde

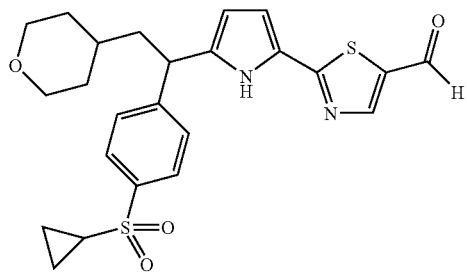

A mixture of [2-(5-{1-[4-(cyclopropylsulfonyl)phenyl]-2-(tetrahydro-2H-pyran-4-yl)ethyl}-1H-pyrrol-2-yl)-1,3-thiazol-5-yl]methanol (0.49 g), Dess-Martin reagent (0.50 g) and acetonitrile (10 mL) was stirred at room temperature overnight. To the reaction mixture was added saturated aqueous sodium hydrogen carbonate, and the mixture was extracted with ethyl acetate. The ethyl acetate layer was washed with saturated brine, dried (MgSO$_4$) and concentrated. The obtained residue was subjected to silica gel column chromatography, and the title compound (0.46 g, yield 98%) was obtained as yellow crystals from a fraction eluted with ethyl acetate-hexane (4:1, volume ratio). melting point 175-176° C. MS: 471 (MH$^+$).

Example 159

N-{[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methyl}-2-(ethylsulfanyl)ethanamine

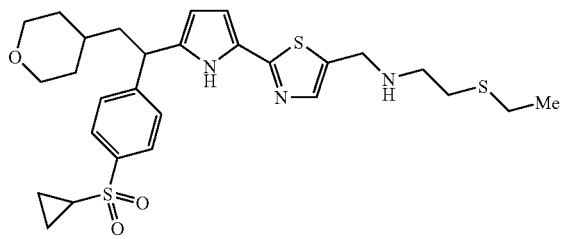

A mixture of 2-(5-{1-[4-(cyclopropylsulfonyl)phenyl]-2-(tetrahydro-2H-pyran-4-yl)ethyl}-1H-pyrrol-2-yl)-1,3-thiazole-5-carbaldehyde (0.31 g), 2-(ethylsulfanyl)ethanamine (0.14 g), acetic acid (1 drop) and tetrahydrofuran (2 mL) was stirred overnight at 50° C. To the reaction mixture was added saturated aqueous sodium hydrogen carbonate, and the mixture was extracted with ethyl acetate. The ethyl acetate layer was m washed with saturated brine, dried (MgSO$_4$) and concentrated. The obtained residue was dissolved in methanol (4 mL), and sodium borohydride (28 mg) was added at 0° C. The reaction mixture was stirred at room temperature for 1 hr, water was added, and the mixture was extracted with ethyl acetate. The ethyl acetate layer was washed with saturated brine, dried (MgSO$_4$) and concentrated. The obtained residue was subjected to silica gel column chromatography, and the title compound (0.37 g, quantitatively) was obtained as a yellow oil from a fraction eluted with tetrahydrofuran-hexane (3:1, volume ratio). MS: 471 (MH$^+$).

$^1$H NMR (300 MHz, CDCl$_3$) δ0.98-1.07 (2 H, m), 1.20-1.68 (10H, m), 1.78-2.09 (2 H, m), 2.39-2.57 (3 H, m), 2.66-2.73 (2 H, m), 2.79-2.88 (2H, m), 3.20-3.32 (2 H, m), 3.86-4.01 (4 H, m), 4.11 (1 H, t, J=8.0 Hz), 6.10 (1 H, t, J=3.3 Hz), 6.57 (1 H, dd, J=2.4, 3.3 Hz), 7.30-7.40 (3 H, m), 7.76-7.83 (2 H, m), 9.27 (1 H, brs).

Example 160

N-{[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methyl}-2-(ethylsulfonyl)ethanamine hydrochloride

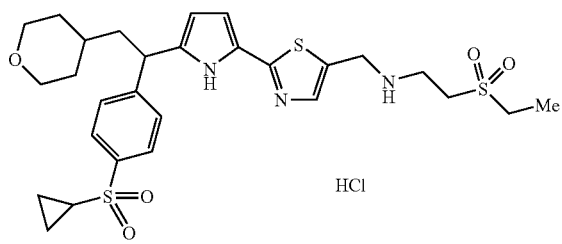

A mixture of N-{[2-(5-{1-[4-(cyclopropylsulfonyl)phenyl]-2-(tetrahydro-2H-pyran-4-yl)ethyl}-1H-pyrrol-2-yl)-1,3-thiazol-5-yl]methyl}-2-(ethylsulfanyl)ethanamine (0.37 g), Oxone (registered trade mark) (0.45 g), water (0.5 mL), tetrahydrofuran (2 mL) and methanol (2 mL) was stirred at room temperature for 4 hr. To the reaction mixture was added saturated aqueous sodium hydrogen carbonate, and the mixture was extracted with ethyl acetate. The ethyl acetate layer was washed with saturated brine, dried (MgSO$_4$) and concentrated. The residue was subjected to silica gel column chromatography to give a yellow oil from a fraction eluted with tetrahydrofuran-hexane (9:1, volume ratio). The obtained oil was dissolved in ethyl acetate, and 4M hydrogen chloride-ethyl acetate solution (1.0 mL) was added. The precipitated solid was collected by filtration, and dried to give the title compound (0.29 g, yield 69%) as yellow crystals. melting point 127-129° C. MS: 592 (MH$^+$).

Example 161

Ethyl (2E)-3-[2-(5-[(1-[4-(cyclopropylsulfonyl)phenyl]-2-(tetrahydro-2H-pyran-4-yl)ethyl]-1H-pyrrol-2-yl)-1,3-thiazol-5-yl]propenoate

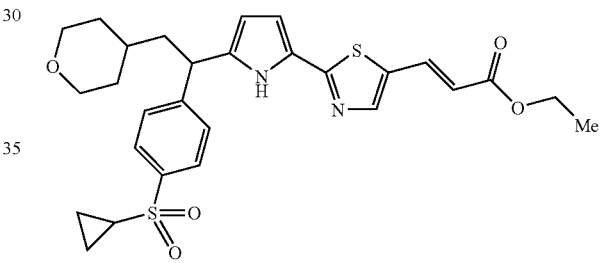

To a suspension of sodium hydride (60%, oil, 0.26 g) in N,N-dimethylformamide (10 mL) was slowly added a mixture of 2-(5-{1-[4-(cyclopropylsulfonyl)phenyl]-2-(tetrahydro-2H-pyran-4-yl)ethyl}-1H-pyrrol-2-yl)-1,3-thiazole-5-carbaldehyde (1.28 g), ethyl diethylphosphonoacetate (0.61 g) and tetrahydrofuran (4 mL) at 0° C. The reaction mixture was stirred at room temperature for 4 hr, 10% citric acid was added, and the mixture was extracted with ethyl acetate. The ethyl acetate layer was washed successively with saturated aqueous sodium hydrogen carbonate and saturated brine, dried (MgSO$_4$) and concentrated. The residue was subjected to silica gel column chromatography, and the title compound (0.84 g, yield 59%) was obtained as a yellow amorphous solid from a fraction eluted with ethyl acetate-hexane (2:1, volume ratio). MS: 541 (MH$^+$).

$^1$H NMR (300 MHz, CDCl$_3$) δ0.99-1.08 (2 H, m), 1.20-1.70 (10H, m), 1.82-2.12 (2 H, m), 2.40-2.50 (1 H, m), 3.20-3.33 (2 H, m), 3.87-3.96 (2 H, m), 4.14 (1 H, t, J=8.7 Hz), 4.24 (2 H, q, J=7.1 Hz), 6.08 (1 H, dd, J=0.6, 15.6 Hz), 6.16 (1 H, t, J=3.2 Hz), 6.69 (1 H, dd, J=2.6, 3.8 Hz), 7.32-7.39 (2 H, m), 7.66 (1 H, s), 7.72 (1 H, dd, J=0.6, 15.6 Hz), 7.78-7.85 (2 H, m), 9.18 (1 H, brs).

Example 162

Ethyl 3-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]propanoate

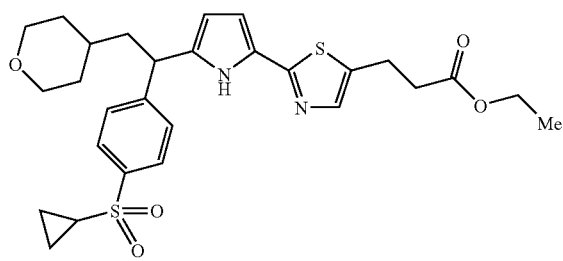

A mixture of ethyl (2E)-3-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]propenoate (0.78 g), 10% palladium carbon (containing 50% water, 0.15 g), tetrahydrofuran (10 mL) and ethanol (5 mL) was stirred under hydrogen atmosphere at room temperature for 2 days. The insoluble material was filtered off, and the filtrate was concentrated. The obtained residue was subjected to silica gel column chromatography, and the title compound (0.58 g, yield 79%) was obtained as a yellow amorphous solid from a fraction eluted with ethyl acetate-hexane (2:1, volume ratio). MS: 543 (MH$^+$).

$^1$H NMR (300 MHz, CDCl$_3$) δ0.98-1.06 (2 H, m), 1.22-1.44 (8 H, m), 1.49-1.65 (2 H, m), 1.77-2.05 (2 H, m), 2.38-2.49 (1H, m), 2.64 (2 H, t, J=7.1 Hz), 3.11 (2 H, t, J=7.1 Hz), 3.19-3.30 (2 H, m), 3.85-3.94 (2 H, m), 4.07 (1 H, t, J=8.0 Hz), 4.14 (2 H, q, J=7.1 Hz), 6.09 (1 H, t, J=3.3 Hz), 6.53 (1 H, dd, J=2.4, 3.3 Hz), 7.25-7.31 (3 H, m), 7.63-7.69 (2 H, m), 9.43 (1 H, brs).

Example 163

3-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]propanoic acid 1/2 calcium salt

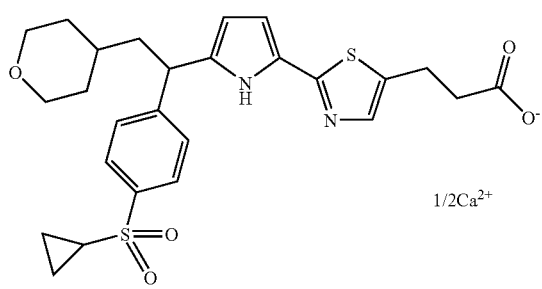

A mixture of ethyl 3-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]propanoate (0.46 g), 1M aqueous sodium hydroxide solution (1.7 mL), methanol (3 mL) and tetrahydrofuran (6 mL) was stirred at room temperature overnight. To the reaction mixture was added 1M hydrochloric acid (1.7 mL), and the mixture was extracted with ethyl acetate. The ethyl acetate layer was washed with saturated brine, dried (MgSO$_4$) and concentrated to give a yellow amorphous solid. To a mixture of the obtained amorphous solid, 1M aqueous sodium hydroxide solution (1.0 mL), methanol (1 mL) and water (10 mL) was added a solution of calcium chloride (94 mg) in water (2 ml). The precipitated solid was collected by filtration, washed with water, and dried to give the title compound (0.34 g) as yellow crystals. melting point>194° C. (decomposition). MS: 515 (MH$^+$).

Example 164

2-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]-1,1-dimethoxypropan-2-ol

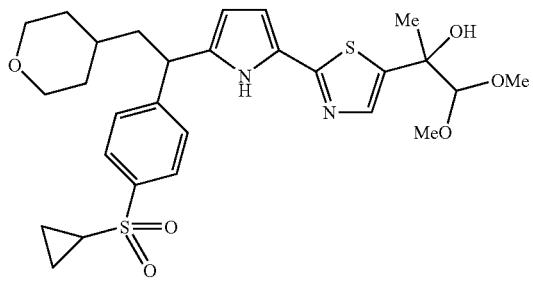

A mixture of 5-[4-(cyclopropylsulfonyl)phenyl]-1-[5-(1-hydroxy-2,2-dimethoxy-1-methylethyl)-1,3-thiazol-2-yl]-6-(tetrahydro-2H-pyran-4-yl)hexane-1,4-dione (1.14 g), ammonium acetate (0.76) and acetic acid (8 mL) was stirred at 100° C. for 1 hr. The reaction mixture was neutralized with 8M aqueous sodium hydroxide solution, and extracted with ethyl acetate. The ethyl acetate layer was washed with saturated aqueous sodium hydrogen carbonate and saturated brine, dried (MgSO$_4$) and concentrated. The residue was subjected to silica gel column chromatography, and the title compound (0.55 g, yield 50%) was obtained as a yellow amorphous solid from a fraction eluted with ethyl acetate-hexane (9:1, volume ratio). MS: 561 (MH$^+$).

$^1$H NMR (300 MHz, CDCl$_3$) δ0.98-1.07 (2 H, m), 1.22-1.67 (10H, m), 1.76-1.90 (1 H, m), 1.95-2.07 (1 H, m), 2.38-2.49 (1 H, m), 3.01 (1 H, d, J=2.4 Hz), 3.20-3.32 (2 H, m), 3.48 (3 H, s), 3.57 (3 H, s), 3.85-3.95 (2 H, m), 4.09 (1 H, t, J=8.0 Hz), 4.20 (1 H, s), 6.10 (1 H, t, J=3.1 Hz), 6.56 (1 H, dd, J=2.6, 3.5 Hz), 7.25-7.34 (2 H, m), 7.47 (1 H, d, J=0.9 Hz), 7.74-7.81 (2 H, m), 9.31 (1 H, brs).

Example 165

5-{2-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethyl}-1,3,4-oxadiazol-2(3H)-one

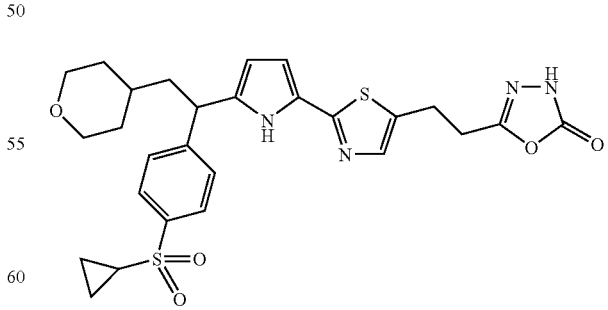

A mixture of ethyl 3-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]propanoate (0.48 g), hydrazine hydrate (0.22 g) and ethanol (6 mL) was stirred with heating under reflux for 2 days. The reaction mixture was concentrated, and then the resulting crystals were washed with cold ethanol and dried to give yellow crystals (0.31 g). A mixture of the obtained crystals, 1,1'-carbonylbis(1H-imidazole) (0.14 g) and tetrahydrofuran (10 mL) was stirred at room temperature for 6 hr. The reaction mixture was concentrated, and the obtained residue was subjected to silica gel column chromatography, and the title compound (0.23 g, yield 47%) was obtained as a colorless amorphous solid from a fraction eluted with ethyl acetate. MS: 555 (MH$^+$).

$^1$H NMR (300 MHz, CDCl$_3$) δ0.96-1.06 (2 H, m), 1.24-1.46 (5 H, m), 1.53-1.65 (2 H, m), 1.79-2.10 (2 H, m), 2.38-2.48 (1H, m), 2.89-2.99 (2 H, m), 3.18-3.33 (4 H, m), 3.85-3.96 (2 H, m), 4.19 (1 H, t, J=7.8 Hz), 6.09 (1 H, t, J=3.0 Hz), 6.58 (1 H, t, J=3.0 Hz), 7.35-7.43 (3 H, m), 7.74-7.81 (2H, m), 9.90 (1 H, brs), 11.23 (1 H, brs).

Example 166

Optically Active Form of 1-[2-(5-{1-[4-(cyclopropyl-sulfonyl)phenyl]-2-(tetrahydro-2H-pyran-4-yl)ethyl}-1H-pyrrol-2-yl)-1,3-thiazol-5-yl]ethanol

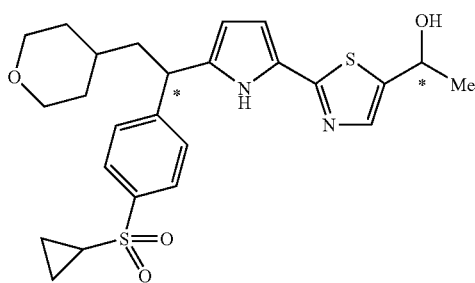

1-[2-(5-[1-[4-(Cyclopropylsulfonyl)phenyl]-2-(tetrahydro-2H-pyran-4-yl)ethyl]-1H-pyrrol-2-yl)-1,3-thiazol-5-yl]ethanol (951 mg) was subjected to supercritical fluid chromatography using CHIRALCEL OD-H (manufactured by DAICEL CHEMICAL INDUSTRY LTD.). Using carbon dioxide-ethanol (700:300, volume ratio) as a mobile phase, the solution was eluted at flow rate 50 mL/min, at 100 bar and at 35° C., and the fraction was separated at retention time 7.6 min to give the title compound (222 mg) as colorless crystals. The obtained crystals were recrystallized from acetonitrile. melting point 105-106° C. MS: 487 (MH$^+$).

Example 167

Optically Active form of 1-[2-(5-{1-[4-(cyclopropyl-sulfonyl)phenyl]-2-(tetrahydro-2H-pyran-4-yl)ethyl}-1H-pyrrol-2-yl)-1,3-thiazol-5-yl]ethanol

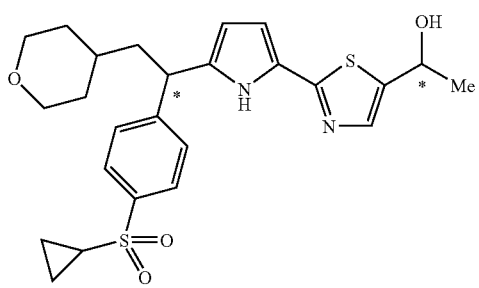

1-[2-(5-{1-[4-(Cyclopropylsulfonyl)phenyl]-2-(tetrahydro-2H-pyran-4-yl)ethyl}-1H-pyrrol-2-yl)-1,3-thiazol-5-yl]ethanol (951 mg) was subjected to supercritical fluid chromatography using CHIRALCEL OD-H (manufactured by DAICEL CHEMICAL INDUSTRY LTD.). Using carbon dioxide-ethanol (700:300, volume ratio) as a mobile phase, the solution was eluted at flow rate 50 mL/min, at 100 bar and at 35° C., and the fraction was separated at retention time 8.7 min to give the title compound (224 mg) as colorless crystals. The obtained crystals were recrystallized from acetonitrile. melting point 112-114° C. MS: 487 (MH$^+$).

Example 168

Optically Active Form of 1-[2-(5-{1-[4-(cyclopropyl-sulfonyl)phenyl]-2-(tetrahydro-2H-pyran-4-yl)ethyl}-1H-pyrrol-2-yl)-1,3-thiazol-5-yl]ethanol

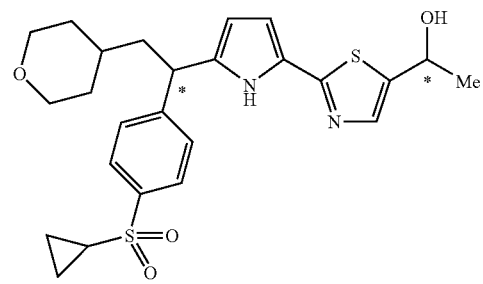

1-[2-(5-{1-[4-(Cyclopropylsulfonyl)phenyl]-2-(tetrahydro-2H-pyran-4-yl)ethyl}-1H-pyrrol-2-yl)-1,3-thiazol-5-yl]ethanol (951 mg) was subjected to supercritical fluid chromatography using CHIRALCEL OD-H (manufactured by DAICEL CHEMICAL INDUSTRY LTD.). Using carbon dioxide-ethanol (700:300, volume ratio) as a mobile phase, the solution was eluted at flow rate 50 mL/min, at 100 bar and at 35° C., and the fraction was separated at retention time 10.8 min to give the title compound (207 mg) as colorless crystals. The obtained crystals were recrystallized from acetonitrile. melting point 115-116° C. MS: 487 (MH$^+$).

Example 169

Optically Active Form of 1-[2-(5-{1-[4-(cyclopropyl-sulfonyl)phenyl]-2-(tetrahydro-2H-pyran-4-yl)ethyl}-1H-pyrrol-2-yl)-1,3-thiazol-5-yl]ethanol

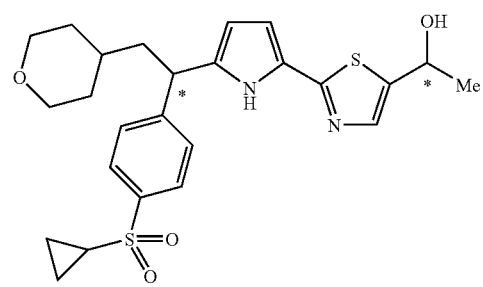

1-[2-(5-{1-[4-(Cyclopropylsulfonyl)phenyl]-2-(tetrahydro-2H-pyran-4-yl)ethyl}-1H-pyrrol-2-yl)-1,3-thiazol-5-yl]ethanol (951 mg) was subjected to supercritical fluid chromatography using CHIRALCEL OD-H (manufactured by DAICEL CHEMICAL INDUSTRY LTD.). Using carbon dioxide-ethanol (700:300, volume ratio) as a mobile phase, the solution was eluted at flow rate 50 mL/min, at 100 bar and at 35° C., and the fraction was separated at retention time 17.0 min to give the title compound (209 mg) as colorless crystals. The obtained crystals were recrystallized from acetonitrile. melting point 105-106° C. MS: 487 (MH$^+$).

Example 170

1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]-2,2,2-trifluoroethanol

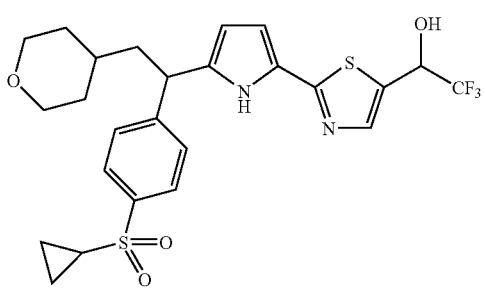

A mixture of 5-[4-(cyclopropylsulfonyl)phenyl]-6-(tetrahydro-2H-pyran-4-yl)-1-[5-(2,2,2-trifluoro-1-hydroxyethyl)-1,3-thiazol-2-yl]hexane-1,4-dione (0.45 g), ammonium acetate (0.31 g) and acetic acid (6 mL) was stirred at 80° C. for 3 hr. The reaction mixture was neutralized with 8M sodium hydroxide, and extracted with ethyl acetate. The ethyl acetate layer was washed with saturated brine, dried (MgSO$_4$) and concentrated. The residue was subjected to basic silica gel column chromatography, and the title compound (0.28, yield 65%) was obtained as a yellow amorphous solid from a fraction eluted with ethyl acetate-hexane (9:1, volume ratio). MS: 541 (MH$^+$).
$^1$H NMR (300 MHz, CDCl$_3$) δ1.00-1.10 (2 H, m), 1.20-1.70 (5 H, m), 1.80-2.10 (2 H, m), 2.40-2.52 (1 H, m), 2.80-2.98 (1H, m), 3.17-3.44 (2 H, m), 3.84-4.20 (3 H, m), 5.20-5.44 (1 H, m), 6.09-6.17 (1 H, m), 6.62-6.68 (1 H, m), 7.28-7.50 (3 H, m), 7.75-7.96 (2 H, m), 9.48 (1 H, brs).

Example 171

1-[2-(5-[1-[4-(methylsulfonyl)phenyl]-2-(tetrahydro-2H-pyran-4-yl)ethyl]-1H-pyrrol-2-yl)-1,3-thiazol-5-yl]ethanol

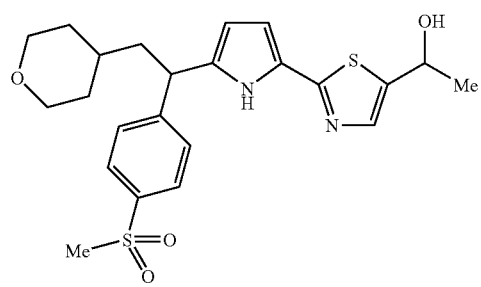

A mixture of 1-[5-(1-hydroxyethyl)-1,3-thiazol-2-yl]-5-[4-(methylsulfonyl)phenyl]-6-(tetrahydro-2H-pyran-4-yl)hexane-1,4-dione (0.57 g), ammonium acetate (0.46 g) and acetic acid (5 mL) was stirred at 90° C. for 3 hr. The reaction mixture was neutralized with 8M aqueous sodium hydroxide solution, and extracted with ethyl acetate. The ethyl acetate layer was concentrated, 2M aqueous sodium hydroxide solution (1 mL), tetrahydrofuran (4 mL) and methanol (4 mL) were added to the residue, and the mixture was stirred with heating under reflux for 2 hr. Water was added to the reaction mixture, and the mixture was extracted with ethyl acetate. The ethyl acetate layer was washed with saturated brine, dried (MgSO$_4$) and concentrated. The residue was subjected to basic silica gel column chromatography, and the title compound (0.19 g, yield 34%) was obtained as a yellow amorphous solid from a fraction eluted with tetrahydrofuran-hexane (3:1, volume ratio). MS: 461 (MH$^+$).
$^1$H NMR (300 MHz, CDCl$_3$) δ1.22-1.70 (8 H, m), 1.80-2.08 (2 H, m), 2.40 (1 H, d, J=4.5 Hz), 3.30-3.52 (2 H, m), 3.85-3.95 (2 H, m), 4.11 (1 H, t, J=7.8 Hz), 5.06-5.16 (1 H, m), 6.09 (1 H, dd, J=2.7, 3.6 Hz), 6.58 (1 H, dd, J=2.7, 3.6 Hz), 7.32-7.39 (3 H, m), 7.80-7.86 (2 H, m), 9.28 (1 H, brs).

Example 172

1-[2-(5-{1-[3-chloro-4-(methylsulfonyl)phenyl]-2-(tetrahydro-2H-pyran-4-yl)ethyl}-1H-pyrrol-2-yl)-1,3-thiazol-5-yl]ethanol

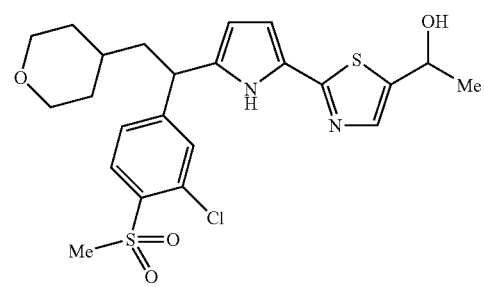

A mixture of 5-[3-chloro-4-(methylsulfonyl)phenyl]-1-[5-(1-hydroxyethyl)-1,3-thiazol-2-yl]-6-(tetrahydro-2H-pyran-4-yl)hexane-1,4-dione (0.66 g), ammonium acetate (0.50 g) and acetic acid (5 mL) was stirred at 90° C. for 3 hr. The reaction mixture was neutralized with 8M aqueous sodium hydroxide solution, and extracted with ethyl acetate. The ethyl acetate layer was concentrated, 2M aqueous sodium hydroxide solution (1.5 mL), tetrahydrofuran (4 mL) and methanol (4 mL) were added to the residue, and the mixture was stirred with heating under reflux for 2 hr. Water was added to the reaction mixture, and the mixture was extracted with ethyl acetate. The ethyl acetate layer was washed with saturated brine, dried (MgSO$_4$) and concentrated. The residue was subjected to basic silica gel column chromatography, and the title compound (0.19 g, yield 34%) was obtained as a yellow amorphous solid from a fraction eluted with ethyl acetate. MS: 495 (MH$^+$).
$^1$H NMR (300 MHz, CDCl$_3$) δ1.23-1.66 (8 H, m), 1.76-1.88 (1 H, m), 1.95-2.06 (1 H, m), 2.55 (1 H, d, J=4.5 Hz), 3.20-3.33 (5 H, m), 3.86-3.96 (2 H, m), 4.05 (1 H, t, J=8.1 Hz), 5.07-5.18 (1 H, m), 6.09 (1 H, t, J=3.2 Hz), 6.58 (1 H, dd, J=2.6, 3.8 Hz), 7.21 (1 H, d, J=8.1 Hz), 7.30 (1 H, s), 7.37 (1 H, s), 8.01 (1 H, d, J=8.1 Hz), 9.52 (1 H, brs).

Example 173

1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]-2-methylpropane-1,2-diol

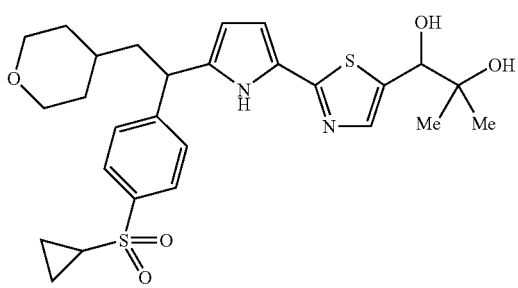

A mixture of 5-[4-(cyclopropylsulfonyl)phenyl]-1-[5-(1,2-dihydroxy-2-methylpropyl)-1,3-thiazol-2-yl]-6-(tetrahydro-2H-pyran-4-yl)hexane-1,4-dione (0.52 g), ammonium acetate (0.37 g) and acetic acid (4 mL) was stirred at 90° C. for 2 hr. The reaction mixture was neutralized with 8M aqueous sodium hydroxide solution, and extracted with ethyl acetate. The ethyl acetate layer was washed with saturated brine, dried (MgSO$_4$) and concentrated. The residue was subjected to silica gel column chromatography, and the title compound (0.28 g, yield 56%) was obtained as a yellow amorphous solid from a fraction eluted with ethyl acetate. MS: 531 (MH$^+$).

$^1$H NMR (300 MHz, CDCl$_3$) δ0.98-1.68 (15 H, m), 1.80-2.08 (2H, m), 2.28 (1 H, s), 2.38-2.49 (1 H, m), 2.97 (1 H, brs), 3.20-3.32 (2 H, m), 3.85-3.95 (2 H, m), 4.10 (1 H, t, J=7.2 Hz), 4.70 (1 H, d, J=3.3 Hz), 6.08-6.13 (1 H, m), 6.60 (1 H, t, J=2.9 Hz), 7.30-7.42 (3 H, m), 7.75-7.83 (2 H, m), 9.31 (1 H, brs).

Example 174

2-methyl-1-[2-(5-{1-[4-(methylsulfonyl)phenyl]-2-(tetrahydro-2H-pyran-4-yl)ethyl}-1H-pyrrol-2-yl)-1,3-thiazol-5-yl]propane-1,2-diol

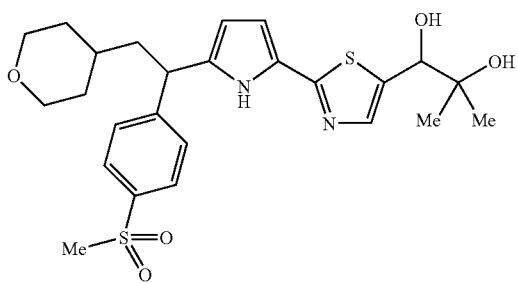

A mixture of 1-[5-(1,2-dihydroxy-2-methylpropyl)-1,3-thiazol-2-yl]-5-[4-(methylsulfonyl)phenyl]-6-(tetrahydro-2H-pyran-4-yl)hexane-1,4-dione (0.51 g), ammonium acetate (0.39 g) and acetic acid (5 mL) was stirred at 90° C. for 2 hr. The reaction mixture was neutralized with 8M aqueous sodium hydroxide solution, and extracted with ethyl acetate. The ethyl acetate layer was washed with saturated brine, dried (MgSO$_4$) and concentrated. The residue was subjected to silica gel column chromatography, and the title compound (0.38 g, yield 77%) was obtained as a yellow amorphous solid from a fraction eluted with ethyl acetate. MS: 505 (MH$^+$).

$^1$H NMR (300 MHz, CDCl$_3$) δ1.10-1.44 (11 H, m), 1.48-1.66 (2 H, m), 1.79-2.08 (2 H, m), 2.39 (1 H, brs), 3.03 (3 H, s), 3.14-3.30 (3 H, m), 3.84-3.94 (2 H, m), 4.10 (1 H, t, J=8.1 Hz), 4.69 (1 H, d, J=3.0 Hz), 6.08 (1 H, q, J=3.2 Hz), 6.59 (1 H, t, J=3.2 Hz), 7.30-7.40 (3 H, m), 7.78-7.84 (2H, m), 9.50 (1 H, brs).

Example 175

2-methyl-1-[6-(5-{1-[5-(methylsulfanyl)pyridin-2-yl]-2-(tetrahydro-2H-pyran-4-yl)ethyl}-1H-pyrrol-2-yl)pyridin-3-yl]propane-1,2-diol

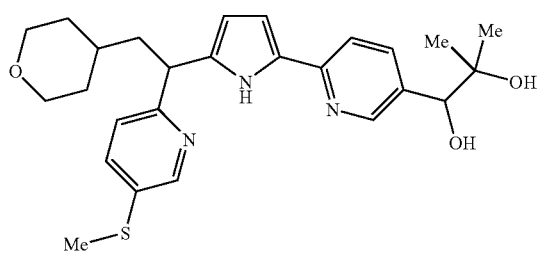

A mixture of 1-[5-(1,2-dihydroxy-2-methylpropyl)pyridin-2-yl]-5-[5-(methylsulfanyl)pyridin-2-yl]-6-(tetrahydro-2H-pyran-4-yl)hexane-1,4-dione (0.49 g), ammonium acetate (0.39 g) and acetic acid (5 mL) was stirred at 80° C. for 3 hr. The reaction mixture was neutralized with 8M aqueous sodium hydroxide solution, and extracted with ethyl acetate. The ethyl acetate layer was washed with saturated brine, dried (MgSO$_4$) and concentrated. The residue was subjected to basic silica gel column chromatography, and the title compound (0.37 g, yield 79%) was obtained as a colorless amorphous form from a fraction eluted with ethyl acetate. MS: 468 (MH$^+$).

$^1$H NMR (300 MHz, CDCl$_3$) δ1.09 (3H, s), 1.23-1.68 (8 H, m), 1.88-2.07 (2 H, m), 2.38 (1 H, brs), 2.47 (3 H, s), 3.10 (1H, brs), 3.21-3.33 (2 H, m), 3.85-3.95 (2 H, m), 4.18 (1 H, t, J=7.8 Hz), 4.49 (1 H, s), 6.08 (1 H, q, J=3.1 Hz), 6.58 (1H, t, J=3.1 Hz), 7.08 (1 H, dd, J=0.6, 8.4 Hz), 7.43 (1 H, d, J=8.4 Hz), 7.47 (1 H, dd, J=2.4, 8.4 Hz), 7.64 (1 H, td, J=2.4, 8.4 Hz), 8.35 (1 H, t, J=2.4 Hz), 8.46 (1 H, d, J=2.4 Hz), 9.95 (1 H, brs).

Example 176

2-methyl-1-[6-(5-{1-[5-(methylsulfonyl)pyridin-2-yl]-2-(tetrahydro-2H-pyran-4-yl)ethyl}-1H-pyrrol-2-yl)pyridin-3-yl]propane-1,2-diol

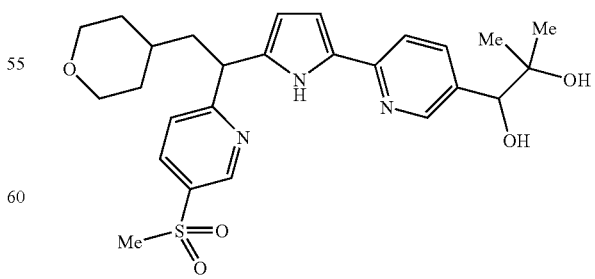

To a mixture of 2-methyl-1-[6-(5-{1-[5-(methylsulfanyl)pyridin-2-yl]-2-(tetrahydro-2H-pyran-4-yl)ethyl}-1H-pyrrol-2-yl)pyridin-3-yl]propane-1,2-diol (0.37 g), water (4 mL)

and acetonitrile (6 mL) was added sodium percarbonate (0.25 g), and the mixture was stirred at room temperature for 2 hr. To the reaction mixture was added sodium percarbonate (0.10 g), and the mixture was stirred at room temperature for 1 hr. To the reaction mixture was added saturated aqueous sodium sulfite solution, and the mixture was extracted with ethyl acetate. The ethyl acetate layer was washed with saturated brine, dried (MgSO$_4$) and concentrated. The residue was subjected to basic silica gel column chromatography, and the title compound (0.33 g, yield 84%) was obtained as a pale-yellow amorphous solid from a fraction eluted with tetrahydrofuran-hexane (4:1, volume ratio). MS: 500 (MH$^+$).

$^1$H NMR (300 MHz, CDCl$_3$) δ1.09 (3H, s), 1.18-1.75 (11 H, m), 1.97-2.18 (2 H, m), 2.36 (1 H, brs), 3.07 (3 H, s), 3.09 (1H, brs), 3.20-3.33 (2 H, m), 3.85-3.95 (2 H, m), 4.34 (1 H, t, J=8.0 Hz), 4.50 (1 H, s), 6.13 (1 H, t, J=3.1 Hz), 6.59 (1 H, t, J=3.1 Hz), 7.36 (1 H, d, J=8.4 Hz), 7.45 (1 H, d, J=8.4 Hz), 7.66 (1 H, td, J=2.4, 8.4 Hz), 8.08 (1 H, dd, J=2.4, 8.4 Hz), 8.36 (1 H, s), 9.09 (1 H, d, J=2.4 Hz), 9.97 (1 H, brs).

Example 177

1-[6-(5-[1-[4-(cyclopropylsulfonyl)phenyl]-2-(tetrahydro-2H-pyran-4-yl)ethyl]-1H-pyrrol-2-yl)pyridin-3-yl]-2-methoxyethanol

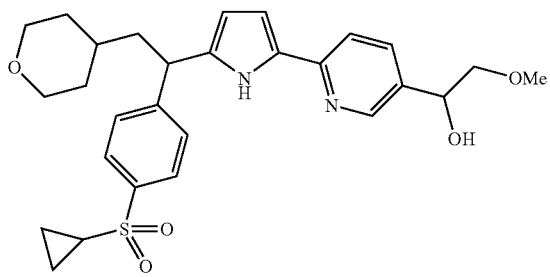

A mixture of 5-[4-(cyclopropylsulfonyl)phenyl]-1-{5-[2-methoxy-1-(tetrahydro-2H-pyran-2-yloxy)ethyl]pyridin-2-yl}-6-(tetrahydro-2H-pyran-4-yl)hexane-1,4-dione (0.70 g), ammonium acetate (0.42 g) and acetic acid (5 mL) was stirred at 80° C. for 3 hr. The reaction mixture was neutralized with 8M aqueous sodium hydroxide solution, and extracted with ethyl acetate. The ethyl acetate layer was washed with saturated brine, dried (MgSO$_4$) and concentrated. The residue was subjected to basic silica gel column chromatography, and the title compound (0.39 g, yield 69%) was obtained as a pale-yellow amorphous solid from a fraction eluted with ethyl acetate. MS: 511 (MH$^+$).

$^1$H NMR (300 MHz, CDCl$_3$) δ0.97-1.06 (2 H, m), 1.24-1.68 (7 H, m), 1.81-1.93 (1 H, m), 2.00-2.11 (1 H, m), 2.38-2.48 (1H, m), 2.94 (1 H, brs), 3.20-3.55 (7 H, m), 3.86-3.95 (2 H, m), 4.15 (1 H, t, J=8.0 Hz), 4.82-4.89 (1 H, m), 6.13 (1 H, t, J=3.2 Hz), 6.63 (1 H, dd, J=2.7, 3.6 Hz), 7.34-7.39 (2 H, m), 7.48 (1 H, d, J=8.0 Hz), 7.64 (1 H, td, J=2.1, 8.0 Hz), 7.76-7.82 (2 H, m), 8.35 (1 H, t, J=2.1 Hz), 9.38 (1 H, brs).

Example 178

2-methoxy-1-[6-(5-{1-[4-(methylsulfonyl)phenyl]-2-(tetrahydro-2H-pyran-4-yl)ethyl}-1H-pyrrol-2-yl) pyridin-3-yl]ethanol

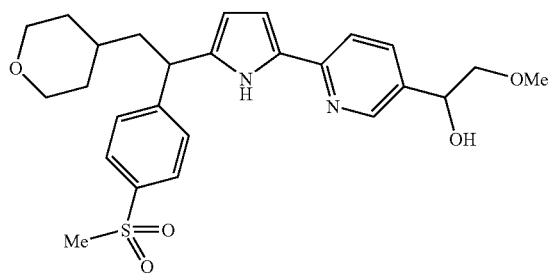

A mixture of 1-{5-[(2-methoxy-1-(tetrahydro-2H-pyran-2-yloxy)ethyl]pyridin-2-yl}-5-[4-(methylsulfonyl)phenyl]-6-(tetrahydro-2H-pyran-4-yl)hexane-1,4-dione (1.05 g), ammonium acetate (0.70 g) and acetic acid (5 mL) was stirred at 80° C. for 3 hr. The reaction mixture was neutralized with 8M aqueous sodium hydroxide solution, and extracted with ethyl acetate. The ethyl acetate layer was washed with saturated brine, dried (MgSO$_4$) and concentrated. The residue was subjected to basic silica gel column chromatography, and the title compound (0.65 g, yield 73%) was obtained as a pale-yellow amorphous solid from a fraction eluted with ethyl acetate. MS: 485 (MH$^+$).

$^1$H NMR (300 MHz, CDCl$_3$) δ1.24-1.68 (5 H, m), 1.80-1.92 (1 H, m), 1.98-2.10 (1 H, m), 2.98 (1 H, brs), 3.02 (3 H, s), 3.20-3.55 (7 H, m), 3.86-3.95 (2 H, m), 4.14 (1 H, t, J=7.8 Hz), 4.82-4.88 (1 H, m), 6.12 (1 H, t, J=3.2 Hz), 6.63 (1 H, dd, J=2.4, 3.6 Hz), 7.33-7.40 (2 H, m), 7.48 (1 H, d, J=8.1 Hz), 7.64 (1 H, td, J=2.4, 8.1 Hz), 7.80-7.86 (2 H, m), 8.35 (1 H, t, J=2.4 Hz), 9.46 (1 H, brs).

Example 179

Ethyl [4-(5-{1-[4-(cyclopropylsulfonyl)phenyl]-2-(tetrahydro-2H-pyran-4-yl)ethyl}-1H-pyrrol-2-yl)-1H-imidazol-1-yl]acetate

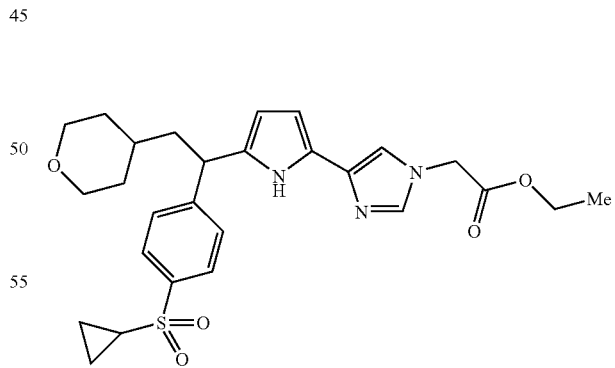

A mixture of ethyl (4-{5-[4-(cyclopropylsulfonyl)phenyl]-4-oxo-6-(tetrahydro-2H-pyran-4-yl)hexanoyl}-1H-imidazol-1-yl)acetate (1.05 g), ammonium acetate (0.70 g) and acetic acid (5 mL) was stirred at 80° C. for 3 hr. The reaction mixture was neutralized with 8M aqueous sodium hydroxide solution, and extracted with ethyl acetate. The ethyl acetate layer was washed with saturated brine, dried (MgSO₄) and concentrated. The residue was subjected to basic silica gel column chromatography, and the fraction eluted with ethyl acetate was concentrated. The obtained residue was subjected to silica gel column chromatography, and the title compound (0.44 g, yield 51%) was obtained as a pale-yellow amorphous solid from a fraction eluted with tetrahydrofuran-hexane (5:1, volume ratio). MS: 512 (MH⁺).

¹H NMR (300 MHz, CDCl₃) δ0.97-1.05 (2 H, m), 1.23-1.67 (10H, m), 1.78-1.89 (1 H, m), 1.98-2.09 (1 H, m), 2.38-2.48 (1 H, m), 3.20-3.32 (2 H, m), 3.85-3.94 (2 H, m), 4.11 (1H, t, J=7.7 Hz), 4.24 (2 H, q, J=7.1 Hz), 4.64 (2 H, s), 6.04 (1 H, t, J=3.0 Hz), 6.23 (1 H, t, J=3.0 Hz), 7.01 (1 H, d, J=1.2 Hz), 7.32-7.38 (3 H, m), 7.74-7.79 (2 H, m), 9.04 (1H, brs).

Example 180

2-(2-{1-[4-(cyclopropylsulfonyl)phenyl]-2-(tetrahydro-2H-pyran-4-yl)ethyl}-4-fluoro-1H-imidazol-5-yl)pyridine

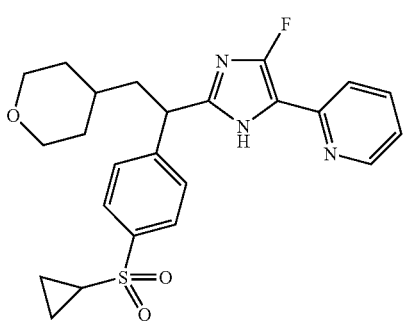

To a solution of 2-(2-{1-[4-(cyclopropylsulfonyl)phenyl]-2-(tetrahydro-2H-pyran-4-yl)ethyl}-1H-imidazol-5-yl)pyridine (0.750 g) in acetonitrile (20 mL) was added xenon difluoride (434 mg), and the mixture was stirred at room temperature for 30 min, and at 0° C. for 63 hr. To the reaction mixture was added saturated aqueous sodium hydrogen carbonate solution, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=10:90-100:0, volume ratio) and preparative thin layer chromatography to give the title compound (0.008 g, yield 1%) as a yellow oil. MS: 456 (MH⁺).

¹H NMR (300 MHz, CDCl₃) δ0.99-1.08 (2 H, m), 1.23-1.46 (5 H, m), 1.52-1.65 (2 H, m), 1.84-1.97 (1 H, m), 2.18-2.30 (1H, m), 2.40-2.52 (1 H, m), 3.19-3.33 (2 H, m), 3.86-3.95 (2 H, m), 4.06-4.14 (1 H, m), 7.07-7.15 (1 H, m), 7.45 (2H, d, J=8.7 Hz), 7.59-7.66 (1 H, m), 7.68-7.77 (1 H, m), 7.84 (2 H, d, J=8.3 Hz), 8.37-8.44 (1 H, m).

Example 181

Methyl [2-{1-[4-(cyclopropylsulfonyl)phenyl]-2-(tetrahydro-2H-pyran-4-yl)ethyl}-5-(1,3-thiazol-2-yl)-1H-pyrrol-3-yl]carbamate

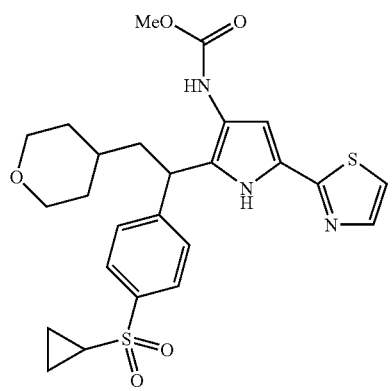

A mixture of 2-[(1-[4-(cyclopropylsulfonyl)phenyl]-2-(tetrahydro-2H-pyran-4-yl)ethyl]-5-(1,3-thiazol-2-yl)-1H-pyrrole-3-carboxylic acid (60 mg), diphenylphosphoryl azide (43 μL), triethylamine (38 μL) and acetonitrile (4 mL) was stirred at room temperature for 5 hr. To the reaction mixture was added methanol (6 mL), and the mixture was stirred at 60° C. for 16 hr. To the reaction solution were added ethyl acetate and water. The ethyl acetate layer was separated and washed with saturated brine, dried (MgSO₄) and concentrated. The residue was subjected to silica gel column chromatography to give a colorless oil from a fraction eluted with ethyl acetate-hexane (6:4-8:2, volume ratio). The obtained oil was crystallized from diethyl ether-hexane to give the title compound (38 mg, yield 60%) as colorless crystals. MS: 516 (MH⁺). melting point 120-122° C.

Example 182

2-{5-[(E)-1-[3-chloro-4-(methylsulfanyl)phenyl]-2-(tetrahydro-2H-pyran-4-yl)ethenyl]-4-iodo-1H-imidazol-2-yl}pyridine

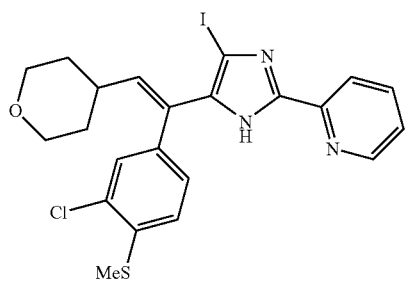

To a solution of 1-[3-chloro-4-(methylsulfanyl)phenyl]-1-(4-iodo-2-(pyridin-2-yl)-1-{[2-(trimethylsilyl)ethoxy]methyl}-1H-imidazol-5-yl)-2-(tetrahydro-2H-pyran-4-yl)ethanol (0.520 g) in ethanol (10 mL) was added 3M hydrochloric acid (10 mL), and the mixture was stirred at 80° C. for 1.5 hr. To the reaction mixture was added saturated aqueous sodium hydrogen carbonate solution, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=5:95-60:40, volume ratio) to give the title compound (0.343 g, yield 84%) as a colorless oil. MS: 358 (MH$^+$).

$^1$H NMR (300 MHz, CDCl$_3$) δ1.52-1.75 (6 H, m), 2.48 (1 H, s), 2.53 (2 H, s), 3.28-3.42 (2 H, m), 3.90-3.98 (2 H, m), 6.04-6.16 (1 H, m), 6.85-7.01 (1 H, m), 7.05-7.10 (1 H, m), 7.14-7.28 (1 H, m), 7.70-7.86 (1 H, m), 8.09-8.20 (1H, m), 8.31-8.38 (1 H, m), 10.62 (1 H, s).

Example 183

2-(5-{1-[3-chloro-4-(methylsulfonyl)phenyl]-2-(tetrahydro-2H-pyran-4-yl)ethyl}-1H-imidazol-2-yl)pyridine

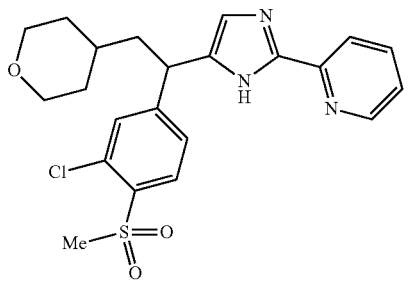

To a solution of 2-{5-[(E)-1-[3-chloro-4-(methylsulfanyl)phenyl]-2-(tetrahydro-2H-pyran-4-yl)ethenyl]-4-iodo-1H-imidazol-2-yl}pyridine (0.340 g) in a mixed solvent of tetrahydrofuran (3 mL), methanol (3 mL) and water (3 mL) was added Oxone (registered trade mark) (777 mg) under ice-cooling, and the mixture was stirred at 0° C. for 30 min. To the reaction mixture was added saturated aqueous sodium hydrogen carbonate solution, and the mixture was extracted with ethyl acetate. The extract was washed successively with water and saturated brine, dried over anhydrous sodium sulfate, and concentrated under reduced pressure. To a solution of the residue in a mixed solvent of acetonitrile (10 mL) and water (5 mL) was added sodium percarbonate (198 mg) under ice-cooling. The reaction solution was warmed to room temperature, and the mixture was stirred at room temperature for 2 hr. A saturated aqueous ammonium chloride solution was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=50:50-100:0, volume ratio) to give a colorless oil. To a solution of the obtained oil in methanol (5 mL) were added 10% palladium carbon (30 mg), diphenylsulfide (0.7 μL) and triethylamine (0.29 mL). The reaction solution was purged with hydrogen, and stirred at room temperature for 16 hr. The reaction mixture was filtered, and the filtrate was concentrated under reduced pressure. The residue was purified by silica gel column chromatography (ethyl acetate:hexane=50:50-100:0, volume ratio) and recrystallized from hexane-ethyl acetate to give the title compound (0.047 g, yield 17%) as colorless crystals. melting point 106-109° C. MS: 446 (MH$^+$).

Example 184

2-{4-chloro-5-[(E)-1-[3-chloro-4-(methylsulfanyl)phenyl]-2-(tetrahydro-2H-pyran-4-yl)ethenyl]-1H-imidazol-2-yl}pyridine

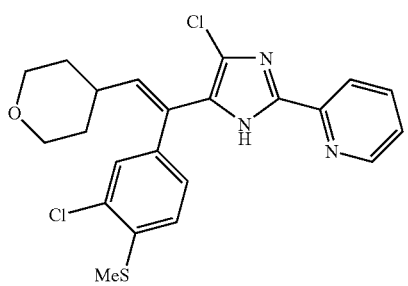

To a solution of 1-[3-chloro-4-(methylsulfanyl)phenyl]-1-(4-chloro-2-(pyridin-2-yl)-1-{[2-(trimethylsilyl)ethoxy]methyl}-1H-imidazol-5-yl)-2-(tetrahydro-2H-pyran-4-yl)ethanol (1.47 g) in ethanol (40 mL) was added 3M hydrochloric acid (40 mL), and the mixture was stirred at 80° C. for 1.5 hr. To the reaction mixture was added saturated aqueous sodium hydrogen carbonate solution, and the mixture was extracted with ethyl acetate. The extract was washed successively with water and saturated brine, dried over anhydrous magnesium sulfate and concentrated under reduced pressure. The residue was purified by silica gel column chromatography (ethyl acetate:hexane=30:70-80:20, volume ratio) to give the title compound (1.10 g, yield 100%) as a colorless amorphous solid. MS: 446 (MH$^+$).

$^1$H NMR (300 MHz, CDCl$_3$) δ1.47-1.73 (4 H, m), 2.32-2.57 (4 H, m), 3.25-3.43 (2 H, m), 3.87-4.01 (2 H, m), 6.11-6.22 (1H, m), 6.86-7.15 (3 H, m), 7.16-7.25 (1 H, m), 7.71-7.86 (1 H, m), 8.04-8.15 (1 H, m), 8.29-8.38 (1 H, m), 10.50 (1 H, s).

Example 185

2-{4-chloro-5-[(E)-1-[3-chloro-4-(methylsulfonyl)phenyl]-2-(tetrahydro-2H-pyran-4-yl)ethenyl]-1H-imidazol-2-yl}pyridine

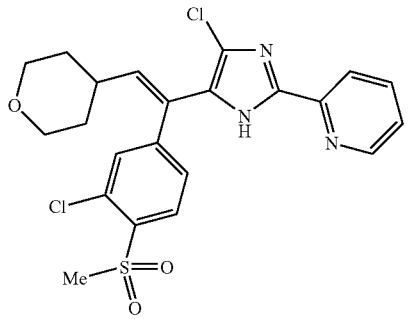

To a solution of 2-{4-chloro-5-[(E)-1-[3-chloro-4-(methylsulfanyl)phenyl]-2-(tetrahydro-2H-pyran-4-yl)ethenyl]-1H-imidazol-2-yl}pyridine (1.10 g) in a mixed solvent of tetrahydrofuran (10 mL), methanol (10 mL) and water (10 mL) was added Oxone (registered trade mark) (3.02 g) under ice-cooling, and the mixture was stirred at 0° C. for 30 min. To the reaction mixture was added saturated aqueous sodium hydrogen carbonate solution, and the mixture was extracted with ethyl acetate. The extract was washed successively with water and saturated brine, dried over anhydrous sodium sulfate, and concentrated under reduced pressure. To a solution of the residue in a mixed solvent of acetonitrile (20 mL) and water (10 mL) was added sodium percarbonate (772 mg) under ice-cooling. The reaction solution was warmed to room temperature, and the mixture was stirred at room temperature for 3 hr. A saturated aqueous ammonium chloride solution was added to the reaction mixture, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=40:60-100:0, volume ratio) to give the title compound (0.471 g, yield 40%) as a colorless amorphous solid. MS: 478 (MH$^+$).

$^1$H NMR (300 MHz, CDCl$_3$) δ1.47-1.73 (4 H, m), 2.27-2.45 (1 H, m), 3.27-3.49 (5 H, m), 3.89-4.00 (2 H, m), 6.18 (1 H, d, J=10.2 Hz), 7.16 (1 H, dd, J=8.1, 1.7 Hz), 7.23-7.31 (2 H, m), 7.76-7.84 (1 H, m), 8.06 (2 H, d, J=8.1 Hz), 8.38 (1 H, d, J=4.9 Hz), 11.05 (1 H, s).

Example 186

2-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)pyridine

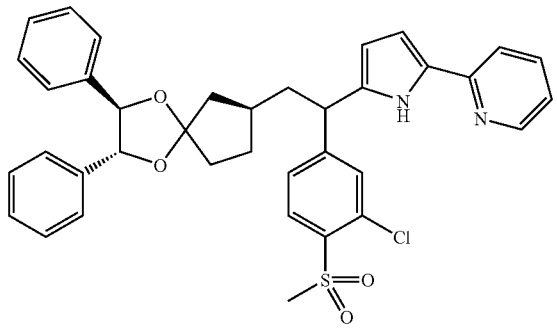

To a solution of 5-[3-chloro-4-(methylsulfonyl)phenyl]-6-[(2R,3R,7R)-2,3-diphenyl-1,4-dioxaspiro[4.4]non-7-yl]-1-(pyridin-2-yl)hexane-1,4-dione (698 mg) in acetic acid (5 mL) was added ammonium acetate (1.31 g), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (580 mg, yield 85%) was obtained as a pale-yellow amorphous solid from a fraction eluted with ethyl acetate-hexane (1:1, volume ratio).

$^1$H NMR (300 MHz, CDCl$_3$) δ1.40-2.42 (9 H, m), 3.23 (3 H, s), 3.98-4.06 (1 H, m), 4.64-4.73 (2 H, m), 6.12-6.17 (1 H, m), 6.61-6.66 (1 H, m), 6.96-7.04 (1 H, m), 7.14-7.23 (4H, m), 7.27-7.40 (8 H, m), 7.46-7.53 (1 H, m), 7.56-7.65 (1 H, m), 8.04 (1 H, dd, J=5.0, 7.8 Hz), 8.34-8.42 (1 H, m), 9.32-9.56 (1 H, m).

Example 187

(3R)-3-{2-[3-chloro-4-(methylsulfonyl)phenyl]-2-(5-(pyridin-2-yl)-1H-pyrrol-2-yl)ethyl}cyclopentanone

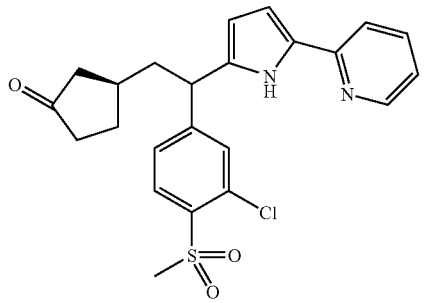

To a solution of 2-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)pyridine (580 mg) in tetrahydrofuran (4.5 mL) was added 1M hydrochloric acid (4.5 mL), and the mixture was stirred at 55° C. for 5 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (360 mg, yield 90%) was obtained as a white amorphous solid from a fraction eluted with ethyl acetate-hexane (2:1, volume ratio). MS: 443 (MH$^+$).

$^1$H NMR (300 MHz, CDCl$_3$) δ1.40-2.42 (9 H, m), 3.23 (3 H, s), 3.98-4.06 (1 H, m), 4.64-4.73 (2 H, m), 6.12-6.17 (1 H, m), 6.61-6.66 (1 H, m), 6.96-7.04 (1 H, m), 7.14-7.23 (4H, m), 7.27-7.40 (8 H, m), 7.46-7.53 (1 H, m), 7.56-7.65 (1 H, m), 8.04 (1 H, dd, J=5.0, 7.8 Hz), 8.34-8.42 (1 H, m), 9.32-9.56 (1 H, m).

Example 188

[2-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)-1,3-thiazol-5-yl]methanol

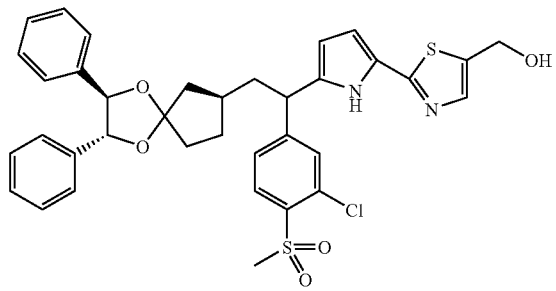

To a solution of 5-[3-chloro-4-(methylsulfonyl)phenyl]-6-[(2R,3R,7R)-2,3-diphenyl-1,4-dioxaspiro[4.4]non-7-yl]-1-{5-[(tetrahydro-2H-pyran-2-yloxy)methyl]-1,3-thiazol-2-yl}hexane-1,4-dione (416 mg) in acetic acid (2.5 mL) was added ammonium acetate (659 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (151 mg, yield 42%) was obtained as a pale-yellow amorphous solid from a fraction eluted with ethyl acetate-hexane (19:1, volume ratio). MS: 675 (MH+).

$^1$H NMR (300 MHz, CDCl$_3$) δ1.40-1.54 (1 H, m), 1.62-2.35 (8 H, m), 2.54 (1 H, brs), 3.23 (3 H, s), 3.92-4.03 (1 H, m), 4.63-4.73 (2 H, m), 4.76-4.83 (2 H, m), 6.06-6.17 (1 H, m), 6.54-6.65 (1 H, m), 7.13-7.39 (13 H, m), 8.01 (1 H, dd, J=5.0, 8.2 Hz), 9.72 (1 H, d, J=17.0 Hz).

Example 189

(3R)-3-(2-[3-chloro-4-(methylsulfonyl)phenyl]-2-{5-[5-(hydroxymethyl)-1,3-thiazol-2-yl]-1H-pyrrol-2-yl}ethyl)cyclopentanone

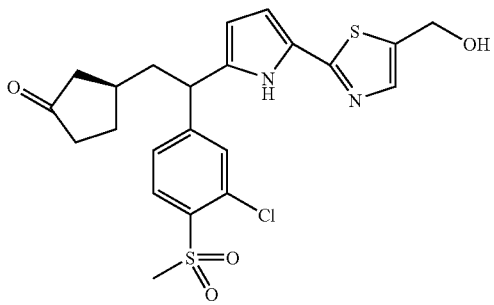

To a solution of [2-(5-{1-[3-chloro-4-(methylsulfonyl)phenyl]-2-[(2R,3R,7R)-2,3-diphenyl-1,4-s dioxaspiro[4.4]non-7-yl]ethyl}-1H-pyrrol-2-yl)-1,3-thiazol-5-yl]methanol (151 mg) in tetrahydrofuran (1 mL) was added 1M hydrochloric acid (1 ml), and the mixture was stirred at 55° C. for 16 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (65.8 mg, yield 61%) was obtained as a pale-yellow amorphous solid from a fraction eluted with ethyl acetate-hexane (9:1, volume ratio). MS: 479 (MH+).

$^1$H NMR (300 MHz, CDCl$_3$) δ1.47-1.61 (1 H, m), 1.71-1.88 (1 H, m), 1.93-2.42 (8 H, m), 3.25 (3 H, s), 3.93-4.03 (1 H, m), 4.83 (2 H, d, J=5.7 Hz), 6.08-6.17 (1 H, m), 6.57-6.64 (1H, m), 7.21-7.25 (1 H, m), 7.34 (1 H, dd, J=1.5, 3.8 Hz), 7.41 (1 H, d, J=2.6 Hz), 8.03 (1 H, d, J=8.3 Hz), 9.55-9.66 (1 H, m).

Example 190

2-(5-{1-[3-chloro-4-(methylsulfonyl)phenyl]-2-(tetrahydro-2H-pyran-4-yl)ethyl}-1H-pyrrol-2-yl)pyridine

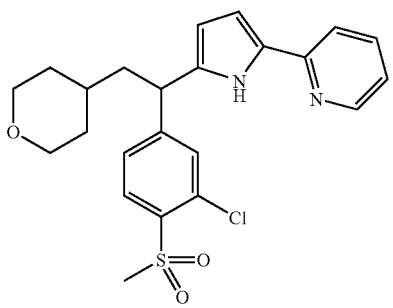

To a solution of 5-[3-chloro-4-(methylsulfonyl)phenyl]-1-(pyridin-2-yl)-6-(tetrahydro-2H-pyran-4-yl)hexane-1,4-dione (1.13 g) in acetic acid (12.2 mL) was added ammonium acetate (3.01 g), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (855 mg, yield 79%) was obtained as a pale-yellow amorphous solid from a fraction eluted with ethyl acetate-hexane (1:1, volume ratio). MS: 445 (MH+).

$^1$H NMR (300 MHz, CDCl$_3$) δ1.20-1.69 (6 H, m), 1.78-1.92 (1 H, m), 1.97-2.13 (1 H, m), 3.20-3.37 (5 H, m), 3.87-3.98 (2H, m), 6.14 (1 H, t, J=3.2 Hz), 6.61-6.67 (1 H, m), 6.98-7.06 (1 H, m), 7.24-7.31 (1 H, m), 7.36 (1 H, s), 7.46-7.54 (1 H, m), 7.57-7.66 (1 H, m), 8.05 (1 H, d, J=8.0 Hz), 8.39 (1 H, d, J=4.9 Hz), 9.39 (1 H, brs).

Example 191

[2-(5-{1-[3-chloro-4-(methylsulfonyl)phenyl]-2-(tetrahydro-2H-pyran-4-yl)ethyl}-1H-pyrrol-2-yl)-1,3-thiazol-5-yl]methyl acetate

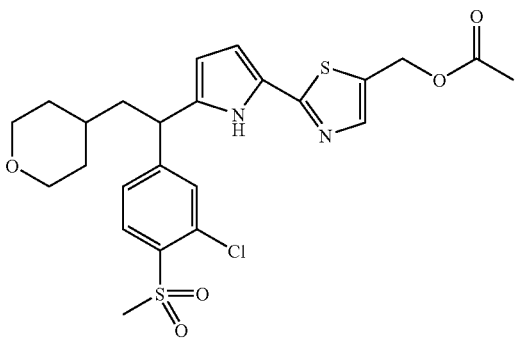

To a solution of 5-[3-chloro-4-(methylsulfonyl)phenyl]-6-(tetrahydro-2H-pyran-4-yl)-1-{5-[(tetrahydro-2H-pyran-2-yloxy)methyl]-1,3-thiazol-2-yl}hexane-1,4-dione (366 mg) in acetic acid (3.1 mL) was added ammonium acetate (773 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (103 mg, yield 31%) was obtained as a pale-yellow amorphous solid from a fraction eluted with ethyl acetate-hexane (1:1, volume ratio). MS: 523 (MH+).

$^1$H NMR (300 MHz, CDCl$_3$) δ1.23-1.68 (6 H, m), 1.79-1.93 (1 H, m), 1.98-2.12 (4 H, m), 3.22-3.36 (5 H, m), 3.89-3.97 (2H, m), 4.06-4.14 (1 H, m), 5.23 (2 H, s), 6.12 (1 H, t, J=3.2 Hz), 6.59-6.64 (1 H, m), 7.26-7.30 (1 H, m), 7.34 (1 H, s), 7.54 (1 H, s), 8.06 (1 H, d, J=8.3 Hz), 9.03 (1 H, brs).

Example 192

[2-(5-[1-[3-chloro-4-(methylsulfonyl)phenyl]-2-(tetrahydro-2H-pyran-4-yl)ethyl]-1H-pyrrol-2-yl)-1,3-thiazol-5-yl]methanol

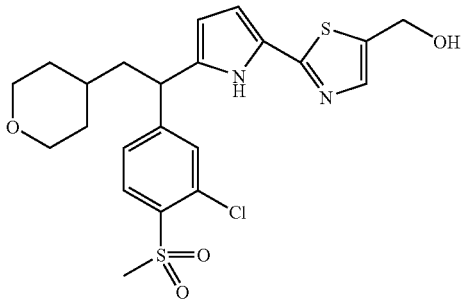

To a solution of 5-[3-chloro-4-(methylsulfonyl)phenyl]-6-(tetrahydro-2H-pyran-4-yl)-1-{5-[(tetrahydro-2H-pyran-2-yloxy)methyl]-1,3-thiazol-2-yl}hexane-1,4-dione (366 mg) in acetic acid (3.1 mL) was added ammonium acetate (773 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (117 mg, yield 39%) was obtained as a pale-yellow amorphous solid from a fraction eluted with ethyl acetate-hexane (19:1, volume ratio). MS: 481 (MH$^+$).

$^1$H NMR (300 MHz, CDCl$_3$) δ1.23-1.68 (5 H, m), 1.78-1.92 (1 H, m), 1.97-2.11 (2 H, m), 3.22-3.36 (5 H, m), 3.87-3.98 (2H, m), 4.04-4.16 (1 H, m), 4.83 (2 H, d, J=5.7 Hz), 6.12 (1H, t, J=3.2 Hz), 6.58-6.63 (1 H, m), 7.25-7.31 (1 H, m), 7.35 (1 H, d, J=1.5 Hz), 7.44 (1 H, s), 8.06 (1 H, d, J=8.3 Hz), 9.19 (1 H, brs).

Example 193

2-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)pyrazine

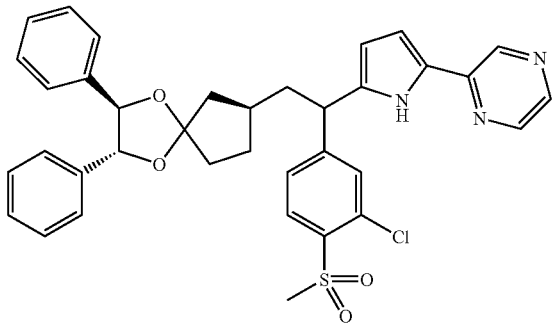

To a solution of 5-[3-chloro-4-(methylsulfonyl)phenyl]-6-[(2R,3R,7R)-2,3-diphenyl-1,4-dioxaspiro[4.4]non-7-yl]-1-(pyrazin-2-yl)hexane-1,4-dione (284 mg) in acetic acid (2.2 mL) was added ammonium acetate (530 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (94.3 mg, yield 34%) was obtained as a pale-yellow amorphous solid from a fraction eluted with ethyl acetate-hexane (4:1, volume ratio).

$^1$H NMR (300 MHz, CDCl$_3$) δ1.42-2.40 (9 H, m), 3.25 (3 H, s), 4.03-4.19 (1 H, m), 4.65-4.74 (2 H, m), 6.18-6.23 (1 H, m), 6.74-6.81 (1 H, m), 7.15-7.24 (4 H, m), 7.27-7.39 (7H, m), 7.42 (1 H, dd, J=1.0, 6.3 Hz), 8.09 (1 H, dd, J=5.1, 7.9 Hz), 8.25 (1 H, t, J=2.1 Hz), 8.31 (1 H, d, J=1.7 Hz), 8.81 (1 H, s), 9.16 (1 H, brs).

Example 194

(3R)-3-{2-[3-chloro-4-(methylsulfonyl)phenyl]-2-(5-(pyrazin-2-yl)-1H-pyrrol-2-yl)ethyl}cyclopentanone

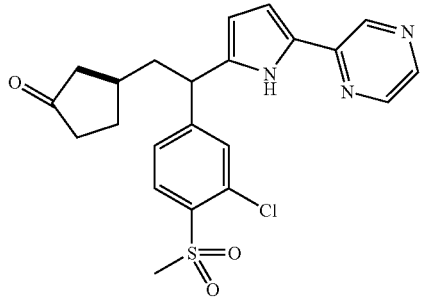

To a solution of 2-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)pyrazine (94.3 mg) in tetrahydrofuran (1 mL) was added 1M hydrochloric acid (1 mL), and the mixture was stirred at 50° C. for 24 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (44.7 mg, yield 68%) was obtained as a white amorphous solid from a fraction eluted with ethyl acetate-hexane (9:1, volume ratio). MS: 444 (MH$^+$).

$^1$H NMR (300 MHz, CDCl$_3$) δ1.59-2.45 (9 H, m), 3.26 (3 H, s), 4.05-4.17 (1 H, m), 6.23 (1 H, t, J=3.1 Hz), 6.79 (1 H, t, J=3.0 Hz), 7.33-7.38 (1 H, m), 7.42 (1 H, t, J=2.0 Hz), 8.11 (1 H, d, J=8.1 Hz), 8.27 (1 H, d, J=2.6 Hz), 8.31-8.35 (1 H, m), 8.81 (1 H, d, J=1.5 Hz), 9.11 (1 H, brs).

Example 195

6-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)pyridine-3-carbaldehyde

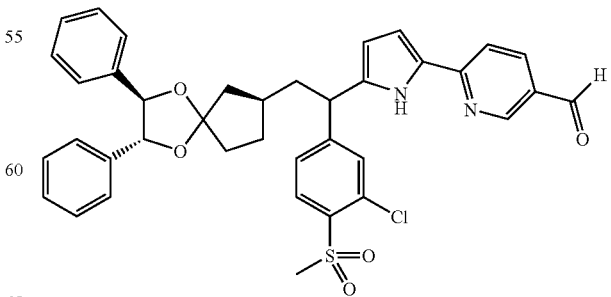

To a solution of 5-[3-chloro-4-(methylsulfonyl)phenyl]-1-[5-(1,3-dioxolan-2-yl)pyridin-2-yl]-6-[(2R,3R,7R)-2,3- diphenyl-1,4-dioxaspiro[4.4]non-7-yl]hexane-1,4-dione (276 mg) in acetic acid (2 mL) was added ammonium acetate (466 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (80.0 mg, yield 32%) was obtained as a pale-yellow amorphous solid from a fraction eluted with ethyl acetate-hexane (1:1, volume ratio).

$^1$H NMR (300 MHz, CDCl$_3$) δ1.40-2.42 (9 H, m), 3.25 (3 H, s), 4.03-4.14 (1 H, m), 4.64-4.75 (2 H, m), 6.22 (1 H, t, J=2.6 Hz), 6.81-6.86 (1 H, m), 7.15-7.24 (4 H, m), 7.27-7.38 (8 H, m), 7.55-7.63 (1 H, m), 8.02-8.11 (2 H, m), 8.80 (1 H, d, J=4.7 Hz), 9.54 (1 H, brs), 9.97 (1 H, d, J=1.5 Hz).

Example 196

[6-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)pyridin-3-yl]methanol

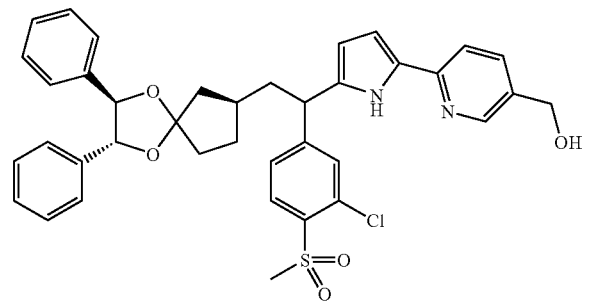

To a solution of 6-(5-{1-[3-chloro-4-(methylsulfonyl)phenyl]-2-[(2R,3R,7R)-2,3-diphenyl-1,4-5-dioxaspiro[4.4]non-7-yl]ethyl}-1H-pyrrol-2-yl)pyridine-3-carbaldehyde (80.0 mg) in a mixed solvent of tetrahydrofuran (1 mL) and methanol (1 mL) was added sodium borohydride (13.6 mg), and the mixture was stirred at 0° C. for 10 min. A saturated aqueous ammonium chloride solution was added to the reaction mixture, and the mixture was extracted with ethyl acetate. The extract was dried over anhydrous magnesium sulfate and concentrated under reduced pressure. The residue was subjected to silica gel column chromatography, and the title compound (35.6 mg, yield 44%) was obtained as a pale-yellow amorphous solid from a fraction eluted with ethyl acetate-hexane (9:1, volume ratio).

$^1$H NMR (300 MHz, CDCl$_3$) δ1.38-2.37 (9 H, m), 3.22 (3 H, s), 3.99 (1 H, brs), 4.56-4.75 (4 H, m), 6.10-6.19 (1 H, m), 6.61-6.68 (1 H, m), 7.10-7.40 (12 H, m), 7.46-7.54 (1 H, m), 7.59-7.67 (1 H, m), 7.96-8.04 (1 H, m), 8.27 (1 H, d, J=2.1 Hz), 9.84 (1 H, brs).

Example 197

(3R)-3-(2-[3-chloro-4-(methylsulfonyl)phenyl]-2-[(5-[5-(hydroxymethyl)pyridin-2-yl]-1H-pyrrol-2-yl]ethyl)cyclopentanone

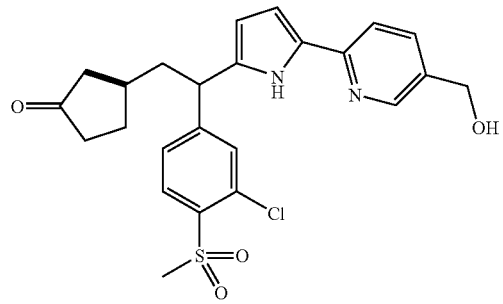

To a solution of [6-(5-{1-[3-chloro-4-(methylsulfonyl)phenyl]-2-[(2R,3R,7R)-2,3-diphenyl-1,4-dioxaspiro[4.4]non-7-yl]ethyl}-1H-pyrrol-2-yl)pyridin-3-yl]methanol (35.6 mg) in tetrahydrofuran (1 mL) was added 1M hydrochloric acid (1 mL), and the mixture was stirred at 50° C. for 16 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (16.0 mg, yield 64%) was obtained as a white amorphous solid from a fraction eluted with ethyl acetate-hexane (99:1, volume ratio). MS: 473 (MH$^+$).

$^1$H NMR (300 MHz, CDCl$_3$) δ1.72-2.45 (9 H, m), 3.24 (3 H, s), 4.03 (1 H, t, J=7.8 Hz), 4.68 (2 H, s), 6.13-6.20 (1 H, m), 6.66 (1 H, d, J=2.6 Hz), 7.25-7.32 (1 H, m), 7.37 (1 H, s), 7.52 (1 H, d, J=8.3 Hz), 7.66 (1 H, dd, J=2.1, 8.3 Hz), 8.04 (1 H, dd, J=2.5, 8.2 Hz), 8.34 (1 H, s), 9.64 (1 H, brs).

Example 198

5-(methylsulfonyl)-2-[1-(5-(pyridin-2-yl)-1H-pyrrol-2-yl)-2-(tetrahydro-2H-pyran-4-yl)ethyl]pyridine

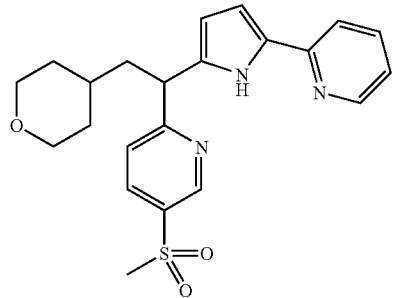

To a solution of 5-[5-(methylsulfanyl)pyridin-2-yl]-1-(pyridin-2-yl)-6-(tetrahydro-2H-pyran-4-yl)hexane-1,4-dione (27.7 mg) in acetic acid (0.35 mL) was added ammonium acetate (85.7 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. To a solution of the obtained residue in a mixed solvent of tetrahydrofuran (0.5 mL), water (0.5 mL) and methanol (0.5 mL) was added Oxone (registered trademark) (51 mg), and the mixture was stirred at room temperature for 4 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (12.4 mg, yield 43%) was obtained as a colorless amorphous solid from a fraction eluted with ethyl acetate-hexane (9:1, volume ratio). MS: 473 (MH$^+$).

$^1$H NMR (300 MHz, CDCl$_3$) δ1.16-2.18 (7 H, m), 3.08 (3 H, s), 3.22-3.37 (2 H, m), 3.84-3.98 (2 H, m), 4.34 (1 H, t, J=7.9 Hz), 6.15 (1 H, t, J=3.0 Hz), 6.61 (1 H, t, J=2.8 Hz), 6.97-7.06 (1 H, m), 7.36 (1 H, d, J=8.1 Hz), 7.46-7.52 (1H, m), 7.56-7.63 (1 H, m), 8.09 (1 H, dd, J=2.2, 8.2 Hz), 8.44 (1 H, dd, J=0.9, 4.9 Hz), 9.12 (1 H, d, J=1.9 Hz), 9.92 (1 H, brs).

Example 199

2-(5-{1-[3-fluoro-4-(methylsulfanyl)phenyl]-2-(tetrahydro-2H-pyran-4-yl)ethyl}-1H-pyrrol-2-yl)pyridine

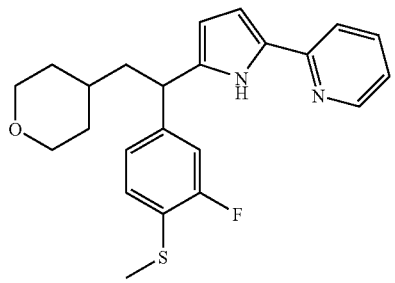

To a solution of 5-[3-fluoro-4-(methylsulfanyl)phenyl]-1-(pyridin-2-yl)-6-(tetrahydro-2H-pyran-4-yl)hexane-1,4-dione (127 mg) in acetic acid (2 mL) was added ammonium acetate (377% mg), and the mixture was stirred at 110° C. for 2 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (98.8 mg, yield 81%) was obtained as a colorless amorphous solid from a fraction eluted with ethyl acetate-hexane (1:1, volume ratio).

$^1$H NMR (300 MHz, CDCl$_3$) δ1.22-1.91 (6 H, m), 1.94-2.07 (1 H, m), 2.44 (3 H, s), 3.22-3.34 (2 H, m), 3.84-3.96 (2 H, m), 4.03 (1 H, t, J=7.9 Hz), 6.09 (1 H, t, J=3.0 Hz), 6.62 (1 H, dd, J=2.4, 3.6 Hz), 6.85-7.02 (3 H, m), 7.19 (1 H, t, J=7.8 Hz), 7.46-7.51 (1 H, m), 7.55-7.62 (1 H, m), 8.34-8.40 (1 H, m), 9.33 (1 H, brs).

Example 200

2-(5-{1-[3-fluoro-4-(methylsulfonyl)phenyl]-2-(tetrahydro-2H-pyran-4-yl)ethyl}-1H-pyrrol-2-yl)pyridine

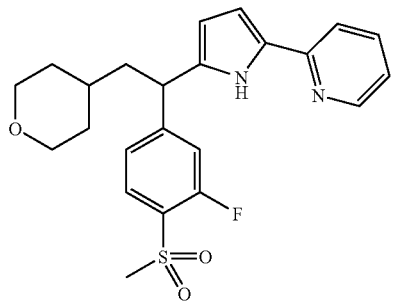

To a mixture of 2-(5-[1-[3-fluoro-4-(methylsulfanyl)phenyl]-2-(tetrahydro-2H-pyran-4-yl)ethyl]-1H-pyrrol-2-yl)pyridine (97.8 mg), tetrahydrofuran (2 mL), water (2 mL) and methanol (2 mL) was added Oxone (registered trademark) (159 mg), and the mixture was stirred at room temperature for 4 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (41.2 mg, yield 41%) was obtained as a pale-yellow amorphous solid from a fraction eluted with ethyl acetate-hexane (9:1, volume ratio). MS: 429 (MH$^+$).

$^1$H NMR (300 MHz, CDCl$_3$) δ1.23-1.70 (5 H, m), 1.80-1.94 (1 H, m), 1.99-2.14 (1 H, m), 3.20 (3 H, s), 3.24-3.35 (2 H, m), 3.86-3.99 (2 H, m), 4.15 (1 H, t, J=7.8 Hz), 6.14 (1 H, t, J=3.1 Hz), 6.64 (1 H, dd, J=2.4, 3.6 Hz), 6.99-7.11 (2 H, m), 7.16-7.22 (1 H, m), 7.48-7.53 (1 H, m), 7.58-7.65 (1 H, m), 7.87 (1 H, t, J=7.6 Hz), 8.37-8.43 (1 H, m), 9.28 (1 H, brs).

Example 201

2-(5-{1-[3-fluoro-4-(methylsulfanyl)phenyl]-2-(tetrahydro-2H-pyran-4-yl)ethyl}-1H-pyrrol-2-yl)pyrazine

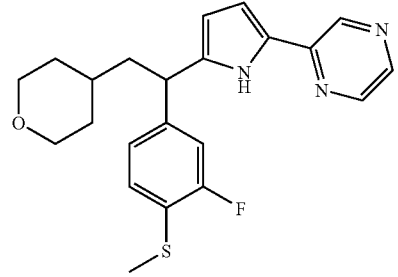

To a solution of 5-[3-fluoro-4-(methylsulfanyl)phenyl]-1-(pyrazin-2-yl)-6-(tetrahydro-2H-pyran-4-yl)hexane-1,4-dione (438 mg) in acetic acid (5 mL) was added ammonium acetate (1.29 g), and the mixture was stirred at 110° C. for 2.5 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (367 mg, yield 88%) was obtained as a colorless amorphous solid from a fraction eluted with ethyl acetate-hexane (1:1, volume ratio). MS: 398 (MH$^+$).

$^1$H NMR (300 MHz, CDCl$_3$) δ1.21-1.72 (5 H, m), 1.83-1.94 (1 H, m), 1.95-2.07 (1 H, m), 2.45 (3 H, s), 3.23-3.34 (2 H, m), 3.88-3.98 (2 H, m), 4.06 (1 H, t, J=8.0 Hz), 6.16 (1 H, t, J=3.2 Hz), 6.73-6.77 (1 H, m), 6.91 (1 H, dd, J=1.9, 11.0 Hz), 6.98 (1 H, dd, J=1.9, 8.3 Hz), 7.22 (1 H, t, J=8.0 Hz), 8.22 (1 H, d, J=2.7 Hz), 8.28-8.31 (1 H, m), 8.78 (1 H, d, J=1.5 Hz), 8.99 (1 H, brs).

Example 202

2-(5-{1-[3-fluoro-4-(methylsulfonyl)phenyl]-2-(tetrahydro-2H-pyran-4-yl)ethyl}-1H-pyrrol-2-yl)pyrazine

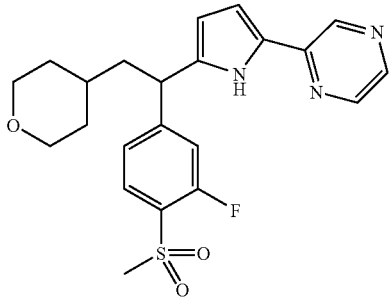

To a mixture of 2-(5-[(1-[3-fluoro-4-(methylsulfanyl)phenyl]-2-(tetrahydro-2H-pyran-4-yl)ethyl]-1H-5 pyrrol-2-yl)pyrazine (359 mg), tetrahydrofuran (6 mL), water (6 mL) and methanol (6 mL) was added Oxone (registered trademark) (583 mg), and the mixture was stirred at room temperature for 4 hr. The reaction mixture was diluted with ethyl acetate, and washed with saturated aqueous sodium m hydrogen carbonate solution. The ethyl acetate layer was dried (MgSO$_4$) and concentrated. The residue was subjected to silica gel column chromatography, and the title compound (135 mg, yield 36%) was obtained as a pale-yellow amorphous solid from a fraction eluted with ethyl acetate-hexane (9:1, volume 1.5 ratio). MS: 430 (MH$^+$).

$^1$H NMR (300 MHz, CDCl$_3$) δ1.21-1.71 (5 H, m), 1.82-1.96 (1 H, m), 2.01-2.14 (1 H, m), 3.21 (3 H, s), 3.30 (2 H, t, J=11.6 Hz), 3.94 (2 H, d, J=11.7 Hz), 4.18 (1 H, t, J=7.8 Hz), 6.20 (1 H, t, J=3.2 Hz), 6.76-6.81 (1 H, m), 7.10 (1 H, d, J=10.9 Hz), 7.21 (1 H, dd, J=1.1, 8.1 Hz), 7.90 (1 H, t, J=7.6 Hz), 8.23-8.35 (2 H, m), 8.81 (1 H, d, J=1.5 Hz), 9.11 (1 H, brs).

Example 203

2-(5-{1-[4-(methylsulfonyl)phenyl]-2-(tetrahydrofuran-3-yl)ethyl}-1H-pyrrol-2-yl)pyridine

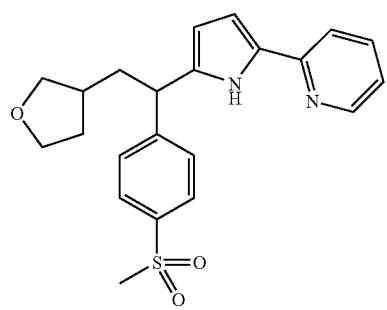

To a solution of 5-[4-(methylsulfonyl)phenyl]-1-(pyridin-2-yl)-6-(tetrahydrofuran-3-yl)hexane-1,4-dione (43.5 mg) in acetic acid (0.53 mL) was added ammonium acetate (129 mg), and the mixture was stirred at 110° C. for 2 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (27.4 mg, yield 66%) was obtained as a colorless amorphous solid from a fraction eluted with ethyl acetate-hexane (19:1, volume ratio).

$^1$H NMR (300 MHz, CDCl$_3$) δ1.45-1.67 (1 H, m), 1.91-2.34 (4 H, m), 3.04 (3 H, s), 3.33-3.45 (1 H, m), 3.62-3.93 (3 H, m), 3.99-4.10 (1 H, m), 6.13-6.19 (1 H, m), 6.64 (1 H, dd, J=2.4, 3.4 Hz), 6.97-7.05 (1 H, m), 7.40-7.52 (3 H, m), 7.55-7.65 (1 H, m), 7.83-7.92 (2 H, m), 8.35-8.41 (1 H, 9.21 (1 H, brs).

Example 204

2-(5-[(1-[4-(methylsulfonyl)phenyl]-2-(tetrahydrofuran-3-yl)ethyl]-1H-pyrrol-2-yl)pyrazine

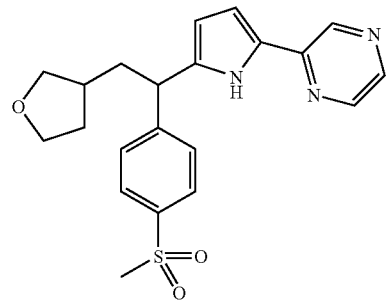

To a solution of 5-[4-(methylsulfonyl)phenyl]-1-(pyrazin-2-yl)-6-(tetrahydrofuran-3-yl)hexane-1,4-dione (100 mg) in acetic acid (1.2 mL) was added ammonium acetate (296 mg), and the mixture was stirred at 110° C. for 2 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (81.9 mg, yield 86%) was obtained as a colorless amorphous solid from a fraction eluted with ethyl acetate-hexane (19:1, volume ratio).

$^1$H NMR (300 MHz, CDCl$_3$) δ1.48-1.67 (1 H, m), 1.91-2.32 (4 H, m), 3.05 (3 H, s), 3.31-3.48 (1 H, m), 3.64-3.93 (3 H, m), 4.01-4.12 (1 H, m), 6.18-6.25 (1 H, m), 6.77 (1 H, t, J=3.0 Hz), 7.44 (2 H, d, J=8.3 Hz), 7.90 (2 H, d, J=8.3 Hz), 8.24 (1 H, d, J=2.6 Hz), 8.30-8.33 (1 H, m), 8.80 (1 H, d, J=1.1 Hz), 9.03 (1 H, brs).

Example 205

2-({[tert-butyl(diphenyl)silyl]oxy}methyl)-5-(5-{1-[4-(cyclopropylsulfonyl)phenyl]-2-(tetrahydro-2H-pyran-4-yl)ethyl}-1H-pyrrol-2-yl)-1,3,4-thiadiazole

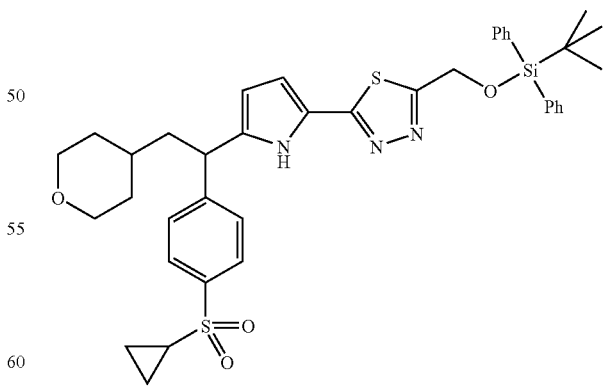

To a solution of 1-[5-({[tert-butyl(diphenyl)silyl]oxy}methyl)-1,3,4-thiadiazol-2-yl]-5-[4-(cyclopropylsulfonyl)phenyl]-6-(tetrahydro-2H-pyran-4-yl)hexane-1,4-dione (168 mg) in acetic acid (2.3 mL) was added ammonium acetate (283 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO₄) and concentrated. The residue was subjected to silica gel column chromatography, and the title compound (122 mg, yield 74%) was obtained as a pale-yellow amorphous solid from a fraction eluted with ethyl acetate-hexane (4:1, volume ratio).

¹H NMR (300 MHz, CDCl₃) δ0.82-1.72 (18 H, m), 1.82-2.15 (2H, m), 2.41-2.53 (1 H, m), 3.23-3.37 (2 H, m), 3.87-3.99 (2 H, m), 4.13-4.23 (1 H, m), 5.02 (2 H, s), 6.19 (1 H, t, J=3.1 Hz), 6.66 (1 H, dd, J=2.5, 3.7 Hz), 7.34-7.50 (8 H, m), 7.63-7.71 (4 H, m), 7.85 (2 H, d, J=8.3 Hz), 9.16 (1 H, brs).

Example 206

[5-(5-{1-[4-(cyclopropylsulfonyl)phenyl]-2-(tetrahydro-2H-pyran-4-yl)ethyl}-1H-pyrrol-2-yl)-1,3,4-thiadiazol-2-yl]methanol

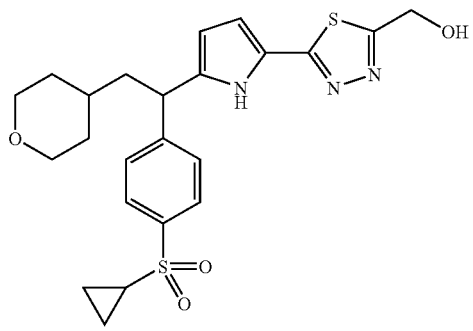

To a solution of 2-({[tert-butyl(diphenyl)silyl]oxy}methyl)-5-(5-{1-[4-(cyclopropylsulfonyl)phenyl]-2-(tetrahydro-2H-pyran-4-yl)ethyl}-1H-pyrrol-2-yl)-1,3,4-thiadiazole (122 mg) in tetrahydrofuran (1.2 mL) was added tetrabutylammonium fluoride (0.44 mL: 1M tetrahydrofuran solution), and the mixture was stirred at room temperature for 30 min. The reaction mixture was diluted with ethyl acetate, and washed with saturated brine. The ethyl acetate layer was dried (MgSO₄) and concentrated. The residue was subjected to silica gel column chromatography, and the title compound (51.3 mg, yield 63%) was obtained as white crystals from a fraction eluted with ethyl acetate-hexane (19:1, volume ratio). melting point 208.5-208.6° C. MS: 474 (MH⁺).

¹H NMR (300 MHz, CDCl₃) δ0.94-1.43 (7 H, m), 1.53-1.66 (2 H, m), 1.81-1.94 (1 H, m), 2.03-2.17 (1 H, m), 2.75-2.86 (1H, m), 3.16 (2 H, t, J=11.4 Hz), 3.72-3.84 (2 H, m), 4.31 (1 H, t, J=8.0 Hz), 4.80 (2 H, d, J=5.7 Hz), 6.10-6.21 (2 H, m), 6.63-6.68 (1 H, m), 7.60 (2 H, d, J=8.3 Hz), 7.81 (2 H, d, J=8.3 Hz), 11.93 (1 H, brs).

Example 207

2-(5-{1-[4-(methylsulfonyl)phenyl]-2-(tetrahydrofuran-2-yl)ethyl}-1H-pyrrol-2-yl)pyridine

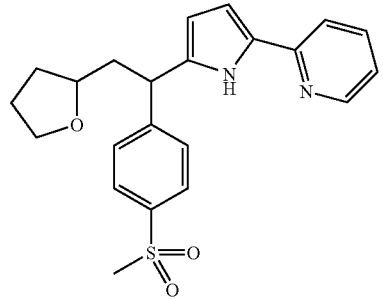

To a solution of 5-[4-(methylsulfonyl)phenyl]-1-(pyridin-2-yl)-6-(tetrahydrofuran-2-yl)hexane-1,4-dione (302 mg) in acetic acid (7.3 mL) was added ammonium acetate (897 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO₄) and concentrated. The residue was subjected to silica gel column chromatography, and the title compound (177 mg, yield 61%) was obtained as a colorless amorphous solid from a fraction eluted with ethyl acetate-hexane (9:1, volume ratio). MS: 397 (MH⁺).

¹H NMR (300 MHz, CDCl₃) δ1.41-1.58 (1 H, m), 1.76-2.18 (4 H, m), 2.21-2.40 (1 H, m), 2.97-3.08 (3 H, m), 3.48-3.99 (3H, m), 4.27-4.41 (1 H, m), 6.03-6.11 (1 H, m), 6.59-6.66 (1 H, m), 6.94-7.05 (1 H, m), 7.43-7.52 (3 H, m), 7.55-7.64 (1 H, m), 7.80-7.94 (2 H, m), 8.32-8.44 (1 H, m), 9.32-9.73 (1 H, m).

Example 208

2-methoxy-1-[2-(5-{1-[5-(methylsulfanyl)pyridin-2-yl]-2-(tetrahydro-2H-pyran-4-yl)ethyl}-1H-pyrrol-2-yl)-1,3-thiazol-5-yl]ethanol

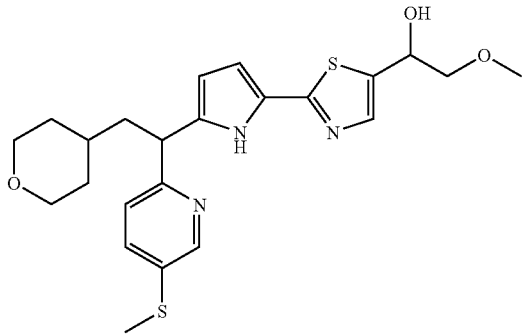

To a solution of 1-[5-(1-hydroxy-2-methoxyethyl)-1,3-thiazol-2-yl]-5-[5-(methylsulfanyl)pyridin-2-yl]-6-(tetrahydro-2H-pyran-4-yl)hexane-1,4-dione (103 mg) in acetic acid (1.7 mL) was added ammonium acetate (265 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO₄) and concentrated. The residue was subjected to silica gel column chromatography, and the title compound (62.8 mg, yield 64%) was obtained as a pale-yellow amorphous solid from a fraction eluted with ethyl acetate-hexane (19:1, volume ratio).

¹H NMR (300 MHz, CDCl₃) δ1.20-2.02 (8 H, m), 2.48 (3 H, s), 3.04-3.34 (3 H, m), 3.45 (3 H, d, J=1.1 Hz), 3.51-3.59 (1H, m), 3.61-3.67 (1 H, m), 3.89 (2 H, d, J=11.3 Hz), 5.11 (1H, dd, J=3.7, 7.3 Hz), 6.01-6.09 (1 H, m), 6.51-6.57 (1 H, m), 7.00-7.10 (1 H, m), 7.42-7.53 (2 H, m), 8.45-8.51 (1H, m), 9.91 (1 H, brs).

Example 209

2-methoxy-1-[2-(5-[(1-[5-(methylsulfonyl)pyridin-2-yl]-2-(tetrahydro-2H-pyran-4-yl)ethyl]-1H-pyrrol-2-yl)-1,3-thiazol-5-yl]ethanol

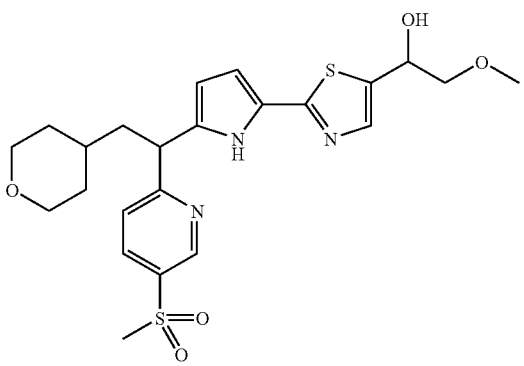

To a mixture of 2-methoxy-1-[2-(5-{1-[5-(methylsulfanyl)pyridin-2-yl]-2-(tetrahydro-2H-pyran-4-5 yl)ethyl}-1H-pyrrol-2-yl)-1,3-thiazol-5-yl]ethanol (62.8 mg), tetrahydrofuran (1 mL), water (1 mL) and methanol (1 mL) was added Oxone (registered trademark) (157 mg), and the mixture was stirred at room temperature for 3 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (40 mg, yield 59%) was obtained as a white amorphous solid from a fraction eluted with ethyl acetate-hexane (49:1, volume ratio). MS: 492 (MH$^+$).

$^1$H NMR (300 MHz, CDCl$_3$) δ1.13-1.73 (4 H, m), 1.89-2.14 (3 H, m), 3.08 (3 H, s), 3.25 (2 H, t, J=11.4 Hz), 3.44 (3 H, s), 3.50-3.70 (3 H, m), 3.89 (2 H, d, J=11.4 Hz), 4.28 (1 H, t, J=7.8 Hz), 5.11 (1 H, dd, J=3.6, 7.0 Hz), 6.08-6.13 (1 H, m), 6.53-6.58 (1 H, m), 7.33 (1 H, dd, J=1.9, 8.0 Hz), 7.50 (1 H, s), 8.08 (1 H, d, J=9.1 Hz), 9.07 (1 H, s), 10.03 (1 H, brs).

Example 210

5-chloro-2-(5-{1-[5-(methylsulfanyl)pyridin-2-yl]-2-(tetrahydro-2H-pyran-4-yl)ethyl}-1H-pyrrol-2-yl)pyridine

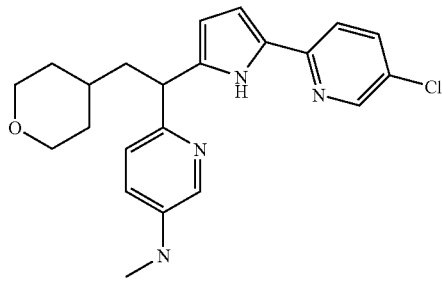

To a solution (3 mL) of 4-[5-(methylsulfanyl)pyridin-2-yl]-5-(tetrahydro-2H-pyran-4-yl)pent-1-en-3-one (89.0 mg) in ethanol-tetrahydrofuran (1:1) were added 5-chloropyridine-2-carbaldehyde (86.5 mg), 3-benzyl-5-(2-hydroxyethyl)-4-methyl-1,3-thiazol-3-ium chloride (8.2 mg) and triethylamine (17 μL), and the mixture was stirred with heating under reflux for 2 h After cooling to room temperature, the reaction mixture was diluted with ethyl acetate and washed with water. The ethyl acetate layer was dried (MgSO$_4$) and concentrated. To a solution of the obtained residue (MS: 433 (M)) in acetic acid (2 mL) was added ammonium acetate (376 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (117 mg, yield 92%) was obtained as a pale-yellow amorphous solid from a fraction eluted with ethyl acetate-hexane (1:1, volume ratio).

$^1$H NMR (300 MHz, CDCl$_3$) δ1.24-1.48 (2 H, m), 1.55-1.83 (3 H, m), 1.97-2.04 (2 H, m), 2.48 (3 H, s), 3.21-3.34 (2 H, m), 3.85-3.96 (2 H, m), 4.17 (1 H, t, 8.0 Hz), 6.09 (1 H, t, J=3.0 Hz), 6.54-6.58 (1 H, m), 7.08 (1 H, d, J=8.0 Hz), 7.39 (1 H, d, J=8.0 Hz), 7.45-7.55 (2 H, m), 8.37 (1 H, d, J=1.9 Hz), 8.51 (1 H, d, J=2.7 Hz), 9.86 (1 H, brs).

Example 211

5-chloro-2-(5-{1-[5-(methylsulfonyl)pyridin-2-yl]-2-(tetrahydro-2H-pyran-4-yl)ethyl}-1H-pyrrol-2-yl)pyridine

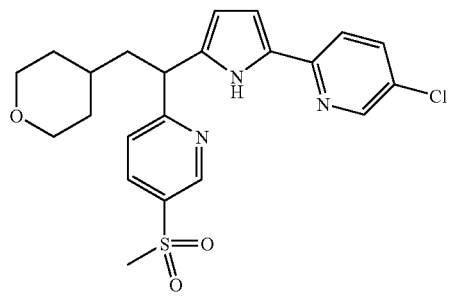

To a mixture of 5-chloro-2-(5-{1-[5-(methylsulfanyl)pyridin-2-yl]-2-(tetrahydro-2H-pyran-4-yl)ethyl}-1H-pyrrol-2-yl)pyridine (117 mg), tetrahydrofuran (2 mL), water (2 mL) and methanol (2 mL) was added Oxone (registered trademark) (207 mg), and the mixture was stirred at room temperature for 4 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (64.6 mg, yield 52%) was obtained as a white amorphous solid from a fraction eluted with ethyl acetate-hexane (2:1, volume ratio). MS: 446 (MH$^+$).

$^1$H NMR (300 MHz, CDCl$_3$) δ1.22-1.48 (2 H, m), 1.53-1.84 (3 H, m), 1.97-2.16 (2 H, m), 3.08 (3 H, s), 3.21-3.34 (2 H, m), 3.85-3.98 (2 H, m), 4.33 (1 H, t, J=7.9 Hz), 6.14 (1 H, t, J=3.1 Hz), 6.58 (1 H, dd, J=2.6, 3.4 Hz), 7.34-7.44 (2 H, m), 7.56 (1 H, dd, J=2.4, 8.5 Hz), 8.11 (1 H, dd, J=2.4, 8.1 Hz), 8.39 (1 H, d, J=2.4 Hz), 9.12 (1 H, d, J=2.4 Hz), 9.85 (1 H, brs).

Example 212

2-{1-[5-(5-chloro-1,3-thiazol-2-yl)-1H-pyrrol-2-yl]-2-(tetrahydro-2H-pyran-4-yl)ethyl}-5-(methylsulfanyl)pyridine

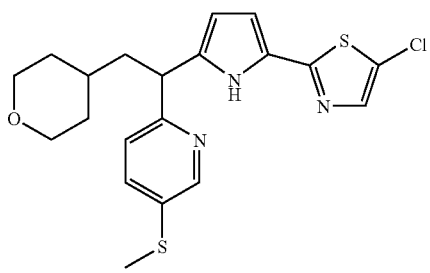

To a solution of 1-(5-chloro-1,3-thiazol-2-yl)-5-[5-(methylsulfanyl)pyridin-2-yl]-6-(tetrahydro-2H-pyran-4-yl)hexane-1,4-dione (83.9 mg) in acetic acid (1.8 mL) was added ammonium acetate (278 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (83.9 mg, yield 89%) was obtained as a pale-yellow amorphous solid from a fraction eluted with ethyl acetate-hexane (1:1, volume ratio).

$^1$H NMR (300 MHz, CDCl$_3$) δ1.19-1.43 (2 H, m), 1.51-2.01 (5 H, m), 2.48 (3 H, s), 3.20-3.34 (2 H, m), 3.90 (2 H, d, J=11.0 Hz), 4.11-4.18 (1 H, m), 6.03-6.08 (1 H, m), 6.46-6.52 (1 H, m), 7.07 (1 H, d, J=8.3 Hz), 7.41 (1 H, s), 7.48 (1 H, dd, J=2.3, 8.3 Hz), 8.49 (1 H, d, J=2.3 Hz), 9.88 (1 H, brs).

Example 213

2-{1-[5-(5-chloro-1,3-thiazol-2-yl)-1H-pyrrol-2-yl]-2-(tetrahydro-2H-pyran-4-yl)ethyl}-5-(methylsulfonyl)pyridine

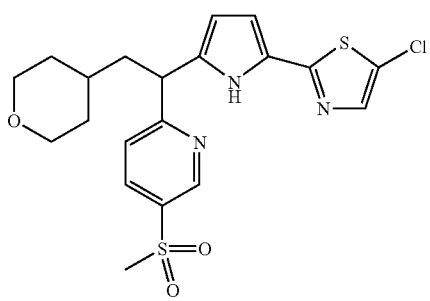

To a mixture of 2-{1-[5-(5-chloro-1,3-thiazol-2-yl)-1H-pyrrol-2-yl]-2-(tetrahydro-2H-pyran-4-yl)ethyl}-5-s (methylsulfanyl)pyridine (83.9 mg), tetrahydrofuran (1.5 mL), water (1.5 mL) and methanol (1.5 mL) was added Oxone (registered trademark) (148 mg), and the mixture was stirred at room temperature for 4 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (41.1 mg, yield 45%) was obtained as a pale-yellow amorphous solid from a fraction eluted with ethyl acetate-hexane (3:1, volume ratio). MS: 452 (MH$^+$).

$^1$H NMR (300 MHz, CDCl$_3$) δ1.21-1.70 (5 H, m), 1.93-2.12 (2 H, m), 3.09 (3 H, s), 3.21-3.35 (2 H, m), 3.86-3.97 (2 H, m), 4.31 (1 H, t, J=8.0 Hz), 6.11 (1 H, dd, J=2.6, 3.6 Hz), 6.50 (1 H, dd, J=2.6, 3.6 Hz), 7.38 (1 H, d, J=8.1 Hz), 7.44 (1 H, s), 8.13 (1 H, dd, J=2.4, 8.3 Hz), 9.13 (1 H, d, J=2.3 Hz), 9.70 (1 H, brs).

Example 214

1-[6-(5-{1-[5-(methylsulfanyl)pyridin-2-yl]-2-(tetrahydro-2H-pyran-4-yl)ethyl}-1H-pyrrol-2-yl)pyridin-3-yl]ethanol

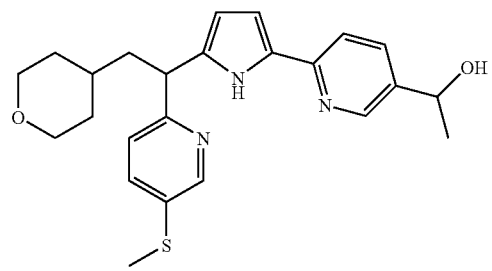

To a solution of 1-[5-(1-{[tert-butyl(dimethyl)silyl]oxy}ethyl)pyridin-2-yl]-5-[5-s (methylsulfanyl)pyridin-2-yl]-6-(tetrahydro-2H-pyran-4-yl)hexane-1,4-dione (123 mg) in acetic acid (1.7 mL) was added ammonium acetate (273 mg), and the mixture was stirred at 110° C. for 30 min, cooled to room temperature, and neutralized with saturated aqueous sodium hydrogen carbonate solution. The reaction mixture was diluted with ethyl acetate and washed with water. The ethyl acetate layer was dried (MgSO$_4$) and concentrated. To a solution of the obtained residue in tetrahydrofuran (2 mL) was added tetrabutylammonium fluoride (1M tetrahydrofuran solution, 1.77 mL), and the mixture was stirred at room temperature for 1.5 hr. The reaction mixture was diluted with ethyl acetate, and washed with saturated brine. The ethyl acetate layer was dried (MgSO$_4$) and concentrated. The residue was subjected to silica gel column chromatography, and the title compound (76.1 mg, yield 81%) was obtained as a colorless amorphous solid from a fraction eluted with ethyl acetate-hexane (19:1, volume ratio).

$^1$H NMR (300 MHz, CDCl$_3$) δ1.21-1.45 (3 H, m), 1.49 (3 H, d, J=6.4 Hz), 1.61 (2 H, d, J=11.7 Hz), 2.01 (2 H, t, J=7.0 Hz), 2.17-2.57 (4 H, m), 3.26 (2 H, t, J=11.5 Hz), 3.89 (2 H, d, J=11.4 Hz), 4.12-4.21 (1 H, m), 4.88 (1 H, q, J=6.4 Hz), 6.09 (1 H, t, J=3.0 Hz), 6.59 (1 H, d, J=2.7 Hz), 7.06 (1 H, d, J=8.0 Hz), 7.45 (2 H, d, J=8.3 Hz), 7.58-7.65 (1 H, m), 8.38 (1 H, s), 8.46 (1 H, s), 10.06 (1 H, brs).

Example 215

1-[6-(5-{1-[5-(methylsulfonyl)pyridin-2-yl]-2-(tetrahydro-2H-pyran-4-yl)ethyl}-1H-pyrrol-2-yl)pyridin-3-yl]ethanol

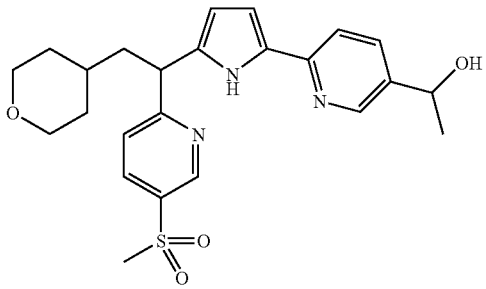

To a mixture of 1-[6-(5-{1-[5-(methylsulfanyl)pyridin-2-yl]-2-(tetrahydro-2H-pyran-4-yl)ethyl}-1H-pyrrol-2-yl)pyridin-3-yl]ethanol (76.1 mg), tetrahydrofuran (1 mL), water (1 mL) and methanol (1 mL) was added Oxone (registered trademark) (133 mg), and the mixture was stirred at room temperature for 4 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (40.3 mg, yield 49%) was obtained as a white amorphous solid from a fraction eluted with ethyl acetate-hexane (19:1, volume ratio). MS: 456 (MH$^+$).

$^1$H NMR (300 MHz, CDCl$_3$) δ1.23-1.70 (7 H, m), 1.74-1.90 (1 H, m), 1.98-2.18 (2 H, m), 3.08 (3 H, s), 3.22-3.36 (2 H, m), 3.84-3.97 (2 H, m), 4.31-4.40 (1 H, m), 4.88-4.98 (1 H, m), 6.14 (1 H, t, J=3.1 Hz), 6.58-6.62 (1 H, m), 7.38 (1 H, d, J=8.3 Hz), 7.48 (1 H, d, J=8.5 Hz), 7.62-7.68 (1 H, m), 8.11 (1 H, dd, J=2.4, 8.3 Hz), 8.44 (1 H, s), 9.13 (1 H, d, J=2.3 Hz), 9.81 (1 H, brs).

Example 216

1-[6-(5-{2-cyclopentyl-1-[5-(methylsulfanyl)pyridin-2-yl]ethyl}-1H-pyrrol-2-yl)pyridin-3-yl]ethanol

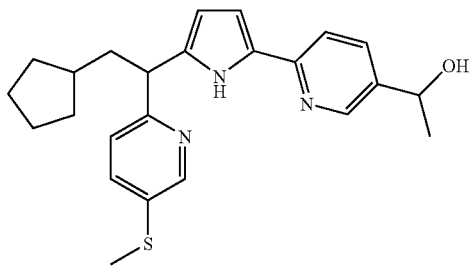

To a solution of 1-[5-(1-{[tert-butyl(dimethyl)silyl]oxy}ethyl)pyridin-2-yl]-6-cyclopentyl-5-s [5-(methylsulfanyl)pyridin-2-yl]hexane-1,4-dione (848 mg) in acetic acid (11 mL) was added ammonium acetate (1.93 g), and the mixture was stirred at 110° C. for 45 min. After cooling to room temperature, the mixture was neutralized with saturated aqueous sodium hydrogen carbonate solution. The reaction m mixture was diluted with ethyl acetate and washed with water. The ethyl acetate layer was dried (MgSO$_4$) and concentrated. To a solution of the obtained residue in tetrahydrofuran (6.3 mL) was added tetrabutylammonium fluoride (1M tetrahydrofuran solution, 6.28 mL), and the mixture was stirred at room temperature for 1.5 hr. The reaction mixture was diluted with ethyl acetate and washed with saturated brine. The ethyl acetate layer was dried (MgSO$_4$) and concentrated. The residue was subjected to silica gel column chromatography, and the title compound (313 mg, yield 49%) was obtained as a colorless amorphous solid from a fraction eluted with ethyl acetate-hexane (19:1, volume ratio). MS: 408 (MH$^+$).

$^1$H NMR (300 MHz, CDCl$_3$) δ1.01-1.97 (12 H, m), 2.09 (2 H, t, J=7.3 Hz), 2.47 (3 H, s), 4.09 (1 H, t, J=7.9 Hz), 4.90 (1 H, q, J=6.6 Hz), 6.10 (1 H, t, J=3.1 Hz), 6.58 (1 H, dd, J=2.5, 3.5 Hz), 7.11 (1 H, d, J=7.5 Hz), 7.42-7.52 (2 H, m), 7.61 (1H; dd, J=2.3, 8.3 Hz), 8.41 (1 H, d, J=1.7 Hz), 8.51 (1 H, d, J=2.3 Hz), 9.88 (1 H, brs).

Example 217

1-[6-(5-{2-cyclopentyl-1-[5-(methylsulfonyl)pyridin-2-yl]ethyl}-1H-pyrrol-2-yl)pyridin-3-yl]ethanol

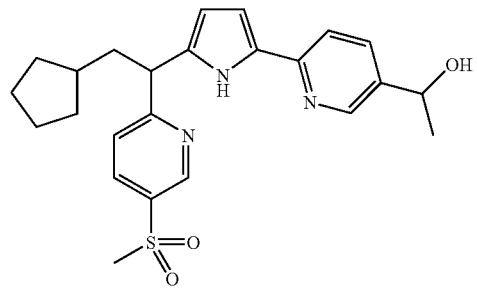

To a mixture of 1-[6-(5-{2-cyclopentyl-1-[5-(methylsulfanyl)pyridin-2-yl]ethyl}-1H-pyrrol-2-yl)pyridin-3-yl]ethanol (313 mg), tetrahydrofuran (5.5 mL), water (5.5 mL) and methanol (5.5 mL) was added Oxone (registered trademark) (566 mg), and the mixture was stirred at room temperature for 2 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (128 mg, yield 38%) was obtained as a white amorphous solid from a fraction eluted with ethyl acetate-hexane (9:1, volume ratio). MS: 440 (MH$^+$).

$^1$H NMR (300 MHz, CDCl$_3$) δ1.04-1.22 (2 H, m), 1.37-2.00 (12H, m), 2.15 (2 H, t, J=7.4 Hz), 3.08 (3 H, s), 4.25 (1 H, t, J=7.8 Hz), 4.92 (1 H, q, J=6.3 Hz), 6.14 (1 H, t, J=3.2 Hz), 6.57-6.62 (1 H, m), 7.39 (1 H, d, J=8.3 Hz), 7.47 (1 H, d, J=8.3 Hz), 7.64 (1 H, dd, J=1.9, 8.3 Hz), 8.05-8.13 (1 H, m), 8.43 (1 H, s), 9.12 (1 H, s), 9.88 (1 H, brs).

Example 218

1-[6-(5-{2-cyclopentyl-1-[5-(methylsulfanyl)pyridin-2-yl]ethyl}-1H-pyrrol-2-yl)pyridin-3-yl]ethane-1,2-diol

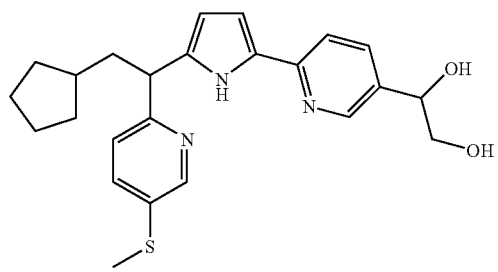

To a solution of 1-[5-(1,2-bis{[tert-butyl(dimethyl)silyl]oxy}ethyl)pyridin-2-yl]-6-cyclopentyl-5-[5-(methylsulfanyl)pyridin-2-yl]hexane-1,4-dione (682 mg) in acetic acid (7 mL) was added ammonium acetate (1.26 g), and the mixture was stirred at 110° C. for 45 min. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. To a solution of the obtained residue in tetrahydrofuran (4 mL) was added tetrabutylammonium fluoride (1M tetrahydrofuran solution, 8.16 mL), and the mixture was stirred at room temperature for 1.5 hr. The reaction mixture was diluted with ethyl acetate, and washed with saturated brine. The ethyl acetate layer was dried (MgSO$_4$) and concentrated. The residue was subjected to silica gel column chromatography, and the title compound (230 mg, yield 53%) was obtained as a colorless amorphous solid from a fraction eluted with ethyl acetate-hexane (99:1, volume ratio). MS: 424 (MH$^+$).

$^1$H NMR (300 MHz, CDCl$_3$) δ0.80-1.84 (9 H, m), 2.03-2.14 (2 H, m), 2.46 (3 H, s), 3.63-3.82 (2 H, m), 4.09 (1 H, t, J=7.8 Hz), 4.81 (1 H, dd, J=3.6, 7.7 Hz), 6.10 (1 H, t, J=3.1 Hz), 6.58 (1 H, d, J=2.6 Hz), 7.09 (1 H, d, J=8.1 Hz), 7.45 (2 H, t, J=7.7 Hz), 7.60 (1 H, dt, J=2.0, 8.3 Hz), 8.35 (1 H, s), 8.44 (1 H, d, J=2.1 Hz), 10.10 (1 H, brs).

Example 219

1-[6-(5-{2-cyclopentyl-1-[5-(methylsulfonyl)pyridin-2-yl]ethyl}-1H-pyrrol-2-yl)pyridin-3-yl]ethane-1,2-diol

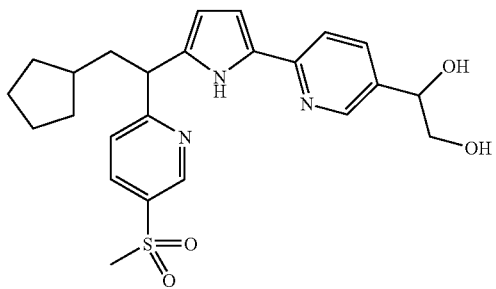

To a mixture of 1-[6-(5-{2-cyclopentyl-1-[5-(methylsulfanyl)pyridin-2-yl]ethyl}-1H-pyrrol-2-yl)pyridin-3-yl]ethane-1,2-diol (124 mg), tetrahydrofuran (2 mL), water (2 mL) and methanol (2 mL) was added Oxone (registered trademark) (216 mg), and the mixture was stirred at room temperature for 2 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (57.1 mg, yield 43%) 15 was obtained as a white amorphous solid from a fraction eluted with ethyl acetate-hexane (99:1, volume ratio). MS: 456 (MH$^+$).

$^1$H NMR (300 MHz, CDCl$_3$) δ1.04-1.22 (4 H, m), 1.36-1.83 (8 H, m), 2.14 (2 H, t, J=6.8 Hz), 3.07 (3 H, s), 3.66-3.71 (1 H, m), 3.74-3.81 (1 H, m), 4.25 (1 H, t, J=8.0 Hz), 4.81 (1 H, dd, J=3.6, 7.8 Hz), 6.15 (1 H, t, J=3.0 Hz), 6.58-6.63 (1 H, m), 7.38 (1 H, d, J=8.0 Hz), 7.46 (1 H, d, J=8.3 Hz), 7.62 (1H, d, J=8.3 Hz), 8.09 (1 H, dd, J=2.3, 8.3 Hz), 8.38 (1 H, s), 9.09 (1 H, d, J=2.3 Hz), 10.04 (1 H, brs).

Example 220

1-(6-{5-[(E)-1-[4-(cyclopropylsulfonyl)phenyl]-2-(tetrahydro-2H-pyran-4-yl)ethenyl]-1H-pyrrol-2-yl}pyridin-3-yl)-2-methylpropane-1,2-diol

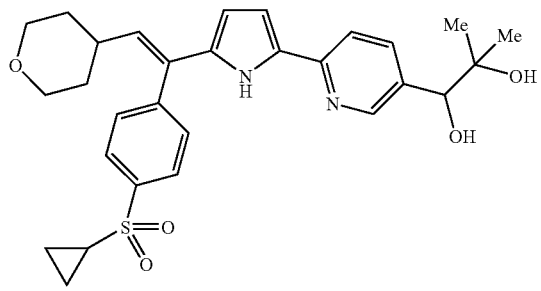

A mixture of (5E)-5-[4-(cyclopropylsulfonyl)phenyl]-1-[5-(1,2-dihydroxy-2-methylpropyl)pyridin-2-yl]-6-(tetrahydro-2H-pyran-4-yl)hex-5-ene-1,4-dione (4.79 g), ammonium acetate (3.40 g) and acetic acid (15 mL) was stirred at 90° C. for 2 hr. Water was added to the reaction mixture, and the mixture was neutralized with 8N aqueous sodium hydroxide solution. The precipitated solid was collected by filtration, washed with water, and dried. The obtained solid was dissolved in tetrahydrofuran, and the solution was treated with activated carbon and concentrated. Cold ethyl acetate was added to the obtained residue to allow crystallization. The crystals were collected by filtration, washed with cold ethyl acetate and dried to give the title compound (3.38 g, yield 73%) as pale-yellow crystals. melting point 196-197° C. MS: 523 (MH$^+$).

Example 221

[5-(5-{1-[4-(methylsulfonyl)phenyl]-2-(tetrahydro-2H-pyran-4-yl)ethyl}-1H-pyrrol-2-yl)-1,3,4-thiadiazol-2-yl]methanol

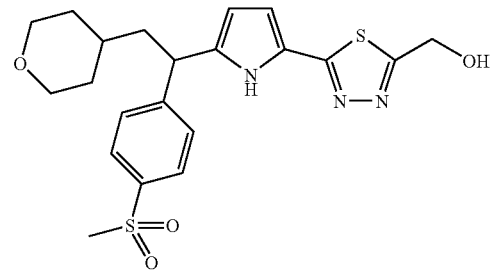

To a solution of 1-[5-({[tert-butyl(diphenyl)silyl]oxy}methyl)-1,3,4-thiadiazol-2-yl]-5-[4-(methylsulfonyl)phenyl]-6-(tetrahydro-2H-pyran-4-yl)hexane-1,4-dione (1.95 g) in acetic acid (20 mL) was added ammonium acetate (3.41 g), and the mixture was stirred at 110° C. for 30 min. The reaction mixture was cooled to room temperature, and neutralized with saturated aqueous sodium hydrogen carbonate solution. The reaction mixture was diluted with ethyl acetate and washed with water. The ethyl acetate layer was washed with saturated brine, dried (MgSO$_4$) and concentrated to give a crude product (1.9 g). To a solution of the obtained crude product in tetrahydrofuran (10 mL) was added tetrabutylammonium fluoride (1M tetrahydrofuran solution) (5 mL) at room temperature. The reaction mixture was stirred at room temperature for 10 min and concentrated. The residue was subjected to silica gel column chromatography, and the title compound (1.0 g, yield 81%) was obtained as white crystals from a fraction eluted with ethyl acetate. melting point 199-201° C. MS: 448 (MH+).

¹H NMR (300 MHz, DMSO-d₆) δ1.08-1.44 (3 H, m), 1.53-1.66 (2H, m), 1.81-1.96 (1 H, m), 2.01-2.18 (1 H, m), 3.08-3.22 (5 H, m), 3.78 (2 H, d, J=10.6 Hz), 4.31 (1H, t, J=8.0 Hz), 4.80 (2 H, d, J=5.3 Hz), 6.09-6.22 (2 H, m), 6.65 (1 H, brs), 7.61 (2 H, d, J=8.0 Hz), 7.85 (2 H, d, J=8.0 Hz), 11.93 (1 H, brs).

Example 222

5-(5-{1-[4-(methylsulfonyl)phenyl]-2-(tetrahydro-2H-pyran-4-yl)ethyl}-1H-pyrrol-2-yl)-1,3,4-thiadiazole-2-carbaldehyde

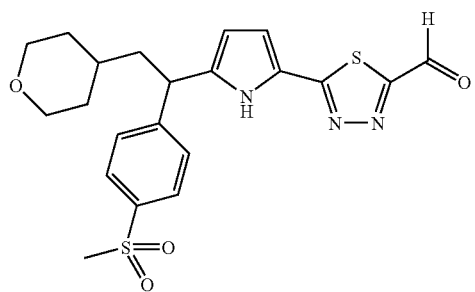

To a solution of [5-(5-{1-[4-(methylsulfonyl)phenyl]-2-(tetrahydro-2H-pyran-4-yl)ethyl}-1H-pyrrol-2-yl)-1,3,4-thiadiazol-2-yl]methanol (700 mg) in acetonitrile (10 mL) was added Dess-Martin reagent (796 mg) and the mixture was stirred at room temperature for 15 hr and at 80° C. for 30 min. The reaction mixture was cooled to room temperature, saturated aqueous sodium hydrogen carbonate solution was added and the mixture was stirred for 20 min. The insoluble material was removed by filtration through celite, and the filtrate was diluted with ethyl acetate and washed with water. The ethyl acetate layer was washed with saturated brine, dried (MgSO₄) and concentrated to give the title compound (700 mg, yield 100%) as a yellow amorphous solid.

¹H NMR (300 MHz, CDCl₃) δ1.25-1.42 (3 H, m), 1.53-1.71 (2 H, m), 1.88-1.99 (1 H, m), 2.02-2.17 (1 H, m), 3.08 (3 H, s), 3.28 (2 H, t, J=11.4 Hz), 3.87-3.99 (2 H, m), 4.23 (1 H, t, J=7.9 Hz), 6.27 (1 H, t, J=3.3 Hz), 6.84 (1 H, dd, J=2.6, 3.8 Hz), 7.39 (2 H, d, J=8.3 Hz), 7.88 (2 H, d, J=8.3 Hz), 9.73 (1H, brs), 10.15 (1 H, s).

Example 223

1-[5-(5-{1-[4-(methylsulfonyl)phenyl]-2-(tetrahydro-2H-pyran-4-yl)ethyl}-1H-pyrrol-2-yl)-1,3,4-thiadiazol-2-yl]ethanol

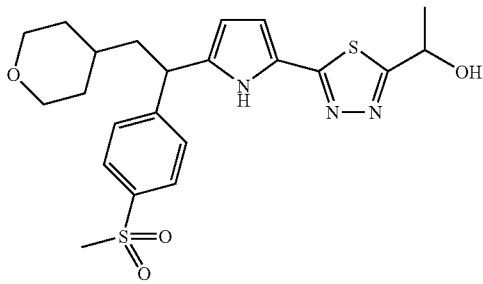

To a solution of 5-(5-{1-[4-(methylsulfonyl)phenyl]-2-(tetrahydro-2H-pyran-4-yl)ethyl}-1H-pyrrol-2-yl)-1,3,4-thiadiazole-2-carbaldehyde (700 mg) in tetrahydrofuran (10 mL) was added methylmagnesium bromide (1M tetrahydrofuran solution) (3.46 mL) and the mixture was stirred at room temperature for 10 min. Saturated aqueous ammonium chloride solution was added to the reaction mixture, and the mixture was extracted with ethyl acetate. The ethyl acetate layer was washed with saturated brine, dried (MgSO₄) and concentrated. The residue was subjected to silica gel column chromatography, and the title compound (460 mg, yield 63%) was obtained as a pale-yellow amorphous solid from a fraction eluted with ethyl acetate-methanol (9:1, volume ratio). MS: 462 (MH+).

¹H NMR (300 MHz, DMSO-d₆) δ1.48 (3 H, dd, J=6.4, 1.5 Hz), 1.59 (2 H, d, J=13.2 Hz), 1.81-1.96 (1 H, m), 2.01-2.16 (1 H, m), 3.09-3.21 (5 H, m), 3.33 (3 H, s), 3.78 (2 H, d, J=10.2 Hz), 4.31 (1 H, t, J=8.1 Hz), 5.05 (1 H, dq, J=6.0, 6.2 Hz), 6.17 (1 H, t), 6.28 (1 H, d, J=4.9 Hz), 6.64 (1 H, dd, J=2.5, 3.5 Hz), 7.61 (2 H, d, J=8.3 Hz), 7.85 (2 H, d, J=8.3 Hz), 11.91 (1 H, brs).

Example 224

5-(5-{1-[4-(cyclopropylsulfonyl)phenyl]-2-(tetrahydro-2H-pyran-4-yl)ethyl}-1H-pyrrol-2-yl)-1,3,4-thiadiazole-2-carbaldehyde

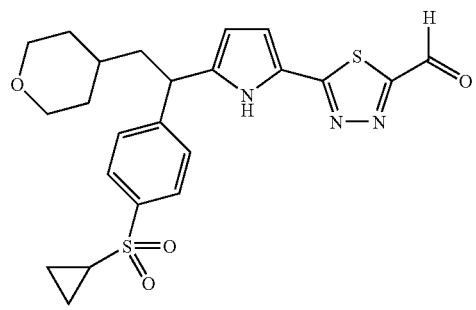

To a solution of [5-(5-{1-[4-(cyclopropylsulfonyl)phenyl]-2-(tetrahydro-2H-pyran-4-yl)ethyl}-1H-pyrrol-2-yl)-1,3,4-thiadiazol-2-yl]methanol (700 mg) in acetonitrile (10 mL) was added Dess-Martin reagent (752 mg), and the mixture was stirred at 80° C. for 30 min. The reaction mixture was cooled to room temperature, saturated aqueous sodium hydrogen carbonate solution was added and the mixture was stirred for 20 min. The insoluble material was removed by filtration through celite, and the filtrate was diluted with ethyl acetate and washed with water. The ethyl acetate layer was washed with saturated brine, dried (MgSO₄) and concentrated to give the title compound (700 mg, yield 100%) as a yellow amorphous solid.

¹H NMR (300 MHz, CDCl₃) δ1.05 (2 H, dd, J=1.9, 8.0 Hz), 1.28-1.51 (5 H, m), 1.51-1.70 (2 H, m), 1.73 (2 H, s), 1.83-2.00 (1 H, m), 2.00-2.17 (1 H, m), 2.41-2.59 (1 H, m), 3.28 (2 H, t, J=11.4 Hz), 3.92 (2 H, dd, J=4.7, 10.8 Hz), 4.22 (1 H, t, J=8.0 Hz), 6.27 (1 H, d, J=3.0 Hz), 6.85 (1 H, dd, J=2.3, 3.8 Hz), 7.38 (2 H, d, J=8.3 Hz), 7.84 (2 H, d, J=8.3 Hz), 9.58 (1 H, brs), 10.15 (1 H, s).

Example 225

1-[5-(5-{1-[4-(cyclopropylsulfonyl)phenyl]-2-(tetrahydro-2H-pyran-4-yl)ethyl}-1H-pyrrol-2-yl)-1,3,4-thiadiazol-2-yl]ethanol

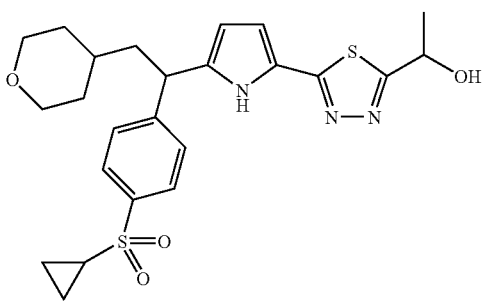

To a solution of 5-(5-{1-[4-(cyclopropylsulfonyl)phenyl]-2-(tetrahydro-2H-pyran-4-yl)ethyl}-1H-pyrrol-2-yl)-1,3,4-thiadiazole-2-carbaldehyde (700 mg) in tetrahydrofuran (10 mL) was added methylmagnesium bromide (1M tetrahydrofuran solution) (3.27 mL) and the mixture was stirred at room temperature for 10 min. Saturated aqueous ammonium chloride solution was added to the reaction mixture, and the mixture was extracted with ethyl acetate. The ethyl acetate layer was washed with saturated brine, dried (MgSO$_4$) and concentrated. The residue was subjected to silica gel column chromatography to give a pale-yellow amorphous solid from a fraction eluted with ethyl acetate-methanol (9:1, volume ratio). The pale-yellow amorphous solid was purified by preparative HPLC to give the title compound (301 mg, yield 42%) as a colorless amorphous solid. MS: 488 (MH$^+$).

$^1$H NMR (300 MHz, DMSO-d$_6$) δ0.92-1.04 (2 H, m), 1.06-1.14 (2H, m), 1.15-1.36 (3 H, m), 1.48 (3 H, dd, J=6.4, 1.5 Hz), 1.52-1.67 (2 H, m), 1.79-1.94 (1 H, m), 2.03-2.18 (1 H, m), 2.72-2.88 (1 H, m), 3.15 (2 H, t, J=11.4 Hz), 3.78 (2 H, d, J=11.0 Hz), 4.31 (1 H, t, J=8.0 Hz), 4.99-5.14 (1 H, m), 6.15-6.21 (1 H, m), 6.29 (1 H, d, J=4.9 Hz), 6.60-6.68 (1H, m), 7.60 (2 H, d, J=8.0 Hz), 7.81 (2 H, d, J=8.3 Hz), 11.92 (1 H, brs).

Example 226

4-{[5-(5-{1-[4-(cyclopropylsulfonyl)phenyl]-2-(tetrahydro-2H-pyran-4-yl)ethyl}-1H-pyrrol-2-yl)-1,3,4-thiadiazol-2-yl]methyl}thiomorpholine monooxide

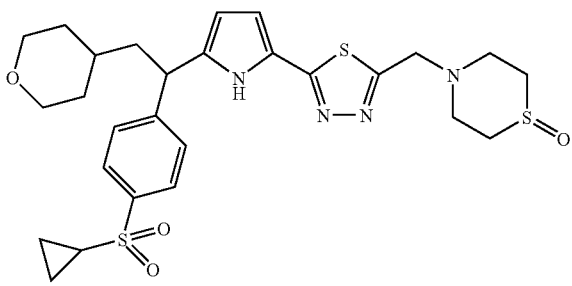

To a solution of 5-(5-{1-[4-(cyclopropylsulfonyl)phenyl]-2-(tetrahydro-2H-pyran-4-yl)ethyl}-1H-pyrrol-2-yl)-1,3,4-thiadiazole-2-carbaldehyde (300 mg) in tetrahydrofuran (20 mL) were added thiomorpholine monooxide hydrochloride (149 mg), sodium triacetoxyborohydride (270 mg) and triethylamine (177 μL) and the mixture was stirred at room temperature for 18 hr. Saturated aqueous sodium hydrogen carbonate solution was added to the reaction mixture, and the mixture was extracted with ethyl acetate. The ethyl acetate layer was washed with saturated brine, dried (MgSO$_4$) and concentrated. The residue was subjected to basic silica gel column chromatography to give a pale-yellow amorphous solid from a fraction eluted with ethyl acetate-methanol (9:1, volume ratio). The pale-yellow amorphous solid was purified by preparative HPLC to give the title compound (87 mg, yield 24%) as a pale-yellow amorphous solid. MS: 575 (MH$^+$).

$^1$H NMR (300 MHz, CDCl$_3$) δ1.04 (2 H, dd, J=8.0, 2.2 Hz), 1.29-1.47 (5 H, m), 1.50-1.73 (2 H, m), 1.78-1.96 (1 H, m), 1.99-2.14 (1 H, m), 2.46 (1 H, tt, J=4.8, 8.0 Hz), 2.74-2.99 (6 H, m), 3.15-3.36 (4 H, m), 3.85-3.97 (2 H, m), 3.99 (2 H, s), 4.18 (1 H, t, J=7.6 Hz), 6.18 (1 H, t, J=3.2 Hz), 6.62 (1 H, dd, J=3.7, 2.5 Hz), 7.38 (2 H, d, J=8.3 Hz), 7.83 (2 H, d, J=8.5 Hz), 9.32 (1 H, brs).

Example 227

1-{[5-(5-{1-[4-(cyclopropylsulfonyl)phenyl]-2-(tetrahydro-2H-pyran-4-yl)ethyl}-1H-pyrrol-2-yl)-1,3,4-thiadiazol-2-yl]methyl}azetidin-3-ol

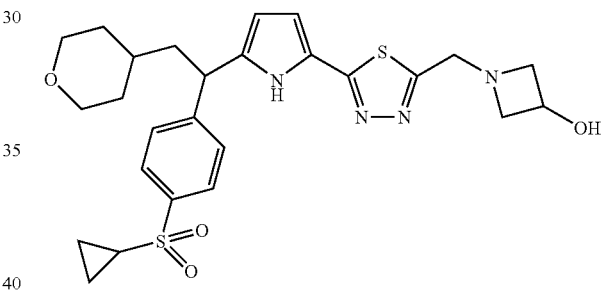

To a solution of 5-(5-{1-[4-(cyclopropylsulfonyl)phenyl]-2-(tetrahydro-2H-pyran-4-yl)ethyl}-1H-pyrrol-2-yl)-1,3,4-thiadiazole-2-carbaldehyde (300 mg) in tetrahydrofuran (20 mL) were added 3-hydroxyazetidine hydrochloride (105 mg), sodium triacetoxyborohydride (270 mg) and triethylamine (177 μL) and the mixture was stirred at room temperature for 18 hr. Saturated aqueous sodium hydrogen carbonate solution was added to the reaction mixture, and the mixture was extracted with ethyl acetate. The ethyl acetate layer was washed with saturated brine, dried (MgSO$_4$) and concentrated. The residue was subjected to basic silica gel column chromatography to give pale-yellow amorphous solid from a fraction eluted with ethyl acetate-methanol (9:1, volume ratio). The pale-yellow amorphous solid was purified by preparative HPLC to give the title compound (97 mg, yield 29%) as a pale-yellow amorphous solid. MS: 529 (MH$^+$).

$^1$H NMR (300 MHz, CDCl$_3$) δ1.03 (2 H, dd, J=7.9, 2.1 Hz), 1.24-1.46 (5 H, m), 1.51-1.71 (2 H, m), 1.82-1.95 (1 H, m), 1.98-2.12 (1 H, m), 2.45 (1 H, dt, J=4.0, 8.1 Hz), 3.09 (2 H, dd, J=6.0, 7.5 Hz), 3.27 (2 H, t, J=11.3 Hz), 3.69-3.81 (2 H, m), 3.85-3.97 (2 H, m), 3.99 (2 H, s), 4.18 (1 H, t, J=7.9 Hz), 4.42-4.58 (1 H, m), 6.16 (1 H, t, J=3.2 Hz), 6.57-6.64 (1 H, m), 7.37 (2 H, d, J=8.3 Hz), 7.82 (2 H, d, J=8.3 Hz), 9.44 (1 H, brs).

Example 228

4-{[5-(5-{1-[4-(cyclopropylsulfonyl)phenyl]-2-(tetrahydro-2H-pyran-4-yl)ethyl}-1H-pyrrol-2-yl)-1,3,4-thiadiazol-2-yl]methyl}morpholine

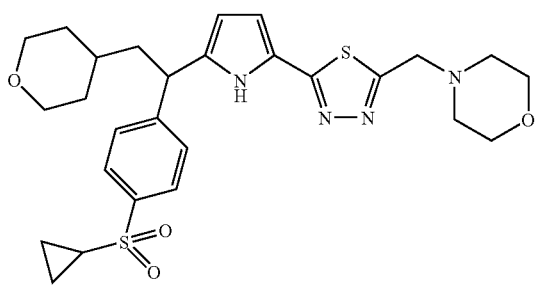

To a solution of 5-(5-{1-[4-(cyclopropylsulfonyl)phenyl]-2-(tetrahydro-2H-pyran-4-yl)ethyl}-1H-pyrrol-2-yl)-1,3,4-thiadiazole-2-carbaldehyde (300 mg) in tetrahydrofuran (20 mL) were added morpholine (83 mg), sodium triacetoxyborohydride (270 mg) and triethylamine (177 µL) and the mixture was stirred at room temperature for 18 hr. Saturated aqueous sodium hydrogen carbonate solution was added to the reaction mixture, and the mixture was extracted with ethyl acetate. The ethyl acetate layer was washed with saturated brine, dried (MgSO$_4$) and concentrated. The residue was subjected to basic silica gel column chromatography, and the title compound (141 mg, yield 41%) was obtained as a colorless amorphous solid from a fraction eluted with ethyl acetate. MS: 543 (MH$^+$).

$^1$H NMR (300 MHz, CDCl$_3$) δ1.04 (2 H, dd, J=2.4, 8.0 Hz), 1.30-1.46 (5 H, m), 1.51-1.70 (2 H, m), 1.80-1.96 (1 H, m), 1.98-2.15 (1 H, m), 2.36-2.52 (1 H, m), 2.52-2.63 (4 H, m), 3.20-3.35 (2 H, m), 3.67-3.76 (4 H, m), 3.86-4.00 (2H, m), 3.90 (2 H, s), 4.12-4.23 (1 H, m), 6.18 (1 H, t, J=3.2 Hz), 6.61 (1 H, t, J=3.1 Hz), 7.37 (2 H, d, J=8.3 Hz), 7.83 (2 H, d, J=8.1 Hz), 9.27 (1 H, brs).

Example 229

2-({[5-(5-{1-[4-(cyclopropylsulfonyl)phenyl]-2-(tetrahydro-2H-pyran-4-yl)ethyl}-1H-pyrrol-2-yl)-1,3,4-thiadiazol-2-yl]methyl}amino)ethanol

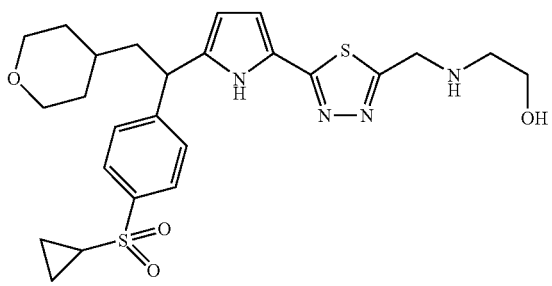

To a solution of 5-(5-{1-[4-(cyclopropylsulfonyl)phenyl]-2-(tetrahydro-2H-pyran-4-yl)ethyl}-1H-pyrrol-2-yl)-1,3,4-thiadiazole-2-carbaldehyde (300 mg) in methanol (10 mL) was added 2-aminoethanol (250 µL) at room temperature, and the mixture was stirred at 80° C. for 1 hr. The reaction mixture was cooled to room temperature, sodium tetrahydroborate (72 mg) was added to the reaction mixture, and the mixture was stirred at room temperature for 30 min. Saturated aqueous sodium hydrogen carbonate solution was added to the reaction mixture, and the mixture was extracted with ethyl acetate. The ethyl acetate layer was washed with saturated brine, dried (MgSO$_4$) and concentrated. The residue was subjected to basic silica gel column chromatography to give a pale-yellow amorphous solid from a fraction eluted with ethyl acetate-methanol (9:1, volume ratio). The pale-yellow amorphous solid was subjected to silica gel column chromatography, and the title compound (188 mg, yield 57%) was obtained as a colorless amorphous solid from a fraction eluted with ethyl acetate-methanol (8:2, volume ratio). MS: 517 (MH$^+$).

$^1$H NMR (300 MHz, CDCl$_3$) δ1.04 (2 H, dd, J=2.1, 7.7 Hz), 1.25-1.47 (5 H, m), 1.54-1.78 (2 H, m), 1.82-1.98 (1 H, m), 1.99-2.18 (1 H, m), 2.46 (1 H, tt, J=4.9, 8.0 Hz), 2.83-2.93 (2 H, m), 3.21-3.38 (2 H, m), 3.66-3.72 (2 H, m), 3.87-4.00 (2 H, m), 4.16 (1 H, t), 4.21 (2 H, s), 6.17 (1 H, t, J=3.2 Hz), 6.61 (1 H, dd, J=2.5, 3.7 Hz), 7.38 (2 H, d, J=8.3 Hz), 7.83 (2 H, d, J=8.5 Hz), 9.31 (1 H, brs).

Example 230

2-({[6-(5-{1-[4-(cyclopropylsulfonyl)phenyl]-2-(tetrahydro-2H-pyran-4-yl)ethyl}-1H-pyrrol-2-yl)pyridin-3-yl]methyl}sulfonyl)ethanol

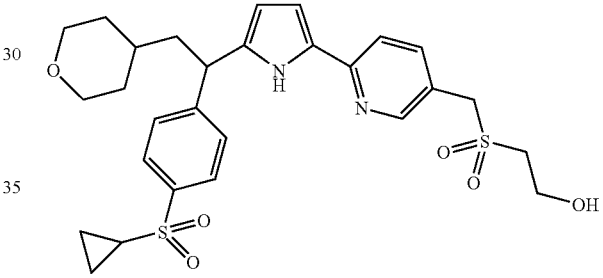

To a solution of tert-butyl 2-{1-[4-(cyclopropylsulfonyl)phenyl]-2-(tetrahydro-2H-pyran-4-yl)ethyl}-5-[5-(hydroxymethyl)pyridin-2-yl]-1H-pyrrole-1-carboxylate (3 g) in tetrahydrofuran (10 mL) were added methanesulfonyl chloride (0.5 mL) and triethylamine (1.1 mL), and the mixture was stirred at room temperature for 2 hr. Saturated aqueous ammonium chloride solution was added to the reaction mixture, and the mixture was extracted with ethyl acetate. The ethyl acetate layer was washed with saturated brine, dried (MgSO$_4$) and concentrated. The residue was subjected to silica gel column chromatography to give a pale-yellow amorphous solid (1 g) from a fraction eluted with ethyl acetate. To a solution of the obtained amorphous solid (1 g) in N,N-dimethylformamide (30 µL) were added 2-mercaptoethanol (242 mg) and potassium carbonate (643 mg), and the mixture was stirred at 50° C. for 15 hr. 1M Hydrochloric acid (20 mL) was added to the reaction mixture, and the mixture was further stirred at 80° C. for 2 hr. Water was added to the reaction mixture, and the mixture was extracted with ethyl acetate. The ethyl acetate layer was washed with saturated brine, dried (MgSO$_4$) and concentrated to give a pale-yellow amorphous solid (900 mg). To a mixture of the obtained amorphous solid (900 mg), tetrahydrofuran (5 mL), methanol (9 mL) and water (1 mL) was added Oxone (registered trademark) (2.31 g), and the mixture was stirred at room temperature for 2 days. Sodium sulfite (3 g) was added to the reaction mixture, and the mixture was stirred for 30 min. Water was added to the reaction mixture, and the mixture was extracted with ethyl acetate. The ethyl acetate layer was washed with saturated brine, dried (MgSO₄) and concentrated. The residue was subjected to silica gel column chromatography to give a yellow amorphous solid from a fraction eluted with ethyl acetate. The yellow amorphous solid was purified by preparative HPLC to give the title compound (201 mg, yield 6.8%) as a yellow amorphous solid. MS: 559 (MH⁺).

¹H NMR (300 MHz, CDCl₃) δ1.02 (2 H, dd, J=8.0, 1.9 Hz), 1.18-1.49 (5 H, m), 1.58 (2 H, d, J=15.5 Hz), 1.85 (2 H, dt, J=3.3, 6.7 Hz), 1.95-2.12 (1 H, m), 2.46 (1 H, td, J=3.8, 8.3 Hz), 3.00-3.15 (2 H, m), 3.18-3.36 (2 H, m), 3.61-3.81 (2 H, m), 3.83-3.99 (2 H, m), 4.02-4.23 (3 H, m), 4.30 (2 H, s), 6.16 (1 H, t, J=3.0 Hz), 6.61-6.74 (1 H, m), 7.38 (2 H, d, J=8.3 Hz), 7.51 (1 H, d, J=8.3 Hz), 7.71 (1 H, dd, J=1.9, 8.3 Hz), 7.81 (2 H, d, J=8.3 Hz), 8.36 (1 H, s), 9.63 (1 H, brs).

Example 231

2-[6-(5-{1-[4-(cyclopropylsulfonyl)phenyl]-2-(tetrahydro-2H-pyran-4-yl)ethyl}-1H-pyrrol-2-yl)pyridin-3-yl]-2-methoxyethanol

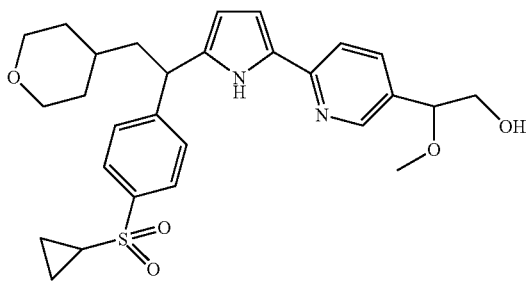

To a solution of trimethylsulfoxonium iodide (947 mg) in dimethylsulfoxide (5 mL) was added sodium hydride (oil, about 60%) (129 mg) and the mixture was stirred at room temperature m for 1 hr. The reaction mixture was added dropwise to a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (1 g) in dimethylsulfoxide (5 mL) and the mixture was stirred at room temperature for 1 hr. Water was added to the reaction mixture, and the mixture was extracted with ethyl acetate. The ethyl acetate layer was washed with saturated brine, dried (MgSO₄) and concentrated to give a crude product (1.0 g). The obtained crude product was dissolved in methanol (10 mL), sodium methoxide (64 mg) was added at room temperature, and the mixture was stirred for 2 hr. Saturated aqueous ammonium chloride solution was added to the reaction mixture, and the mixture was extracted with ethyl acetate. The ethyl acetate layer was washed with saturated brine, dried (MgSO₄) and concentrated. The residue was subjected to silica gel column chromatography to give a pale-yellow amorphous solid from a fraction eluted with ethyl acetate. The obtained pale-yellow amorphous solid was purified by preparative HPLC to give the title compound (310 mg, yield 28%) as a colorless amorphous solid. MS: 511 (MH⁺).

¹H NMR (600 MHz, CDCl₃) δ1.00-1.05 (2 H, m), 1.41-1.51 (1 H, m), 1.56-1.62 (1 H, m), 1.62-1.68 (1 H, m), 1.90 (1 H, ddd, J=7.0, 7.7, 14.3 Hz), 2.07 (1 H, dt, J=7.7, 13.6 Hz), 2.44 (1H, tt, J=4.9, 7.9 Hz), 3.23-3.31 (2 H, m), 3.29 (1 H, s), 3.30 (1 H, s), 3.62 (1 H, dt, J=4.2, 11.7 Hz), 3.67 (1 H, ddd, J=2.2, 8.1, 11.7 Hz), 3.88-3.95 (1 H, m), 4.18 (1 H, t, J=7.9 Hz), 4.23-4.31 (1 H, m), 6.16 (1 H, t, J=3.3 Hz), 6.66 (1 H, dd, J=2.6, 3.3 Hz), 7.40 (2 H, m), 7.50 (1 H, d, J=8.4 Hz), 7.56 (1 H, dd, J=2.2, 8.4 Hz), 7.82 (2 H, m), 8.31 (1 H, d, J=1.8 Hz), 9.32 (1 H, brs).

Example 232

1-{[6-(5-{1-[4-(cyclopropylsulfonyl)phenyl]-2-(tetrahydro-2H-pyran-4-yl)ethyl}-1H-pyrrol-2-yl)pyridin-3-yl](hydroxy)methyl}cyclobutanol

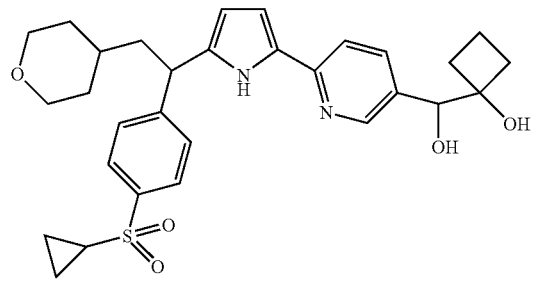

To a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (940 mg) in acetic acid (10 mL) were added cyclobutanone (2.1 g) and 20% aqueous titanium trichloride solution (3.1 g), and the mixture was stirred under argon at room temperature for 16 hr. The reaction mixture was diluted with ethyl acetate, and neutralized with saturated aqueous sodium hydrogen carbonate solution, and filtered through celite to remove the insoluble material. The filtrate was extracted with ethyl acetate. The ethyl acetate layer was washed with saturated brine, dried (MgSO₄) and concentrated. The residue was subjected to silica gel column chromatography to give a pale-yellow amorphous solid from a fraction eluted with ethyl acetate. The obtained pale-yellow amorphous solid was purified by preparative HPLC to give the title compound (75 mg, yield 6.9%) as a colorless amorphous solid. MS: 537 (MH⁺).

¹H NMR (300 MHz, CDCl₃) δ0.95-1.10 (2 H, m), 1.15-1.47 (5 H, m), 1.59 (2 H, t, J=14.4 Hz), 1.68-1.96 (4 H, m), 1.96-2.15 (3 H, m), 2.20-2.37 (1 H, m), 2.43 (1 H, tt, J=4.8, 7.9 Hz), 3.17-3.36 (2 H, m), 3.90 (2 H, d, J=9.8 Hz), 4.04-4.19 (1 H, m), 4.61 (1 H, d, J=6.4 Hz), 6.14 (1 H, d, J=2.7 Hz), 6.65 (1 H, s), 7.35 (2 H, d, J=7.6 Hz), 7.49 (1 H, t, J=7.4 Hz), 7.66-7.77 (1 H, m), 7.78 (2 H, d, J=6.8 Hz), 8.17-8.39 (1 H, m), 9.71 (1 H, brs).

Example 233

1-[6-(5-{1-[4-(cyclopropylsulfonyl)phenyl]-2-(tetrahydro-2H-pyran-4-yl)ethyl}-1H-pyrrol-2-yl)pyridin-3-yl]-2-(methylsulfonyl)ethanol

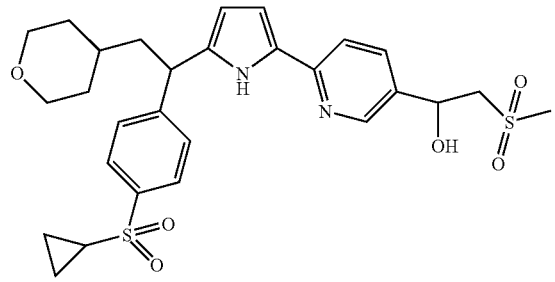

To a solution of dimethylsulfone (446 mg) in tetrahydrofuran (10 mL) was added dropwise lithium hexamethyldisilazide (1.6M tetrahydrofuran solution) (2.7 mL) at −78° C., and the mixture was stirred for 1 hr. To the reaction mixture was added dropwise a solution of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (1 g) in tetrahydrofuran (5 mL), and the mixture was stirred for 1 hr. Water was added to the reaction mixture, and the mixture was extracted with ethyl acetate. The ethyl acetate layer was washed with saturated brine, dried (MgSO$_4$) and concentrated. The residue was subjected to silica gel column chromatography to give a pale-yellow amorphous solid from a fraction eluted with ethyl acetate-methanol (9:1, volume ratio). The obtained pale-yellow amorphous solid was subjected to basic silica gel column chromatography to give a pale-yellow amorphous solid from a fraction eluted with ethyl acetate-methanol (9:1, volume ratio). The pale-yellow amorphous solid was purified by preparative HPLC to give the title compound (270 mg, yield 22%) as a colorless amorphous solid. MS: 559 (MH$^+$).

$^1$H NMR (300 MHz, CDCl$_3$) δ1.02 (1 H, dd, J=2.0, 7.8 Hz), 1.21-1.44 (5 H, m), 1.50-1.66 (2 H, m), 1.78-1.93 (1 H, m), 1.95-2.11 (1 H, m), 2.43 (1 H, tt, J=4.8, 7.9 Hz), 3.07 (3 H, s), 3.12 (2 H, d, J=15.4 Hz), 3.26 (2 H, t, J=11.6 Hz), 3.38-3.53 (1 H, m), 3.90 (2 H, d, J=11.3 Hz), 4.04-4.21 (1 H, m), 5.31 (1 H, d, J=10.4 Hz), 6.16 (1 H, t, J=3.1 Hz), 6.68 (1 H, d, J=2.6 Hz), 7.33 (2 H, d, J=8.3 Hz), 7.45-7.54 (1 H, m), 7.63 (1 H, dt, J=2.3, 8.4 Hz), 7.76 (2 H, d, J=8.5 Hz), 8.28 (1 H, dd, J=2.0, 4.6 Hz), 9.60 (1 H, brs).

Example 234

Methyl [6-(5-{1-[4-(cyclopropylsulfonyl)phenyl]-2-(tetrahydro-2H-pyran-4-yl)ethyl}-1H-pyrrol-2-yl)pyridin-3-yl]acetate

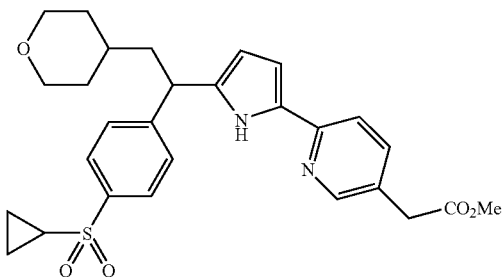

A mixture of 6-(5-{1-[4-(cyclopropylsulfonyl)phenyl]-2-(tetrahydro-2H-pyran-4-yl)ethyl}-1H-pyrrol-2-yl)pyridine-3-carbaldehyde (3.0 g), methyl (methylsulfinyl)methyl sulfide (2.43 g), 40% benzyltrimethylammonium hydroxide methanol solution (5 mL), and tetrahydrofuran (50 mL) was heated under reflux for 24 hr. Water was added to the reaction mixture and the mixture was extracted with ethyl acetate. The ethyl acetate layer was washed with saturated brine, dried (MgSO$_4$) and concentrated. A mixture of the residue and 10% hydrogen chloride methanol solution (60 mL) was heated under reflux for 15 hr, and cooled to room temperature. To the reaction mixture was basified with saturated aqueous sodium hydrogen carbonate and the mixture was extracted with ethyl acetate. The ethyl acetate layer was washed with saturated brine, dried (MgSO$_4$) and concentrated. The residue was subjected to silica gel column chromatography, and the title compound (2.02 g, yield 64%) was obtained as a brown amorphous solid from a fraction eluted with ethyl acetate-hexane (1:1-2:1, volume ratio). MS: 509 (MH$^+$).

$^1$H NMR (300 MHz, CDCl$_3$) δ0.93-1.08 (2 H, m), 1.16-1.72 (8 H, m), 1.81-1.96 (1 H, m), 1.99-2.15 (1 H, m), 2.36-2.52 (1H, m), 3.18-3.37 (2 H, m), 3.58 (2 H, s), 3.70 (3 H, s), 3.84-3.98 (2 H, m), 6.09-6.21 (1 H, m), 6.56-6.70 (1 H, m), 7.38 (2 H, d, J=7.95 Hz), 7.43-7.50 (1 H, m), 7.52-7.60 (1 H, m), 7.81 (2 H, d, J=8.33 Hz), 8.28 (1 H, d, J=1.51 Hz), 9.27 (1 H, brs).

Example 235

2-(5-{1-[4-(cyclopropylsulfonyl)phenyl]-2-(tetrahydro-2H-pyran-4-yl)ethyl}-1H-pyrrol-2-yl)-5-[(5-methyl-1,3,4-oxadiazol-2-yl)methyl]pyridine

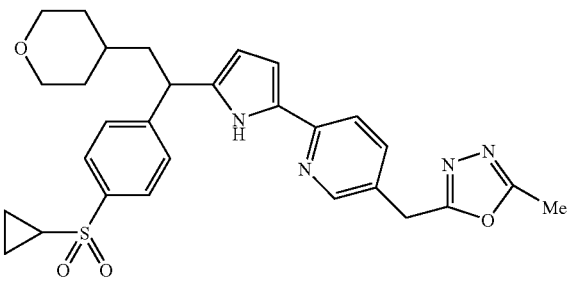

To a mixture of [6-(5-{1-[4-(cyclopropylsulfonyl)phenyl]-2-(tetrahydro-2H-pyran-4-yl)ethyl}-1H-pyrrol-2-yl)pyridin-3-yl]acetic acid (350 mg), 4-methylmorpholine (90 mg) and tetrahydrofuran (20 mL) was added isobutyl chlorocarbonate (140 mg) at 0° C. The reaction mixture was stirred at 0° C. for 1 hr, and the insoluble material was filtered off. The filtrate was added dropwise to a mixture of hydrazine monohydrate (180 mg) and tetrahydrofuran (10 mL) at 0° C. The reaction mixture was stirred at 0° C. for 1 hr. Aqueous ammonium chloride solution was added to the reaction mixture, and the mixture was extracted with ethyl acetate. The ethyl acetate layer was washed with saturated brine, dried (MgSO$_4$) and concentrated. A mixture of the obtained residue, trimethyl orthoacetate (250 mg), methanesulfonic acid (13 mg) and tetrahydrofuran (30 mL) was heated under reflux for 3 hr. To the reaction mixture was added saturated aqueous sodium hydrogen carbonate and the mixture was extracted with ethyl acetate. The ethyl acetate layer was washed with saturated brine, dried (MgSO$_4$) and concentrated. The residue was subjected to silica gel column chromatography, and the title compound (60 mg, yield 16%) was obtained as a pale-yellow amorphous solid from a fraction eluted with ethyl acetate-hexane (1:3-3:1, volume ratio). MS: 533 (MH$^+$).

$^1$H NMR (300 MHz, CDCl$_3$) δ0.94-1.06 (2 H, m), 1.20-1.70 (7 H, m), 1.81-1.95 (1 H, m), 1.98-2.12 (1 H, m), 2.37-2.52 (4 H, m), 3.19-3.36 (2 H, m), 3.84-3.97 (2 H, m), 4.05-4.21 (3 H, m), 6.15 (1 H, t, J=3.03 Hz), 6.59-6.69 (1 H, m), 7.38 (2 H, d, J=8.33 Hz), 7.42-7.52 (1 H, m), 7.53-7.60 (1 H, m), 7.81 (2 H, d, J=8.33 Hz), 8.33 (1 H, d, J=1.51 Hz), 9.33 (1 H, brs).

Example 236

2-[6-(5-{1-[4-(cyclopropylsulfonyl)phenyl]-2-(tetrahydro-2H-pyran-4-yl)ethyl}-1H-pyrrol-2-yl)pyridin-3-yl]ethanol

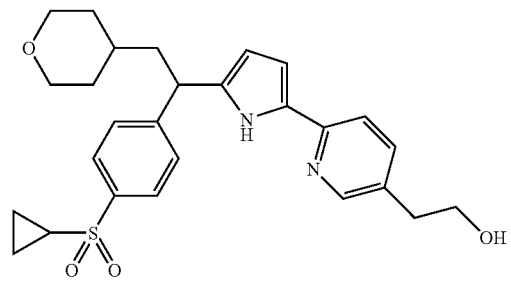

To a mixture of methyl [6-(5-{1-[4-(cyclopropylsulfonyl)phenyl]-2-(tetrahydro-2H-pyran-4-yl)ethyl}-1H-pyrrol-2-yl)pyridin-3-yl]acetate (400 mg), tetrahydrofuran (10 mL) and methanol (2 mL) was added lithium borohydride (85 mg) at room temperature, and the mixture was stirred at room temperature for 3 hr. To the reaction mixture was added water and the mixture was extracted with ethyl acetate. The ethyl acetate layer was washed with saturated brine, dried (MgSO$_4$) and concentrated. The residue was subjected to silica gel column chromatography to give the title compound as a crude product from a fraction eluted with hexane-ethyl acetate-methanol (1:4:0-0:95:5, volume ratio), the crude product was subjected to preparative HPLC to give the title compound (150 mg, yield 39%) as a pale-yellow amorphous solid. MS: 481 (MH$^+$).

$^1$H NMR (300 MHz, CDCl$_3$) δ0.93-1.07 (2 H, m), 1.21-1.72 (8 H, m), 1.81-1.95 (1 H, m), 2.00-2.13 (1 H, m), 2.35-2.52 (1 H, m), 2.81 (2 H, t, J=6.44 Hz), 3.21-3.35 (2 H, m), 3.70-4.02 (4 H, m), 4.17 (1 H, t, J=7.76 Hz), 6.14 (1 H, t, J=3.22 Hz), 6.55-6.68 (1 H, m), 7.34-7.53 (4 H, m), 7.82 (2 H, d, J=8.33 Hz), 8.23 (1 H, s), 9.26 (1 H, brs.).

Example 237

2-(5-{1-[4-(cyclopropylsulfonyl)phenyl]-2-(tetrahydro-2H-pyran-4-yl)ethyl}-1H-pyrrol-2-yl)-5-(1H-1,2,4-triazol-1-ylmethyl)pyridine

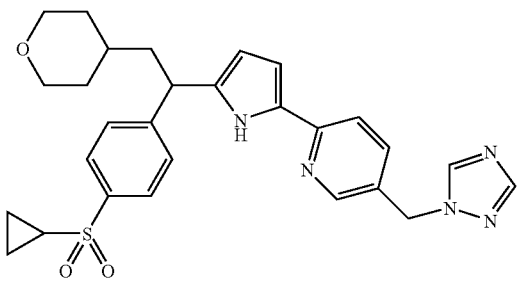

To a mixture of [6-(5-[1-[4-(cyclopropylsulfonyl)phenyl]-2-(tetrahydro-2H-pyran-4-yl)ethyl]-1H-pyrrol-2-yl)pyridin-3-yl]methanol (430 mg), tributylphosphine (280 mg), 1,2,4-triazole (76 mg) and tetrahydrofuran (30 mL) was added 1,1'-(azodicarbonyl)dipiperidine (350 mg) at room temperature, and the mixture was stirred at room temperature for 15 hr. To the mixture were added 1,2,4-triazole (76 mg) and tributylphosphine (280 mg), 1,1'-(azodicarbonyl)dipiperidine (350 mg) was further added at room temperature, and the mixture was stirred at room temperature for 4 hr. The reaction mixture was concentrated, ethyl acetate was added to the residue, and the insoluble material was filtered off. The filtrate was concentrated, and the residue was subjected to silica gel column chromatography to give the title compound as a crude product from a fraction eluted with ethyl acetate-methanol (100:0-90:10, volume ratio), and the crude product was subjected to preparative HPLC to give the title compound as an oil. The oil was crystallized from acetonitrile-diethyl ether, and further recrystallized from acetone-hexane to give the title compound (38 mg, yield 8%) as colorless crystals. MS: 518 (MH$^+$). melting point 152-153° C.

Example 238

2-(3-chloro-5-{1-[4-(cyclopropylsulfonyl)phenyl]-2-(tetrahydro-2H-pyran-4-yl)ethyl}-1H-pyrrol-2-yl)pyridine

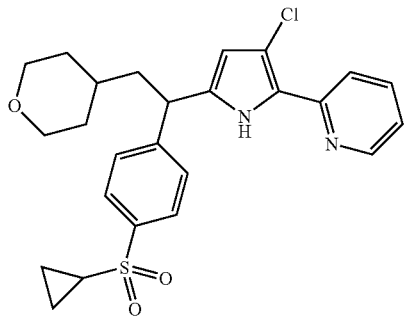

To a solution of 2-(5-{1-[4-(cyclopropylsulfonyl)phenyl]-2-(tetrahydro-2H-pyran-4-yl)ethyl}-1H-pyrrol-2-yl)pyridine (200 mg) in tetrahydrofuran (5 mL) was added N-chlorosuccinimide (61.2 mg) at 0° C., and the mixture was stirred overnight at room temperature, and further at 50° C. for 1 day. After cooling to room temperature, the reaction mixture was diluted with ethyl acetate, and washed with saturated aqueous sodium hydrogen carbonate. The ethyl acetate layer was washed with saturated brine, dried (MgSO$_4$) and concentrated. The residue was subjected to silica gel column chromatography, and the title compound (60.0 mg, yield 28%) was obtained as a pale-yellow amorphous solid from a fraction eluted with ethyl acetate-hexane (2:1, volume ratio). MS: 471 (MH$^+$).

$^1$H NMR (300 MHz, CDCl$_3$) δ0.94-1.09 (2 H, m), 1.28-1.45 (5 H, m), 1.51-1.56 (1 H, m), 1.60-1.69 (1 H, m), 1.77-1.92 (1H, m), 1.95-2.04 (1 H, m), 2.36-2.51 (1 H, m), 3.20-3.36 (2 H, m), 3.86-3.98 (2 H, m), 4.05-4.15 (1 H, m), 6.13 (1 H, d, J=2.6 Hz), 7.02-7.11 (1 H, m), 7.32-7.42 (2 H, m), 7.63-7.73 (1 H, m), 7.79-7.87 (2 H, m), 8.06-8.16 (1 H, m), 8.35-8.47 (1 H, m), 9.44 (1 H, brs).

Example 239

2-(4-chloro-5-{1-[4-(cyclopropylsulfonyl)phenyl]-2-(tetrahydro-2H-pyran-4-yl)ethyl}-1H-pyrrol-2-yl)pyridine

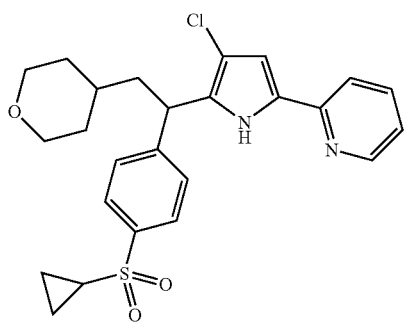

To a solution of 2-(5-{1-[4-(cyclopropylsulfonyl)phenyl]-2-(tetrahydro-2H-pyran-4-yl)ethyl}-1H-pyrrol-2-yl)pyridine (200 mg) in tetrahydrofuran (5 mL) was added N-chlorosuccinimide (61.2 mg) at 0° C., and the mixture was stirred

Example 240

Ethyl 5-{1-[4-(cyclopropylsulfonyl)phenyl]-2-(tetrahydro-2H-pyran-4-yl)ethyl}-1H-pyrrole-2-carboxylate

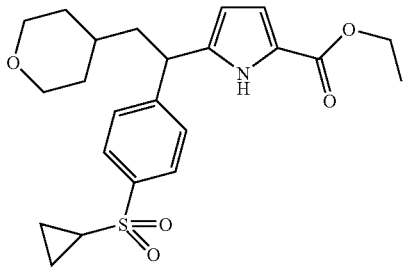

To a solution of 4-[4-(cyclopropylsulfonyl)phenyl]-5-(tetrahydro-2H-pyran-4-yl)pent-1-en-3-one (500 mg) in a mixed solvent of ethanol (15 mL) and tetrahydrofuran (5 mL) were added ethyl glyoxylate (polymer type, 47% toluene solution) (623 mg), 3-benzyl-5-(2-hydroxyethyl)-4-methyl-1,3-thiazol-3-ium chloride (43 mg) and triethylamine (86 μL), and the mixture was heated under reflux under argon atmosphere for 30% min. After cooling to room temperature, the reaction mixture was diluted with ethyl acetate and washed with water. The ethyl acetate layer was washed with saturated brine, dried (MgSO$_4$) and concentrated. The residue was dissolved in acetic acid (5 mL), ammonium acetate (1.7 g) was added, and the mixture was stirred at 110° C. for 30 min. After cooling to room temperature, the mixture was neutralized with saturated aqueous sodium hydrogen carbonate solution. The reaction mixture was diluted with ethyl acetate and washed with water. The ethyl acetate layer was washed with saturated brine, dried (MgSO$_4$) and concentrated. The residue was subjected to silica gel column chromatography, and the title compound (210 mg, yield 34%) was obtained as a pale-yellow amorphous solid from a fraction eluted with hexane-ethyl acetate (1:1, volume ratio). MS: 432 (MH$^+$).

$^1$H NMR (300 MHz, CDCl$_3$) δ1.04 (2 H, dd, J=2.0, 7.8 Hz), 1.22-1.46 (8 H, m), 1.58 (2 H, dd, J=1.9, 18.8 Hz), 1.82-1.98 (1H, m), 1.98-2.12 (1 H, m), 2.46 (1 H, tt, J=4.9, 8.0 Hz), 3.27 (2 H, t, J=11.4 Hz), 3.92 (2 H, dd, J=4.4, 6.5 Hz), 4.16 (1 H, t, J=8.0 Hz), 4.28 (2 H, q, J=7.2 Hz), 6.09-6.21 (1 H, m), 6.85 (1 H, dd, J=2.4, 3.8 Hz), 7.36 (2 H, d, J=8.3 Hz), 7.83 (2 H, d, J=8.3 Hz), 8.87 (1 H, brs).

overnight at room temperature, and further at 50° C. for 1 day. After cooling to room temperature, the reaction mixture was diluted with ethyl acetate, and washed with saturated aqueous sodium hydrogen carbonate. The ethyl acetate layer was washed with saturated brine, dried (MgSO$_4$) and concentrated. The residue was subjected to silica gel column chromatography, and the title compound (49.0 mg, yield 23%) was obtained as a pale-yellow amorphous solid from a fraction eluted with ethyl acetate-hexane (2:1, volume ratio). MS: 471 (MH$^+$).

$^1$H NMR (300 MHz, CDCl$_3$) δ0.93-1.08 (2 H, m), 1.29-1.48 (5 H, m), 1.54-1.60 (1 H, m), 1.65-1.78 (1 H, m), 1.92-2.03 (1H, m), 2.07-2.18 (1 H, m), 2.36-2.50 (1 H, m), 3.23-3.36 (2 H, m), 3.92 (2 H, dd, J=5.1, 10.9 Hz), 4.42 (1 H, dd, J=7.0, 9.4 Hz), 6.59 (1 H, s), 6.99-7.12 (1 H, m), 7.40-7.51 (3 H, m), 7.58-7.72 (1 H, m), 7.79-7.87 (2 H, m), 8.38-8.47 (1H, m), 9.42 (1 H, brs).

Example 241

5-{1-[4-(cyclopropylsulfonyl)phenyl]-2-(tetrahydro-2H-pyran-4-yl)ethyl}-1H-pyrrole-2-carboxylic acid

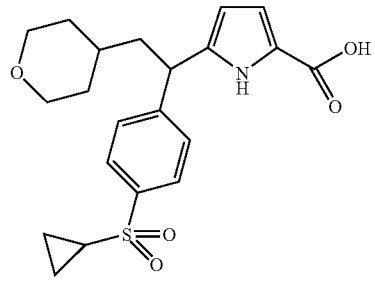

To a solution of ethyl 5-{1-[4-(cyclopropylsulfonyl)phenyl]-2-(tetrahydro-2H-pyran-4-yl)ethyl}-1H-pyrrole-2-carboxylate (1.5 g) in a mixed solvent of ethanol (15 mL) and tetrahydrofuran (15 ml) was added 1N aqueous sodium hydroxide solution (10 mL), and the mixture was stirred at 70° C. for 3 hr. After cooling to room temperature, the reaction mixture was concentrated, the residue was diluted with ethyl acetate, and 1N hydrochloric acid (10 mL) was added. The mixture was extracted with ethyl acetate. The ethyl acetate layer was washed with saturated brine, dried (MgSO$_4$) and concentrated. The residue was subjected to silica gel column chromatography, and the title compound (1.3 g, yield 93%) was obtained as a pale-yellow amorphous solid from a fraction eluted with ethyl acetate. MS: 404 (MH$^+$).

$^1$H NMR (300 MHz, CDCl$_3$) δ1.03 (2 H, dd, J=2.3, 8.0 Hz), 1.20-1.44 (5 H, m), 1.48-1.70 (2 H, m), 1.77-1.97 (1 H, m), 1.97-2.11 (1 H, m), 2.38-2.53 (1 H, m), 3.26 (2 H, t, J=11.4 Hz), 3.82-3.99 (2 H, m), 4.13-4.23 (1 H, m), 6.13-6.19 (1 H, m), 6.93-7.02 (1 H, m), 7.36 (2 H, d, J=8.3 Hz), 7.81 (2 H, d, J=8.3 Hz), 9.34 (1 H, brs).

Example 242

5-{1-[4-(cyclopropylsulfonyl)phenyl]-2-(tetrahydro-2H-pyran-4-yl)ethyl}-1H-pyrrole-2-carboxamide

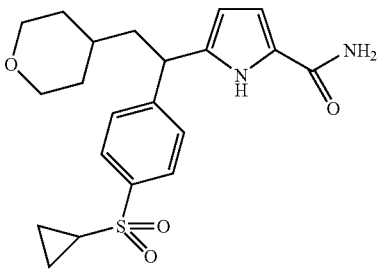

To a solution of 5-{1-[4-(cyclopropylsulfonyl)phenyl]-2-(tetrahydro-2H-pyran-4-yl)ethyl}-1H-pyrrole-2-carboxylic acid (1.3 g) in N,N-dimethylformamide (15 mL) were added 1-ethyl-3-(3-dimethylaminopropyl)carbodiimide hydrochloride (980 mg) and 1-hydroxybenzotriazole ammonium salt (926 mg), and the mixture was stirred at room temperature for 3 days. Water was added to the reaction mixture, and the mixture was extracted with ethyl acetate. The ethyl acetate layer was washed with saturated brine, dried (MgSO$_4$) and concentrated. The residue was subjected to silica gel column chromatography, and the title compound (910 mg, yield 70%) was obtained as a colorless amorphous solid from a fraction eluted with ethyl acetate. MS: 403 (MH$^+$).

$^1$H NMR (300 MHz, CDCl$_3$) δ1.01 (2 H, dd, J=2.1, 7.8 Hz), 1.18-1.40 (5 H, m), 1.46-1.64 (2 H, m), 1.74-1.90 (1 H, m), 2.02 (1 H, dt, J=7.0, 13.7 Hz), 2.35-2.58 (1 H, m), 3.11-3.32 (2 H, m), 3.86 (2 H, t, J=10.8 Hz), 4.17 (1 H, t, J=8.0 Hz), 5.81 (2 H, brs), 6.04-6.15 (1 H, m), 6.53-6.65 (1 H, m), 7.34 (2 H, d, J=8.7 Hz), 7.74 (2 H, d, J=8.3 Hz), 10.06 (1H, brs).

Example 243

Ethyl 5-{1-[4-(methylsulfonyl)phenyl]-2-(tetrahydro-2H-pyran-4-yl)ethyl}-1H-pyrrole-2-carboxylate

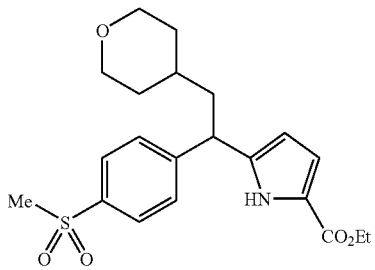

To a mixture of 4-[4-(methylsulfonyl)phenyl]-5-(tetrahydro-2H-pyran-4-yl)pent-1-en-3-one (350 mg), ethyl glyoxylate (polymer type, 47% toluene solution) (260 mg), triethylamine (0.31 mL), ethanol (15 mL) and tetrahydrofuran (5 mL) was added 3-benzyl-5-(2-hydroxyethyl)-4-methyl-1,3-thiazol-3-ium chloride (280 mg) and the mixture was heated under reflux for 1 hr under argon atmosphere. The reaction mixture was concentrated, water was added to the residue and the mixture was extracted with ethyl acetate. The ethyl acetate layer was washed with saturated brine, dried (MgSO$_4$) and concentrated. A mixture of the obtained residue, ammonium acetate (1.36 g) and acetic acid (10 mL) was stirred at 120° C. for 2 hr. The reaction mixture was concentrated, saturated aqueous sodium hydrogen carbonate solution was added to the residue, and the mixture was extracted with ethyl acetate. The ethyl acetate layer was washed with saturated brine, dried (MgSO$_4$) and concentrated. The residue was subjected to silica gel column chromatography, and the title compound (140 mg, yield 31%) was obtained as a pale-brown oil from a fraction eluted with hexane-ethyl acetate (1:1-1:2, volume ratio). MS: 406 (MH$^+$).
$^1$H NMR (300 MHz, CDCl$_3$) δ1.29-1.44 (6 H, m), 1.59 (2 H, t, J=13.44 Hz), 1.80-1.95 (1 H, m), 1.97-2.11 (1 H, m), 3.05 (3 H, s), 3.19-3.34 (2 H, m), 3.91 (2 H, d, J=11.36 Hz), 4.14-4.21 (1 H, m), 4.28 (2 H, q, J=7.07 Hz), 6.13 (1 H, t, J=3.22 Hz), 6.82-6.88 (1 H, m), 7.37 (2 H, d, J=8.33 Hz), 7.86 (2 H, d, J=8.33 Hz), 9.01 (1 H, brs).

Example 244

2-[1-methyl-1-(5-(pyridin-2-yl)-1H-pyrrol-2-yl)-2-(tetrahydro-2H-pyran-4-yl)ethyl]-5-(methylsulfanyl)pyridine

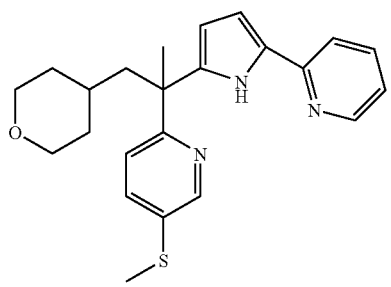

To a solution of 5-methyl-5-[5-(methylsulfanyl)pyridin-2-yl]-1-(pyridin-2-yl)-6-(tetrahydro-2H-pyran-4-yl)hexane-1,4-dione (60.7 mg) in acetic acid (1 mL) was added ammonium acetate (181 mg), and the mixture was stirred at 110° C. for 1 hr. After cooling to room temperature, the mixture was neutralized with saturated aqueous sodium hydrogen carbonate solution. The reaction mixture was diluted with ethyl acetate and washed with water. The ethyl acetate layer was dried (MgSO$_4$) and concentrated. The residue was subjected to silica gel column chromatography, and the title compound (84.0 mg, yield 82%) was obtained as a pale-yellow amorphous solid from a fraction eluted with ethyl acetate-hexane (4:1, volume ratio).
$^1$H NMR (300 MHz, CDCl$_3$) δ1.14-1.33 (5 H, m), 1.49-1.66 (1 H, m), 1.78 (3 H, s), 2.05-2.13 (1 H, m), 2.21-2.30 (1 H, m), 2.48 (3 H, s), 3.17-3.32 (2 H, m), 3.73-3.83 (2 H, m), 6.08-6.13 (1 m), 6.56-6.60 (1 H, m), 6.93-7.01 (1 H, m), 7.12 (1 H, d, J=8.3 Hz), 7.42-7.49 (2 H, m), 7.53-7.61 (1 H, m), 8.42 (1 H, d, J=4.9 Hz), 8.54 (1 H, d, J=1.9 Hz), 9.89 (1 H, brs).

Example 245

2-[1-methyl-1-(5-(pyridin-2-yl)-1H-pyrrol-2-yl)-2-(tetrahydro-2H-pyran-4-yl)ethyl]-5-(methylsulfonyl)pyridine

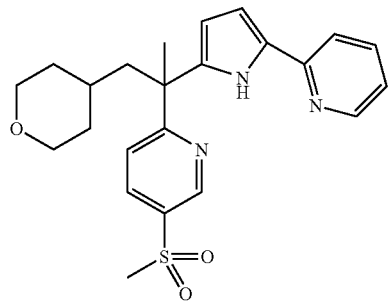

To a mixture of 2-[1-methyl-1-(5-(pyridin-2-yl)-1H-pyrrol-2-yl)-2-(tetrahydro-2H-pyran-4-yl)ethyl]-5-(methylsulfanyl)pyridine (84.0 mg), tetrahydrofuran (1 mL), water (1 mL) and methanol (1 mL) was added Oxone (registered trademark) (157 mg), and the mixture was stirred at room temperature for 1.5 hr. The reaction mixture was diluted with ethyl acetate, and washed with saturated aqueous sodium hydrogen carbonate solution. The ethyl acetate layer was dried (MgSO$_4$) and concentrated. The residue was subjected to silica gel column chromatography, and the title compound (55.5 mg, yield 61%) was obtained as white crystals from a fraction eluted with ethyl acetate-hexane (2:1, volume ratio). melting point 135-136° C. MS: 426 (MH$^+$).
$^1$H NMR (300 MHz, CDCl$_3$) δ1.15-1.35 (4 H, m), 1.49-1.70 (1 H, m), 1.84 (3 H, s), 2.10-2.21 (1 H, m), 2.24-2.35 (1 H, m), 3.08 (3 H, s), 3.17-3.34 (2 H, m), 3.72-3.88 (2H, m), 6.15 (1 H, t, J=3.2 Hz), 6.57-6.63 (1 H, m), 6.97-7.04 (1H, m), 7.40 (1 H, d, J=8.7 Hz), 7.46-7.51 (1 H, m), 7.55-7.63 (1 H, m), 8.07 (1 H, dd, J=2.7, 8.3 Hz), 8.43 (1 H, d, J=4.9 Hz), 9.14 (1 H, d, J=2.3 Hz), 9.81 (1 H, brs).

Experimental Example 1

Measurement of GK Activation Value

To each well of a 384-well black plate (Nalge Nunc International K.K.) was added 5 μL of 50% dimethyl sulfoxide solution containing test compound diluted to 100 μmol/L. Then, GST-hLGK1 obtained in Reference Example 2A was diluted with measurement buffer (containing 50 mM HEPES (pH 7.4), 200 mM KCl, 5 mM MgCl$_2$, 2.5 mM DTT and 50

μM 2'-(or-3')—O—(N-methylanthraniloyl) adenosine 5'-triphosphate (Mant-ATP) (Jena BioScience)) to 6 μg/mL and 35 μL thereof was added to each well.

Each well was stood at 37° C. for 10 min, 25 mM D-glucose solution (10 μL) was added to start the reaction. The final concentration of the test compound was 10 μmol/L.

Each, well after the reaction was stood at 37° C. for 60 min, and the reaction was quenched by adding 25 μL of a quenching solution (containing 200 mM HEPES (pH 7.4), 20 mM $MgCl_2$, 200 mM EDTA, 0.03% Triton-X 100, 0.3% Coating 3 reagent (Caliper Life Sciences, Inc.)).

2'-(or-3')-O-(N-methylanthraniloyl)adenosine 5'-triphosphate (Mant-ATP, substrate) and Mant-ADP (reaction resultant product) were separated from each well after the reaction by a microchip type capillary electrophoresis apparatus 250 HTS (Caliper Life Sciences, Inc.). The reaction rate [(reaction resultant product peak height)/(reaction resultant product peak height+substrate peak height)×100(%)] was calculated from the ratio of the substrate peak height and reaction resultant product peak height obtained by fluorescence detection (excitation wavelength 355 nm, measurement wavelength 460 nm) and used as the index of GK activity.

As a control group, the reaction rate was calculated in the same manner as above except that "solution in 50% dimethyl sulfoxide (without test compound)" was used instead of "solution of test compound in 50% dimethyl sulfoxide".

The reaction rate of the well (test compound addition group) added with the test compound was divided by the reaction rate of the control group and the obtained percentage was taken as the GK activation value (Emax) of the test compound. The results are shown in Table 1.

TABLE 1

| Example No. | Emax (%) |
|---|---|
| 1 | 195 |
| 2 | 168 |
| 3 | 180 |
| 4 | 227 |
| 5 | 167 |
| 6 | 198 |
| 7 | 179 |
| 8 | 225 |
| 9 | 173 |
| 10 | 193 |
| 11 | 160 |
| 14 | 185 |
| 17 | 188 |
| 21 | 157 |
| 24 | 190 |
| 29 | 218 |
| 34 | 178 |
| 42 | 156 |
| 53 | 148 |
| 59 | 151 |
| 62 | 153 |
| 63 | 154 |
| 91 | 142 |
| 127 | 139 |

TABLE 1-continued

| Example No. | Emax (%) |
|---|---|
| 151 | 167 |
| 160 | 155 |
| 164 | 148 |
| 172 | 148 |
| 177 | 171 |
| 197 | 142 |
| 225 | 141 |
| 227 | 129 |
| 228 | 145 |
| 237 | 152 |

As is clear from Table 1, the compound of the present invention has a superior glucokinase activating action.

Formulation Example 1

Production of Capsule

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3), and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

Industrial Applicability

The glucokinase activator of the present invention has superior activity, and is useful as a medicament such as an agent for the prophylaxis or treatment of diabetes, obesity and the like and the like.

This application is based on patent application Nos. 2007-120136 and 2008-106925 filed in Japan, the contents of which are incorporated in full herein by this reference.

The invention claimed is:

1. A compound represented by the formula (I)

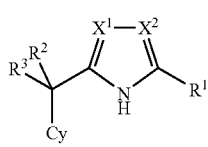

(I)

wherein
$R^1$ is
a 5- or 6-membered nitrogen-containing heterocyclic group represented by the formula

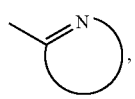

which is optionally substituted;

$R^2$ is an optionally substituted alkyl group, an optionally substituted 4- to 7-membered cyclic group, —$OR^6$ wherein $R^6$ is an optionally substituted alkyl group or an optionally substituted 4- to 7-membered cyclic group, or an optionally substituted amino group;

$R^3$ is a hydrogen atom or an optionally substituted alkyl group, or $R^2$ and $R^3$ in combination (i) optionally form, together with the carbon atom they are bonded to, cyclopropane substituted by an optionally substituted 4- to 7-membered cyclic group, or (ii) optionally form =N—$OR^7$ or =CH—$R^7$ wherein $R^7$ is an optionally substituted alkyl group or an optionally substituted 4- to 7-membered cyclic group;

Cy is an optionally substituted 6-membered cyclic group, which is optionally condensed with an optionally substituted 5- or 6-membered ring; and $X^1$ and $X^2$ are both optionally substituted carbon atoms, provided that when Cy is a benzene ring, then $R^2$ should not be pyrrolyl; or a salt thereof.

2. The compound of claim 1, wherein $R^2$ is an optionally substituted $C_{1-6}$ alkyl group.

3. The compound of claim 1, wherein $R^3$ is a hydrogen atom or a $C_{1-6}$ alkyl group.

4. The compound of claim 1, wherein Cy is an optionally substituted 6-membered aromatic group.

5. The compound or salt of claim 1, wherein $X^2$ is a carbon atom optionally substituted by one substituent selected from the group consisting of a halogen atom and a $C_{1-4}$ alkyl group optionally substituted by 1 to 3 $C_{1-6}$ alkoxy-carbonyl groups.

6. The compound of claim 1, wherein
R$^1$ is a 5- or 6-membered nitrogen-containing heterocyclic group represented by the formula

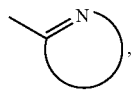

which is optionally substituted,
R$^2$ is an optionally substituted C$_{1-6}$ alkyl group, and
X$^1$ and X$^2$ are both optionally substituted carbon atoms.

7. The compound 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethane-1,2-diol or a salt thereof.

8. The compound 1-[6-(5-{1-[4-(cyclopropylsulfonyl)phenyl]-2-(tetrahydro-2H-pyran-4-yl)ethyl}-1H-pyrrol-2-yl)pyridin-3-yl]ethane-1,2-diol or a salt thereof.

9. The compound 2-[6-(5-{1-[4-(cyclopropylsulfonyl)phenyl]-2-(tetrahydro-2H-pyran-4-yl)ethyl}-1H-pyrrol-2-yl)pyridin-3-yl]propane-1,3-diol or a salt thereof.

10. The compound 1-acetyl-4-{[6-(5-{1-[4-(cyclopropylsulfonyl)phenyl]-2-(tetrahydro-2H-pyran-4-yl)ethyl}-1H-pyrrol-2-yl)pyridin-3-yl]methyl}piperazine or a salt thereof.

11. The compound 1-[6-(5-{1-[3-chloro-4-(methylsulfonyl)phenyl]-2-(tetrahydro-2H-pyran-4-yl)ethyl}-1H-pyrrol-2-yl)pyridin-3-yl]ethane-1,2-diol or a salt thereof.

12. The compound 1-[6-(5-{1-[4-(cyclopropylsulfonyl)phenyl]-2-(tetrahydro-2H-pyran-4-yl)ethyl}-1H-pyrrol-2-yl)pyridin-3-yl]-2-methylpropane-1,2-diol or a salt thereof.

13. The compound 1-[2-(5-{1-[4-(cyclopropylsulfonyl)phenyl]-2-(tetrahydro-2H-pyran-4-yl)ethyl}-1H-pyrrol-2-yl)-1,3-thiazol-5-yl]ethanol or a salt thereof.

14. The compound 1-[2-(5-{1-[3-chloro-4-(methylsulfonyl)phenyl]-2-(tetrahydro-2H-pyran-4-yl)ethyl}-1H-pyrrol-2-yl)-1,3-thiazol-5-yl]ethanol or a salt thereof.

15. The compound 3-(2-[3-chloro-4-(methylsulfonyl)phenyl]-2-{5-[5-(hydroxymethyl)pyridin-2-yl]-1H-pyrrol-2-yl}ethyl)cyclopentanone or a salt thereof.

16. A prodrug of the compound of claim 1.

17. A medicament comprising a compound represented by the formula

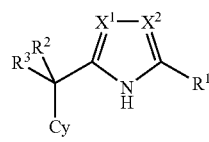

(I)

wherein
R$^1$ is
a 5- or 6-membered nitrogen-containing heterocyclic group represented by the formula

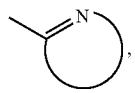

which is optionally substituted;
R$^2$ is an optionally substituted alkyl group, an optionally substituted 4- to 7-membered cyclic group, —OR$^6$ wherein R$^6$ is an optionally substituted alkyl group or an optionally substituted 4- to 7-membered cyclic group, or an optionally substituted amino group;
R$^3$ is a hydrogen atom or an optionally substituted alkyl group, or
R$^2$ and R$^3$ in combination
(i) optionally form, together with the carbon atom they are bonded to, cyclopropane substituted by an optionally substituted 4- to 7-membered cyclic group, or
(ii) optionally form =N—OR$^7$ or =CH—R$^7$ wherein R$^7$ is an optionally substituted alkyl group or an optionally substituted 4- to 7-membered cyclic group;
Cy is an optionally substituted 6-membered cyclic group, which is optionally condensed with an optionally substituted 5- or 6-membered ring; and
X$^1$ and X$^2$ are both optionally substituted carbon atoms, provided that when Cy is a benzene ring, then R$_2$ should not be pyrrolyl;
or a salt thereof or a produg thereof.

18. The medicament of claim 17, which is a glucokinase activator.

19. The medicament of claim 17, which is an agent for the prophylaxis or treatment of diabetes or obesity.

20. A method of activating a glucokinase in a mammal, which comprises administering, to the mammal, a compound represented by the formula

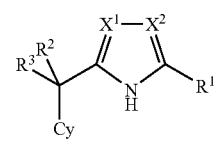

(I)

wherein
R$^1$ is
(i) a group represented by —COR$^4$
wherein
R$^4$ is an optionally substituted alkyl group, an optionally substituted cycloalkyl group, —OR$^5$ wherein R$^5$ is a hydrogen atom or an optionally substituted alkyl group, or an optionally substituted amino group, or
(ii) a 5- or 6-membered nitrogen-containing heterocyclic group represented by the formula

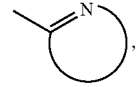

which is optionally substituted;
R$^2$ is an optionally substituted alkyl group, an optionally substituted 4- to 7-membered cyclic group, —OR$^6$ wherein R$^6$ is an optionally substituted alkyl group or an optionally substituted 4- to 7-membered cyclic group, or an optionally substituted amino group;
R$^3$ is a hydrogen atom or an optionally substituted alkyl group, or
R$^2$ and R$^3$ in combination
(i) optionally form, together with the carbon atom they are bonded to, cyclopropane substituted by an optionally substituted 4- to 7-membered cyclic group, or
(ii) optionally form =N—OR$^7$ or =CH—R$^7$ wherein R$^7$ is an optionally substituted alkyl group or an optionally substituted 4- to 7-membered cyclic group;
Cy is an optionally substituted 6-membered cyclic group, which is optionally condensed with an optionally substituted 5- or 6-membered ring; and
X$^1$ and X$^2$ are each independently an optionally substituted carbon atom, or a nitrogen atom, or a salt thereof or a prodrug thereof in an amount effective for activating glucokinase.

21. A method for the treatment of diabetes or obesity in a mammal, which comprises administering a therapeutically effective amount of a compound represented by the formula

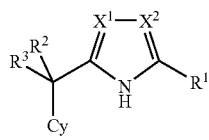

(I)

wherein
$R^1$ is
(i) a group represented by —$COR^4$
   wherein
   $R^4$ is an optionally substituted alkyl group, an optionally substituted cycloalkyl group, —$OR^5$ wherein $R^5$ is a hydrogen atom or an optionally substituted alkyl group, or an optionally substituted amino group, or
(ii) a 5- or 6-membered nitrogen-containing heterocyclic group represented by the formula

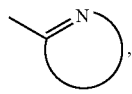

which is optionally substituted;
$R^2$ is an optionally substituted alkyl group, an optionally substituted 4- to 7-membered cyclic group, —$OR^6$ wherein $R^6$ is an optionally substituted alkyl group or an optionally substituted 4- to 7-membered cyclic group, or an optionally substituted amino group;
$R^3$ is a hydrogen atom or an optionally substituted alkyl group, or
$R^2$ and $R^3$ in combination
(i) optionally form, together with the carbon atom they are bonded to, cyclopropane substituted by an optionally substituted 4- to 7-membered cyclic group, or
(ii) optionally form =N—$OR^7$ or =CH—$R^7$ wherein $R^7$ is an optionally substituted alkyl group or an optionally substituted 4- to 7-membered cyclic group;
Cy is an optionally substituted 6-membered aromatic group, which is optionally condensed with an optionally substituted 5- or 6-membered ring; and
$X^1$ and $X^2$ are each independently an optionally substituted carbon atom, or a nitrogen atom,
or a salt thereof or a prodrug thereof to the mammal.

22. The compound or salt of claim 1, wherein $R^2$ is a $C_{1-6}$ alkyl group optionally substituted by an optionally substituted 4- or 7-membered cyclic group.

23. The compound or salt of claim 1, wherein $R^2$ is a $C_{1-6}$ alkyl group substituted by an optionally substituted 4- or 7-membered cyclic group.

24. A pharmaceutical composition comprising a compound or salt according to claim 1 and a pharmacologically acceptable carrier.

* * * * *

UNITED STATES PATENT AND TRADEMARK OFFICE
CERTIFICATE OF CORRECTION

PATENT NO.         : 8,318,746 B2
APPLICATION NO.    : 12/451130
DATED              : November 27, 2012
INVENTOR(S)        : Tsuneo Yasuma et al.

It is certified that error appears in the above-identified patent and that said Letters Patent is hereby corrected as shown below:

In the Claims:

Claim 2, in column 312, lines 58 and 59:
"The compound of claim 1, wherein $R^2$ is an optionally substituted $C_{1-6}$ alkyl group.",
should read
--The compound or salt of claim 1, wherein $R^2$ is an optionally substituted $C_{1-6}$ alkyl group.--.

Claim 3, in column 312, lines 60 and 61:
"The compound of claim 1, wherein $R^3$ is a hydrogen atom or a $C_{1-6}$ alkyl group.",
should read
--The compound or salt of claim 1, wherein $R^3$ is a hydrogen atom or a $C_{1-6}$ alkyl group.--.

Claim 4, in column 312, lines 62 and 63:
"The compound of claim 1, wherein Cy is an optionally substituted 6-membered aromatic group.", should read
--The compound or salt of claim 1, wherein Cy is an optionally substituted 6-membered aromatic group.--.

Claim 6, in column 313, line 1:
"The compound of claim 1, wherein",
should read
--The compound or salt of claim 1, wherein--.

Signed and Sealed this
Fourteenth Day of May, 2013

Teresa Stanek Rea
*Acting Director of the United States Patent and Trademark Office*

Claim 16, in column 313, line 40:

"A prodrug of the compound of claim 1.", should read

--A prodrug of the compound or salt of claim 1.--.

SEQUENCE LISTING

<160> NUMBER OF SEQ ID NOS: 4

<210> SEQ ID NO 1
<211> LENGTH: 27
<212> TYPE: DNA
<213> ORGANISM: Artificial
<220> FEATURE:
<223> OTHER INFORMATION: primer for cloning glucokinase

```
<400> SEQUENCE: 1
cagctctcca tccaagcagc cgttgct                                              27

<210> SEQ ID NO 2
<211> LENGTH: 21
<212> TYPE: DNA
<213> ORGANISM: Artificial
<220> FEATURE:
<223> OTHER INFORMATION: primer for cloning glucokinase

<400> SEQUENCE: 2
ggcggcctgg gtcctgacaa g                                                    21

<210> SEQ ID NO 3
<211> LENGTH: 69
<212> TYPE: DNA
<213> ORGANISM: Artificial
<220> FEATURE:
<223> OTHER INFORMATION: primer for cloning glucokinase

<400> SEQUENCE: 3
ggatccatgc ccagaccaag atcccaactc ccacaaccca actcccaggt agagcagatc          60
ctggcagag                                                                  69

<210> SEQ ID NO 4
<211> LENGTH: 24
<212> TYPE: DNA
<213> ORGANISM: Artificial
<220> FEATURE:
<223> OTHER INFORMATION: primer for cloning glucokinase

<400> SEQUENCE: 4
gaattcctgg cccagcatac aggc                                                 24
```